(12) United States Patent
Sullivan et al.

(10) Patent No.: US 12,390,524 B2
(45) Date of Patent: *Aug. 19, 2025

(54) COMPOSITIONS AND METHODS FOR INDUCING IMMUNE RESPONSES

(71) Applicant: Arcturus Therapeutics, Inc., San Diego, CA (US)

(72) Inventors: Sean Michael Sullivan, Escondido, CA (US); Daiki Matsuda, San Diego, CA (US); Kiyoshi Tachikawa, San Diego, CA (US); Padmanabh Chivukula, San Diego, CA (US); Priya Prakash Karmali, San Diego, CA (US); Jared Henry Davis, Poway, CA (US); Yanjie Bao, San Diego, CA (US)

(73) Assignee: Arcturus Therapeutics, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/351,392

(22) Filed: Jul. 12, 2023

(65) Prior Publication Data
US 2024/0115692 A1  Apr. 11, 2024

Related U.S. Application Data

(63) Continuation of application No. 17/196,890, filed on Mar. 9, 2021, now Pat. No. 11,759,515.

(60) Provisional application No. 63/073,900, filed on Sep. 2, 2020, provisional application No. 62/987,191, filed on Mar. 9, 2020.

(51) Int. Cl.
| | | |
|---|---|---|
| *A61K 39/215* | (2006.01) | |
| *A61K 9/51* | (2006.01) | |
| *A61K 38/00* | (2006.01) | |
| *A61K 39/00* | (2006.01) | |
| *A61K 39/12* | (2006.01) | |
| *A61K 47/10* | (2017.01) | |
| *A61K 47/20* | (2006.01) | |
| *A61K 47/26* | (2006.01) | |
| *C07K 14/005* | (2006.01) | |
| *C07K 14/18* | (2006.01) | |
| *C12N 7/00* | (2006.01) | |
| *C12N 15/86* | (2006.01) | |

(52) U.S. Cl.
CPC .......... *A61K 39/215* (2013.01); *A61K 9/5123* (2013.01); *A61K 39/12* (2013.01); *A61K 47/10* (2013.01); *A61K 47/20* (2013.01); *A61K 47/26* (2013.01); *C07K 14/005* (2013.01); *C07K 14/1808* (2013.01); *C12N 7/00* (2013.01); *C12N 15/86* (2013.01); *A61K 38/00* (2013.01); *A61K 2039/53* (2013.01); *C12N 2770/20022* (2013.01); *C12N 2770/20034* (2013.01); *C12N 2770/36122* (2013.01); *C12N 2770/36134* (2013.01); *C12N 2830/42* (2013.01); *C12N 2830/50* (2013.01)

(58) Field of Classification Search
CPC .... A61K 39/215; A61K 9/5123; A61K 39/12; A61K 47/10; A61K 47/20; A61K 47/26; A61K 38/00; A61K 2039/53; A61K 39/395; A61K 2039/507; A61K 2039/884; A61K 2039/55555; A61K 2039/572; A61K 2039/575; C07K 14/005; C07K 14/1808; C07K 2317/76; C07K 16/2818; C07K 16/2827; C12N 7/00; C12N 15/86; C12N 2770/20022; C12N 2770/20034; C12N 2770/36122; C12N 2770/36134; C12N 2830/42; C12N 2830/50; C12N 2740/13071; C12N 2760/16134; C12N 2760/16171; C12N 2740/13034; A61P 35/00; A61P 31/14; A61P 31/16; Y02A 50/30

See application file for complete search history.

(56) References Cited

U.S. PATENT DOCUMENTS

| | | | |
|---|---|---|---|
| 7,332,322 B2 | 2/2008 | Frolov et al. | |
| 7,425,337 B2 | 9/2008 | Smith et al. | |
| 7,442,381 B2 | 10/2008 | Smith et al. | |
| 8,093,367 B2 | 1/2012 | Kore et al. | |
| 8,158,601 B2 | 4/2012 | Chen et al. | |
| 8,304,529 B2 | 11/2012 | Kore et al. | |
| 8,961,995 B2 | 2/2015 | Frolov et al. | |
| 9,254,265 B2 | 2/2016 | Geall et al. | |
| 9,295,646 B2 | 3/2016 | Brito et al. | |
| 9,730,997 B2 | 8/2017 | Perri et al. | |
| 9,770,463 B2 | 9/2017 | Geall et al. | |

(Continued)

FOREIGN PATENT DOCUMENTS

| | | |
|---|---|---|
| EP | 2591114 B1 | 6/2016 |
| EP | 3471778 A2 | 4/2019 |

(Continued)

OTHER PUBLICATIONS

Shustov AV, et. al. VEEV replicon vector YFV-C1, complete sequence. GenBank: DQ322637.1. Dep. Jan. 16, 2006. (Year: 2006).*

(Continued)

*Primary Examiner* — Rachel B Gill
(74) *Attorney, Agent, or Firm* — Greenberg Traurig, LLP

(57) ABSTRACT

Provided herein are nucleic acid molecules encoding viral replication proteins and antigenic proteins or fragments thereof. Also provided herein are compositions that include nucleic acid molecules encoding viral replication and antigenic proteins, and lipids. Nucleic acid molecules provided herein are useful for inducing immune responses.

22 Claims, 11 Drawing Sheets

Specification includes a Sequence Listing.

(56) References Cited

U.S. PATENT DOCUMENTS

| | | | |
|---|---|---|---|
| 10,238,733 B2 | 3/2019 | Brito et al. | |
| 10,487,105 B2 | 11/2019 | Chivukula et al. | |
| 11,135,283 B2 | 10/2021 | Berglund et al. | |
| 11,744,887 B2 | 9/2023 | Sullivan et al. | |
| 11,759,515 B2 | 9/2023 | Sullivan et al. | |
| 2009/0075384 A1* | 3/2009 | Kamrud | A61P 37/04 |
| | | | 435/235.1 |
| 2009/0155301 A1 | 6/2009 | Mason et al. | |
| 2011/0171255 A1 | 7/2011 | Kliver et al. | |
| 2011/0207223 A1 | 8/2011 | Tang et al. | |
| 2011/0256175 A1 | 10/2011 | Hope et al. | |
| 2012/0027803 A1 | 2/2012 | Manoharan et al. | |
| 2012/0128760 A1 | 5/2012 | Manoharan et al. | |
| 2012/0156251 A1 | 6/2012 | Brito et al. | |
| 2013/0171241 A1 | 7/2013 | Geall | |
| 2013/0195968 A1 | 8/2013 | Geall et al. | |
| 2014/0227346 A1 | 8/2014 | Geall et al. | |
| 2014/0242152 A1 | 8/2014 | Geall et al. | |
| 2015/0024002 A1 | 1/2015 | Perri et al. | |
| 2016/0074500 A1 | 3/2016 | Pushko et al. | |
| 2016/0348132 A1 | 12/2016 | Rayner et al. | |
| 2018/0036398 A1 | 2/2018 | Hagen et al. | |
| 2018/0104359 A1 | 4/2018 | Kamrud | |
| 2018/0169268 A1 | 6/2018 | Payne et al. | |
| 2018/0171340 A1 | 6/2018 | Kamrud et al. | |
| 2018/0273576 A1 | 9/2018 | Hogrefe et al. | |
| 2018/0327471 A1 | 11/2018 | Limphong et al. | |
| 2019/0091329 A1 | 3/2019 | Brito et al. | |
| 2019/0224299 A1 | 7/2019 | Kamrud et al. | |
| 2019/0321458 A1 | 10/2019 | Sahin et al. | |
| 2019/0374650 A1 | 12/2019 | Moon et al. | |
| 2020/0010849 A1 | 1/2020 | Blair et al. | |
| 2020/0113830 A1 | 4/2020 | Geall et al. | |
| 2020/0113831 A1 | 4/2020 | Geall et al. | |
| 2020/0222332 A1 | 7/2020 | Irvine et al. | |
| 2020/0230058 A1 | 7/2020 | Geall et al. | |
| 2020/0230225 A1* | 7/2020 | Vogels | C12N 15/86 |
| 2020/0297634 A1 | 9/2020 | Karmali et al. | |
| 2020/0330585 A1 | 10/2020 | Mogler et al. | |
| 2021/0030859 A1 | 2/2021 | Bucala et al. | |
| 2021/0284974 A1 | 9/2021 | Chivukula et al. | |
| 2021/0290752 A1 | 9/2021 | Sullivan et al. | |
| 2021/0290756 A1 | 9/2021 | Sullivan et al. | |
| 2022/0347298 A1 | 11/2022 | Sullivan et al. | |
| 2022/0395570 A1* | 12/2022 | Rauch | A61K 47/543 |
| 2022/0401550 A1 | 12/2022 | Simon-loriere et al. | |
| 2023/0219996 A1 | 7/2023 | Matsuda et al. | |
| 2024/0115691 A1 | 4/2024 | Sullivan et al. | |

FOREIGN PATENT DOCUMENTS

| | | |
|---|---|---|
| EP | 3433369 B1 | 3/2020 |
| EP | 2729126 B1 | 12/2020 |
| WO | 2008119827 A1 | 10/2008 |
| WO | 2009079185 A2 | 6/2009 |
| WO | 2009086558 A1 | 7/2009 |
| WO | 2009127060 A1 | 10/2009 |
| WO | 2010048536 A2 | 4/2010 |
| WO | 2010054406 A1 | 5/2010 |
| WO | 2010088537 A2 | 8/2010 |
| WO | 2010129709 A1 | 11/2010 |
| WO | 2011153493 A2 | 12/2011 |
| WO | 2012006369 A2 | 1/2012 |
| WO | 2012006380 A2 | 1/2012 |
| WO | 2012170431 A2 | 12/2012 |
| WO | 2014170493 A2 | 10/2014 |
| WO | 2015051169 A2 | 4/2015 |
| WO | 2015061491 A1 | 4/2015 |
| WO | 2016184822 A1 | 11/2016 |
| WO | 2017083356 A1 | 5/2017 |
| WO | 2017223085 A2 | 12/2017 |
| WO | 2018078053 A1 | 5/2018 |
| WO | 2018208856 A1 | 11/2018 |
| WO | 2018222890 A1 | 12/2018 |
| WO | 2018222926 A1 | 12/2018 |
| WO | 2019023566 A1 | 1/2019 |
| WO | 2020014654 A1 | 1/2020 |
| WO | 2020035609 A2 | 2/2020 |
| WO | 2020254535 A1 | 12/2020 |
| WO | 2020254804 A1 | 12/2020 |
| WO | 2020255055 A1 | 12/2020 |
| WO | 2021067181 A1 | 4/2021 |
| WO | 2021183563 A1 | 9/2021 |
| WO | 2021183564 A1 | 9/2021 |
| WO | 2023010128 A2 | 2/2023 |

OTHER PUBLICATIONS

Keyer VV, et. al. Non-structural polyprotein [Cloning vector pCMV-VEE-GFP]. GenBank: QCD25069.1, Dep. Apr. 27, 2019. (Year: 2019).*

(Apr. 27, 2019) "Cloning Vector pCMV-VEE-GFP", Complete Sequence, GenBank ID: MH891622.1, 7 pages.

International Search Report and Written Opinion for Application No. PCT/US21/21572, mailed on Jul. 20, 2021, 11 pages.

International Search Report and Written Opinion for Application No. PCT/US21/21573, mailed on Jul. 1, 2021, 12 pages.

International Search Report and Written Opinion for Application No. PCT/US22/74337, mailed on Dec. 30, 2022, 16 pages.

(Jul. 18, 2020) "Surface Glycoprotein [Severe Acute Respiratory Syndrome Coronavirus 2]", GenBank ID: YP_009724390, 3 pages.

Altschul et al. (Oct. 5, 1990) "Basic Local Alignment Search Tool", Journal of Molecular Biology, 215(3):403-410.

Altschul et al. (Sep. 1, 1997) "Gapped BLAST and PSI-BLAST: A New Generation of Protein Database Search Programs", Nucleic Acids Research, 25(17):3389-3402.

Baden et al. (Feb. 4, 2021) "Efficacy and Safety of the mRNA-1273 SARS-CoV-2 Vaccine", The New England Journal of Medicine, 384(5):403-416.

Bochicchio et al. (2014) "Liposomes as siRNA Delivery Vectors", Current Drug Metabolism, 15(9):882-892.

Boles et al. (2017) "Synthetic Construct H7N9 HA Gene, Complete CDS", GenBank KY199425.1, National Library of Medicine, 4 pages.

Both et al. (Mar. 1, 1975) "Methylation-Dependent Translation of Viral Messenger RNAs In Vitro", Proceedings of the National Academy of Sciences, 72(3): 1189-1193.

Bouloy et al. (Jul. 1, 1980) "Both The 7-Methyl and The 2'-O-Methyl Groups in the Cap of mRNA Strongly Influence Its Ability to Act as Primer for Influenza Virus RNA Transcription", Proceedings of the National Academy of Sciences, 77(7):3952-3956.

Chan et al. (Sep. 19, 2016) "Cross-reactive antibodies enhance live attenuated virus infection for increased immunogenicity", Nature Microbiology, 1(12):16164 (10 pages).

Chan et al. (Oct. 5, 2017) "Early Molecular Correlates of Adverse Events Following Yellow Fever Vaccination", JCI Insight, 2(19):e96031 (12 pages).

Chan et al. (Aug. 2019) "Metabolic Perturbations and Cellular Stress Underpin Susceptibility to Symptomatic Live-attenuated Yellow Fever Infection", Nature Medicine, 25(8):1218-1224 (21 pages).

Chu et al. (Aug. 1978) "Paradoxical Observations on the 5' Terminus of Ovalbumin Messenger Ribonucleic Acid", Journal of Biological Chemistry, 253(15):5228-5231.

Cirelli et al. (May 16, 2019) "Slow Delivery Immunization Enhances Hiv Neutralizing Antibody and Germinal Center Responses via Modulation of Immunodominance", Cell, 177(5):1153-1171.e28 (57 pages).

Conticello et al. (Aug. 22, 2008) "Interaction Between Antibody-diversification Enzyme Aid and Spliceosome-associated Factor CTNNBL1", Molecular Cell, 31(4):474-484.

Corbett et al. (Oct. 22, 2020) "SARS-CoV-2 mRNA Vaccine Design Enabled by Prototype Pathogen Preparedness", Nature, 586(7830):567-571.

Corbett et al. (Jun. 11, 2020) "SARS-CoV-2 mRNA Vaccine Development Enabled by Prototype Pathogen Preparedness", bioRxiv., 39 pages.

(56) References Cited

OTHER PUBLICATIONS

Dabkowska et al. (Mar. 7, 2012) "The Effect of Neutral Helper Lipids on the Structure of Cationic Lipid Monolayers", Journal of the Royal Society Interface, 9(68):548-561.
Dua et al. (Apr.-Jun. 2012) "Liposome: Methods of Preparation and Applications", International Journal of Pharmaceutical Studies and Research, 3(3):14-20.
Dupuis et al. (Sep. 1, 2000) "Distribution of Dna Vaccines Determines Their Immunogenicity After Intramuscular Injection in Mice", The Journal of Immunology, 165(5):2850-2858.
Ehrchen et al. (Sep. 2009) "The Endogenous Toll-like Receptor 4 Agonist S1OOA8/S1OOA9 (Calprotectin) as Innate Amplifier of Infection, Autoimmunity, and Cancer", Journal of Leukocyte Biology, 86(3):557-566.
Enright et al. (Dec. 12, 2003) "MicroRNA targets in Drosophil", Genome Biology, 5:R1 (14 pages).
Geall et al. (Sep. 4, 2012) "Nonviral Delivery of Self-amplifying Rna Vaccines", Proceedings of the National Academy of Sciences, 109(36):14604-14609.
Groom et al. (Mar. 10, 2011) "CXCR3 in T Cell Function", Experimental Cell Research, 317(5):620-631.
Gustafsson et al. (Jul. 2004) "Codon Bias and Heterologous Protein Expression", Trends in Biotechnoloov, 22(7):346-353.
Hashem et al. (Oct. 8, 2019) "A Highly Lmmunogenic, Protective, and Safe Adenovirus-based Vaccine Expressing Middle East Respiratory Syndrome Coronavirus S1-cd40I Fusion Protein in a Transgenic Human Dipeptidyl Peptidase 4 Mouse Model", The Journal of Infectious Diseases, 220(10):1558-1567.
Hassett et al. (Apr. 15, 2019) "Optimization of Lipid Nanoparticles for Intramuscular Administration of mRNA Vaccines", Molecular Therapy—Nucleic Acids, 15:1-11.
Higgins et al. (Apr. 2019) "Programming Isotype-specific Plasma Cell Function", Trends Immunology, 40(4):345-357.
Honda-Okubo et al. (Mar. 2015) "Severe Acute Respiratory Syndrome-associated Coronavirus Vaccines Formulated with Delta Inulin Adjuvants Provide Enhanced Protection While Ameliorating Lung Eosinophilic Immunopathology", Journal of Virological Methods, 89(6):2995-3007.
Hsieh et al. (Sep. 18, 2020) "Structure-based design of prefusion-stabilized SARS-CoV-2 spikes", Science, 369(6510):1501-1505 (10 pages).
Huang et al. (Aug. 15, 2011) "In Vivo Delivery of RNAI with Lipid-Based Nanoparticles", Annual Review of Biomedical Engineering, 13:507-530.
Hyde et al. (Aug. 3, 2015) "The 5' and 3' Ends of Alphavirus RNAs-non-coding Is Not Non-functional", Virus Research, 206:99-107 (8 pages).
Ishikawa et al. (Sep. 27, 2009) "Preparation of Eukaryotic mRNA having Differently Methylated Adenosine at the 5'-Terminus and the Effect of the Methyl Group in Translation", Nucleic Acids Symposium, 53(1):129-130.
Jackson et al. (Feb. 4, 2020) "The Promise of mRNA Vaccines: a Biotech and Industrial Perspective", NPJ Vaccines, 5:11 (6 pages).
Jin et al. (Jul. 5, 2010) "Immunomodulatory Effects of dsRNA and Its Potential as Vaccine Adjuvant", Journal of Biomedicine and Biotechnology, 2010:690438.
Jokerst et al. (Jun. 2011) "Nanoparticle PEGylation for Imaging and Therapy", Nanomedicine (Lond), 6(4):715-728.
Kalnin et al. (2021) "Immunogenicity and efficacy of mRNA COVID-19 vaccine MRT5500 in preclinical animal models", NPJ Vaccines, 6(61):12 pages.
Karlin et al. (Jun. 1993) "Applications and Statistics for Multiple High-Scoring Segments in Molecular Sequences", Proceedings of the National Academy of Sciences, 90(12):5873-5877.
Karlin et al. (Mar. 1990) "Methods for Assessing the Statistical Significance of Molecular Sequence Features by Using General Scoring Schemes", Proceedings of the National Academy of Sciences, 87(6):2264-2268.

Kasturi et al. (Feb. 24, 2011) "Programming the Magnitude and Persistence of Antibody Responses with Innate Immunity", Nature, 470(7335):543-547 (20 pages).
Kawabata et al. (1995) "The Fate of Plasmid DNA After Intravenous Injection in Mice: Involvement of Scavenger Receptors in Its Hepatic Uptake", Pharmaceutical Research, 12:825-830.
Keech et al. (Dec. 10, 2020) "Phase 1-2 Trial of a SARS-CoV-2 Recombinant Spike Protein Nanoparticle Vaccine", The New England Journal of Medicine, 383:2320-2332.
Kirchdoerfer et al. (Oct. 24, 2018) "Stabilized Coronavirus Spikes Are Resistant to Conformational Changes Induced by Receptor Recognition or Proteolysis", Science Reports. 8(1):15701 (11 pages).
Kowalski et al. (Apr. 2019) "Delivering the Messenger: Advances in Technologies for Therapeutic mRNA Delivery", Molecular Therapy, 27(4):710-728.
Kozak Marilyn. (Nov. 1990) "Downstream Secondary Structure Facilitates Recognition of Initiator Codons by Eukaryotic Ribosomes", Proceedings of the National Academy of Sciences, 87(21):8301-8305.
Kozak Marilyn. (Jul. 1988) "Leader Length and Secondary Structure Modulate mRNA Function Under Conditions of Stress.", Molecular and Cellular Biology, 8(7):2737-2744.
Kozak Marilyn. (Oct. 25, 1991) "Structural Features In Eukaryotic mRNAs That Modulate The Initiation of Translation", Journal of Biological Chemistry, 266(30):19867-19870.
Kozak Marilyn. (Feb. 1989) "The Scanning Model for Translation: An Update", Journal of Cell Biology, 108(2):229-241.
Kreiter et al. (Jan. 1, 2008) "Increased Antigen Presentation Efficiency by Coupling Antigens to MHC Class I Trafficking Signals", Journal of Immunology, 180(1):309-318.
Kulasegaran-Shylini et al. (Apr. 25, 2009) "The 5'UTR-specific Mutation in VEEV TC-83 Genome Has a Strong Effect on RNA Replication and Subgenomic RNA Synthesis, but Not on Translation of the Encoded Proteins", Virology, 387(1):211-221 (24 pages).
Kulkarni et al. (Jun. 2018) "Lipid Nanoparticles Enabling Gene Therapies: From Concepts to Clinical Utility", Nucleic Acid Therapeutics, 28(3):146-157.
Lasic Dand. (Jul. 1, 1998) "Novel Applications of Liposomes", Trends in Biotechnology, 16(7):307-321.
Li et al. (Jan. 2011) "Biosynthesis of Nanoparticles by Microorganisms and Their Applications", Journal of Nanomaterials, Article ID 270974, 2011:17 Pages.
Li et al. (Aug. 3, 2010) "Stealth Nanoparticles: High Density but Sheddable PEG is a Key for Tumor Targeting", Journal of Controlled Release, 145(3):178-181.
Lin et al. (Jan. 2014) "Lipid-based Nanoparticles in the Systemic Delivery of siRNA", Nanomedicine, 9(1):105-120.
Love et al. (Feb. 2, 2010) "Lipid-like materials for low-dose, In Vivo Gene Silencing", Proceedings of the National Academy of Sciences, 107(5):1864-1869.
Magini et al. (Aug. 15, 2016) "Self-amplifying mRNA Vaccines Expressing Multiple Conserved Influenza Antigens Confer Protection Against Homologous and Heterosubtypic Viral Challenge", PLoS one, 11(8):e0161193 (25 pages).
Maruggi et al. (Dec. 2013) "Engineered Alphavirus Replicon Vaccines Based on Known Attenuated Viral Mutants Show Limited Effects on Immunogenicity", Virology, 447(1-2):254-264.
Maruggi et al. (Apr. 10, 2019) "mRNA as a Transformative Technology for Vaccine Development to control Infectious Diseases", Molecular Therapy, 27(4):757-772.
Muthukrishnan et al. (May 1, 1975) "5'-Terminal 7-Methylguanosine in Eukaryotic mRNA is Required for Translation", Nature, 255:33-37.
Olmedillas et al. (May 6, 2021) "Structure-based design of a highly stable, covalently-linked SARS-CoV-2 spike trimer with improved structural properties and immunogenicity", bioRxiv, 51 pages.
Patil et al. (Jan. 2014) "Novel Methods for Liposome Preparation", Chemistry and Physics of Lipids, 177:8-18.
Pearson et al. (2013) "An Introduction to Sequence Similarity ("Homology") Searching", Current Protocols in Bioinformatics Book, 42:3.1.1-3.1.8.

(56) References Cited

OTHER PUBLICATIONS

Pearson et al. (Apr. 1988) "Improved Tools for Biological Sequence Comparison", Proceedings of the National Academy of Sciences, 85:2444-2448.

Pepini et al. (May 15, 2017) "Induction of an IFN-mediated Antiviral Response by a Self-amplifying RNA Vaccine: Implications for Vaccine Design", The Journal of Immunology, 198(10):4012-4024 (13 pages).

Petkov et al. (Jun. 4, 2018) "DNA Immunization Site Determines the Level of Gene Expression and the Magnitude, but Not the Type of the Induced Immune Response", PLoS One, 13(6): e0197902 (22 pages).

Polack et al. (Dec. 31, 2020) "Safety and Efficacy of the BNT162b2 mRNA Covid-19 Vaccine", The New England Journal of Medicine, 383:2603-2615.

Querec et al. (Jan. 2009) "Systems Biology Approach Predicts Immunogenicity of the Yellow Fever Vaccine in Humans", National Immunology, 10(1):116-125 (26 pages).

Querec et al. (2007) "Understanding the Role of Innate Immunity in the Mechanism of Action of the Live Attenuated Yellow Fever Vaccine 17D", Advances in Experimental Medicine and Biology, 590:43-53.

Ramanathan et al. (Sep. 19, 2016) "mRNA Capping: Biological Functions and Applications", Nucleic Acids Research, 44(16):7511-7526.

Rodriguez-Gascon et al., (Apr. 10, 2014) "Development of Nucleic Acid Vaccines: Use of Self-Amplifying RNA in Lipid Nanoparticles", International Journal of Nanomedicine, 9:1833-1843.

Sahin et al. (Dec. 11, 2020) "BNT162b2 Induces SARS-CoV-2-Neutralising Antibodies and T cells in Humans", medRxiv, 49 pages.

Sahin et al. (May 27, 2021) "BNT162b2 vaccine induces neutralizing antibodies and poly-specific T cells in humans", Nature, 595:572-577.

Saltl et al. (Dec. 15, 2011) "Granzyme B Regulates Antiviral CD8+ T Cell Responses", Journal of Immunology, 187(12):6301-6309 (19 pages).

Sercombe et al. (Dec. 1, 2015) "Advances and Challenges of Liposome Assisted Drug Delivery", Frontiers in Pharmacology, 6(286):13 Pages.

Slansky et al. (Oct. 2000) "Enhanced Antigen-Specific Antitumor Immunity with Altered Peptide Ligands that Stabilize the MHC-Peptide-TCR Complex", Immunity, 13(4):529-538.

Tam et al. (Oct. 4, 2016) "Sustained Antigen Availability During Germinal Center Initiation Enhances Antibody Responses to Vaccination", Proceedings of the National Academy of Sciences, 113(43):e6639-e6648.

Taverniti et al. (Jan. 9, 2015) "Elimination of Cap Structures Generated by mRNA Decay Involves the New Scavenger mRNA Decapping Enzyme Aph1/FHIT Together with DcpS", Nucleic Acids Research, 43(1):482-492.

Thompson et al. (Mar. 7, 2006) "Mucosal and Systemic Adjuvant Activity of Alphavirus Replicon Particles", Proceedings of the National Academy of Sciences, 103(10):3722-3727.

U.S. Appl. No. 16/823,212, "Method of Making Lipid-Encapsulated RNA Nanoparticles", 95 pages.

Villalobos et al. (Jun. 6, 2006) "Gene Designer: A Synthetic Biology Tool for Constructing Artificial DNA Segments", BMC Bioinformatics, 7:285 (8 pages).

Von Herrath et al. (Jun. 2003) "Immune Responsiveness, Tolerance and dsRNA: Implications for Traditional Paradigms", Trends in Immunology, 24(6):289-293 (4 pages).

Wootton et al. (Jun. 1993) "Statistics of Local Complexity in Amino Acid Sequences and Sequence Databases", Computers & Chemistry, 17(2):149-163.

Wrapp et al. (Mar. 13, 2020) "Cryo-EM Structure of the 2019-nCoV Spike in the Prefusion Conformation", Science, 367(6483):1260-1263.

Wu et al. (Mar. 12, 2020) "A New Coronavirus Associated with Human Respiratory Disease in China", Nature, 579(7798):265-269.

Yu et al. (Sep. 2000) "April and TALL-I and Receptors BCMA and TACI: System for Regulating Humoral Immunity", Nature Immunology, 1(3):252-256.

Extended European Search Report for Application No. EP 21767978.6, mailed on Apr. 30, 2024, 11 pages.

Extended European Search Report for Application No. EP 21768525.4, mailed on Mar. 22, 2024, 10 pages.

Kim et al. (2014) "Enhancement of Protein 1-15 Expression by Alphavirus Replicons by Designing Self-replicating Subgenomic RNAs", Proceedings of the National Academy of Sciences of the United States of America, 111 (29):10708-10713.

Lundstrom, Kenneth (2016) "Replicon RNA Viral 1-15 Vectors as Vaccines", Vaccines, 4(4):39.

Lundstrom, Kenneth (2018) "Self-Replicating RNA Viruses for RNA Therapeutics", Molecules, 23(12):3310.

* cited by examiner

COMPOSITIONS AND METHODS FOR INDUCING IMMUNE RESPONSES

CROSS-REFERENCES TO RELATED APPLICATIONS

This application claims the benefit of U.S. Provisional Application No. 62/987,191, filed Mar. 9, 2020 and U.S. Provisional Application No. 63/073,900, filed Sep. 2, 2020.

REFERENCE TO A SEQUENCE LISTING

The instant application contains a Sequence Listing which has been submitted electronically in XML format and is hereby incorporated by reference in its entirety. Said XML copy, created on Jul. 12, 2023 is named 2023 Jul. 11 Sequence_Listing_ST26 049386-530C01US.xml and is 322,134 bytes in size.

Reference is also made to the Sequence Listing filed with U.S. application Ser. No. 17/196,890, which was submitted electronically in ASCII format and is also hereby incorporated by reference in its entirety. Said ASCII copy, created on Mar. 8, 2021 is named 049386-530001US_SequenceListing_ST25.txt and is 390,698 bytes in size.

TECHNICAL FIELD

The present disclosure relates generally to inducing immune responses against infectious agents and tumor antigens and more specifically to self-transcribing and replicating RNA for antigen expression.

BACKGROUND

Infectious diseases and cancer represent significant burdens on health worldwide. According to the World Health Organization (WHO), lower respiratory tract infection was the deadliest infectious disease worldwide in 2016, causing approximately 3 million deaths. Current control measures to curb the rapid worldwide spread of infection diseases, such as national lockdowns, closure of work places and schools, and reduction of international travel are threatening to result in a global economic recession to an extent not seen since the Great Depression.

Cancer is the second leading cause of death globally, accounting for approximately 9.6 million deaths worldwide in 2018. Cancer is a large group of diseases that can affect almost any organ or tissue in the body. Cancer burden continues to grow globally, exerting physical, emotional, and financial strains on patients and health care providers. Self-replicating ribonucleic acids (RNAs), e.g., derived from viral replicons, are useful for expression of proteins, such as heterologous proteins, for a variety of purposes, such as expression of therapeutic proteins and expression of antigens for vaccines. A desirable property of such replicons is the ability for sustained expression of the protein.

Few treatments for infections caused by viruses and eukaryotic organisms are available, and resistance to antibiotics for the treatment of bacterial infections is increasing. In addition, rapid responses, including rapid vaccine development, are required to effectively control emerging infectious diseases and pandemics. Moreover, many cancer treatments include costly and painful surgeries and chemotherapies that are often unsuccessful or only modestly prolong life despite serious side effects. Thus, there exists a need for the prevention and/or treatment of infectious diseases and cancer.

SUMMARY

In one aspect, the present disclosure provides a nucleic acid molecule comprising a first polynucleotide encoding one or more viral replication proteins, wherein the first polynucleotide is codon-optimized as compared to a wild-type polynucleotide encoding the one or more viral replication proteins; and a second polynucleotide comprising a first transgene encoding a first antigenic protein or a fragment thereof.

In some embodiments, the one or more viral replication proteins may be alphavirus proteins or rubivirus proteins.

In some embodiments, the alphavirus proteins are from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), Buggy Creek Virus (BCRV), or any combination thereof.

In some embodiments, the first polynucleotide encodes a polyprotein comprising an alphavirus nsP1 protein, an alphavirus nsP2 protein, an alphavirus nsP3 protein, an alphavirus nsP4 protein, or any combination thereof.

In some embodiments, the first polynucleotide encodes a polyprotein comprising an alphavirus nsP1 protein, an alphavirus nsP2 protein, an alphavirus nsP3 protein, or any combination thereof, and an alphavirus nsP4 protein.

In some embodiments, the nucleic acid molecule further comprises a first intergenic region between a sequence encoding the polyprotein comprising an alphavirus nsP1 protein, an alphavirus nsP2 protein, an alphavirus nsP3 protein, or any combination thereof, and a sequence encoding an alphavirus nsP4 protein.

In some embodiments, the first intergenic region comprises an alphavirus sequence.

In some embodiments, the first polynucleotide comprises a sequence having at least 80% identity to a sequence of SEQ ID NO:72.

In some embodiments, the nucleic acid molecule further comprises a 5' untranslated region (UTR), such as a viral 5' UTR, a non-viral 5' UTR, or a combination of viral and non-viral 5' UTR sequences. In some embodiments, the 5' UTR comprises an alphavirus 5' UTR.

In some embodiments, the alphavirus 5' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 5' UTR sequence.

In some embodiments, the 5' UTR comprises a sequence of SEQ ID NO:73, SEQ ID NO:74, or SEQ ID NO:75.

In some embodiments, the nucleic acid molecule further comprises a 3' untranslated region (UTR). In some embodiments, the 3' UTR comprises a viral 3' UTR, a non-viral 3' UTR, or a combination of viral and non-viral 3' UTR sequences. In some embodiments, the 3' UTR comprises an alphavirus 3' UTR.

In some embodiments, the alphavirus 3' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 3' UTR sequence.

In some embodiments, the 3' UTR comprises a poly-A sequence. In some embodiments, the 3' UTR comprises a sequence of SEQ ID NO:76.

In some embodiments, the antigenic protein is a viral protein, a bacterial protein, a fungal protein, a protozoan protein, a parasite protein, or a tumor protein.

In some embodiments, the viral protein is an orthomyxovirus protein, a paramyxovirus protein, a picornavirus protein, a flavivirus protein, a filovirus protein, a rhabdovirus protein, a togavirus protein, an arterivirus protein, a bunyavirus protein, an arenavirus protein, a reovirus protein, a bornavirus protein, a retrovirus protein, an adenovirus protein, a herpesvirus protein, a polyomavirus protein, a papillomavirus protein, a poxvirus protein, or a hepadnavirus protein.

In some embodiments, the antigenic protein is an influenza virus protein, a respiratory syncytial virus (RSV) protein, a human immunodeficiency virus (HIV) protein, a hepatitis C virus (HCV) protein, a cytomegalovirus (CMV) protein, a Lassa Fever Virus (LFV) protein, an Ebola Virus (EBOV) protein, a *Mycobacterium* protein, a *Bacillus* protein, a *Yersinia* protein, a *Streptococcus* protein, a *Pseudomonas* protein, a *Shigella* protein, a *Campylobacter* protein, a *Salmonella* protein, a *Plasmodium* protein, or a *Toxoplasma* protein.

In some embodiments, the tumor protein is a kidney cancer, renal cancer, urinary bladder cancer, prostate cancer, uterine cancer, breast cancer, cervical cancer, ovarian cancer, lung cancer, liver cancer, stomach cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, or sarcoma protein.

In some embodiments, the second polynucleotide comprises at least two transgenes.

In some embodiments, a second transgene encodes a second antigenic protein or a fragment thereof or an immunomodulatory protein.

In some embodiments, the second polynucleotide further comprises a sequence encoding a 2A peptide, an internal ribosomal entry site (IRES), or a combination thereof, located between transgenes.

In some embodiments, the immunomodulatory protein is a cytokine, a chemokine, or an interleukin.

In some embodiments, the first and second transgenes encode viral proteins, bacterial proteins, fungal proteins, protozoan proteins, parasite proteins, tumor proteins, immunomodulatory proteins, or any combination thereof.

In some embodiments, the first polynucleotide is located 5' of the second polynucleotide.

In some embodiments, the nucleic acid molecule further comprises a second intergenic region located between the first polynucleotide and the second polynucleotide.

In some embodiments, the second intergenic region comprises a sequence having at least 85% identity to a sequence of SEQ ID NO:77.

In some embodiments, the nucleic acid molecule is a DNA molecule; or an RNA molecule, wherein T is substituted with U.

In some embodiments, the DNA molecule further comprises a promoter. In some embodiments, the promoter is located 5' of the 5'UTR.

In some embodiments, the promoter is a T7 promoter, a T3 promoter, or an SP6 promoter.

In some embodiments, the RNA molecule is a self-replicating RNA molecule.

In some embodiments, the RNA molecule further comprises a 5' cap. In some embodiments, the 5' cap has a Cap 1 structure, a Cap 1 (m6A) structure, a Cap 2 structure, a Cap 0 structure, or any combination thereof.

In another aspect, provided herein is a nucleic acid molecule comprising a sequence of SEQ ID NO:78; or a sequence of SEQ ID NO:72, SEQ ID NO:73, SEQ ID NO:76, and SEQ ID NO:77, wherein T is substituted with U.

In some embodiments, the nucleic acid molecule is an RNA molecule.

In some embodiments, the nucleic acid molecule further comprises a 5' cap having a Cap 1 structure.

In yet another aspect, provided herein is a nucleic acid molecule comprising a first polynucleotide comprising a sequence having at least 80% identity to a sequence of SEQ ID NO:72; and a second polynucleotide comprising a first transgene encoding a first antigenic protein or a fragment thereof.

In some embodiments, the nucleic acid molecule further comprises a 5' untranslated region (UTR).

In some embodiments, the 5' UTR comprises a viral 5' UTR, a non-viral 5' UTR, or a combination of viral and non-viral 5' UTR sequences. In some embodiments, the 5' UTR comprises an alphavirus 5' UTR.

In some embodiments, the alphavirus 5' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 5' UTR sequence.

In some embodiments, the 5' UTR comprises a sequence of SEQ ID NO:73, SEQ ID NO:74, or SEQ ID NO:75.

In some embodiments, the nucleic acid molecule further comprises a 3' untranslated region (UTR).

In some embodiments, the 3' UTR comprises a viral 3' UTR, a non-viral 3' UTR, or a combination of viral and non-viral 3' UTR sequences. In some embodiments, the 3' UTR comprises an alphavirus 3' UTR.

In some embodiments, the alphavirus 3' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 3' UTR sequence.

In some embodiments, the 3' UTR comprises a poly-A sequence.

In some embodiments, the 3' UTR comprises a sequence of SEQ ID NO:76.

In some embodiments, the antigenic protein is a viral protein, a bacterial protein, a fungal protein, a protozoan protein, a parasite protein, or a tumor protein.

In some embodiments, the viral protein is an orthomyxovirus protein, a paramyxovirus protein, a picornavirus protein, a flavivirus protein, a filovirus protein, a rhabdovirus protein, a togavirus protein, an arterivirus protein, a bunyavirus protein, an arenavirus protein, a reovirus protein, a bornavirus protein, a retrovirus protein, an adenovirus protein, a herpesvirus protein, a polyomavirus protein, a papillomavirus protein, a poxvirus protein, or a hepadnavirus protein.

In some embodiments, the antigenic protein is an influenza virus protein, a respiratory syncytial virus (RSV) protein, a human immunodeficiency virus (HIV) protein, a hepatitis C virus (HCV) protein, a cytomegalovirus (CMV) protein, a Lassa Fever Virus (LFV) protein, an Ebola Virus (EBOV) protein, a *Mycobacterium* protein, a *Bacillus* protein, a *Yersinia* protein, a *Streptococcus* protein, a *Pseudomonas* protein, a *Shigella* protein, a *Campylobacter* protein, a *Salmonella* protein, a *Plasmodium* protein, or a *Toxoplasma* protein.

In some embodiments, the tumor protein is a kidney cancer, renal cancer, urinary bladder cancer, prostate cancer, uterine cancer, breast cancer, cervical cancer, ovarian cancer, lung cancer, liver cancer, stomach cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, or sarcoma protein.

In some embodiments, the second polynucleotide comprises at least two transgenes. In some embodiments, a second transgene encodes a second antigenic protein or a fragment thereof or an immunomodulatory protein.

In some embodiments, the second polynucleotide further comprises a sequence encoding a 2A peptide, an internal ribosomal entry site (IRES), or a combination thereof, located between transgenes.

In some embodiments, the immunomodulatory protein is a cytokine, a chemokine, or an interleukin.

In some embodiments, the first and second transgenes encode viral proteins, bacterial proteins, fungal proteins, protozoan proteins, parasite proteins, tumor proteins, immunomodulatory proteins, or any combination thereof.

In some embodiments, the first polynucleotide is located 5' of the second polynucleotide.

In some embodiments, the nucleic acid molecule further comprises a second intergenic region located between the first polynucleotide and the second polynucleotide. In some embodiments, the second intergenic region comprises a sequence having at least 85% identity to a sequence of SEQ ID NO:77.

In some embodiments, the nucleic acid molecule is a DNA molecule; or an RNA molecule, wherein T is substituted with U.

In some embodiments, the DNA molecule further comprises a promoter. In some embodiments, the promoter is located 5' of the 5'UTR.

In some embodiments, the promoter is a T7 promoter, a T3 promoter, or an SP6 promoter.

In some embodiments, the RNA molecule is a self-replicating RNA molecule.

In some embodiments, the RNA molecule further comprises a 5' cap. In some embodiments, the 5' cap has a Cap 1 structure, a Cap 1 (m6A) structure, a Cap 2 structure, a Cap 0 structure, or any combination thereof.

In yet another aspect, provided herein is a composition comprising any one of the nucleic acid molecules described herein.

In some embodiments, the lipid comprises an ionizable cationic lipid. In some embodiments, the ionizable cationic lipid has a structure of

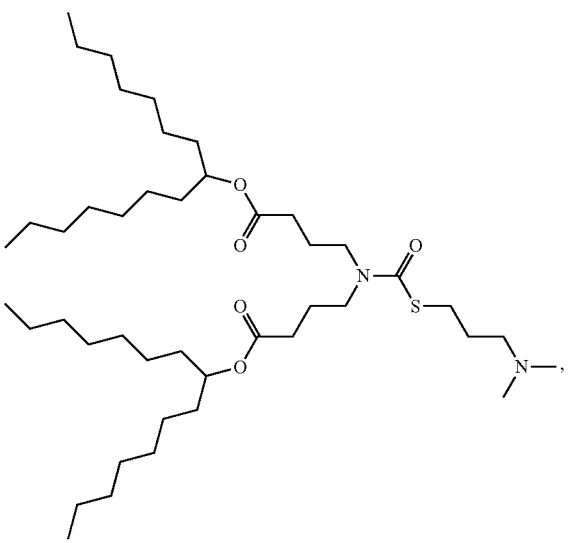

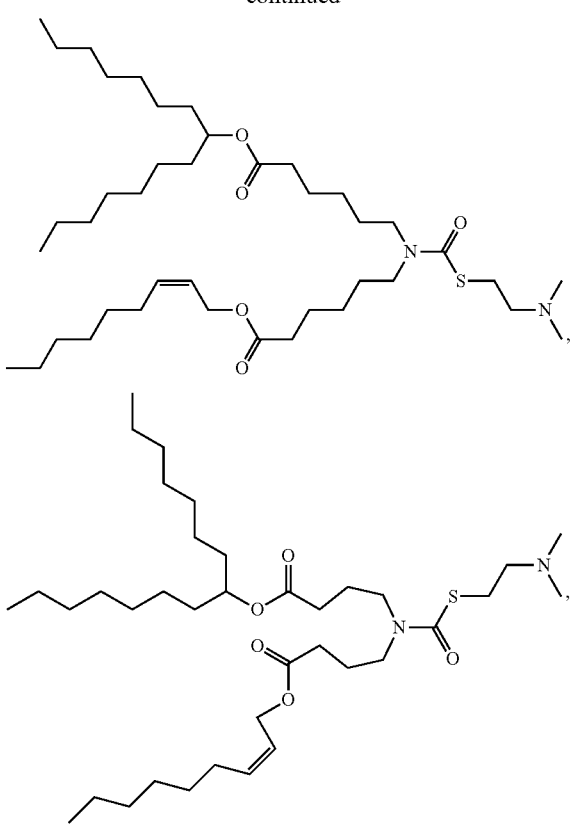

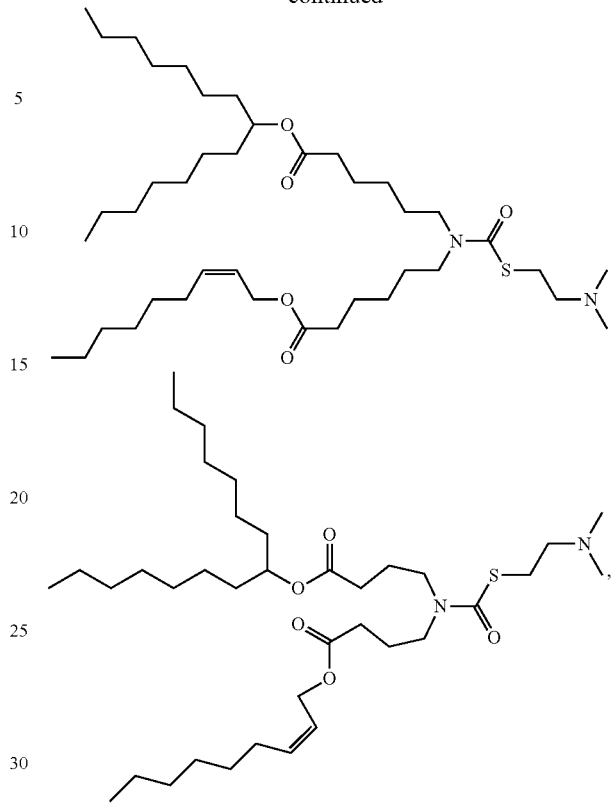

or a pharmaceutically acceptable salt thereof.

In yet another aspect, provided herein is a pharmaceutical composition comprising any one of the nucleic acid molecules described herein, and a lipid formulation.

In some embodiments, the lipid formulation comprises an ionizable cationic lipid. In some embodiments, the ionizable cationic lipid has a structure of

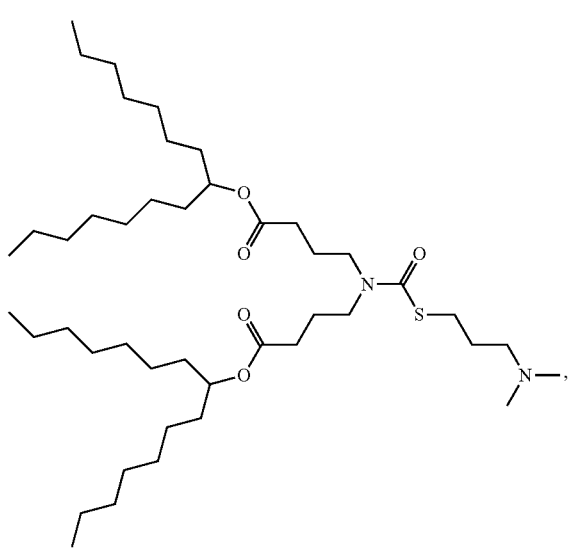

or a pharmaceutically acceptable salt thereof.

In yet another aspect, provided herein is a method of inducing an immune response in a subject comprising administering to the subject an effective amount of any one of the nucleic acid molecules described herein.

In some embodiments, the method comprises administering the nucleic acid molecule intramuscularly, subcutaneously, intradermally, transdermally, intranasally, orally, sublingually, intravenously, intraperitoneally, topically, by aerosol, or by a pulmonary route.

In yet another aspect, provided herein is a method of inducing an immune response in a subject comprising administering to the subject an effective amount of any one of the compositions described herein.

In some embodiments, the method comprises administering the composition intramuscularly, subcutaneously, intradermally, transdermally, intranasally, orally, sublingually, intravenously, intraperitoneally, topically, by aerosol, or by a pulmonary route.

In yet another aspect, provided herein is a method of inducing an immune response in a subject comprising administering to the subject an effective amount of any one of the pharmaceutical compositions described herein.

In some embodiments, the method may comprise administering the pharmaceutical composition intramuscularly, subcutaneously, intradermally, transdermally, intranasally, orally, sublingually, intravenously, intraperitoneally, topically, by aerosol, or by a pulmonary route.

In yet another aspect, the present disclosure provides any of the nucleic acid molecules described herein for use in inducing an immune response to the first antigenic protein or fragment thereof.

In yet another aspect, the present disclosure provides use of any one of the nucleic acid molecules described herein in the manufacture of a medicament for inducing an immune response to the first antigenic protein or fragment thereof.

DETAILED DESCRIPTION

Figure 1:
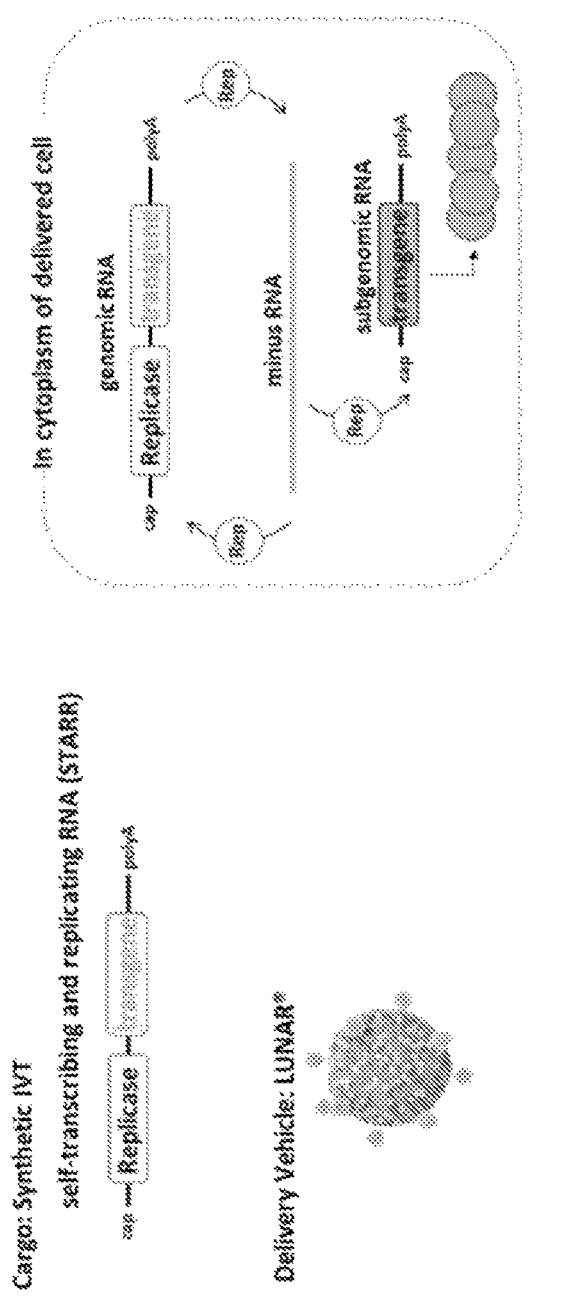
FIG. 1 shows a schematic illustrating one aspect of STARR™ technology.

The present disclosure relates to self-replicating RNAs and nucleic acids encoding the same for expression of transgenes such as antigenic proteins and tumor antigens, for example. Also provided herein are methods of administration (e.g., to a host, such as a mammalian subject) of self-replicating RNAs, whereby the self-replicating RNA is translated in vivo and the heterologous protein-coding sequence is expressed and, e.g., can elicit an immune response to the heterologous protein-coding sequence in the recipient or provide a therapeutic effect, where the heterologous protein-coding sequence is a therapeutic protein. Self-replicating RNAs provided herein are useful as vaccines that can be rapidly generated and that can be effective at low and/or single doses. The present disclosure further relates to methods of inducing an immune response using self-replicating RNAs provided herein.

Definitions

As used herein, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth.

"About" as used herein when referring to a measurable value such as an amount, a temporal duration, and the like, is meant to encompass variations of +20%, or ±10%, or ±5%, or even ±1% from the specified value, as such variations are appropriate for the disclosed methods or to perform the disclosed methods.

As used herein, the term "fragment," when referring to a protein or nucleic acid, for example, means any shorter sequence than the full-length protein or nucleic acid. Accordingly, any sequence of a nucleic acid or protein other than the full-length nucleic acid or protein sequence can be a fragment. In some aspects, a protein fragment includes an epitope. In other aspects, a protein fragment is an epitope.

As used herein, the term "nucleic acid" refers to any deoxyribonucleic acid (DNA) molecule, ribonucleic acid (RNA) molecule, or nucleic acid analogues. A DNA or RNA molecule can be double-stranded or single-stranded and can be of any size. Exemplary nucleic acids include, but are not limited to, chromosomal DNA, plasmid DNA, cDNA, cell-free DNA (cfDNA), mitochondrial DNA, chloroplast DNA, viral DNA, mRNA, tRNA, rRNA, long non-coding RNA, siRNA, micro RNA (miRNA or miR), hnRNA, and viral RNA. Exemplary nucleic analogues include peptide nucleic acid, morpholino- and locked nucleic acid, glycol nucleic acid, and threose nucleic acid. As used herein, the term "nucleic acid molecule" is meant to include fragments of nucleic acid molecules as well as any full-length or non-fragmented nucleic acid molecule, for example. As used herein, the terms "nucleic acid" and "nucleic acid molecule" can be used interchangeably, unless context clearly indicates otherwise.

As used herein, the term "protein" refers to any polymeric chain of amino acids. The terms "peptide" and "polypeptide" can be used interchangeably with the term protein, unless context clearly indicates otherwise, and can also refer to a polymeric chain of amino acids. The term "protein" encompasses native or artificial proteins, protein fragments and polypeptide analogs of a protein sequence. A protein may be monomeric or polymeric. The term "protein" encompasses fragments and variants (including fragments of variants) thereof, unless otherwise contradicted by context.

In general, "sequence identity" or "sequence homology," which can be used interchangeably, refer to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby or the amino acid sequence of a polypeptide, and comparing these sequences to a second nucleotide or amino acid sequence.

As used herein, the term "percent (%) sequence identity" or "percent (%) identity," also including "homology," refers to the percentage of amino acid residues or nucleotides in a sequence that are identical with the amino acid residues or nucleotides in a reference sequence after aligning the sequences and introducing gaps, if necessary, to achieve the maximum percent sequence identity, and not considering any conservative substitutions as part of the sequence identity. Thus, two or more sequences (polynucleotide or amino acid) can be compared by determining their "percent identity," also referred to as "percent homology." The percent identity to a reference sequence (e.g., nucleic acid or amino acid sequences), which may be a sequence within a longer molecule (e.g., polynucleotide or polypeptide), may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul et al., J. Mol. Biol. 215:403-410 (1990); Karlin and Altschul, Proc. Natl. Acad. sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17: 149-163 (1993). Ranges of desired degrees of sequence identity are approximately 80% to 100% and integer values in between. Percent identities between a reference sequence and a claimed sequence can be at least 80%, at least 85%, at least 90%, at least 95%, at least 98%, at least 99%, at least 99.5%, or at least 99.9%. In general, an exact match indicates 100% identity over the length of the reference sequence. Additional programs and methods for comparing sequences and/or assessing sequence identity include the Needleman-Wunsch algorithm (see, e.g., the EMBOSS Needle aligner available at ebi.ac.uk/Tools/psa/emboss needle/, optionally with default settings), the Smith-Waterman algorithm (see, e.g., the EMBOSS Water aligner available at ebi.ac.uk/Tools/psa/emboss water/, optionally with default settings), the similarity search method of Pearson and Lipman, 1988, Proc. Natl. Acad. Sci. USA 85, 2444, or computer programs which use these algorithms (GAP, BESTFIT, FASTA, BLAST P, BLAST N and TFASTA in Wisconsin Genetics Software Package, Genetics Computer Group. 575 Science Drive, Madison, Wis.). In some aspects, reference to percent sequence identity refers to sequence identity as measured using BLAST (Basic Local Alignment Search Tool). In other aspects, ClustalW is used for multiple sequence alignment. Optimal alignment may be assessed using any suitable parameters of a chosen algorithm, including default parameters.

The term "expression" refers to the process by which a nucleic acid sequence or a polynucleotide is transcribed from a DNA template (such as into mRNA or other RNA transcript) and/or the process by which a transcribed mRNA or other RNA is subsequently translated into peptides, polypeptides, or proteins. Transcripts and encoded polypeptides may be collectively referred to as "gene product."

As used herein, "operably linked," "operable linkage," "operatively linked," or grammatical equivalents thereof refer to juxtaposition of genetic elements, e.g., a promoter, an enhancer, a polyadenylation sequence, etc., wherein the elements are in a relationship permitting them to operate in the expected manner. For instance, a regulatory element, which can comprise promoter and/or enhancer sequences, is operatively linked to a coding region if the regulatory element helps initiate transcription of the coding sequence. There may be intervening residues between the regulatory element and coding region so long as this functional relationship is maintained.

As used herein, the term "drug" or "medicament," means a pharmaceutical formulation or composition as described herein.

The phrases "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

As used herein, the terms "self-replicating RNA," "self-transcribing and self-replicating RNA," "self-amplifying RNA (saRNA)," and "replicon" may be used interchangeably, unless context clearly indicates otherwise. Generally, the term "replicon" or "viral replicon" refers to a self-replicating subgenomic RNA derived from a viral genome that includes viral genes encoding non-structural proteins important for viral replication and that lacks viral genes encoding structural proteins. A self-replicating RNA can encode further subgenomic RNAs that are not able to self-replicate.

Nucleic Acid Molecules

In some embodiments, provided herein are nucleic acid molecules comprising: (i) a first polynucleotide encoding one or more viral replication proteins, wherein the first polynucleotide is codon-optimized as compared to a wild-type polynucleotide encoding the one or more viral replication proteins; and (ii) a second polynucleotide comprising a first transgene encoding a first antigenic protein or a fragment thereof.

An RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

Also provided herein, in some embodiments, are nucleic acid molecules comprising: (i) a first polynucleotide comprising a sequence having at least 80% identity to a sequence of SEQ ID NO:72; and (ii) a second polynucleotide comprising a first transgene encoding a first antigenic protein or a fragment thereof.

Codon Optimization

In some embodiments, first polynucleotides of nucleic acid molecules provided herein encoding one or more viral replication proteins include codon-optimized sequences. As used herein, the term "codon-optimized" means a polynucleotide, nucleic acid sequence, or coding sequence has been redesigned as compared to a wild-type or reference polynucleotide, nucleic acid sequence, or coding sequence by choosing different codons without altering the amino acid sequence of the encoded protein. Accordingly, codon-optimization generally refers to replacement of codons with synonymous codons to optimize expression of a protein while keeping the amino acid sequence of the translated protein the same. Codon optimization of a sequence can increase protein expression levels (Gustafsson et al., Codon bias and heterologous protein expression. 2004, Trends Biotechnol 22: 346-53) of the encoded proteins, for example, and provide other advantages. Variables such as codon usage preference as measured by codon adaptation index (CAI), for example, the presence or frequency of U and other nucleotides, mRNA secondary structures, cis-regulatory sequences, GC content, and other variables may correlate with protein expression levels (Villalobos et al., Gene Designer: a synthetic biology tool for constructing artificial DNA segments. 2006, BMC Bioinformatics 7:285).

Any method of codon optimization can be used to codon optimize polynucleotides and nucleic acid molecules provided herein, and any variable can be altered by codon optimization. Accordingly, any combination of codon optimization methods can be used. Exemplary methods include the high codon adaptation index (CAI) method, the Low U method, and others. The CAI method chooses a most frequently used synonymous codon for an entire protein coding sequence. As an example, the most frequently used codon for each amino acid can be deduced from 74,218 protein-coding genes from a human genome. The Low U method targets U-containing codons that can be replaced with a synonymous codon with fewer U moieties, generally without changing other codons. If there is more than one choice for replacement, the more frequently used codon can be selected. Any polynucleotide, nucleic acid sequence, or codon sequence provided herein can be codon-optimized. This method may be used in conjunction with the disclosed RNAs to design coding sequences that are to be synthesized with, for example, 5-methoxyuridine or N1-methyl pseudouridine. Methods of codon optimization in combination with the use of a modified nucleotide monomer are described in U.S. 2018/0327471, the contents of which are herein incorporated by reference.

In some embodiments, the nucleotide sequence of any region of the RNA or DNA templates described herein may be codon optimized. Preferably, the primary cDNA template may include reducing the occurrence or frequency of appearance of certain nucleotides in the template strand. For example, the occurrence of a nucleotide in a template may be reduced to a level below 25% of said nucleotides in the template. In further examples, the occurrence of a nucleotide in a template may be reduced to a level below 20% of said nucleotides in the template. In some examples, the occurrence of a nucleotide in a template may be reduced to a level below 16% of said nucleotides in the template. Preferably, the occurrence of a nucleotide in a template may be reduced to a level below 15%, and preferably may be reduced to a level below 12% of said nucleotides in the template.

In some embodiments, the nucleotide reduced is uridine. For example, the present disclosure provides nucleic acids with altered uracil content wherein at least one codon in the wild-type sequence has been replaced with an alternative codon to generate a uracil-altered sequence. Altered uracil sequences can have at least one of the following properties:
(i) an increase or decrease in global uracil content (i.e., the percentage of uracil of the total nucleotide content in the nucleic acid of a section of the nucleic acid, e.g., the open reading frame);
(ii) an increase or decrease in local uracil content (i.e., changes in uracil content are limited to specific subsequences);
(iii) a change in uracil distribution without a change in the global uracil content;
(iv) a change in uracil clustering (e.g., number of clusters, location of clusters, or distance between clusters); or
(v) combinations thereof.

In some embodiments, the percentage of uracil nucleobases in the nucleic acid sequence is reduced with respect to the percentage of uracil nucleobases in the wild-type nucleic acid sequence. For example, 30% of nucleobases may be uracil in the wild-type sequence but the nucleobases that are uracil are preferably lower than 15%, preferably lower than 12% and preferably lower than 10% of the nucleobases in the nucleic acid sequences of the disclosure. The percentage uracil content can be determined by dividing the number of uracil in a sequence by the total number of nucleotides and multiplying by 100.

In some embodiments, the percentage of uracil nucleobases in a subsequence of the nucleic acid sequence is reduced with respect to the percentage of uracil nucleobases in the corresponding subsequence of the wild-type sequence. For example, the wild-type sequence may have a 5'-end region (e.g., 30 codons) with a local uracil content of 30%, and the uracil content in that same region could be reduced to preferably 15% or lower, preferably 12% or lower and preferably 10% or lower in the nucleic acid sequences of the disclosure. These subsequences can also be part of the wild-type sequences of the heterologous 5' and 3' UTR sequences of the present disclosure.

In some embodiments, codons in the nucleic acid sequence of the disclosure reduce or modify, for example, the number, size, location, or distribution of uracil clusters that could have deleterious effects on protein translation. Although lower uracil content is desirable in certain aspects, the uracil content, and in particular the local uracil content, of some subsequences of the wild-type sequence can be greater than the wild-type sequence and still maintain beneficial features (e.g., increased expression).

In some embodiments, the uracil-modified sequence induces a lower Toll-Like Receptor (TLR) response when compared to the wild-type sequence. Several TLRs recognize and respond to nucleic acids. Double-stranded (ds) RNA, a frequent viral constituent, has been shown to activate TLR3. Single-stranded (ss)RNA activates TLR7. RNA oligonucleotides, for example RNA with phosphorothioate internucleotide linkages, are ligands of human TLR8. DNA containing unmethylated CpG motifs, characteristic of bacterial and viral DNA, activate TLR9.

As used herein, the term "TLR response" is defined as the recognition of single-stranded RNA by a TLR7 receptor, and preferably encompasses the degradation of the RNA and/or physiological responses caused by the recognition of the single-stranded RNA by the receptor. Methods to determine and quantify the binding of an RNA to a TLR7 are known in the art. Similarly, methods to determine whether an RNA has triggered a TLR7-mediated physiological response (e.g., cytokine secretion) are well known in the art. In some embodiments, a TLR response can be mediated by TLR3, TLR8, or TLR9 instead of TLR7. Suppression of TLR7-mediated response can be accomplished via nucleoside modification. RNA undergoes over a hundred different nucleoside modifications in nature. Human rRNA, for example, has ten times more pseudouracil ('P) and 25 times more 2'-O-methylated nucleosides than bacterial rRNA. Bacterial RNA contains no nucleoside modifications, whereas mammalian RNAs have modified nucleosides such as 5-methylcytidine (m5C), N6-methyladenosine (m6A), inosine and many 2'-O-methylated nucleosides in addition to N7-methylguanosine (m7G).

In some embodiments, the uracil content of polynucleotides disclosed herein is less than about 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total nucleobases in the sequence in the reference sequence. In some embodiments, the uracil content of polynucleotides disclosed herein is between about 5% and about 25%. In some embodiments, the uracil content of polynucleotides disclosed herein is between about 15% and about 25%.

In some embodiments, first polynucleotides of nucleic acid molecules provided herein comprise a sequence having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:72. In some embodiments, first polynucleotides of nucleic acid molecules provided herein comprise a sequence of SEQ ID NO:72.

In some aspects, first polynucleotides and second polynucleotides of nucleic acid molecules provided herein are included in the same (i.e., a single) or in separate nucleic acid molecules. Generally, first polynucleotides and second polynucleotides of nucleic acid molecules provided herein are included in a single nucleic acid molecule. In one aspect, the first polynucleotide is located 5' of the second polynucleotide. In one aspect, first polynucleotides and second polynucleotides of nucleic acid molecules provided herein are included in separate nucleic acid molecules. In yet another aspect, first polynucleotides and second polynucleotides are included in two separate nucleic acid molecules.

In some aspects, first polynucleotides and second polynucleotides are included in the same (i.e., a single) nucleic acid molecule. First polynucleotides and second polynucleotides of nucleic acid molecules provided herein can be contiguous, i.e., adjacent to each other without nucleotides in between. In one aspect, an intergenic region is located between the first polynucleotide and the second polynucleotide. In another aspect, the intergenic region located between the first polynucleotide and the second polynucleotide is a second intergenic region, with a first intergenic region included in the first polynucleotide as described below. As used herein, the terms "intergenic region" and intergenic sequence" can be used interchangeably, unless context clearly indicates otherwise.

An intergenic region located between the first polynucleotide and the second polynucleotide can be of any length and can have any nucleotide sequence. As an example, the intergenic region between the first polynucleotide and the second polynucleotide can include about one nucleotide, about two nucleotides, about three nucleotides, about four nucleotides, about five nucleotides, about six nucleotides, about seven nucleotides, about eight nucleotides, about nine nucleotides, about ten nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, about 50 nucleotides, about 60 nucleotides, about 70 nucleotides, about 80 nucleotides, about 90 nucleotides, about 100 nucleotides, about 125 nucleotides, about 150 nucleotides, about 175 nucleotides, about 200 nucleotides, about 250 nucleotides, about 300 nucleotides, about 350 nucleotides, about 400 nucleotides, about 450 nucleotides, about 500 nucleotides, about 600 nucleotides, about 700 nucleotides, about 800 nucleotides, about 1,000 nucleotides, about 1,500 nucleotides, about 2,000 nucleotides, about 2,500 nucleotides, about 3,000 nucleotides, about 3,500 nucleotides, about 4,000 nucleotides, about 4,500 nucleotides, about 5,000 nucleotides, about 6,000 nucleotides, about 7,000 nucleotides, about 8,000 nucleotides, about 9,000 nucleotides, about 10,000 nucleotides, and any number or range in between. In one aspect, the intergenic region between first and second polynucleotides includes about 10-100 nucleotides, about 10-200 nucleotides, about 10-300 nucleotides, about 10-400 nucleotides, or about 10-500 nucleotides. In another aspect, the intergenic region between first and second polynucleotides includes about 1-10 nucleotides, about 1-20 nucleotides, about 1-30 nucleotides, about 1-40 nucleotides, or about 1-50 nucleotides. In yet another aspect, the region includes about 44 nucleotides. In one aspect, the intergenic region between first and second polynucleotides of nucleic acid molecules provided herein is a second intergenic region.

In one aspect, the intergenic region between first and second polynucleotides includes a viral sequence. The intergenic region between first and second polynucleotides can include a sequence from any virus, such as alphaviruses and rubiviruses, for example. In one aspect, the intergenic region between the first polynucleotide and the second polynucleotide comprises an alphavirus sequence, such as a sequence from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), ONyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (STNV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), Buggy Creek Virus (BCRV), or any combination thereof. In another aspect, the intergenic region between first and second polynucleotides comprises a sequence from Venezuelan Equine Encephalitis Virus (VEEV). In yet another aspect, the intergenic region between first and second polynucleotides comprises a sequence having at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to SEQ ID NO:77. In a further aspect, the intergenic region between first and second polynucleotides comprises a sequence of SEQ ID NO:77. In yet a further aspect, the intergenic region between first and second polynucleotides is a second intergenic region comprising a sequence having at least 85% identity to SEQ ID NO:77.

Natural and Modified Nucleotides

A self-replicating RNA of the disclosure can comprise one or more chemically modified nucleotides. Examples of nucleic acid monomers include non-natural, modified, and chemically-modified nucleotides, including any such nucleotides known in the art. Nucleotides can be artificially modified at either the base portion or the sugar portion. In nature, most polynucleotides comprise nucleotides that are "unmodified" or "natural" nucleotides, which include the purine bases adenine (A) and guanine (G), and the pyrimidine bases thymine (T), cytosine (C) and uracil (U). These bases are typically fixed to a ribose or deoxy ribose at the 1' position. The use of RNA polynucleotides comprising chemically modified nucleotides have been shown to improve RNA expression, expression rates, half-life and/or expressed protein concentrations. RNA polynucleotides comprising chemically modified nucleotides have also been useful in optimizing protein localization thereby avoiding deleterious bio-responses such as immune responses and/or degradation pathways.

Examples of modified or chemically-modified nucleotides include 5-hydroxycytidines, 5-alkylcytidines, 5-hydroxyalkylcytidines, 5-carboxycytidines, 5-formylcytidines, 5-alkoxycytidines, 5-alkynylcytidines, 5-halocytidines, 2-thiocytidines, N4-alkylcytidines, N4-aminocytidines, N4-acetylcytidines, and N4,N4-dialkylcytidines.

Examples of modified or chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; N4-methylcytidine, N4-aminocytidine, N4-acetylcytidine, and N4,N4-dimethylcytidine.

Examples of modified or chemically-modified nucleotides include 5-hydroxyuridines, 5-alkyluridines, 5-hydroxyalkyluridines, 5-carboxyuridines, 5-carboxyalkylesteruridines, 5-formyluridines, 5-alkoxyuridines, 5-alkynyluridines, 5-halouridines, 2-thiouridines, and 6-alkyluridines.

Examples of modified or chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine (also referred to herein as "5MeOU"), 5-propynyluridine, 5-bromouridine, 5-fluorouridine, 5-iodouridine, 2-thiouridine, and 6-methyluridine.

Examples of modified or chemically-modified nucleotides include 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'O-methyluridine, and 3,2'-O-dimethyluridine.

Examples of modified or chemically-modified nucleotides include N6-methyladenosine, 2-aminoadenosine, 3-methyladenosine, 8-azaadenosine, 7-deazaadenosine, 8-oxoadenosine, 8-bromoadenosine, 2-methylthio-N6-methyladenosine, N6-isopentenyladenosine, 2-methylthio-N6-isopentenyladenosine, N6-(cis-hydroxyisopentenyl) adenosine, 2-methylthio-N6-(cis-hydroxyisopentenyl) adenosine, N6-glycinylcarbamoyladenosine, N6-threonylcarbamoyl-adenosine, N6-methyl-N6-threonylcarbamoyl-adenosine, 2-methylthio-N6-threonylcarbamoyl-adenosine, N6,N6-dimethyladenosine, N6-hydroxynorvalylcarbamoyladenosine, 2-methylthio-N6-hydroxynorvalylcarbamoyl-adenosine, N6-acetyl-adenosine, 7-methyl-adenine, 2-methylthio-adenine, 2-methoxy-adenine, alpha-thio-adenosine, 2'-O-methyl-adenosine, N6,2'-O-dimethyl-adenosine, N6,N6,2'-O-trimethyl-adenosine, 1,2'-O-dimethyl-adenosine, 2'-O-ribosyladenosine, 2-amino-N6-methyl-purine, 1-thio-adenosine, 2'-F-ara-adenosine, 2'-F-adenosine, 2'-OH-ara-adenosine, and N6-(19-amino-pentaoxanonadecyl)-adenosine.

Examples of modified or chemically-modified nucleotides include N1-alkylguanosines, N2-alkylguanosines, thienoguanosines, 7-deazaguanosines, 8-oxoguanosines, 8-bromoguanosines, O6-alkylguanosines, xanthosines, inosines, and N1-alkylinosines.

Examples of modified or chemically-modified nucleotides include N1-methylguanosine, N2-methylguanosine, thienoguanosine, 7-deazaguanosine, 8-oxoguanosine, 8-bromoguanosine, O6-methylguanosine, xanthosine, inosine, and N1-methylinosine.

Examples of modified or chemically-modified nucleotides include pseudouridines. Examples of pseudouridines include Nhalkylpseudouridines, N1-cycloalkylpseudouridines, N1-hydroxypseudouridines, N1-hydroxyalkylpseudouridines, N1-phenylpseudouridines, N1-phenylalkylpseudouridines, N1-aminoalkylpseudouridines, N3-alkylpseudouridines, N6-alkylpseudouridines, N6-alkoxypseudouridines, N6-hydroxypseudouridines, N6-hydroxyalkylpseudouridines, N6-morpholinopseudouridines, N6-phenylpseudouridines, and N6-halopseudouridines. Examples of pseudouridines include N1-alkyl-N6-alkylpseudouridines, N1-alkyl-N6-alkoxypseudouridines, N1-alkyl-N6-hydroxypseudouridines, N1-alkyl-N6-hydroxyalkylpseudouridines, N1-alkyl-N6-morpholinopseudouridines, N1-alkyl-N6-phenylpseudouridines, and N1-alkyl-N6-halopseudouridines. In these examples, the alkyl, cycloalkyl, and phenyl substituents may be unsubstituted, or further substituted with alkyl, halo, haloalkyl, amino, or nitro substituents.

Examples of pseudouridines include N1-methylpseudouridine (also referred to herein as "N1MPU"),N1-ethylpseudouridine, N1-propylpseudouridine, N1-cyclopropylpseudouridine, N1-phenylpseudouridine, N1-aminomethylpseudouridine, N3-methylpseudouridine, N1-hydroxypseudouridine, and N1-hydroxymethylpseudouridine.

Examples of nucleic acid monomers include modified and chemically-modified nucleotides, including any such nucleotides known in the art.

Examples of modified and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of modified and chemically-modified nucleotide monomers include 3'-end stabilized nucleotides, 3'-glyceryl nucleotides, 3'-inverted abasic nucleotides, and 3'-inverted thymidine.

Examples of modified and chemically-modified nucleotide monomers include locked nucleic acid nucleotides (LNA), 2'-O,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides. In an exemplary embodiment, the modified monomer is a locked nucleic acid nucleotide (LNA).

Examples of modified and chemically-modified nucleotide monomers include 2',4'-constrained 2'-O-methoxyethyl (cMOE) and 2'-O-Ethyl (cEt) modified DNAs.

Examples of modified and chemically-modified nucleotide monomers include 2'-amino nucleotides, 2'-O-amino nucleotides, 2'-C-allyl nucleotides, and 2'-O-allyl nucleotides.

Examples of modified and chemically-modified nucleotide monomers include N6-methyladenosine nucleotides.

Examples of modified and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of modified and chemically-modified nucleotide monomers include 2'-O-aminopropyl substituted nucleotides.

Examples of modified and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Example of base modifications described above can be combined with additional modifications of nucleoside or nucleotide structure, including sugar modifications and linkage modifications. Certain modified or chemically-modified nucleotide monomers may be found in nature.

Preferred nucleotide modifications include N1-methylpseudouridine and 5-methoxyuridine.

Viral Replication Proteins and Polynucleotides Encoding Them

Provided herein, in some embodiments, are nucleic acid molecules comprising a first polynucleotide encoding one or more viral replication proteins. As used herein, the term "replication protein" or "viral replication protein" refers to any protein or any protein subunit of a protein complex that functions in replication of a viral genome. Generally, viral replication proteins are non-structural proteins. Viral replication proteins encoded by nucleic acid molecules provided herein can function in the replication of any viral genome. The viral genome can be a single-stranded positive-sense RNA genome, a single-stranded negative-sense RNA genome, a double-stranded RNA genome, a single-stranded positive-sense DNA genome, a single-stranded negative-sense DNA genome, or a double-stranded DNA genome. Viral genomes can include a single nucleic acid molecule or more than one nucleic acid molecule. Nucleic acid molecules provided herein can encode one or more viral replication proteins from any virus or virus family, including animal viruses and plant viruses, for example. Viral replication proteins encoded by first polynucleotides included in nucleic acid molecules provided herein can be expressed from self-replicating RNA.

First polynucleotide sequences of nucleic acid molecules provided herein can encode one or more togavirus replication proteins. In some aspects, the one or more viral replication proteins encoded by first polynucleotides of nucleic acid molecules provided herein are alphavirus proteins. In some embodiments, the one or more viral replication proteins encoded by first polynucleotides of nucleic acid molecules provided herein are rubivirus proteins. First polynucleotide sequences of nucleic acid molecules provided herein can encode any alphavirus replication protein and any rubivirus replication protein. Exemplary replication proteins from alphaviruses include proteins from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), Buggy Creek Virus (BCRV), and any combination thereof. Exemplary rubivirus replication proteins include proteins from rubella virus.

Viral replication proteins encoded by first polynucleotides of nucleic acid molecules provided herein can be expressed as one or more polyproteins or as separate or single proteins. Generally, polyproteins are precursor proteins that are cleaved to generate individual or separate proteins. Accordingly, proteins derived from a precursor polyprotein can be expressed from a single open reading frame (ORF). As used herein, the term "ORF" refers to a nucleotide sequence that begins with a start codon, generally ATG, and that ends with a stop codon, such as TAA, TAG, or TGA, for example. It will be appreciated that T is present in DNA, while U is present in RNA. Accordingly, a start codon of ATG in DNA corresponds to AUG in RNA, and the stop codons TAA, TAG, and TGA in DNA correspond to UAA, UAG, and UGA in RNA. It will further be appreciated that for any sequence provided in the present disclosure, T is present in DNA, while U is present in RNA. Accordingly, for any sequence provided herein, T present in DNA is substituted with U for an RNA molecule, and U present in RNA is substituted with T for a DNA molecule.

The protease cleaving a polyprotein can be a viral protease or a cellular protease. In some aspects, the first polynucleotide of nucleic acid molecules provided herein encodes a polyprotein comprising an alphavirus nsP1 protein, an alphavirus nsP2 protein, an alphavirus nsP3 protein, an alphavirus nsP4 protein, or any combination thereof. In other aspects, the first polynucleotide of nucleic acid molecules provided herein encodes a polyprotein comprising an alphavirus nsP1 protein, an alphavirus nsP2 protein, an alphavirus nsP3 protein, or any combination thereof, and an alphavirus nsP4 protein. In some aspects, the polyprotein is a VEEV polyprotein. In other aspects, the alphavirus nsP1, nsP2, nsP3, and nsP4 proteins are VEEV proteins.

In one aspect, first polynucleotides of nucleic acid molecules provided herein lack a stop codon between sequences encoding an nsP3 protein and an nsP4 protein. Accordingly, in some aspects, first polynucleotides of nucleic acid molecules provided herein encode a P1234 polyprotein comprising nsP1, nsP2, nsP3, and nsP4. First polynucleotides of nucleic acid molecules provided herein can also include a stop codon between sequences encoding an nsP3 and an nsP4 protein. Accordingly, in some aspects, first polynucleotides of nucleic acid molecules provided herein encode a P123 polyprotein comprising nsP1, nsP2, and nsP3 and a P1234 polyprotein comprising nsP1, nsP2, nsP3, and nsP4 as a result of stop codon readthrough, for example. In other aspects, first polynucleotides of nucleic acid molecules provided herein encode a polyprotein having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:79. In some embodiments, first polynucleotides of nucleic acid molecules provided herein encode a polyprotein having a sequence of SEQ ID NO:79. Further exemplary polyproteins comprise a sequence of SEQ ID NO:80 or SEQ ID NO:81. In one aspect, nsP2 and nsP3 proteins include mutations. Exemplary mutations include G1309R and 51583G mutations of VEEV proteins. In another aspect, the nsP1, nsP2, and nsP4 proteins are VEEV proteins, and the nsP3 protein is a chikungunya virus (CHIKV) nsP3 protein.

In some aspects, first polynucleotides of nucleic acid molecules provided herein can include a first intergenic region. In some aspects, the first intergenic region is located between a sequence encoding a polyprotein comprising an alphavirus nsP1 protein, an alphavirus nsP2 protein, an alphavirus nsP3 protein, or any combination thereof, and a sequence encoding an alphavirus nsP4 protein. A first intergenic region can comprise any sequence, such as any viral or non-viral sequence. In one aspect, the first intergenic region comprises a viral sequence. In another aspect, the first intergenic region comprises an alphavirus sequence. In yet another aspect, the alphavirus is VEEV. In one aspect, nsP2 and nsP3 proteins include mutations. Exemplary mutations include G1309R and S1583G mutations of VEEV proteins. In another aspect, the nsP1, nsP2, and nsP4 proteins are VEEV proteins, and the nsP3 protein is a chikungunya virus (CHIKV) nsP3 protein.

5' Untranslated Region (5' UTR)

Nucleic acid molecules provided herein can further comprise untranslated regions (UTRs). Untranslated regions, including 5' UTRs and 3' UTRs, for example, can affect RNA stability and/or efficiency of RNA translation, such as translation of cellular and viral mRNAs, for example. 5' UTRs and 3' UTRs can also affect stability and translation of viral genomic RNAs and self-replicating RNAs, including virally derived self-replicating RNAs or replicons. Exemplary viral genomic RNAs whose stability and/or efficiency of translation can be affected by 5' UTRs and 3' UTRs include the genome nucleic acid of positive-sense RNA viruses. Both genome nucleic acid of positive-sense RNA viruses and self-replicating RNAs, including virally derived self-replicating RNAs or replicons, can be translated upon infection or introduction into a cell.

In some aspects, nucleic acid molecules provided herein further include a 5' untranslated region (5' UTR). Any 5' UTR sequence can be included in nucleic acid molecules provided herein. In some embodiments, nucleic acid molecules provided herein include a viral 5' UTR. In one aspect, nucleic acid molecules provided herein include a non-viral 5' UTR. Any non-viral 5' UTR can be included in nucleic acid molecules provided herein, such as 5' UTRs of transcripts expressed in any cell or organ, including muscle, skin, subcutaneous tissue, liver, spleen, lymph nodes, antigen-presenting cells, and others. In another aspect, nucleic acid molecules provided herein include a 5' UTR comprising viral and non-viral sequences. Accordingly, a 5' UTR included in nucleic acid molecules provided herein can comprise a combination of viral and non-viral 5' UTR sequences. In some aspects, the 5' UTR included in nucleic acid molecules provided herein is located upstream of or 5' of the first polynucleotide that encodes one or more viral replication proteins. In other aspects, the 5' UTR is located 5' of or upstream of the first polynucleotide of nucleic acid molecules provided herein that encodes one or more viral replication proteins, and the first polynucleotide is located 5' of or upstream of the second polynucleotide of nucleic acid molecules provided herein.

In one aspect, the 5' UTR of nucleic acid molecules provided herein comprises an alphavirus 5' UTR. A 5' UTR from any alphavirus can be included in nucleic acid molecules provided herein, including 5' UTR sequences from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (STNV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV). In another aspect, the 5' UTR comprises a sequence having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:73, SEQ ID NO:74, or SEQ ID NO:75. In yet another aspect, the 5' UTR comprises a sequence of SEQ ID NO:73, SEQ ID NO:74, or SEQ ID NO:75.

In some embodiments, the 5' UTR comprises a sequence selected from the 5' UTRs of human IL-6, alanine aminotransferase 1, human apolipoprotein E, human fibrinogen alpha chain, human transthyretin, human haptoglobin, human alpha-1-antichymotrypsin, human antithrombin, human alpha-1-antitrypsin, human albumin, human beta globin, human complement C3, human complement C5, SynK (thylakoid potassium channel protein derived from the cyanobacteria, *Synechocystis* sp.), mouse beta globin, mouse albumin, and a tobacco etch virus, or fragments of any of the foregoing. Preferably, the 5' UTR is derived from a tobacco etch virus (TEV). Preferably, an mRNA described herein comprises a 5' UTR sequence that is derived from a gene expressed by *Arabidopsis thaliana*. Preferably, the 5' UTR sequence of a gene expressed by *Arabidopsis thaliana* is AT1G58420. Examples of 5 UTRs and 3' UTRs are described in PCT/US2018/035419, the contents of which are herein incorporated by reference. Preferred 5' UTR sequences comprise SEQ ID NOs: 5, 25-27 and 28-45: as shown in Table 1.

TABLE 1

5' UTR Sequences

| Name | Sequence | Seq ID No.: |
|---|---|---|
| EV | UCAACACAACAUAUACAAAACAAACGAAUCUCAAGCAAUC AAGCAUUCUACUUCUAUUGCAGCAAUUUAAAUCAUUUCU UUUAAAGCAAAAGCAAUUUUCUGAAAAUUUUCACCAUUU ACGAACGAUAG | SEQ ID NO: 5 |
| AT1G58420 | AUUAUUACAUCAAAACAAAAAGCCGCCA | SEQ ID NO: 6 |
| ARC5-2 | CUUAAGGGGCGCUGCCUACGGAGGUGGCAGCCAUCUCCU UCUCGGCAUCAAGCUUACCAUGGUGCCCCAGGCCCUGCUC UUGGUCCCGCUGCUGGUGUUCCCCCUCUGCUUCGGCAAGU UCCCCAUCUACACCAUCCCCGACAAGCUGGGGCCGUGGAG CCCCAUCGACAUCCACCACCUGUCCUGCCCCAACAACCUCG UGGUCGAGGACGAGGGCUGCACCAACCUGAGCGGGUUCUC CUAC | SEQ ID NO: 7 |
| HCV | UGAGUGUCGU ACAGCCUCCA GGCCCCCCCC UCCCGGGAGA GCCAUAGUGG UCUGCGGAACCGGUGAGUAC ACCGGAAUUG CCGGGAAGAC UGGGUCCUUU CUUGGAUAAA CCCACUCUAUGCCCGGCCAU UUGGGCGUGC CCCCGCAAGA CUGCUAGCCG AGUAGUGUUG GGUUGCG | SEQ ID NO: 8 |
| HUMAN ALBUMIN | AAUUAUUGGUUAAAGAAGUAUAUUAGUGCUAAUUUCCCU CCGUUUGUCCUAGCUUUUCUCUUCUGUCAACCCCACACGC CUUUGGCACA | SEQ ID NO: 9 |
| EMCV | CUCCCUCCCC CCCCCCUAAC GUUACUGGCC GAAGCCGCUU GGAAUAAGGC CGGUGUGCGU UUGUCUAUAU GUUAUUUUCC ACCAUAUUGC CGUCUUUUGG CAAUGUGAGG GCCCGGAAAC CUGGCCCUGU CUUCUUGACG AGCAUUCCUA GGGGUCUUUC CCCUCUCGCC AAAGGAAUGC AAGGUCUGUU GAAUGUCGUG AAGGAAGCAG UUCCUCUGGA AGCUUCUUGA AGACAAACAA CGUCUGUAGC GACCCUUUGC AGGCAGCGGA ACCCCCCACC UGGCGACAGG UGCCUCUGCG GCCAAAAGCC ACGUGUAUAA GAUACACCUG CAAAGGCGGC ACAACCCCAG UGCCACGUUG UGAGUUGGAU AGUUGUGGAA AGAGUCAAAU GGCUCUCCUC AAGCGUAUUC AACAAGGGGC UGAAGGAUGC CCAGAAGGUA CCCCAUUGUA UGGGAUCUGA UCUGGGGCCU CGGUGCACAU GCUUUACGUG UGUUUAGUCG AGGUUAAAAA ACGUCUAGGC CCCCGAACC ACGGGACGU GGUUUUCCUU UGAAAAACAC GAUGAUAAU | SEQ ID NO: 10 |
| AT1G67090 | CACAAAGAGUAAAGAAGAACA | SEQ ID NO: 25 |
| AT1G35720 | AACACUAAAAGUAGAAGAAAA | SEq ID NO: 26 |
| AT5G45900 | CUCAGAAAGAUAAGAUCAGCC | SEQ ID NO: 27 |
| AT5G61250 | AACCAAUCGAAAGAAACCAAA | SEQ ID NO: 28 |
| AT5G46430 | CUCUAAUCACCAGGAGUAAAA | SEQ ID NO: 29 |
| AT5G47110 | GAGAGAGAUCUUAACAAAAAA | SEQ ID NO: 30 |
| AT1G03110 | UGUGUAACAACAACAACAACA | SEQ ID NO: 31 |
| AT3G12380 | CCGCAGUAGGAAGAGAAAGCC | SEQ ID NO: 32 |
| AT5G45910 | AAAAAAAAAAGAAAUCAUAAA | SEQ ID NO: 33 |

TABLE 1-continued

5' UTR Sequences

| Name | Sequence | Seq ID No.: |
| --- | --- | --- |
| AT1G07260 | GAGAGAAGAAAGAAGAAGACG | SEQ ID NO: 34 |
| AT3G55500 | CAAUUAAAAAUACUUACCAAA | SEQ ID NO: 35 |
| AT3G46230 | GCAAACAGAGUAAGCGAAACG | SEQ ID NO: 36 |
| AT2G36170 | GCGAAGAAGACGAACGCAAAG | SEQ ID NO: 37 |
| AT1G10660 | UUAGGACUGUAUUGACUGGCC | SEQ ID NO: 38 |
| AT4G14340 | AUCAUCGGAAUUCGGAAAAAG | SEQ ID NO: 39 |
| AT1G49310 | AAAACAAAAGUUAAAGCAGAC | SEQ ID NO: 40 |
| AT4G14360 | UUUAUCUCAAAUAAGAAGGCA | SEQ ID NO: 41 |
| AT1G28520 | GGUGGGGAGGUGAGAUUUCUU | SEQ ID NO: 42 |
| AT1G20160 | UGAUUAGGAAACUACAAAGCC | SEQ ID NO: 43 |
| AT5G37370 | CAUUUUUCAAUUUCAUAAAAC | SEQ ID NO: 44 |
| AT4G11320 | UUACUUUUAAGCCCAACAAAA | SEQ ID NO: 45 |
| AT5G40850 | GGCGUGUGUGUGUUGUUGA | SEQ ID NO: 46 |
| AT1G06150 | GUGGUGAAGGGGAAGGUUUAG | SEQ ID NO: 47 |
| AT2G26080 | UUGUUUUUUUUGGUUUGGUU | SEQ ID NO: 48 |

3' Untranslated Region (3' UTR)

In some aspects, nucleic acid molecules provided herein further include a 3' untranslated region (3' UTR). Any 3' UTR sequence can be included in nucleic acid molecules provided herein. In one aspect, nucleic acid molecules provided herein include a viral 3' UTR. In another aspect, nucleic acid molecules provided herein include a non-viral 3' UTR. Any non-viral 3' UTR can be included in nucleic acid molecules provided herein, such as 3' UTRs of transcripts expressed in any cell or organ, including muscle, skin, subcutaneous tissue, liver, spleen, lymph nodes, antigen-presenting cells, and others. In some aspects, nucleic acid molecules provided herein include a 3' UTR comprising viral and non-viral sequences. Accordingly, a 3' UTR included in nucleic acid molecules provided herein can comprise a combination of viral and non-viral 3' UTR sequences. In one aspect, the 3' UTR is located 3' of or downstream of the second polynucleotide of nucleic acid molecules provided herein that comprises a first transgene encoding a first antigenic protein or a fragment thereof. In another aspect, the 3' UTR is located 3' of or downstream of the second polynucleotide of nucleic acid molecules provided herein that comprises a first transgene encoding a first antigenic protein or a fragment thereof, and the second polynucleotide is located 3' of or downstream of the first polynucleotide of nucleic acid molecules provided herein.

In one aspect, the 3' UTR of nucleic acid molecules provided herein comprises an alphavirus 3' UTR. A 3' UTR from any alphavirus can be included in nucleic acid molecules provided herein, including 3' UTR sequences from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV). In another aspect, the 3' UTR comprises a sequence having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:5. In yet another aspect, the 3' UTR comprises a poly-A sequence. In a further aspect, the 3' UTR comprises a sequence of SEQ ID NO:5.

In some embodiments, the 3' UTR comprises a sequence selected from the 3' UTRs of alanine aminotransferase 1, human apolipoprotein E, human fibrinogen alpha chain, human haptoglobin, human antithrombin, human alpha globin, human beta globin, human complement C3, human growth factor, human hepcidin, MALAT-1, mouse beta globin, mouse albumin, and Xenopus beta globin, or fragments of any of the foregoing. In some embodiments, the 3' UTR is derived from Xenopus beta globin. Exemplary 3' UTR sequences include SEQ ID NOs: 16-22 as shown in Table 2.

TABLE 2

3' UTR sequences.

| Name | Sequence | Seq ID No.: |
|---|---|---|
| XBG | CUAGUGACUGACUAGGAUCUGGUUACCACUAAACCAG CCUCAAGAACACCCGAAUGGAGUCUCUAAGCUACAUA AUACCAACUUACACUUACAAAAUGUUGUCCCCCAAAA UGUAGCCAUUCGUAUCUGCUCCUAAUAAAAAGAAAGU UUCUUCACAU | SEQ ID NO: 16 |
| HUMAN HAPTOGLOBIN | UGCAAGGCUGGCCGGAAGCCCUUGCCUGAAAGCAAGA UUUCAGCCUGGAAGAGGGCAAAGUGGACGGGAGUGG ACAGGAGUGGAUGCGAUAAGAUGUGGUUUGAAGCUG AUGGGUGCCAGCCCUGCAUUGCUGAGUCAAUCAAUAA AGAGCUUUCUUUUGACCCAU | SEQ ID NO: 17 |
| HUMAN APOLIPOPROTEINE | ACGCCGAAGCCUGCAGCCAUGCGACCCCACGCCACCCC GUGCCUCCUGCCUCCGCGCAGCCUGCAGCGGGAGACC CUGUCCCCGCCCCAGCCGUCCUCCUGGGGUGGACCCU AGUUUAAUAAAGAUUCACCAAGUUUCACGCA | SEQ ID NO: 18 |
| HCV | UAGAGCGGCAAACCCUAGCUACACUCCAUAGCUAGUU UCUUUUUUUUUGUUUUUUUUUUUUUUUUUUUUUUU UUUUUUUUUUUUUUUCCUUUCUUUUCCUUCUUUUU UUCCUCUUUUCUUGGUGGCUCCAUCUUAGCCCUAGUC ACGGCUAGCUGUGAAAGGUCCGUGAGCCGCAUGACUG CAGAGAGUGCCGUAACUGGUCUCUCUGCAGAUCAUGU | SEQ ID NO: 19 |
| MOUSE ALBUMIN | ACACAUCACAACCACAACCUUCUCAGGCUACCCUGAG AAAAAAAGACAUGAAGACUCAGGACUCAUCUUUUCUG UUGGUGUAAAAUCAACACCCUAAGGAACACAAAUUUC UUUAAACAUUUGACUUCUUGUCUCUGUGCUGCAAUUA AUAAAAAAUGGAAAGAAUCUAC | SEQ ID NO: 20 |
| HUMAN ALPHA GLOBIN | GCUGGAGCCUCGGUAGCCGUUCCUCCUGCCCGCUGGG CCUCCCAACGGGCCCUCCUCCCCUCCUUGCACCGGCCC UUCCUGGUCUUUGAAUAAAGUCUGAGUGGGCAGCA | SEQ ID NO: 21 |
| EMCV | UAGUGCAGUCAC UGGCACAACG CGUUGCCCGG UAAGCCAAUC GGGUAUACAC GGUCGUCAUACUGCAGACAG GGUUCUUCUA CUUUGCAAGA UAGUCUAGAG UAGUAAAAUA AAUAGUAUAAG | SEQ ID NO: 22 |

Triple Stop Codon

In some embodiments, the self-replicating RNA may comprise a sequence immediately downstream of a coding region (i.e., ORF) that creates a triple stop codon. A triple stop codon is a sequence of three consecutive stop codons. The triple stop codon can ensure total insulation of an expression cassette and may be incorporated to enhance the efficiency of translation. In some embodiments, a self-replicating RNA of the disclosure may comprise a triple combination of any of the sequences UAG, UGA, or UAA immediately downstream of a ORF described herein. The triple combination can be three of the same codons, three different codons, or any other permutation of the three stop codons.

Translation Enhancers and Kozak Sequences

For translation initiation, proper interactions between ribosomes and mRNAs must be established to determine the exact position of the translation initiation region. However, ribosomes also must dissociate from the translation initiation region to slide toward the downstream sequence during mRNA translation. Translation enhancers upstream from initiation sequences of mRNAs enhance the yields of protein biosynthesis. Several studies have investigated the effects of translation enhancers. In some embodiments, an mRNA described herein comprises a translation enhancer sequence. These translation enhancer sequences enhance the translation efficiency of a self-replicating RNA of the disclosure and thereby provide increased production of the protein encoded by the mRNA. The translation enhancer region may be located in the 5' or 3' UTR of an mRNA sequence. Examples of translation enhancer regions include naturally-occurring enhancer regions from the TEV 5' UTR and the *Xenopus* beta-globin 3' UTR. Exemplary 5' UTR enhancer sequences include but are not limited to those derived from mRNAs encoding human heat shock proteins (HSP) including HSP70-P2, HSP70-M1 HSP72-M2, HSP17.9 and HSP70-P1. Preferred translation enhancer sequences used in accordance with the embodiments of the present disclosure are represented by SEQ ID Nos: 11-15 as shown in Table 3.

TABLE 3

5' UTR Enhancers

| Name | Sequence | Seq ID No.: |
|---|---|---|
| HSP70-P2 | GUCAGCUUUCAAACUCUUUGUUUCUUGUUUGUUGAUUGAGAAUA | SEQ ID NO: 11 |

TABLE 3-continued

5' UTR Enhancers

| Name | Sequence | Seq ID No.: |
|---|---|---|
| HSP70-M1 | CUCUCGCCUGAGAAAAAAAAUCCACGAACCAAUUUCUCAGCAACCAGCAGCACG | SEQ ID NO: 12 |
| HSP72-M2 | ACCUGUGAGGGUUCGAAGGAAGUAGCAGUGUUUUUUGUUCCUAGAGGAAGAG | SEQ ID NO: 13 |
| HSP17.9 | ACACAGAAACAUUCGCAAAAACAAAAUCCCAGUAUCAAAAUUCUUCUCUUUUUUUCAUAUUUCGCAAAGAC | SEQ ID NO: 14 |
| HSP70-P1 | CAGAAAAAUUUGCUACAUUGUUUCACAAACUUCAAAUAUUAUUCAUUUAUUU | SEQ ID NO: 15 |

In some embodiments, a self-replicating RNA of the disclosure comprises a Kozak sequence. As is understood in the art, a Kozak sequence is a short consensus sequence centered around the translational initiation site of eukaryotic mRNAs that allows for efficient initiation of translation of the mRNA. See, for example, Kozak, Marilyn (1988) Mol. and Cell Biol, 8:2737-2744; Kozak, Marilyn (1991) J. Biol. Chem, 266: 19867-19870; Kozak, Marilyn (1990) Proc Natl. Acad. Sci. USA, 87:8301-8305; and Kozak, Marilyn (1989) J. Cell Biol, 108:229-241. It ensures that a protein is correctly translated from the genetic message, mediating ribosome assembly and translation initiation. The ribosomal translation machinery recognizes the AUG initiation codon in the context of the Kozak sequence. A Kozak sequence may be inserted upstream of the coding sequence for the protein of interest, downstream of a 5' UTR or inserted upstream of the coding sequence for the protein of interest and downstream of a 5' UTR. In some embodiments, a self-replicating RNA described herein comprises a Kozak sequence having the amino acid sequence GCCACC (SEQ ID NO: 23). Preferably a self-replicating RNA described herein comprises a partial Kozak sequence "p" having the amino acid sequence GCCA (SEQ ID NO: 24).

Transgenes

Transgenes included in nucleic acid molecules provided herein can encode an antigenic protein or a fragment thereof. In some embodiments, second polynucleotides of nucleic acid molecules provided herein comprise a first transgene. A first transgene included in second polynucleotides of nucleic acid molecules provided herein can encode a first antigenic protein or a fragment thereof. A transgene included in second polynucleotides of nucleic acid molecules provided herein can comprise a sequence encoding the full amino acid sequence of an antigenic protein or a sequence encoding any suitable portion or fragment of the full amino acid sequence of an antigenic protein. Any antigenic protein can be encoded by transgenes included in nucleic acid molecules provided herein. In one aspect, the antigenic protein is a viral protein, a bacterial protein, a fungal protein, a protozoan protein, a parasite protein, or a tumor protein or tumor antigen. Transgenes included in nucleic acid molecules provided herein can be expressed from a subgenomic RNA.

In another embodiment, the antigenic protein, when administered to a mammalian subject, raises an immune response to a pathogen, optionally wherein the pathogen is bacterial, viral, fungal, protozoan, or cancerous. In some more particular embodiments, the antigenic protein is expressed on the outer surface of the pathogen; while in other more particular embodiments, the antigen may be a non-surface antigen, e.g., useful as a T-cell epitope. The immunogen may elicit an immune response against a pathogen (e.g. a bacterium, a virus, a fungus or a parasite) but, in some other embodiments, it elicits an immune response against an allergen or a tumor antigen. The immune response may comprise an antibody response (usually including IgG) and/or a cell mediated immune response. The polypeptide immunogen will typically elicit an immune response that recognizes the corresponding pathogen (or allergen or tumor) polypeptide, but in some embodiments, the polypeptide may act as a mimotope to elicit an immune response that recognizes a saccharide. The immunogen will typically be a surface polypeptide e.g. an adhesin, a hemagglutinin, an envelope glycoprotein, a spike glycoprotein, etc.

Any viral, bacterial, fungal, protozoan, parasite, or tumor protein can be encoded by transgenes included in nucleic acid molecules provided herein. A protein from any infectious agent can be encoded by transgenes included in nucleic acid molecules provided herein. As used herein, the term "infectious agent" refers to any agent capable of infecting an organism, including humans and animals, and causing disease or deterioration in health. The terms "infectious agent" and "infectious pathogen" may be used interchangeably, unless context clearly indicates otherwise.

In some aspects, the viral protein encoded by transgenes included in nucleic acid molecules provided herein is an orthomyxovirus protein, a paramyxovirus protein, a picornavirus protein, a flavivirus protein, a filovirus protein, a rhabdovirus protein, a togavirus protein, an arterivirus protein, a bunyavirus protein, an arenavirus protein, a reovirus protein, a bornavirus protein, a retrovirus protein, an adenovirus protein, a herpesvirus protein, a polyomavirus protein, a papillomavirus protein, a poxvirus protein, or a hepadnavirus protein. In other aspects, the antigenic protein is an influenza virus protein, a respiratory syncytial virus (RSV) protein, a human immunodeficiency virus (HIV) protein, a hepatitis C virus (HCV) protein, a cytomegalovirus (CMV) protein, a Lassa Fever Virus (LFV) protein, an Ebola Virus (EBOV) protein, a Mycobacterium protein, a Bacillus protein, a Yersinia protein, a Streptococcus protein, a Pseudomonas protein, a Shigella protein, a Campylobacter protein, a Salmonella protein, a Plasmodium protein, or a Toxoplasma protein.

In one aspect, the antigenic protein is from a prokaryotic organism, including gram positive bacteria, gram negative bacteria, or other bacteria, such as Bacillus (e.g., Bacillus anthracis), Mycobacterium (e.g., Mycobacterium tuberculosis, Mycobacterium Leprae), Shigella (e.g., Shigella sonnei, Shigella dysenteriae, Shigella flexneri), Helicobacter (e.g., Helicobacter pylori), Salmonella (e.g., Salmonella enterica, Salmonella typhi, Salmonella typhimurium), Neisseria (e.g., *Neisseria gonorrhoeae, Neisseria meningitidis*), *Moraxella* (e.g., *Moraxella catarrhalis*), *Haemophilus* (e.g., *Haemophilus influenzae*), *Klebsiella* (e.g., *Klebsiella pneumoniae*), *Legionella* (e.g., *Legionella pneumophila*), *Pseudomonas* (e.g., *Pseudomonas aeruginosa*), *Acinetobacter* (e.g., *Acinetobacter baumannii*), *Listeria* (e.g., *Listeria monocytogenes*), *Staphylococcus* (e.g., *Staphylococcus aureus*), *Streptococcus* (e.g., *Streptococcus pneumoniae, Streptococcus pyogenes, Streptococcus agalactiae*), *Corynebacterium* (e.g., *Corynebacterium diphtheria*), *Clostridium* (e.g., *Clostridium botulinum, Clostridium tetani, Clostridium difficile*), *Chlamydia* (e.g., *Chlamydia* pneumonia, *Chlamydia trachomatis*), *Caphylobacter* (e.g., *Caphylobacter jejuni*), *Bordetella* (e.g., *Bordetella pertussis*), *Enterococcus* (e.g., *Enterococcus faecalis, Enterococcus faecum*), *Vibrio* (e.g., *Vibrio cholerae*), *Yersinia* (e.g., *Yersinia pestis*), *Burkholderia* (e.g., *Burkholderia cepacia* complex), *Coxiella* (e.g., *Coxiella burnetti*), *Francisella* (e.g., *Francisella tularensis*), and *Escherichia* (e.g., enterotoxigenic, enterohemorrhagic or Shiga toxin producing *E. coli*, such as ETEC, EHEC, EPEC, EIEC, and EAEC)). In another aspect, the antigenic protein is from a eukaryotic organism, including protists and fungi, such as *Plasmodium* (e.g., *Plasmodium falciparum, Plasmodium vivax, Plasmodium ovale, Plasmodium malariae, Plasmodium* diarrhea), *Candida* (e.g., *Candida albicans*), *Aspergillus* (e.g., *Aspergillus fumigatus*), *Cryptococcus* (e.g., *Cryptococcus neoformans*), *Histoplasma* (e.g., *Histoplasma capsulatum*), *Pneumocystis* (e.g., *Pneumocystis jirovecii*), and *Coccidiodes* (e.g., *Coccidiodes immitis*).

In one aspect, the antigenic protein encoded by first transgenes of second polynucleotides included in nucleic acid molecules provided herein is an influenza virus protein or a fragment thereof. In another aspect, the second polynucleotide includes one or more transgenes encoding one or more influenza virus proteins or fragments thereof. Exemplary influenza virus proteins that can be encoded by transgenes of second polynucleotides included in nucleic acid molecules provided herein include proteins from any human or animal virus, including influenza A virus, influenza B virus, influenza C virus, influenza D virus, or any combination thereof. Exemplary influenza proteins include hemagglutinin (HA), neuraminidase (NA), M2, M1, NP, NS1, NS2, PA, PB1, PB2, and PB1-F2. Hemagglutinin proteins from any influenza virus subtype, such as H1-H18 and any emerging hemagglutinin, and neuraminidase proteins from any influenza virus subtype, such as N1-N11 and any emerging neuraminidase, can be antigenic proteins encoded by transgenes included in second polynucleotides of nucleic acid molecules provided herein. Any suitable fragment of influenza virus proteins can be encoded by transgenes included in second polynucleotides of nucleic acid molecules provided herein, including, for example, one or more helper T lymphocyte (HTL) epitope, one or more cytotoxic T lymphocyte (CTL) epitope, or any combination thereof.

Transgenes included in second polynucleotides of nucleic acid molecules provided herein can express tumor proteins or tumor antigens. Tumor proteins or tumor antigens can be from any tumor, including solid and liquid tumors, for example. As used herein, the terms "tumor protein" or "tumor antigen," which may be used interchangeably unless context clearly indicates otherwise, refer to any protein antigen that is present on the surface of a tumor cell or expressed in a tumor cell. Tumor proteins or tumor antigens include tumor-specific antigens that are present on tumor cells but generally not on other cells and tumor-associated antigens that are generally present on tumor cells and on normal cells. Tumor proteins or tumor antigens also include neoantigens. As used herein, the term "neoantigen" refers to tumor-specific mutations that can be unique to a patient's cancer or tumor.

As used herein, the term "tumor" refers to a mass or lump of tissue that is formed by an accumulation of abnormal cells. A tumor can be benign (i.e., not cancer), malignant (i.e., cancer), or premalignant (i.e., precancerous). The terms "tumor" and "neoplasm" can be used interchangeably. Generally, a cancerous tumor is malignant. As used herein, the term "solid tumor" refers to an abnormal mass of tissue that usually does not contain cysts or liquid areas. Exemplary solid tumors include sarcomas and carcinomas. As used herein, the term "liquid tumors" refers to tumors or cancers present in body fluids such as blood and bone marrow. Exemplary liquid tumors include hematopoietic tumors, such as leukemias and lymphomas, notwithstanding the ability of lymphomas to grow as solid tumors by growing in a lymph node, for example. The term "liquid tumor" can be used interchangeably with the term "blood cancer," unless context clearly indicates otherwise.

Exemplary tumor proteins or tumor antigens include products of mutated oncogenes, products of mutated tumor suppressor genes, products of mutated genes other than oncogenes or tumor suppressors, tumor antigens produced by oncogenic viruses, altered cell surface glycoproteins, oncofetal antigens, and others. Tumor proteins or tumor antigens also include immune regulatory molecules, such as immune checkpoint inhibitors and immune stimulatory molecules. Tumor antigens further include altered cell surface glycolipids. In some aspects, the tumor protein or tumor antigen encoded by transgenes included in second polynucleotides of nucleic acid molecules provided herein is a kidney cancer, renal cancer, urinary bladder cancer, prostate cancer, uterine cancer, breast cancer, cervical cancer, ovarian cancer, lung cancer, liver cancer, stomach cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, or sarcoma protein. Exemplary tumor proteins or tumor antigens include KRAS, NRAS, HRAS, HER2, BRCA1, BRCA2, carcinoembryonic antigen (CEA), MUC1, guanylyl-cyclase C, NY-ESO-1, melanoma-associated antigen (e.g., MAGE-1, MAGE-3), p53, survivin, alphafetoprotein (AFP), CA-125, epithelial tumor antigen (ETA), tyrosinase, prostate-specific antigen (PSA), prostate-specific membrane antigen (PSMA), prostate stem cell antigen (PSCA), human aspartyl (asparaginyl) β-hydroxylase (HAAH), EphA2, and others.

In some aspects, the tumor protein or tumor antigen encoded by transgenes included in nucleic acid molecules provided herein is a wild-type protein or a fragment or epitope thereof. In other aspects, the tumor protein or tumor antigen encoded by transgenes included in second polynucleotides of nucleic acid molecules provided herein is a mutant protein or a fragment or epitope thereof. In one aspect, the tumor protein or tumor antigen is KRAS, NRAS, HRAS, HER2, BRCA1, BRCA2, carcinoembryonic antigen (CEA), MUC1, guanylyl-cyclase C, NY-ESO-1, melanoma-associated antigen (e.g., MAGE-1, MAGE-3), p53, survivin, alphafetoprotein (AFP), CA-125, epithelial tumor antigen (ETA), tyrosinase, prostate-specific antigen (PSA), prostate-specific membrane antigen (PSMA), prostate stem cell antigen (PSCA), human aspartyl (asparaginyl) β-hydroxylase (HAAH), EphA2, or any mutant thereof. In another aspect, the tumor protein or tumor antigen is KRAS or a fragment or epitope thereof. In another aspect, the tumor protein or tumor antigen is KRASG12D, KRASG12C, KRASG12V, or KRASG13D. Any KRAS that includes any mutation can be encoded by transgenes included in second polynucleotides of nucleic acid molecules provided herein.

In some aspects, transgenes included in second polynucleotides of nucleic acid molecules provided herein encode a reporter or a marker, including selectable markers. Reporters and markers can include fluorescent proteins, such as green fluorescent protein (GFP), red fluorescent protein (RFP), yellow fluorescent protein (YFP), luciferase enzymes, such as firefly and *Renilla* luciferases, and antibiotic selection markers, for example.

In some aspects, the second polynucleotide of nucleic acid molecules provided herein comprises at least two transgenes. Any number of transgenes can be included in second polynucleotides of nucleic acid molecules provided herein, such as one, two, three, four, five, six, seven, eight, nine, ten, or more transgenes. In one aspect, the second polynucleotide of nucleic acid molecules provided herein includes a second transgene encoding a second antigenic protein or a fragment thereof or an immunomodulatory protein. In one aspect, the second polynucleotide further comprises an internal ribosomal entry site (IRES), a sequence encoding a 2A peptide, or a combination thereof, located between transgenes. As used herein, the term "2A peptide" refers to a small (generally 18-22 amino acids) sequence that allows for efficient, stoichiometric production of discrete protein products within a single reading frame through a ribosomal skipping event within the 2A peptide sequence. As used herein, the term "internal ribosomal entry site" or "IRES" refers to a nucleotide sequence that allows for the initiation of protein translation of a messenger RNA (mRNA) sequence in the absence of an AUG start codon or without using an AUG start codon. An IRES can be found anywhere in an mRNA sequence, such as at or near the beginning, at or near the middle, or at or near the end of the mRNA sequence, for example.

Any number of transgenes included in second polynucleotides of nucleic acid molecules provided herein can be expressed via any combination of 2A peptide and IRES sequences. For example, a second transgene located 3' of a first transgene can be expressed via a 2A peptide sequence or via an IRES sequence. As another example, a second transgene located 3' of a first transgene and a third transgene located 3' of the second transgene can be expressed via 2A peptide sequences located between the first and second transgenes and the second and third transgenes, via an IRES sequence located between the first and second transgenes and the second and third transgenes, via a 2A peptide sequence located between the first and second transgenes and an IRES located between the second and third transgenes, or via an IRES sequence located between the first and second transgenes and a 2A peptide sequence located between the second and third transgenes. Similar configurations and combinations of 2A peptide and IRES sequences located between transgenes are contemplated for any number of transgenes included in second polynucleotides of nucleic acid molecules provided herein. In addition to expression via 2A peptide and IRES sequences, two or more transgenes included in nucleic acid molecules provided herein can also be expressed from separate subgenomic RNAs.

A second, third, fourth, fifth, sixth, seventh, eighth, ninth, tenth, etc., transgene included in second polynucleotides of nucleic acid molecules provided herein can encode an immunomodulatory protein or a functional fragment or functional variant thereof. Any immunomodulatory protein or a functional fragment or functional variant thereof can be encoded by a transgene included in second polynucleotides.

As used herein, the terms "functional variant" or "functional fragment" refer to a molecule, including a nucleic acid or protein, for example, that comprises a nucleotide and/or amino acid sequence that is altered by one or more nucleotides and/or amino acids compared to the nucleotide and/or amino acid sequences of the parent or reference molecule. For a protein, a functional variant is still able to function in a manner that is similar to the parent molecule. In other words, the modifications in the amino acid and/or nucleotide sequence of the parent molecule do not significantly affect or alter the functional characteristics of the molecule encoded by the nucleotide sequence or containing the amino acid sequence. The functional variant may have conservative sequence modifications including nucleotide and amino acid substitutions, additions and deletions. These modifications can be introduced by standard techniques known in the art, such as site-directed mutagenesis and random PCR-mediated mutagenesis. Functional variants can also include, but are not limited to, derivatives that are substantially similar in primary structural sequence, but which contain, e.g., in vitro or in vivo modifications, chemical and/or biochemical, that are not found in the parent molecule. Such modifications include, inter alia, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI-anchor formation, hydroxylation, iodination, methylation, myristoylation, oxidation, pegylation, proteolytic processing, phosphorylation, prenylation, racemization, selenoylation, sulfation, transfer-RNA-mediated addition of amino acids to proteins such as arginylation, ubiquitination, and the like.

In one aspect, a second transgene included in second polynucleotides of nucleic acid molecules provided herein encodes a cytokine, a chemokine, or an interleukin. Exemplary cytokines include interferons, TNF-α, TGF-β, G-CSF, and GM-CSF. Exemplary chemokines include CCL3, CCL26, and CXCL7. Exemplary interleukins include IL-I, IL-2, IL-3, IL-4, IL-5, IL-6, IL-7, IL-8, IL-10, IL-12, IL-15, IL-18, IL-21, and IL-23. Any transgene or combination of transgenes encoding any cytokine, chemokine, interleukin, or combinations thereof, can be included in second polynucleotides of nucleic acid molecules provided herein.

In one aspect, first and second transgenes included in second polynucleotides of nucleic acid molecules provided herein encode viral proteins, bacterial proteins, fungal proteins, protozoan proteins, parasite proteins, tumor proteins, immunomodulatory proteins, or any combination thereof. In yet another aspect, first, second, third, fourth, fifth, sixth, seventh, eighth, ninth, tenth, or more transgenes included in second polynucleotides of nucleic acid molecules provided herein encode viral proteins, bacterial proteins, fungal proteins, protozoan proteins, parasite proteins, tumor proteins, immunomodulatory proteins, or any combination thereof.

DNA and RNA Molecules

Nucleic acid molecules provided herein can be DNA molecules or RNA molecules. It will be appreciated that T present in DNA is substituted with U in RNA, and vice versa. In one aspect, nucleic acid molecules provided herein are DNA molecules. In another aspect, DNA molecules provided herein further comprise a promoter. As used herein, the term "promoter" refers to a regulatory sequence that initiates transcription. A promoter can be operably linked to first and second polynucleotides of nucleic acid molecules provided herein. Generally, promoters included in DNA molecules provided herein include promoters for in vitro transcription (IVT). Any suitable promoter for in vitro transcription can be included in DNA molecules provided herein, such as a T7 promoter, a T3 promoter, an SP6 promoter, and others. In one aspect, DNA molecules provided herein comprise a T7 promoter. In another aspect, the promoter is located 5' of the 5' UTR included in DNA molecules provided herein. In yet another aspect, the promoter is a T7 promoter located 5' of the 5' UTR included in DNA molecules provided herein. In yet another aspect, the promoter overlaps with the 5' UTR. A promoter and a 5' UTR can overlap by about one nucleotide, about two nucleotides, about three nucleotides, about four nucleotides, about five nucleotides, about six nucleotides, about seven nucleotides, about eight nucleotides, about nine nucleotides, about ten nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, about 50 nucleotides, or more nucleotides.

In some aspects, DNA molecules provided herein include a promoter for in vivo transcription. Generally, the promoter for in vivo transcription is an RNA polymerase II (RNA pol II) promoter. Any RNA pol II promoter can be included in DNA molecules provided herein, including constitutive promoters, inducible promoters, and tissue-specific promoters. Exemplary constitutive promoters include a cytomegalovirus (CMV) promoter, an EF1α promoter, an SV40 promoter, a PGK1 promoter, a Ubc promoter, a human beta actin promoter, a CAG promoter, and others. Any tissue-specific promoter can be included in DNA molecules provided herein. In one aspect, the RNA pol II promoter is a muscle-specific promoter, skin-specific promoter, subcutaneous tissue-specific promoter, liver-specific promoter, spleen-specific promoter, lymph node-specific promoter, or a promoter with any other tissue specificity. DNA molecules provided herein can also include an enhancer. Any enhancer that increases transcription can be included in DNA molecules provided herein.

In some aspects, nucleic acid molecules provided herein are RNA molecules. An RNA molecule provided herein can be generated by in vitro transcription (IVT) of DNA molecules provided herein. In one aspect, RNA molecules provided herein are self-replicating RNA molecules. In another aspect, RNA molecules provided herein further comprise a 5' cap. Any 5' cap can be included in RNA molecules provided herein, including 5' caps having a Cap 1 structure, a Cap 1 (m6A) structure, a Cap 2 structure, a Cap 0 structure, or any combination thereof. In one aspect, RNA molecules provided herein include a 5' cap having Cap 1 structure. In yet another aspect, RNA molecules provided herein are self-replicating RNA molecules comprising a 5' cap having a Cap 1 structure. In a further aspect, RNA molecules provided herein comprise a cap having a Cap 1 structure, wherein a m7G is linked via a 5'-5' triphosphate to the 5' end of the 5' UTR. In yet a further aspect, RNA molecules provided herein comprise a cap having a Cap 1 structure, wherein a m7G is linked via a 5'-5' triphosphate to the 5' end of the 5' UTR comprising a sequence of SEQ ID NO:73. Any method of capping can be used, including, but not limited to using a Vaccinia Capping enzyme (New England Biolabs, Ipswich, Mass.) and co-transcriptional capping or capping at or shortly after initiation of in vitro transcription (IVT), by for example, including a capping agent as part of an in vitro transcription (IVT) reaction. (Nuc. Acids Symp. (2009) 53:129).

Provided herein, in some embodiments, are nucleic acid molecules comprising (a) a sequence of SEQ ID NO:78; or (b) a sequence of SEQ ID NO:72, SEQ ID NO:73, SEQ ID NO:76, and SEQ ID NO:77, wherein T is substituted with U. In one aspect, nucleic acid molecules provided herein are RNA molecules. In another aspect, RNA molecules provided herein further comprise a 5' cap having a Cap 1 structure. Any RNA molecules provided herein can be self-replicating RNA molecules.

Only those mRNAs that carry the Cap structure are active in Cap dependent translation; "decapitation" of mRNA results in an almost complete loss of their template activity for protein synthesis (Nature, 255:33-37, (1975); J. Biol. Chem., vol. 253:5228-5231, (1978); and Proc. Natl. Acad. Sci. USA, 72:1189-1193, (1975)).

Another element of eukaryotic mRNA is the presence of 2'-O-methyl nucleoside residues at transcript position 1 (Cap 1), and in some cases, at transcript positions 1 and 2 (Cap 2). The 2'-O-methylation of mRNA provides higher efficacy of mRNA translation in vivo (Proc. Natl. Acad. Sci. USA, 77:3952-3956 (1980)) and further improves nuclease stability of the 5'-capped mRNA. The mRNA with Cap 1 (and Cap 2) is a distinctive mark that allows cells to recognize the bona fide mRNA 5' end, and in some instances, to discriminate against transcripts emanating from infectious genetic elements (Nucleic Acid Research 43: 482-492 (2015)).

Some examples of 5' cap structures and methods for preparing mRNAs comprising the same are given in WO2015/051169A2, WO/2015/061491, US 2018/0273576, and U.S. Pat. Nos. 8,093,367, 8,304,529, and 10,487,105. In some embodiments, the 5' cap is m7GpppAmpG, which is known in the art. In some embodiments, the 5' cap is m7GppppG or m7GpppGm, which are known in the art. Structural formulas for embodiments of 5' cap structures are provided below.

In some embodiments, a self-replicating RNA of the disclosure comprises a 5' cap having the structure of Formula (Cap I).

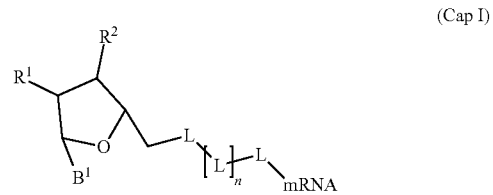

(Cap I)

wherein $B^1$ is a natural or modified nucleobase; $R^1$ and $R^2$ are each independently selected from a halogen, OH, and $OCH_3$; each L is independently selected from the group consisting of phosphate, phophorothioate, and boranophosphate wherein each L is linked by diester bonds; n is 0 or 1. and mRNA represents an mRNA of the present disclosure linked at its 5' end. In some embodiments $B^1$ is G, $m^7G$, or A. In some embodiments, n is 0. In some embodiments n is 1. In some embodiments, $B^1$ is A or $m^6A$ and $R^1$ is $OCH_3$; wherein G is guanine, $m^7G$ is 7-methylguanine, A is adenine, and $m^6A$ is $N^6$-methyladenine.

In some embodiments, a self-replicating RNA of the disclosure comprises a 5' cap having the structure of Formula (Cap II).

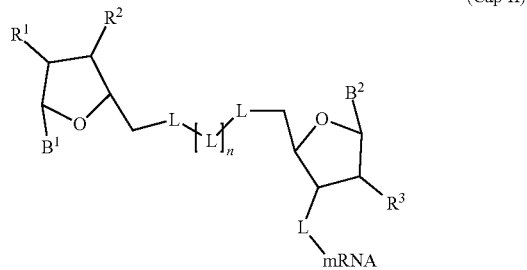

(Cap II)

wherein $B^1$ and $B^2$ are each independently a natural or modified nucleobase; $R^1$, $R^2$, and $R^3$ are each independently selected from a halogen, OH, and $OCH_3$; each L is independently selected from the group consisting of phosphate, phophorothioate, and boranophosphate wherein each L is linked by diester bonds; mRNA represents an mRNA of the present disclosure linked at its 5' end; and n is 0 or 1. In some embodiments $B^1$ is G, $m^7G$, or A. In some embodiments, n is 0. In some embodiments, n is 1. In some embodiments, $B^1$ is A or $m^6A$ and $R^1$ is $OCH_3$; wherein G is guanine, $m^7G$ is 7-methylguanine, A is adenine, and $m^6A$ is $N^6$-methyladenine.

In some embodiments, a self-replicating RNA of the disclosure comprises a 5' cap having the structure of Formula (Cap III).

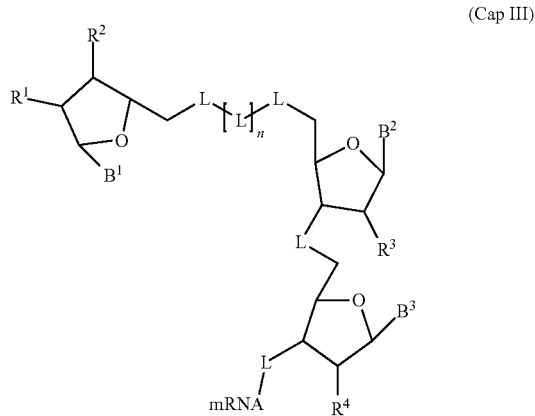

(Cap III)

wherein $B^1$, $B^2$, and $B^3$ are each independently a natural or modified nucleobase; $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH.

In some embodiments $B^1$ is G, $m^7G$, or A. In some embodiments, $B^1$ is A or $m^6A$ and $R^1$ is $OCH_3$; wherein G is guanine, $m^7G$ is 7-methylguanine, A is adenine, and $m^6A$ is $N^6$-methyladenine. In some embodiments, n is 1.

In some embodiments, a self-replicating RNA of the disclosure comprises a m7GpppG 5' cap analog having the structure of Formula (Cap IV).

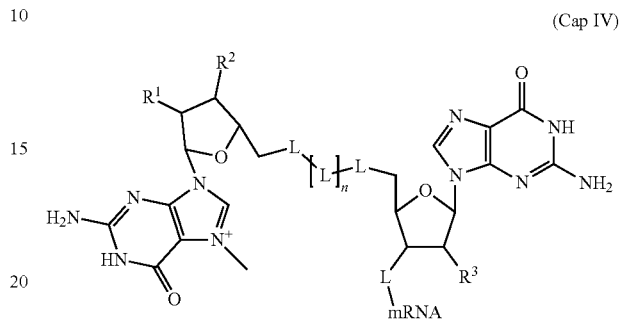

(Cap IV)

wherein, $R^1$, $R^2$, and $R^3$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; n is 0 or 1. In some embodiments, at least one of $R^1$, $R^2$, and $R^3$ is OH. In some embodiments, the 5' cap is $m^7GpppG$ wherein $R^1$, $R^2$, and $R^3$ are each OH, n is 1, and each L is a phosphate. In some embodiments, n is 1. In some embodiments, the 5' cap is m7GpppGm, wherein $R^1$ and $R^2$ are each OH, $R^3$ is $OCH_3$, each L is a phosphate, mRNA is the mRNA encoding an enzyme having OTC activity linked at its 5' end, and n is 1.

In some embodiments, a self-replicating RNA of the disclosure comprises a m7Gpppm7G 5' cap analog having the structure of Formula (Cap V).

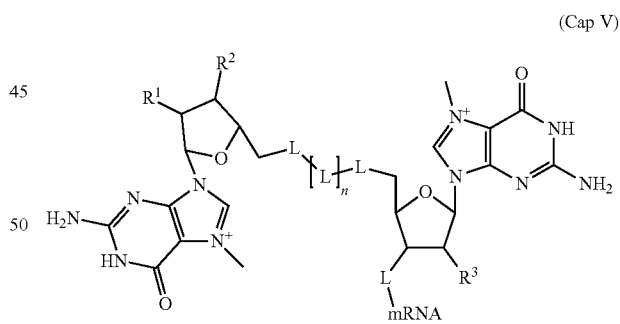

(Cap V)

wherein, $R^1$, $R^2$, and $R^3$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^3$ is OH. In some embodiments, n is 1.

In some embodiments, a self-replicating RNA of the disclosure comprises a m7Gpppm7GpN, 5' cap analog, wherein N is a natural or modified nucleotide, the 5' cap analog having the structure of Formula (Cap VI).

(Cap VI)

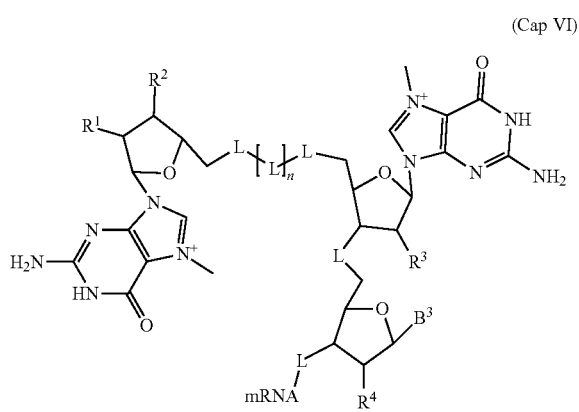

wherein B³ is a natural or modified nucleobase; R¹, R², R³, and R⁴ are each independently selected from a halogen, OH, and OCH₃; each L is independently selected from the group consisting of phosphate, phosphorothioate, and boranophosphate wherein each L is linked by diester bonds; mRNA represents an mRNA of the present disclosure linked at its 5' end; and n is 0 or 3. In some embodiments, at least one of R¹, R², R³, and R⁴ is OH. In some embodiments B¹ is G, m⁷G, or A. In some embodiments, B¹ is A or m⁶A and R¹ is OCH₃; wherein G is guanine, m⁷G is 7-methylguanine, A is adenine, and m⁶A is N⁶-methyladenine. In some embodiments, n is 1.

In some embodiments, a self-replicating RNA of the disclosure comprises a m7Gpppm7GpG 5' cap analog having the structure of Formula (Cap VII).

(Cap VII)

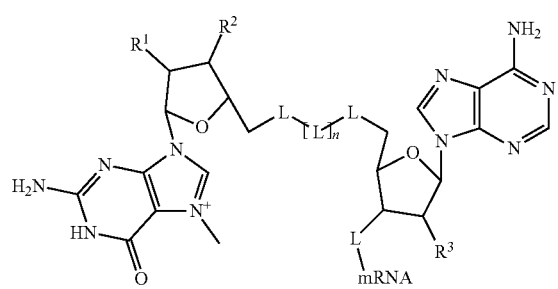

wherein, R¹, R², R³, and R⁴ are each independently selected from a halogen, OH, and OCH₃; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of R¹, R², R³, and R⁴ is OH. In some embodiments, n is 1.

In some embodiments, a self-replicating RNA of the disclosure comprises a m7Gpppm7Gpm7G 5' cap analog having the structure of Formula (Cap VIII).

(Cap VIII)

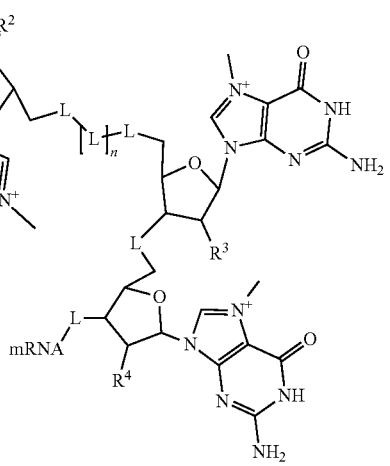

wherein, R¹, R², R³, and R⁴ are each independently selected from a halogen, OH, and OCH₃; each L is independently selected from the group consisting of phosphate, phosphorothioate, and boranophosphate wherein each L is linked by diester bonds; mRNA represents an mRNA of the present disclosure linked at its 5' end; n is 0 or 1. In some embodiments, at least one of R¹, R², R³, and R⁴ is OH. In some embodiments, n is 1.

In some embodiments, a self-replicating RNA of the disclosure comprises a m7GpppA 5' cap analog having the structure of Formula (Cap IX).

(Cap IX)

wherein, R¹, R², and R³ are each independently selected from a halogen, OH, and OCH₃; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of R¹, R², and R³ is OH. In some embodiments, n is 1.

In some embodiments, a self-replicating RNA of the disclosure comprises a m7GpppApN 5' cap analog, wherein N is a natural or modified nucleotide, and the 5' cap has the structure of Formula (Cap X).

(Cap X)

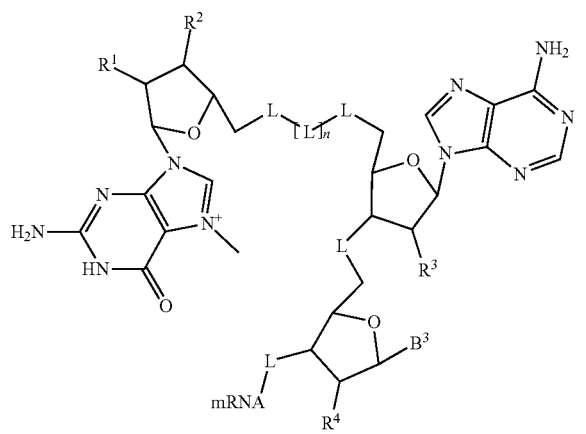

wherein $B^3$ is a natural or modified nucleobase; $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments $B^3$ is G, $m^7G$, A or $m^6A$; wherein G is guanine, $m^7G$ is 7-methylguanine, A is adenine, and $m^6A$ is $N^6$-methyladenine. In some embodiments, n is 1.

In some embodiments, a self-replicating RNA of the disclosure comprises a m7GpppAmpG 5' cap analog having the structure of Formula (Cap XI).

(Cap XI)

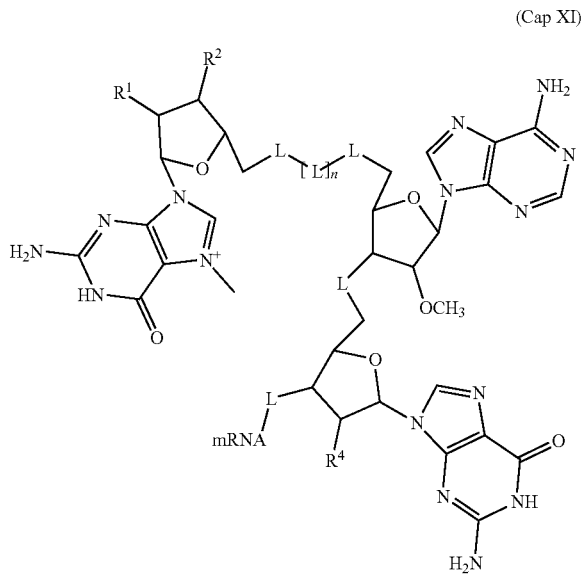

wherein, $R^1$, $R^2$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^4$ is OH. In some embodiments, the compound of Formula Cap XI is m7GpppAmpG, wherein $R^1$, $R^2$, and $R^4$ are each OH, n is 1, and each L is a phosphate linkage. In some embodiments, n is 1.

In some embodiments, a self-replicating RNA of the disclosure comprises a m7GpppApm7G 5' cap analog having the structure of Formula (Cap XII).

(Cap XII)

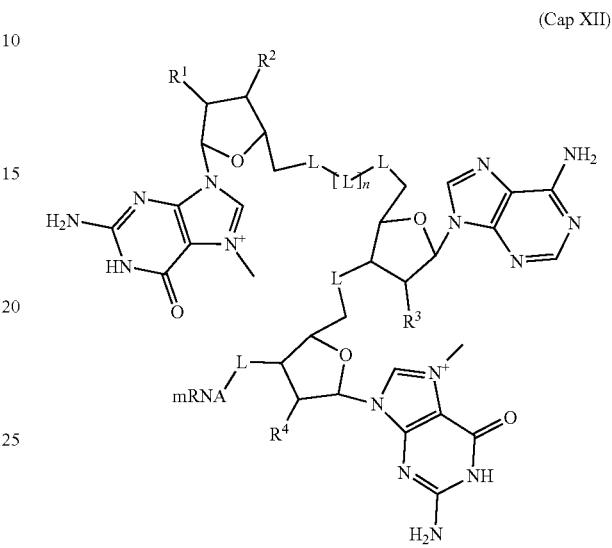

wherein, $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments, n is 1.

In some embodiments, a self-replicating RNA of the disclosure comprises a m7GpppAmpm7G 5' cap analog having the structure of Formula (Cap XIII).

(Cap XIII)

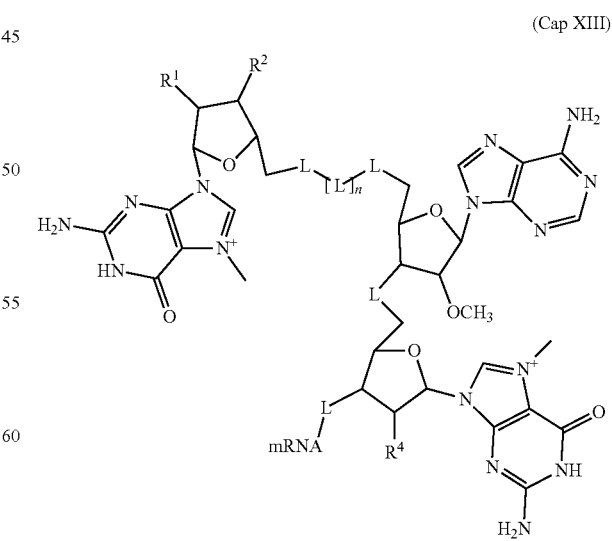

wherein, $R^1$, $R^2$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^4$ is OH. In some embodiments, n is 1.

Poly-Adenine (Poly-A) Tail

Polyadenylation is the addition of a poly(A) tail, a chain of adenine nucleotides usually about 100-120 monomers in length, to a mRNA. In eukaryotes, polyadenylation is part of the process that produces mature mRNA for translation and begins as the transcription of a gene terminates. The 3'-most segment of a newly made pre-mRNA is first cleaved off by a set of proteins; these proteins then synthesize the poly(A) tail at the 3' end. The poly(A) tail is important for the nuclear export, translation, and stability of mRNA. The tail is shortened over time, and, when it is short enough, the mRNA is enzymatically degraded. However, in a few cell types, mRNAs with short poly(A) tails are stored for later activation by re-polyadenylation in the cytosol.

Preferably, a self-replicating RNA of the disclosure comprises a 3' tail region, which can serve to protect the RNA from exonuclease degradation. The tail region may be a 3'poly(A) and/or 3'poly(C) region. Preferably, the tail region is a 3' poly(A) tail. As used herein a "3' poly(A) tail" is a polymer of sequential adenine nucleotides that can range in size from, for example: 10 to 250 sequential adenine nucleotides; 60-125 sequential adenine nucleotides, 90-125 sequential adenine nucleotides, 95-125 sequential adenine nucleotides, 95-121 sequential adenine nucleotides, 100 to 121 sequential adenine nucleotides, 110-121 sequential adenine nucleotides; 112-121 sequential adenine nucleotides; 114-121 adenine sequential nucleotides; or 115 to 121 sequential adenine nucleotides. Preferably, a 3' poly(A) tail as described herein comprise 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 sequential adenine nucleotides. 3' Poly(A) tails can be added using a variety of methods known in the art, e.g., using poly(A) polymerase to add tails to synthetic or in vitro transcribed RNA. Other methods include the use of a transcription vector to encode poly(A) tails or the use of a ligase (e.g., via splint ligation using a T4 RNA ligase and/or T4 DNA ligase), wherein poly(A) may be ligated to the 3' end of a sense RNA. In some embodiments, a combination of any of the above methods is utilized.

Design and Synthesis of Self-Replicating RNA

The constructs for exemplary self-replicating RNA sequences of the present disclosure are provided in Table 4.

TABLE 4

Comparison of STARR[TM] self-replicating RNA of the disclosure with comparative self-replicating RNA as described

| Construct | Position | Sequence Type | Sequence |
|---|---|---|---|
| STARR[TM] (SEQ ID NO: 49) | 5' UTR | nucleotide | ATGGGCGGCGCATGAGAGAAGCCCAGACCAATTACCT ACCCAAA |
| STARR[TM] (SEQ ID NO: 50) | non-structural gene ORF | nucleotide | ATGGAGAAAGTTCACGTTGACATCGAGGAAGACAGCC CATTCCTCAGAGCTTTGCAGCGGAGCTTCCCGCAGTTT GAGGTAGAAGCCAAGCAGGTCACTGATAATGACCATG CTAATGCCAGAGCGTTTTCGCATCTGGCTTCAAAACTG ATCGAAACGGAGGTGGACCCATCCGACACGATCCTTG ACATTGGAAGTGCGCCCGCCCGCAGAATGTATTCTAA GCACAAGTATCATTGTATCTGTCCGATGAGATGTGCGG AAGATCCGGACAGATTGTATAAGTATGCAACTAAGCT GAAGAAAAACTGTAAGGAAATAACTGATAAGGAATTG GACAAGAAAATGAAGGAGCTGGCCGCCGTCATGAGCG ACCCTGACCTGGAAACTGAGACTATGTGCCTCCACGA CGACGAGTCGTGTCGCTACGAAGGGCAAGTCGCTGTT TACCAGGATGTATACGCCGTCGACGGCCCCACCAGCC TGTACCACCAGGCCAACAAGGGCGTGAGGGTGGCCTA CTGGATCGGCTTCGACACCACACCCTTCATGTTCAAGA ACCTGGCCGGCGCCTACCCCAGCTACAGCACCAACTG GGCCGACGAGACCGTGCTGACCGCCAGGAACATCGGC CTGTGCAGCAGCGACGTGATGGAGAGGAGCCGGAGAG GCATGAGCATCCTGAGGAAGAAATACCTGAAGCCCAG CAACAACGTGCTGTTCAGCGTGGGCAGCACCATCTAC CACGAGAAGAGGGACCTGCTCAGGAGCTGGCACCTGC CCAGCGTGTTCCACCTGAGGGGCAAGCAGAACTACAC CTGCAGGTGCGAGACCATCGTGAGCTGCGACGGCTAC GTGGTGAAGAGGATCGCCATCAGCCCCGGCCTGTACG GCAAGCCCAGCGGCTACGCCGCTACAATGCACAGGGA GGGCTTCCTGTGCTGCAAGGTGACCGACACCCTGAAC GGCGAGAGGGTGAGCTTCCCCGTGTGCACCTACGTGC CCGCCACCCTGTGCGACCAGATGACCGGCATCCTGGC CACCGACGTGAGCGCCGACGACGCCCAGAAGCTGCTC GTGGGCCTGAACCAGAGGATCGTGGTCAACGGCAGGA CCCAGAGGAACACCAACACAATGAAGAACTACCTGCT GCCCGTGGTGGCCCAGGCTTTCGCCAGGTGGGCCAAG GAGTACAAGGAGGACCAGGAAGACGAGAGGCCCCTG GGCCTGAGGGACAGGCAGCTGGTGATGGGCTGCTGCT GGGCCTTCAGGCGGCACAAGATCACCAGCATCTACAA GAGGCCCGACACCCAGACCATCATCAAGGTGAACAGC GACTTCCACAGCTTCGTGCTGCCCAGGATCGGCAGCA ACACCCTGGAGATCGGCCTGAGGACCCGGATCAGGAA |

TABLE 4-continued

Comparison of STARR™ self-replicating RNA of the disclosure with comparative self-replicating RNA as described

| Construct | Position | Sequence Type | Sequence |
|---|---|---|---|
| | | | GATGCTGGAGGAACACAAGGAGCCCAGCCCACTGATC |
| | | | ACCGCCGAGGACGTGCAGGAGGCCAAGTGCGCTGCCG |
| | | | ACGAGGCCAAGGAGGTGAGGGAGGCCGAGGAACTGA |
| | | | GGGCCGCCCTGCCACCCCTGGCTGCCGACGTGGAGGA |
| | | | ACCCACCCTGGAAGCCGACGTGGACCTGATGCTGCAG |
| | | | GAGGCCGGCGCCGGAAGCGTGGAGACACCCAGGGGC |
| | | | CTGATCAAGGTGACCAGCTACGACGGCGAGGACAAGA |
| | | | TCGGCAGCTACGCCGTGCTGAGCCCACAGGCCGTGCT |
| | | | GAAGTCCGAGAAGCTGAGCTGCATCCACCCACTGGCC |
| | | | GAGCAGGTGATCGTGATCACCCACAGCGGCAGGAAGG |
| | | | GCAGGTACGCCGTGGAGCCCTACCACGGCAAGGTGGT |
| | | | CGTGCCCGAGGGCCACGCCATCCCCGTGCAGGACTTC |
| | | | CAGGCCCTGAGCGAGAGCGCCACCATCGTGTACAACG |
| | | | AGAGGGAGTTCGTGAACAGGTACCTGCACCATATCGC |
| | | | CACCCACGGCGGAGCCCTGAACACCGACGAGGAATAC |
| | | | TACAAGACCGTGAAGCCCAGCGAGCACGACGGCGAGT |
| | | | ACCTGTACGACATCGACAGGAAGCAGTGCGTGAAGAA |
| | | | AGAGCTGGTGACCGGCCTGGGACTGACCGGCGAGCTG |
| | | | GTGGACCCACCCTTCCACGAGTTCGCCTACGAGAGCCT |
| | | | GAGGACCAGACCCGCCGCTCCCTACCAGGTGCCCACC |
| | | | ATCGGCGTGTACGGCGTGCCCGGCAGCGGAAAGAGCG |
| | | | GCATCATCAAGAGCGCCGTGACCAAGAAAGACCTGGT |
| | | | GGTCAGCGCCAAGAAAGAGAACTGCGCCGAGATCATC |
| | | | AGGGACGTGAAGAAGATGAAAGGCCTGGACGTGAAC |
| | | | GCGCGCACCGTGGACAGCGTGCTGCTGAACGGCTGCA |
| | | | AGCACCCCGTGGAGACCCTGTACATCGACGAGGCCTT |
| | | | CGCTTGCCACGCCGGCACCCTGAGGGCCCTGATCGCC |
| | | | ATCATCAGGCCCAAGAAAGCCGTGCTGTGCGGCGACC |
| | | | CCAAGCAGTGCGGCTTCTTCAACATGATGTGCCTGAAG |
| | | | GTGCACTTCAACCACGAGATCTGCACCCAGGTGTTCCA |
| | | | CAAGAGCATCAGCAGGCGGTGCACCAAGAGCGTGACC |
| | | | AGCGTCGTGAGCACCCTGTTCTACGACAAGAAAATGA |
| | | | GGACCACCAACCCCAAGGAGACCAAAATCGTGATCGA |
| | | | CACCACAGGCAGCACCAAGCCCAAGCAGGACGACCTG |
| | | | ATCCTGACCTGCTTCAGGGGCTGGGTGAAGCAGCTGC |
| | | | AGATCGACTACAAGGGCAACGAGATCATGACCGCCGC |
| | | | TGCCAGCCAGGGCCTGACCAGGAAGGGCGTGTACGCC |
| | | | GTGAGGTACAAGGTGAACGAGAACCCACTGTACGCTC |
| | | | CCACCAGCGAGCACGTGAACGTGCTGCTGACCAGGAC |
| | | | CGAGGACAGGATCGTGTGGAAGACCCTGGCCGGCGAC |
| | | | CCCTGGATCAAGACCCTGACCGCCAAGTACCCCGGCA |
| | | | ACTTCACCGCCACCATCGAAGAGTGGCAGGCCGAGCA |
| | | | CGACGCCATCATGAGGCACATCCTGGAGAGGCCCGAC |
| | | | CCCACCGACGTGTTCCAGAACAAGGCCAACGTGTGCT |
| | | | GGGCCAAGGCCCTGGTGCCCGTGCTGAAGACCGCCGG |
| | | | CATCGACATGACCACAGAGCAGTGGAACACCGTGGAC |
| | | | TACTTCGAGACCGACAAGGCCCACAGCGCCGAGATCG |
| | | | TGCTGAACCAGCTGTGCGTGAGGTTCTTCGGCCTGGAC |
| | | | CTGGACAGCGGCCTGTTCAGCGCCCCCACCGTGCCACT |
| | | | GAGCATCAGGAACAACCACTGGGACAACAGCCCCAGC |
| | | | CCAAACATGTACGGCCTGAACAAGGAGGTGGTCAGGC |
| | | | AGCTGAGCAGGCGGTACCCACAGCTGCCCAGGGCCGT |
| | | | GGCCACCGGCAGGGTGTACGACATGAACACCGGCACC |
| | | | CTGAGGAACTACGACCCCAGGATCAACCTGGTGCCCG |
| | | | TGAACAGGCGGCTGCCCCACGCCCTGGTGCTGCACCA |
| | | | CAACGAGCACCCACAGAGCGACTTCAGCTCCTTCGTG |
| | | | AGCAAGCTGAAAGGCAGGACCGTGCTGGTCGTGGGCG |
| | | | AGAAGCTGAGCGTGCCCGGCAAGATGGTGGACTGGCT |
| | | | GAGCGACAGGCCCGAGGCCACCTTCCGGGCCAGGCTG |
| | | | GACCTCGGCATCCCCGGCGACGTGCCCAAGTACGACA |
| | | | TCATCTTCGTGAACGTCAGGACCCCATACAAGTACCAC |
| | | | CATTACCAGCAGTGCGAGGACCACGCCATCAAGCTGA |
| | | | GCATGCTGACCAAGAAGGCCTGCCTGCACCTGAACCC |
| | | | CGGAGGCACCTGCGTGAGCATCGGCTACGGCTACGCC |
| | | | GACAGGGCCAGCGAGAGCATCATTGGCGCCATCGCCA |
| | | | GGCTGTTCAAGTTCAGCAGGGTGTGCAAACCCAAGAG |
| | | | CAGCCTGGAGGAAACCGAGGTGCTGTTCGTGTTCATC |
| | | | GGCTACGACCGGAAGGCCAGGACCCACAACCCCTACA |
| | | | AGCTGAGCAGCACCCTGACAAACATCTACACCGGCAG |
| | | | CAGGCTGCACGAGGCCGGCTGCGCCCCCAGCTACCAC |
| | | | GTGGTCAGGGGCGATATCGCCACCGCCACCGAGGGCG |
| | | | TGATCATCAACGCTGCCAACAGCAAGGGCCAGCCCGG |
| | | | AGGCGGAGTGTGCGGCGCCCTGTACAAGAAGTTCCCC |
| | | | GAGAGCTTCGACCTGCAGCCCATCGAGGTGGGCAAGG |

TABLE 4-continued

Comparison of STARR™ self-replicating RNA of the disclosure with comparative self-replicating RNA as described

| Construct | Position | Sequence Type | Sequence |
|---|---|---|---|
| | | | CCAGGCTGGTGAAGGGCGCCGCTAAGCACATCATCCA |
| | | | CGCCGTGGGCCCCAACTTCAACAAGGTGAGCGAGGTG |
| | | | GAAGGCGACAAGCAGCTGGCCGAAGCCTACGAGAGC |
| | | | ATCGCCAAGATCGTGAACGACAATAACTACAAGAGCG |
| | | | TGGCCATCCCACTGCTCAGCACCGGCATCTTCAGCGGC |
| | | | AACAAGGACAGGCTGACCCAGAGCCTGAACCACCTGC |
| | | | TCACCGCCCTGGACACCACCGATGCCGACGTGGCCAT |
| | | | CTACTGCAGGGACAAGAAGTGGGAGATGACCCTGAAG |
| | | | GAGGCCGTGGCCAGGCGGGAGGCCGTGGAAGAGATCT |
| | | | GCATCAGCGACGACTCCAGCGTGACCGAGCCCGACGC |
| | | | CGAGCTGGTGAGGGTGCACCCCAAGAGCTCCCTGGCC |
| | | | GGCAGGAAGGGCTACAGCACCAGCGACGGCAAGACCT |
| | | | TCAGCTACCTGGAGGGCACCAAGTTCCACCAGGCCGC |
| | | | TAAGGACATCGCCGAGATCAACGCTATGTGGCCCGTG |
| | | | GCCACCGAGGCCAACGAGCAGGTGTGCATGTACATCC |
| | | | TGGGCGAGAGCATGTCCAGCATCAGGAGCAAGTGCCC |
| | | | CGTGGAGGAAAGCGAGGCCAGCACACCCACCCAGCACC |
| | | | CTGCCCTGCCTGTGCATCCACGCTATGACACCCGAGAG |
| | | | GGTGCAGCGGCTGAAGGCCAGCAGGCCCGAGCAGATC |
| | | | ACCGTGTGCAGCTCCTTCCCACTGCCCAAGTACAGGAT |
| | | | CACCGGCGTGCAGAAGATCCAGTGCAGCCAGCCCATC |
| | | | CTGTTCAGCCCAAAGGTGCCCGCCTACATCCACCCCAG |
| | | | GAAGTACCTGGTGGAGACCCCACCCGTGGACGAGACA |
| | | | CCCGAGCCAAGCGCCGAGAACCAGAGCACCGAGGGC |
| | | | ACACCCGAGCAGCCACCCCTGATCACCGAGGACGAGA |
| | | | CAAGGACCCGGACCCCAGAGCCCATCATTATCGAGGA |
| | | | AGAGGAAGAGGACAGCATCAGCCTGCTGAGCGACGGC |
| | | | CCCACCCACCAGGTGCTGCAGGTGGAGGCCGACATCC |
| | | | ACGGCCCACCCAGCGTGTCCAGCTCCAGCTGGAGCAT |
| | | | CCCACACGCCAGCGACTTCGACGTGGACAGCCTGAGC |
| | | | ATCCTGGACACCCTGGAGGGCGCCAGCGTGACCTCCG |
| | | | GCGCCACCAGCGCCGAGACCAACAGCTACTTCGCCAA |
| | | | GAGCATGGAGTTCCTGGCCAGGCCCGTGCCAGCTCCC |
| | | | AGGACCGTGTTCAGGAACCCACCCCACCCAGCTCCCA |
| | | | GGACCAGGACCCCAAGCCTGGCTCCCAGCAGGGCCTG |
| | | | CAGCAGGACCAGCCTGGTGAGCACCCCACCCGGCGTG |
| | | | AACAGGGTGATCACCAGGGAGGAACTGGAGGCCCTGA |
| | | | CACCCAGCAGGACCCCCAGCAGGTCCGTGAGCAGGAC |
| | | | TAGTCTGGTGTCCAACCCACCCGGCGTGAACAGGGTG |
| | | | ATCACCAGGGAGGAATTCGAGGCCTTCGTGGCCCAGC |
| | | | AACAGAGACGGTTCGACGCCGGCGCCTACATCTTCAG |
| | | | CAGCGACACCGGCCAGGGACACCTGCAGCAAAAGAGC |
| | | | GTGAGGCAGACCGTGCTGAGCGAGGTGGTGCTGGAGA |
| | | | GGACCGAGCTGGAAATCAGCTACGCCCCCAGGCTGGA |
| | | | CCAGGAGAAGGAGGAACTGCTCAGGAAGAAACTGCA |
| | | | GCTGAACCCCACCCCAGCCAACAGGAGCAGGTACCAG |
| | | | AGCAGGAAGGTGGAGAACATGAAGGCCATCACCGCCA |
| | | | GGCGGATCCTGCAGGGCCTGGGACACTACCTGAAGGC |
| | | | CGAGGGCAAGGTGGAGTGCTACAGGACCCTGCACCCC |
| | | | GTGCCACTGTACAGCTCCAGCGTGAACAGGGCCTTCTC |
| | | | CAGCCCCAAGGTGGCCGTGGAGGCCTGCAACGCTATG |
| | | | CTGAAGGAGAACTTCCCCACCGTGGCCAGCTACTGCA |
| | | | TCATCCCCGAGTACGACGCCTACCTGGACATGGTGGA |
| | | | CGGCGCCAGCTGCTGCCTGGACACCGCCAGCTTCTGCC |
| | | | CCGCCAAGCTGAGGAGCTTCCCCAAGAAACACAGCTA |
| | | | CCTGGAGCCCACCATCAGGAGCGCCGTGCCCAGCGCC |
| | | | ATCCAGAACACCCTGCAGAACGTGCTGGCCGCTGCCA |
| | | | CCAAGAGGAACTGCAACGTGACCCAGATGAGGGAGCT |
| | | | GCCCGTGCTGGACAGCGCTGCCTTCAACGTGGAGTGCT |
| | | | TCAAGAAATACGCCTGCAACAACGAGTACTGGGAGAC |
| | | | CTTCAAGGAGAACCCCATCAGGCTGACCGAAGAGAAC |
| | | | GTGGTGAACTACATCACCAAGCTGAAGGGCCCCAAGG |
| | | | CCGCTGCCCTGTTCGCTAAGACCCACAACCTGAACATG |
| | | | CTGCAGGACATCCCAATGGACAGGTTCGTGATGGACC |
| | | | TGAAGAGGGACGTGAAGGTGACACCCGGCACCAAGCA |
| | | | CACCGAGGAGAGGCCCAAGGTGCAGGTGATCCAGGCC |
| | | | GCTGACCCACTGGCCACCGCCTACCTGTGCGGCATCCA |
| | | | CAGGGAGCTGGTGAGGCGGCTGAACGCCGTGCTGCTG |
| | | | CCCAACATCCACACCCTGTTCGACATGAGCGCCGAGG |
| | | | ACTTCGACGCCATCATCGCCGAGCACTTCCAGCCCGGC |
| | | | GACTGCGTGCTGGAGACCGACATCGCCAGCTTCGACA |
| | | | AGAGCGAGGATGACGCTATGGCCCTGACCGCTCTGAT |
| | | | GATCCTGGAGGACCTGGGCGTGGACGCCGAGCTGCTC |
| | | | ACCCTGATCGAGGCTGCCTTCGGCGAGATCAGCTCCAT |

TABLE 4-continued

Comparison of STARR™ self-replicating RNA of the disclosure with comparative self-replicating RNA as described

| Construct | Position | Sequence Type | Sequence |
|---|---|---|---|
| | | | CCACCTGCCCACCAAGACCAAGTTCAAGTTCGGCGCT<br>ATGATGAAAAGCGGAATGTTCCTGACCCTGTTCGTGA<br>ACACCGTGATCAACATTGTGATCGCCAGCAGGGTGCT<br>GCGGGAGAGGCTGACCGGCAGCCCCTGCGCTGCCTTC<br>ATCGGCGACGACAACATCGTGAAGGGCGTGAAAAGCG<br>ACAAGCTGATGGCCGACAGGTGCGCCACCTGGCTGAA<br>CATGGAGGTGAAGATCATCGACGCCGTGGTGGGCGAG<br>AAGGCCCCCTACTTCTGCGGCGGATTCATCCTGTGCGA<br>CAGCGTGACCGGCACCGCCTGCAGGGTGGCCGACCCC<br>CTGAAGAGGCTGTTCAAGCTGGGCAAGCCACTGGCCG<br>CTGACGATGAGCACGACGATGACAGGCGGAGGGCCCT<br>GCACGAGGAAAGCACCAGGTGGAACAGGGTGGGCAT<br>CCTGAGCGAGCTGTGCAAGGCCGTGGAGAGCAGGTAC<br>GAGACCGTGGGCACCAGCATCATCGTGATGGCTATGA<br>CCCACACTGGCCAGCTCCGTCAAGAGCTTCTCCTACCTG<br>AGGGGGGCCCCTATAACTCTCTACGGCTAA |
| STARR™<br>(SEQ ID NO: 51) | non-structural gene ORF | amino acid | MEKVHVDIEEDSPFLRALQRSFPQFEVEAKQVTDNDHAN<br>ARAFSHLASKLIETEVDPSDTILDIGSAPARRMYSKHKYH<br>CICPMRCAEDPDRLYKYATKLKKNCKEITDKELDKKMK<br>ELAAVMSDPDLETETMCLHDDESCRYEGQVAVYQDVY<br>AVDGPTSLYHQANKGVRVAYWIGFDTTPFMFKNLAGAY<br>PSYSTNWADETVLTARNIGLCSSDVMERSRRGMSILRKK<br>YLKPSNNVLFSVGSTIYHEKRDLLRSWHLPSVFHLRGKQ<br>NYTCRCETIVSCDGYVVKRIAISPGLYGKPSGYAATMHR<br>EGFLCCKVTDTLNGERVSFPVCTYVPATLCDQMTGILAT<br>DVSADDAQKLLVGLNQRIVVNGRTQRNTNTMKNYLLPV<br>VAQAFARWAKEYKEDQEDERPLGLRDRQLVMGCCWAF<br>RRHKITSIYKRPDTQTIIKVNSDFHSFVLPRIGSNTLEIGLR<br>TRIRKMLEEHKEPSPLITAEDVQEAKCAADEAKEVREAE<br>ELRAALPPLAADVEEPTLEADVDLMLQEAGAGSVETPRG<br>LIKVTSYDGEDKIGSYAVLSPQAVLKSEKLSCIHPLAEQVI<br>VITHSGRKGRYAVEPYHGKVVVPEGHAIPVQDFQALSES<br>ATIVYNEREFVNRYLHHIATHGGALNTDEEYYKTVKPSE<br>HDGEYLYDIDRKQCVKKELVTGLGLTGELVDPPFHEFAY<br>ESLRTRPAAPYQVPTIGVYGVPGSGKSGIIKSAVTKKDLV<br>VSAKKENCAEIIRDVKKMKGLDVNARTVDSVLLNGCKH<br>PVETLYIDEAFACHAGTLRALIAIIRPKKAVLCGDPKQCG<br>FFNMMCLKVHFNHEICTQVFHKSISRRCTKSVTSVVSTLF<br>YDKKMRTTNPKETKIVIDTTGSTKPKQDDLILTCFRGWV<br>KQLQIDYKGNEIMTAAASQGLTRKGVYAVRYKVNENPL<br>YAPTSEHVNVLLTRTEDRIVWKTLAGDPWIKTLTAKYPG<br>NFTATIEEWQAEHDAIMRHILERPDPTDVFQNKANVCWA<br>KALVPVLKTAGIDMTTEQWNTVDYFETDKAHSAEIVLN<br>QLCVRFFGLDLDSGLFSAPTVPLSIRNNHWDNSPSPNMY<br>GLNKEVVRQLSRRYPQLPRAVATGRVYDMNTGTLRNYD<br>PRINLVPVNRRLPHALVLHHNEHPQSDFSSFVSKLKGRTV<br>LVVGEKLSVPGKMVDWLSDRPEATFRARLDLGIPGDVP<br>KYDIIFVNVRTPYKYHHYQQCEDHAIKLSMLTKKACLHL<br>NPGGTCVSIGYGYADRASESIIGAIARLFKFSRVCKPKSSL<br>EETEVLFVFIGYDRKARTHNPYKLSSTLTNIYTGSRLHEA<br>GCAPSYHVVRGDIATATEGVIINAANSKGQPGGGVCGAL<br>YKKFPESFDLQPIEVGKARLVKGAAKHIIHAVGPNFNKVS<br>EVEGDKQLAEAYESIAKIVNDNNYKSVAIPLLSTGIFSGN<br>KDRLTQSLNHLLTALDTTDADVAIYCRDKKWEMTLKEA<br>VARREAVEEICISDDSSVTEPDAELVRVHPKSSLAGRKGY<br>STSDGKTFSYLEGTKFHQAAKDIAEINAMWPVATEANEQ<br>VCMYILGESMSSIRSKCPVEESEASTPPSTLPCLCIHAMTP<br>ERVQRLKASRPEQITVCSSFPLPKYRITGVQKIQCSQPILFS<br>PKVPAYIHPRKYLVETPPVDETPEPSAENQSTEGTPEQPPL<br>ITEDETRTRTPEPIIIEEEEEDSISLLSDGPTHQVLQVEADIH<br>GPPSVSSSSWSIPHASDFDVDSLSILDTLEGASVTSGATSA<br>ETNSYFAKSMEFLARPVPAPRTVFRNPPHPAPRTRTPSLA<br>PSRACSRTSLVSTPPGVNRVITREELEALTPSRTPSRSVSR<br>TSLVSNPPGVNRVITREEFEAFVAQQQRRFDAGAYIFSSD<br>TGQGHLQQKSVRQTVLSEVVLERTELEISYAPRLDQEKE<br>ELLRKKLQLNPTPANRSRYQSRKVENMKAITARRILQGL<br>GHYLKAEGKVECYRTLHPVPLYSSSVNRAFSSPKVAVEA<br>CNAMLKENFPTVASYCIIPEYDAYLDMVDGASCCLDTAS<br>FCPAKLRSFPKKHSYLEPTIRSAVPSAIQNTLQNVLAAAT<br>KRNCNVTQMRELPVLDSAAFNVECFKKYACNNEYWETF<br>KENPIRLTEENVVNYITKLKGPKAAALFAKTHNLNMLQD<br>IPMDRFVMDLKRDVKVTPGTKHTEERPKVQVIQAADPL<br>ATAYLCGIHRELVRRLNAVLLPNIHTLFDMSAEDFDAIIA |

TABLE 4-continued

Comparison of STARR™ self-replicating RNA of the disclosure with comparative self-replicating RNA as described

| Construct | Position | Sequence Type | Sequence |
|---|---|---|---|
| | | | EHFQPGDCVLETDIASFDKSEDDAMALTALMILEDLGVD AELLTLIEAAFGEISSIHLPTKTKFKFGAMMKSGMFLTLF VNTVINIVIASRVLRERLTGSPCAAFIGDDNIVKGVKSDK LMADRCATWLNMEVKIIDAVVGEKAPYFCGGFILCDSVT GTACRVADPLKRLFKLGKPLAADDEHDDDRRRALHEES TRWNRVGILSELCKAVESRYETVGTSIIVMAMTTLASSV KSFSYLRGAPITLYG* |
| STARR™ (SEQ ID NO: 52) | intergenic region | nucleotide | CCTGAATGGACTACGACATAGTCTAGTCCGCCAAGGC CGCCACC |
| STARR™ | transgene ORF | nucleotide | n/a (depends on gene of our interest) |
| STARR™ (SEQ ID NO: 53) | 3' UTR | nucleotide | ACTCGAGTATGTTACGTGCAAAGGTGATTGTCACCCCC CGAAAGACCATATTGTGACACACCCTCAGTATCACGC CCAAACATTTACAGCCGCGGTGTCAAAAACCGCGTGG ACGTGGTTAACATCCCTGCTGGGAGGATCAGCCGTAA TTATTATAATTGGCTTGGTGCTGGCTACTATTGTGGCC ATGTACGTGCTGACCAACCAGAAACATAATTGAATAC AGCAGCAATTGGCAAGCTGCTTACATAGAACTCGCGG CGATTGGCATGCCGCCTTAAAATTTTTATTTTATTTTTT CTTTTCTTTTCCGAATCGGATTTTGTTTTTAATATTTCA AAAAAAAAAAAAAAAAAAAAAAATCTAGAAAAAAA AAAAAAAAAAAAAAAAAAAAAAAAAAAAAAAA AAAAAAAAAAAAAAAAAAAAAAAAAAAAAAAA AAAAAAAAAAAAAAAAAAAAA |
| Comparitive | 5' UTR | nucleotide | unknown |
| Original (SEQ ID NO: 54) | non-structural gene ORF | nucleotide | ATGCCCGAGAAGGTGCACGTGGACATCGAGGAGGACA GCCCCTTCCTGAGGGCCCTGCAGAGGAGCTTCCCACA GTTCGAAGTGGAGGCCAAGCAGGTGACCGACAACGAC CACGCCAACGCCAGGGCCTTCAGCCACCTGGCCAGCA AGCTGATCGAGACCGAGGTGGACCCCAGCGACACCAT CCTGGACATCGGCAGCGCCCCAGCCAGGAGAATGTAC AGCAAGCACAAGTACCACTGCATCTGCCCCATGAGGT GCGCCGAGGACCCCGACAGGCTGTACAAGTACGCCAC CAAACTGAAGAAGAACTGCAAGGAGATCACCGACAA GGAGCTGGACAAGAAAATGAAGGAGCTGGCCGCCGTG ATGAGCGACCCCGACCTGGAGACCGAGACAATGTGCC TGCACGACGACGAGAGCTGCAGGTACGAGGGCCAGGT GGCCGTCTACCAGGACGTGTACGCCGTCGACGGCCCC ACCAGCCTGTACCACCAGGCCAACAAGGGCGTGAGGG TGGCCTACTGGATCGGCTTCGACACCACACCCTTCATG TTCAAGAACCTGGCCGGCGCCTACCCCAGCTACAGCA CCAACTGGGCCGACGAGACCGTGCTGACCGCCAGGAA CATCGGCCTGTGCAGCAGCGACGTGATGGAGAGGAGC CGGAGAGGCATGAGCATCCTGAGGAAGAAATACCTGA AGCCCAGCAACAACGTGCTGTTCAGCGTGGGCAGCAC CATCTACCACGAGAAGAGGGACCTGCTCAGGAGCTGG CACCTGCCCAGCGTGTTCCACCTGAGGGGCAAGCAGA ACTACACCTGCAGGTGCGAGACCATCGTGAGCTGCGA CGGCTACGTGGTGAAGAGGATCGCCATCAGCCCCGGC CTGTACGGCAAGCCCAGCGGCTACGCCGCTACAATGC ACAGGGAGGGCTTCCTGTGCTGCAAGGTGACCGACAC CCTGAACGGCGAGAGGGTGAGCTTCCCCGTGTGCACC TACGTGCCCGCCACCCTGTGCGACCAGATGACCGGCA TCCTGGCCACCGACGTGAGCGCCGACGACGCCCAGAA GCTGCTCGTGGGCCTGAACCAGAGGATCGTGGTCAAC GGCAGGACCCAGAGGAACACCAACACAATGAAGAAC TACCTGCTGCCCGTGGTGGCCCAGGCTTTCGCCAGGTG GGCCAAGGAGTACAAGGAGGACCAGGAAGACGAGAG GCCCCTGGGCCTGAGGGACAGGCAGCTGGTGATGGGC TGCTGCTGGGCCTTCAGGCGGCACAAGATCACCAGCA TCTACAAGAGGCCCGACACCCAGACCATCATCAAGGT GAACAGCGACTTCCACAGCTTCGTGCTGCCCAGGATC GGCAGCAACACCCTGGAGATCGGCCTGAGGGACCGGA TCAGGAAGATGCTGGAGGAACACAAGGAGCCCAGCCC ACTGATCACCGCCGAGGACGTGCAGGAGGCCAAGTGC GCTGCCGACGAGGCCAAGGAGGTGAGGGAGGCCGAG GAACTGAGGGCCGCCCTGCCACCCCTGGCTGCCGACG TGGAGGAACCCACCCTGGAAGCCGACGTGGACCTGAT |

TABLE 4-continued

Comparison of STARR<sup>TM</sup> self-replicating RNA of the disclosure with comparative self-replicating RNA as described

| Construct | Position | Sequence Type | Sequence |
|---|---|---|---|
| | | | GCTGCAGGAGGCCGGCGCCGGAAGCGTGGAGACACCC |
| | | | AGGGGCCTGATCAAGGTGACCAGCTACGACGGCGAGG |
| | | | ACAAGATCGGCAGCTACGCCGTGCTGAGCCCACAGGC |
| | | | CGTGCTGAAGTCCGAGAAGCTGAGCTGCATCCACCCA |
| | | | CTGGCCGAGCAGGTGATCGTGATCACCCACAGCGGCA |
| | | | GGAAGGGCAGGTACGCCGTGGAGCCCTACCACGGCAA |
| | | | GGTGGTCGTGCCCGAGGGCCACGCCATCCCCGTGCAG |
| | | | GACTTCCAGGCCCTGAGCGAGAGCGCCACCATCGTGT |
| | | | ACAACGAGAGGGAGTTCGTGAACAGGTACCTGCACCA |
| | | | TATCGCCACCCACGGCGGAGCCCTGAACACCGACGAG |
| | | | GAATACTACAAGACCGTGAAGCCCAGCGAGCACGACG |
| | | | GCGAGTACCTGTACGACATCGACAGGAAGCAGTGCGT |
| | | | GAAGAAAGAGCTGGTGACCGGCCTGGGACTGACCGGC |
| | | | GAGCTGGTGGACCCACCCTTCCACGAGTTCGCCTACGA |
| | | | GAGCCTGAGGACCAGACCCGCCGCTCCCTACCAGGTG |
| | | | CCCACCATCGGCGTGTACGGCGTGCCCGGCAGCGGAA |
| | | | AGAGCGGCATCATCAAGAGCGCCGTGACCAAGAAAGA |
| | | | CCTGGTGGTCAGCGCCAAGAAAGAGAACTGCGCCGAG |
| | | | ATCATCAGGGACGTGAAGAAGATGAAAGGCCTGGACG |
| | | | TGAACGCGCGCACCGTGGACAGCGTGCTGCTGAACGG |
| | | | CTGCAAGCACCCCGTGGAGACCCTGTACATCGACGAG |
| | | | GCCTTCGCTTGCCACGCCGGCACCCTGAGGGCCCTGAT |
| | | | CGCCATCATCAGGCCCAAGAAAGCCGTGCTGTGCGGC |
| | | | GACCCCAAGCAGTGCGGCTTCTTCAACATGATGTGCCT |
| | | | GAAGGTGCACTTCAACCACGAGATCTGCACCCAGGTG |
| | | | TTCCACAAGAGCATCAGCAGGCGGTGCACCAAGAGCG |
| | | | TGACCAGCGTCGTGAGCACCCTGTTCTACGACAAGAA |
| | | | AATGAGGACCACCAACCCCAAGGAGACCAAAATCGTG |
| | | | ATCGACACCACAGGCAGCACCAAGCCCAAGCAGGACG |
| | | | ACCTGATCCTGACCTGCTTCAGGGGCTGGGTGAAGCA |
| | | | GCTGCAGATCGACTACAAGGGCAACGAGATCATGACC |
| | | | GCCGCTGCCAGCCAGGGCCTGACCAGGAAGGGCGTGT |
| | | | ACGCCGTGAGGTACAAGGTGAACGAGAACCCACTGTA |
| | | | CGCTCCCACCAGCGAGCACGTGAACGTGCTGCTGACC |
| | | | AGGACCGAGGACAGGATCGTGTGGAAGACCCTGGCCG |
| | | | GCGACCCCTGGATCAAGACCCTGACCGCCAAGTACCC |
| | | | CGGCAACTTCACCGCCACCATCGAAGAGTGGCAGGCC |
| | | | GAGCACGACGCCATCATGAGGCACATCCTGGAGAGGC |
| | | | CCGACCCCACCGACGTGTTCCAGAACAAGGCCAACGT |
| | | | GTGCTGGGCCAAGGCCCTGGTGCCCGTGCTGAAGACC |
| | | | GCCGGCATCGACATGACCACAGAGCAGTGGAACACCG |
| | | | TGGACTACTTCGAGACCGACAAGGCCCACAGCGCCGA |
| | | | GATCGTGCTGAACCAGCTGTGCGTGAGGTTCTTCGGCC |
| | | | TGGACCTGGACAGCGGCCTGTTCAGCGCCCCCACCGT |
| | | | GCCACTGAGCATCAGGAACAACCACTGGGACAACAGC |
| | | | CCCAGCCCAAACATGTACGGCCTGAACAAGGAGGTGG |
| | | | TCAGGCAGCTGAGCAGGCGGTACCCACAGCTGCCCAG |
| | | | GGCCGTGGCCACCGGCAGGGTGTACGACATGAACACC |
| | | | GGCACCCTGAGGAACTACGACCCCAGGATCAACCTGG |
| | | | TGCCCGTGAACAGGCGGCTGCCCCACGCCCTGGTGCT |
| | | | GCACCACAACGAGCACCCACAGAGCGACTTCAGCTCC |
| | | | TTCGTGAGCAAGCTGAAAGGCAGGACCGTGCTGGTCG |
| | | | TGGGCGAGAAGCTGAGCGTGCCCGGCAAGATGGTGGA |
| | | | CTGGCTGAGCGACAGGCCCGAGGCCACCTTCCGGGCC |
| | | | AGGCTGGACCTCGGCATCCCCGGCGACGTGCCCAAGT |
| | | | ACGACATCATCTTCGTGAACGTCAGGACCCCATACAA |
| | | | GTACCACCATTACCAGCAGTGCGAGGACCACGCCATC |
| | | | AAGCTGAGCATGCTGACCAAGAAGGCCTGCCTGCACC |
| | | | TGAACCCCGGAGGCACCTGCGTGAGCATCGGCTACGG |
| | | | CTACGCCGACAGGGCCAGCGAGAGCATCATTGGCGCC |
| | | | ATCGCCAGGCTGTTCAAGTTCAGCAGGGTGTGCAAAC |
| | | | CCAAGAGCAGCCTGGAGGAAACCGAGGTGCTGTTCGT |
| | | | GTTCATCGGCTACGACCGGAAGGCCAGGACCCACAAC |
| | | | CCCTACAAGCTGAGCAGCACCCTGACAAACATCTACA |
| | | | CCGGCAGCAGGCTGCACGAGGCCGGCTGCGCCCCCAG |
| | | | CTACCACGTGGTCAGGGGCGATATCGCCACCGCCACC |
| | | | GAGGGCGTGATCATCAACGCTGCCAACAGCAAGGGCC |
| | | | AGCCCGGAGGCGGAGTGTGCGGCGCCCTGTACAAGAA |
| | | | GTTCCCCGAGAGCTTCGACCTGCAGCCCATCGAGGTG |
| | | | GGCAAGGCCAGGCTGGTGAAGGGCGCCGCTAAGCACA |
| | | | TCATCCACGCCGTGGGCCCCAACTTCAACAAGGTGAG |
| | | | CGAGGTGGAAGGCGACAAGCAGCTGGCCGAAGCCTAC |
| | | | GAGAGCATCGCCAAGATCGTGAACGACAATAACTACA |
| | | | AGAGCGTGGCCATCCCACTGCTCAGCACCGGCATCTTC |

TABLE 4-continued

Comparison of STARR™ self-replicating RNA of the disclosure with comparative self-replicating RNA as described

| Construct | Position | Sequence Type | Sequence |
|---|---|---|---|
| | | | AGCGGCAACAAGGACAGGCTGACCCAGAGCCTGAACC |
| | | | ACCTGCTCACCGCCCTGGACACCACCGATGCCGACGT |
| | | | GGCCATCTACTGCAGGGACAAGAAGTGGGAGATGACC |
| | | | CTGAAGGAGGCCGTGGCCAGGCGGGAGGCCGTGGAA |
| | | | GAGATCTGCATCAGCGACGACTCCAGCGTGACCGAGC |
| | | | CCGACGCCGAGCTGGTGAGGGTGCACCCCAAGAGCTC |
| | | | CCTGGCCGGCAGGAAGGGCTACAGCACCAGCGACGGC |
| | | | AAGACCTTCAGCTACCTGGAGGGCACCAAGTTCCACC |
| | | | AGGCCGCTAAGGACATCGCCGAGATCAACGCTATGTG |
| | | | GCCCGTGGCCACCGAGGCCAACGAGCAGGTGTGCATG |
| | | | TACATCCTGGGCGAGAGCATGTCCAGCATCAGGAGCA |
| | | | AGTGCCCCGTGGAGGAAAGCGAGGCCAGCACACCACC |
| | | | CAGCACCCTGCCCTGCCTGTGCATCCACGCTATGACAC |
| | | | CCGAGAGGGTGCAGCGGCTGAAGGCCAGCAGGCCCGA |
| | | | GCAGATCACCGTGTGCAGCTCCTTCCCACTGCCCAAGT |
| | | | ACAGGATCACCGGCGTGCAGAAGATCCAGTGCAGCCA |
| | | | GCCCATCCTGTTCAGCCCAAAGGTGCCCGCCTACATCC |
| | | | ACCCCAGGAAGTACCTGGTGGAGACCCCACCCGTGGA |
| | | | CGAGACACCCGAGCCAAGCGCCGAGAACCAGAGCACC |
| | | | GAGGGCACACCCGAGCAGCCACCCCTGATCACCGAGG |
| | | | ACGAGACAAGGACCCGGACCCCAGAGCCCATCATTAT |
| | | | CGAGGAAGAGGAAGAGGACAGCATCAGCCTGCTGAG |
| | | | CGACGGCCCCACCCACCAGGTGCTGCAGGTGGAGGCC |
| | | | GACATCCACGGCCCACCCAGCGTGTCCAGCTCCAGCT |
| | | | GGAGCATCCCACACGCCAGCGACTTCGACGTGGACAG |
| | | | CCTGAGCATCCTGGACACCCTGGAGGGCGCCAGCGTG |
| | | | ACCTCCGGCGCCACCAGCGCCGAGACCAACAGCTACT |
| | | | TCGCCAAGAGCATGGAGTTCCTGGCCAGGCCCGTGCC |
| | | | AGCTCCCAGGACCGTGTTCAGGAACCCACCCCACCCA |
| | | | GCTCCCAGGACCAGGACCCCAAGCCTGGCTCCCAGCA |
| | | | GGGCCTGCAGCAGGACCAGCCTGGTGAGCACCCCACC |
| | | | CGGCGTGAACAGGGTGATCACCAGGGAGGAACTGGAG |
| | | | GCCCTGACACCCAGCAGGACCCCCAGCAGGTCCGTGA |
| | | | GCAGGACTAGTCTGGTGTCCAACCCACCCGGCGTGAA |
| | | | CAGGGTGATCACCAGGGAGGAATTCGAGGCCTTCGTG |
| | | | GCCCAGCAACAGAGACGGTTCGACGCCGGCGCCTACA |
| | | | TCTTCAGCAGCGACACCGGCCAGGGACACCTGCAGCA |
| | | | AAAGAGCGTGAGGCAGACCGTGCTGAGCGAGGTGGTG |
| | | | CTGGAGAGGACCGAGCTGGAAATCAGCTACGCCCCCA |
| | | | GGCTGGACCAGGAGAAGGAGGAACTGCTCAGGAAGA |
| | | | AACTGCAGCTGAACCCCACCCCAGCCAACAGGAGCAG |
| | | | GTACCAGAGCAGGAAGGTGGAGAACATGAAGGCCATC |
| | | | ACCGCCAGGCGGATCCTGCAGGGCCTGGGACACTACC |
| | | | TGAAGGCCGAGGGCAAGGTGGAGTGCTACAGGACCCT |
| | | | GCACCCCGTGCCACTGTACAGCTCCAGCGTGAACAGG |
| | | | GCCTTCTCCAGCCCCAAGGTGGCCGTGGAGGCCTGCA |
| | | | ACGCTATGCTGAAGGAGAACTTCCCCACCGTGGCCAG |
| | | | CTACTGCATCATCCCCGAGTACGACGCCTACCTGGACA |
| | | | TGGTGGACGGCGCCAGCTGCTGCCTGGACACCGCCAG |
| | | | CTTCTGCCCCGCCAAGCTGAGGAGCTTCCCCAAGAAA |
| | | | CACAGCTACCTGGAGCCCACCATCAGGAGCGCCGTGC |
| | | | CCAGCGCCATCCAGAACACCCTGCAGAACGTGCTGGC |
| | | | CGCTGCCACCAAGAGGAACTGCAACGTGACCCAGATG |
| | | | AGGGAGCTGCCCGTGCTGGACAGCGCTGCCTTCAACG |
| | | | TGGAGTGCTTCAAGAAATACGCCTGCAACAACGAGTA |
| | | | CTGGGAGACCTTCAAGGAGAACCCCATCAGGCTGACC |
| | | | GAAGAGAACGTGGTGAACTACATCACCAAGCTGAAGG |
| | | | GCCCCAAGGCCGCTGCCCTGTTCGCTAAGACCCACAA |
| | | | CCTGAACATGCTGCAGGACATCCCAATGGACAGGTTC |
| | | | GTGATGGACCTGAAGAGGGACGTGAAGGTGACACCCG |
| | | | GCACCAAGCACACCGAGGAGAGGCCCAAGGTGCAGGT |
| | | | GATCCAGGCCGCTGACCCACTGGCCACCGCCTACCTGT |
| | | | GCGGCATCCACGGGGAGCTGGTGAGGCGGCTGAACGC |
| | | | CGTGCTGCTGCCCAACATCCACACCCTGTTCGACATGA |
| | | | GCGCCGAGGACTTCGACGCCATCATCGCCGAGCACTT |
| | | | CCAGCCCGGCGACTGCGTGCTGGAGACCGACATCGCC |
| | | | AGCTTCGACAAGAGCGAGGATGACGCTATGGCCCTGA |
| | | | CCGCTCTGATGATCCTGGAGGACCTGGGCGTGGACGC |
| | | | CGAGCTGCTCACCCTGATCGAGGCTGCCTTCGGCGAG |
| | | | ATCAGCTCCATCCACCTGCCCACCAAGACCAAGTTCAA |
| | | | GTTCGGCGCTATGATGAAAGCGGAATGTTCCTGACC |
| | | | CTGTTCGTGAACACCGTGATCAACATTGTGATCGCCAG |
| | | | CAGGGTGCTGCGGGAGAGGCTGACCGGCAGCCCCTGC |
| | | | GCTGCCTTCATCGGCGACGACAACATCGTGAAGGGCG |

TABLE 4-continued

Comparison of STARR™ self-replicating RNA of the disclosure with comparative self-replicating RNA as described

| Construct | Position | Sequence Type | Sequence |
|---|---|---|---|
| | | | TGAAAAGCGACAAGCTGATGGCCGACAGGTGCGCCAC<br>CTGGCTGAACATGGAGGTGAAGATCATCGACGCCGTG<br>GTGGGCGAGAAGGCCCCCTACTTCTGCGGCGGATTCA<br>TCCTGTGCGACAGCGTGACCGGCACCGCCTGCAGGGT<br>GGCCGACCCCCTGAAGAGGCTGTTCAAGCTGGGCAAG<br>CCACTGGCCGCTGACGATGAGCACGACGATGACAGGO<br>GGAGGGCCCTGCACGAGGAAAGCACCAGGTGGAACA<br>GGGTGGGCATCCTGAGCGAGCTGTGCAAGGCCGTGGA<br>GAGCAGGTACGAGACCGTGGGCACCAGCATCATCGTG<br>ATGGCTATGACCACACTGGCCAGCTCCGTCAAGAGCTT<br>CTCCTACCTGAGGGGGGCCCCTATAACTCTCTACGGCT<br>AA |
| Comparitive (SEQ ID NO: 55) | non-structural gene ORF | amino acid | MPEKVHVDIEEDSPFLRALQRSFPQFEVEAKQVTDNDHA<br>NARAFSHLASKLIETEVDPSDTILDIGSAPARRMYSKHKY<br>HCICPMRCAEDPDRLYKYATKLKKNCKEITDKELDKKM<br>KELAAVMSDPDLETETMCLHDDESCRYEGQVAVYQDV<br>YAVDGPTSLYHQANKGVRVAYWIGFDTTPFMFKNLAGA<br>YPSYSTNWADETVLTARNIGLCSSDVMERSRRGMSILRK<br>KYLKPSNNVLFSVGSTIYHEKRDLLRSWHLPSVFHLRGK<br>QNYTCRCETIVSCDGYVVKRIAISPGLYGKPSGYAATMH<br>REGFLCCKVTDTLNGERVSFPVCTYVPATLCDQMTGILA<br>TDVSADDAQKLLVGLNQRIVVNGRTQRNTNTMKNYLLP<br>VVAQAFARWAKEYKEDQEDERPLGLRDRQLVMGCCWA<br>FRRHKITSIYKRPDTQTIIKVNSDFHSFVLPRIGSNTLEIGL<br>RTRIRKMLEEHKEPSPLITAEDVQEAKCAADEAKEVREA<br>EELRAALPPLAADVEEPTLEADVDLMLQEAGAGSVETPR<br>GLIKVTSYDGEDKIGSYAVLSPQAVLKSEKLSCIHPLAEQ<br>VIVITHSGRKGRYAVEPYHGKVVVPEGHAIPVQDFQALS<br>ESATIVYNEREFVNRYLHHIATHGGALNTDEEYYKTVKP<br>SEHDGEYLYDIDRKQCVKKELVTGLGLTGELVDPPFHEF<br>AYESLRTRPAAPYQVPTIGVYGVPGSGKSGIIKSAVTKKD<br>LVVSAKKENCAEIIRDVKKMKGLDVNARTVDSVLLNGC<br>KHPVETLYIDEAFACHAGTLRALIAIIRPKKAVLCGDPKQ<br>CGFFNMMCLKVHFNHEICTQVFHKSISRRCTKSVTSVVS<br>TLFYDKKMRTTNPKETKIVIDTTGSTKPKQDDLILTCFRG<br>WVKQLQIDYKGNEIMTAAASQGLTRKGVYAVRYKVNE<br>NPLYAPTSEHVNVLLTRTEDRIVWKTLAGDPWIKTLTAK<br>YPGNFTATIEEWQAEHDAIMRHILERPDPTDVFQNKANV<br>CWAKALVPVLKTAGIDMTTEQWNTVDYFETDKAHSAEI<br>VLNQLCVRFFGLDLDSGLFSAPTVPLSIRNNHWDNSPSPN<br>MYGLNKEVVRQLSRRYPQLPRAVATGRVVDMNTGTLR<br>NYDPRINLVPVNRRLPHALVLHHNEHPQSDFSSFVSKLK<br>GRTVLVVGEKLSVPGKMVDWLSDRPEATFRARLDLGIP<br>GDVPKYDIIFVNVRTPYKYHHYQQCEDHAIKLSMLTKKA<br>CLHLNPGGTCVSIGYGYADRASESIIGAIARLPKFSRVCKP<br>KSSLEETEVLFVFIGYDRKARTHNPYKLSSTLTNIYTGSRL<br>HEAGCAPSYHVVRGDIATATEGVIINAANSKGQPGGGVC<br>GALYKKFPESFDLQPIEVGKARLVKGAAKHIIHAVGPNF<br>NKVSEVEGDKQLAEAYESIAKIVNDNNYKSVAIPLLSTGI<br>FSGNKDRLTQSLNHLLTALDTTDADVAIYCRDKKWEMT<br>LKEAVARREAVEEICISDDSSVTEPDAELVRVHPKSSLAG<br>RKGYSTSDGKTFSYLEGTKFHQAAKDIAEINAMWPVATE<br>ANEQVCMYILGESMSSIRSKCPVEESEASTPPSTLPCLCIH<br>AMTPERVQRLKASRPEQITVCSSFPLPKYRITGVQKIQCS<br>QPILFSPKVPAYIHPRKYLVETPPVDETPEPSAENQSTEGT<br>PEQPPLITEDETRTRTPEPIIIEEEEEDSISLLSDGPTHQVLQ<br>VEADIHGPPSVSSSSWSIPHASDFDVDSLSILDTLEGASVT<br>SGATSAETNSYFAKSMEFLARPVPAPRTVFRNPPHPAPRT<br>RTPSLAPSRACSRTSLVSTPPGVNRVITREELEALTPSRTP<br>SRSVSRTSLVSNPPGVNRVITREEFEAPVAQQQRRFDAGA<br>YIFSSDTGQGHLQQKSVRQTVLSEVVLERTELEISYAPRL<br>DQEKEELLRKKLQLNPTPANRSRYQSRKVENMKAITARR<br>ILQGLGHYLKAEGKVECYRTLHPVPLYSSSVNRAFSSPK<br>VAVEACNAMLKENFPTVASYCIIPEYDAYLDMVDGASC<br>CLDTASFCPAKLRSFPKKHSYLEPTIRSAVPSAIQNTLQNV<br>LAAATKRNCNVTQMRELPVLDSAAFNVECFKKYACNNE<br>YWETFKENPIRLTEENVVNYITKLKGPKAAALFAKTHNL<br>NMLQDIPMDRFVMDLKRDVKVTPGTKHTEERPKVQVIQ<br>AADPLATAYLCGIHRELVRRLNAVLLPNIHTLFDMSAED<br>FDAIIAEHFQPGDCVLETDIASFDKSEDDAMALTALMILE<br>DLGVDAELLTLIEAAFGEISSIHLPTKTKFKFGAMMKSGM<br>FLTLFVNTVINIVIASRVLRERLTGSPCAAFIGDDNIVKGV<br>KSDKLMADRCATWLNMEVKIIDAVVGEKAPYFCGGFIL |

TABLE 4-continued

Comparison of STARR™ self-replicating RNA of the disclosure with comparative self-replicating RNA as described

| Construct | Position | Sequence Type | Sequence |
|---|---|---|---|
| | | | CDSVTGTACRVADPLKRLFKLGKPLAADDEHDDDRRRA LHEESTRWNRVGILSELCKAVESRYETVGTSIIVMAMTTL ASSVKSFSYLRGAPITLYG* |
| Comparitive | intergenic region | nucleotide | unknown |
| Comparitive | 3' UTR | nucleotide | unknown |

RNA sequences can include any combination of the RNA sequences listed in Table 4. In some embodiments, RNA sequences of the present disclosure include any combination of the RNA sequences listed in Table 4 in which 0% to 100%, 1% to 100%, 25% to 100%, 50% to 100% and 75% to 100% of the uracil nucleotides of the mRNA sequences are modified. In some embodiments, 1% to 100% of the uracil nucleotides are N1-methylpseudouridine or 5-methoxyuridine. In some embodiments, 100% of the uracil nucleotides are N1-methylpseudouridine. In some embodiments, 100% of the uracil nucleotides are 5-methoxyuridine.

A self-replicating RNA of the disclosure may be obtained by any suitable means. Methods for the manufacture of self-replicating RNA are known in the art and would be readily apparent to a person of ordinary skill. A self-replicating RNA of the disclosure may be prepared according to any available technique including, but not limited to chemical synthesis, in vitro transcription (IVT) or enzymatic or chemical cleavage of a longer precursor, etc.

In some embodiments, a self-replicating RNA of the disclosure is produced from a primary complementary DNA (cDNA) construct. The cDNA constructs can be produced on an RNA template by the action of a reverse transcriptase (e.g., RNA-dependent DNA-polymerase). The process of design and synthesis of the primary cDNA constructs described herein generally includes the steps of gene construction, RNA production (either with or without modifications) and purification. In the IVT method, a target polynucleotide sequence encoding a self-replicating RNA of the disclosure is first selected for incorporation into a vector which will be amplified to produce a cDNA template. Optionally, the target polynucleotide sequence and/or any flanking sequences may be codon optimized. The cDNA template is then used to produce a self-replicating RNA of the disclosure through in vitro transcription (IVT). After production, the self-replicating RNA of the disclosure may undergo purification and clean-up processes. The steps of which are provided in more detail below.

The step of gene construction may include, but is not limited to gene synthesis, vector amplification, plasmid purification, plasmid linearization and clean-up, and cDNA template synthesis and clean-up. Once a protein of interest is selected for production, a primary construct is designed. Within the primary construct, a first region of linked nucleosides encoding the polypeptide of interest may be constructed using an open reading frame (ORF) of a selected nucleic acid (DNA or RNA) transcript. The ORF may comprise the wild type ORF, an isoform, variant or a fragment thereof. As used herein, an "open reading frame" or "ORF" is meant to refer to a nucleic acid sequence (DNA or RNA) which is capable of encoding a polypeptide of interest. ORFs often begin with the start codon, ATG and end with a nonsense or termination codon or signal.

The cDNA templates may be transcribed to produce a self-replicating RNA of the disclosure using an in vitro transcription (IVT) system. The system typically comprises a transcription buffer, nucleotide triphosphates (NTPs), an RNase inhibitor and a polymerase. The NTPs may be selected from, but are not limited to, those described herein including natural and unnatural (modified) NTPs. The polymerase may be selected from, but is not limited to, T7 RNA polymerase, T3 RNA polymerase and mutant polymerases such as, but not limited to, polymerases able to incorporate modified nucleic acids.

The primary cDNA template or transcribed RNA sequence may also undergo capping and/or tailing reactions. A capping reaction may be performed by methods known in the art to add a 5' cap to the 5' end of the primary construct. Methods for capping include, but are not limited to, using a Vaccinia Capping enzyme (New England Biolabs, Ipswich, Mass.) or capping at initiation of in vitro transcription, by for example, including a capping agent as part of the IVT reaction. (Nuc. Acids Symp. (2009) 53:129). A poly(A) tailing reaction may be performed by methods known in the art, such as, but not limited to, 2' O-methyltransferase and by methods as described herein. If the primary construct generated from cDNA does not include a poly-T, it may be beneficial to perform the poly(A)-tailing reaction before the primary construct is cleaned.

The present disclosure also provides expression vectors comprising a nucleotide sequence encoding a self-replicating RNA that is preferably operably linked to at least one regulatory sequence. Regulatory sequences are art-recognized and are selected to direct expression of the encoded polypeptide.

Accordingly, the term regulatory sequence includes promoters, enhancers, and other expression control elements. The design of the expression vector may depend on such factors as the choice of the host cell to be transformed and/or the type of protein desired to be expressed.

The present disclosure also provides polynucleotides (e.g. DNA, RNA, cDNA, mRNA, etc.) directed to a self-replicating RNA of the disclosure that may be operably linked to one or more regulatory nucleotide sequences in an expression construct, such as a vector or plasmid. In certain embodiments, such constructs are DNA constructs. Regulatory nucleotide sequences will generally be appropriate for a host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the embodiments of the present disclosure. The promoters may be either naturally occurring promoters, or hybrid promoters that combine elements of more than one promoter.

An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

The present disclosure also provides a host cell transfected with a self-replicating RNA or DNA described herein. The host cell may be any prokaryotic or eukaryotic cell. For example, a polypeptide encoded by a self-replicating RNA may be expressed in bacterial cells such as *E. coli*, insect cells (e.g., using a baculovirus expression system), yeast, or mammalian cells. Other suitable host cells are known to those skilled in the art.

The present disclosure also provides a host cell comprising a vector comprising a polynucleotide which encodes a self-replicating RNA sequence provided herein.

A host cell transfected with an expression vector comprising a self-replicating RNA of the disclosure can be cultured under appropriate conditions to allow expression of the amplification of the self-replicating RNA and translation of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art.

The expressed proteins described herein can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptide.

Compositions and Pharmaceutical Compositions

Provided herein, in some embodiments, are compositions comprising any of the nucleic acid molecules provided herein. Compositions provided herein can include a lipid. Any lipid can be included in compositions provided herein. In one aspect, the lipid is an ionizable cationic lipid. Any ionizable cationic lipid can be included in compositions comprising nucleic acid molecules provided herein.

Also provided herein, in some embodiments, are pharmaceutical compositions comprising any of the nucleic acid molecules provided herein and a lipid formulation. Any lipid can be included in lipid formulations of pharmaceutical compositions provided herein. In one aspect, lipid formulations of pharmaceutical compositions provided herein include an ionizable cationic lipid. Exemplary ionizable cationic lipids of compositions and pharmaceutical compositions provided herein include the following:

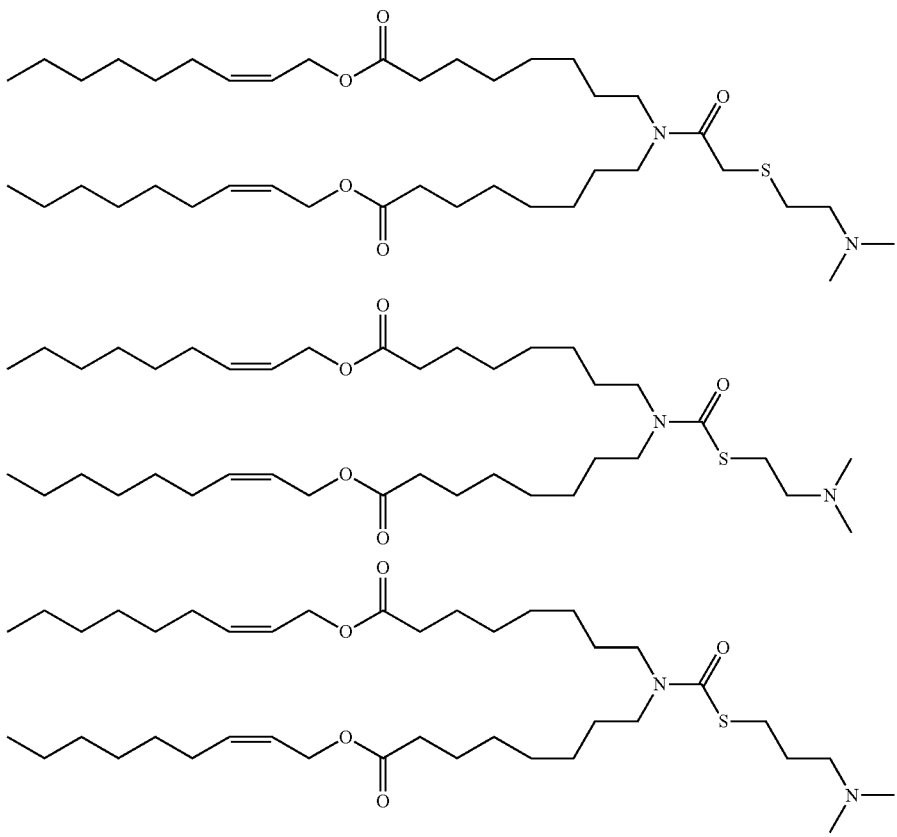

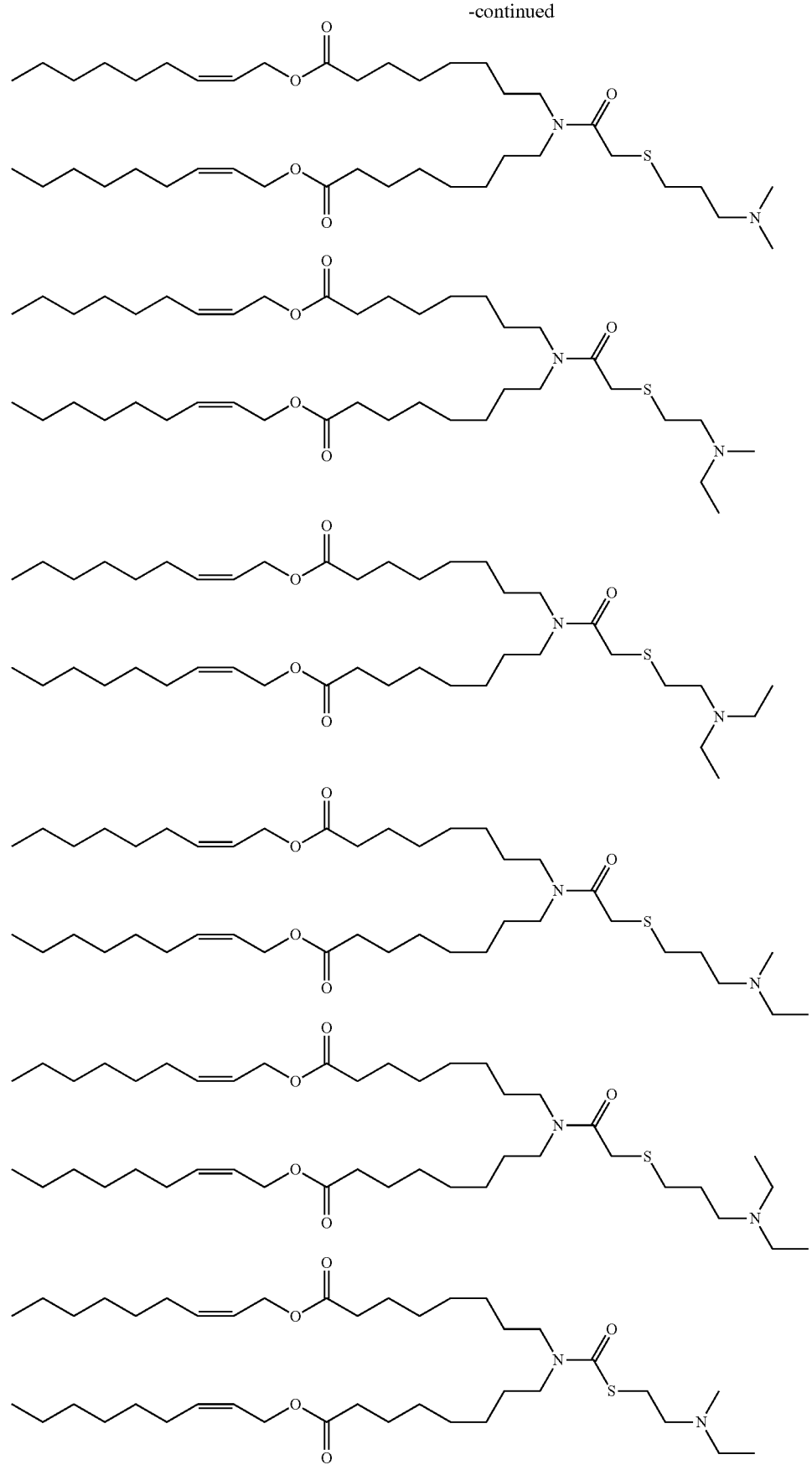

-continued
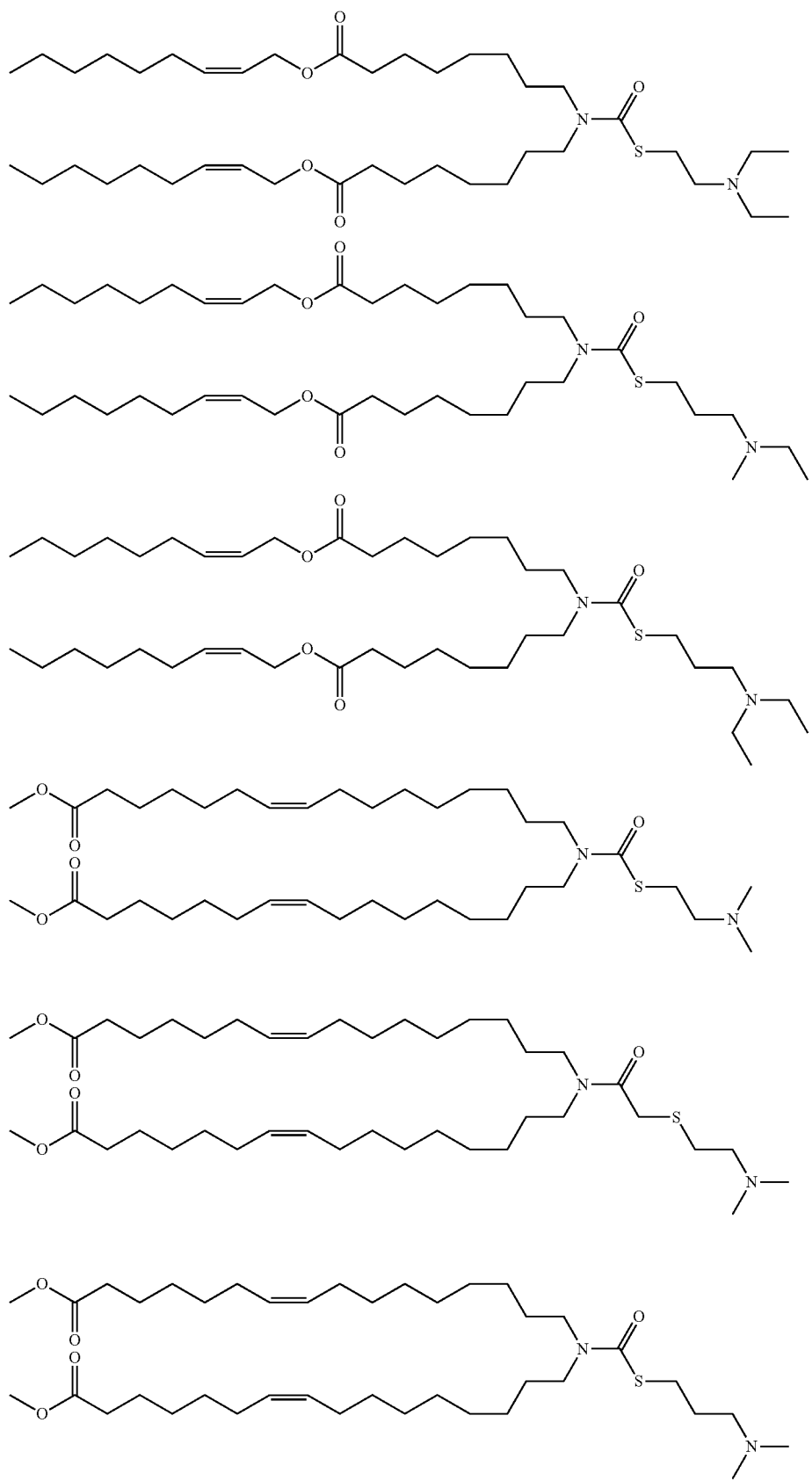

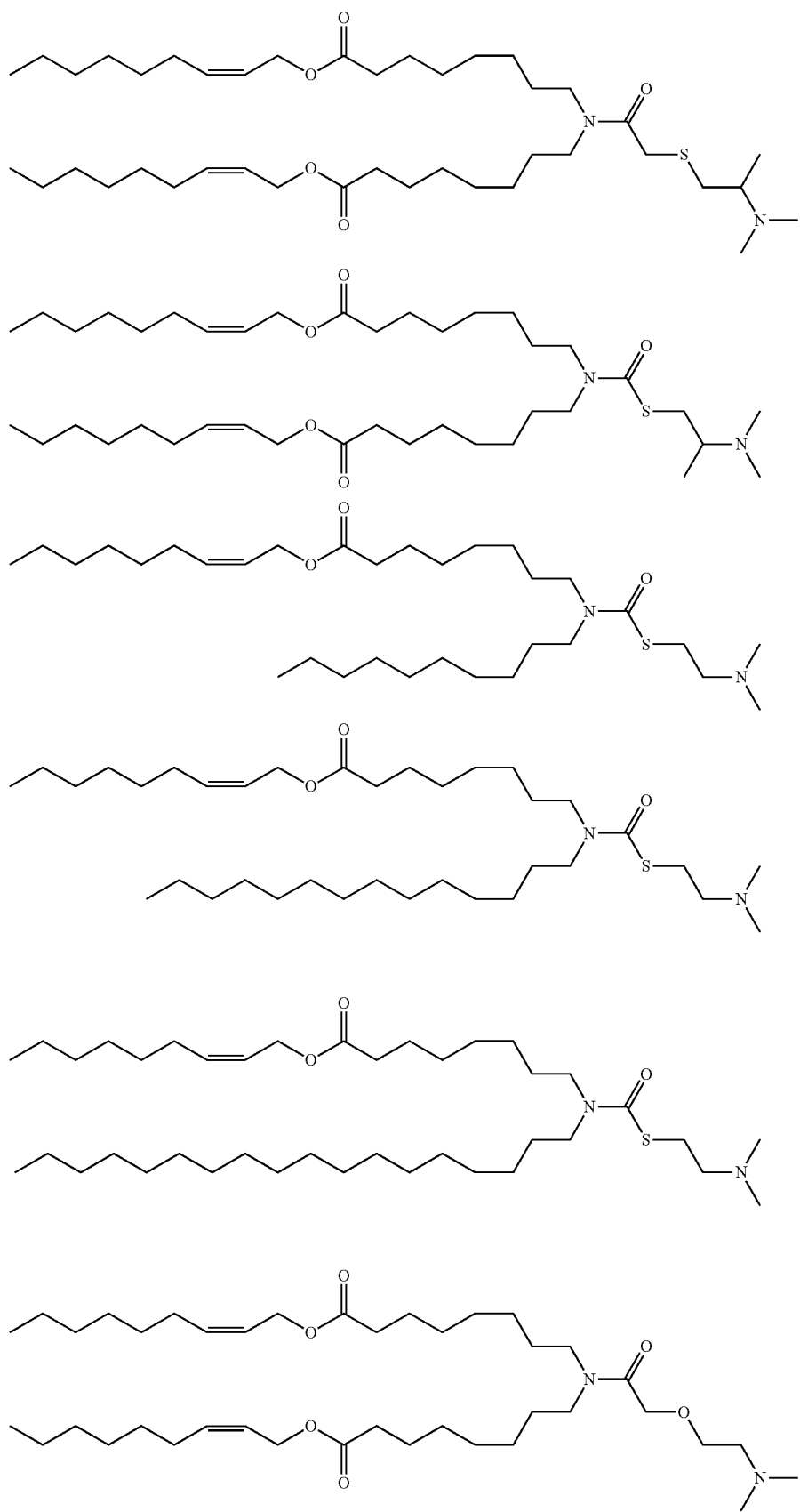

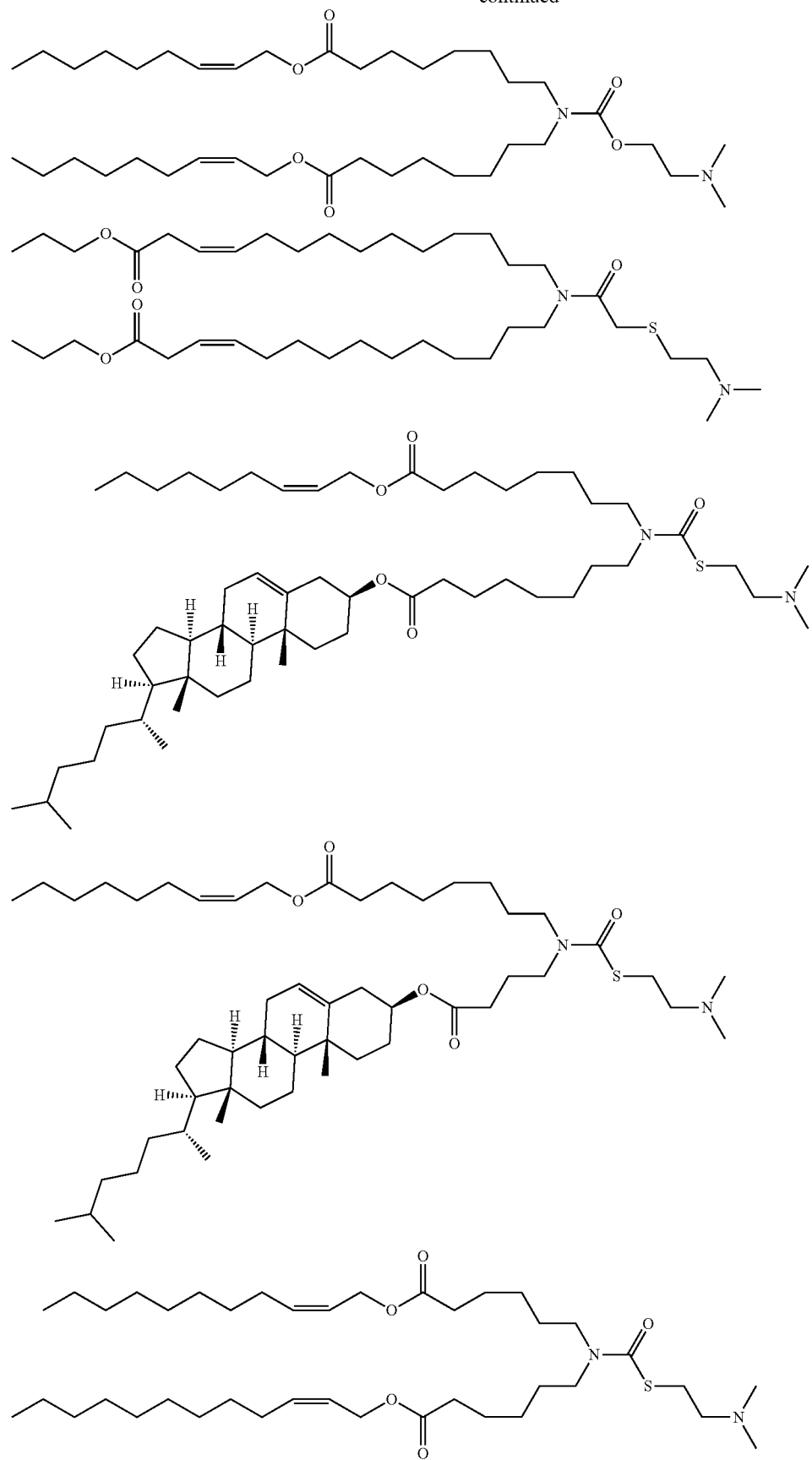

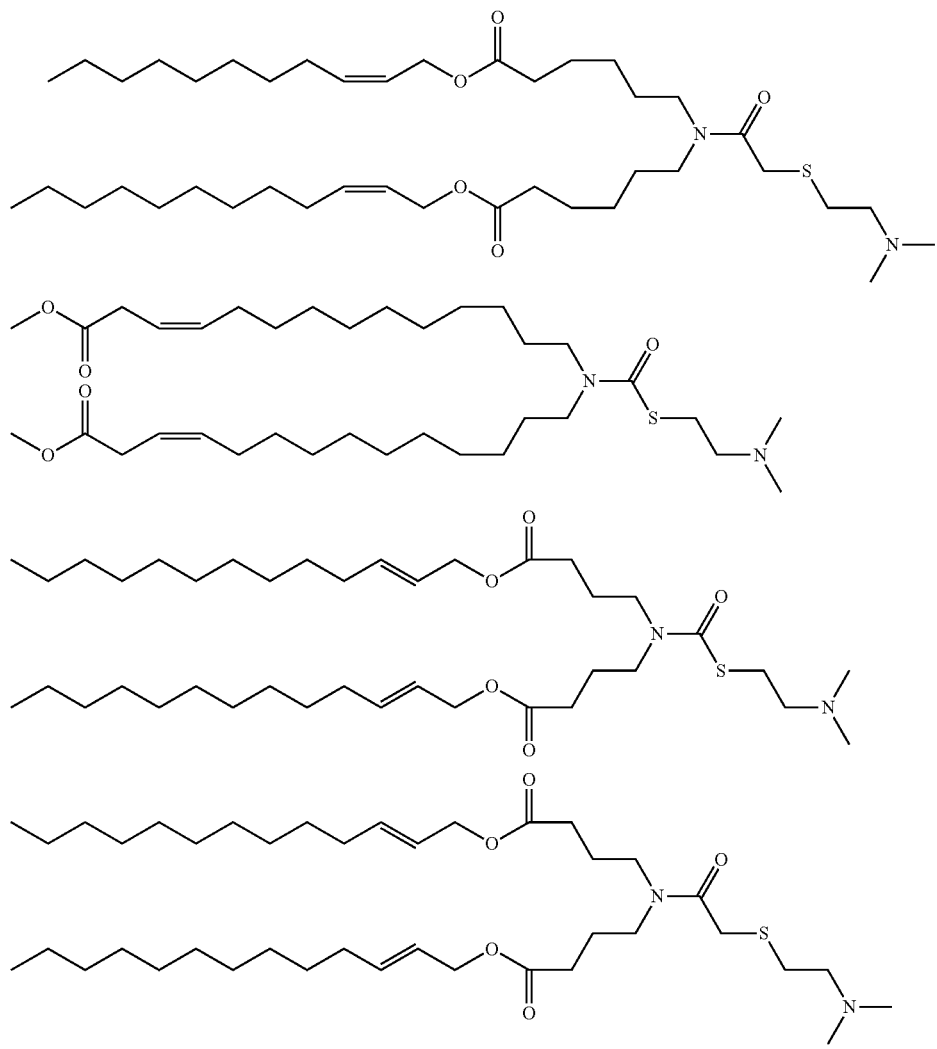
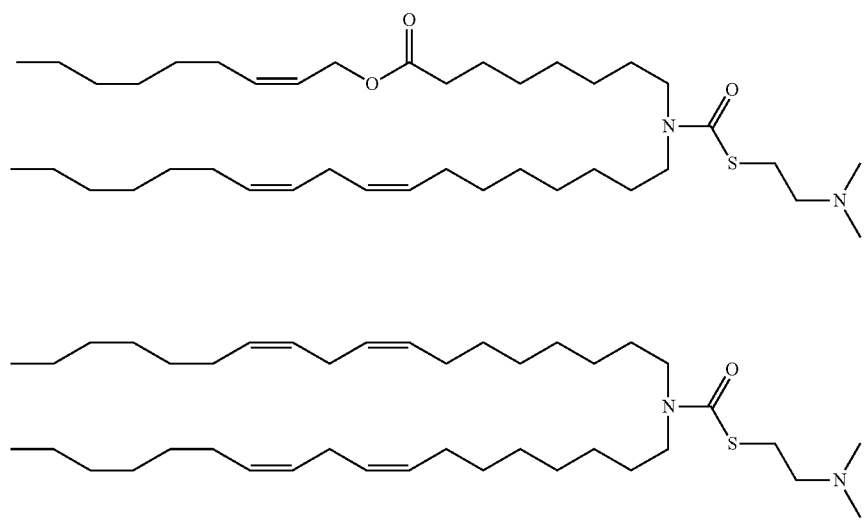

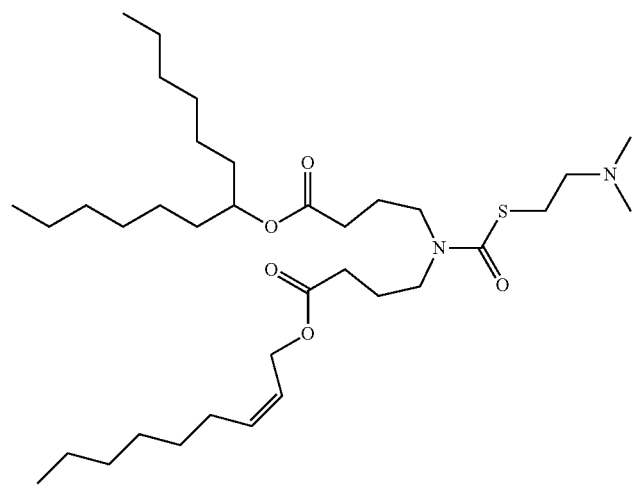
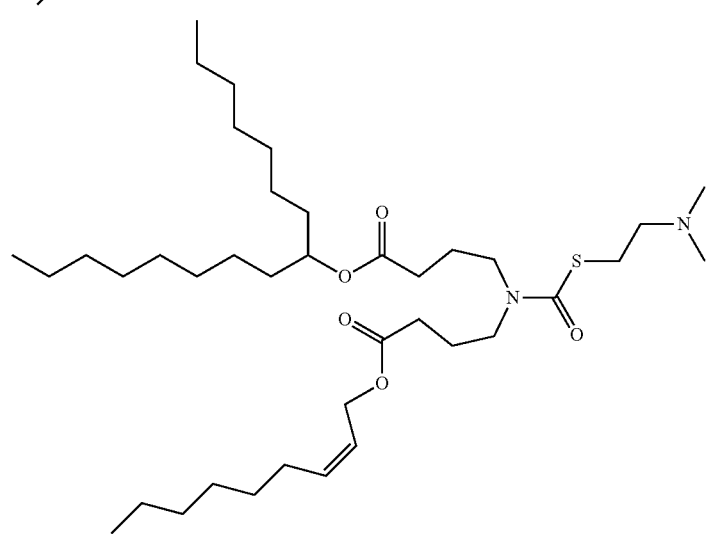
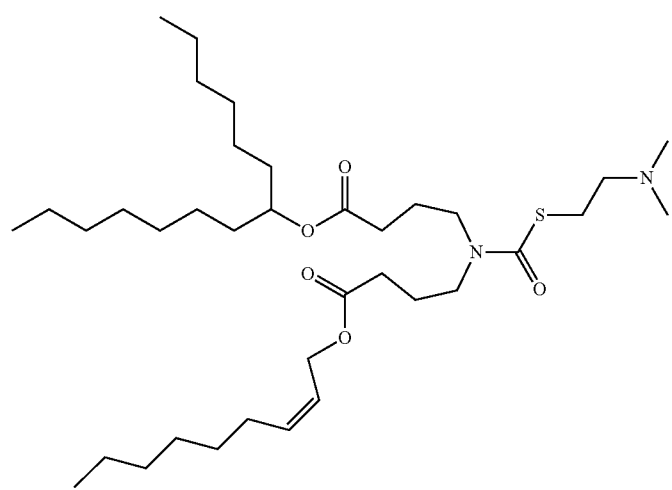

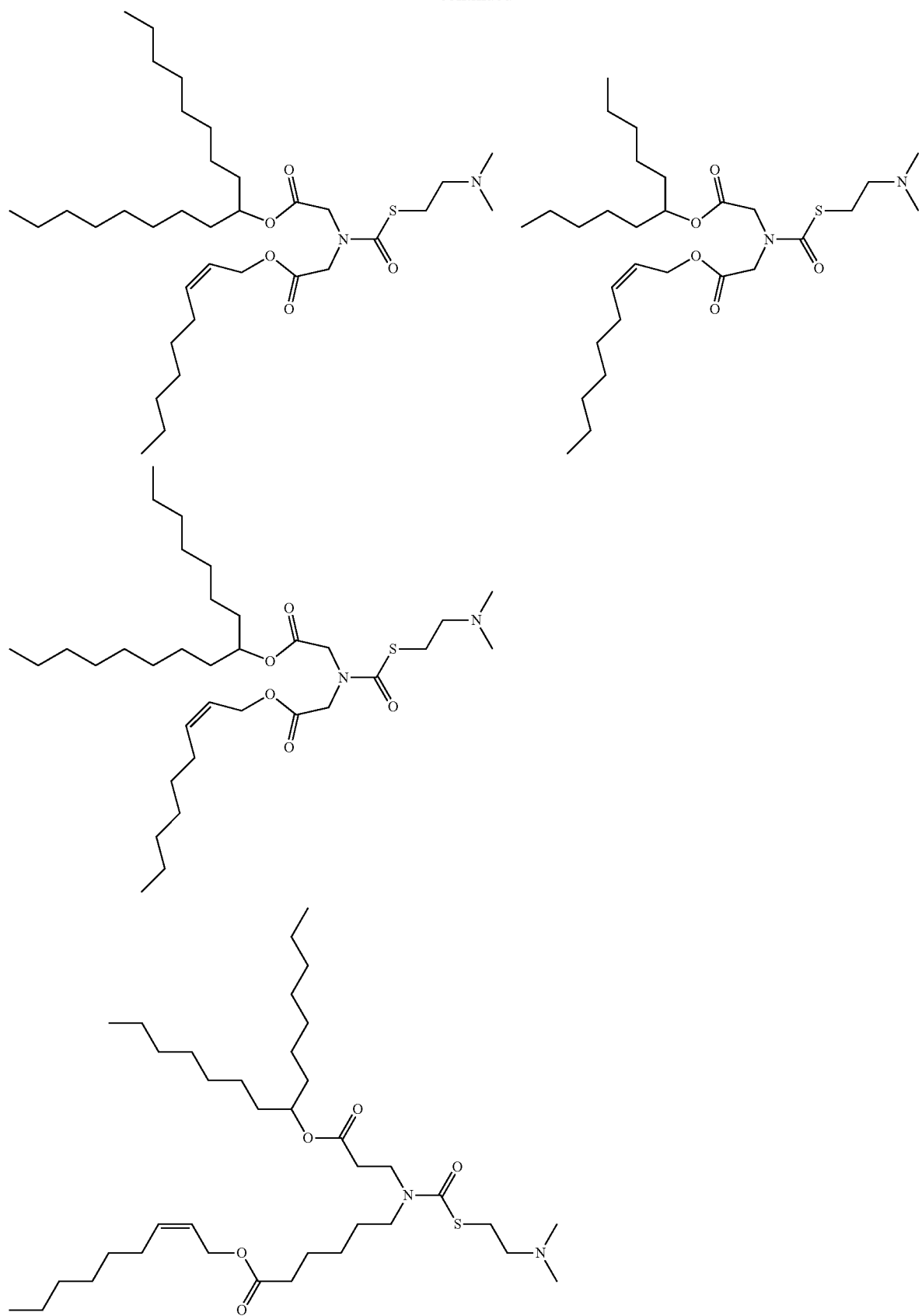

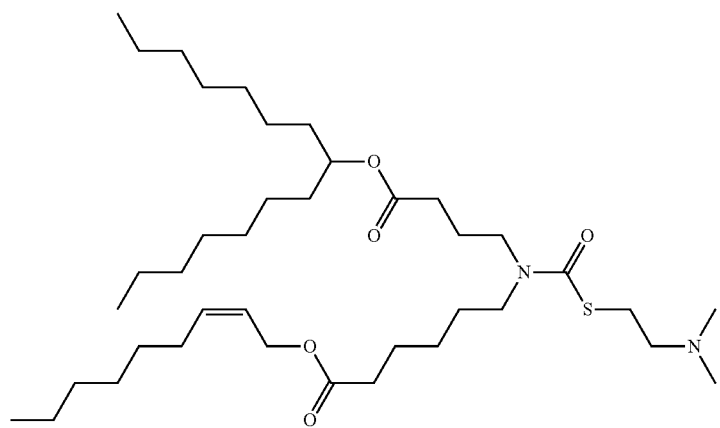
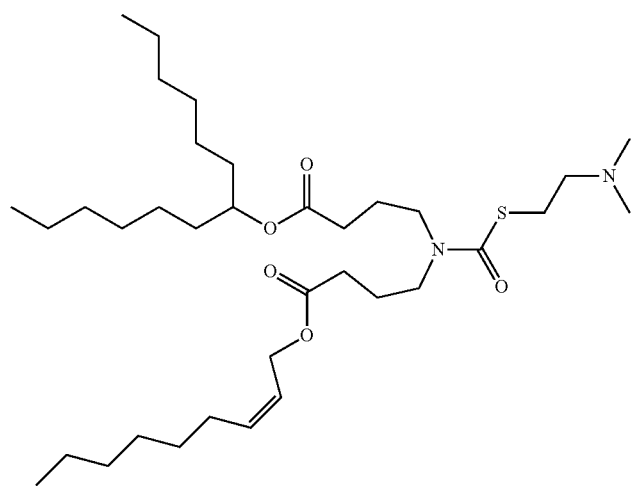
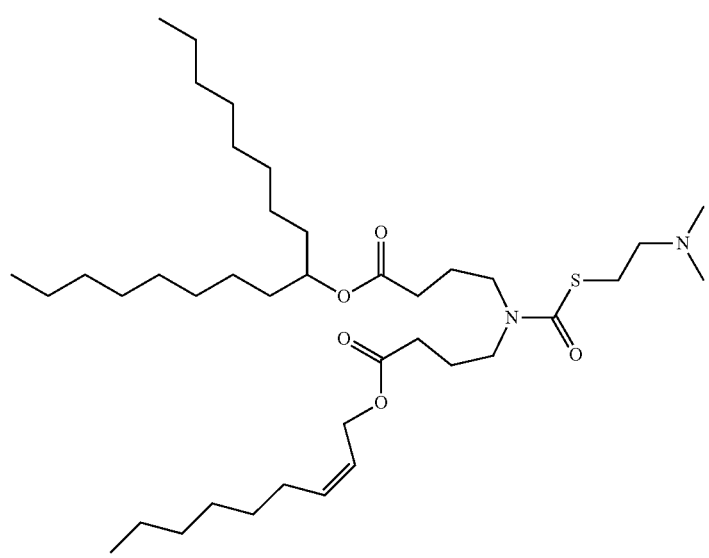

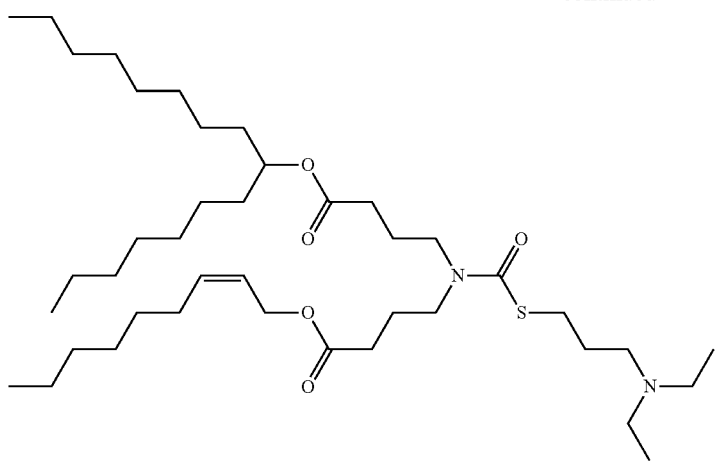
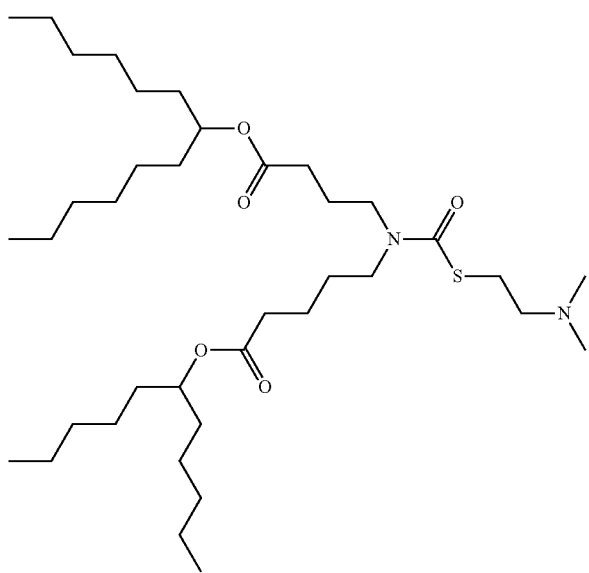
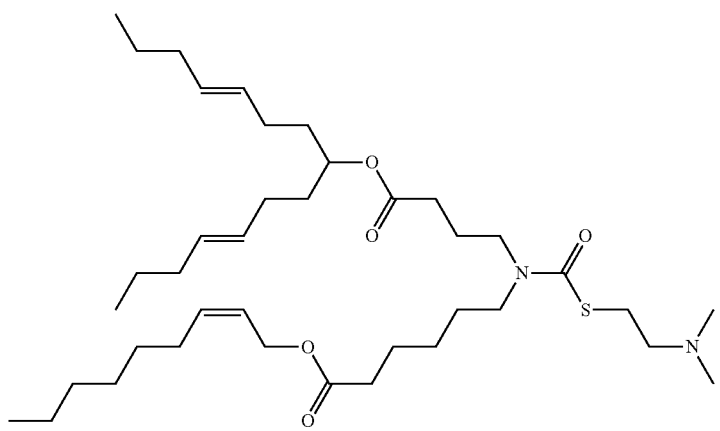

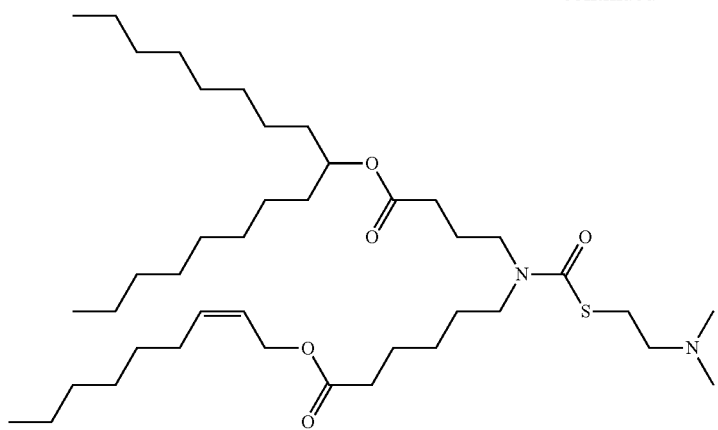
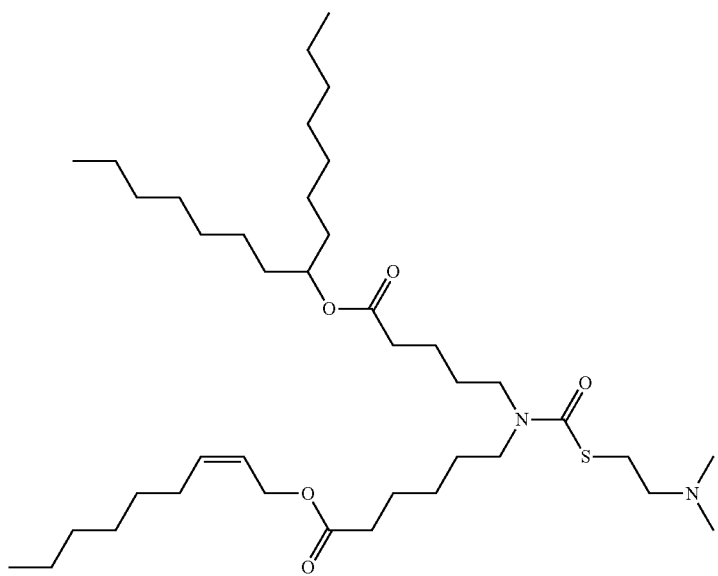
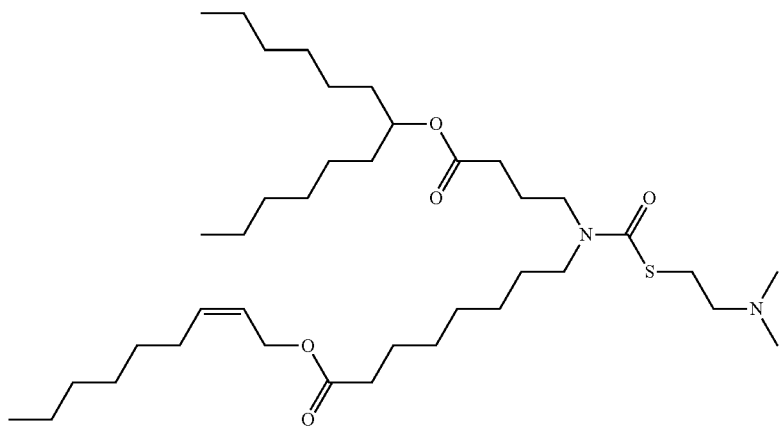

-continued
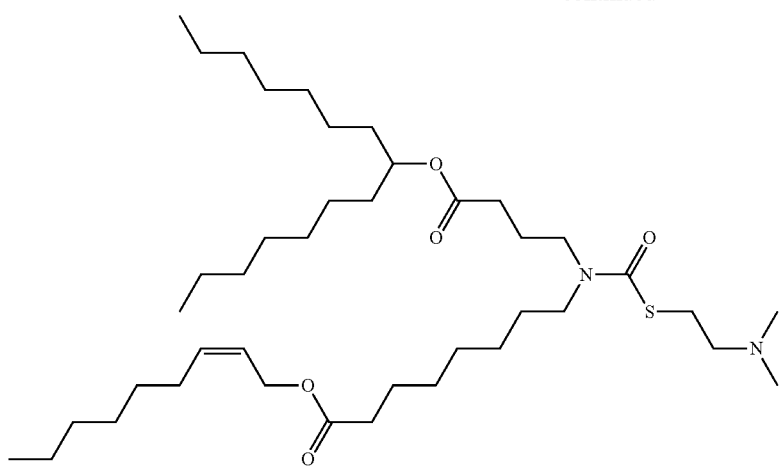
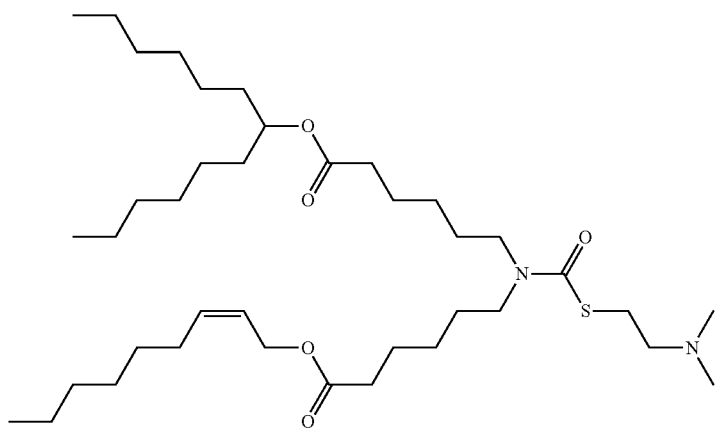
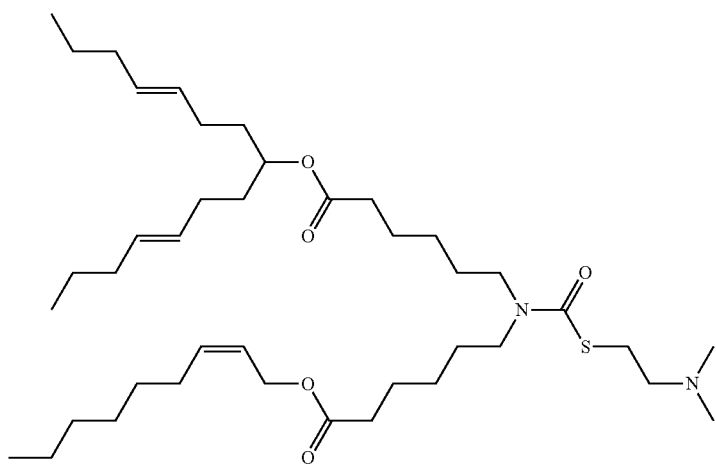

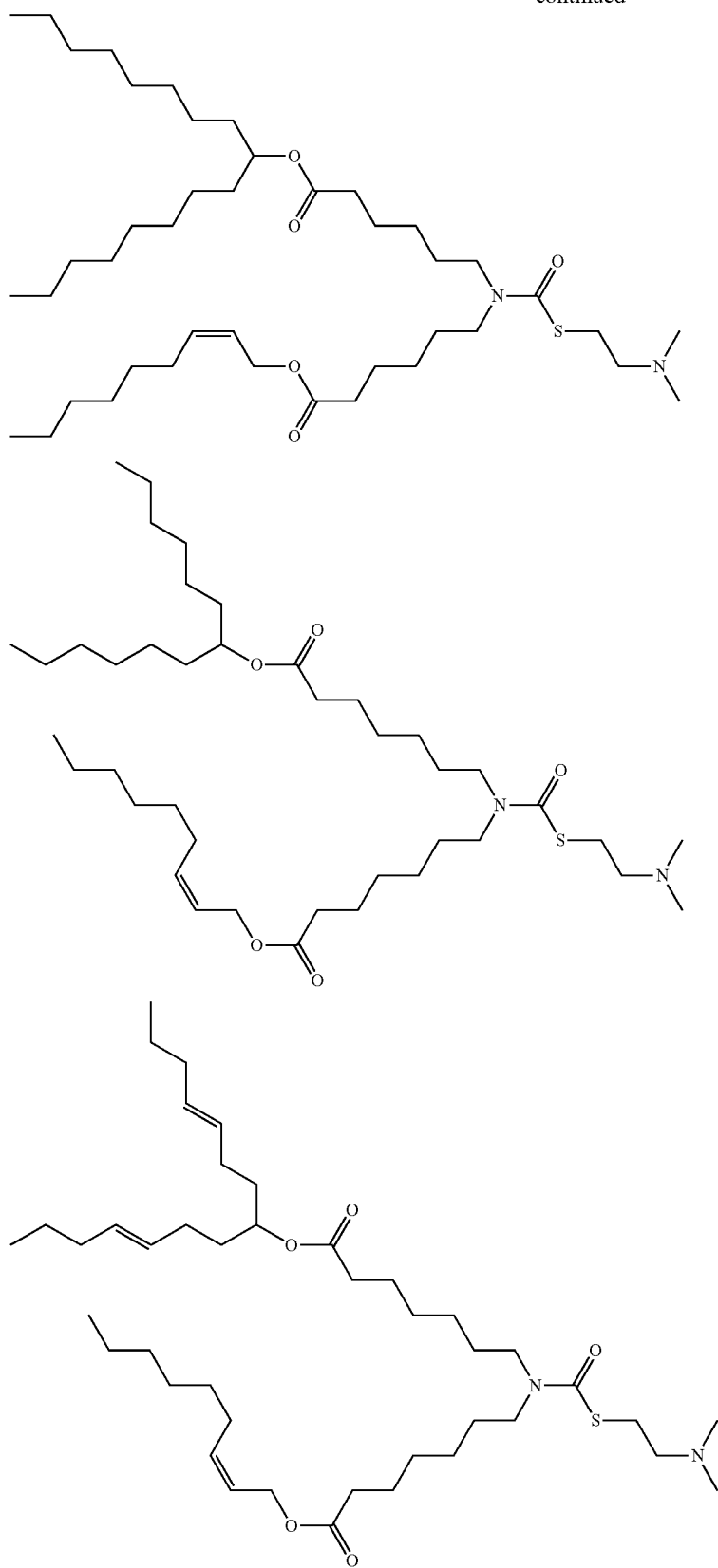

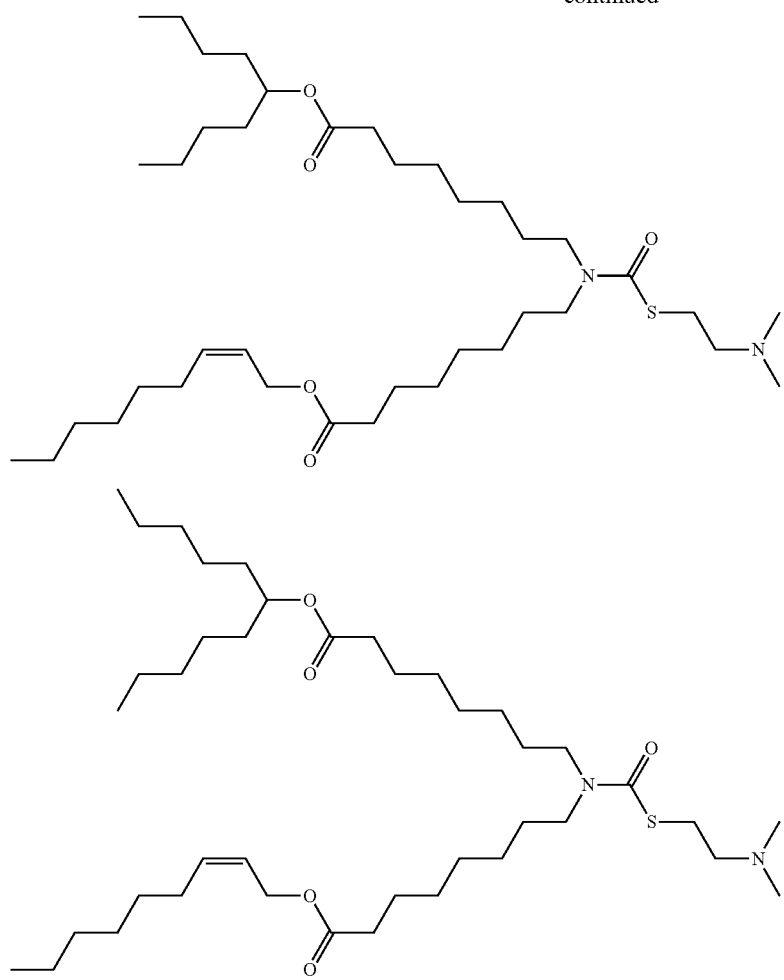
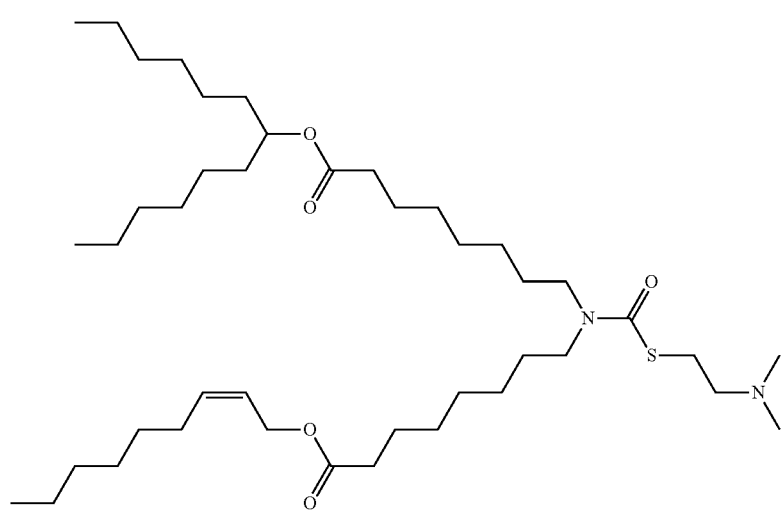

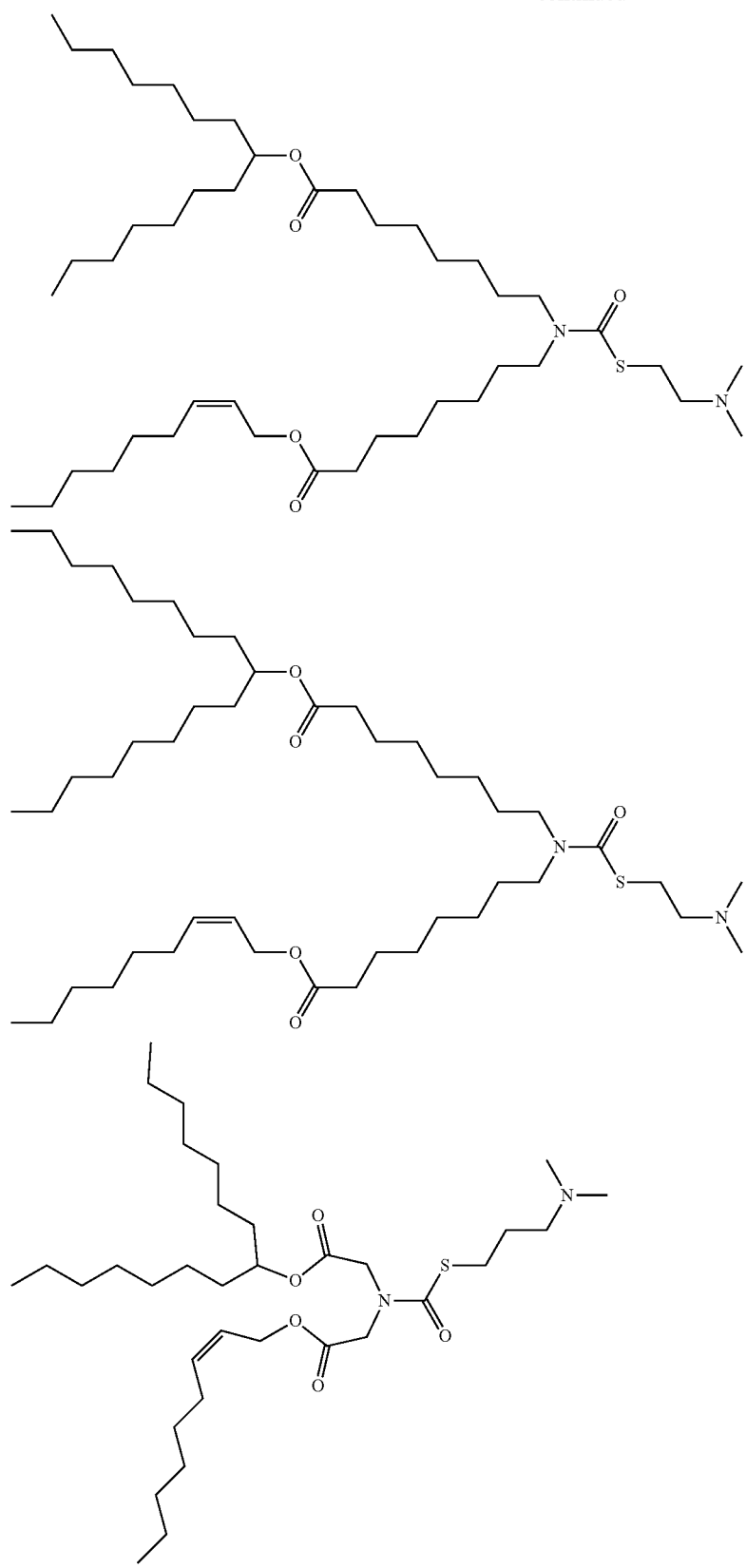

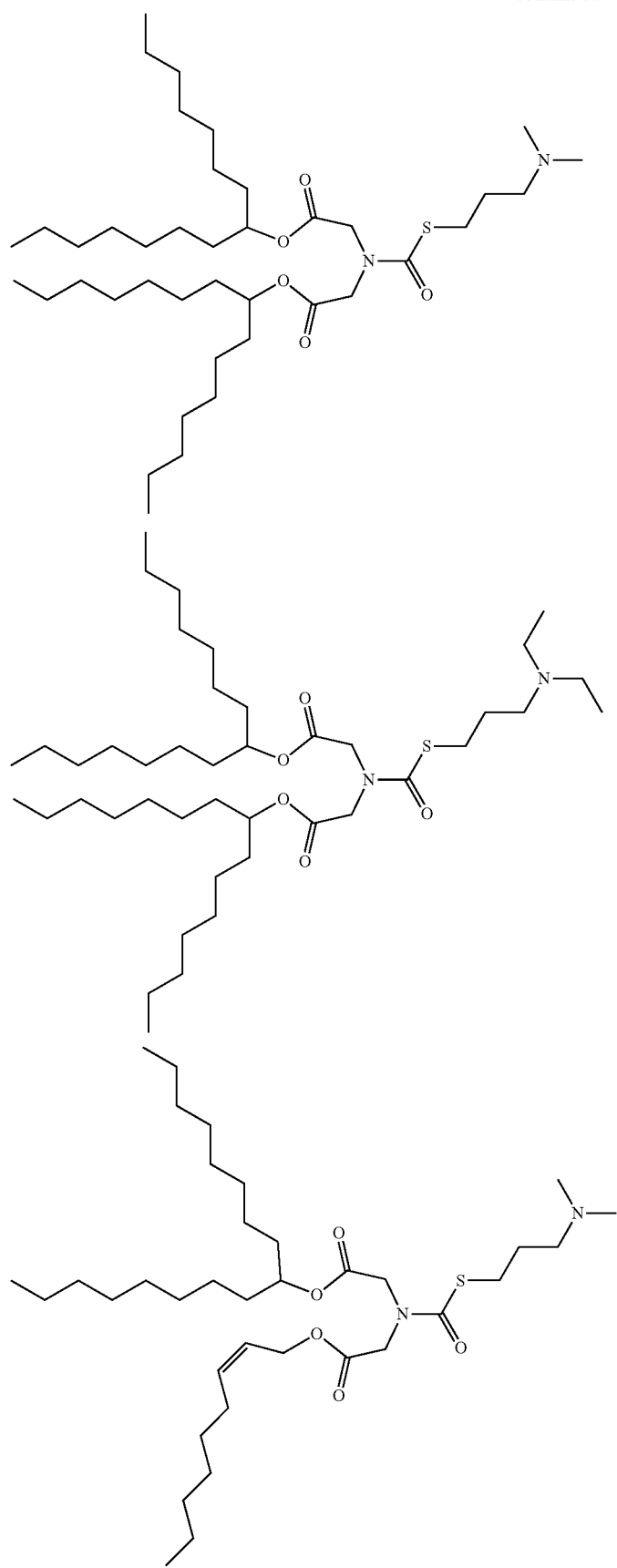

-continued
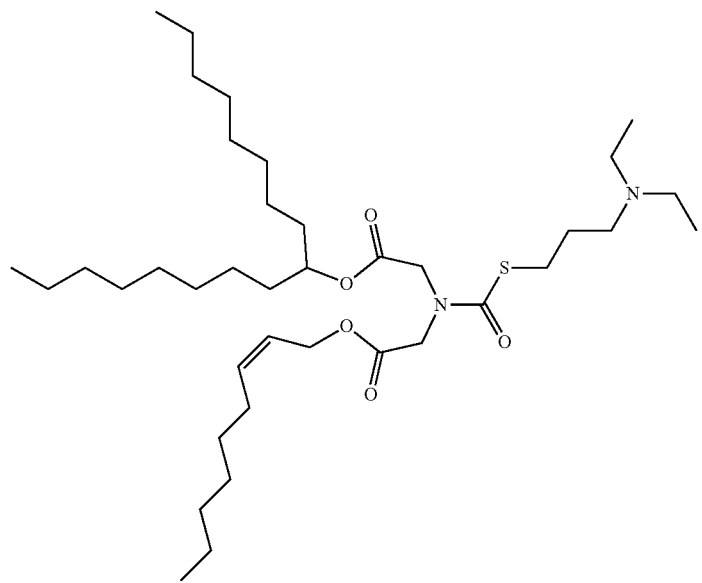
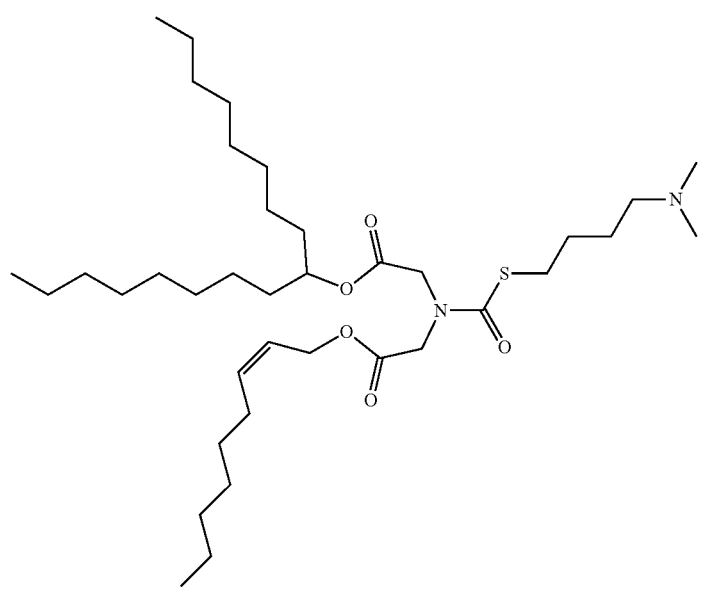

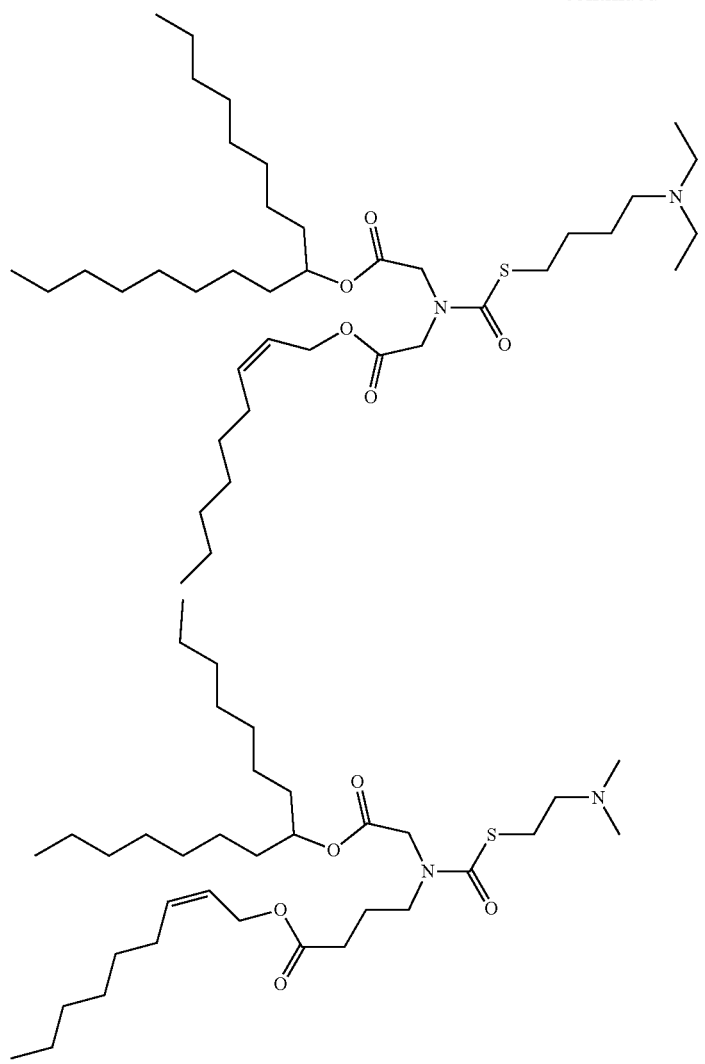
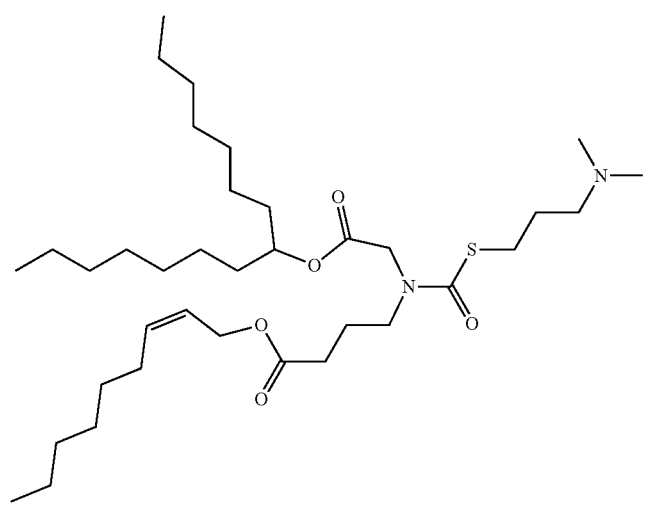

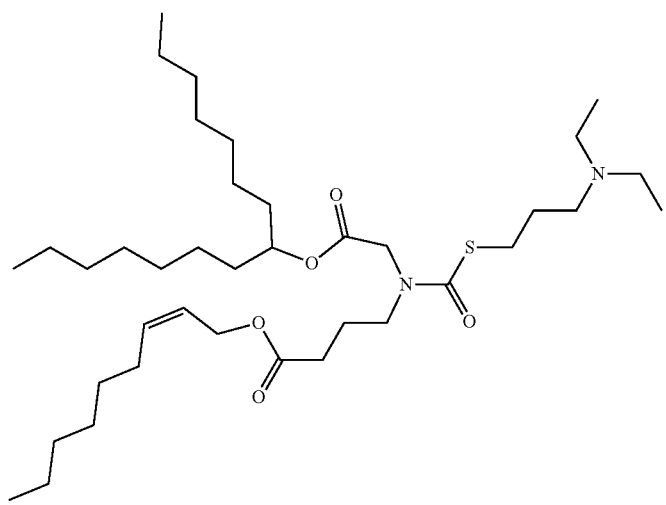
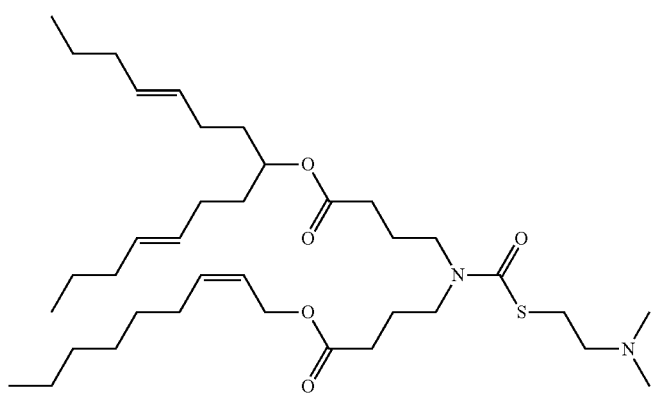
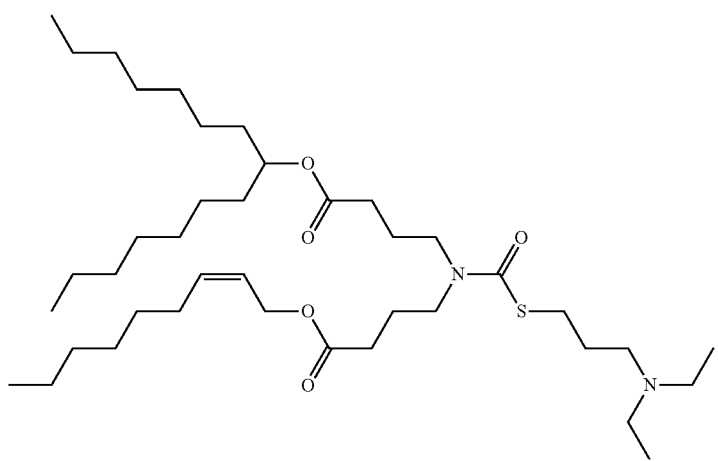

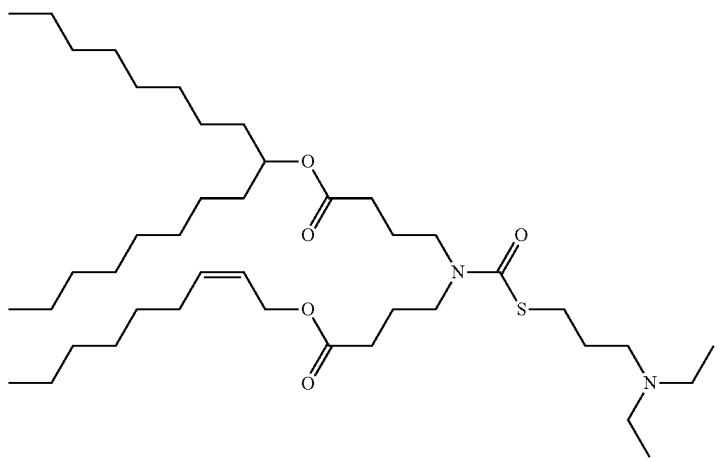
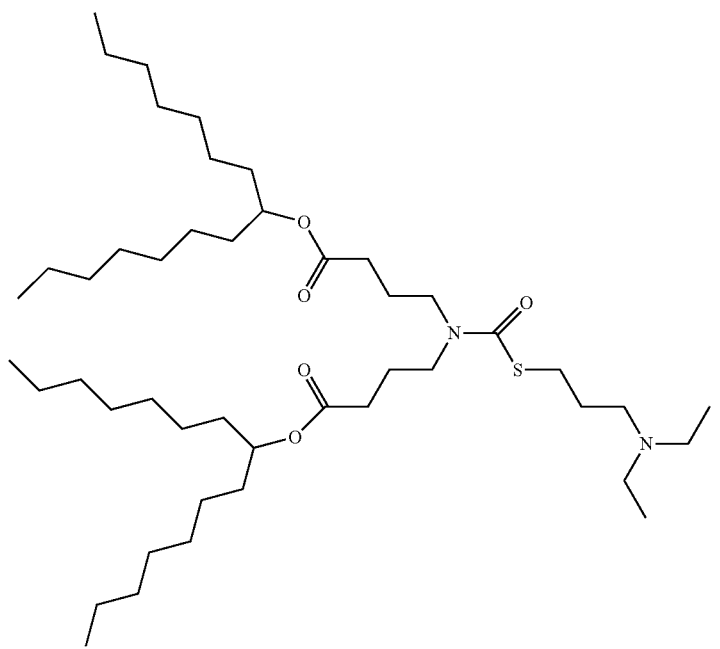
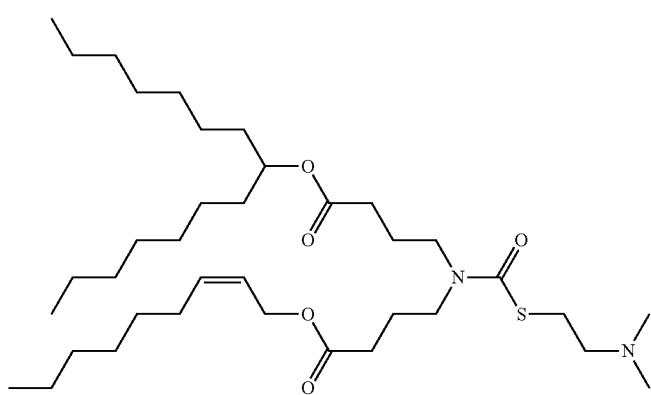

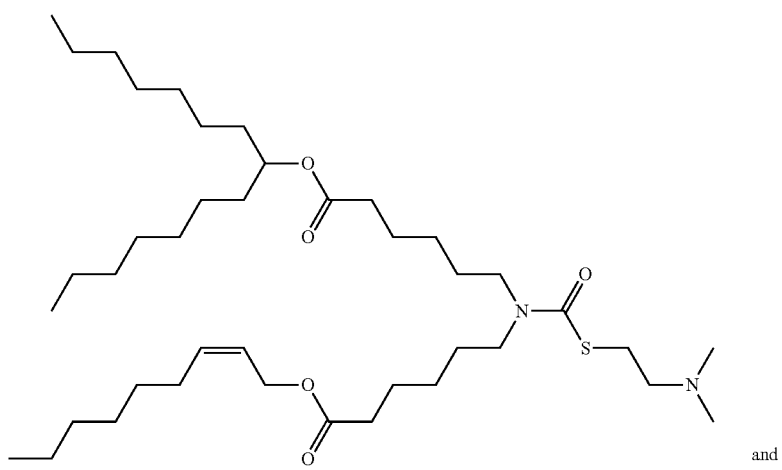
and
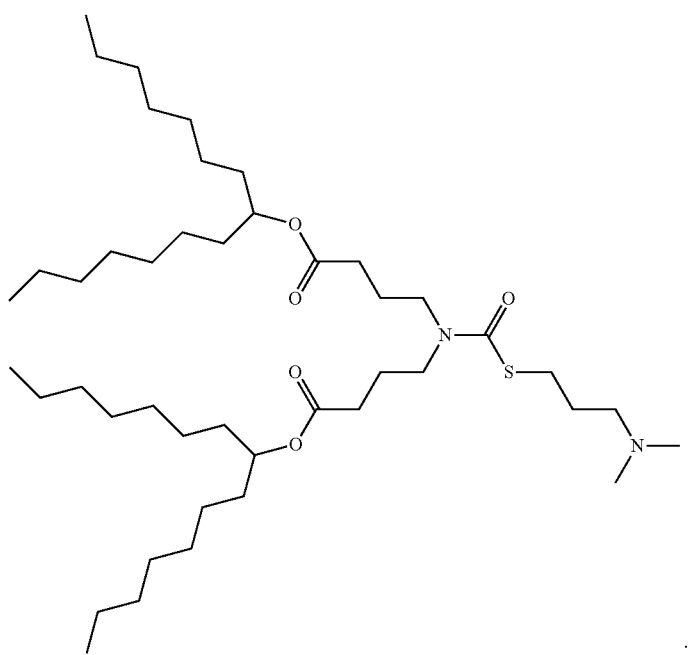 [SMILES: CCCCCCCC(CCCCCCC)OC(=O)CCCN(CCCC(=O)OC(CCCCCCC)CCCCCCC)C(=O)SCCCN(C)C]

In one aspect, the ionizable cationic lipid of compositions provided herein has a structure of

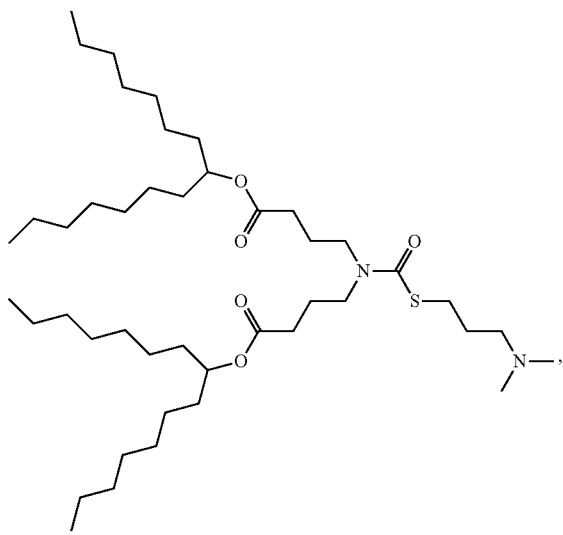 [SMILES: CCCCCCCC(CCCCCCC)OC(=O)CCCN(CCCC(=O)OC(CCCCCCC)CCCCCCC)C(=O)SCCCN(C)C]

or a pharmaceutically acceptable salt thereof.

In another aspect, the ionizable cationic lipid of compositions provided herein has a structure of

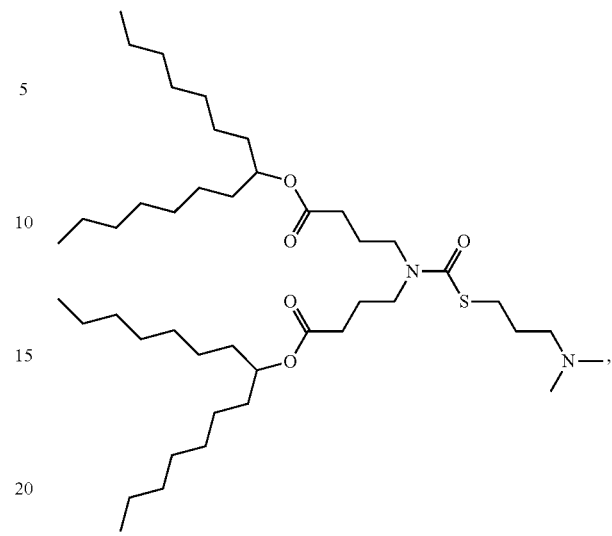

or a pharmaceutically acceptable salt thereof.

In one aspect, the ionizable cationic lipid included in lipid formulations of pharmaceutical compositions provided herein has a structure of

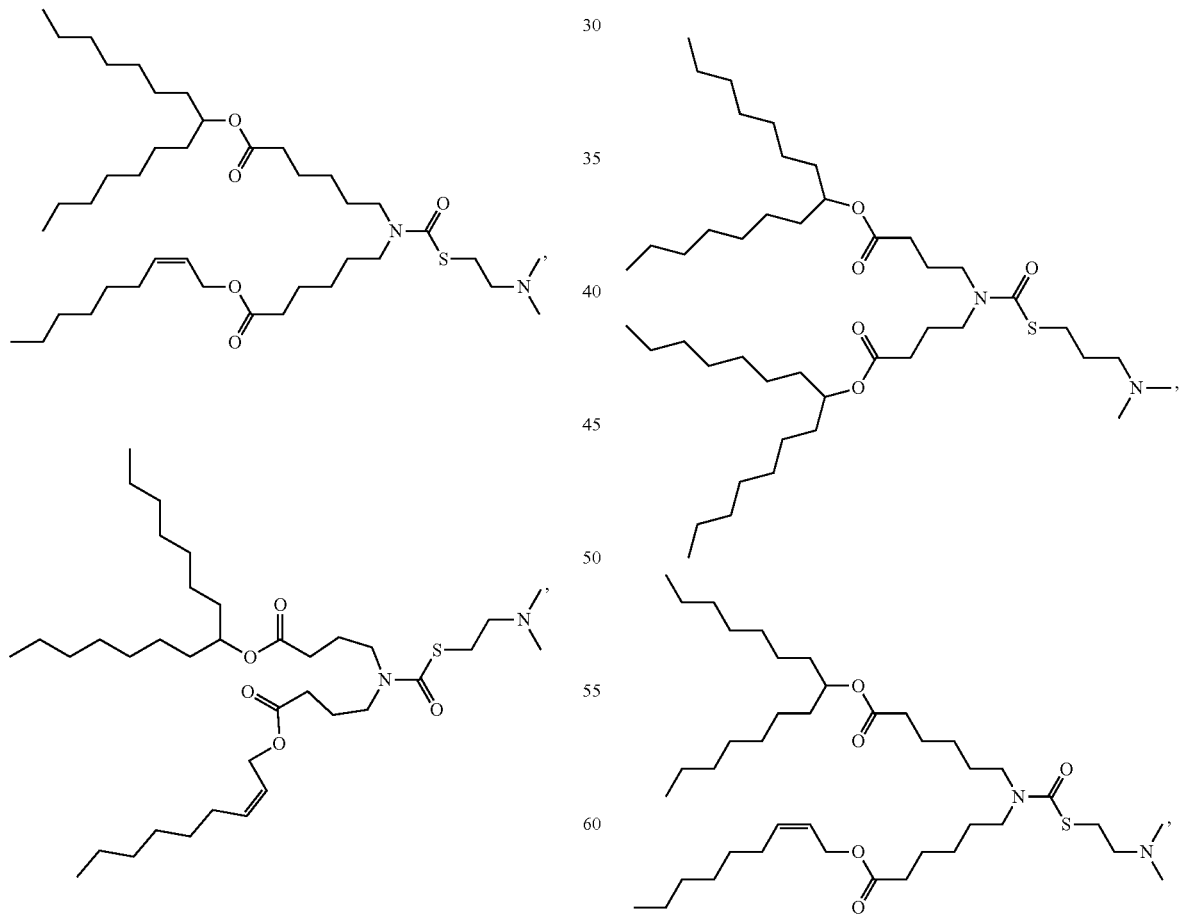

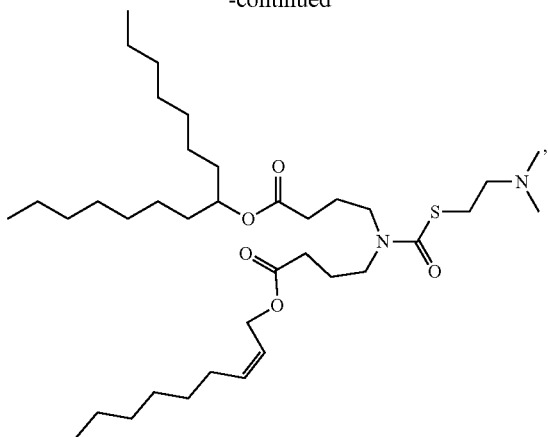

or a pharmaceutically acceptable salt thereof.

In another aspect, the ionizable cationic lipid included in lipid formulations of pharmaceutical compositions provided herein has a structure of

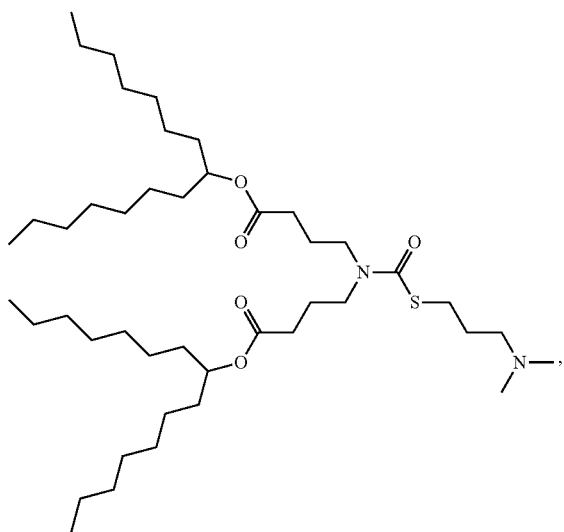

or a pharmaceutically acceptable salt thereof.

Lipid Formulations/LNPs

Therapies based on the intracellular delivery of nucleic acids to target cells face both extracellular and intracellular barriers. Indeed, naked nucleic acid materials cannot be easily systemically administered due to their toxicity, low stability in serum, rapid renal clearance, reduced uptake by target cells, phagocyte uptake and their ability in activating the immune response, all features that preclude their clinical development. When exogenous nucleic acid material (e.g., mRNA) enters the human biological system, it is recognized by the reticuloendothelial system (RES) as foreign pathogens and cleared from blood circulation before having the chance to encounter target cells within or outside the vascular system. It has been reported that the half-life of naked nucleic acid in the blood stream is around several minutes (Kawabata K, Takakura Y, Hashida M Pharm Res. 1995 June; 12(6):825-30). Chemical modification and a proper delivery method can reduce uptake by the RES and protect nucleic acids from degradation by ubiquitous nucleases, which increase stability and efficacy of nucleic acid-based therapies. In addition, RNAs or DNAs are anionic hydrophilic polymers that are not favorable for uptake by cells, which are also anionic at the surface. The success of nucleic acid-based therapies thus depends largely on the development of vehicles or vectors that can efficiently and effectively deliver genetic material to target cells and obtain sufficient levels of expression in vivo with minimal toxicity.

Moreover, upon internalization into a target cell, nucleic acid delivery vectors are challenged by intracellular barriers, including endosome entrapment, lysosomal degradation, nucleic acid unpacking from vectors, translocation across the nuclear membrane (for DNA), release at the cytoplasm (for RNA), and so on. Successful nucleic acid-based therapy thus depends upon the ability of the vector to deliver the nucleic acids to the target sites inside of the cells in order to obtain sufficient levels of a desired activity such as expression of a gene.

While several gene therapies have been able to successfully utilize a viral delivery vector (e.g., AAV), lipid-based formulations have been increasingly recognized as one of the most promising delivery systems for RNA and other nucleic acid compounds due to their biocompatibility and their ease of large-scale production. One of the most significant advances in lipid-based nucleic acid therapies happened in August 2018 when Patisiran (ALN-TTR02) was the first siRNA therapeutic approved by the Food and Drug Administration (FDA) and by the European Commission (EC). ALN-TTR02 is an siRNA formulation based upon the so-called Stable Nucleic Acid Lipid Particle (SNALP) transfecting technology. Despite the success of Patisiran, the delivery of nucleic acid therapeutics, including mRNA, via lipid formulations is still under ongoing development.

Some art-recognized lipid-formulated delivery vehicles for nucleic acid therapeutics include, according to various embodiments, polymer based carriers, such as polyethyleneimine (PEI), lipid nanoparticles and liposomes, nanoliposomes, ceramide-containing nanoliposomes, multivesicular liposomes, proteoliposomes, both natural and synthetically-derived exosomes, natural, synthetic and semi-synthetic lamellar bodies, nanoparticulates, micelles, and emulsions. These lipid formulations can vary in their structure and composition, and as can be expected in a rapidly evolving field, several different terms have been used in the art to describe a single type of delivery vehicle. At the same time, the terms for lipid formulations have varied as to their intended meaning throughout the scientific literature, and this inconsistent use has caused confusion as to the exact meaning of several terms for lipid formulations. Among the several potential lipid formulations, liposomes, cationic liposomes, and lipid nanoparticles are specifically described in detail and defined herein for the purposes of the present disclosure.

Liposomes

Conventional liposomes are vesicles that consist of at least one bilayer and an internal aqueous compartment. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). They generally present as spherical vesicles and can range in size from 20 nm to a few microns. Liposomal formulations can be prepared as a colloidal dispersion or they can be lyophilized to reduce stability risks and to improve the shelf-life for liposome-based drugs. Methods of preparing liposomal compositions are known in the art and would be within the skill of an ordinary artisan.

Liposomes that have only one bilayer are referred to as being unilamellar, and those having more than one bilayer are referred to as multilamellar. The most common types of liposomes are small unilamellar vesicles (SUV), large unilamellar vesicle (LUV), and multilamellar vesicles (MLV). In contrast to liposomes, lysosomes, micelles, and reversed micelles are composed of monolayers of lipids. Generally, a liposome is thought of as having a single interior compartment, however some formulations can be multivesicular liposomes (MVL), which consist of numerous discontinuous internal aqueous compartments separated by several non-concentric lipid bilayers.

Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9:1833-1843). In their use as drug delivery vehicles, because a liposome has an aqueous solution core surrounded by a hydrophobic membrane, hydrophilic solutes dissolved in the core cannot readily pass through the bilayer, and hydrophobic compounds will associate with the bilayer. Thus, a liposome can be loaded with hydrophobic and/or hydrophilic molecules. When a liposome is used to carry a nucleic acid such as RNA, the nucleic acid will be contained within the liposomal compartment in an aqueous phase.

Cationic Liposomes

Liposomes can be composed of cationic, anionic, and/or neutral lipids. As an important subclass of liposomes, cationic liposomes are liposomes that are made in whole or part from positively charged lipids, or more specifically a lipid that comprises both a cationic group and a lipophilic portion. In addition to the general characteristics profiled above for liposomes, the positively charged moieties of cationic lipids used in cationic liposomes provide several advantages and some unique structural features. For example, the lipophilic portion of the cationic lipid is hydrophobic and thus will direct itself away from the aqueous interior of the liposome and associate with other nonpolar and hydrophobic species. Conversely, the cationic moiety will associate with aqueous media and more importantly with polar molecules and species with which it can complex in the aqueous interior of the cationic liposome. For these reasons, cationic liposomes are increasingly being researched for use in gene therapy due to their favorability towards negatively charged nucleic acids via electrostatic interactions, resulting in complexes that offer biocompatibility, low toxicity, and the possibility of the large-scale production required for in vivo clinical applications. Cationic lipids suitable for use in cationic liposomes are listed herein below.

Lipid Nanoparticles

In contrast to liposomes and cationic liposomes, lipid nanoparticles (LNP) have a structure that includes a single monolayer or bilayer of lipids that encapsulates a compound in a solid phase. Thus, unlike liposomes, lipid nanoparticles do not have an aqueous phase or other liquid phase in its interior, but rather the lipids from the bilayer or monolayer shell are directly complexed to the internal compound thereby encapsulating it in a solid core. Lipid nanoparticles are typically spherical vesicles having a relatively uniform dispersion of shape and size. While sources vary on what size qualifies a lipid particle as being a nanoparticle, there is some overlap in agreement that a lipid nanoparticle can have a diameter in the range of from 10 nm to 1000 nm. However, more commonly they are considered to be smaller than 120 nm or even 100 nm.

For lipid nanoparticle nucleic acid delivery systems, the lipid shell is formulated to include an ionizable cationic lipid which can complex to and associate with the negatively charged backbone of the nucleic acid core. Ionizable cationic lipids with apparent pKa values below about 7 have the benefit of providing a cationic lipid for complexing with the nucleic acid's negatively charged backbone and loading into the lipid nanoparticle at pH values below the pKa of the ionizable lipid where it is positively charged. Then, at physiological pH values, the lipid nanoparticle can adopt a relatively neutral exterior allowing for a significant increase in the circulation half-lives of the particles following i.v. administration. In the context of nucleic acid delivery, lipid nanoparticles offer many advantages over other lipid-based nucleic acid delivery systems including high nucleic acid encapsulation efficiency, potent transfection, improved penetration into tissues to deliver therapeutics, and low levels of cytotoxicity and immunogenicity.

Prior to the development of lipid nanoparticle delivery systems for nucleic acids, cationic lipids were widely studied as synthetic materials for delivery of nucleic acid medicines. In these early efforts, after mixing together at physiological pH, nucleic acids were condensed by cationic lipids to form lipid-nucleic acid complexes known as lipoplexes. However, lipoplexes proved to be unstable and characterized by broad size distributions ranging from the submicron scale to a few microns. Lipoplexes, such as the Lipofectamine® reagent, have found considerable utility for in vitro transfection. However, these first-generation lipoplexes have not proven useful in vivo. The large particle size and positive charge (imparted by the cationic lipid) result in rapid plasma clearance, hemolytic and other toxicities, as well as immune system activation.

In some aspects, nucleic acid molecules provided herein and lipids or lipid formulations provided herein form a lipid nanoparticle (LNP).

In other aspects, nucleic acid molecules provided herein are incorporated into a lipid formulation (i.e., a lipid-based delivery vehicle).

In the context of the present disclosure, a lipid-based delivery vehicle typically serves to transport a desired RNA to a target cell or tissue. The lipid-based delivery vehicle can be any suitable lipid-based delivery vehicle known in the art. In some aspects, the lipid-based delivery vehicle is a liposome, a cationic liposome, or a lipid nanoparticle containing a self-replicating RNA of the disclosure. In some aspects, the lipid-based delivery vehicle comprises a nanoparticle or a bilayer of lipid molecules and a self-replicating RNA of the disclosure. In some aspects, the lipid bilayer further comprises a neutral lipid or a polymer. In some aspects, the lipid formulation comprises a liquid medium. In some aspects, the formulation further encapsulates a nucleic acid. In some aspects, the lipid formulation further comprises a nucleic acid and a neutral lipid or a polymer. In some aspects, the lipid formulation encapsulates the nucleic acid.

The description provides lipid formulations comprising one or more self-replicating RNA molecules encapsulated within the lipid formulation. In some aspects, the lipid formulation comprises liposomes. In some aspects, the lipid formulation comprises cationic liposomes. In some aspects, the lipid formulation comprises lipid nanoparticles.

In some aspects, the self-replicating RNA is fully encapsulated within the lipid portion of the lipid formulation such that the RNA in the lipid formulation is resistant in aqueous solution to nuclease degradation. In other aspects, the lipid formulations described herein are substantially non-toxic to animals such as humans and other mammals.

The lipid formulations of the disclosure also typically have a total lipid:RNA ratio (mass/mass ratio) of from about 1:1 to about 100:1, from about 1:1 to about 50:1, from about 2:1 to about 45:1, from about 3:1 to about 40:1, from about 5:1 to about 45:1, or from about 10:1 to about 40:1, or from about 15:1 to about 40:1, or from about 20:1 to about 40:1; or from about 25:1 to about 45:1; or from about 30:1 to about 45:1; or from about 32:1 to about 42:1; or from about 34:1 to about 42:1. In some aspects, the total lipid:RNA ratio (mass/mass ratio) is from about 30:1 to about 45:1. The ratio may be any value or subvalue within the recited ranges, including endpoints.

The lipid formulations of the present disclosure typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, or about 150 nm, and are substantially non-toxic. The diameter may be any value or subvalue within the recited ranges, including endpoints. In addition, nucleic acids, when present in the lipid nanoparticles of the present disclosure, generally are resistant in aqueous solution to degradation with a nuclease.

In some aspects, the lipid formulations comprise a self-replicating RNA, a cationic lipid (e.g., one or more cationic lipids or salts thereof described herein), a phospholipid, and a conjugated lipid that inhibits aggregation of the particles (e.g., one or more PEG-lipid conjugates). The lipid formulations can also include cholesterol. In one aspect, the cationic lipid is an ionizable cationic lipid.

In the nucleic acid-lipid formulations, the RNA may be fully encapsulated within the lipid portion of the formulation, thereby protecting the nucleic acid from nuclease degradation. In some aspects, a lipid formulation comprising an RNA is fully encapsulated within the lipid portion of the lipid formulation, thereby protecting the nucleic acid from nuclease degradation. In certain aspects, the RNA in the lipid formulation is not substantially degraded after exposure of the particle to a nuclease at 37° C. for at least 20, 30, 45, or 60 minutes. In certain other aspects, the RNA in the lipid formulation is not substantially degraded after incubation of the formulation in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In some aspects, the RNA is complexed with the lipid portion of the formulation. One of the benefits of the formulations of the present disclosure is that the nucleic acid-lipid compositions are substantially non-toxic to animals such as humans and other mammals.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a lipid formulation, measuring the resulting fluorescence, and comparing it to the fluorescence observed upon addition of a small amount of nonionic detergent. Detergent-mediated disruption of the lipid layer releases the encapsulated nucleic acid, allowing it to interact with the membrane-impermeable dye. Nucleic acid encapsulation may be calculated as $E=(I0-I)/I0$, where/and I0 refers to the fluorescence intensities before and after the addition of detergent.

In some aspects, the present disclosure provides a nucleic acid-lipid composition comprising a plurality of nucleic acid-liposomes, nucleic acid-cationic liposomes, or nucleic acid-lipid nanoparticles. In some aspects, the nucleic acid-lipid composition comprises a plurality of RNA-liposomes. In some aspects, the nucleic acid-lipid composition comprises a plurality of RNA-cationic liposomes. In some aspects, the nucleic acid-lipid composition comprises a plurality of RNA-lipid nanoparticles.

In some aspects, the lipid formulations comprise RNA that is fully encapsulated within the lipid portion of the formulation, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% (or any fraction thereof or range therein) of the particles have the RNA encapsulated therein. The amount may be any value or subvalue within the recited ranges, including endpoints. The RNA included in any RNA-lipid composition or RNA-lipid formulation provided herein can be a self-replicating RNA.

Depending on the intended use of the lipid formulation, the proportions of the components can be varied, and the delivery efficiency of a particular formulation can be measured using assays known in the art.

In some aspects, nucleic acid molecules provided herein are lipid formulated. The lipid formulation is preferably selected from, but not limited to, liposomes, cationic liposomes, and lipid nanoparticles. In one aspect, a lipid formulation is a cationic liposome or a lipid nanoparticle (LNP) comprising:

(a) an RNA of the present disclosure,
(b) a cationic lipid,
(c) an aggregation reducing agent (such as polyethylene glycol (PEG) lipid or PEG-modified lipid),
(d) optionally a non-cationic lipid (such as a neutral lipid), and
(e) optionally, a sterol.

In another aspect, the cationic lipid is an ionizable cationic lipid. Any ionizable cationic lipid can be included in lipid formulations, including exemplary cationic lipids provided herein.

Cationic Lipids

In one aspect, the lipid nanoparticle formulation comprises (i) at least one cationic lipid; (ii) a helper lipid; (iii) a sterol (e.g., cholesterol); and (iv) a PEG-lipid. In another aspect, the cationic lipid is an ionizable cationic lipid. In yet another aspect, the lipid nanoparticle formulation comprises (i) at least one cationic lipid; (ii) a helper lipid; (iii) a sterol (e.g., cholesterol); and (iv) a PEG-lipid, in a molar ratio of about 40-70% ionizable cationic lipid:about 2-15% helper lipid:about 20-45% sterol; about 0.5-5% PEG-lipid. In a further aspect, the cationic lipid is an ionizable cationic lipid.

In one aspect, the lipid nanoparticle formulation consists of (i) at least one cationic lipid; (ii) a helper lipid; (iii) a sterol (e.g., cholesterol); and (iv) a PEG-lipid. In another aspect, the cationic lipid is an ionizable cationic lipid. In yet another aspect, the lipid nanoparticle formulation consists of (i) at least one cationic lipid; (ii) a helper lipid; (iii) a sterol (e.g., cholesterol); and (iv) a PEG-lipid, in a molar ratio of about 40-70% ionizable cationic lipid:about 2-15% helper lipid:about 20-45% sterol; about 0.5-5% PEG-lipid. In a further aspect, the cationic lipid is an ionizable cationic lipid.

In the presently disclosed lipid formulations, the cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-y-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA·Cl), 1,2-Dilinoleoyl-3-trimethylaminopropane chloride salt (DLin-TAP·Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanediol (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl4-(dimethylamino) butanoate (MC3), 1,1'-(2-(4-(2-((2-(bis(2-hydroxydodecyl) amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6,9,28 31-tetraen-19-yl 4-(dimethylamino) butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31 Z)-heptatriaconta-6,9,28,31-tetraen-19-yloxy)-N,N-dimethylbutan-1-amine (MC4 Ether), or any combination thereof. Other cationic lipids include, but are not limited to, N,N-distearyl-N,N-dimethylammonium bromide (DDAB), 3P—(N—(N',N'-dimethylaminoethane)-carbamoyl)cholesterol (DC-Choi), N-(1-(2,3-dioleyloxy)propyl)-N-2-(sperminecarboxamido) ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-11,31-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107(5), 1864-69, 2010, the contents of which are herein incorporated by reference.

The RNA-lipid formulations of the present disclosure can comprise a helper lipid, which can be referred to as a neutral helper lipid, non-cationic lipid, non-cationic helper lipid, anionic lipid, anionic helper lipid, or a neutral lipid. It has been found that lipid formulations, particularly cationic liposomes and lipid nanoparticles have increased cellular uptake if helper lipids are present in the formulation. (Curr. Drug Metab. 2014; 15(9):882-92). For example, some studies have indicated that neutral and zwitterionic lipids such as 1,2-dioleoylsn-glycero-3-phosphatidylcholine (DOPC), Di-Oleoyl-Phosphatidyl-Ethanoalamine (DOPE) and 1,2-DiStearoyl-sn-glycero-3-PhosphoCholine (DSPC), being more fusogenic (i.e., facilitating fusion) than cationic lipids, can affect the polymorphic features of lipid-nucleic acid complexes, promoting the transition from a lamellar to a hexagonal phase, and thus inducing fusion and a disruption of the cellular membrane. (Nanomedicine (Lond). 2014 January; 9(1):105-20). In addition, the use of helper lipids can help to reduce any potential detrimental effects from using many prevalent cationic lipids such as toxicity and immunogenicity.

Non-limiting examples of non-cationic lipids suitable for lipid formulations of the present disclosure include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lyso-phosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, palmitoyl, stearoyl, or oleoyl.

Additional examples of non-cationic lipids include sterols such as cholesterol and derivatives thereof. As a helper lipid, cholesterol increases the spacing of the charges of the lipid layer interfacing with the nucleic acid making the charge distribution match that of the nucleic acid more closely. (J. R. Soc. Interface. 2012 Mar. 7; 9(68): 548-561). Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In some aspects, the cholesterol derivative is a polar analogue such as cholesteryl-(4'-hydroxy)-butyl ether.

In some aspects, the helper lipid present in the lipid formulation comprises or consists of a mixture of one or more phospholipids and cholesterol or a derivative thereof. In other aspects, the neutral lipid present in the lipid formulation comprises or consists of one or more phospholipids, e.g., a cholesterol-free lipid formulation. In yet other aspects, the neutral lipid present in the lipid formulation comprises or consists of cholesterol or a derivative thereof, e.g., a phospholipid-free lipid formulation.

Other examples of helper lipids include nonphosphorous containing lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, and sphingomyelin.

Other suitable cationic lipids include those having alternative fatty acid groups and other dialkylamino groups, including those, in which the alkyl substituents are different (e.g., N-ethyl-N-methylamino-, and N-propyl-N-ethylamino-). These lipids are part of a subcategory of cationic lipids referred to as amino lipids. In some embodiments of the lipid formulations described herein, the cationic lipid is an amino lipid. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of C14 to C22 may be used. Other scaffolds can also be used to separate the amino group and the fatty acid or fatty alkyl portion of the amino lipid.

In some embodiments, the lipid formulation comprises the cationic lipid with Formula I according to the patent application PCT/EP2017/064066. In this context, the disclosure of PCT/EP2017/064066 is also incorporated herein by reference.

In some embodiments, amino or cationic lipids of the present disclosure are ionizable and have at least one protonatable or deprotonatable group, such that the lipid is positively charged at a pH at or below physiological pH (e.g., pH 7.4), and neutral at a second pH, preferably at or above physiological pH. Of course, it will be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the disclosure. In certain embodiments, the protonatable lipids have a pKa of the protonatable group in the range of about 4 to about 11. In some embodiments, the ionizable cationic lipid has a pKa of about 5 to about 7. In some embodiments, the pKa of an ionizable cationic lipid is about 6 to about 7.

In some embodiments, the lipid formulation comprises an ionizable cationic lipid of Formula I:

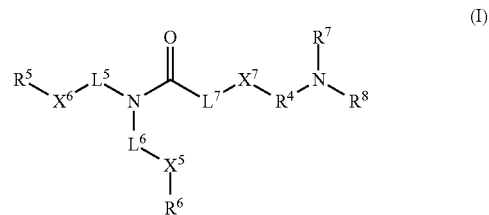

or a pharmaceutically acceptable salt or solvate thereof, wherein R5 and R6 are each independently selected from the group consisting of a linear or branched C1-C31 alkyl, C2-C31 alkenyl or C2-C31 alkynyl and cholesteryl; L5 and L6 are each independently selected from the group consisting of a linear C1-C20 alkyl and C2-C20 alkenyl; X5 is —C(O)O—, whereby —C(O)O—R6 is formed or —OC(O)— whereby —OC(O)—R6 is formed; X6 is —C(O)O— whereby —C(O)O—R5 is formed or —OC(O)— whereby —OC(O)—R5 is formed; X7 is S or O; L7 is absent or lower alkyl; R4 is a linear or branched C1-C6 alkyl; and R7 and R8 are each independently selected from the group consisting of a hydrogen and a linear or branched C1-C6 alkyl.

In some embodiments, X7 is S.

In some embodiments, X5 is —C(O)O—, whereby —C(O)O—R6 is formed and X6 is —C(O)O— whereby —C(O)O—R5 is formed.

In some embodiments, R7 and R8 are each independently selected from the group consisting of methyl, ethyl and isopropyl.

In some embodiments, L5 and L6 are each independently a C1-C10 alkyl. In some embodiments, L5 is C1-C3 alkyl, and L6 is C1-C5 alkyl. In some embodiments, L6 is C1-C2 alkyl. In some embodiments, L5 and L6 are each a linear C7 alkyl. In some embodiments, L5 and L6 are each a linear C9 alkyl.

In some embodiments, R5 and R6 are each independently an alkenyl. In some embodiments, R6 is alkenyl. In some embodiments, R6 is C2-C9 alkenyl. In some embodiments, the alkenyl comprises a single double bond. In some embodiments, R5 and R6 are each alkyl. In some embodiments, R5 is a branched alkyl. In some embodiments, R5 and R6 are each independently selected from the group consisting of a C9 alkyl, C9 alkenyl and C9 alkynyl. In some embodiments, R5 and R6 are each independently selected from the group consisting of a C11 alkyl, C11 alkenyl and C11 alkynyl. In some embodiments, R5 and R6 are each independently selected from the group consisting of a C7 alkyl, C7 alkenyl and C7 alkynyl. In some embodiments, R5 is —CH((CH2)pCH3)2 or —CH((CH2)pCH3)((CH2)p-1CH3), wherein p is 4-8. In some embodiments, p is 5 and L5 is a C1-C3 alkyl. In some embodiments, p is 6 and L5 is a C3 alkyl. In some embodiments, p is 7. In some embodiments, p is 8 and L5 is a C1-C3 alkyl. In some embodiments, R5 consists of —CH((CH2)pCH3)((CH2)p-1CH3), wherein p is 7 or 8.

In some embodiments, R4 is ethylene or propylene. In some embodiments, R4 is n-propylene or isobutylene.

In some embodiments, L7 is absent, R4 is ethylene, X7 is S and R7 and R8 are each methyl. In some embodiments, L7 is absent, R4 is n-propylene, X7 is S and R7 and R8 are each methyl. In some embodiments, L7 is absent, R4 is ethylene, X7 is S and R7 and R8 are each ethyl.

In some embodiments, X7 is S, X5 is —C(O)O—, whereby —C(O)O—R6 is formed, X6 is —C(O)O— whereby —C(O)O—R5 is formed, L5 and L6 are each independently a linear C3-C7 alkyl, L7 is absent, R5 is —CH((CH2)pCH3)2, and R6 is C7-C12 alkenyl. In some further embodiments, p is 6 and R6 is C9 alkenyl.

In some embodiments, the lipid formulation can comprise an ionizable cationic lipid selected from the group consisting of LIPID #1 to LIPID #8:

TABLE 5

| LIPID # | STRUCTURE |
| --- | --- |
| 1 | 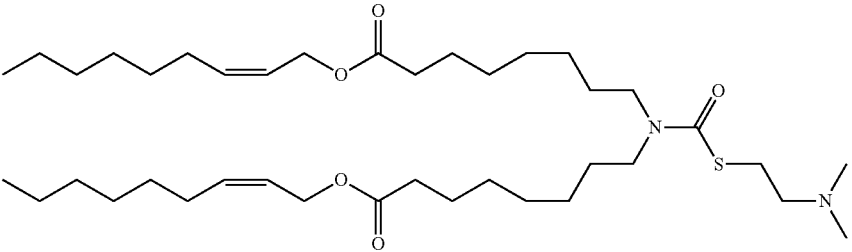 [SMILES: CCCCCC/C=C\COC(=O)CCCCCCCN(CCCCCCCC(=O)OC/C=C\CCCCCC)C(=O)SCCN(C)C] |
| 2 | 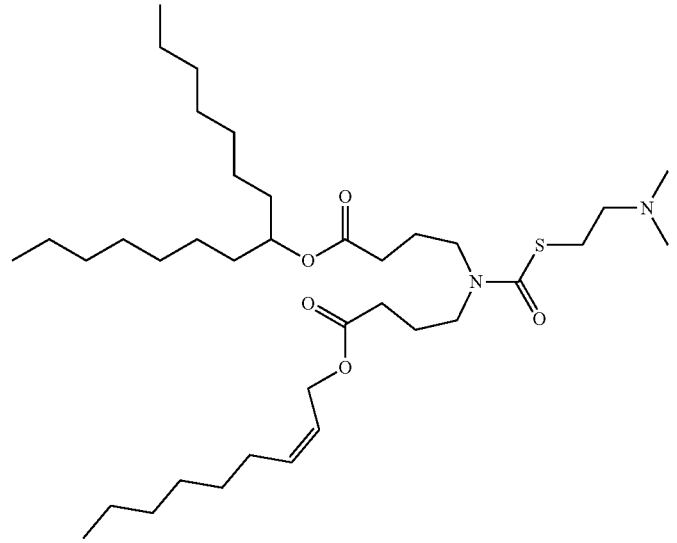 [SMILES: CCCCCC/C=C\COC(=O)CCCN(CCCC(=O)OC(CCCCCCC)CCCCCCC)C(=O)SCCN(C)C] |
| 3 | 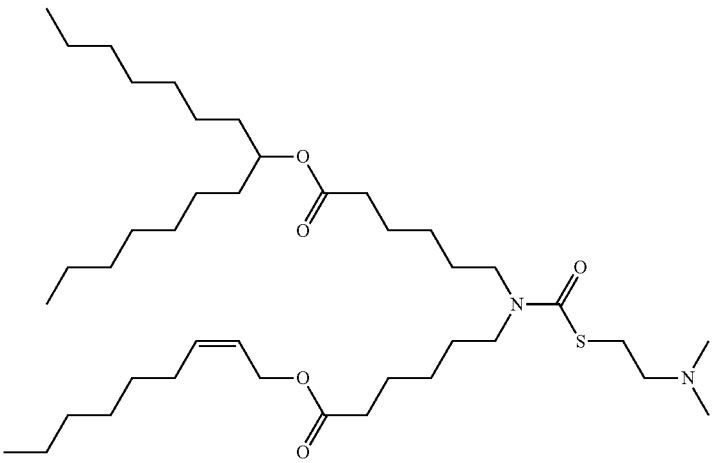 [SMILES: CCCCCC/C=C\COC(=O)CCCCCN(CCCCCC(=O)OC(CCCCCCC)CCCCCCC)C(=O)SCCN(C)C] |

TABLE 5-continued
| LIPID # | STRUCTURE |
|---|---|
| 4 | 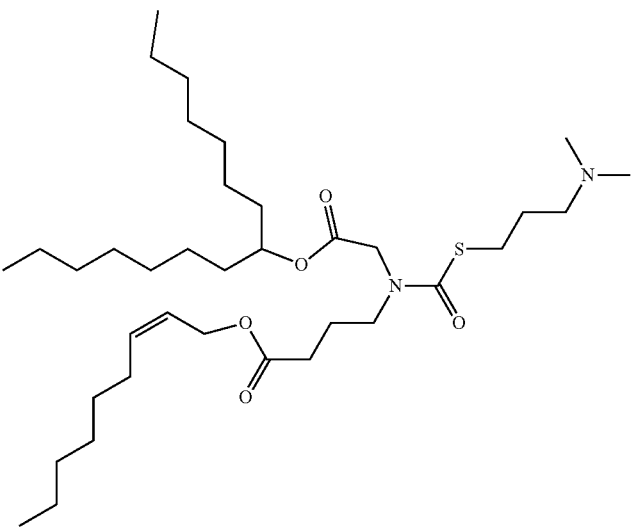 [SMILES: CCCCCC/C=C\COC(=O)CCCN(CC(=O)OC(CCCCCCC)CCCCCCC)C(=O)SCCCN(C)C] |
| 5 | 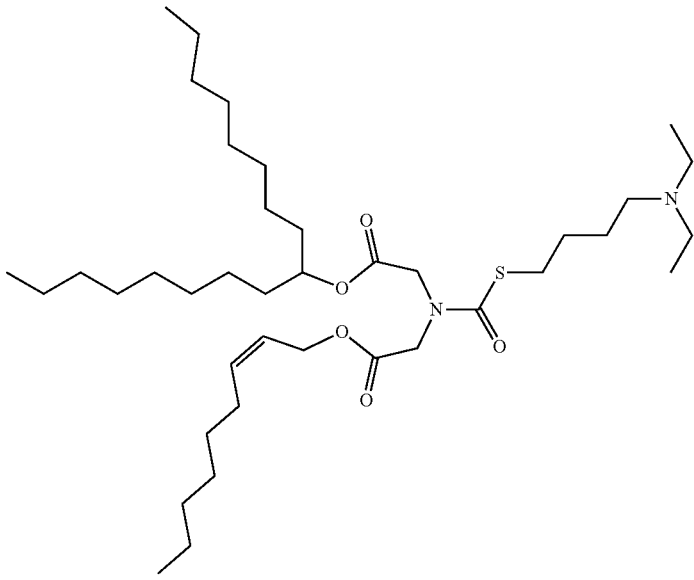 [SMILES: CCCCCC/C=C\COC(=O)CN(CC(=O)OC(CCCCCCCC)CCCCCCCC)C(=O)SCCCCN(CC)CC] |
| 6 | 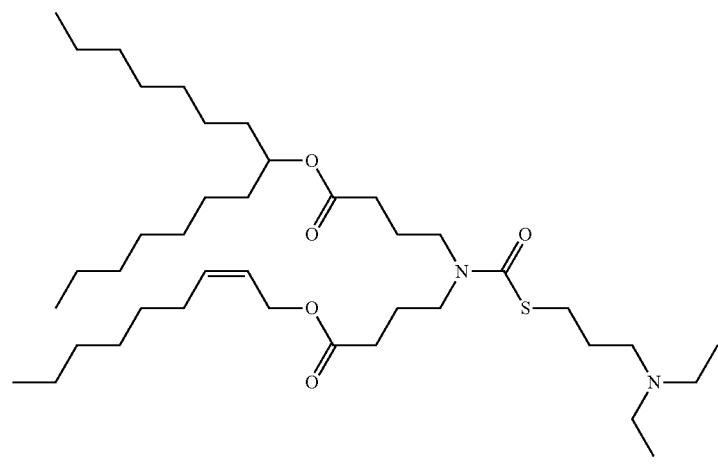 [SMILES: CCCCCC/C=C\COC(=O)CCCN(CCCC(=O)OC(CCCCCCC)CCCCCCC)C(=O)SCCCN(CC)CC] |

TABLE 5-continued
| LIPID # | STRUCTURE |
|---|---|
| 7 | 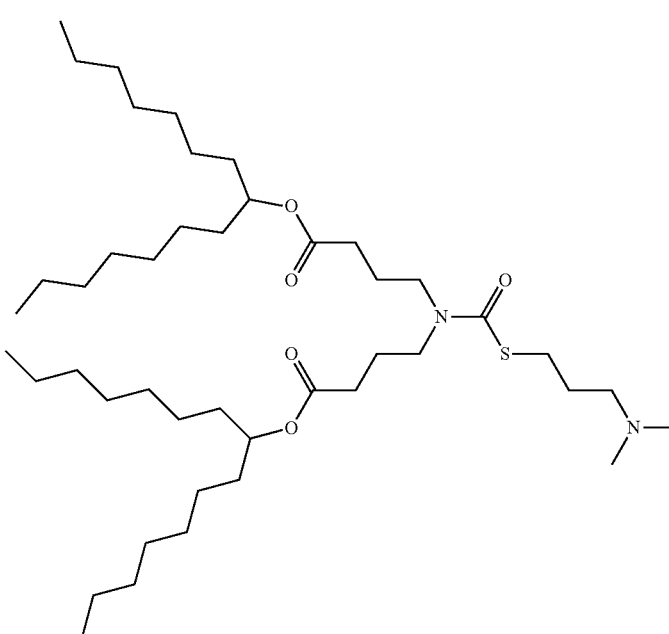 [SMILES: CCCCCCCC(CCCCCCC)OC(=O)CCCN(CCCC(=O)OC(CCCCCCC)CCCCCCC)C(=O)SCCCN(C)C] |
| 8 | 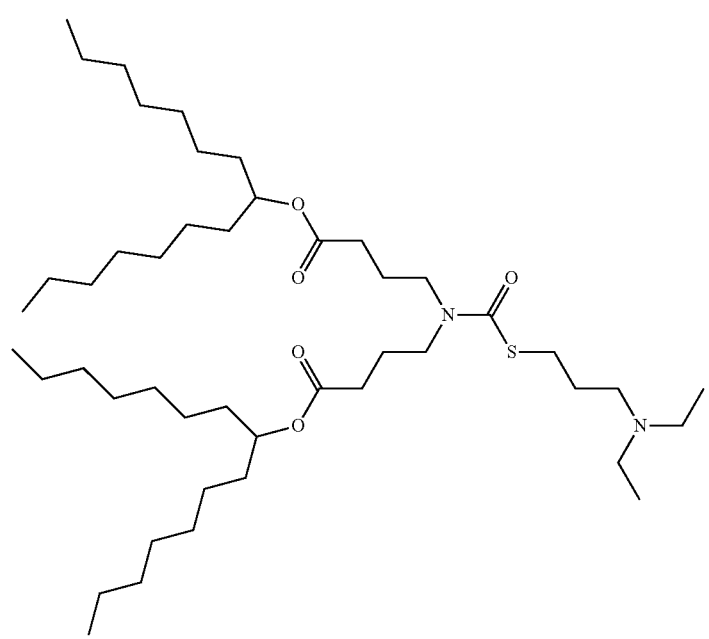 [SMILES: CCCCCCCC(CCCCCCC)OC(=O)CCCN(CCCC(=O)OC(CCCCCCC)CCCCCCC)C(=O)SCCCN(CC)CC] |

In some embodiments, the lipid formulation comprises an ionizable cationic lipid having a structure selected from

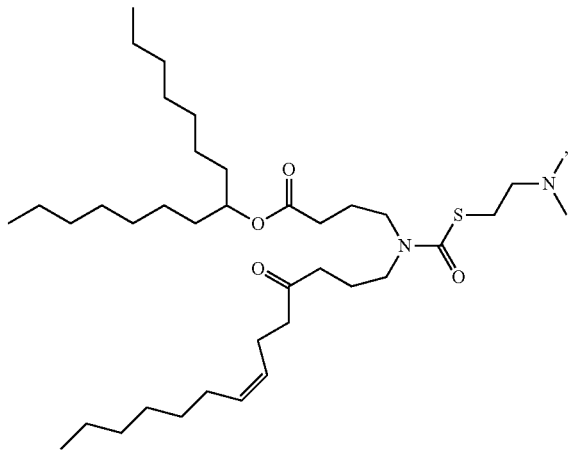

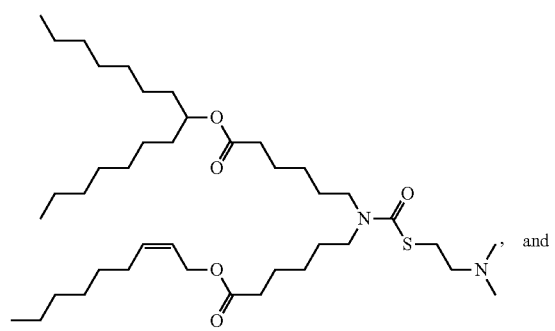

and

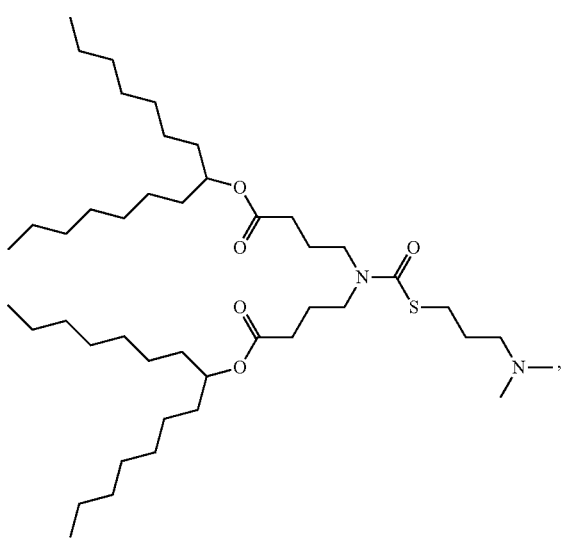

or a pharmaceutically acceptable salt thereof.
In some preferred embodiments, the lipid formulation comprises an ionizable cationic lipid having the structure

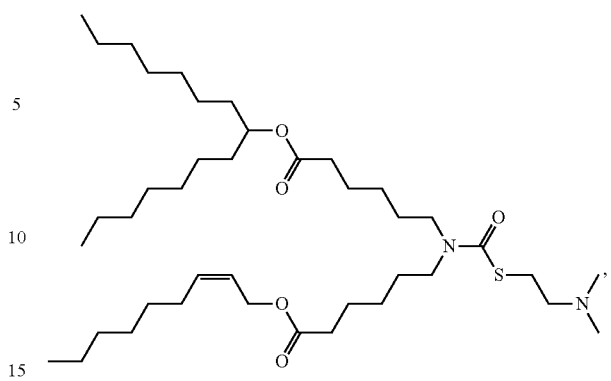

or a pharmaceutically acceptable salt thereof.

In embodiments, any one or more lipids recited herein may be expressly excluded.

In some aspects, the helper lipid comprises from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid formulation.

The cholesterol or cholesterol derivative in the lipid formulation may comprise up to about 40 mol %, about 45 mol %, about 50 mol %, about 55 mol %, or about 60 mol % of the total lipid present in the lipid formulation. In some aspects, the cholesterol or cholesterol derivative comprises about 15 mol % to about 45 mol %, about 20 mol % to about 40 mol %, about 25 mol % to about 35 mol %, or about 28 mol % to about 35 mol %; or about 25 mol %, about 26 mol %, about 27 mol %, about 28 mol %, about 29 mol %, about 30 mol %, about 31 mol %, about 32 mol %, about 33 mol %, about 34 mol %, about 35 mol %, about 36 mol %, or about 37 mol % of the total lipid present in the lipid formulation.

In some aspects, the phospholipid component in the mixture may comprise from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid formulation.

The percentage of helper lipid present in the lipid formulation is a target amount, and the actual amount of helper lipid present in the formulation may vary, for example, by ±5 mol %.

A lipid formulation that includes a cationic lipid compound or ionizable cationic lipid compound may be on a molar basis about 30-70% cationic lipid compound, about 25-40% cholesterol, about 2-15% helper lipid, and about 0.5-5% of a polyethylene glycol (PEG) lipid, wherein the percent is of the total lipid present in the formulation. In some aspects, the composition is about 40-65% cationic lipid compound, about 25-35% cholesterol, about 3-9% helper lipid, and about 0.5-3% of a PEG-lipid, wherein the percent is of the total lipid present in the formulation.

The formulation may be a lipid particle formulation, for example containing 8-30% nucleic acid compound, 5-30% helper lipid, and 0-20% cholesterol; 4-25% cationic lipid, 4-25% helper lipid, 2-25% cholesterol, 10-35% cholesterol-PEG, and 5% cholesterol-amine; or 2-30% cationic lipid, 2-30% helper lipid, 1-15% cholesterol, 2-35% cholesterol-PEG, and 1-20% cholesterol-amine; or up to 90% cationic lipid and 2-10% helper lipids, or even 100% cationic lipid.

Lipid Conjugates

The lipid formulations described herein may further comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof. Furthermore, lipid delivery vehicles can be used for specific targeting by attaching ligands (e.g., antibodies, peptides, and carbohydrates) to its surface or to the terminal end of the attached PEG chains (Front Pharmacol. 2015 Dec. 1; 6:286).

In some aspects, the lipid conjugate is a PEG-lipid. The inclusion of polyethylene glycol (PEG) in a lipid formulation as a coating or surface ligand, a technique referred to as PEGylation, helps to protect nanoparticles from the immune system and their escape from RES uptake (Nanomedicine (Lond). 2011 June; 6(4):715-28). PEGylation has been used to stabilize lipid formulations and their payloads through physical, chemical, and biological mechanisms. Detergent-like PEG lipids (e.g., PEG-DSPE) can enter the lipid formulation to form a hydrated layer and steric barrier on the surface. Based on the degree of PEGylation, the surface layer can be generally divided into two types, brush-like and mushroom-like layers. For PEG-DSPE-stabilized formulations, PEG will take on the mushroom conformation at a low degree of PEGylation (usually less than 5 mol %) and will shift to brush conformation as the content of PEG-DSPE is increased past a certain level (Journal of Nanomaterials. 2011; 2011:12). PEGylation leads to a significant increase in the circulation half-life of lipid formulations (Annu. Rev. Biomed. Eng. 2011 Aug. 15; 130:507-30; J. Control Release. 2010 Aug. 3; 145(3):178-81).

Examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), PEG conjugated to ceramides, PEG conjugated to cholesterol or a derivative thereof, and mixtures thereof.

PEG is a linear, water-soluble polymer of ethylene PEG repeating units with two terminal hydroxyl groups. PEGs are classified by their molecular weights and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-NH2).

The PEG moiety of the PEG-lipid conjugates described herein may comprise an average molecular weight ranging from about 550 daltons to about 10,000 daltons. In certain aspects, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons). In some aspects, the PEG moiety has an average molecular weight of about 2,000 daltons or about 750 daltons. The average molecular weight may be any value or subvalue within the recited ranges, including endpoints.

In certain aspects, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In one aspect, the linker moiety is a non-ester-containing linker moiety. Exemplary non-ester-containing linker moieties include, but are not limited to, amido (—C(O)NH—), amino (—NR—), carbonyl (—C(O)—), carbamate (—NHC(O)O—), urea (—NHC(O)NH—), disulfide (—S—S—), ether (—O—), succinyl (—(O)CCH2CH2C(O)—), succinamidyl (—NHC(O)CH2CH2C(O)NH—), ether, as well as combinations thereof (such as a linker containing both a carbamate linker moiety and an amido linker moiety). In one aspect, a carbamate linker is used to couple the PEG to the lipid.

In some aspects, an ester-containing linker moiety is used to couple the PEG to the lipid. Exemplary ester-containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available or can be isolated or synthesized using conventional techniques known to those of skill in the art. Phosphatidylethanolamines containing saturated or unsaturated fatty acids with carbon chain lengths in the range of C10 to C20 are preferred. Phosphatidylethanolamines with mono- or di-unsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoyl-phosphatidylethanolamine (DOPE), and distearoyl-phosphatidylethanolamine (DSPE).

In some aspects, the PEG-DAA conjugate is a PEG-didecyloxypropyl (C10) conjugate, a PEG-dilauryloxypropyl (C12) conjugate, a PEG-dimyristyloxypropyl (C14) conjugate, a PEG-dipalmityloxypropyl (C16) conjugate, or a PEG-distearyloxypropyl (C18) conjugate. In some aspects, the PEG has an average molecular weight of about 750 or about 2,000 daltons. In some aspects, the terminal hydroxyl group of the PEG is substituted with a methyl group.

In addition to the foregoing, other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl, methacrylamide, polymethacrylamide, and polydimethylacrylamide, polylactic acid, polyglycolic acid, and derivatized celluloses such as hydroxymethylcellulose or hydroxyethylcellulose.

In some aspects, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.6 mol % (or any fraction thereof or range therein) of the total lipid present in the lipid formulation. In other embodiments, the lipid conjugate (e.g., PEG-lipid) comprises about 0.5%, 0.6%, 0.7%, 0.8%, 0.9%, 1.0%, 1.2%, 1.3%, 1.4%, 1.5%, 1.6%, 1.7%, 1.8%, 1.9%, 2.0%, 2.5%, 3.0%, 3.5%, 4.0%, 4.5%, or 5%, (or any fraction thereof or range therein) of the total lipid present in the lipid formulation. The amount may be any value or subvalue within the recited ranges, including endpoints.

The percentage of lipid conjugate (e.g., PEG-lipid) present in the lipid formulations of the disclosure is a target amount, and the actual amount of lipid conjugate present in the formulation may vary, for example, by ±0.5 mol %. One of ordinary skill in the art will appreciate that the concentration of the lipid conjugate can be varied depending on the lipid conjugate employed and the rate at which the lipid formulation is to become fusogenic.

Mechanism of Action for Cellular Uptake of Lipid Formulations

In some aspects, lipid formulations for the intracellular delivery of nucleic acids, particularly liposomes, cationic liposomes, and lipid nanoparticles, are designed for cellular uptake by penetrating target cells through exploitation of the target cells' endocytic mechanisms where the contents of the lipid delivery vehicle are delivered to the cytosol of the target cell. (Nucleic Acid Therapeutics, 28(3):146-157, 2018). Prior to endocytosis, functionalized ligands such as PEG-lipid at the surface of the lipid delivery vehicle are shed from the surface, which triggers internalization into the target cell. During endocytosis, some part of the plasma membrane of the cell surrounds the vector and engulfs it into a vesicle that then pinches off from the cell membrane, enters the cytosol and ultimately enters and moves through the endolysosomal pathway. For ionizable cationic lipid-containing delivery vehicles, the increased acidity as the endosome ages results in a vehicle with a strong positive charge on the surface. Interactions between the delivery vehicle and the endosomal membrane then result in a membrane fusion event that leads to cytosolic delivery of the payload. For RNA payloads, the cell's own internal translation processes will then translate the RNA into the encoded protein. The encoded protein can further undergo postranslational processing, including transportation to a targeted organelle or location within the cell or excretion from the cell.

By controlling the composition and concentration of the lipid conjugate, one can control the rate at which the lipid conjugate exchanges out of the lipid formulation and, in turn, the rate at which the lipid formulation becomes fusogenic. In addition, other variables including, e.g., pH, temperature, or ionic strength, can be used to vary and/or control the rate at which the lipid formulation becomes fusogenic. Other methods which can be used to control the rate at which the lipid formulation becomes fusogenic will become apparent to those of skill in the art upon reading this disclosure. Also, by controlling the composition and concentration of the lipid conjugate, one can control the liposomal or lipid particle size.

Lipid Formulation Manufacture

There are many different methods for the preparation of lipid formulations comprising a nucleic acid. (Curr. Drug Metabol. 2014, 15, 882-892; Chem. Phys. Lipids 2014, 177, 8-18; Int. J. Pharm. Stud. Res. 2012, 3, 14-20). The techniques of thin film hydration, double emulsion, reverse phase evaporation, microfluidic preparation, dual assymetric centrifugation, ethanol injection, detergent dialysis, spontaneous vesicle formation by ethanol dilution, and encapsulation in preformed liposomes are briefly described herein.

Thin Film Hydration

In Thin Film Hydration (TFH) or the Bangham method, the lipids are dissolved in an organic solvent, then evaporated through the use of a rotary evaporator leading to a thin lipid layer formation. After the layer hydration by an aqueous buffer solution containing the compound to be loaded, Multilamellar Vesicles (MLVs) are formed, which can be reduced in size to produce Small or Large Unilamellar vesicles (LUV and SUV) by extrusion through membranes or by the sonication of the starting MLV.

Double Emulsion

Lipid formulations can also be prepared through the Double Emulsion technique, which involves lipids dissolution in a water/organic solvent mixture. The organic solution, containing water droplets, is mixed with an excess of aqueous medium, leading to a water-in-oil-in-water (W/O/W) double emulsion formation. After mechanical vigorous shaking, part of the water droplets collapse, giving Large Unilamellar Vesicles (LUVs).

Reverse Phase Evaporation

The Reverse Phase Evaporation (REV) method also allows one to achieve LUVs loaded with nucleic acid. In this technique a two-phase system is formed by phospholipids dissolution in organic solvents and aqueous buffer. The resulting suspension is then sonicated briefly until the mixture becomes a clear one-phase dispersion. The lipid formulation is achieved after the organic solvent evaporation under reduced pressure. This technique has been used to encapsulate different large and small hydrophilic molecules including nucleic acids.

Microfluidic Preparation

The Microfluidic method, unlike other bulk techniques, gives the possibility of controlling the lipid hydration process. The method can be classified in continuous-flow microfluidic and droplet-based microfluidic, according to the way in which the flow is manipulated. In the microfluidic hydrodynamic focusing (MHF) method, which operates in a continuous flow mode, lipids are dissolved in isopropyl alcohol which is hydrodynamically focused in a microchannel cross junction between two aqueous buffer streams. Vesicles size can be controlled by modulating the flow rates, thus controlling the lipids solution/buffer dilution process. The method can be used for producing oligonucleotide (ON) lipid formulations by using a microfluidic device consisting of three-inlet and one-outlet ports.

Dual Asymmetric Centrifugation

Dual Asymmetric Centrifugation (DAC) differs from more common centrifugation as it uses an additional rotation around its own vertical axis. An efficient homogenization is achieved due to the two overlaying movements generated: the sample is pushed outwards, as in a normal centrifuge, and then it is pushed towards the center of the vial due to the additional rotation. By mixing lipids and an NaCl-solution a viscous vesicular phospholipid gel (VPC) is achieved, which is then diluted to obtain a lipid formulation dispersion. The lipid formulation size can be regulated by optimizing DAC speed, lipid concentration and homogenization time.

Ethanol Injection

The Ethanol Injection (EI) method can be used for nucleic acid encapsulation. This method provides the rapid injection of an ethanolic solution, in which lipids are dissolved, into an aqueous medium containing nucleic acids to be encapsulated, through the use of a needle. Vesicles are spontaneously formed when the phospholipids are dispersed throughout the medium.

Detergent Dialysis

The Detergent dialysis method can be used to encapsulate nucleic acids. Briefly lipid and plasmid are solubilized in a detergent solution of appropriate ionic strength, after removing the detergent by dialysis, a stabilized lipid formulation is formed. Unencapsulated nucleic acid is then removed by ion-exchange chromatography and empty vesicles by sucrose density gradient centrifugation. The technique is highly sensitive to the cationic lipid content and to the salt concentration of the dialysis buffer, and the method is also difficult to scale.

Spontaneous Vesicle Formation by Ethanol Dilution

Stable lipid formulations can also be produced through the Spontaneous Vesicle Formation by Ethanol Dilution method in which a stepwise or dropwise ethanol dilution provides the instantaneous formation of vesicles loaded with nucleic acid by the controlled addition of lipid dissolved in ethanol to a rapidly mixing aqueous buffer containing the nucleic acid.

Encapsulation in Preformed Liposomes

The entrapment of nucleic acids can also be obtained starting with preformed liposomes through two different methods: (1) A simple mixing of cationic liposomes with nucleic acids which gives electrostatic complexes called "lipoplexes", where they can be successfully used to transfect cell cultures, but are characterized by their low encapsulation efficiency and poor performance in vivo; and (2) a liposomal destabilization, slowly adding absolute ethanol to a suspension of cationic vesicles up to a concentration of 40% v/v followed by the dropwise addition of nucleic acids achieving loaded vesicles; however, the two main steps characterizing the encapsulation process are too sensitive, and the particles have to be downsized.

Excipients

The pharmaceutical compositions disclosed herein can be formulated using one or more excipients to: (1) increase stability; (2) increase cell transfection; (3) permit a sustained or delayed release (e.g., from a depot formulation of the polynucleotide, primary construct, or RNA); (4) alter the biodistribution (e.g., target the polynucleotide, primary construct, or RNA to specific tissues or cell types); (5) increase the translation of encoded protein in vivo; and/or (6) alter the release profile of encoded protein in vivo.

The pharmaceutical compositions described herein may be prepared by any method known or hereafter developed in the art of pharmacology. In general, such preparatory methods include the step of associating the active ingredient (i.e., nucleic acid) with an excipient and/or one or more other accessory ingredients. A pharmaceutical composition in accordance with the present disclosure may be prepared, packaged, and/or sold in bulk, as a single unit dose, and/or as a plurality of single unit doses.

Pharmaceutical compositions may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired.

In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, liposomes, lipid nanoparticles, polymers, lipoplexes, core-shell nanoparticles, peptides, proteins, cells transfected with primary DNA construct, or RNA (e.g., for transplantation into a subject), hyaluronidase, nanoparticle mimics and combinations thereof.

Accordingly, the pharmaceutical compositions described herein can include one or more excipients, each in an amount that together increases the stability of the nucleic acid in the lipid formulation, increases cell transfection by the nucleic acid, increases the expression of the encoded protein, and/or alters the release profile of encoded proteins. Further, the RNA of the present disclosure may be formulated using self-assembled nucleic acid nanoparticles.

Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference in its entirety). The use of a conventional excipient medium may be contemplated within the scope of the embodiments of the present disclosure, except insofar as any conventional excipient medium may be incompatible with a substance or its derivatives, such as by producing any undesirable biological effect or otherwise interacting in a deleterious manner with any other component(s) of the pharmaceutical composition.

The pharmaceutical compositions of this disclosure may further contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the disclosure, the RNA-lipid formulation may be administered in a time release formulation, for example in a composition which includes a slow release polymer. The active agent can be prepared with carriers that will protect against rapid release, for example a controlled release vehicle such as a polymer, microencapsulated delivery system, or a bioadhesive gel. Prolonged delivery of the RNA, in various compositions of the disclosure can be brought about by including in the composition agents that delay absorption, for example, aluminum monostearate hydrogels and gelatin.

Methods of Inducing Immune Responses

Provided herein, in some embodiments, are methods of inducing an immune response in a subject. Any type of immune response can be induced using the methods provided herein, including adaptive and innate immune responses. In one aspect, immune responses induced using the methods provided herein include an antibody response, a cellular immune response, or both an antibody response and a cellular immune response.

Methods of inducing an immune response provided herein include administering to a subject an effective amount of any nucleic acid molecule provided herein. In one aspect, methods of inducing an immune response include administering to a subject an effective amount of any composition comprising a nucleic acid molecule and a lipid provided herein. In another aspect, methods of inducing an immune response include administering to a subject an effective amount of any pharmaceutical composition comprising a nucleic acid molecule and a lipid formulation provided herein. In some aspects, nucleic acid molecules, compositions, and pharmaceutical composition provided here are vaccines that can elicit a protective or a therapeutic immune response, for example.

As used herein, the term "subject" refers to any individual or patient on which the methods disclosed herein are performed. The term "subject" can be used interchangeably with the term "individual" or "patient." The subject can be a human, although the subject may be an animal, as will be appreciated by those in the art. Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. As used herein, the term "effective amount" or "therapeutically effective amount" refers to that amount of a nucleic acid molecule, composition, or pharmaceutical composition described herein that is sufficient to effect the intended application, including but not limited to inducing an immune response and/or disease treatment, as defined herein. The therapeutically effective amount may vary depending upon the intended application (e.g., inducing an immune response, treatment, application in vivo), or the subject or patient and disease condition being treated, e.g., the weight and age of the subject, the species, the severity of the disease condition, the manner of administration and the like, which can readily be determined by one of ordinary skill in the art. The term also applies to a dose that will induce a particular response in a target cell. The specific dose will vary depending on the particular nucleic acid molecule, composition, or pharmaceutical composition chosen, the dosing regimen to be followed, whether it is administered in combination with other compounds, timing of administration, the tissue to which it is administered, and the physical delivery system in which it is carried.

Exemplary doses of nucleic acid molecules that can be administered include about 0.01 µg, about 0.02 µg, about 0.03 µg, about 0.04 µg, about 0.05 µg, about 0.06 µg, about 0.07 µg, about 0.08 µg, about 0.09 µg, about 0.1 µg, about 0.2 µg, about 0.3 µg, about 0.4 µg, about 0.5 µg, about 0.6 µg, about 0.7 µg, about 0.8 µg, about 0.9 µg, about 1.0 µg, about 1.5 µg, about 2.0 µg, about 2.5 µg, about 3.0 µg, about 3.5 µg, about 4.0 µg, about 4.5 µg, about 5.0 µg, about 5.5 µg about 6.0 µg, about 6.5 µg about 7.0 µg, about 7.5 µg, about 8.0 µg, about 8.5 µg, about 9.0 µg, about 9.5 µg, about 10 µg, about 11 µg, about 12 µg, about 13µ, about 14 µg, about 15 µg, about 16 µg, about 17 µg, about 18 µg, about 19 µg, about 20 µg, about 21 µg, about 22 µg, about 23 µg, about 24 µg, about 25 µg, about 26 µg, about 27 µg, about 28 µg, about 29 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 125 µg, about 150 µg, about 175 µg, about 200 µg, about 250 µg, about 300 µg, about 350 µg, about 400 µg, about 450 µg, about 500 µg, about 600 µg, about 700 µg, about 800 µg, about 900 µg, about 1,000 µg, or more, and any number or range in between. In one aspect, the nucleic acid molecules are RNA molecules. In another aspect, the nucleic acid molecules are DNA molecules. Nucleic acid molecules can have a unit dosage comprising about 0.01 µg to about 1,000 µg or more nucleic acid in a single dose.

In some aspects, compositions provided herein that can be administered include about 0.01 µg, about 0.02 µg, about 0.03 µg, about 0.04 µg, about 0.05 µg, about 0.06 µg, about 0.07 µg, about 0.08 µg, about 0.09 µg, about 0.1 µg, about 0.2 µg, about 0.3 µg, about 0.4 µg, about 0.5 µg, about 0.6 µg, about 0.7 µg, about 0.8 µg, about 0.9 µg, about 1.0 µg, about 1.5 µg, about 2.0 µg, about 2.5 µg, about 3.0 µg, about 3.5 µg, about 4.0 µg, about 4.5 µg, about 5.0 µg, about 5.5 µg, about 6.0 µg, about 6.5 µg, about 7.0 µg, about 7.5 µg, about 8.0 µg, about 8.5 µg, about 9.0 µg, about 9.5 µg, about 10 µg, about 11 µg, about 12 µg, about 13 µg, about 14 µg, about 15 µg, about 16 µg, about 17 µg, about 18 µg, about 19 µg, about 20 µg, about 21 µg, about 22 µg, about 23 µg, about 24 µg, about 25 µg, about 26 µg, about 27 µg, about 28 µg, about 29 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 125 µg, about 150 µg, about 175 µg, about 200 µg, about 250 µg, about 300 µg, about 350 µg, about 400 µg, about 450 µg, about 500 µg, about 600 µg, about 700 µg, about 800 µg, about 900 µg, about 1,000 µg, or more, and any number or range in between, nucleic acid and lipid. In other aspects, pharmaceutical compositions provided herein that can be administered include about 0.01 µg, about 0.02 µg, about 0.03 µg, about 0.04 µg, about 0.05 µg, about 0.06 µg, about 0.07 µg, about 0.08 µg, about 0.09 µg, about 0.1 µg, about 0.2 µg, about 0.3 µg, about 0.4 µg, about 0.5 µg, about 0.6 µg, about 0.7 µg, about 0.8 µg, about 0.9 µg, about 1.0 µg, about 1.5 µg, about 2.0 µg, about 2.5 µg, about 3.0 µg, about 3.5 µg, about 4.0 µg, about 4.5 µg, about 5.0 µg, about 5.5 µg, about 6.0 µg, about 6.5 µg, about 7.0 µg, about 7.5 µg, about 8.0 µg, about 8.5 µg, about 9.0 µg, about 9.5 µg, about 10 µg, about 11 µg, about 12 µg, about 13 µg, about 14 µg, about 15 µg, about 16 µg, about 17 µg, about 18 µg, about 19 µg, about 20 µg, about 21 µg, about 22 µg, about 23 µg, about 24 µg, about 25 µg, about 26 µg, about 27 µg, about 28 µg, about 29 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 125 µg, about 150 µg, about 175 µg, about 200 µg, about 250 µg, about 300 µg, about 350 µg, about 400 µg, about 450 µg, about 500 µg, about 600 µg, about 700 µg, about 800 µg, about 900 µg, about 1,000 µg, or more, and any number or range in between, nucleic acid and lipid formulation.

In one aspect, compositions provided herein can have a unit dosage comprising about 0.01 µg to about 1,000 µg or more nucleic acid and lipid in a single dose. In another aspect, pharmaceutical compositions provided herein can have a unit dosage comprising about 0.01 µg to about 1,000 µg or more nucleic acid and lipid formulation in a single dose. A vaccine unit dosage can correspond to the unit dosage of nucleic acid molecules, compositions, or pharmaceutical compositions provided herein and that can be administered to a subject. In one aspect, vaccine compositions of the instant disclosure have a unit dosage comprising about 0.01 µg to about 1,000 µg or more nucleic acid and lipid formulation in a single dose. In another aspect, vaccine compositions of the instant disclosure have a unit dosage comprising about 0.01 µg to about 50 µg nucleic acid and lipid formulation in a single dose. In yet another aspect, vaccine compositions of the instant disclosure have a unit dosage comprising about 0.2 µg to about 20 µg nucleic acid and lipid formulation in a single dose.

A dosage form of the composition of this disclosure can be solid, which can be reconstituted in a liquid prior to administration. The solid can be administered as a powder. The solid can be in the form of a capsule, tablet, or gel. In some embodiments, the pharmaceutical composition comprises a nucleic acid lipid formulation that has been lyophilized.

In a preferred embodiment, the dosage form of the pharmaceutical compositions described herein can be a liquid suspension of self-replicating RNA lipid nanoparticles described herein. In some embodiments, the liquid suspension is in a buffered solution. In some embodiments, the buffered solution comprises a buffer selected from the group consisting of HEPES, MOPS, TES, and TRIS. In some embodiments, the buffer has a pH of about 7.4. In some preferred embodiments, the buffer is HEPES. In some further embodiments, the buffered solution further comprises a cryoprotectant. In some embodiments, the cryoprotectant is selected from a sugar and glycerol or a combination of a sugar and glycerol. In some embodiments, the sugar is a dimeric sugar. In some embodiments, the sugar is sucrose. In some preferred embodiments, the buffer comprises HEPES, sucrose, and glycerol at a pH of 7.4. In some embodiments, the suspension is frozen during storage and thawed prior to administration. In some embodiments, the suspension is frozen at a temperature below about 70° C. In some embodiments, the suspension is diluted with sterile water during intravenous administration. In some embodiments, intravenous administration comprises diluting the suspension with about 2 volumes to about 6 volumes of sterile water. In some embodiments, the suspension comprises about 0.1 mg to about 3.0 mg self-replicating RNA/mL, about 15 mg/mL to about 25 mg/mL of an ionizable cationic lipid, about 0.5 mg/mL to about 2.5 mg/mL of a PEG-lipid, about 1.8 mg/mL to about 3.5 mg/mL of a helper lipid, about 4.5 mg/mL to about 7.5 mg/mL of a cholesterol, about 7 mg/mL to about 15 mg/mL of a buffer, about 2.0 mg/mL to about 4.0 mg/mL of NaCl, about 70 mg/mL to about 110 mg/mL of sucrose, and about 50 mg/mL to about 70 mg/mL of glycerol. In some embodiments, a lyophilized self-replicating RNA-lipid nanoparticle formulation can be resuspended in a buffer as described herein.

In some embodiments, the compositions of the disclosure are administered to a subject such that a self-replicating RNA concentration of at least about 0.05 mg/kg, at least about 0.1 mg/kg, at least about 0.5 mg/kg, at least about 1.0 mg/kg, at least about 2.0 mg/kg, at least about 3.0 mg/kg, at least about 4.0 mg/kg, at least about 5.0 mg/kg of body weight is administered in a single dose or as part of single treatment cycle. In some embodiments, the compositions of the disclosure are administered to a subject such that a total amount of at least about 0.1 mg, at least about 0.5 mg, at least about 1.0 mg, at least about 2.0 mg, at least about 3.0 mg, at least about 4.0 mg, at least about 5.0 mg, at least about 6.0 mg, at least about 7.0 mg, at least about 8.0 mg, at least about 9.0 mg, at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 105 mg, at least about 110 mg, at least about 115 mg, at least about 120 mg, or at least about 125 mg self-replicating RNA is administered in one or more doses up to a maximum dose of about 300 mg, about 350 mg, about 400 mg, about 450 mg, or about 500 mg self-replicating RNA.

Any route of administration can be included in methods provided herein. In some aspects, nucleic acid molecules, compositions, and pharmaceutical compositions provided herein are administered intramuscularly, subcutaneously, intradermally, transdermally, intranasally, orally, sublingually, intravenously, intraperitoneally, topically, by aerosol, or by a pulmonary route, such as by inhalation or by nebulization, for example. In some embodiments, the pharmaceutical compositions described are administered systemically. Suitable routes of administration include, for example, rectal, vaginal, transmucosal, or intestinal administration; parenteral delivery, including intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments, the pharmaceutical composition is administered intravenously.

Pharmaceutical compositions may be administered to any desired tissue. In some embodiments, the self-replicating RNA delivered is expressed in a tissue different from the tissue in which the lipid formulation or pharmaceutical composition was administered. In preferred embodiments, self-replicating RNA is delivered and expressed in the liver.

In other aspects, nucleic acid molecules, compositions, and pharmaceutical compositions provided herein are administered intramuscularly.

In some aspects, the subject in which an immune response is induced is a healthy subject. As used herein, the term "healthy subject" refers to a subject not having a condition or disease, including an infectious disease or cancer, for example, or not having a condition or disease against which an immune response is induced. Accordingly, in some aspects, a nucleic acid molecule, composition, or pharmaceutical composition provided herein is administered prophylactically to prevent an infectious disease or cancer, for example. In other aspects, the subject in which an immune response is induced has cancer. The subject may suffer from any cancer or have any tumor, including solid and liquid tumors. In one aspect, the cancer is kidney cancer, renal cancer, urinary bladder cancer, prostate cancer, uterine cancer, breast cancer, cervical cancer, ovarian cancer, lung cancer, liver cancer, stomach cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, or sarcoma. Accordingly, a nucleic acid molecule, composition, or pharmaceutical composition provided herein can be administered therapeutically, i.e., to treat a condition or disease, such as cancer, after the onset of the condition or disease.

As used herein, the terms "treat," "treatment," "therapy," "therapeutic," and the like refer to obtaining a desired pharmacologic and/or physiologic effect, including, but not limited to, alleviating, delaying or slowing the progression, reducing the effects or symptoms, preventing onset, inhibiting, ameliorating the onset of a diseases or disorder, obtaining a beneficial or desired result with respect to a disease, disorder, or medical condition, such as a therapeutic benefit and/or a prophylactic benefit. "Treatment," as used herein, includes any treatment of a disease in a mammal, particularly in a human, and includes: (a) preventing the disease from occurring in a subject, including a subject which is predisposed to the disease or at risk of acquiring the disease but has not yet been diagnosed as having it; (b) inhibiting the disease, i.e., arresting its development; and (c) relieving the disease, i.e., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some aspects, for prophylactic benefit, treatment or compositions for treatment, including pharmaceutical compositions, are administered to a subject at risk of developing a particular disease, or to a subject reporting one or more of the physiological symptoms of a disease, even though a diagnosis of this disease may not have been made. The methods of the present disclosure may be used with any mammal or other animal. In some aspects, treatment results in a decrease or cessation of symptoms. A prophylactic effect includes delaying or eliminating the appearance of a disease or condition, delaying or eliminating the onset of symptoms of a disease or condition, slowing, halting, or reversing the progression of a disease or condition, or any combination thereof.

Nucleic acid molecules, compositions, and pharmaceutical compositions provided herein can be administered once or multiple times. Accordingly, nucleic acid molecules, compositions, and pharmaceutical compositions provided herein can be administered one, two, three, four, five, six, seven, eight, nine, ten, or more times. Timing between two or more administrations can be one week, two weeks, three weeks, four weeks, five weeks, six weeks, seven weeks, eight weeks, nine weeks, weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or more weeks, and any number or range in between. In some aspects, timing between two or more administrations is one month, two months, three months, four months, five months, six months, seven months, eight months, nine months, ten months, 11 months, 12 months, 13 months, 14 months, 15 months, months, 16 months, 17 months, 18 months, 19 months, 20 months, 21 months, 22 months, 23 months, 24 months, or more months, and any number or range in between. In other aspects, timing between two or more administrations can be one year, two years, three years, four years, five years, six years, seven years, eight years, nine years, ten years, or more years, and any number or range in between, Timing between the first and any subsequent administration can be the same or different. In one aspect, nucleic acid molecules, compositions, or pharmaceutical compositions provided herein are administered once.

More than one nucleic acid molecule, composition, or pharmaceutical composition can be administered in the methods provided herein. In one aspect, two or more nucleic acid molecules, compositions, or pharmaceutical compositions provided herein are administered simultaneously. In another aspect, two or more nucleic acid molecules, compositions, or pharmaceutical compositions provided herein are administered sequentially. Simultaneous and sequential administrations can include any number and any combination of nucleic acid molecules, compositions, or pharmaceutical compositions provided herein. Multiple nucleic acid molecules, compositions, or pharmaceutical compositions that are administered together or sequentially can include transgenes encoding different antigenic proteins or fragments thereof. In this manner, immune responses against different antigenic targets can be induced. Two, three, four, five, six, seven, eight, nine, ten, or more nucleic acid molecules, compositions, or pharmaceutical compositions including transgenes encoding different antigenic proteins or fragments thereof can be administered simultaneously or sequentially. Any combination of nucleic acid molecules, compositions, and pharmaceutical compositions including any combination of transgenes can be administered simultaneously or sequentially. In some aspects, administration is simultaneous. In other aspects, administration is sequential. Timing between two or more administrations can be one week, two weeks, three weeks, four weeks, five weeks, six weeks, seven weeks, eight weeks, nine weeks, weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or more weeks, and any number or range in between. In some aspects, timing between two or more administrations is one month, two months, three months, four months, five months, six months, seven months, eight months, nine months, ten months, 11 months, 12 months, 13 months, 14 months, 15 months, months, 16 months, 17 months, 18 months, 19 months, 20 months, 21 months, 22 months, 23 months, 24 months, or more months, and any number or range in between. In other aspects, timing between two or more administrations can be one year, two years, three years, four years, five years, six years, seven years, eight years, nine years, ten years, or more years, and any number or range in between, Timing between the first and any subsequent administration can be the same or different. Nucleic acid molecules, compositions, and pharmaceutical compositions provided herein can be administered with any other vaccine or treatment.

Following administration of the composition to the subject, the protein product encoded by the self-replicating RNA of the disclosure (e.g., an antigen) is detectable in the target tissues for at least about one to seven days or longer. For example, the protein product may be detectable in the target tissues at a concentration (e.g., a therapeutic concentration) of at least about 0.025-1.5 µg/ml (e.g., at least about 0.050 µg/ml, at least about 0.075 µg/ml, at least about 0.1 µg/ml, at least about 0.2 µg/ml, at least about 0.3 µg/ml, at least about 0.4 µg/ml, at least about 0.5 µg/ml, at least about 0.6 µg/ml, at least about 0.7 µg/ml, at least about 0.8 µg/ml, at least about 0.9 µg/ml, at least about 1.0 µg/ml, at least about 1.1 µg/ml, at least about 1.2 µg/ml, at least about 1.3 µg/ml, at least about 1.4 µg/ml, or at least about 1.5 µg/ml), for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 days or longer following administration of the composition to the subject.

In some embodiments, a pharmaceutical composition of the present disclosure is administered to a subject once per month. In some embodiments, a pharmaceutical composition of the present disclosure is administered to a subject twice per month. In some embodiments, a pharmaceutical composition of the present disclosure is administered to a subject three times per month. In some embodiments, a pharmaceutical composition of the present disclosure is administered to a subject four times per month.

Alternatively, the compositions of the present disclosure may be administered in a local rather than systemic manner, for example, via injection of the pharmaceutical composition directly into a targeted tissue, preferably in a depot or sustained release formulation. Local delivery can be affected in various ways, depending on the tissue to be targeted. For example, aerosols containing compositions of the present disclosure can be inhaled (for nasal, tracheal, or bronchial delivery); compositions of the present disclosure can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing compositions of the present disclosure complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

The self-replicating RNA, formulations thereof, or encoded proteins described herein may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. Preferably, the methods of treatment of the present disclosure encompass the delivery of pharmaceutical, prophylactic, diagnostic, or imaging compositions in combination with agents that may improve their bioavailability, reduce and/or modify their metabolism, inhibit their excretion, and/or modify their distribution within the body. As a non-limiting example, a self-replicating RNA of the disclosure may be used in combination with a pharmaceutical agent for immunizing or vaccinating a subject. In general, it is expected that agents utilized in combination with the presently disclosed self-replicating RNA and formulations thereof be utilized at levels that do not exceed the levels at which they are utilized individually. In some embodiments, the levels utilized in combination will be lower than those utilized individually. In one embodiment, the combinations, each or together may be administered according to the split dosing regimens as are known in the art.

Ranges: throughout this disclosure, various aspects can be presented in range format. It should be understood that any description in range format is merely for convenience and brevity and not meant to be limiting. Accordingly, the description of a range should be considered to have specifically disclosed all possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example 1, 2, 2.1, 2.2, 2.5, 3, 4, 4.75, 4.8, 4.85, 4.95, 5, 5.5, 5.75, 5.9, 5.00, and 6. This applies to a range of any breadth.

Example 1

This example describes characterization of self-replicating (STARR™) technology using firefly luciferase transgene expression. In vitro transcripts were formulated with lipid nanoparticles (LNP) at a concentration of 0.1 mg/ml, and injected intramuscularly in both legs of female BALB/C mice (n=3) at a dose of 5 ug per leg. Expression of firefly luciferase (FLuc) was measured by IVIS Lumina LT Series III (PerkinElmer) by administering 100 ul of 1.5 mg Xenolight D-luciferin (PerkinElmer) in PBS via intraperitoneal injection ~10 min prior to the measurement. Six data points per group of mice were obtained at each time point (FIGS. 2A-2D).

Figure 2A:
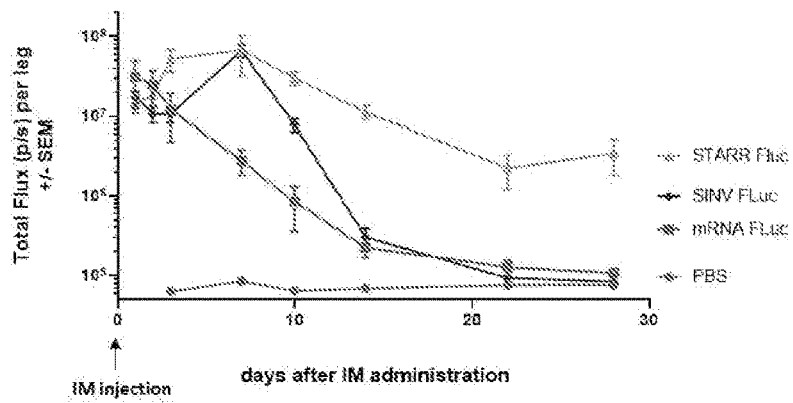
FIGS. 2A-2D show characterization of STARR™ technology with firefly luciferase transgene expression. (2A) Firefly luciferase (FLuc) expression from STARR™ Fluc, SINV FLuc, and mRNA FLuc was monitored up to day 28 by In Vivo Imaging System (IVIS). The average of total flux (p/s) from 6 injection sites in a mouse group was plotted at each time point with a standard error of mean, SEM. (2B) IVIS picture of three mice (6 injection sites) per group on day 14 is shown for each group that was administered with the test article labeled below the picture. (2C) Luciferase expression from mice that were intramuscularly injected with STARR™ FLuc was monitored by IVIS up to 63 days post administration. (2D) Effect of prior administration of replicon backbone was examined for STARR™ (upper panel) and SINV (lower panel). Replicon encoding FLuc was IM injected at 7 days post dose of replicon with homologous backbone with an irrelevant gene/sequence (labeled STARR™ irr or SINV irr) at day 0. As a reference, a mouse group with PBS administration at day 0 was included in each of STARR™ and SINV group.
Figure 2B:
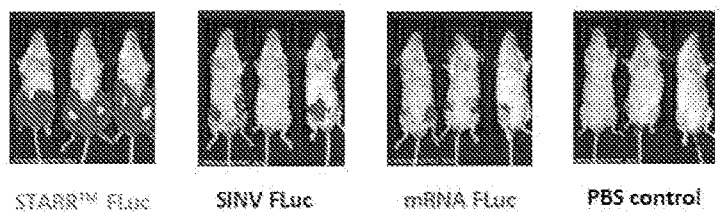
Figure 2C:
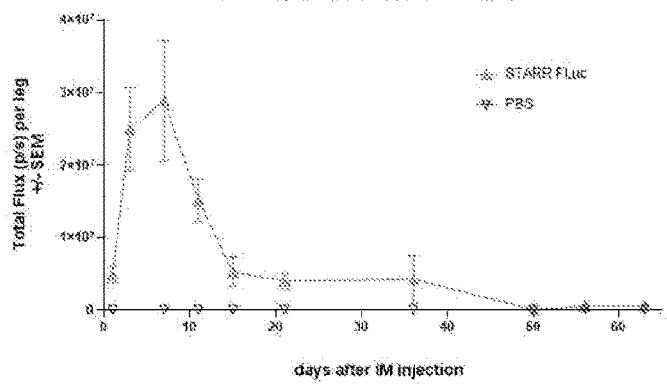
Figure 2D:
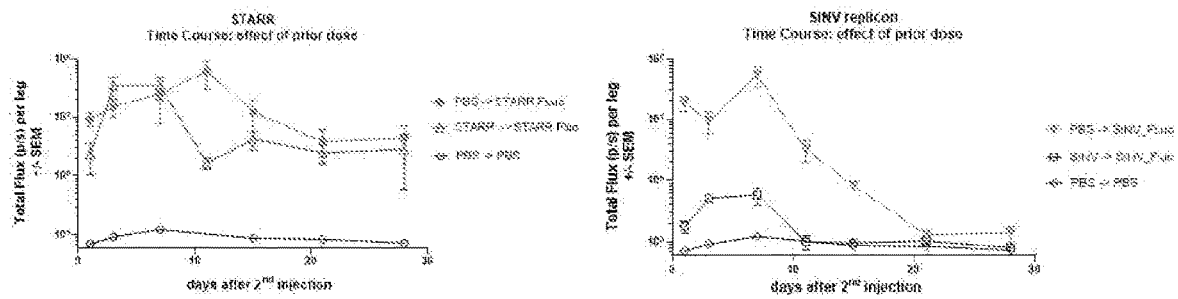

Firefly luciferase (FLuc) expression was monitored from STARR™ Fluc, SINV FLuc, and mRNA FLuc up to day 28 by In Vivo Imaging System (IVIS). Enhanced levels and durations of transgene expression from STARR™ were observed. The expression from STARR™ Fluc peaked around day 3 to 7 and declined until day 22. Fluc expression from SINV FLuc also peaked on day 10, however, the expression was reduced at a significantly faster rate than STARR™ FLuc. Additionally, the expression on day 3 was significantly lower than STARR™ FLuc. FLuc expression from the conventional mRNA backbone was highest at day 1, the earliest time point in this study, and declined at a slightly faster rate than that of STARR™—Fluc (FIG. 2A). FIG. 2B shows that at 14 days post dosing, FLuc expression from STARR™ FLuc was higher than the other groups by about two orders of magnitude. FIG. 2D shows that the effect of the STARR™ backbone remained minimal throughout the experimental period (up to day 28), while prior administration of STNV replicon backbone resulted in a reduction of FLuc transgene expression by ~2 orders of magnitude.

Figure 3:
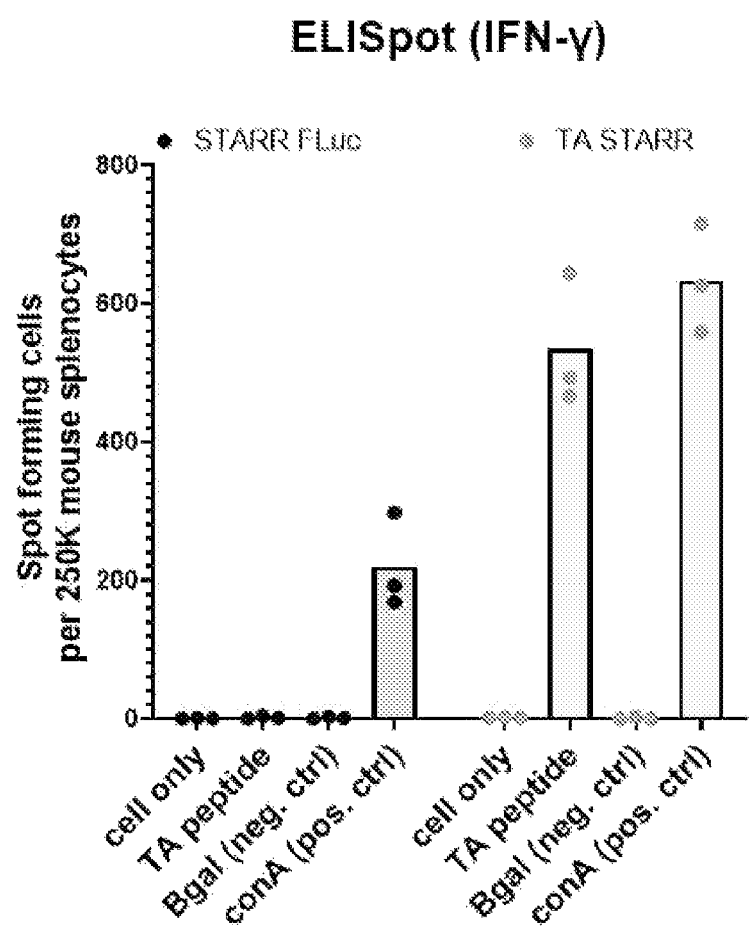
FIG. 3 shows that STARR™ elicits antigen-specific IFN-gamma response. Enzyme-linked immune absorbent spot ELISpot was used to count the number of splenocytes that were specifically stimulated by an antigen peptide of the same amino acid sequence encoded in TA STARR™. Neither no peptide (cell only) nor irrelevant peptide (Bgal) elicited significant IFN-gamma from splenocytes from mice vaccinated with STARR™ FLuc or TA STARR™. Stimulation with AH1-A5 peptide resulted in the detection of IFN-gamma-producing cells specifically from the mice that were vaccinated with TA STARR™. Concanavalin A (ConA) was used as a positive control of IFN-gamma production.
Figure 4A:
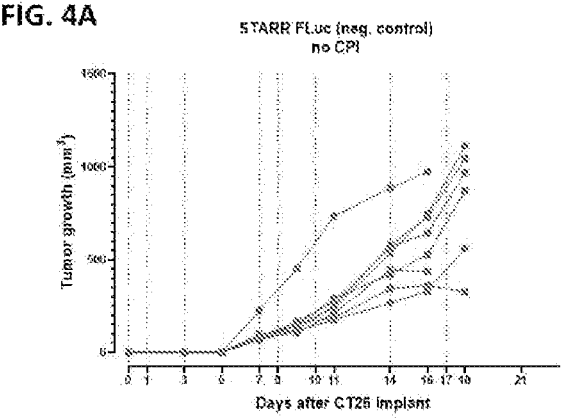
FIGS. 4A-4F illustrate reduced tumor growth rate by TA STARR™ vaccination in a CT26 syngeneic mouse model. CT26 murine colorectal carcinoma cells ($5\times10^5$) were subcutaneously implanted in 10-week old female BALB/c mice (n=8 per group). On days 1 and 8, the mice were vaccinated with STARR™ FLuc, a negative control, or TA STARR™, which encodes AH1A5 epitope. Tumor growth was monitored in mice vaccinated with (4A) STARR™ FLuc without checkpoint inhibitor treatment; (4B) STARR™ FLuc with a combination anti-PD1/PDL1 treatment; (4C) STARR™ FLuc with a combination anti-CTLA4 treatment; (4D) STARR™ vaccine without checkpoint inhibitor treatment; (4E) STARR™ vaccine with a combination treatment of anti-PD1 and anti-PDL1; and (4F) STARR™ vaccine with a combination treatment of anti-CTLA4. The individual tumor growth curves from a mouse group that were administered with STARR™ FLuc and TA STARR™ are shown in upper and lower panels, respectively.
Figure 4B:
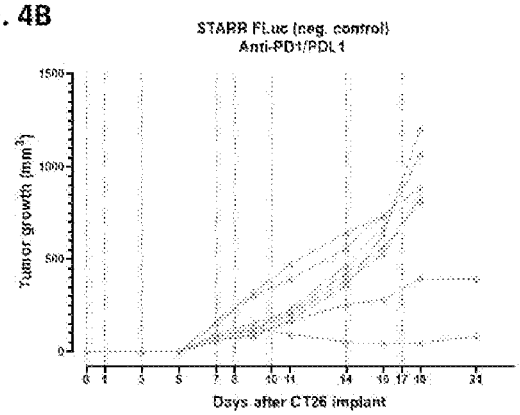
Figure 4C:
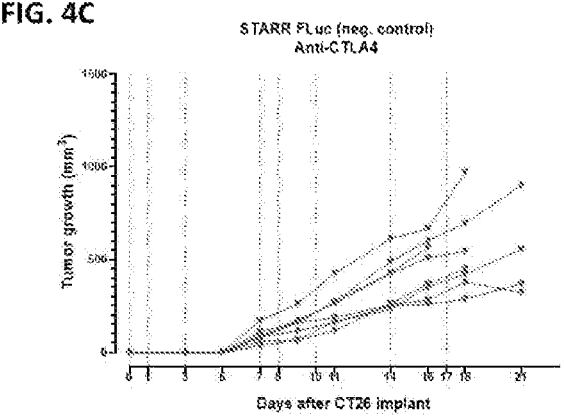
Figure 4D:
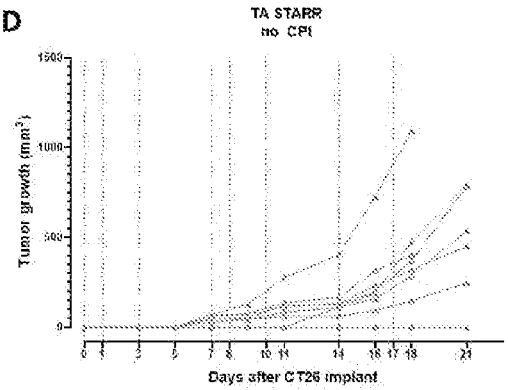
Figure 4E:
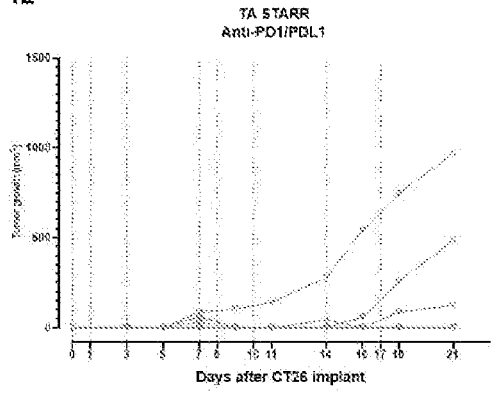
Figure 4F:
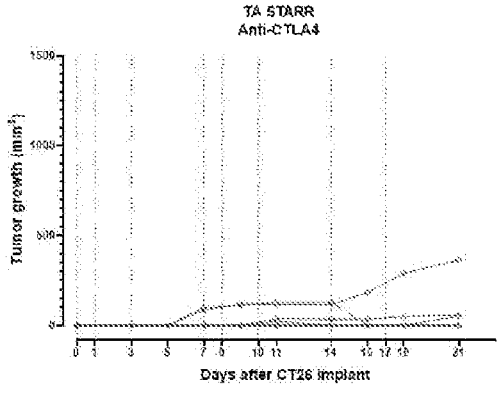

A cancer vaccine substrate, TA STARR™, was constructed next with the STARR™ backbone that encodes AH1A5 epitope from gp70, an envelope glycoprotein of endogenous Murine leukemia virus. AH1 (SPSYVYHQF) (SEQ ID NO:110) is an H-2Ld-restricted antigen of gp70423-431, which is expressed in tumor cells such as the CT26 colorectal cancer cell line, but not expressed in most of the normal tissues. AH1-A5 is a mutated sequence with SPSYAYHQF (SEQ ID NO:111) (the mutation underlined) with enhanced affinity to the T cell receptor (Slansky, et al., 2000, Immunity 13: 529-538). The open reading frame of the TA STARR™ subgenomic RNA contains a cassette with a signal peptide from the HLA class I antigen, gp70 sequence containing AH1A5 epitope, ovalbumin epitope (OVA323-339), and MHC class I trafficking signal (Kreiter, et al. 2008, J Immunol 180: 309-318). Three female BALB/c mice were intramuscularly injected with 10 ug of LNP formulated STARR™ transcripts, STARR™ FLuc or TA STARR™, on day 0 and day 7. On day 16, the spleens were harvested and the splenocytes were isolated. Splenocytes ($2.5 \times 10^5$ cells) were incubated with or without AH1A5 (SPSYAYHQF) (SEQ ID NO:111), beta-gal peptide (TPHPARIGL) (SEQ ID NO:112) at 1 ug/ml, and 1× Concanavalin A (Life Technologies). ELISpot detecting murine IFN-gamma (ImmunoSpot) was performed according to the manufacturer's instructions. As can be seen in FIG. 3, TA STARR™ elicited antigen-specific IFN-gamma responses.

Figure 5:
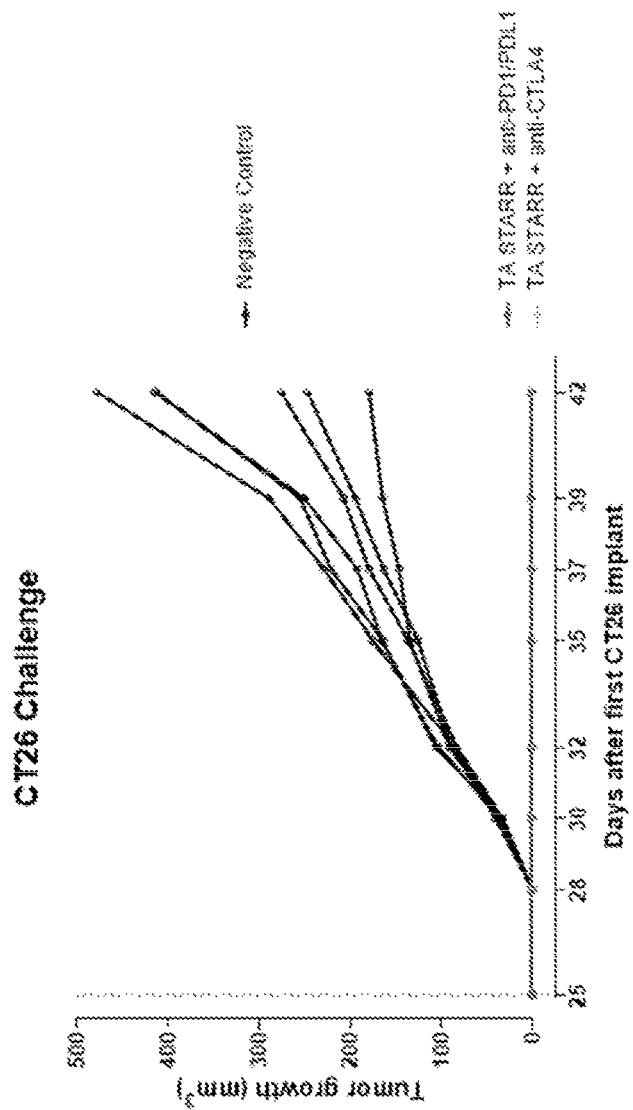
FIG. 5 illustrates prolonged protection by combination treatment of TA STARR™ Vaccine with checkpoint inhibitors. Mice that were treated with TA STARR™ combined with anti-PD1/PDL1 or anti-CTLA4 were found to be resistant to tumor development following the CT26 challenge at day 25 to 42. Naïve mice were used as a control for the CT26 tumor growth.

BALB/c mice, 10 week-old female, were subcutaneously implanted in the right flank with $5 \times 10^5$ cells of CT26 cells in PBS. A day later, LNP formulated STARR™ RNA was injected intramuscularly in the left leg at a dose of 10 ug in 100 ul. The mice were administered another booster shot on day 8 with the same dose. For a group with combination treatment of anti-mouse PD1 (RMP1-14, BioXCell) and anti-mouse PDL1 (10F.9G2, BioXcell), the combined checkpoint inhibitor (100 ug each) was administered via intraperitoneal injection in the right quadrant twice weekly for two weeks starting on day 3. For a group with the treatment of anti-mouse CTLA4 (9H10, BioxCell), 200 ug of the checkpoint inhibitor was administered in the same manner but starting on day 7. Five mice of the group with the combo treatment of TA STARR™ vaccine and the checkpoint inhibitors remained tumor-free on day 25, and were further challenged by subcutaneous implantation of CT26 (5×105 cells) in the right flank where the implantation site was slightly above the first implantation site. Naïve mice were used as a control group. The tumor growth was monitored for another 17 days (i.e. up to day 42 since the first CT26 implantation) before euthanization. FIGS. 4A-4F illustrate reduced tumor growth resulting from TA STARR™ vaccination and FIG. 5 shows prolonged protection resulting from treatment with the TA STARR™ vaccine in combination with checkpoint inhibitors.

Figure 6A:
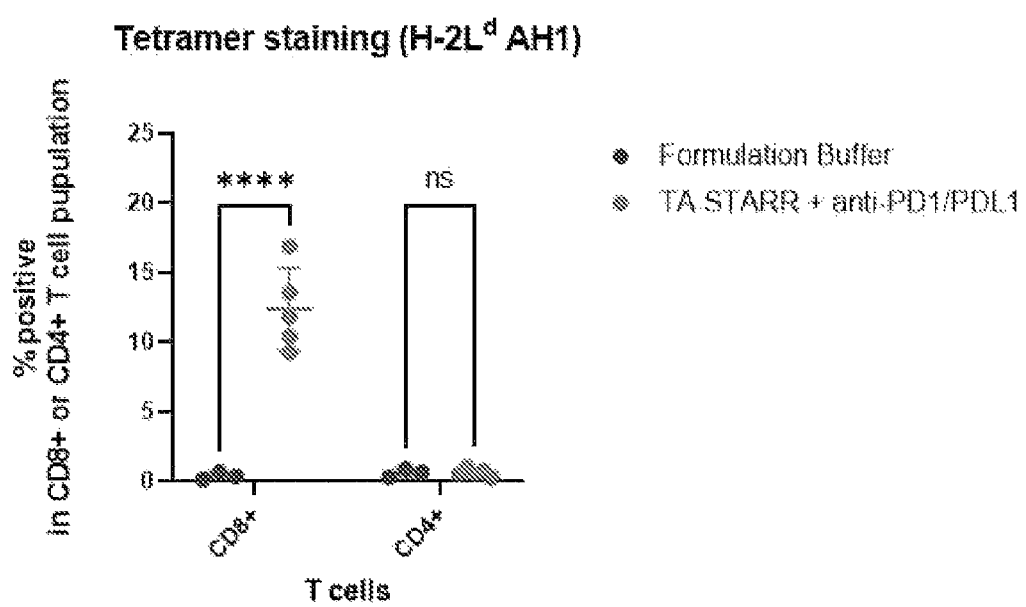
FIGS. 6A-6C show results from AH1-tetramer staining of CD8+ T-cells in the form of (6A) a graph and (6B and 6C) plots. Splenocytes from the mice group with combination treatment of TA STARR™ and anti-PD1/PDL1 at day 42 were stained with AH1 (H-2Ld)-tetramer. The staining was specific to CD8+ T cells from the mouse group with TA STARR™ treatment, and the population represented 9-17% of total CD8+ T cells from the splenocytes.
Figure 6B:
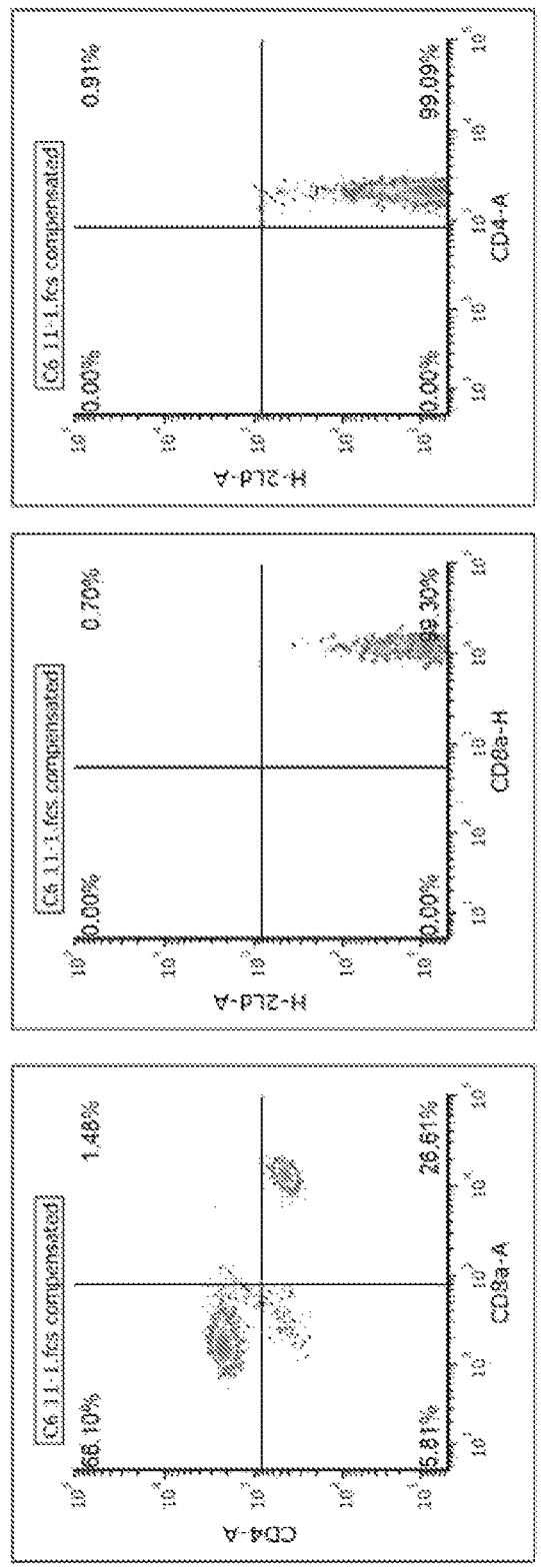
Figure 6C:
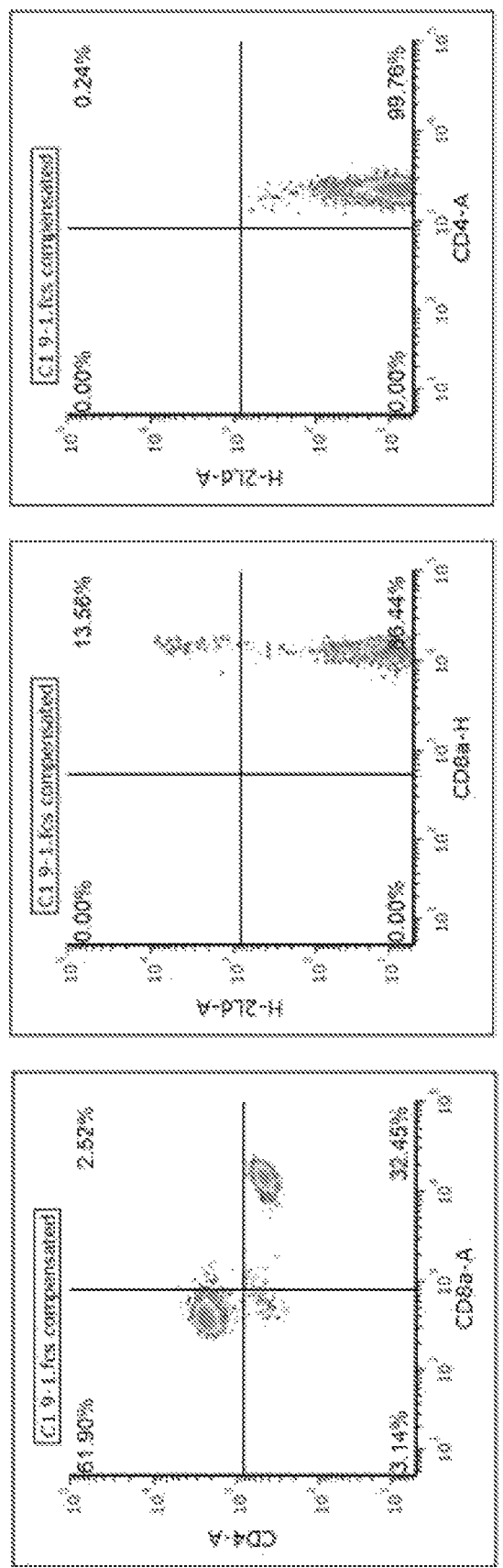
Figure 7:
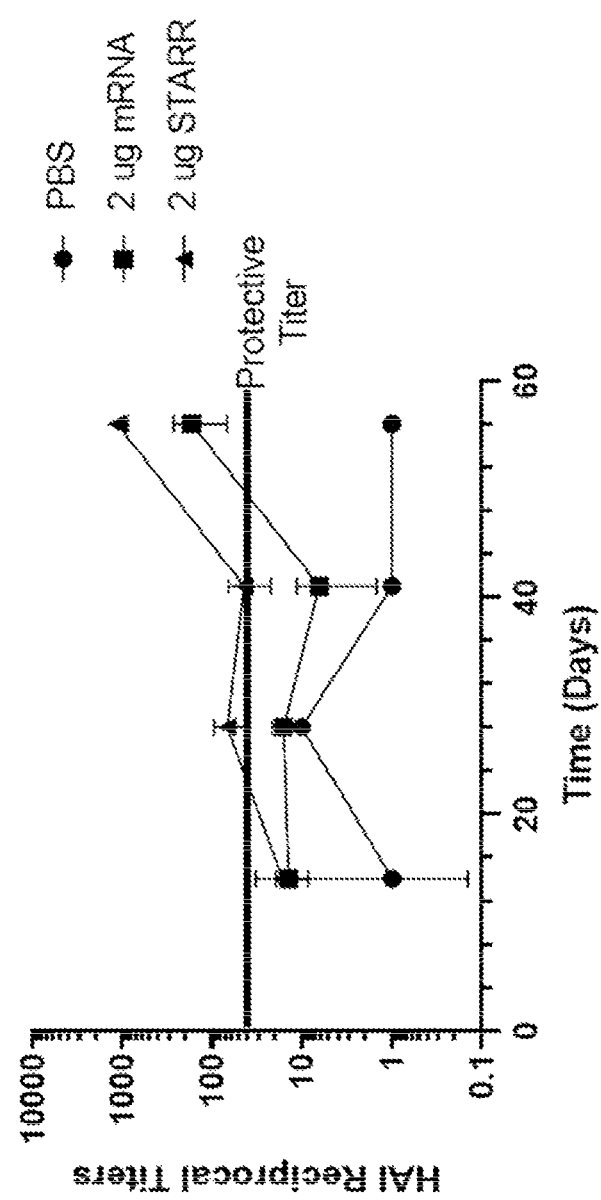
FIG. 7 shows HAI titers obtained for self-replicating RNA (STARR™) and mRNA constructs encoding the hemagglutinin of influenza virus A/California/07/2009 (H1N1).
Figure 8A:
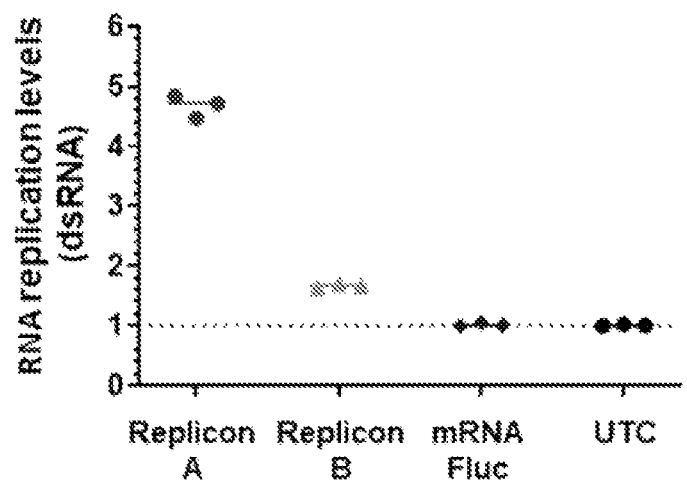
FIGS. 8A-8B show (8A) RNA replication levels and (8B) luciferase reporter gene expression levels for the indicated self-replicating (replicon) RNAs as compared to mRNA.
Figure 8B:
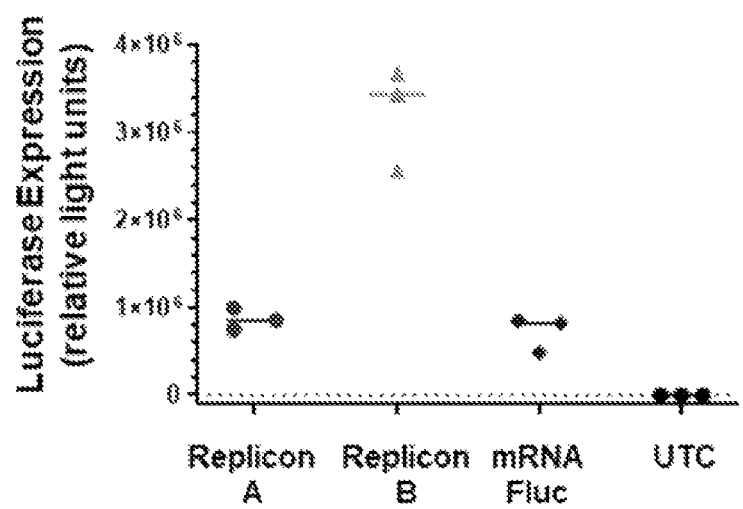
Figure 9A:
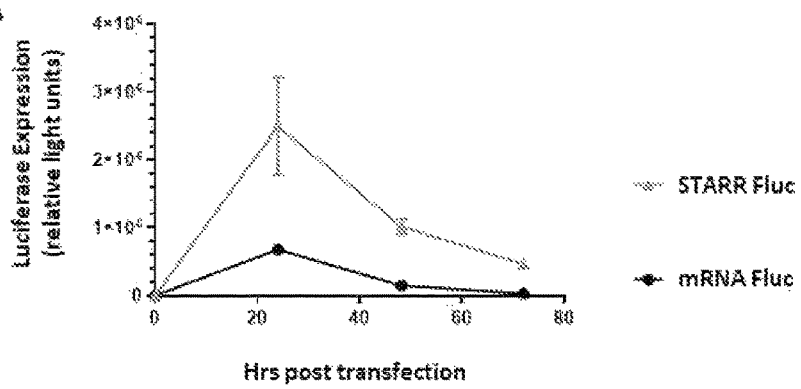
FIGS. 9A-9C shows duration of luciferase reporter gene expression for self-replicating (replicon) RNA (STARR™), such as (9A) STARR™ FLuc, (9B) STARR™ FLuc IRES-E3L, and (9C) STARR™ FLuc IRES E3L (short 3' UTR) as compared to mRNA.
Figure 9B:
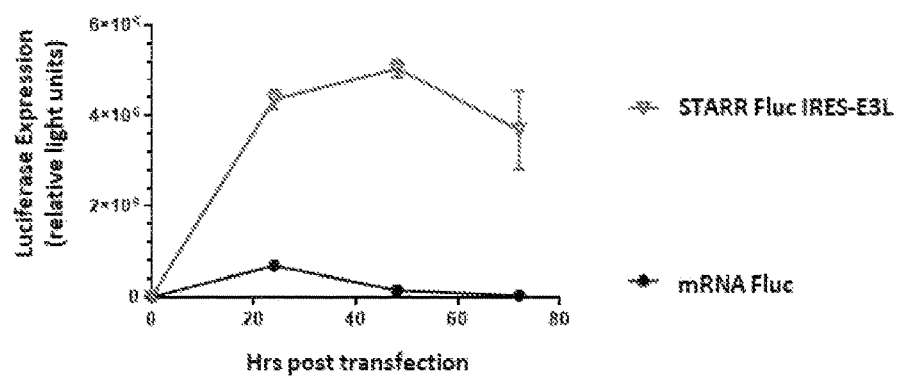
Figure 9C:
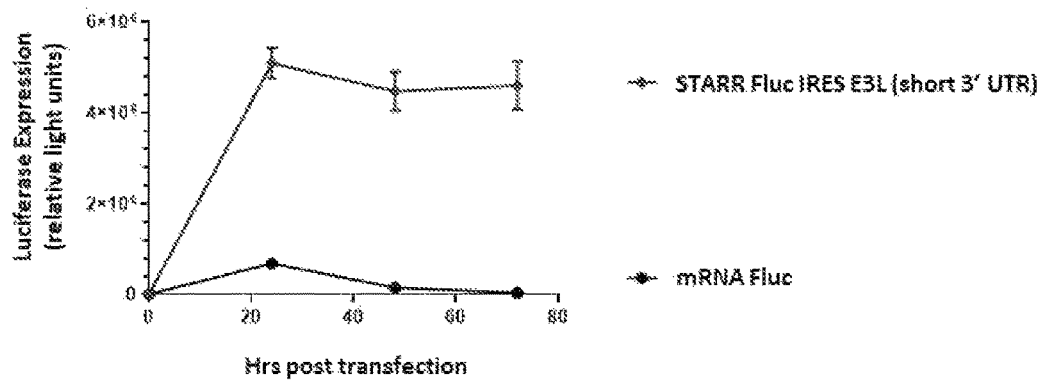

Splenocytes from the combination treatment group with TA STARR™ and anti-PD1/PDL1 were harvested for tetramer staining with AH1 peptide. Splenocytes from the control group with the LNP formulation buffer with the same dosing schedule were used as a negative control. The splenocytes ($2 \times 10^6$ cells) were incubated with AH1 (H-2Ld)-tetramer (MBL) followed by appropriate fluorescent-labeled antibodies (Alexa Fluor 488 anti-CD8a (53-6.7), Pacific Orange anti-CD4 (RM4-5), and Pacific Blue anti-mouse CD3E (145-2C11), (eBioscience) and DRAQ7 (Invitrogen) by following the manufacture's recommendation, and 500 K events were analyzed by ZE5 Cell Analyzer (Bio-Rad). Results are shown in FIGS. 6A-6C.

TABLE 6

Transgene ORF nucleotide sequence

| mARM # | RNA back bone | transgene | Sequence |
|---|---|---|---|
| 2809 (SEQ ID NO: 84) | STARR$^{TM}$ | Fluc | AUGGAAGAUGCCAAAAACAUUAAGAAGGGCCCAGCGCCAUUCUACC CACUCGAAGACGGGACCGCCGGCGAGCAGCUGCACAAAGCCAUGAA GCGCUACGCCCUGGUGCCCGGCACCAUCGCCUUUACCGACGCACAU AUCGAGGUGGACAUUACCUACGCCGAGUACUUCGAGAUGAGCGUUC GGCUGGCAGAAGCUAUGAAGCGCUAUGGGCUGAAUACAAACCAUCG GAUCGUGGUGUGCAGCGAGAAUAGCUUGCAGUUCUUCAUGCCCGUG UUGGGUGCCCUGUUCAUCGGUGUGGCUGUGGCCCCAGCUAACGACA UCUACAACGAGCGCGAGCUGCUGAACAGCAUGGGCAUCAGCCAGCC CACCGUCGUAUUCGUGAGCAAGAAAGGGCUGCAAAAGAUCCUCAAC GUGCAAAAGAAGCUACCGAUCAUACAAAAGAUCAUCAUCAUGGAUA GCAAGACCGACUACCAGGGCUUCCAAAGCAUGUACACCUUCGUGAC UUCCCAUUUGCCACCCGGCUUCAACGAGUACGACUUCGUGCCCGAG AGCUUCGACCGGGACAAAACCAUCGCCCUGAUCAUGAACAGUAGUG GCAGUACCGGAUUGCCCAAGGGCGUAGCCCUACCGCACCGCACCGC UUGUGUCCGAUUCAGUCAUGCCCGCGACCCCAUCUUCGGCAACCAG AUCAUCCCCGACACCGCUAUCCUCAGCGUGGUGCCAUUUCACCACG GCUUCGGCAUGUUCACCACGCUGGGCUACUUGAUCUGCGGCUUUCG GGUCGUGCUCAUGUACCGCUUCGAGGAGGAGCUAUUCUUGCGCAGC UUGCAAGACUAUAAGAUUCAAUCUGCCCUGCUGGUGCCCACACUAU UUAGCUUCUUCGCUAAGAGCACUCUCAUCGACAAGUACGACCUAAG CAACUUGCACGAGAUCGCCAGCGGCGGGGCGCCGCUCAGCAAGGAG GUAGGUGAGGCCGUGGCCAAACGCUUCCACCUACCAGGCAUCCGAC AGGGCUACGGCCUGACAGAAACAACCAGCGCCAUUCUGAUCACCCC CGAAGGGGACGACAAGCCUGGCGCAGUAGGCAAGGUGGUGCCCUUC UUCGAGGCUAAGGUGGUGGACUUGGACACCGGUAAGACACUGGGUG UGAACCAGCGCGGCGAGCUGUGCGUCCGUGGCCCCAUGAUCAUGAG CGGCUACGUUAACAACCCCGAGGCUACAAACGCUCUCAUCGACAAG GACGGCUGGCUGCACAGCGGCGACAUCGCCUACUGGGACGAGGACG AGCACUUCUUCAUCGUGGACCGGCUGAAGUCCCUGAUCAAAUACAA GGGCUACCAGGUAGCCCCAGCCGAACUGGAGAGCAUCCUGCUGCAA CACCCCAACAUCUUCGACGCCGGGGUCGCCGGCCUGCCCGACGACG AUGCCGGCGAGCUGCCCGCCGCAGUCGUCGUGCUGGAACACGGUAA AACCAUGACCGAGAAGGAGAUCGUGGACUAUGUGGCCAGCCAGGUU ACAACCGCCAAGAAGCUGCGCGGUGGUGUUGUGUUCGUGGACGAGG UGCCUAAAGGACUGACCGGCAAGUUGGACGCCCGCAAGAUCCGCGA GAUUCUCAUUAAGGCCAAGAAGGGCGGCAAGAUCGCCGUGUAA |
| 2842 (SEQ ID NO: 85) | SINV replicon | Fluc | AUGGAAGAUGCCAAAAACAUUAAGAAGGGCCCAGCGCCAUUCUACC CACUCGAAGACGGGACCGCCGGCGAGCAGCUGCACAAAGCCAUGAA GCGCUACGCCCUGGUGCCCGGCACCAUCGCCUUUACCGACGCACAU AUCGAGGUGGACAUUACCUACGCCGAGUACUUCGAGAUGAGCGUUC GGCUGGCAGAAGCUAUGAAGCGCUAUGGGCUGAAUACAAACCAUCG GAUCGUGGUGUGCAGCGAGAAUAGCUUGCAGUUCUUCAUGCCCGUG UUGGGUGCCCUGUUCAUCGGUGUGGCUGUGGCCCCAGCUAACGACA UCUACAACGAGCGCGAGCUGCUGAACAGCAUGGGCAUCAGCCAGCC CACCGUCGUAUUCGUGAGCAAGAAAGGGCUGCAAAAGAUCCUCAAC GUGCAAAAGAAGCUACCGAUCAUACAAAAGAUCAUCAUCAUGGAUA GCAAGACCGACUACCAGGGCUUCCAAAGCAUGUACACCUUCGUGAC UUCCCAUUUGCCACCCGGCUUCAACGAGUACGACUUCGUGCCCGAG AGCUUCGACCGGGACAAAACCAUCGCCCUGAUCAUGAACAGUAGUG GCAGUACCGGAUUGCCCAAGGGCGUAGCCCUACCGCACCGCACCGC UUGUGUCCGAUUCAGUCAUGCCCGCGACCCCAUCUUCGGCAACCAG AUCAUCCCCGACACCGCUAUCCUCAGCGUGGUGCCAUUUCACCACG GCUUCGGCAUGUUCACCACGCUGGGCUACUUGAUCUGCGGCUUUCG |

TABLE 6-continued

| | | | |
|---|---|---|---|
| | | | GGUCGUGCUCAUGUACCGCUUCGAGGAGGAGCUAUUCUUGCGCAGC<br>UUGCAAGACUAUAAGAUUCAAUCUGCCCUGCUGGUGCCCACACUAU<br>UUAGCUUCUUCGCUAAGAGCACUCUCAUCGACAAGUACGACCUAAG<br>CAACUUGCACGAGAUCGCCAGCGGCGGGGCGCCGCUCAGCAAGGAG<br>GUAGGUGAGGCCGUGGCCAAACGCUUCCACCUACCAGGCAUCCGAC<br>AGGGCUACGGCCUGACAGAAACAACCAGCGCCAUUCUGAUCACCCC<br>CGAAGGGGACGACAAGCCUGGCGCAGUAGGCAAGUGGUGCCCUUC<br>UUCGAGGCUAAGGUGGUGGACUUGGACACCGGUAAGACACUGGGUG<br>UGAACCAGCGCGGCGAGCUGUGCGUCCGUGGCCCCAUGAUCAUGAG<br>CGGCUACGUUAACAACCCCGAGGCUACAAACGCUCUCAUCGACAAG<br>GACGGCUGGCUGCACAGCGGCGACAUCGCCUACUGGGACGAGGACG<br>AGCACUUCUUCAUCGUGGACCGGCUGAAGUCCCUGAUCAAAUACAA<br>GGGCUACCAGGUAGCCCCAGCCGAACUGGAGAGCAUCCUGCUGCAA<br>CACCCCAACAUCUUCGACGCCGGGGUCGCCGGCCUGCCCGACGACG<br>AUGCCGGCGAGCUGCCCGCCGCAGUCGUCGUGCUGGAACACGGUAA<br>AACCAUGACCGAGAAGGAGAUCGUGGACUAUGUGGCCAGCCAGGUU<br>ACAACCGCCAAGAAGCUGCGCGGUGGUGUUGUGUUCGUGGACGAGG<br>UGCCUAAAGGACUGACCGGCAAGUUGGACGCCCGCAAGAUCCGCGA<br>GAUUCUCAUUAAGGCCAAGAAGGGCGGCAAGAUCGCCGUGUAA |
| 1782<br>(SEQ<br>ID<br>NO: 86) | mRNA<br>(TEV-<br>XbG) | Fluc | AUGGAAGAUGCCAAAAACAUUAAGAAGGGCCCAGCGCCAUUCUACC<br>CACUCGAAGACGGGACCGCCGGCGAGCAGCUGCACAAAGCCAUGAA<br>GCGCUACGCCCUGGUGCCCGGCACCAUCGCCUUUACCGACGCACAU<br>AUCGAGGUGGACAUUACCUACGCCGAGUACUUCGAGAUGAGCGUUC<br>GGCUGGCAGAAGCUAUGAAGCGCUAUGGGCUGAAUACAAACCAUCG<br>GAUCGUGGUGUGCAGCGAGAAUAGCUUGCAGUUCUUCAUGCCCGUG<br>UUGGGUGCCCUGUUCAUCGGUGUGGCUGUGGCCCCAGCUAACGACA<br>UCUACAACGAGCGCGAGCUGCUGAACAGCAUGGGCAUCAGCCAGCC<br>CACCGUCGUAUUCGUGAGCAAGAAAGGGCUGCAAAAGAUCCUCAAC<br>GUGCAAAAGAAGCUACCGAUCAUACAAAAGAUCAUCAUCAUGGAUA<br>GCAAGACCGACUACCAGGGCUUCCAAAGCAUGUACACCUUCGUGAC<br>UUCCCAUUUGCCACCCGGCUUCAACGAGUACGACUUCGUGCCCGAG<br>AGCUUCGACCGGGACAAAACCAUCGCCCUGAUCAUGAACAGUAGUG<br>GCAGUACCGGAUUGCCCAAGGGCGUAGCCCUACCGCACCGCACCGC<br>UUGUGUCCGAUUCAGUCAUGCCCGCGACCCCAUCUUCGGCAACCAG<br>AUCAUCCCCGACACCGCUAUCCUCAGCGUGGUGCCAUUUCACCACG<br>GCUUCGGCAUGUUCACCACGCUGGGCUACUUGAUCUGCGGCUUUCG<br>GGUCGUGCUCAUGUACCGCUUCGAGGAGGAGCUAUUCUUGCGCAGC<br>UUGCAAGACUAUAAGAUUCAAUCUGCCCUGCUGGUGCCCACACUAU<br>UUAGCUUCUUCGCUAAGAGCACUCUCAUCGACAAGUACGACCUAAG<br>CAACUUGCACGAGAUCGCCAGCGGCGGGGCGCCGCUCAGCAAGGAG<br>GUAGGUGAGGCCGUGGCCAAACGCUUCCACCUACCAGGCAUCCGAC<br>AGGGCUACGGCCUGACAGAAACAACCAGCGCCAUUCUGAUCACCCC<br>CGAAGGGGACGACAAGCCUGGCGCAGUAGGCAAGUGGUGCCCUUC<br>UUCGAGGCUAAGGUGGUGGACUUGGACACCGGUAAGACACUGGGUG<br>UGAACCAGCGCGGCGAGCUGUGCGUCCGUGGCCCCAUGAUCAUGAG<br>CGGCUACGUUAACAACCCCGAGGCUACAAACGCUCUCAUCGACAAG<br>GACGGCUGGCUGCACAGCGGCGACAUCGCCUACUGGGACGAGGACG<br>AGCACUUCUUCAUCGUGGACCGGCUGAAGUCCCUGAUCAAAUACAA<br>GGGCUACCAGGUAGCCCCAGCCGAACUGGAGAGCAUCCUGCUGCAA<br>CACCCCAACAUCUUCGACGCCGGGGUCGCCGGCCUGCCCGACGACG<br>AUGCCGGCGAGCUGCCCGCCGCAGUCGUCGUGCUGGAACACGGUAA<br>AACCAUGACCGAGAAGGAGAUCGUGGACUAUGUGGCCAGCCAGGUU<br>ACAACCGCCAAGAAGCUGCGCGGUGGUGUUGUGUUCGUGGACGAGG<br>UGCCUAAAGGACUGACCGGCAAGUUGGACGCCCGCAAGAUCCGCGA<br>GAUUCUCAUUAAGGCCAAGAAGGGCGGCAAGAUCGCCGUGUAA |
| 2847<br>(SEQ ID<br>NO: 87) | STARR™ | KRAS<br>epitope wt | AUGAAGUUGGUGGUUGUGGGGGCCGGGGGUGUUGGCAAAAGCGCCC<br>UUACAAUUUGA |
| 2862<br>(SEQ ID<br>NO: 88) | SINV<br>replicon | Empty | AUGGAUCCUAGACGCUACGCCCCAAUGAUCCGACCAGCAAAACUCG<br>AUGUACUUCCGAGGAACUGA |
| 3060<br>(SEQ<br>ID<br>NO: 89) | STARR™ | Signal<br>peptide-<br>gp70 with<br>AH1A5-<br>MITD | AUGAGAGUGACAGCCCCUAGAACCUUACUGCUUCUGCUUUGGGGAG<br>CUGUUGCUCUGACAGAGACAUGGGCUGGAUCUCUGGAGGCGGGGAC<br>CGGCCAGGGCCUGUGCAUCGGCGCCGUGCCCAAGACCCACCAGGUG<br>CUGUGCAACACCACCCAGAAGACCAGCGACGGCAGCUACUACCUGG<br>CCGCUCCCACCGGCACCACCUGGGCCUGCAGCACCGGCCUGACCCC<br>UUGCAUCAGCACCACCAUCCUGAACCUGACCACCGACUACUGCGUG<br>CUGGUGGAGCUGUGGCCCAGGGUGACCUACCACAGCCCCAGCUACG<br>CCUACCACCAGUUCGAGAGGAGGGCCAAGUACAAGAGGGAGCCCGU<br>GAGCCUGACCCUGGCCCUGCUGCUGGGCGGCCUGACAAUGGGCGGC<br>AUCGCCGCCGGCAUCGGCACCGGCACCACCGCCCUGGUGGCCACCA<br>AGCAGUUCCAGCAGCUGCAGGCCGCCAUGCACGACGACCUGAAGGA<br>GGUGGAGAAGUCCAUCACCAACCUGGAGAAGUCCCUGACCAGCCUG<br>AGCGAGGUGGUGCUGCAGAACAGGAGGGGCCUGGACCUGCUGUUCC<br>UGAAGGAGGGCGGCCUGUGCGCCGCCCUGAAGGAGGAGUGCUGCCU<br>GUACGCCGACCACACCGGCCUGGUGAUCGUGGGCAUUGUCGCUGGC |

TABLE 6-continued

| | | | |
|---|---|---|---|
| | | | CUGGCCGUCCUCGCCGUGGUGGUGAUUGGAGCUGUGGUCGCAGCUG<br>UUAUGUGCAGAAGAAAGUCAUCCGGCGGAAAGGGAGGCUCCUACUC<br>UCAGGCUGCUUCUGCUACAGUGCCUAGAGCUCUUAUGUGUUUAUCU<br>CAGCUGUAA |
| 3061<br>(SEQ<br>ID<br>NO: 90) | STARR™ | Signal<br>peptide-<br>AH1A5 OVA-<br>MITD | AUGAGAGUGACAGCCCCUAGAACCUUACUGCUUCUGCUUUGGGGAG<br>CUGUUGCUCUGACAGAGACAUGGGCUGGAUCUUACCACAGCCCCAG<br>CUACGCCUACCACCAGUUCGAGAGGGGGGAGGAGGCUCCGGGGGA<br>GGAGGCUCCCUGAAGAUCAGCCAGGCCGUGCACGCCGCCCACGCCG<br>AGAUCAACGAGGCCGGCCGGGAGGUGAUCGUGGGCAUUGUCGCUGG<br>CCUGGCCGUCCUCGCCGUGGUGGUGAUUGGAGCUGUGGUCGCAGCU<br>GUUAUGUGCAGAAGAAAGUCAUCCGGCGGAAAGGGAGGCUCCUACU<br>CUCAGGCUGCUUCUGCUACAGUGCCUAGAGCUCUUAUGUGUUUAUC<br>UCAGCUGUAA |
| 3076<br>(SEQ<br>ID<br>NO: 91) | STARR™ | Signal<br>peptide-<br>gp70 with<br>AH1A5-<br>MITD-FLAG | AUGAGAGUGACAGCCCCUAGAACCUUACUGCUUCUGCUUUGGGGAG<br>CUGUUGCUCUGACAGAGACAUGGGCUGGAUCUCUGAGCGAGGUGAC<br>CGGCCAGGGCCUGUGCAUCGGCGCCGUGCCCAAGACCCACCAGGUG<br>CUGUGCAACACCACCCAGAAGACCAGCGACGGCAGCUACUACCUGG<br>CCGCUCCCACCGGCACCACCUGGGCCUGCAGCACCGGCCUGACCCC<br>UUGCAUCAGCACCACCAUCCUGAACCUGACCACCGACUACUGCGUG<br>CUGGUGGAGCUGUGGCCCAGGGUGACCUACCACAGCCCCAGCUACG<br>CCUACCACCAGUUCGAGAGGGAGGGCCAAGUACAAGAGGGAGCCCGU<br>GAGCCUGACCCUGGCCCUGCUGCUGGGCGGCCUGACAAUGGGCGGC<br>AUCGCCGCCGGCGUGGGCACCGGCACCACCGCCCUGGUGGCCACCC<br>AGCAGUUCCAGCAGCUGCAGGCCGCCAUGCACGACGACCUGAAGGA<br>GGUGGAGAAGUCCAUCACCAACCUGGAGAAGUCCCUGACCAGCCUG<br>AGCGAGGUGGUGCUGCAGAACAGGAGGGGCCUGGACCUGCUGUUCC<br>UGAAGGAGGGCGGCCUGUGCGCCGCCCUGAAGGAGGAGUGCUGCCU<br>GUACGCCGACCACACCGGCCUGGUGAUCGUGGGCAUUGUCGCUGGC<br>CUGGCCGUCCUCGCCGUGGUGGUGAUUGGAGCUGUGGUCGCAGCUG<br>UUAUGUGCAGAAGAAAGUCAUCCGGCGGAAAGGGAGGCUCCUACUC<br>UCAGGCUGCUUCUGCUACAGUGCCUAGAGCUCUUAUGUGUUUAUCU<br>CAGCUGGGCGGCGGAGGCAGCGACUACAAGGACGACGAUGACAAGU<br>AA |
| 3068<br>(SEQ<br>ID<br>NO: 92) | STARR | Signal<br>peptide-<br>AH1A5 OVA-<br>MITD-FLAG | AUGAGAGUGACAGCCCCUAGAACCUUACUGCUUCUGCUUUGGGGAG<br>CUGUUGCUCUGACAGAGACAUGGGCUGGAUCUUACCACAGCCCCAG<br>CUACGCCUACCACCAGUUCGAGAGGGGGGAGGAGGCUCCGGGGGA<br>GGAGGCUCCCUGAAGAUCAGCCAGGCCGUGCACGCCGCCCACGCCG<br>AGAUCAACGAGGCCGGCCGGGAGGUGAUCGUGGGCAUUGUCGCUGG<br>CCUGGCCGUCCUCGCCGUGGUGGUGAUUGGAGCUGUGGUCGCAGCU<br>GUUAUGUGCAGAAGAAAGUCAUCCGGCGGAAAGGGAGGCUCCUACU<br>CUCAGGCUGCUUCUGCUACAGUGCCUAGAGCUCUUAUGUGUUUAUC<br>UCAGCUGGGCGGCGGAGGCAGCGACUACAAGGACGACGAUGACAAG<br>UAA |
| Transgene ORF amino acid sequence ||||
| mARM<br># | | transgene<br>description | Sequence |
| 2809,<br>2842,<br>1782<br>(SEQ<br>ID<br>NO: 93) | | Fluc | MEDAKNIKKGPAPFYPLEDGTAGEQLHKAMKRYALVPGTIAFTDAH<br>IEVDITYAEYFEMSVRLAEAMKRYGLNTNHRIVVCSENSLQFFMPV<br>LGALFIGVAVAPANDIYNERELLNSMGISQPTVVFVSKKGLQKILN<br>VQKKLPIIQKIIIMDSKTDYQGFQSMYTFVTSHLPPGFNEYDFVPE<br>SFDRDKTIALIMNSSGSTGLPKGVALPHRTACVRFSHARDPIFGNQ<br>IIPDTAILSVVPFHHGFGMFTTLGYLICGFRVVLMYRFEEELFLRS<br>LQDYKIQSALLVPTLFSFFAKSTLIDKYDLSNLHEIASGGAPLSKE<br>VGEAVAKRFHLPGIRQGYGLTETTSAILITPEGDDKPGAVGKVVPF<br>FEAKVVDLDTGKTLGVNQRGELCVRGPMIMSGYVNNPEATNALIDK<br>DGWLHSGDIAYWDEDEHFFIVDRLKSLIKYKGYQVAPAELESILLQ<br>HPNIFDAGVAGLPDDDAGELPAAVVVLEHGKTMTEKEIVDYVASQV<br>TTAKKLRGGVVFVDEVPKGLTGKLDARKIREILIKAKKGGKIAV* |
| 2847<br>(SEQ ID<br>NO: 94) | | KRAS<br>epitope wt | MKLVVVGAGGVGKSALTI* |
| 2862<br>(SEQ ID<br>NO: 95) | | empty | MDPRRYAPMIRPAKLDVLPRN* |
| 3060<br>(SEQ<br>ID<br>NO: 96) | | Signal<br>peptide-<br>gp70 with<br>AH1A5-<br>MITD | MRVTAPRTLLLLLWGAVALTETWAGSLSEVTGQGLCIGAVPKTHQV<br>LCNTTQKTSDGSYYLAAPTGTTWACSTGLTPCISTTILNLTTDYCV<br>LVELWPRVTYHSPSYAYHQFERRAKYKREPVSLTLALLLGGLTMGG<br>IAAGVGTGTTALVATQQFQQLQAAMHDDLKEVEKSITNLEKSLTSL<br>SEVVLQNRRGLDLLFLKEGGLCAALKEECCLYADHTGLVIVGIVAG<br>LAVLAVVVIGAVVAVMCRRKSSGGKGGSYSQAASATVPRALMCLS<br>QL* |

TABLE 6-continued

| | | |
|---|---|---|
| 3061 (SEQ ID NO: 97) | Signal peptide-AH1A5 OVA-MITD | MRVTAPRTLLLLLWGAVALTETWAGSYHSPSYAYHQFERGGGGSGG GGSLKISQAVHAAHAEINEAGREVIVGIVAGLAVLAVVVIGAVVAA VMCRRKSSGGKGGSYSQAASATVPRALMCLSQL* |
| 3076 (SEQ ID NO: 98) | Signal peptide-gp70 with AH1A5-MITD-FLAG | MRVTAPRTLLLLLWGAVALTETWAGSLSEVTGQGLCIGAVPKTHQV LCNTTQKTSDGSYYLAAPTGTTWACSTGLTPCISTTILNLTTDYCV LVELWPRVTYHSPSYAYHQFERRAKYKREPVSLTLALLLGGLTMGG IAAGVGTGTTALVATQQFQQLQAAMHDDLKEVEKSITNLEKSLTSL SEVVLQNRRGLDLLFLKEGGLCAALKEECCLYADHTGLVIVGIVAG LAVLAVVVIGAVVAAVMCRRKSSGGKGGSYSQAASATVPRALMCLS QLGGGGSDYKDDDDK* |
| 3068 (SEQ ID NO: 99) | Signal peptide-AH1A5 OVA-MITD-FLAG | MRVTAPRTLLLLLWGAVALTETWAGSYHSPSYAYHQFERGGGGSGG GGSLKISQAVHAAHAEINEAGREVIVGIVAGLAVLAVVVIGAVVAA VMCRRKSSGGKGGSYSQAASATVPRALMCLSQLGGGGSDYKDDDDK * |

| | whole RNA sequence | | |
|---|---|---|---|
| mARM # | brief name | | Sequence |
| 2809 (SEQ ID NO: 100) | STARR™ Fluc | 2809 | AUGGGCGGCGCAUGAGAGAAGCCCAGACCAAUUACCUACCCAAAAU GGAGAAAGUUCACGUUGACAUCGAGGAAGACAGCCCAUUCCUCAGA GCUUUGCAGCGGAGCUUCCCGCAGUUUGAGGUAGAAGCCAAGCAGG UCACUGAUAAUGACCAUGCUAAUGCCAGAGCGUUUCGCAUCUGGC UUCAAAACUGAUCGAAACGGAGGUGGACCCAUCCGACACGAUCCUU GACAUUGGAAGUGCGCCCGCCCGCAGAAUGUAUUCUAAGCACAAGU AUCAUUGUAUCUGUCCGAUGAGAUGUGCGGAAGAUCCGGACAGAUU GUAUAAGUAUGCAACUAAGCUGAAGAAAAACUGUAAGGAAAUAACU GAUAAGGAAUUGGACAAGAAAAUGAAGGAGCUGGCCGCCGUCAUGA GCGACCCUGACCUGGAAACUGAGACUAUGUGCGCCUCCACGACGACGA GUCGUGUCGCUACGAAGGGCAAGUCGCUGUUUACCAGGAUGUAUAC GCCGUCGACGGCCCCACCAGCCUGUACCACCAGGCCAACAAGGGCG UGAGGGUGGCCUACUGGAUCGGCUUCGACACCACACCCUUCAUGUU CAAGAACCUGGCCGGCGCCUACCCCAGCUACAGCACCAACUGGGCC GACGAGACCGUGCUGACCGCCAGGAACAUCGGCCUGUGCAGCAGCG ACGUGAUGGAGAGGAGCCGAGAGGCAUGAGCAUCCUGAGGAAGAA AUACCUGAAGCCCAGCAACAACGUGCUGUUCAGCGUGGGCAGCACC AUCUACCACGAGAAGAGGGACCUGCUCAGGAGCUGGCACCUGCCCA GCGUGUUCCACCUGAGGGGCAAGCAGAACUACACCUGCAGGUGCGA GACCAUCGUGAGCUGCGACGGCUACGUGGUGAAGAGGAUCGCCAUC AGCCCCGGCCUGUACGGCAAGCCCAGCGGCUACGCCGCUACAAUGC ACAGGGAGGGCUUCCUGUGCUGCAAGGUGACCGACACCCUGAACGG CGAGAGGGUGAGCUUCCCCGUGUGCACCUACGUGCCCGCCACCCUG UGCGACCAGAUGACCGGCAUCCUGGCCACCGACGUGAGCGCCGACG ACGCCCAGAAGCUGCUCGUGGGCCUGAACCAGAGGAUCGUGGUCAA CGGCAGGACCCAGAGGAACACCAACACAAUGAAGAACUACCUGCUG CCCGUGGUGGCCCAGGCUUUCGCCAGGUGGGCCAAGGAGUACAAGG AGGACCAGGAAGACGAGAGGCCCCUGGGCCUGAGGGACAGGCAGCU GGUGAUGGGCUGCUGCUGGGCCUUCAGGCGGCACAAGAUCACCAGC AUCUACAAGAGGCCCGACACCCAGACCAUCAUCAAGGUGAACAGCG ACUUCCACAGCUUCGUGCUGCCCAGGAUCGGCAGCAACACCCUGGA GAUCGGCCUGAGGACCCGGAUCAGGAAGAUGCUGGAGGAACACAAG GAGCCCAGCCCACUGAUCACCGCCGAGGACGUGCAGGAGGCCAAGU GCGCCUGCCGACGAGGCCAAGGAGGUGAGGGAGGCCGAGGAACUGAG GGCCGCCCUGCCACCCCUGGCUGCCGACGUGGAGGAACCCACCCUG GAAGCCGACGUGACCUGAUGCUGCAGGAGGCCGGCGCCGGAAGCG UGGAGACACCCAGGGGCCUGAUCAAGGUGACCAGCUACGACGGCGA GGACAAGAUCGGCAGCUACGCCGUGCUGUGAGCCCACAGGCCGUGCUG AAGUCCGAGAAGCUGAGCUGCAUCCACCCACUGGCCGAGCAGGUGA UCGUGAUCACCCACAGCGGCAGGAAGGGCAGGUACGCCGUGGAGCC CUACCACGGCAAGGUGGUCGUGCCCGAGGGCACGCCAUCCCCGUG CAGGACUUCCAGGCCCUGAGCGAGAGCGCCACCAUCGUGUACAACG AGAGGGAGUUCGUGAACAGGUACCUGCACCAUAUCGCCACCCACGG CGGAGCCCUGAACACCGACGAGGAAUACUACAAGACCGUGAAGCCC AGCGAGCACGACGGCGAGUACCUGUACGACAUCGACAGGAAGCAGU GCGUGAAGAAAGAGCUGGUGACCGGCCUGGGACUGACCGGCGAGCU GGUGGACCCACCCUUCCACGAGUUCGCCUACGAGAGCCUGAGGACC AGACCCGCCGCUCCCUACCAGGUGCCCACCAUCGGCGUGACGGCG UGCCCGGCAGCGGAAAGAGCGGCAUCAUCAAGAGCGCCGUGACCAA GAAAGACCUGGUGGUCAGCGCCAAGAAAGAGAACUGCGCCGAGAUC AUCAGGGACGUGAAGAAGAUGAAGGGACUGGACGUGGAACGCGCGCA CCGUGGACAGCGUGCUGCUGAACGGCUGCAAGCACCCCGUGGAGAC CCUGUACAUCGACGAGGCCUUCGCUUGCCACGCCGGCACCCUGAGG GCCCUGAUCGCCAUCAUCAGGCCCAAGAAAGCCGUGCUGUGCGGCG ACCCCAAGCAGUGCGGCUUCUUCAACAUGAUGUGCCUGAAGGUGCA CUUCAACCACGAGAUCUGCACCCAGGUGUUCCACAAGAGCAUCAGC |

TABLE 6-continued

```
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGCCCUGAACAAGGAGGUGGUCAGGCAGCUGACGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCAGCUACCACGU
GGUCAGGGGCGAUAUCGCCACCGCCACCGAGGGCGUGAUCACAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCCGAGUACGACGCCUACCUGGACAUGGUGGACGGCGCC
AGCUGCUGCCUGGACACCGCCAGCUUCUGCCCCGCCAAGCUGAGGA
GCUUCCCCAAGAAACACAGCUACCUGGAGCCCACCAUCAGGAGCGC
```

TABLE 6-continued

```
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACGUGGAGUGCUUCAAGAAAUACGC
CUGCAACAACGAGUACUGGGAGACCUUCAAGGAGAACCCCAUCAGG
CUGACCGAAGAGAACGUGGUGAACUACAUCACCAAGCUGAAGGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
GUGAAGGUGACACCCGGCACCAAGCACACCGAGGAGAGGCCCAAGG
UGCAGGUGAUCCAGGCCGCUGACCCACUGGCCACCGCCUACCUGUG
CGGCAUCCACAGGGAGCUGGUGAGGCGGCUGAACGCCGUGCUGCUG
CCCAACAUCCACACCCUGUUCGACAUGAGCGCCGAGGACUUCGACG
CCAUCAUCGCCGAGCACUUCCAGCCCGGCGACUGCGUGCUGGAGAC
CGACAUCGCCAGCUUCGACAAGAGCGAGGAUGACGCUAUGGCCCUG
ACCGCUCUGAUGAUCCUGGAGGACCUGGGCGUGGACGCCGAGCUGC
UCACCCUGAUCGAGGCUGCCUUCGGCGAGAUCAGCUCCAUCCACCU
GCCCACCAAGACCAAGUUCAAGUUCGGCGCUAUGAUGAAAAGCGGA
AUGUUCUGACCCUGUUCGUGAACACCGUGAUCAACAUUGUGAUCG
CCAGCAGGGUGCUGCGGGAGAGGCUGACCGGCAGCCCCUGCGCUGC
CUUCAUCGGCGACGACAACAUCGUGAAGGGCGUGAAAAGCGACAAG
CUGAUGGCCGACAGGUGCGCCACCUGGCUGAACAUGGAGGUGAAGA
UCAUCGACGCCGUGGUGGGCGAGAAGGCCCCCUACUUCUGCGGCGG
AUUCAUCCUGUGCGACAGCGUGACCGGCACCGCCUGCAGGGUGGCC
GACCCCCUGAAGAGGCUGUUCAAGCUGGGCAAGCCACUGGCCGCUG
ACGAUGAGCACGACGAUGACAGGCGGAGGGCCCUGCACGAGGAAAG
CACCAGGUGGAACAGGGUGGGCAUCCUGAGCGAGCUGUGCAAGGCC
GUGGAGAGCAGGUACGAGACCGUGGGCACCAGCAUCAUCGUGAUGG
CUAUGACCACACUGGCCAGCUCCGUCAAGAGCUUCUCCUACCUGAG
GGGGGCCCCUAUAACUCUCUACGGCUAACCUGAAUGGACUACGACA
UAGUCUAGUCCGCCAAGGCCGCCACCAUGGAAGAUGCCAAAAACAU
UAAGAAGGGCCCAGCGCCAUUCUACCCACUCGAAGACGGGACCGCC
GGCGAGCAGCUGCACAAAGCCAUGAAGCGCUACGCCCUGGUGCCCG
GCACCAUCGCCUUUACCGACGCACAUAUCGAGGUGGACAUUACCUA
CGCCGAGUACUUCGAGAUGAGCGUUCGGCUGGCAGAAGCUAUGAAG
CGCUAUGGGCUGAAUACAAACCAUCGGAUCGUGGUGUGCAGCGAGA
AUAGCUUGCAGUUCUUCAUGCCCGUGUUGGGUGCCCUGUUCAUCGG
UGUGGCUGUGGCCCCAGCUAACGACAUCUACAACGAGCGCGAGCUG
CUGAACAGCAUGGGCAUCAGCCAGCCCACCGUCGUAUUCGUGAGCA
AGAAAGGGCUGCAAAAGAUCCUCAACGUGCAAAAGAAGCUACCGAU
CAUACAAAAGAUCAUCAUCAUGGAUAGCAAGACCGACUACCAGGGC
UUCCAAAGCAUGUACACCUUCGUGACUUCCCAUUUGCCACCCGGCU
UCAACGAGUACGACUUCGUGCCCGAGAGCUUCGACCGGGACAAAAC
CAUCGCCCUGAUCAUGAACAGUAGUGGCAGUACCGGAUUGCCCAAG
GGCGUAGCCCUACCGCACCGCACCGCUUGUGUCCGAUUCAGUCAUG
CCCGCGACCCCAUCUUCGGCAACCAGAUCAUCCCCGACACCGCUAU
CCUCAGCGUGGUGCCAUUUCACCACGGCUUCGGCAUGUUCACCACG
CUGGGCUACUUGAUCUGCGGCUUUCGGGUCGUGCUCAUGUACCGCU
U

TABLE 6-continued

```
CAGAGCAUUUCGCAUCUGGCCAGUAAACUAAUCGAGCUGGAGGUU
CCUACCACAGCGACGAUCUUGGACAUAGGCAGCGCACCGGCUCGUA
GAAUGUUUUCCGAGCACCAGUAUCAUUGUGUCUGCCCCAUGCGUAG
UCCAGAAGACCCGGACCGCAUGAUGAAAUAUGCCAGUAAACUGGCG
GAAAAAGCGUGCAAGAUUACAAACAAGAACUUGCAUGAGAAGAUUA
AGGAUCUCCGGACCGUACUUGAUACGCCGGAUGCUGAAACACCAUC
GCUCUGCUUUCACAACGAUGUUACCUGCAACAUGCGUGCCGAAUAU
UCCGUCAUGCAGGACGUGUAUAUCAACGCUCCCGGAACUAUCUAUC
AUCAGGCUAUGAAAGGCGUGCGGACCCUGUACUGGAUUGGCUUCGA
CACCACCCAGUUCAUGUUCUCGGCUAUGGCAGGUUCGUACCCUGCG
UACAACACCAACUGGGCCGACGAGAAAGUCCUUGAAGCGCGUAACA
UCGGACUUUGCAGCACAAAGCUGAGUGAAGGUAGGACAGGAAAAUU
GUCGAUAAUGAGGAAGAAGGAGUUGAAGCCCGGGUCGCGGGUUUAU
UUCUCCGUAGGAUCGACACUUUAUCCAGAACACAGAGCCAGCUUGC
AGAGCUGGCAUCUUCCAUCGGUGUUCCACUUGAAUGGAAAGCAGUC
GUACACUUGCCGCUGUGAUACAGUGGUGAGUUGCGAAGGCUACGUA
GUGAAGAAAAUCACCAUCAGUCCCGGGAUCACGGGAGAAACCGUGG
GAUACGCGGUUACACACAAUAGCGAGGGCUUCUUGCUAUGCAAAGU
UACUGACACAGUAAAAGGAGAACGGGUAUCGUUCCCUGUGUGCACG
UACAUCCCGGCCACCAUAUGCGAUCAGAUGACUGGUAUAAUGGCCA
CGGAUAUAUCACCUGACGAUGCACAAAAACUUCUGGUUGGGCUCAA
CCAGCGAAUUGUCAUUAACGGUAGGACUAACAGGAACACCAACACC
AUGCAAAAUUACCUUCUGCCGAUCAUAGCACAAGGGUUCAGCAAAU
GGGCUAAGGAGCGCAAGGAUGAUCUUGAUAACGAGAAAAUGCUGGG
UACUAGAGAACGCCAAGCUUACGUAUGGCUGCUUGUGGGCGUUUCGC
ACUAAGAAAGUACAUUCGUUUUAUCGCCCACCUGGAACGCAGACCU
GCGUAAAAGUCCCAGCCUCUUUUAGCGCUUUUCCCAUGUCGUCCGU
AUGGACGACCUCUUUGCCCAUGUCGCUGAGGCAGAAAUUGAAACUG
GCAUUGCAACCAAAGAAGGAGGAAAAACUGCUGCAGGUCUCGGAGG
AAUUAGUCAUGGAGGCCAAGGCUGCUUUUGAGGAUGCUCAGGAGGA
AGCCAGAGCGGAGAAGCUCCGAGAAGCACUUCCACCAUUAGUGGCA
GACAAAGGCAUCGAGGCAGCCGCAGAGUUGUCUGCGAAGUGGAGG
GGCUCCAGGCGGACAUCGGAGCAGCAUUAGUUGAAACCCCGCGCGG
UCACGUAAGGAUAAUACCUCAAGCAAAUGACCGUAUGAUCGGACAG
UAUAUCGUUGUCUCGCCAAACUCUGUGCUGAAGAAUGCCAAACUCG
CACCAGCGCACCCGCUAGCAGAUCAGGUUAAGAUCAUAACACACUC
CGGAAGAUCAGGAAGGUACGCGGUCGAACCAUACGACGCUAAAGUA
CUGAUGCCAGCAGGAGGUGCCGUACCAUGGCCAGAAUUCCUAGCAC
UGAGUGAGAGCGCCACGUUAGUGUACAACGAAAGAGAGUUUGUGAA
CCGCAAACUAUACCACAUUGCCAUGCAUGGCCCCGCCAAGAAUACA
GAAGAGGAGCAGUACAAGGUUACAAAGGCAGAGCUUGCAGAAACAG
AGUACGUGUUUGACGUGGACAAGAAGCGUUGCGUUAAGAAGGAAGA
AGCCUCAGGUCUGGUCCUCUCGGGAGAACUGACCAACCCUCCCUAU
CAUGAGCUAGCUCUGGAGGGACUGAAGACCCGACCUGCGGUCCCGU
ACAAGGUCGAAACAAUAGGAGUGAUAGGCACACCGGGGUCGGGCAA
GUCAGCUAUUAUCAAGUCAACUGUCACGGCACGAGAUCUUGUUACC
AGCGGAAAGAAAGAAAAUUGUCGCGAAAUUGAGGCCGACGUGCUAA
GACUGAGGGGUAUGCAGAUUACGUCGAAGACAGUAGAUUCGGUUAU
GCUCAACGGAUGCCACAAAGCCGUAGAAGUGCUGUACGUUGACGAA
GCGUUCGCGUGCCACGCAGGAGCACUACUUGCCUUGAUUGCUAUCG
UCAGGCCCCGCAAGAAGGUAGUACUAUGCGGAGACCCCAUGCAAUG
CGGAUUCUUCAACAUGAUGCAACUAAAGGUACAUUUCAAUCACCCU
GAAAAAGACAUAUGCACCAAGACAUUCUACAAGUAUAUCUCCCGGC
GUUGCACACAGCCAGUUACAGCUAUUGUAUCGACACUGCAUUACGA
UGGAAAGAUGAAAACCACGAACCCGUGCAAGAAGAACAUUGAAAUC
GAUAUUACAGGGGCCACAAAGCCGAAGCCAGGGGAUAUCAUCCUGA
CAUGUUUCCGCGGGUGGGUUAAGCAAUUGCAAAUCGACUAUCCCGG
ACAUGAAGUAAAUGCAGCCGCGGCCUCACAAGGGCUAACCAGAAAA
GGAGUGUAUGCCGUCCGGCAAAAAGUCAAUGAAAACCCACUGUACG
CGAUCACAUCAGAGCAUGUGAACGUGUUGCUCACCCGCACUGAGGA
CAGGCUAGUGUGGAAAACCUUGCAGGGCGACCCAUGGAUUAAGCAG
CUCACUAACAUACCUAAAGGAAACUUUCAGGCUACUAUAGAGGACU
GGGAAGCUGAACACAAGGGAAUAAUUGCUGCAAUAAACAGCCCCAC
UCCCCGUGCCAAUCCGUUCAGCUGCAAGACCAACGUUUGCUGGGCG
AAAGCAUUGGAACCGAUACUAGCCACGGCCGGUAUCGUACUUACCG
GUUGCCAGUGGAGCGAACUGUUCCCACAGUUUGCGGAUGACAAACC
ACAUUCGGCCAUUUACGCCUUAGACGUAAUUUGCAUUAAGUUUUUC
GGCAUGGACUUGACAAGCGGACUGUUUUCUAAACAGAGCAUCCCAC
UAACGUACCAUCCCGCCGAUUCAGCGAGGCCGGUAGCUCAUUGGGA
CAACAGCCCAGGAACCCGCAAGUAUGGGUACGAUCACGCCAUUGCC
GCCGAACUCUCCCGUAGAUUUCCGGUGUUCCAGCUAGCUGGGAAGG
GCACACAACUUGAUUUGCAGACGGGGAGAACCAGAGUUAUCUCUGC
ACAGCAUAACCUGGUCCGGUGAACCGCAAUCUUCCUCACGCCUUA
GUCCCCGAGUACAAGGAGAAGCAACCCGGCCCGGUCGAAAAAUUCU
UGAACCAGUUCAAACACCACUCAGUACUUGUGGUAUCAGAGGAAAA
AAUUGAAGCUCCCCGUAAGAGAAUCGAAUGGAUCGCCCCGAUUGGC
AUAGCGGUGCAGAUAAGAACUACAACCUGGCUUUCGGGUUUCCGC
CGCAGGCACGGUACGACCUGGUGUUCAUCAACAUUGGAACUAAAUA
CAGAAACCACCACUUUCAGCAGUGCGAAGACCAUGCGGCGACCUUA
AAAACCCUUUCGCGUUCGGCCCUGAAUUGCCUUAACCCAGGAGGCA
```

TABLE 6-continued

```
CCCUCGUGGUGAAGUCCUAUGGCUACGCCGACCGCAACAGUGAGGA
CGUAGUCACCGCUCUUGCCAGAAAGUUUGUCAGGGUGUCUGCAGCG
AGACCAGAUUGUGUCUCAAGCAAUACAGAAAUGUACCUGAUUUUCC
GACAACUAGACAACAGCCGUACACGGCAAUUCACCCCGCACCAUCU
GAAUUGCGUGAUUUCGUCCGUGUAUGAGGGUACAAGAGAUGGAGUU
GGAGCCGCGCCGUCAUACCGCACCAAAAGGGAGAAUAUUGCUGACU
GUCAAGAGGAAGCAGUUGUCAACGCAGCCAAUCCGCUGGGUAGACC
AGGCGAAGGAGUCUGCCGUGCCAUCUAUAAACGUUGGCCGACCAGU
UUUACCGAUUCAGCCACGGAGACAGGCACCGCAAGAAUGACUGUGU
GCCUAGGAAAGAAAGUGAUCCACGCGGUCGGCCCUGAUUUCCGGAA
GCACCCAGAAGCAGAAGCCUUGAAAUUGCUACAAAACGCCUACCAU
GCAGUGGCAGACUUAGUAAAUGAACAUAACAUCAAGUCUGUCGCCA
UUCCACUGCUAUCUACAGGCAUUUACGCAGCCGGAAAAGACCGCCU
UGAAGUAUCACUUAACUGCUUGACAACCGCGCUAGACAGAACUGAC
GCGGACGUAACCAUCUAUUGCCUGGAUAAGAAGUGGAAGGAAAGAA
UCGACGCGGCACUCCAACUUAAGGAGUCUGUAACAGAGCUGAAGGA
UGAAGAUAUGGAGAUCGACGAUGAGUUAGUAUGGAUCCAUCCAGAC
AGUUGCUUGAAGGGAAGAAAGGGAUUCAGUACUACAAAAGGAAAAU
UGUAUUCGUACUUCGAAGGCACCAAAUUCCAUCAAGCAGCAAAAGA
CAUGGCGGAGAUAAAGGUCCUGUUCCCUAAUGACCAGGAAAGUAAU
GAACAACUGUGUGCCUACAUAUUGGGUGAGACCAUGGAAGCAAUCC
GCGAAAAGUGCCCGGUCGACCAUAACCCGUCGUCUAGCCCGCCCAA
AACGUUGCCGUGCCUUUGCAUGUAUGCCAUGACGCCAGAAAGGGUC
CACAGACUUAGAAGCAAUAACGUCAAAGAAGUUACAGUAUGCUCCU
CCACCCCCCUUCCUAAGCACAAAAUUAAGAAUGUUCAGAAGGUUCA
GUGCACGAAAGUAGUCCUGUUUAAUCCGCACACUCCCGCAUUCGUU
CCCGCCCGUAAGUACAUAGAAGUGCCAGAACAGCCUACCGCUCCUC
CUGCACAGGCCGAGGAGGCCCCCGAAGUUGUAGCGACACCGUCACC
AUCUACAGCUGAUAACACCUCGCUUGAUGUCACAGACAUCUCACUG
GAUAUGGAUGACAGUAGCGAAGGCUCACUUUUUUCGAGCUUUAGCG
GAUCGGACAACUCUAUUACUAGUAUGGACAGUUGGUCGUCAGGACC
UAGUUCACUAGAGAUAGUAGACCGAAGGCAGGUGGUGGUGGCUGAC
GUUCAUGCCGUCCAAGAGCCUGCCCCUAUUCCACCGCCAAGGCUAA
AGAAGAUGGCCCGCCUGGCAGCGGCAAGAAAAGAGCCCACUCCACC
GGCAAGCAAUAGCUCUGAGUCCCUCCACCUCUCUUUUGGUGGGGUA
UCCAUGUCCCUCGGAUCAAUUUUCGACGGAGAGACGGCCCGCCAGG
CAGCGGUACAACCCCUGGCAACAGGCCCCACGGAUGUGCCUAUGUC
UUUCGGAUCGUUUUCCGACGGAGAGAUUGAUGAGCUGAGCCGCAGA
GUAACUGAGUCCGAACCCGUCCUGUUUGGAUCAUUUGAACCGGGCG
AAGUGAACUCAAUUAUAUCGUCCCGAUCAGCCGUAUCUUUUCCUCU
ACGCAAGCAGAGACGUAGACGCAGGAGCAGGAGGACUGAAUACUGA
CUAACCGGGUAGGUGGGUACAUAUUUUCGACGGACACAGGCCCUG
GGCACUUGCAAAAGAAGUCCGUUCUGCAGAACCAGCUUACAGAACC
GACCUUGGAGCGCAAUGUCCUGGAAAGAAUUCAUGCCCCGGUGCUC
GACACGUCGAAAGAGGAACAACUCAAACUCAGGUACCAGAUGAUGC
CCACCGAAGCCAACAAAAGUAGGUACCAGUCUCGUAAAGUAGAAAA
UCAGAAAGCCAUAACCACUGAGCGACUACUGUCAGGACUACGACUG
UAUAACUCUGCCACAGAUCAGCCAGAAUGCUAUAAGAUCACCUAUC
CGAAACCAUUGUACUCCAGUAGCGUACCGGCGAACUACUCCGAUCC
ACAGUUCGCUGUAGCUGUCUGUAACAACUAUCUGCAUGAGAACUAU
CCGACAGUAGCAUCUUAUCAGAUUACUGACGAGUACGAUGCUUACU
UGGAUAUGGUAGACGGGACAGUCGCCUGCCUGGACACUGCAACCUU
CUGCCCCGCUAAGCUUAGAAGUUACCCGAAAAAACAUGAGUAUAGA
GCCCCGAAUAUCCGCAGUGCGGUUCCAUCAGCGAUGCAGAACACGC
UACAAAAUGUGCUCAUUGCCGCAACUAAAAGAAAUUGCAACGUCAC
GCAGAUGCGUGAACUGCCAACACUGGACUCAGCGACAUUCAAUGUC
GAAUGCUUUCGAAAAUAUGCAUGUAAUGACGAGUAUUGGGAGGAGU
UCGCUCGGAAGCCAAUUAGGAUUACCACUGAGUUUGUCACCGCAUA
UGUAGCUAGACUGAAAGGCCCUAAGGCCGCCGCACUAUUUGCAAAG
ACGUAUAAUUUGGUCCCAUUGCAAGAAGUGCCUAUGGAUAGAUUCG
UCAUGGACAUGAAAAGAGACGUGAAAGUUACACCAGGCACGAAACA
CACAGAAGAAAGACCGAAAGUACAAGUGAUACAAGCCGCAGAACCC
CUGGCGACUGCUUACUUAUGCGGGAUUCACCGGGAAUUAGUGCGUA
GGCUUACGGCCGUCUUGCUUCCAAACAUUCACACGCUUUUUGACAU
GUCGGCGGAGGAUUUUGAUGCAAUCAUAGCAGAACACUUCAAGCAA
GGCGACCCGGUACUGGAGACGGAUAUCGCAUCAUUCGACAAAAGCC
AAGACGACGCUAUGGCGUUAACCGGUCUGAUGAUCUUGGAGGACCU
GGGUGUGGAUCAACCACUACUCGACUUGAUCGAGUGCGCCUUUGGA
GAAAUAUCAUCCACCCAUCUACCUACGGGUACUCGUUUUAAAUUCG
GGGCGAUGAUGAAAUCCGGAAUGUUCCUCACACUUUUUGUCAACAC
AGUUUUGAAUGUCGUUAUCGCCAGCAGAGUACUAGAGGAGCGGCUU
AAAACGUCCAGAUGUGCAGCGUUCAUUGGCGACGACAACAUCAUAC
AUGGAGUAGUAUCUGACAAAGAAAUGGCUGAGAGGUGCGCCACCUG
GCUCAACAUGGAGGUUAAGAUCAUCGACGCAGUCAUCGGUGAGAGA
CCACCUUACUUUCUGCGGCGGAUUUAUUCUUGCAAGAAUUCGGUUACUU
CCACAGCGUGCCGCGUGGCGGAUCCCCUGAAAAGGCUGUUUAAGUU
GGGUAAACCGCUCCCAGCCGACGACGAGCAAGACGAAGACAGAAGA
CGCGCUCUGCUAGAUGAAACAAAGGCGUGGUUUAGAGUAGGUAUAA
CAGGCACUUUAGCAGUGGCCGUGACGACCCGGUAUGAGGUAGACAA
UAUUACACCUGUCCUACUGGCAUUGAGAACUUUUGCCCAGAGCAAA
```

TABLE 6-continued

|  |  |  | AGAGCAUUCCAAGCCAUCAGAGGGGAAAUAAAGCAUCUCUACGGUG |
|---|---|---|---|
|  |  |  | GUCCUAAAUAGUCAGCAUAGUACAUUUCAUCUGACUAAUACUACAA |
|  |  |  | CACCACCACCAUGGAAGAUGCCAAAAACAUUAAGAAGGGCCCAGCG |
|  |  |  | CCAUUCUACCCACUCGAAGACGGGACCGCCGGCGAGCAGCUGCACA |
|  |  |  | AAGCCAUGAAGCGCUACGCCCUGGUGCCCGGCACCAUCGCCUUUAC |
|  |  |  | CGACGCACAUAUCGAGGUGGACAUUACCUACGCCGAGUACUUCGAG |
|  |  |  | AUGAGCGUUCGGCUGGCAGAAGCUAUGAAGCGCUAUGGGCUGAAUA |
|  |  |  | CAAACCAUCGGAUCUGGGUGUGCAGCGAGAAUAGCUUGCAGUUCUU |
|  |  |  | CAUGCCCGUGUUGGGUGCCCUGUUCAUCGGUGUGGCUGUGGCCCCA |
|  |  |  | GCUAACGACAUCUACAACGAGCGCGAGCUGCUGAACAGCAUGGGCA |
|  |  |  | UCAGCCAGCCCACCGUCGUAUUCGUGAGCAAGAAAGGGCUGCAAAA |
|  |  |  | GAUCCUCAACGUGCAAAAGAAGCUACCGAUCAUACAAAAGAUCAUC |
|  |  |  | AUCAUGGAUAGCAAGACCGACUACCAGGGCUUCCAAAGCAUGUACA |
|  |  |  | CCUUCGUGACUUCCCAUUUGCCACCCGGCUUCAACGAGUACGACUU |
|  |  |  | CGUGCCCGAGAGCUUCGACCGGGACAAAACCAUCGCCCUGAUCAUG |
|  |  |  | AACAGUAGUGGCAGUACCGGAUUGCCCAAGGGCGUAGCCCUACCGC |
|  |  |  | ACCGCACCGCUUGUGUCCGAUUCAGUCAUGCCCGCGACCCCAUCUU |
|  |  |  | CGGCAACCAGAUCAUCCCCGACACCGCUAUCCUCAGCGUGGUGCCA |
|  |  |  | UUUCACCACGGCUUCGGCAUGUUCACCACGCUGGGCUACUUGAUCU |
|  |  |  | GCGGCUUUCGGGUCGUGCUCAUGUACCGCUUCGAGGAGGAGCUAUU |
|  |  |  | CUUGCGCAGCUUGCAAGACUAUAAGAUUCAAUCUGCCCUGCUGGUG |
|  |  |  | CCCACACUAUUUAGCUUCUUCGCUAAGAGCACUCUCAUCGACAAGU |
|  |  |  | ACGACCUAAGCAACUUGCACGAGAUCGCCAGCGGCGGGGCGCCGCU |
|  |  |  | CAGCAAGGAGGUAGGUGAGGCCGUGGCCAAACGCUUCCACCUACCA |
|  |  |  | GGCAUCCGACAGGGCUACGGCCUGACAGAAACAACCAGCGCCAUUC |
|  |  |  | UGAUCACCCCCGAAGGGGACGACAAGCCUGGCGCAGUAGGCAAGGU |
|  |  |  | GGUGCCCUUCUUCGAGGCUAAGGUGGUGGACUUGGACACCGGUAAG |
|  |  |  | ACACUGGGUGUGAACCAGCGCGGCGAGCUGUGCGUCCGUGGCCCCA |
|  |  |  | UGAUCAUGAGCGGCUACGUUAACAACCCCGAGGCUACAAACGCUCU |
|  |  |  | CAUCGACAAGGACGGCUGGCUGCACAGCGGCGACAUCGCCUACUGG |
|  |  |  | GACGAGGACGAGCACUUCUUCAUCGUGGACCGGCUGAAGUCCCUGA |
|  |  |  | UCAAAUACAAGGGCUACCAGGUAGCCCCAGCCGAACUGGAGAGCAU |
|  |  |  | CCUGCUGCAACACCCCAACAUCUUCGACGCCGGGGUCGCCGGCCUG |
|  |  |  | CCCGACGACGAUGCCGGCGAGCUGCCCGCCGCAGUCGUCGUGCUGG |
|  |  |  | AACACGGUAAAACCAUGACCGAGAAGGAGAUCGUGGACUAUGUGGC |
|  |  |  | CAGCCAGGUUACAACCGCCAAGAAGCUGCGCGGUGGUGUUGUGUUC |
|  |  |  | GUGGACGAGGUGCCUAAAGGACUGACCGGCAAGUUGGACGCCCGCA |
|  |  |  | AGAUCCGCGAGAUUCUCAUUAAGGCCAAGAAGGGCGGCAAGAUCGC |
|  |  |  | CGUGUAAACGCGUGCUAGACCAUGGAUCCUAGACGCUACGCCCCAA |
|  |  |  | UGAUCCGACCAGCAAAACUCGAUGUACUUCCGAGGAACUGAUGUGC |
|  |  |  | AUAAUGCAUCAGGCUGGUACAUUAGAUCCCCGCUUACCGCGGGCAA |
|  |  |  | UAUAGCAACACUAAAAACUCGAUGUACUUCCGAGGAAGCGCAGUGC |
|  |  |  | AUAAUGCUGCGCAGUGUUGCCACAUAACCACUAUAUUAACCAUUUA |
|  |  |  | UCUAGCGGACGCCAAAAACUCAAUGUAUUUCUGAGGAAGCGUGGUG |
|  |  |  | CAUAAUGCCACGCAGCGUCUGCAUAACUUUUAUUAUUUCUUUUAUU |
|  |  |  | AAUCAACAAAAUUUUGUUUUUAACAUUUCAAAAAAAAAAAAAAAAA |
|  |  |  | AAAAAAAAUCUAGAAAAAAAAAAAAAAAAAAAAAAAAAAAAAAAAA |
|  |  |  | AAAAAAAAAAAAAAAAAAAAAAAAAAAAAAAAAAAAAAAAAAAAAA |
|  |  |  | AAAAAAAAAAAAAAAAAAAA |
| 1782 (SEQ ID NO: 102) | mRNA Fluc | 1782 | AGGAAACUUAAGUCAACACAACAUAUACAAAACAAACGAAUCUCAA |
|  |  |  | GCAAUCAAGCAUUCUACUUCUAUUGCAGCAAUUUAAAUCAUUUCUU |
|  |  |  | UUAAAGCAAAAGCAAUUUUCUGAAAAUUUUCACCAUUUACGAACGA |
|  |  |  | UAGCCAUGGAAGAUGCCAAAAACAUUAAGAAGGGCCCAGCGCCAUU |
|  |  |  | CUACCCACUCGAAGACGGGACCGCCGGCGAGCAGCUGCACAAAGCC |
|  |  |  | AUGAAGCGCUACGCCCUGGUGCCCGGCACCAUCGCCUUUACCGACG |
|  |  |  | CACAUAUCGAGGUGGACAUUACCUACGCCGAGUACUUCGAGAUGAG |
|  |  |  | CGUUCGGCUGGCAGAAGCUAUGAAGCGCUAUGGGCUGAAUACAAAC |
|  |  |  | CAUCGGAUCUGGGUGUGCAGCGAGAAUAGCUUGCAGUUCUUCAUGC |
|  |  |  | CCGUGUUGGGUGCCCUGUUCAUCGGUGUGGCUGUGGCCCCAGCUAA |
|  |  |  | CGACAUCUACAACGAGCGCGAGCUGCUGAACAGCAUGGGCAUCAGC |
|  |  |  | CAGCCCACCGUCGUAUUCGUGAGCAAGAAAGGGCUGCAAAAGAUCC |
|  |  |  | UCAACGUGCAAAAGAAGCUACCGAUCAUACAAAAGAUCAUCAUCAU |
|  |  |  | GGAUAGCAAGACCGACUACCAGGGCUUCCAAAGCAUGUACACCUUC |
|  |  |  | GUGACUUCCCAUUUGCCACCCGGCUUCAACGAGUACGACUUCGUGC |
|  |  |  | CCGAGAGCUUCGACCGGGACAAAACCAUCGCCCUGAUCAUGAACAG |
|  |  |  | UAGUGGCAGUACCGGAUUGCCCAAGGGCGUAGCCCUACCGCACCGC |
|  |  |  | ACCGCUUGUGUCCGAUUCAGUCAUGCCCGCGACCCCAUCUUCGGCA |
|  |  |  | ACCAGAUCAUCCCCGACACCGCUAUCCUCAGCGUGGUGCCAUUUCA |
|  |  |  | CCACGGCUUCGGCAUGUUCACCACGCUGGGCUACUUGAUCUGCGGC |
|  |  |  | UUUCGGGUCGUGCUCAUGUACCGCUUCGAGGAGGAGCUAUUCUUGC |
|  |  |  | GCAGCUUGCAAGACUAUAAGAUUCAAUCUGCCCUGCUGGUGCCCAC |
|  |  |  | ACUAUUUAGCUUCUUCGCUAAGAGCACUCUCAUCGACAAGUACGAC |
|  |  |  | CUAAGCAACUUGCACGAGAUCGCCAGCGGCGGGGCGCCGCUCAGCA |
|  |  |  | AGGAGGUAGGUGAGGCCGUGGCCAAACGCUUCCACCUACCAGGCAU |
|  |  |  | CCGACAGGGCUACGGCCUGACAGAAACAACCAGCGCCAUUCUGAUC |
|  |  |  | ACCCCCGAAGGGGACGACAAGCCUGGCGCAGUAGGCAAGGUGGUGC |
|  |  |  | CCUUCUUCGAGGCUAAGGUGGUGGACUUGGACACCGGUAAGACACU |
|  |  |  | GGGUGUGAACCAGCGCGGCGAGCUGUGCGUCCGUGGCCCCAUGAUC |
|  |  |  | AUGAGCGGCUACGUUAACAACCCCGAGGCUACAAACGCUCUCAUCG |

| | | | |
|---|---|---|---|
| | | | ACAAGGACGGCUGGCUGCACAGCGGCGACAUCGCCUACUGGGACGA |
| | | | GGACGAGCACUUCUUCAUCGUGGACCGGCUGAAGUCCCUGAUCAAA |
| | | | UACAAGGGCUACCAGGUAGCCCCAGCCGAACUGGAGAGCAUCCUGC |
| | | | UGCAACACCCCAACAUCUUCGACGCCGGGGUCGCCGGCCUGCCCGA |
| | | | CGACGAUGCCGGCGAGCUGCCCGCCGCAGUCGUCGUGCUGGAACAC |
| | | | GGUAAAACCAUGACCGAGAAGGAGAUCGUGGACUAUGUGGCCAGCC |
| | | | AGGUUACAACCGCCAAGAAGCUGCGCGGUGGUGUUGUGUUCGUGGA |
| | | | CGAGGUGCCUAAAGGACUGACCGGCAAGUUGGACGCCCGCAAGAUC |
| | | | CGCGAGAUUCUCAUUAAGGCCAAGAAGGGCGGCAAGAUCGCCGUGU |
| | | | AACUCGAGCUAGUGACUGACUAGGAUCUGGUUACCACUAAACCAGC |
| | | | CUCAAGAACACCCGAAUGGAGUCUCUAAGCUACAUAAUACCAACUU |
| | | | ACACUUACAAAAUGUUGUCCCCCAAAAUGUAGCCAUUCGUAUCUGC |
| | | | UCCUAAUAAAAAGAAAGUUUCUUCACAUUCUAGAAAAAAAAAAAAA |
| | | | AAAAAAAAAAAAAAAAAAAAAAAAAAAAAAAAAAAAAAAAAAAAAA |
| | | | AAAAAAAAAAAAAAAAAAAAAAAAAAAAAAAAAAAAAAAAAAAAAA |
| | | | AAAAAAAAAAAAAAAA |
| 2847 (SEQ ID NO: 103) | STARR™ KRAS wt | 2847 | AUGGGCGGCGCAUGAGAGAAGCCCAGACCAAUUACCUACCCAAAAU GGGAGAAAGUUCACGUUGACAUCGAGGAAGACAGCCCAUUCCUCAGA GCUUUGCAGCGGAGCUUCCCGCAGUUUGAGGUAGAAGCCAAGCAGG UCACUGAUAAUGACCAUGCUAAUGCCAGAGCGUUUUCGCAUCUGGC UUCAAAACUGAUCGAAACGGAGGUGGACCCAUCCGACACGAUCCUU GACAUUGGAAGUGCGCCCGCCCGCAGAAUGUAUUCUAAGCACAAGU AUCAUUGUAUCUGUCCGAUGAGAUGUGCGGAAGAUCCGGACAGAUU GUAUAAGUAUGCAACUAAGCUGAAGAAAAACUGUAAGGAAAUAACU GAUAAGGAAUUGGACAAGAAAAUGAAGGAGCUGGCCGCCGUCAUGA GCGACCCUGACCUGGAAACUGAGACUAUGUGCCUCCACGACGACGA GUCGUGUCGCUACGAAGGGCAAGUCGCUGUUUACCAGGAUGUAUAC GCCGUCGACGGCCCCACCAGCCUGUACCACCAGGCCAACAAGGGCG UGAGGGUGGCCUACUGGAUCGGCUUCGACACCACACCCUUCAUGUU CAAGAACCUGGCCGGCGCCUACCCCAGCUACAGCACCAACUGGGCC GACGAGACCGUGCUGACCGCCAGGAACAUCGGCCUGUGCAGCAGCG ACGUGAUGGAGAGGAGCCGGAGAGGCAUGAGCAUCCUGAGGAAGAA AUACCUGAAGCCCAGCAACAACGUGCUGUUCAGCGUGGGCAGCACC AUCUACCACGAGAAGAGGGACCUGCUCAGGAGCUGGCACCUGCCCA GCGUGUUCCACCUGAGGGGCAAGCAGAACUACACCUGCAGGUGCGA GACCAUCGUGAGCUGCGACGGCUACGUGGUGAAGAGGAUCGCCAUC AGCCCCGGCCUGUACGGCAAGCCCAGCGGCUACGCCGCUACAAUGC ACAGGGAGGGCUUCCUGUGCUGCAAGGUGACCGACACCCUGAACGG CGAGAGGGUGAGCUUCCCCGUGUGCACCUACGUGCCCGCCACCCUG UGCGACCAGAUGACCGGCAUCCUGGCCACCGACGUGAGCGCCGACG ACGCCCAGAAGCUGCUCGUGGGCCUGAACCAGAGGAUCGUGGUCAA CGGCAGGACCCAGAGGAACACCAACACAAUGAAGAACUACCUGCUG CCCGUGGUGGCCCAGGCUUUCGCCAGGUGGGCCAAGGAGUACAAGG AGGACCAGGAAGACGAGAGGCCCCUGGGCCUGAGGGACAGGCAGCU GGUGAUGGGCUGCUGCUGGGCCUUCAGGCGGCACAAGAUCACCAGC AUCUACAAGAGGCCCGACACCCAGACCAUCAUCAAGGUGAACAGCG ACUUCCACAGCUUCGUGCUGCCAGGAUCGGCAGCAACACCCUGGA GAUCGGCCUGAGGACCCGGAUCAGGAAGAUGCUGGAGGAACACAAG GAGCCCAGCCCACUGAUCACCGCCGAGGACGUGCAGGAGGCCAAGU GCGCUGCCGACGAGGCCAAGGAGGUGAGGGAGGCCGAGGAACUGAG GGCCGCCCUGCCACCCCUGGCUGCCGACGUGGAGGAACCCACCCUG GAAGCCGACGUGGACCUGAUGCUGCAGGAGGCCGGCGCCGGAAGCG UGGAGACACCCAGGGGCCUGAUCAAGGUGACCAGCUACGACGGCGA GGACAAGAUCGGCAGCUACGCCGUGCUGAGCCCACAGGCCGUGCUG AAGUCCGAGAAGCUGAGCUGCAUCCACCCACUGGCCGAGCAGGUGA UCGUGAUCACCCACAGCGGCAGGAAGGGCAGGUACGCCGUGGAGCC CUACCACGGCAAGGUGGUCGUGCCCGAGGGCCACGCCAUCCCCGUG CAGGACUUCCAGGCCCUGAGCGAGAGCGCCACCAUCGUGUACAACG AGAGGGAGUUCGUGAACAGGUACCUGCACCAUAUCGCCACCCACGG CGGAGCCCUGAACACCGACGAGGAAUACUACAAGACCGUGAAGCCC AGCGAGCACGACGGCGAGUACCUGUACGACAUCGACAGGAAGCAGU GCGUGAAGAAAGAGCUGGUGACCGGCCUGGGACUGACCGGCGAGCU GGUGGACCCACCCUUCCACGAGUUCGCCUACGAGAGCCUGAGGACC AGACCCGCCGCUCCCUACCAGGUGCCCACCAUCGGCGUGUACGGCG UGCCCGGCAGCGGAAAGAGCGGCAUCAUCAAGAGCGCCGUGACCAA GAAAGACCUGGUGGUCAGCGCCAAGAAAGAGAACUGCGCCGAGAUC AUCAGGGACGUGAAGAAGAUGAAAGGCCUGGACGUGAACGCGCGCA CCGUGGACAGCGUGCUGCUGAACGGCUGCAAGCACCCCGUGGAGAC CCUGUACAUCGACGAGGCCUUCGCUUGCCACGCCGGCACCCUGAGG GCCCUGAUCGCCAUCAUCAGGCCCAAGAAAGCCGUGCUGUGCGGCG ACCCCAAGCAGUGCGGCUUCUUCAACAUGAUGUGCCUGAAGGUGCA CUUCAACCACGAGAUCUGCACCCAGGUGUUCCACAAGAGCAUCAGC AGGCGGUGCACCAAGAGCGUGACCAGCGUCGUGAGCACCCUGUUCU ACGACAAGAAAAUGAGGACCACCAACCCCAAGGAGACCAAAAUCGU GAUCGACACCACAGGCAGCACCAAGCCCAAGCAGGACGACCUGAUC CUGACCUGCUUCAGGGGCUGGGUGAAGCAGCUGCAGAUCGACUACA AGGGCAACGAGAUCAUGACCGCCGCUGCCAGCCAGGGCCUGACCAG GAAGGGCGUGUACGCCGUGAGGUACAAGGUGAACGAGAACCCACUG UACGCUCCCACCAGCGAGCACGUGAACGUGCUGCUGACCAGGACCG |

TABLE 6-continued

```
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACCACCCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCCGAGUACGACGCCUACCUGGACAUGGUGGACGGCGCC
AGCUGCUGCCUGGACACCGCCAGCUUCUGCCCCGCCAAGCUGAGGA
GCUUCCCCAAGAAACACAGCUACCUGGAGCCCACCAUCAGGAGCGC
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACGUGGAGUGCUUCAAGAAAUACGC
CUGCAACAACGAGUACGGGAGACCUUCAAGGAGAACCCCAUCAGG
CUGACCGAAGAGAACGUGGUGAACUACAUCACCAAGCUGAAGGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
```

TABLE 6-continued

|  |  |  | |
|---|---|---|---|
|  |  |  | GUGAAGGUGACACCCGGCACCAAGCACACCGAGGAGAGGCCCAAGG<br>UGCAGGUGAUCCAGGCCGCUGACCCACUGGCCACCGCCUACCUGUG<br>CGGCAUCCACAGGGAGCUGGUGAGGCGGCUGAACGCCGUGCUGCUG<br>CCCAACAUCCACACCCUGUUCGACAUGAGCGCCGAGGACUUCGACG<br>CCAUCAUCGCCGAGCACUUCCAGCCCGGCGACUGCGUGCUGGAGAC<br>CGACAUCGCCAGCUUCGACAAGAGCGAGGAUGACGCUAUGGCCCUG<br>ACCGCUCUGAUGAUCCUGGAGGACCUGGGCGUGGACGCCGAGCUGC<br>UCACCCUGAUCGAGGCUGCCUUCGGCGAGAUCAGCUCCAUCCACCU<br>GCCCACCAAGACCAAGUUCAAGUUCGGCGCUAUGAUGAAAAGCGGA<br>AUGUUCCUGACCCUGUUCGUGAACACCGUGAUCAACAUUGUGAUCG<br>CCAGCAGGGUGCUGCGGGAGAGGCUGACCGGCAGCCCCUGCGCUGC<br>CUUCAUCGGCGACGACAACAUCGUGAAGGGCGUGAAAAGCGACAAG<br>CUGAUGGCCGACAGGUGCGCCACCUGGCUGAACAUGGAGGUGAAGA<br>UCAUCGACGCCGUGGUGGGCGAGAAGGCCCCCUACUUCUGCGGCGG<br>AUUCAUCCUGUGCGACAGCGUGACCGGCACCGCCUGCAGGGUGGCC<br>GACCCCCUGAAGAGGCUGUUCAAGCUGGGCAAGCCACUGGCCGCUG<br>ACGAUGAGCACGACGAUGACAGGCGGAGGGCCCUGCACGAGGAAAG<br>CACCAGGUGGAACAGGGUGGGCAUCCUGAGCGAGCUGUGCAAGGCC<br>GUGGAGAGCAGGUACGAGACCGUGGGCACCAGCAUCAUCGUGAUGG<br>CUAUGACCACACUGGCCAGCUCCGUCAAGAGCUUCUCCUACCUGAG<br>GGGGGCCCCUAUAACUCUCUACGGCUAACCUGAAUGGACUACGACA<br>UAGUCUAGUCCGCCAAGGCCGCCACCCAUGAAGUUGGUGGUUGUGG<br>GGGCCGGGGUGUUGGCAAAAGCGCCCUUACAAUUUGACUCGAGUA<br>UGUUACGUGCAAAGGUGAUUGUCACCCCCCGAAAGACCAUAUUGUG<br>ACACACCCUCAGUAUCACGCCCAAACAUUUACAGCCGCUGGUGUCAA<br>AAACCGCGUGGACGUGGUUAACAUCCCUGCUGGGAGGAUCAGCCGU<br>AAUUAUUAUAAUUGGCUUGGUGCUGGCUACUAUUGUGGCCAUGUAC<br>GUGCUGACCAACCAGAAACAUAAUUGAAUACAGCAGCAAUUGGCAA<br>GCUGCUUACAUAGAACUCGCGGCGAUUGGCAUGCCGCCUUAAAAUU<br>UUUAUUUUAUUUUUUCUUUUCUUUUCCGAAUCGGAUUUUGUUUUUA<br>AUAUUUCAAAAAAAAAAAAAAAAAAAAAAAAAUCUAGAAAAAAAAA<br>AAAAAAAAAAAAAAAAAAAAAAAAAAAAAAAAAAAAAAAAAAAA<br>AAAAAAAAAAAAAAAAAAAAAAAAAAAAAAAAAAAAAAAAA |
| 2862<br>(SEQ<br>ID<br>NO: 104) | SINV<br>empty | 2862 | AUUGACGGCGUAGUACACACUAUUGAAUCAAACAGCCGACCAAUUG<br>CACUACCAUCACAAUGGAGAAGCCAGUAGUAAACGUAGACGUAGAC<br>CCCCAGAGAGUCCGUUUGUCGUGCAACUGCAAAAAAGCCUUCCCGCAAU<br>UUGAGGUAGUAGCACAGCAGGUCACUCCAAAUGACCAUGCUAAUGC<br>CAGAGCAUUUUCGCAUCUGGCCAGUAAACUAAUCGAGCUGGAGGUU<br>CCUACCACAGCGACGAUCUUGGACAUAGGCAGCGCACCGGCUCGUA<br>GAAUGUUUUCCGAGCACCAGUAUCAUUGUGUCUGCCCCAUGCGUAG<br>UCCAGAAGACCCGGACCGCAUGAUGAAAUAUGCCAGUAAACUGGCG<br>GAAAAAGCGUGCAAGAUUACAAACAAGAACUUGCAUGAGAAGAUUA<br>AGGAUCUCCGGACCGUACUUGAUACGCCGGAUGCUGAAACACCAUC<br>GCUCUGCUUUCACAACGAUGUUACCUGCAACAUGCGUGCCGAAUAU<br>UCCGUCAUGCAGGACGUGUAUAUCAACGCUCCCGGAACUAUCUAUC<br>AUCAGGCUAUGAAAGGCGUGCGGACCCUGUACUGGAUUGGCUUCGA<br>CACCCACCCAGUUCAUGUUCUCGGCUAUGGCAGGUUCGUACCCUGCG<br>UACAACACCAACUGGGCCGACGAGAAAGUCCUUGAAGCGCGUAACA<br>UCGGACUUUGCAGCACAAAAGCUGAGUGAAGGUAGGACAGGAAAAUU<br>GUCGAUAAUGAGGAAGAAGGAGUUGAAGCCCGGGUCGCGGGUUUAU<br>UUCUCCGUAGGAUCGACACUUUAUCCAGAACACAGAGCCAGCUUGC<br>AGAGCUGGCAUCUUCCAUCGGUGUUCCACUUGAAUGGAAAGCAGUC<br>GUACACUUGCCGCUGUGAUACAGUGGUGAGUUGCGAAGGCUACGUA<br>GUGAAGAAAAUCACCAUCAGUCCCGGGAUCACGGGAGAAACCGUGG<br>GAUACGCGGUUACACACAAUAGCGAGGGCUUCUUGCUAUGCAAAGU<br>UACUGACACAGUAAAAGGAGAACGGGUAUCGUUCCCUGUGUGCACG<br>UACAUCCGGCCACCAUAUGCGAUCAGAUGACUGGUAUAAUGGCCA<br>CGGAUAUAUCACCUGACGAUGCACAAAAACUUCUGGUUGGGCUCAA<br>CCAGCGAAUUGUCAUUAACGGUAGGACUAACAGGAACACCAACACC<br>AUGCAAAAUUACCUUCUGCCGAUCAUAGCACAAGGGUUCAGCAAAU<br>GGGCUAAGGAGCGCAAGGAUGAUCUUGAUAACGAGAAAAAUGCUGGG<br>UACUAGAGAACGCAAGCUUACGUAUGGCUGCUUGUGGGCGUUUCGC<br>ACUAAGAAAGUACAUUCGUUUUAUCGCCCACCUGGAACGCAGACCU<br>GCGUAAAAGUCCCAGCCUCUUUUAGCGCUUUUCCCAUGUCGUCCGU<br>AUGGACGACCUCUUUGCCCAUGUCGCUGAGGCAGAAAUUGAAACUG<br>GCAUUGCAACCAAAGAAGGAGGAAAAACUGCUGCAGGUCUCGGAGG<br>AAUUAGUCAUGGAGGCCAAGGCUGCUUUUGAGGAUGCUCAGGAGGA<br>AGCCAGAGCGGAGAAGCUCCGAGAAGCACUUCCACCAUUAGUGGCA<br>GACAAAGGCAUCGAGGCAGCCGCAGAAGUUGUCUGCGAAGUGGAGG<br>GGCUCCAGGCGGACAUCGGAGCAGCAUUAGUUGAAACCCCGCGCGG<br>UCACGUAAGGAUAAUACCUCAAGCAAAUGACCGUAUGAUCGGACAG<br>UAUAUCGUUGUCUCGCAAACUCUGUGCUGAAGAAUGCCAAACUCG<br>CACCAGCGCACCCGCUAGCAGAUCAGGUUAAGAUCAUAACACACUC<br>CGGAAGAUCAGGAAGGUACGGGUCGAACCAUACGACGCUAAAGUA<br>CUGAUGCCAGCAGGAGGUGCCGUACCAUGGCCAGAAUUCCUAGCAC<br>UGAGUGAGAGCGCCACGUUAGUGUACAACGAAAGAGAGUUUGUGAA<br>CCGCAAACUAUACCACAUUGCCAUGCAUGGCCCCGCCAAGAAUACA<br>GAAGAGGAGCAGUACAAGGUUACAAAGGCAGAGCUUGCAGAAACAG<br>AGUACGUGUUUGACGUGGACAAGAAGCGUUGCGUUAAGAAGGAAGA |

TABLE 6-continued

```
AGCCUCAGGUCUGGUCCUCUCGGGAGAACUGACCAACCCUCCCUAU
CAUGAGCUAGCUCUGGAGGGACUGAAGACCCGACCUGCGGUCCCGU
ACAAGGUCGAAACAAUAGGAGUGAUAGGCACACCGGGGUCGGGCAA
GUCAGCUAUUAUCAAGUCAACUGUCACGGCACGAGAUCUUGUUACC
AGCGGAAAGAAAGAAAAUUGUCGCGAAAUUGAGGCCGACGUGCUAA
GACUGAGGGGUAUGCAGAUUACGUCGAAGACAGUAGAUUCGGUUAU
GCUCAACGGAUGCCACAAAGCCGUAGAAGUGCUGUACGUUGACGAA
GCGUUCGCGUGCCACGCAGGAGCACUACUUGCCUUGAUUGCUAUCG
UCAGGCCCCGCAAGAAGGUAGUACUAUGCGGAGACCCCAUGCAAUG
CGGAUUCUUCAACAUGAUGCAACUAAAGGUACAUUUCAAUCACCCU
GAAAAAGACAUAUGCACCAAGACAUUCUACAAGUAUAUCUCCCGGC
GUUGCACACAGCCAGUUACAGCUAUUGUAUCGACACUGCAUUACGA
UGGAAGAUGAAAACCACGAACCCGUGCAAGAAGAACAUUGAAAUC
GAUAUUACAGGGGCCACAAAGCCGAAGCCAGGGGAUAUCAUCCUGA
CAUGUUUCCGCGGGUGGGUUAAGCAAUUGCAAAUCGACUAUCCCGG
ACAUGAAGUAAUGACAGCCGCGGCCUCACAAGGGCUAACCAGAAAA
GGAGUGUAUGCCGUCCGGCAAAAAGUCAAUGAAAAACCCACUGUACG
CGAUCAUCAGAGCAUGUGAACGUGUUGCUCACCCGCACUGAGGA
CAGGCUAGUGUGGAAAACCUUGCAGGGCGACCCAUGGAUUAAGCAG
CUCACUAACAUACCUAAAGGAAACUUUCAGGCUACUAUAGAGGACU
GGGAAGCUGAACACAAGGGAAUAAUUGCUGCAAUAAACAGCCCCAC
UCCCCGUGCCAAUCCGUUCAGCUGCAAGACCAACGUUUGCUGGGCG
AAAGCAUUGGAACCGAUACUAGCCACGGCCGGUAUCGUACUUACCG
GUUGCCAGUGGAGCGAACUGUUCCCACAGUUUGCGGAUGACAAACC
ACAUUCGGCCAUUUACGCCUUAGACGUAAUUUGCAUUAAGUUUUUC
GGCAUGGACUUGACAAGCGGACUGUUUUCUAAACAGAGCAUCCCAC
UAACGUACCAUCCCGCCGAUUCAGCGAGGCCGGUAGCUCAUUGGGA
CAACAGCCCAGGAACCCGCAAGUAUGGGUACGAUCACGCCAUUGCC
GCCGAACUCUCCCGUAGAUUUCCGGUGUUCCAGCUAGCUGGGAAGG
GCACACAACUUGAUUUGCAGACGGGGAGAACCAGAGUUAUCUCUGC
ACAGCAUAACCUGGUCCCGGUGAACCGCAAUCUUCCUCACGCCUUA
GUCCCCGAGUACAAGGAGAAGCAACCCGGCCCGGUCGAAAAAUUCU
UGAACCAGUUCAAACACCACUCAGUACUUGUGGGUAUCAGAGGAAAA
AAUUGAAGCUCCCCGUAAGAGAAUCGAAUGGAUCGCCCCGAUUGGC
AUAGCCGGUGCAGAUAAGAACUACAACCUGGCUUUCGGGUUUCCGC
CGCAGGCACGGUACGACCUGGUGUUCAUCAACAUUGGAACUAAAUA
CAGAAACCACCACUUUCAGCAGUGCGAAGACCAUGCGGCGACCUUA
AAAACCCUUUCGCGUUCGGCCCUGAAUUGCCUUAACCCAGGAGGCA
CCCUCGUGGUGAAGUCCUAUGGCUACGCCGACCGCAACAGUGAGGA
CGUAGUCACCGCUCUUGCCAGAAAGUUUGUCAGGGUGUCUGCAGCG
AGACCAGAUUGUGUCUCAAGCAAUACAGAAAUGUACCUGAUUUUCC
GACAACUAGACAACAGCCGUACACGGCAAUUCACCCCGCACCAUCU
GAAUUGCGUGAUUUCGUCCGUGUAUGAGGGUACAAGAGAUGGAGUU
GGAGCCGCGCCGUCAUACCGCACCAAAAGGGAGAAUAUUGCUGACU
GUCAAGAGGAAGCAGUUGUCAACGCAGCCAAUCCGCUGGGUAGACC
AGGCGAAGGAGUCUGCCGUGCCAUCUAUAAACGUUGGCCGACCAGU
UUUACCGAUUCAGCCACGGAGACAGGCACCGCAAGAAUGACUGUGU
GCCUAGGAAAGAAAGUGAUCCACGCGGUCGGCCCUGAUUUCCGGAA
GCACCCAGAAGCAGAAGCCUUGAAAUUGCUACAAAACGCCUACCAU
GCAGUGGCAGAUUAGUAAAUGAACAUAACAUCAAGUCUGUCGCCA
UUCCACUGCUAUCUACAGGCAUUUACGCAGCCGGAAAAGACCGCCU
UGAAGUAUCACUUAACUGCUUGACAACCGCGCUAGACAGAACUGAC
GCGGACGUAACCAUCUAUUGCCUGGAUAAGAAGUGGAAGGAAAGAA
UCGACGCGGCACUCCAACUUUAAGGAGUCUGUAACAGAGCUGAAGGA
UGAAGAUAUGGAGAUCGACGAUGAGUUAGUAUGGAUCCAUCCAGAC
AGUUGCUUGAAGGGAAGAAAGGGAUUCAGUACUACAAAAGGAAAAU
UGUAUUCGUACUUCGAAGGCACCAAAUUCCAUCAAGCAGCAAAAGA
CAUGGCGGAGAUAAAGGUCCUGUUCCCUAAUGACCAGGAAAGUAAU
GAACAACUGUGUGCCUACAUAUUGGGUGAGACCAUGGAAGCAAUCC
GCGAAAAGUGCCCGGUCGACCAUAACCCGUCGUCUAGCCCGCCCAA
AACGUUGCCGUGCCUUUGCAUGUAUGCCAUGACGCCAGAAAGGGUC
CACAGACUUUAGAAGCAAUAACGUCAAAGAAGUUACAGUAUGCUCCU
CCACCCCCCUUCCUAAGCACAAAAUUAAGAAUGUUCAGAAGGUUCA
GUGCACGAAAGUAGUCCUGUUUAAUCCGCACACUCCCGCAUUCGUU
CCCGCCCGUAAGUACAUAGAAGUGCCAGAACAGCCUACCGCUCCUC
CUGCACAGGCCGAGGAGGCCCCCGAAGUUGUAGCGACACCGUCACC
AUCUACAGCUGAUAACACCUCGCUUGAUGUCACAGACAUCUCACUG
GAUAUGGAUGACAGUAGCGAAGGCUCACUUUUUUCGAGCUUUAGCG
GAUCGGACAACUCUAUUACUAGUAUGGACAGUUGGUCGUCAGGACC
UAGUUCACUAGAGAUAGUAGACCGAAGGCAGGUGGUGGUGGCUGAC
GUUCAUGCCGUCCAAGAGCCUGCCCCUAUUCCACCGCCAAGGCUAA
AGAAGAUGGCCCGCCUGGCAGCGGCAAGAAAAAGAGCCCACUCCACC
GGCAAGCAAUAGCUCUGAGUCCCUCCACCUCUCUUUUGGUGGGGUA
UCCAUGUCCCUCGGAUCAAUUUUCGACGGAGAGACGGCCCGCCAGG
CAGCGGUACAACCCCUGGCAACAGGCCCCACGGAUGUGCCUAUGUC
UUUCGGAUCGUUUUCCGACGGAGAGAUUGAUGAGCUGAGCGCAGA
GUAACUGAGUCCGAACCCGUCCUGUUUGGAUCAUUUGAACCGGGCG
AAGUGAACUCAAUUAUAUCGUCCCGAUCAGCCGUAUCUUUUCCUCU
ACGCAAGCAGAGACGUAGACGCAGGAGCAGGAGGACUGAAUACUGA
CUAACCGGGGUAGGUGGGUACAUAUUUCGACGGACACAGGCCCUG
```

TABLE 6-continued

|  |  |  |  |
|---|---|---|---|
|  |  |  | GGCACUUGCAAAAGAAGUCCGUUCUGCAGAACCAGCUUACAGAACC<br>GACCUUGGAGCGCAAUGUCCUGGAAAGAAUUCAUGCCCCGGUGCUC<br>GACACGUCGAAAGAGGAACAACUCAAACUCAGGUACCAGAUGAUGC<br>CCACCGAAGCCAACAAAAGUAGGUACCAGUCUCGUAAAGUAGAAAA<br>UCAGAAAGCCAUAACCACUGAGCGACUACUGUCAGGACUACGACUG<br>UAUAACUCUGCCACAGAUCAGCCAGAAUGCUAUAAGAUCACCUAUC<br>CGAAACCAUUGUACUCCAGUAGCGUACCGGCGAACUACUCCGAUCC<br>ACAGUUCGCUGUAGCUGUCUGUAACAACUAUCUGCAUGAGAACUAU<br>CCGACAGUAGCAUCUUAUCAGAUUACUGACGAGUACGAUGCUUACU<br>UGGAUAUGGUAGACGGGACAGUCGCCUGCCUGGACACUGCAACCUU<br>CUGCCCCGCUAAGCUUAGAAGUUACCCGAAAAAACAUGAGUAUAGA<br>GCCCCGAAUAUCCGCAGUGCGGUUCCAUCAGCGAUGCAGAACACGC<br>UACAAAAUGUGCUCAUUGCCGCAACUAAAAGAAAUUGCAACGUCAC<br>GCAGAUGCGUGAACUGCCAACACUGGACUCAGCGACAUUCAAUGUC<br>GAAUGCUUUCGAAAAUAUGCAUGUAAUGACGAGUAUUGGGAGGAGU<br>UCGCUCGGAAGCCAAUUAGGAUUACCACUGAGUUUGUCACCGCAUA<br>UGUAGCUAGACUGAAAGGCCCUAAGGCCGCCGCACUAUUUGCAAAG<br>ACGUAUAAUUUGGUCCCAUUGCAAGAAGUGCCUAUGGAUAGAUUCG<br>UCAUGGACAUGAAAAGAGACGUGAAAGUUACACCAGGCACGAAACA<br>CACAGAAGAAAGACCGAAAGUACAAGUGAUACAAGCCGCAGAACCC<br>CUGGCGACUGCUUACUUAUGCGGGAUUCACCGGGAAUUAGUGCGUA<br>GGCUUACGGCCGUCUUGCUUCCAAACAUUCACACGCUUUUUGACAU<br>GUCGGCGGAGGAUUUUGAUGCAAUCAUAGCAGAACACUUCAAGCAA<br>GGCGACCCGGUACUGGAGACGGAUAUCGCAUCAUUCGACAAAAGCC<br>AAGACGACGCUAUGGCGUUAACCGGUCUGAUGAUCUUGGAGGACCU<br>GGGUGUGGAUCAACCACUACUCGACUUGAUCGAGUGCGCCUUUGGA<br>GAAAUAUCAUCCACCCAUCUACCUACGGGUACUCGUUUUAAAUUCG<br>GGGCGAUGAUGAAAUCCGGAAUGUUCCUCACACUUUUUGUCAACAC<br>AGUUUUGAAUGUCGUUAUCGCCAGCAGAGAGUACUAGAGGAGCGGCUU<br>AAAACGUCCAGAUGUGCAGCGUUCAUUGGCGACGACAACAUCAUAC<br>AUGGAGUAGUAUCUGACAAAGAAAUGGCUGAGAGGUGCGCCACCUG<br>GCUCAACAUGGAGGUUAAGAUCAUCGACGCAGUCAUCGGUGAGAGA<br>CCACCUUACUUCUGCGGCGGAUUUAUCUUGCAAGAUUCGGUUACUU<br>CCACAGCGUGCCGCGUGGCGGAUCCCCUGAAAAGGCUGUUUAAGUU<br>GGGUAAACCGCUCCCAGCCGACGACGAGCAAGACGAAGACAGAAGA<br>CGCGCUCUGCUAGAUGAAACAAAGGCGUGGUUUAGAGUAGGUAUAA<br>CAGGCACUUUAGCAGUGGCCGUGACGACCCGGUAUGAGGUAGACAA<br>UAUUACACCUGUCCUACUGGCAUUGAGAACUUUUGCCCAGAGCAAA<br>AGAGCAUUCCAAGCCAUCAGAGGGGAAAUAAAGCAUCUCUACGGUG<br>GUCCUAAAUAGUCAGCAUAGUACAUUUCAUCUGACUAAUACUACAA<br>CACCACCACCACGCGUGCUAGACCAUGGAUCCUAGACGCUACGCCC<br>CAAUGAUCCGACCAGCAAAACUCGAUGUACUUCCGAGGAACUGAUG<br>UGCAUAAUGCAUCAGGCUGGUACAUUAGAUCCCCGCUUACCGCGGG<br>CAAUAUAGCAACACUAAAAACUCGAUGUACUUCCGAGGAAGCGCAG<br>UGCAUAAUGCUGCGCAGUGUUGCCACAUAACCACUAUAUUAACCAU<br>UUAUCUAGCGACGCCAAAAACUCAAUGUAUUUCUGAGGAAGCGUG<br>GUGCAUAAUGCCACGCAGCGUCUGCAUAACUUUUAUUAUUUCUUUU<br>AUUAAUCAACAAAAUUUUGUUUUUAACAUUUCAAAAAAAAAAAAA<br>AAAAAAAAAAAUCUAGAAAAAAAAAAAAAAAAAAAAAAAAAAAA<br>AAAAAAAAAAAAAAAAAAAAAAAAAAAAAAAAAAAAAAAAAAAA<br>AAAAAAAAAAAAAAAAAAAAAAA |
| 3060<br>(SEQ<br>ID<br>NO: 105) | STARR<sup>TM</sup><br>gp70 | 3060 | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGUGUGCGGAAGAUCCGGACAGAUU<br>GUAUAAGUAUGCAACUAAGCUGAAGAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGAGAGGCAUGAGCAUCCUGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGACGCUUCCCCGUGUGCACUUACGUGCCGCCACCCUG<br>UGCGACCAGAUGACCGGCAUCCUGGCCACCGACGUGAGCGCCGACG<br>ACGCCCAGAAGCUGCUCGUGGGCCUGAACCAGAGGAUCGUGGUCAA<br>CGGCAGGACCCAGAGGAACACCAACACAAUGAAGAACUACCUGCUG<br>CCCGUGGUGGCCCAGGCUUUCGCCAGGUGGGCCAAGGAGUACAAGG<br>AGGACCAGGAAGACGAGAGGCCCCUGGGCCUGAGGGACAGGCAGCU |

TABLE 6-continued

```
GGUGAUGGGCUGCUGCUGGGCCUUCAGGCGGCACAAGAUCACCAGC
AUCUACAAGAGGCCCGACACCCAGACCAUCAUCAAGGUGAACAGCG
ACUUCCACAGCUUCGUGCUGCCAGGAUCGGCAGCAACACCCUGGA
GAUCGGCCUGAGGACCCGGAUCAGGAGGAAGAUGCUGGAGGAACACAAG
GAGCCCAGCCCACUGAUCACCGCCGAGGACGUGCAGGAGGCCAAGU
GCGCUGCCGACGAGGCCAAGGAGGUGAGGGAGGCCGAGGAACUGAG
GGCCGCCCUGCCACCCUGGCUGCCGACGUGGAGGAACCCACCCUG
GAAGCCGACGUGGACCUGAUGCUGCAGGAGGCCGGCGCCGGAAGCG
UGGAGACACCCAGGGGCCUGAUCAAGGUGACCAGCUACGACGGCGA
GGACAAGAUCGGCAGCUACGCCGUGCUGAGCCCACAGGCCGUGCUG
AAGUCCGAGAAGCUGAGCUGCAUCCACCCACUGGCCGAGCAGGUGA
UCGUGAUCACCCACAGCGGCAGGAAGGGCAGGUACGCCGUGGAGCC
CUACCACGGCAAGGUGGUCGUGCCCGAGGGCCACGCCAUCCCCGUG
CAGGACUUCCAGGCCCUGAGCGAGAGCGCCACCAUCGUGUACAACG
AGAGGGAGUUCGUGAACAGGUACCUGCACCAUAUCGCCACCCACGG
CGGAGCCCUGAACACCGACGAGGAAUACUACAAGACCGUGAAGCCC
AGCGAGCACGACGGCGAGUACCUGUACGACAUCGACAGGAAGCAGU
GCGUGAAGAAAGAGCUGGUGACCGGCCUGGGACUGACCGGCGAGCU
GGUGGACCCACCCUUCCACGAGUUCGCCUACGAGAGCCUGAGGACC
AGACCCGCCGCUCCCUACCAGGUGCCCACCAUCGGCGUGUACGGCG
UGCCCGGCAGCGGAAAGAGCGGCAUCAUCAAGAGCGCCGUGACCAA
GAAAGACCUGGUGGUCAGCGCCAAGAAAGAGAACUGCGCCGAGAUC
AUCAGGGACGUGAAGAAGAUGAAAGGCCUGGACGUGAACGCGCGCA
CCGUGGACAGCGUGCUGCUGAACGGCUGCAAGCACCCCGUGGAGAC
CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
```

TABLE 6-continued

```
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCCGAGUACGACGCCUACCUGGACAUGGUGGACGGCGCC
AGCUGCUGCCUGGACACCGCCAGCUUCUGCCCCGCCAAGCUGAGGA
GCUUCCCCAAGAAACACAGCUACCUGGAGCCCACCAUCAGGAGCGC
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACGUGGAGUGCUUCAAGAAAUACGC
CUGCAACAACGAGUACUGGGAGACCUUCAAGGAGAACCCCAUCAGG
CUGACCGAAGAGAACGUGGUGAACUACAUCACCAAGCUGAAGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
GUGAAGGUGACACCCGGCACCAAGCACACCGAGGAGAGGCCCAAGG
UGCAGGUGAUCCAGGCCGCUGACCCACUGGCCACCGCCUACCUGUG
CGGCAUCCACAGGGAGCUGGUGAGGCGGCUGAACGCCGUGCUGCUG
CCCAACAUCCACACCCUGUUCGACAUGAGCGCCGAGGACUUCGACG
CCAUCAUCGCCGAGCACUUCCAGCCCGGCGACUGCGUGCUGGAGAC
CGACAUCGCCAGCUUCGACAAGAGCGAGGAUGACGCUAUGGCCCUG
ACCGCUCUGAUGAUCCUGGAGGACCUGGGCGUGGACGCCGAGCUGC
UCACCCUGAUCGAGGCUGCCUUCGGCGAGAUCAGCUCCAUCCACCU
GCCCACCAAGACCAAGUUCAAGUUCGGCGCUAUGAUGAAAAGCGGA
AUGUUCCUGACCCUGUUCGUGAACACCGUGAUCAACAUUGUGAUCG
CCAGCAGGGUGCUGCGGGAGAGGCUGACCGGCAGCCCCUGCGCUGC
CUUCAUCGGCGACGACAACAUCGUGAAGGGCGUGAAAAGCGACAAG
CUGAUGGCCGACAGGUGCGCCACCUGGCUGAACAUGGAGGUGAAGA
UCAUCGACGCCGUGGUGGGCGAGAAGGCCCCCUACUUCUGCGGCGG
AUUCAUCCUGUGCGACAGCGUGACCGGCACCGCCUGCAGGGUGGCC
GACCCCCUGAAGAGGCUGUUCAAGCUGGGCAAGCCACUGGCCGCUG
ACGAUGAGCACGACGAUGACAGGCGGAGGGCCCUGCACGAGGAAAG
CACCAGGUGGAACAGGGUGGGCAUCCUGAGCGAGCUGUGCAAGGCC
GUGGAGAGCAGGUACGAGACCGUGGGCCACCAGCAUCAUCGUGAUGG
CUAUGACCACACUGGCCAGCUCCGUCAAGAGCUUCUCCUACCUGAG
GGGGGCCCCUAUAACUCUCUACGGCUAACCUGAAUGGACUACGACA
UAGUCUAGUCCGCCAAGGCCGCCACCAUGAGAGUGACAGCCCCUAG
AACCUUACUGCUUCUGCUUUGGGGAGCUGUUGCUGUGACAGAGACA
UGGGCUGGAUCUCUGAGCGAGGUGACCGGCCAGGGCCUGUGCAUCG
GCGCCGUGCCCAAGACCCACCAGGUGCUGUGCAACACCACCCAGAA
GACCAGCGACGGCAGCUACUACCUGGCCGCUCCCACCGGCACCACC
UGGGCCUGCAGCACCGGCCUGACCCCUUGCAUCAGCACCACCAUCC
UGAACCUGACCACCGACUACUGCGUGCUGGUGGAGCUGUGGCCCAG
GGUGACCUACCACAGCCCCAGCUACGCCUACCACCAGUUCGAGAGG
AGGGCCAAGUACAAGAGGGAGCCCGUGAGCCUGACCCUGGCCCUGC
UGCUGGGCGGCCUGACAAUGGGCGGCAUCGCCGCCGGCGUGGGCAC
CGGCACCACCGCCCUGGUGGCCACCCAGCAGUUCCAGCAGCUGCAG
GCCGCCAUGCACGACGACCUGAAGGAGGUGGAGAAGUCCAUCACCA
ACCUGGAGAAGUCCCUGACCAGCCUGAGCGAGGUGGUGCUGCAGAA
CAGGAGGGGCCUGGACCUGCUGUUCCUGAAGGAGGGCGGCCUGUGC
GCCGCCCUGAAGGAGGAGUGCUGCUGCUGCUGCCGACCACACCGGCC
UGGUGAUCGUGGGCAUUGUCGCUGGCCUGGCCGUCCUCGCCGUGGU
GGUGAUGGAGCUGUGGUCGCAGCUGUUAUGUGCAGAAGAAAGUCA
UCCGGCGGAAAGGGAGGCUCCUACUCUCAGGCUGCUUCUGCUACAG
UGCCUAGAGCUCUUUAUGUGUUUAUCUCAGCUGUAAACUCGAGUAUG
UUACGUGCAAAGGUGAUUGUCACCCCCGAAAGACCAUAUUGUGAC
ACACCCUCAGUAUCACGCCCAAACAUUUACAGCCGCGGUGUCAAAA
ACCGCGUGGACGUGGUUAACAUCCCUGCUGGGAGGAUCAGCCGUAA
UUAUUAUAAUUGGCUUGGUGCUGGCUACUAUUGUGGCCAUGUACGU
GCUGACCAACCAGAAACAUAAUUGAAUACAGCAGCAAUUGGCAAGC
```

| | | | |
|---|---|---|---|
| | | | UGCUUACAUAGAACUCGCGGCGAUUGGCAUGCCGCCUUAAAAUUUU<br>UAUUUUAUUUUUCUUUUCUUUUCCGAAUCGGAUUUUGUUUUUAAU<br>AUUUCAAAAAAAAAAAAAAAAAAAAAAAAAUCUAGAAAAAAAAAAA<br>AAAAAAAAAAAAAAAAAAAAAAAAAAAAAAAAAAAAAAAAAAAAAA<br>AAAAAAAAAAAAAAAAAAAAAAAAAAAAAAAAAAAAAAAA |
| 3061<br>(SEQ<br>ID<br>NO: 106) | STARR™<br>AH1A5 | 3061 | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGYGAYGGAGAGGGAGCCGGAGAGGCAYGAGCAYCCYGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGAGCUUCCCCGUGUGCACCUACGUGCCGCCACCCUG<br>UGCGACCAGAUGACCGGCAUCCUGGCCACCGACGUGAGCGCCGACG<br>ACGCCCAGAAGCUGCUCGUGGGCCUGAACCAGAGGAUCGUGGUCAA<br>CGGCAGGACCCAGAGGAACACCAACACAAUGAAGAACUACCUGCUG<br>CCCGUGGUGGCCCAGGCUUUCGCCAGGUGGGCCAAGGAGUACAAGG<br>AGGACCAGGAAGACGAGAGGCCCCUGGGCCUGAGGGACAGGCAGCU<br>GGUGAUGGGCUGCUGCUGGGCCUUCAGGCGGCACAAGAUCACCAGC<br>AUCUACAAGAGGCCCGACACCCAGACCAUCAUCAAGGUGAACAGCG<br>ACUUCCACAGCUUCGUGCUGCCCAGGAUCGGCAGCAACACCCUGGA<br>GAUCGGCCUGAGGACCCGGAUCAGGAAGAUGCUGGAGGAACACAAG<br>GAGCCCAGCCCACUGAUCACCGCCGAGGACGUGCAGGAGGCCAAGU<br>GCGCUGCCGACGAGGCCAAGGAGGUGAGGGAGGCCGAGGAACUGAG<br>GGCCGCCUGCCACCCCUGGCUGCCGACGUGGAGGAACCCACCCUG<br>GAAGCCGACGUGGACCUGAUGCUGCAGGAGGCCGGCGCCGGAAGCG<br>UGGAGACACCCAGGGGCCUGAUCAAGGUGACCAGCUACGACGGCGA<br>GGACAAGAUCGGCAGCUACGCCGUGCUGAGCCCACAGGCCGUGCUG<br>AAGUCCGAGAAGCUGAGCUGCAUCCACCCACUGGCCGAGCAGGUGA<br>UCGUGAUCACCCACAGCGGCAGGAAGGGCAGGUACGCCGUGGAGCC<br>CUACCACGGCAAGGUGGUCUGUGCCCGAGGGCCACGCCAUCCCCGUG<br>CAGGACUUCCAGGCCCUGAGCGAGAGCGCCACCAUCGUGUACAACG<br>AGAGGGAGUUCGUGAACAGGUACCUGCACCAUAUCGCCACCCACGG<br>CGGAGCCCUGAACACCGACGAGGAAUACUACAAGACCGUGAAGCCC<br>AGCGAGCACGACGGCGAGUACCUGUACGACAUCGACAGGAAGCAGU<br>GCGUGAAGAAAGAGCUGGUGACCGGCCUGGGACUGACCGGCGAGCU<br>GGUGGACCCACCCUUCCACGAGUUCGCCUACGAGAGCCUGAGGACC<br>AGACCCGCCGCUCCCUACCAGGUGCCCACCAUCGGCGUGUACGGCG<br>UGCCCGGCAGCGGAAAGAGCGGCAUCAUCAAGAGCGCCGUGACCAA<br>GAAAGACCUGGUGGUCAGCGCCAAGAAAGAGAACUGCGCCGAGAUC<br>AUCAGGGACGUGAAGAAGAUGAAAGGCCUGGACGUGAACGCGCGCA<br>CCGUGGACAGCGUGCUGCUGAACGGCUGCAAGCACCCCGUGGAGAC<br>CCUGUACAUCGACGAGGCCUUCGCUUGCCACGCCGGCACCCUGAGG<br>GCCCUGAUCGCCAUCAUCAGGCCCAAGAAAGCCGUGCUGUGCGGCG<br>ACCCCAAGCAGUGCGGCUUCUUCAACAUGAUGUGCCUGAAGGUGCA<br>CUUCAACCACGAGAUCUGCACCCAGGUGUUCCACAAGAGCAUCAGC<br>AGGCGGUGCACCAAGACGUGACCAGGCGUCGUGAGCACCCUGUUCU<br>ACGACAAGAAAAUGAGGACCACCAACCCCAAGGAGACCAAAAUCGU<br>GAUCGACACCACAGGCAGCACCAAGCCCAAGCAGGACGACCUGAUC<br>CUGACCUGCUUCAGGGGCUGGGUGAAGCAGCUGCAGAUCGACUACA<br>AGGGCAACGAGAUCAUGACCGCCGCUGCCAGCCAGGGCCUGACCAG<br>GAAGGGCGUGUACGCCGUGAGGUACAAGGUGAACGAGAACCCACUG<br>UACGCUCCCACCAGCGAGCACGUGAACGUGCUGCUGACCAGGACCG<br>AGGACAGGAUCGUGUGGAAGACCCUGGCCGGCGACCCCUGGAUCAA<br>GACCCUGACCGCCAAGUACCCCGGCAACUUCACCGCCACCAUCGAA<br>GAGUGGCAGGCCGAGCACGACGCCAUCAUGAGGCACAUCCUGGAGA<br>GGCCCGACCCCACCGACGUGUUCCAGAACAAGGCCAACGUGUGCUG<br>GGCCAAGGCCCUGGUGCCCGUGCUGAAGACCGCCGGCAUCGACAUG<br>ACCACAGAGCAGUGGAACACCGUGGACUACUUCGAGACCGACAAGG<br>CCCACAGCGCCGAGAUCGUGCUGAACCAGCUGUGCGUGAGGUUCUU<br>CGGCCUGGACCUGGACAGCGGCCUGUUCAGCGCCCCCACCGUGCCA<br>CUGAGCAUCAGGAACAACCACUGGGACAACAGCCCCAGCCCAAACA<br>UGUACGCCUGAACAAGGAGGUGGUCAGGCAGCUGAGCAGGCGGUA<br>CCCACAGCUGCCCAGGGCCGUGGCCACCGGCAGGGUGUACGACAUG |

TABLE 6-continued

```
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCCGAGUACGACGCCUACCUGGACAUGGUGGACGGCGCC
AGCUGCUGCUUGGACACCGCCAGCUUCUGCCCCGCCAAGCUGAGGA
GCUUCCCCAAGAAACACAGCUACCUGGAGCCCACCAUCAGGAGCGC
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACUGGGAGUGCUUCAAGAAAUACGC
CUGACCGAAGAGAACGUGGUGAACUACAUCACCAAGCUGAAGGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
GUGAAGGUGACACCCGGCACCAAGCACACCGAGGAGAGGCCCAAGG
UGCAGGUGAUCCAGGCCGCUGACCCACUGGCCACCGCCUACCUGUG
CGGCAUCCACGGGAGCUGGUGAGGCGGCUGAACGCCGUGCUGCUG
CCCAACAUCCACACCCUGUUCGACAUGAGCGCCGAGGACUUCGACG
CCAUCAUCGCCGAGCACUUCCAGCCCGGCGACUGCGUGCUGGAGAC
CGACAUCGCCAGCUUCGACAAGAGCGAGGAUGACGCUAUGGCCCUG
ACCGCUCUGAUGAUCCUGGAGGACCUGGGCGUGGACCCCGAGCUGC
UCACCCUGAUCGAGGCUGCCUUCGGCGAGAUCAGCUCCAUCCACCU
GCCCACCAAGACCAAGUUCAAGUUCGGCGCUAUGAUGAAAAGCGGA
AUGUUCCUGACCCUGUUCGUGAACACCGUGAUCAACAUUGUGAUCG
CCAGCAGGGUGCUGCGGGAGAGGCUGACCGGCAGCCCUGCGCUGC
CUUCAUCGGCGACGACAACAUCGUGAAGGGCGUGAAAAGCGACAAG
```

TABLE 6-continued

| | | | |
|---|---|---|---|
| | | | CUGAUGGCCGACAGGUGCGCCACCUGGCUGAACAUGGAGGUGAAGA |
| | | | UCAUCGACGCCGUGGUGGGCGAGAAGGCCCCCUACUUCUGCGGCGG |
| | | | AUUCAUCCUGUGCGACAGCGUGACCGGCACCGCCUGCAGGGUGGCC |
| | | | GACCCCCUGAAGAGGCUGUUCAAGCUGGGCAAGCCACUGGCCGCUG |
| | | | ACGAUGAGCACGACGAUGACAGGCGGAGGGCCCUGCACGAGGAAAG |
| | | | CACCAGGUGGAACAGGGUGGGCAUCCUGAGCGAGCUGUGCAAGGCC |
| | | | GUGGAGAGCAGGUACGAGACCGUGGGCACCAGCAUCAUCGUGAUGG |
| | | | CUAUGACCACACUGGCCAGCUCCGUCAAGAGCUUCUCCUACCUGAG |
| | | | GGGGGCCCCUAUAACUCUCUACGGCUAACCUGAAUGGACUACGACA |
| | | | UAGUCUAGUCCGCCAAGGCCGCCACCAUGAGAGUGACAGCCCCUAG |
| | | | AACCUUACUGCUUCUGCUUUGGGGAGCUGUUGCUCUGACAGAGACA |
| | | | UGGGCUGGAUCUUACCACAGCCCCAGCUACGCCUACCACCAGUUCG |
| | | | AGAGGGGGGAGGAGGCUCCGGGGGAGGAGGCUCCCUGAAGAUCAG |
| | | | CCAGGCCGUGCACGCCGCCCACGCCGAGAUCAACGAGGCCGGCCGG |
| | | | GAGGUGAUCGUGGGCAUUGUCGCUGGCCUGGCCGUCCUCGCCGUGG |
| | | | UGGUGAUUGGAGCUGUGGUCGCAGCUGUUAUGUGCAGAAGAAAGUC |
| | | | AUCCGGCGGAAAGGGAGGCUCCUACUCUCAGGCUGCUUCUGCUACA |
| | | | GUGCCUAGAGCUCUUAUGUGUUUAUCUCAGCUGUAAACUCGAGUAU |
| | | | GUUACGUGCAAAGGUGAUUGUCACCCCCCGAAAGACCAUAUUGUGA |
| | | | CACACCCUCAGUAUCACGCCCAAACAUUUACAGCCGCGGUGUCAAA |
| | | | AACCGCGUGGACGUGGUUAACAUCCCUGCUGGGAGGAUCAGCCGUA |
| | | | AUUAUUAUAAUUGGCUUGGUGCUGGCUACUAUUGUGGCCAUGUACG |
| | | | UGCUGACCAACCAGAAACAUAAUUGAAUACAGCAGCAAUUGGCAAG |
| | | | CUGCUUACAUAGAACUCGCGGCGAUUGGCAUGCCGCCUUAAAAUUU |
| | | | UUAUUUUAUUUUUUCUUUUCUUUUCCGAAUCGGAUUUUGUUUUUAA |
| | | | UAUUUCAAAAAAAAAAAAAAAAAAAAAAAAAUCUAGAAAAAAAAA |
| | | | AAAAAAAAAAAAAAAAAAAAAAAAAAAAAAAAAAAAAAAAAAAAA |
| | | | AAAAAAAAAAAAAAAAAAAAAAAAAAAAAAAAAAAAAAAAA |
| 3067 (SEQ ID NO: 107) | STARR™ gp70-FLAG | 3067 | AUGGGCGGCGCAUGAGAGAAGCCCAGACCAAUUACCUACCCAAAAU |
| | | | GGAGAAAGUUCACGUUGACAUCGAGGAAGACAGCCCAUUCCUCAGA |
| | | | GCUUUGCAGCGGAGCUUCCCGCAGUUUGAGGUAGAAGCCAAGCAGG |
| | | | UCACUGAUAAUGACCAUGCUAAUGCCAGAGCGUUUUCGCAUCUGGC |
| | | | UUCAAAACUGAUCGAAACGGAGGUGGACCCAUCCGACACGAUCCUU |
| | | | GACAUUGGAAGUGCGCCCGCCCGCAGAAUGUAUUCUAAGCACAAGU |
| | | | AUCAUUGUAUCUGUCCGAUGAGAUGUGCGGAAGAUCCGGACAGAUU |
| | | | GUAUAAGUAUGCAACUAAGCUGAAGAAAAACUGUAAGGAAAUAACU |
| | | | GAUAAGGAAUUGGACAAGAAAAUGAAGGAGCUGGCCGCCGUCAUGA |
| | | | GCGACCCUGACCUGGAAACUGAGACUAUGUGCCUCCACGACGACGA |
| | | | GUCGUGUCGCUACGAAGGGCAAGUCGCUGUUUACCAGGAUGUAUAC |
| | | | GCCGUCGACGGCCCCACCAGCCUGUACCACCAGGCCAACAAGGGCG |
| | | | UGAGGGUGGCCUACUGGAUCGGCUUCGACACCACACCCUUCAUGUU |
| | | | CAAGAACCUGGCCGGCGCCUACCCCAGCUACAGCACCAACUGGGCC |
| | | | GACGAGACCGUGCUGACCGCCAGGAACAUCGGCCUGUGCAGCAGCG |
| | | | ACGUGAUGGAGAGGAGCCGGAGAGGCAUGAGCAUCCUGAGGAAGAA |
| | | | AUACCUGAAGCCCAGCAACAACGUGCUGUUCAGCGUGGGCAGCACC |
| | | | AUCUACCACGAGAAGAGGGACCUGCUCAGGAGCUGGCACCUGCCCA |
| | | | GCGUGUUCCACCUGAGGGGCAAGCAGAACUACACCUGCAGGUGCGA |
| | | | GACCAUCGUGAGCUGCGACGGCUACGUGGUGAAGAGGAUCGCCAUC |
| | | | AGCCCCGGCCUGUACGGCAAGCCCAGCGGCUACGCCGCUACAAUGC |
| | | | ACAGGGAGGGCUUCCUGUGCUGCAAGGUGACCGACACCCUGAACGG |
| | | | CGAGAGGGUGAGCUUCCCCGUGUGCACCUACGUGCCCGCCACCCUG |
| | | | UGCGACCAGAUGACCGGCAUCCUGGCCACCGACGUGAGCGCCGACG |
| | | | ACGCCCAGAAGCUGCUCGUGGGCCUGAACCAGAGGAUCGUGGUCAA |
| | | | CGGCAGGACCCAGAGGAACACCAACACAAUGAAGAACUACCUGCUG |
| | | | CCCGUGGUGGCCCAGGCUUUCGCCAGGUGGGCCAAGGAGUACAAGG |
| | | | AGGACCAGGAAGACGAGAGGCCCCUGGGCUGAGGGACAGGCAGCU |
| | | | GGUGAUGGGCUGCUGCUGGGCCUUCAGGCGGCACAAGAUCACCAGC |
| | | | AUCUACAAGAGGCCCGACACCCAGACCAUCAUCAAGGUGAACAGCG |
| | | | ACUUCCACAGCUUCGUGCUGCCCAGGAUCGGCAGCAACACCCUGGA |
| | | | GAUCGGCCUGAGGACCCGGAUCAGGAAGAUGCUGGAGGAACACAAG |
| | | | GAGCCCAGCCCACUGAUCACCGCCGAGGACGUGCAGGAGGCCAAGU |
| | | | GCGCUGCCGACGAGGCCAAGGAGGUGAGGGAGGCCGAGGAACUGAG |
| | | | GGCCGCCCUGCCACCCCUGGCUGCCGACGUGGAGGAACCCACCCUG |
| | | | GAAGCCGACGUGGACCUGAUGCUGCAGGAGGCCGGCGCCGGAAGCG |
| | | | UGGAGACACCCAGGGGCUGAUCAAGGUGACCAGCUACGACGGCGA |
| | | | GGACAAGAUCGGCAGCUACGCCGUGCUGAGCCCACAGGCCGUGCUG |
| | | | AAGUCCGAGAAGCUGAGCUGCAUCCACCCACUGGCCGAGCAGGUGA |
| | | | UCGUGAUCACCCACAGCGGCAGGAAGGGCAGGUACGCCGUGGAGCC |
| | | | CUACCACGGCAAGGUGGUCGUGCCCGAGGGCACGCCAUCCCCGUG |
| | | | CAGGACUUCCAGGCCCUGAGCGAGAGCGCCACCAUCGUGUACAACG |
| | | | AGAGGGAGUUCGUGAACAGGUACCUGCACCAUAUCGCCACCCACGG |
| | | | CGGAGCCCUGAACACCGACGAGGAAUACUACAAGACCGUGAAGCCC |
| | | | AGCGAGCACGACGGCGAGUACCUGUACGACAUCGACAGGAAGCAGU |
| | | | GCGUGAAGAAAGAGCUGGUGACCGGCUGGGACAGGCAGCU |
| | | | GGUGGACCCACCCUUCCACGAGUUCGCCUACGAGAGCCUGAGGACC |
| | | | AGACCCGCCGCUCCCUACCAGGUGCCCACCAUCGGCGUGUACGGCG |
| | | | UGCCCGGCAGCGGAAAGAGCGGCAUCAUCAAGAGCGCCGUGACCAA |
| | | | GAAAGACCUGGUGGUCAGCGCCAAGAAAGAGAACUGCGCCGAGAUC |
| | | | AUCAGGGACGUGAAGAAGAUGAAAGGCCUGGACGUGAACGCGCGCA |

TABLE 6-continued

```
CCGUGGACAGCGUGCUGCUGAACGGCUGCAAGCACCCCGUGGAGAC
CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCCACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
```

TABLE 6-continued

|  |  |  |  |
|---|---|---|---|
|  |  |  | AGCGUGAACAGGGCCUUCUCCAGCCCCAAGGUGGCCGUGGAGGCCU |
|  |  |  | GCAACGCUAUGCUGAAGGAGAACUUCCCCACCGUGGCCAGCUACUG |
|  |  |  | CAUCAUCCCCGAGUACGACGCCUACCUGGACAUGGUGGACGGCGCC |
|  |  |  | AGCUGCUGCUGGACACCGCCAGCUUCUGCCCCGCCAAGCUGAGGA |
|  |  |  | GCUUCCCCAAGAAACACAGCUACCUGGAGCCCACCAUCAGGAGCGC |
|  |  |  | CGUGCCCAGCGCCAUCCAGAACACCCUGCAGAACGUGCUGGCCGCU |
|  |  |  | GCCACCAAGAGGAACUGCAACGUGACCCAGAUGAGGGAGCUGCCCG |
|  |  |  | UGCUGGACAGCGCUGCCUUCAACGUGGAGUGCUUCAAGAAAUACGC |
|  |  |  | CUGCAACAACGAGUACUGGGAGACCUUCAAGGAGAACCCCAUCAGG |
|  |  |  | CUGACCGAAGAGAACGUGGUGAACUACAUCACCAAGCUGAAGGGCC |
|  |  |  | CCAAGGCCGCUGCCCUGUUCGCUAAGACCCACAACCUGAACAUGCU |
|  |  |  | GCAGGACAUCCCAAUGGACAGGUUCGUGAUGGACCUGAAGAGGGAC |
|  |  |  | GUGAAGGUGACACCCGGCACCAAGCACACCGAGGAGAGGCCCAAGG |
|  |  |  | UGCAGGUGAUCCAGGCCGCUGACCCACUGGCCACCGCCUACCUGUG |
|  |  |  | CGGCAUCCACAGGGAGCUGGUGAGGCGGCUGAACGCCGUGCUGCUG |
|  |  |  | CCCAACAUCCACACCCUGUUCGACAUGAGCGCCGAGGACUUCGACG |
|  |  |  | CCAUCAUCGCCGAGCACUUCCAGCCCGGCGACUGCGUGCUGGAGAC |
|  |  |  | CGACAUCGCCAGCUUCGACAAGAGCGAGGAUGACGCUAUGGCCCUG |
|  |  |  | ACCGCUCUGAUGAUCCUGGAGGACCUGGGCGUGGACGCCGAGCUGC |
|  |  |  | UCACCCUGAUCGAGGCUGCCUUCGGCGAGAUCAGCUCCAUCCACCU |
|  |  |  | GCCCACCAAGACCAAGUUCAAGUUCGGCGCUAUGAUGAAAAGCGGA |
|  |  |  | AUGUUCCUGACCCUGUUCGUGAACACCGUGAUCAACAUUGUGAUCG |
|  |  |  | CCAGCAGGGUGCUGCGGGAGAGGCUGACCGGCAGCCCCUGCGCUGC |
|  |  |  | CUUCAUCGGCGACGACAACAUCGUGAAGGGCGUGAAAAGCGACAAG |
|  |  |  | CUGAUGGCCGACAGGUGCGCCACCUGGCUGAACAUGGAGGUGAAGA |
|  |  |  | UCAUCGACGCCGUGGUGGGCGAGAAGGCCCCCUACUUCUGCGGCGG |
|  |  |  | AUUCAUCCUGUGCGACAGCGUGACCGGCACCGCCUGCAGGGUGGCC |
|  |  |  | GACCCCCUGAAGAGGCUGUUCAAGCUGGGCAAGCCACUGGCCGCUG |
|  |  |  | ACGAUGAGCACGACGAUGACAGGCGGAGGGCCCUGCACGAGGAAAG |
|  |  |  | CACCAGGUGGAACAGGGUGGGCAUCCUGAGCGAGCUGUGCAAGGCC |
|  |  |  | GUGGAGAGCAGGUACGAGACCGUGGGCACCAGCAUCAUCGUGAUGG |
|  |  |  | CUAUGACCACACUGGCCAGCUCCGUCAAGAGCUUCUCCUACCUGAG |
|  |  |  | GGGGGCCCCUAUAACUCUCUACGGCUAACCUGAAUGGACUACGACA |
|  |  |  | UAGUCUAGUCCGCAAGGCCGCCACCAUGAGAGUGACAGCCCCUAG |
|  |  |  | AACCUUACUGCUUCUGCUUUGGGGAGCUGUUGCUCUGACAGAGACA |
|  |  |  | UGGGCUGGAUCUCUGAGCGAGGUGACCGGCCAGGGCCUGUGCAUCG |
|  |  |  | GCGCCGUGCCCAAGACCCACCAGGUGCUGUGCAACACCACCCAGAA |
|  |  |  | GACCAGCGACGGCCAGCUACUACCUGGCCGCUCCCACCGGCACCACC |
|  |  |  | UGGGCCUGCAGCACCGGCUGACCCCUUGCAUCAGCACCACCAUCC |
|  |  |  | UGAACCUGACCACCGACUACUGCGUGCUGGUGAGCUGUGGCCCAG |
|  |  |  | GGUGACCUACCACAGCCCCAGCUACGCCUACCACCAGUUCGAGAGG |
|  |  |  | AGGGCCAAGUACAAGAGGGCCCCGUGAGCCUGACCCUGGCCCUGC |
|  |  |  | UGCUGGGCGGCCUGACAAUGGGCGGCAUCGCCGCCGGCGUGGGCAC |
|  |  |  | CGGCACCACCGCCCUGGUGGCCACCCAGCAGUUCCAGCAGCUGCAG |
|  |  |  | GCCGCCAUGCACGACGACCUGAAGGAGGUGGAGAAGUCCAUCACCA |
|  |  |  | ACCUGGAGAAGUCCCUGACCAGCCUGAGCGAGGUGGUGCUGCAGAA |
|  |  |  | CAGGAGGGGCCUGGACCUGCUGUUCCUGAAGGAGGGCGGCCUGUGC |
|  |  |  | GCCGCCCUGAAGGAGGAGUGCUGCCUGUACGCCGACCACACCGGCC |
|  |  |  | UGGUGAUCGUGGGCAUUGUCGCUGGCCUGGCCGUCCUCGCCGUGGU |
|  |  |  | GGUGAUUGGAGCUGUGGUCGCAGCUGUUAUGUGCAGAAGAAAGUCA |
|  |  |  | UCCGGCGGAAAGGGAGGCUCCUACUCUCAGGCUGCUUCUGCUACAG |
|  |  |  | UGCCUAGAGCUCUUUAUGUGUUUAUCUCAGCUGGGCGGCGGAGGCAG |
|  |  |  | CGACUACAAGGACGACGAUGACAAGUAAACUCGAGUAUGUUACGUG |
|  |  |  | CAAAGGUGAUUGUCACCCCCGAAAGACCAUAUUGUGACACACCCU |
|  |  |  | CAGUAUCACGCCCAAACAUUUACAGCCGCGGUGUCAAAAACCGCGU |
|  |  |  | GGACGUGGUUAACAUCCCUGCUGGGAGGAUCAGCCGUAAUUAUUAU |
|  |  |  | AAUUGGCUUGGUGCUGGCUACUAUUGUGGCCAUGUACGUGCUGACC |
|  |  |  | AACCAGAAACAUAAUUGAAUACAGCAGCAAUUGGCAAGCUGCUUAC |
|  |  |  | AUAGAACUCGCGGCGAUUGGCAUGCCGCCUUAAAAUUUUUAUUUUA |
|  |  |  | UUUUUUCUUUCUUUCCGAAUCGGAUUUUGUUUUUAAUAUUUCAA |
|  |  |  | AAAAAAAAAAAAAAAAAAAAAAUCUAGAAAAAAAAAAAAAAAAAA |
|  |  |  | AAAAAAAAAAAAAAAAAAAAAAAAAAAAAAAAAAAAAAAAAAAAA |
|  |  |  | AAAAAAAAAAAAAAAAAAAAAAAAAAAAAAAAAA |
| 3068 (SEQ ID NO: 108) | STARR™ AH1A 5-FLAG | 3068 | AUGGGCGGCGCAUGAGAGAAGCCCAGACCAAUUACCUACCCAAAAU GGAGAAAGUUCACGUUGACAUCGAGGAAGACAGCCCAUUCCUCAGA GCUUUGCAGCGGAGCUUCCCGCAGUUUGAGGUAGAAGCCAAGCAGG UCACUGAUAAUGACCAUGCUAAUGCCAGAGCGUUUCGCAUCUGGC UUCAAAACUGAUCGAAACGGAGGUGGACCCAUCCGACACGAUCCUU GACAUUGGAAGUGCGCCCGCCCGCAGAAUGUAUUCUAAGCACAAGU AUCAUUGUAUCUGUCCGAUGAGAUGUGCGGAAGAUCCGGACAGAUU GUAUAAGUAUGCAACUAAGCUGAAGAAAAACUGUAAGGAAAUAACU GAUAAGGAAUUGGACAAGAAAAUGAAGGAGCUGGCCGCCGUCAUGA GCGACCCUGACCUGGAAACUGAGACUAUGUGCCUCCACGACGACGA GUCGUGUCGCUACGAAGGGCAAGUCGCUGUUUACCAGGAUGUAUAC GCCGUCGACGGCCCCACCAGCCUGUACCACCAGGCCAACAAGGGCG UGAGGGUGGCCUACUGGAUCGGCUUCGACACCACACCCUUCAUGUU CAAGAACCUGGCCGGCGCCUACCCCAGCUACAGCACCAACUGGGCC GACGAGACCGUGCUGACCGCCAGGAACAUCGGCCUGUGCAGCAGCG ACGUGAUGGAGAGGAGCCGGAGAGGCAUGAGCAUCCUGAGGAAGAA |

TABLE 6-continued

```
AUACCUGAAGCCCAGCAACAACGUGCUGUUCAGCGUGGGCAGCACC
AUCUACCACGAGAAGAGGGACCUGCUCAGGAGCUGGCACCUGCCCA
GCGUGUUCCACCUGAGGGGCAAGCAGAACUACACCUGCAGGUGCGA
GACCAUCGUGAGCUGCGACGGCUACGUGGUGAAGAGGAUCGCCAUC
AGCCCCGGCCUGUACGGCAAGCCCAGCGGCUACGCCGCUACAAUGC
ACAGGGAGGGCUUCCUGUGCUGCAAGGUGACCGACACCCUGAACGG
CGAGAGGGUGAGCUUCCCCGUGUGCACCUACGUGCCCGCCACCCUG
UGCGACCAGAUGACCGGCAUCCUGGCCACCGACGUGAGCGCCGACG
ACGCCCAGAAGCUGCUCGUGGGCCUGAACCAGAGGAUCGUGGUCAA
CGGCAGGACCCAGAGGAACACCAACACAAUGAAGAACUACCUGCUG
CCCGUGGUGGCCCAGGCUUUCGCCAGGUGGGCCAAGGAGUACAAGG
AGGACCAGGAAGACGAGAGGCCCCUGGGCCUGAGGGACAGGCAGCU
GGUGAUGGGCUGCUGCUGGGCCUUCAGGCGGCACAAGAUCACCAGC
AUCUACAAGAGGCCCGACACCCAGACCAUCAUCAAGGUGAACAGCG
ACUUCCACAGCUUCGUGCUGCCCAGGAUCGGCAGCAACACCCUGGA
GAUCGGCCUGAGGACCCGGAUCAGGAAGAUGCUGGAGGAACACAAG
GAGCCCAGCCCACUGAUCACCGCCGAGGACGUGCAGGAGGCCAAGU
GCGCUGCCGACGAGGCCAAGGAGGUGAGGGAGGCCGAGGAACUGAG
GGCCGCCCUGCCACCCCUGGCUGCCGACGUGGAGGAACCCACCCUG
GAAGCCGACGUGGACCUGAUGCUGCAGGAGGCCGGCGCCGGAAGCG
UGGAGACACCCAGGGGCCUGAUCAAGGUGACCAGCUACGACGGCGA
GGACAAGAUCGGCAGCUACGCCGUGCUGAGCCCACAGGCCGUGCUG
AAGUCCGAGAAGCUGAGCUGCAUCCACCCACUGGCCGAGCAGGUGA
UCGUGAUCACCCACAGCGGCAGGAAGGGCAGGUACGCCGUGGAGCC
CUACCACGGCAAGGUGGUCGUGCCCGAGGGCCACGCCAUCCCCGUG
CAGGACUUCCAGGCCCUGAGCGAGAGCGCCACCAUCGUGUACAACG
AGAGGGAGUUCGUGAACAGGUACCUGCACCAUAUCGCCACCCACGG
CGGAGCCCUGAACACCGACGAGGAAUACUACAAGACCGUGAAGCCC
AGCGAGCACGACGGCGAGUACCUGUACGACAUCGACAGGAAGCAGU
GCGUGAAGAAAGAGCUGGUGACCGGCCUGGGACUGACCGGCGAGCU
GGUGGACCCACCCUUCCACGAGUUCGCCUACGAGAGCCUGAGGACC
AGACCCGCCGCUCCCUACCAGGUGCCCACCAUCGGCGUGUACGGCG
UGCCCGGCAGCGGGAAAGAGCGGCAUCAUCAAGAGCGCCGUGACCAA
GAAAGACCUGGUGGUCAGCGCCAAGAAAGAGAACUGCGCCGAGAUC
AUCAGGGACGUGAAGAAGAUGAAAGGCCUGGACGUGAACGCGCGCA
CCGUGGACAGCGUGCUGCUGAACGGCUGCAAGCACCCCGUGGAGAC
CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
```

TABLE 6-continued

```
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUGCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACCACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCGAGUACGACGCCUACCUGGACAUGGUGGACGGCGCC
AGCUGCUGCCUGGACACCGCCAGCUUCUGCCCCGCCAAGCUGAGGA
GCUUCCCCAAGAAACACAGCUACCUGGAGCCCACCAUCAGGAGCGC
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACGUGGAGUGCUUCAAGAAAUACGC
CUGCAACAACGAGUACUGGGAGACCUUCAAGGAGAACCCCAUCAGG
CUGACCGAAGAGAACGUGGUGAACUACAUCACCAAGCUGAAGGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
GUGAAGGUGACACCCGGCACCAAGCACACCGAGGAGAGGCCCAAGG
UGCAGGUGAUCCAGGCCGCUGACCCACUGGCCACCGCCUACCUGUG
CGGCAUCCACAGGGAGCUGGUGAGGCGGCUGAACGCCGUGCUGCUG
CCCAACAUCCACACCCUGUUCGACAUGAGCGCCGAGGACUUCGACG
CCAUCAUCGCCGAGCACUUCCAGCCCGGCGACUGCGUGCUGGAGAC
CGACAUCGCCAGCUUCGACAAGAGCGAGGAUGACGCUAUGGCCCUG
ACCGCUCUGAUGAUCCUGGAGGACCUGGGCGUGGACGCCGAGCUGC
UCACCCUGAUCGAGGCUGCCUUCGGCGAGAUCAGCUCCAUCCACCU
GCCCACCAAGACCAAGUUCAAGUUCGGCGCUAUGAUGAAAAGCGGA
AUGUUCCUGACCCUGUUCGUGAACACCGUGAUCAACAUUGUGAUCG
CCAGCAGGGUGCUGCGGGAGAGGCUGACCGGCAGCCCCUGCCUGC
CUUCAUCGGCGACGACAACAUCGUGAAGGGCGUGAAAAGCGACAAG
CUGAUGGCCGACAGGUGCGCCACCUGGCUGAACAUGGAGGUGAAGA
UCAUCGACGCCGUGGUGGGCGAGAAGGCCCCCUACUUCUGCGGCGG
AUUCAUCCUGUGCGACAGCGUGACCGGCACCGCCUGCAGGGUGGCC
GACCCCCUGAAGAGGCUGUUCAAGCUGGGCAAGCCACUGGCCGCUG
ACGAUGAGCACGACGAUGACAGGCGGAGGGCCCUGCACGAGGAAAG
CACCAGGUGGAACAGGGUGGGCAUCCUGAGCGAGCUGUGCAAGGCC
GUGGAGAGCAGGUACGAGACCGUGGGCACCAGCAUCAUCGUGAUGG
CUAUGACCACACUGGCCAGCUCCGUCAAGAGCUUCUCCUACCCUGAG
GGGGCCCCUAUAACUCUCUACGGCUAACCUGAAUGGACUACGACA
UAGUCUAGUCCGCCAAGGCCGCCACCAUGAGAGUGACAGCCCCUAG
AACCUUACUGCUUCUGCUUUGGGGAGCUGUUGCUCUGACAGAGACA
UGGGCUGGAUCUUACCACAGCCCCAGCUACGCCUACCACCAGUUCG
AGAGGGGGGAGGAGGCUCCGGGGGAGGAGGCUCCCUGAAGAUCAG
CCAGGCCGUGCACGCCGCCCACGCCGAGAUCAACGAGGCCGGCCGG
GAGGUGAUCGUGGGCAUUGUCGCUGGCCUGGCCGUCCUCGCCGUGG
UGGUGAUUGGAGCUGUGGUCGCCAGCUGUUAUGUGCAGAAGAAGUC
AUCCGGCGGAAAGGGAGGCUCCUACUCUCAGGCUGCUUCUGCUACA
GUGCCUAGAGCUCUUUAUGUGUUUAUCUCAGCUGGGCGGCGGAGGCA
GCGACUACAAGGACGACGAUGACAAGUAAACUCGAGUAUGUUACGU
GCAAAGGUGAUUGUCACCCCCCGAAAGACCCAUAUUGUGACACACCC
UCAGUAUCACGCCCAAACAUUUACAGCCGCGGUGUCAAAAACCGCG
```

TABLE 6-continued

```
UGGACGUGGUUAACAUCCCUGCUGGGAGGAUCAGCCGUAAUUAUUA
UAAUUGGCUUGGUGCUGGCUACUAUUGUGGCCAUGUACGUGCUGAC
CAACCAGAAACAUAAUUGAAUACAGCAGCAAUUGGCAAGCUGCUUA
CAUAGAACUCGCGGCGAUUGGCAUGCCGCCUUAAAAUUUUAUUUU
AUUUUUUCUUUUCUUUUCCGAAUCGGAUUUUGUUUUUAAUAUUUCA
AAAAAAAAAAAAAAAAAAAAAAAAUCUAGAAAAAAAAAAAAAAAA
AAAAAAAAAAAAAAAAAAAAAAAAAAAAAAAAAAAAAAAAAAAA
AAAAAAAAAAAAAAAAAAAAAAAAAAAAAAAAAAAA
``` non structural protein of SINV

| mARM # | | | |
|---|---|---|---|
| 2842 and 2862 (SEQ ID NO: 109) | SINV nsP1-4 AA | | MEKPVVNVDVDPQSPFVVQLQKSFPQFEVVAQQVTPNDHANARAFS<br>HLASKLIELEVPTTATILDIGSAPARRMFSEHQYHCVCPMRSPEDP<br>DRMMKYASKLAEKACKITNKNLHEKIKDLRTVLDTPDAETPSLCFH<br>NDVTCNMRAEYSVMQDVYINAPGTIYHQAMKGVRTLYWIGFDTTQF<br>MFSAMAGSYPAYNTNWADEKVLEARNIGLCSTKLSEGRTGKLSIMR<br>KKELKPGSRVYFSVGSTLYPEHRASLQSWHLPSVFHLNGKQSYTCR<br>CDTVVSCEGYVVKKITISPGITGETVGYAVTHNSEGFLLCKVTDTV<br>KGERVSFPVCTYIPATICDQMTGIMATDISPDDAQKLLVGLNQRIV<br>INGRTNRNTNTMQNYLLPIIAQGFSKWAKERKDDLDNEKMLGTRER<br>KLTYGCLWAFRTKKVHSFYRPPGTQTCVKVPASFSAFPMSSVWTTS<br>LPMSLRQKLKLALQPKKEEKLLQVSEELVMEAKAAFEDAQEEARAE<br>KLREALPPLVADKGIEAAAEVVCEVEGLQADIGAALVETPRGHVRI<br>IPQANDRMIGQYIVVSPNSVLKNAKLAPAHPLADQVKIITHSGRSG<br>RYAVEPYDAKVLMPAGGAVPWPEFLALSESATLVYNEREFVNRKLY<br>HIAMHGPAKNTEEEQYKVTKAELAETEYVFDVDKKRCVKKEEASGL<br>VLSGELTNPPYHELALEGLKTRPAVPYKVETIGVIGTPGSGKSAII<br>KSTVTARDLVTSGKKENCREIEADVLRLRGMQITSKTVDSVMLNGC<br>HKAVEVLYVDEAFACHAGALLALIAIVRPRKKVVLCGDPMQCGFFN<br>MMQLKVHFNHPEKDICTKTFYKYISRRCTQPVTAIVSTLHYDGKMK<br>TTNPCKKNIEIDITGATKPKPGDIILTCFRGWVKQLQIDYPGHEVM<br>TAAASQGLTRKGVYAVRQKVNENPLYAITSEHVNVLLTRTEDRLVW<br>KTLQGDPWIKQLTNIPKGNFQATIEDWEAEHKGIIAAINSPTPRAN<br>PPFSCKTNVCWAKALEPILATAGIVLTGCQWSELFPQFADDKPHSAI<br>YALDVICIKFFGMDLTSGLFSKQSIPLTYHPADSARPVAHWDNSPG<br>TRKYGYDHAIAAELSRRFPVFQLAGKGTQLDLQTGRTRVISAQHNL<br>VPVNRNLPHALVPEYKEKQPGPVEKFLNQFKHHSVLVVSEEKIEAP<br>RKRIEWIAPIGIAGADKNYNLAFGFPPQARYDLVFINIGTKYRNHH<br>FQQCEDHAATLKTLSRSALNCLNPGGTLVVKSYGYADRNSEDVVTA<br>LARKFVRVSAARPDCVSSNTEMYLIFRQLDNSRTRQFTPHHLNCVI<br>SSVYEGTRDGVGAAPSYRTKRENIADCQEEAVVNAANPLGRPGEGV<br>CRAIYKRWPTSFTDSATETGTARMTVCLGKKVIHAVGPDFRKHPEA<br>EALKLLQNAYHAVADLVNEHNIKSVAIPLLSTGIYAAGKDRLEVSL<br>NCLTTALDRTDADVTIYCLDKKWKERIDAALQLKESVTELKDEDME<br>IDDELVWIHPDSCLKGRKGFSTTKGKLYSYFEGTKFHQAAKDMAEI<br>KVLFPNDQESNEQLCAYILGETMEAIREKCPVDHNPSSSPPKTLPC<br>LCMYAMTPERVHRLRSNNVKEVTVCSSTPLPKHKIKNVQKVQCTKV<br>VLFNPHTPAFVPARKYIEVPEQPTAPPAQAEEAPEVVATPSPSTAD<br>NTSLDVTDISLDMDDSSEGSLFSSFSGSDNSITSMDSWSSGPSSLE<br>IVDRRQVVVADVHAVQEPAPIPPPRLKKMARLAAARKEPTPPASNS<br>SESLHLSFGGVSMSLGSIFDGETARQAAVQPLATGPTDVPMSFGSF<br>SDGEIDELSRRVTESEPVLFGSFEPGEVNSIISSRSAVSFPLRKQR<br>RRRRSRRTEY*LTGVGGYIFSTDTGPGHLQKKSVLQNQLTEPTLER<br>NVLERIHAPVLDTSKEEQLKLRYQMMPTEANKSRYQSRKVENQKAI<br>TTERLLSGLRLYNSATDQPECYKITYPKPLYSSSVPANYSDPQFAV<br>AVCNNYLHENYPTVASYQITDEYDAYLDMVDGTVACLDTATFCPAK<br>LRSYPKKHEYRAPNIRSAVPSAMQNTLQNVLIAATKRNCNVTQMRE<br>LPTLDSATFNVECFRKYACNDEYWEEFARKPIRITTEFVTAYVARL<br>KGPKAAALFAKTYNLVPLQEVPMDRFVMDMKRDVKVTPGTKHTEER<br>PKVQVIQAAEPLATAYICGIHRELVRRLTAVLLPNIHTLFDMSAED<br>FDAIIAEHFKQGDPVLETDIASFDKSQDDAMALTGLMILEDLGVDQ<br>PLLDLIECAFGEISSTHLPTGTRFKFGAMMKSGMFLTLFVNTVLNV<br>VIASRVLEERLKTSRCAAFIGDDNIIHGVVSDKEMAERCATWLNME<br>VKIIDAVIGERPPYFCGGFILQDSVTSTACRVADPLKRLFKLGKPL<br>PADDEQDEDRRRALLDETKAWFRVGITGTLAVAVTTRYEVDNITPV<br>LLALRTFAQSKRAFQAIRGEIKHLYGGPK |

Example 2

This example describes analysis of the immunogenicity of influenza hemagglutinin (HA) expressed from self-replicating RNA or mRNA.

Self-replicating RNA and mRNA vaccine constructs were designed to encode the full-length hemagglutinin (HA) protein from influenza virus A/California/07/2009 (H1N1) (SEQ ID NO:113 and 114). The mRNA vaccine construct encoding HA included a tobacco etch virus (TEV) 5' UTR and a Xenopus beta-globin (Xbg) 3' UTR. Both self-replicating RNA (SEQ ID NO:56; entire RNA mARM3039) and mRNA vaccine constructs (SEQ ID NO:116; entire RNA sequence mARM3038) were encapsulated in the same lipid nanoparticle (LNP) composition that included four lipid excipients (an ionizable cationic lipid, 1,2-distearoyl-sn-glycero-3-phosphocholine (DSPC), cholesterol, and PEG2000-DMG) dispersed in HEPES buffer (pH 8.0) containing sodium chloride and the cryoprotectants sucrose and glycerol. The N:P ratio of complexing lipid and RNA was approximately 9:1. The ionizable cationic lipid had the following structure:

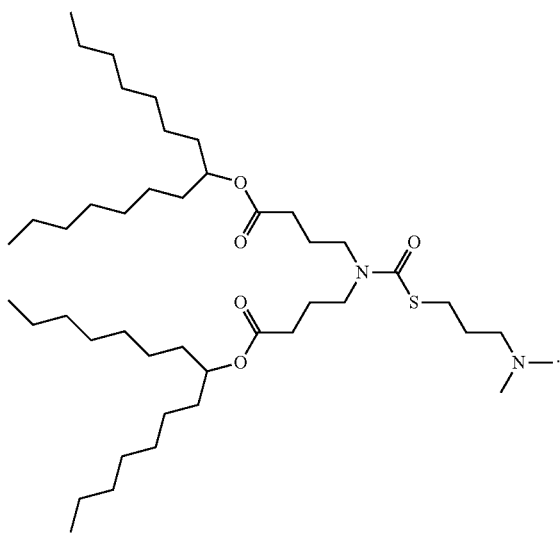 [SMILES: CCCCCCCC(CCCCCCC)OC(=O)CCCN(CCCC(=O)OC(CCCCCCC)CCCCCCC)C(=O)SCCCN(C)C]

Five female, 8-10 week old Balb/c mice were injected intramuscularly with 2 mg of mRNA or self-replicating RNA encoding HA. Mice were bled on days 14, 28, 42, and 56, followed by hemagglutination inhibition (HAI) assay using serially diluted sera. The reciprocal of the highest dilution of serum that caused inhibition of hemagglutination was considered the HAI titer, with a titer of 1/40 being protective against influenza virus infection and four-fold higher titers than baseline indicating seroconversion.

Results in FIG. 7 show that greater HAI titers were obtained with self-replicating RNA encoding HA as compared to mRNA encoding HA. HAI titers for the self-replicating RNA construct encoding HA were greater than HAI titers for the mRNA encoding HA at all time points beginning at day 28. In addition, protective HAI titers were seen for the self-replicating RNA construct encoding HA beginning at day 28 that were maintained for at least 56 days. By contrast, mRNA encoding HA showed protective HAI titers only at day 56 that were lower than HAI titers seen for the self-replicating RNA HA construct. At all other time points, HAI titers for the mRNA construct encoding HA were below the protective titer threshold, with an HAI titer that was comparable to injection with PBS control at day 28.

These results show that the self-replicating RNA construct encoding HA elicited protective HA antibody titers, with greater HAI titers as compared to the mRNA construct encoding HA.

Example 3

This example describes dsRNA production and luciferase expression for self-replicating RNA.

Several self-replicating RNA systems from different alphaviruses were tested for expression in vitro using either green fluorescent protein (GFP) or firefly luciferase (Luc) as reporter genes. Initial transfection of cells with increasing amounts of self-replicating RNA resulted in expression of reporter genes at a lower dose compared to mRNA. However, as the amount of input self-replicating RNA increased, detectable expression of the reporter gene decreased.

Self-replicating RNA produces double stranded RNA (dsRNA) as an intermediate in the amplification process. Overproduction of dsRNA can suppress translation. To evaluate the effect of dsRNA production on transgene expression, dsRNA and the expression of reporter gene luciferase were measured simultaneously. HEK293 cells were transfected with 2 μg of replicon A (SEQ ID NO:115; entire RNA sequence mARM2826) or replicon B (SEQ ID NO:100, entire RNA sequence mARM2809) self-replicating RNA, or mRNA expressing Luc (SEQ ID NO:102, entire mRNA sequence mARM1782) using a commercial RNA transfection reagent. Untransfected cells (UTC) served as a control. dsRNA production (FIG. 8A) was quantified using immunohistochemical staining for dsRNA, followed by fluorescence quantification using a fluorescence scanner 24 hours after transfection. Luciferase expression (FIG. 8B) was assayed by measuring bioluminescence in parallel.

Replicon A produced a 3-fold higher level of dsRNA than replicon B 24 hrs after transfection (FIG. 8A). However, replicon B produced a 2.4-fold higher expression level of luciferase compared to replicon A. Furthermore, the level of luciferase expression from replicon A was equivalent to that observed for mRNA. Thus, even though replicon A had the ability to amplify the amount of replicon RNA and transcribed mRNA encoding luciferase, translation of the amplified mRNA was inhibited, consistent with overproduction of dsRNA inhibiting translation. Furthermore, higher levels of luciferase gene expression were seen for replicon RNA as compared to mRNA at 24, 48, and 72 hours after transfection of HEK293 cells (FIG. 9A). Self-replicating RNA with an expression cassette that included a luciferase reporter gene followed by an IRES and E3L also showed robust luciferase expression (FIGS. 9B, 9C; SEQ ID NOs: 118 and 119). Luciferase expression was also seen for a self-replicating RNA that expressed E3L from a first subgenomic promoter and a luciferase reporter gene from a second subgenomic promoter located 3' of the E3L open reading frame (not shown). Thus, not only did replicon RNA produce higher levels of luciferase gene expression compared to mRNA, but replicon RNA also showed increased duration of expression over a 72-hr period.

Example Sequences

Additional illustrative sequences are provided below, features of which are described in Table 7:

TABLE 7

| SEQ ID NO | Description |
|---|---|
| SEQ ID NO: 72 | nsP1-4 ORF, codon-optimized |
| SEQ ID NO: 73 | 5' UTR |
| SEQ ID NO: 74 | 5' UTR |
| SEQ ID NO: 75 | 5' UTR |
| SEQ ID NO: 76 | 3' UTR |
| SEQ ID NO: 77 | Intergenic region between nsP1-4 ORF and antigenic protein ORF |

TABLE 7-continued

| SEQ ID NO | Description |
|---|---|
| SEQ ID NO: 78 | Replicon sequence comprising SEQ ID NO: 72, SEQ ID NO: 73, SEQ ID NO: 76, and SEQ ID NO: 77 |
| SEQ ID NO: 79 | nsP1-4 protein sequence |
| SEQ ID NO: 80 | nsP1-4 protein sequence |
| SEQ ID NO: 81 | nsP1-4 protein sequence |
| SEQ ID NO: 82 | 5' UTR (TEV) |
| SEQ ID NO: 83 | 3' UTR (Xbg) |

SEQ ID NO: 72

```
ATGGAGAAAGTTCACGTTGACATCGAGGAAGACAGCCCATTCCTCAGAGCTTTG
CAGCGGAGCTTCCCGCAGTTTGAGGTAGAAGCCAAGCAGGTCACTGATAATGAC
CATGCTAATGCCAGAGCGTTTTCGCATCTGGCTTCAAAACTGATCGAAACGGAGG
TGGACCCATCCGACACGATCCTTGACATTGGAAGTGCGCCCGCCCGCAGAATGT
ATTCTAAGCACAAGTATCATTGTATCTGTCCGATGAGATGTGCGGAAGATCCGGA
CAGATTGTATAAGTATGCAACTAAGCTGAAGAAAAACTGTAAGGAAATAACTGA
TAAGGAATTGGACAAGAAAATGAAGGAGCTGGCCGCCGTCATGAGCGACCCTGA
CCTGGAAACTGAGACTATGTGCCTCCACGACGACGAGTCGTGTCGCTACGAAGG
GCAAGTCGCTGTTTACCAGGATGTATACGCCGTCGACGGCCCCACCAGCCTGTAC
CACCAGGCCAACAAGGGCGTGAGGGTGGCCTACTGGATCGGCTTCGACACCACA
CCCTTCATGTTCAAGAACCTGGCCGGCGCCTACCCCAGCTACAGCACCAACTGGG
CCGACGAGACCGTGCTGACCGCCAGGAACATCGGCTGTGCAGCAGCGACGTGA
TGGAGAGGAGCCGGAGAGGCATGAGCATCCTGAGGAAGAAATACCTGAAGCCC
AGCAACAACGTGCTGTTCAGCGTGGGCAGCACCATCTACCACGAGAAGAGGGAC
CTGCTCAGGAGCTGGCACCTGCCCAGCGTGTTCCACCTGAGGGGCAAGCAGAAC
TACACCTGCAGGTGCGAGACCATCGTGAGCTGCGACGGCTACGTGGTGAAGAGG
ATCGCCATCAGCCCCGGCCTGTACGGCAAGCCCAGCGGCTACGCCGCTACAATG
CACAGGGAGGGCTTCCTGTGCTGCAAGGTGACCGACACCCTGAACGGCGAGAGG
GTGAGCTTCCCCGTGTGCACCTACGTGCCCGCCACCCTGTGCGACCAGATGACCG
GCATCCTGGCCACCGACGTGAGCGCCGACGACGCCCAGAAGCTGCTCGTGGGCC
TGAACCAGAGGATCGTGGTCAACGGCAGGACCCAGAGGAACACCAACACAATG
AAGAACTACCTGCTGCCCGTGGTGGCCCAGGCTTTCGCCAGGTGGGCCAAGGAG
TACAAGGAGGACCAGGAAGACGAGAGGCCCCTGGGCCTGAGGGACAGGCAGCT
GGTGATGGGCTGCTGCTGGGCCTTCAGGCGGCACAAGATCACCAGCATCTACAA
GAGGCCCGACACCCAGACCATCATCAAGGTGAACAGCGACTTCCACAGCTTCGT
GCTGCCCAGGATCGGCAGCAACACCCTGGAGATCGGCCTGAGGACCCGGATCAG
GAAGATGCTGGAGGAACACAAGGAGCCCAGCCCACTGATCACCGCCGAGGACGT
GCAGGAGGCCAAGTGCGCTGCCGACGAGGCCAAGGAGGTGAGGGAGGCCGAGG
AACTGAGGGCCGCCCTGCCACCCCTGGCTGCCGACGTGGAGGAACCCACCCTGG
AAGCCGACGTGGACCTGATGCTGCAGGAGGCCGGCGCCGGAAGCGTGGAGACA
CCCAGGGGCCTGATCAAGGTGACCAGCTACGACGGCGAGGACAAGATCGGCAGC
TACGCCGTGCTGAGCCCACAGGCCGTGCTGAAGTCCGAGAAGCTGAGCTGCATC
CACCCACTGGCCGAGCAGGTGATCGTGATCACCCACAGCGGCAGGAAGGGCAGG
TACGCCGTGGAGCCCTACCACGGCAAGGTGGTCGTGCCCGAGGGCCACGCCATC
CCCGTGCAGGACTTCCAGGCCCTGAGCGAGAGCGCCACCATCGTGTACAACGAG
```

-continued

```
AGGGAGTTCGTGAACAGGTACCTGCACCATATCGCCACCCACGGCGGAGCCCTG

AACACCGACGAGGAATACTACAAGACCGTGAAGCCCAGCGAGCACGACGGCGA

GTACCTGTACGACATCGACAGGAAGCAGTGCGTGAAGAAAGAGCTGGTGACCGG

CCTGGGACTGACCGGCGAGCTGGTGGACCCACCCTTCCACGAGTTCGCCTACGA

GAGCCTGAGGACCAGACCCGCCGCTCCCTACCAGGTGCCCACCATCGGCGTGTA

CGGCGTGCCCGGCAGCGGAAAGAGCGGCATCATCAAGAGCGCCGTGACCAAGA

AAGACCTGGTGGTCAGCGCCAAGAAAGAGAACTGCGCCGAGATCATCAGGGAC

GTGAAGAAGATGAAAGGCCTGGACGTGAACGCGCGCACCGTGGACAGCGTGCTG

CTGAACGGCTGCAAGCACCCCGTGGAGACCCTGTACATCGACGAGGCCTTCGCTT

GCCACGCCGGCACCCTGAGGGCCCTGATCGCCATCATCAGGCCCAAGAAAGCCG

TGCTGTGCGGCGACCCCAAGCAGTGCGGCTTCTTCAACATGATGTGCCTGAAGGT

GCACTTCAACCACGAGATCTGCACCCAGGTGTTCCACAAGAGCATCAGCAGGCG

GTGCACCAAGAGCGTGACCAGCGTCGTGAGCACCCTGTTCTACGACAAGAAAAT

GAGGACCACCAACCCCAAGGAGACCAAAATCGTGATCGACACCACAGGCAGCA

CCAAGCCCAAGCAGGACGACCTGATCCTGACCTGCTTCAGGGGCTGGGTGAAGC

AGCTGCAGATCGACTACAAGGGCAACGAGATCATGACCGCCGCTGCCAGCCAGG

GCCTGACCAGGAAGGGCGTGTACGCCGTGAGGTACAAGGTGAACGAGAACCCAC

TGTACGCTCCCACCAGCGAGCACGTGAACGTGCTGCTGACCAGGACCGAGGACA

GGATCGTGTGGAAGACCCTGGCCGGCGACCCCTGGATCAAGACCCTGACCGCCA

AGTACCCCGGCAACTTCACCGCCACCATCGAAGAGTGGCAGGCCGAGCACGACG

CCATCATGAGGCACATCCTGGAGAGGCCCGACCCCACCGACGTGTTCCAGAACA

AGGCCAACGTGTGCTGGGCCAAGGCCCTGGTGCCCGTGCTGAAGACCGCCGGCA

TCGACATGACCACAGAGCAGTGGAACACCGTGGACTACTTCGAGACCGACAAGG

CCCACAGCGCCGAGATCGTGCTGAACCAGCTGTGCGTGAGGTTCTTCGGCCTGGA

CCTGGACAGCGGCCTGTTCAGCGCCCCCACCGTGCCACTGAGCATCAGGAACAA

CCACTGGGACAACAGCCCCAGCCCAAACATGTACGGCCTGAACAAGGAGGTGGT

CAGGCAGCTGAGCAGGCGGTACCCACAGCTGCCCAGGGCCGTGGCCACCGGCAG

GGTGTACGACATGAACACCGGCACCCTGAGGAACTACGACCCCAGGATCAACCT

GGTGCCCGTGAACAGGCGGCTGCCCCACGCCCTGGTGCTGCACCACAACGAGCA

CCCACAGAGCGACTTCAGCTCCTTCGTGAGCAAGCTGAAAGGCAGGACCGTGCT

GGTCGTGGGCGAGAAGCTGAGCGTGCCCGGCAAGATGGTGGACTGGCTGAGCGA

CAGGCCCGAGGCCACCTTCCGGGCCAGGCTGGACCTCGGCATCCCCGGCGACGT

GCCCAAGTACGACATCATCTTCGTGAACGTCAGGACCCCATACAAGTACCACCAT

TACCAGCAGTGCGAGGACCACGCCATCAAGCTGAGCATGCTGACCAAGAAGGCC

TGCCTGCACCTGAACCCCGGAGGCACCTGCGTGAGCATCGGCTACGGCTACGCC

GACAGGGCCAGCGAGAGCATCATTGGCGCCATCGCCAGGCTGTTCAAGTTCAGC

AGGGTGTGCAAACCCAAGAGCAGCCTGGAGGAAACCGAGGTGCTGTTCGTGTTC

ATCGGCTACGACCGGAAGGCCAGGACCCACAACCCCTACAAGCTGAGCAGCACC

CTGACAAACATCTACACCGGCAGCAGGCTGCACGAGGCCGGCTGCGCCCCCAGC

TACCACGTGGTCAGGGGCGATATCGCCACCGCCACCGAGGGCGTGATCATCAAC
```

-continued

```
GCTGCCAACAGCAAGGGCCAGCCCGGAGGCGGAGTGTGCGGCGCCCTGTACAAG

AAGTTCCCCGAGAGCTTCGACCTGCAGCCCATCGAGGTGGGCAAGGCCAGGCTG

GTGAAGGGCGCCGCTAAGCACATCATCCACGCCGTGGGCCCCAACTTCAACAAG

GTGAGCGAGGTGGAAGGCGACAAGCAGCTGGCCGAAGCCTACGAGAGCATCGC

CAAGATCGTGAACGACAATAACTACAAGAGCGTGGCCATCCCACTGCTCAGCAC

CGGCATCTTCAGCGGCAACAAGGACAGGCTGACCCAGAGCCTGAACCACCTGCT

CACCGCCCTGGACACCACCGATGCCGACGTGGCCATCTACTGCAGGGACAAGAA

GTGGGAGATGACCCTGAAGGAGGCCGTGGCCAGGCGGGAGGCCGTGGAAGAGA

TCTGCATCAGCGACGACTCCAGCGTGACCGAGCCCGACGCCGAGCTGGTGAGGG

TGCACCCCAAGAGCTCCCTGGCCGGCAGGAAGGGCTACAGCACCAGCGACGGCA

AGACCTTCAGCTACCTGGAGGGCACCAAGTTCCACCAGGCCGCTAAGGACATCG

CCGAGATCAACGCTATGTGGCCCGTGGCCACCGAGGCCAACGAGCAGGTGTGCA

TGTACATCCTGGGCGAGAGCATGTCCAGCATCAGGAGCAAGTGCCCCGTGGAGG

AAAGCGAGGCCAGCACACCACCCAGCACCCTGCCCTGCCTGTGCATCCACGCTA

TGACACCCGAGAGGGTGCAGCGGCTGAAGGCCAGCAGGCCCGAGCAGATCACC

GTGTGCAGCTCCTTCCCACTGCCCAAGTACAGGATCACCGGCGTGCAGAAGATCC

AGTGCAGCCAGCCCATCCTGTTCAGCCCAAAGGTGCCCGCCTACATCCACCCCAG

GAAGTACCTGGTGGAGACCCCACCCGTGGACGAGACACCCGAGCCAAGCGCCGA

GAACCAGAGCACCGAGGGCACACCCGAGCAGCCACCCCTGATCACCGAGGACG

AGACAAGGACCCGGACCCCAGAGCCCATCATTATCGAGGAAGAGGAAGAGGAC

AGCATCAGCCTGCTGAGCGACGGCCCCACCCACCAGGTGCTGCAGGTGGAGGCC

GACATCCACGGCCCACCCAGCGTGTCCAGCTCCAGCTGGAGCATCCCACACGCC

AGCGACTTCGACGTGGACAGCCTGAGCATCCTGGACACCCTGGAGGGCGCCAGC

GTGACCTCCGGCGCCACCAGCGCCGAGACCAACAGCTACTTCGCCAAGAGCATG

GAGTTCCTGGCCAGGCCCGTGCCAGCTCCCAGGACCGTGTTCAGGAACCCACCCC

ACCCAGCTCCCAGGACCAGGACCCCAAGCCTGGCTCCCAGCAGGGCCTGCAGCA

GGACCAGCCTGGTGAGCACCCCACCCGGCGTGAACAGGGTGATCACCAGGGAGG

AACTGGAGGCCCTGACACCCAGCAGGACCCCCAGCAGGTCCGTGAGCAGGACTA

GTCTGGTGTCCAACCCACCCGGCGTGAACAGGGTGATCACCAGGGAGGAATTCG

AGGCCTTCGTGGCCCAGCAACAGAGACGGTTCGACGCCGGCGCCTACATCTTCA

GCAGCGACACCGGCCAGGGACACCTGCAGCAAAAGAGCGTGAGGCAGACCGTG

CTGAGCGAGGTGGTGCTGGAGAGGACCGAGCTGGAAATCAGCTACGCCCCCAGG

CTGGACCAGGAGAAGGAGGAACTGCTCAGGAAGAAACTGCAGCTGAACCCCAC

CCCAGCCAACAGGAGCAGGTACCAGAGCAGGAAGGTGGAGAACATGAAGGCCA

TCACCGCCAGGCGGATCCTGCAGGGCCTGGGACACTACCTGAAGGCCGAGGGCA

AGGTGGAGTGCTACAGGACCCTGCACCCCGTGCCACTGTACAGCTCCAGCGTGA

ACAGGGCCTTCTCCAGCCCCAAGGTGGCCGTGGAGGCCTGCAACGCTATGCTGA

AGGAGAACTTCCCCACCGTGGCCAGCTACTGCATCATCCCCGAGTACGACGCCTA

CCTGGACATGGTGGACGGCGCCAGCTGCTGCCTGGACACCGCCAGCTTCTGCCCC

GCCAAGCTGAGGAGCTTCCCCAAGAAACACAGCTACCTGGAGCCCACCATCAGG

AGCGCCGTGCCCAGCGCCATCCAGAACACCCTGCAGAACGTGCTGGCCGCTGCC
```

-continued

ACCAAGAGGAACTGCAACGTGACCCAGATGAGGGAGCTGCCCGTGCTGGACAGC
GCTGCCTTCAACGTGGAGTGCTTCAAGAAATACGCCTGCAACAACGAGTACTGG
GAGACCTTCAAGGAGAACCCCATCAGGCTGACCGAAGAGAACGTGGTGAACTAC
ATCACCAAGCTGAAGGGCCCCAAGGCCGCTGCCCTGTTCGCTAAGACCCACAAC
CTGAACATGCTGCAGGACATCCCAATGGACAGGTTCGTGATGGACCTGAAGAGG
GACGTGAAGGTGACACCCGGCACCAAGCACACCGAGGAGAGGCCCAAGGTGCA
GGTGATCCAGGCCGCTGACCCACTGGCCACCGCCTACCTGTGCGGCATCCACAG
GGAGCTGGTGAGGCGGCTGAACGCCGTGCTGCTGCCCAACATCCACACCCTGTTC
GACATGAGCGCCGAGGACTTCGACGCCATCATCGCCGAGCACTTCCAGCCCGGC
GACTGCGTGCTGGAGACCGACATCGCCAGCTTCGACAAGAGCGAGGATGACGCT
ATGGCCCTGACCGCTCTGATGATCCTGGAGGACCTGGGCGTGGACGCCGAGCTG
CTCACCCTGATCGAGGCTGCCTTCGGCGAGATCAGCTCCATCCACCTGCCCACCA
AGACCAAGTTCAAGTTCGGCGCTATGATGAAAAGCGGAATGTTCCTGACCCTGTT
CGTGAACACCGTGATCAACATTGTGATCGCCAGCAGGGTGCTGCGGGAGAGGCT
GACCGGCAGCCCCTGCGCTGCCTTCATCGGCGACGACAACATCGTGAAGGGCGT
GAAAAGCGACAAGCTGATGGCCGACAGGTGCGCCACCTGGCTGAACATGGAGGT
GAAGATCATCGACGCCGTGGTGGGCGAGAAGGCCCCCTACTTCTGCGGCGGATT
CATCCTGTGCGACAGCGTGACCGGCACCGCCTGCAGGGTGGCCGACCCCCTGAA
GAGGCTGTTCAAGCTGGGCAAGCCACTGGCCGCTGACGATGAGCACGACGATGA
CAGGCGGAGGGCCCTGCACGAGGAAAGCACCAGGTGGAACAGGGTGGGCATCC
TGAGCGAGCTGTGCAAGGCCGTGGAGAGCAGGTACGAGACCGTGGGCACCAGC
ATCATCGTGATGGCTATGACCACACTGGCCAGCTCCGTCAAGAGCTTCTCCTACC
TGAGGGGGGCCCCTATAACTCTCTACGGCTAA

ATGGGCGGCGCATGAGAGAAGCCCAGACCAATTACCTACCCAAA SEQ ID NO: 73

GATGGGCGGCGCATGAGAGAAGCCCAGACCAATTACCTACCCAAA SEQ ID NO: 74

GATAGGCGGCGCATGAGAGAAGCCCAGACCAATTACCTACCCAAA SEQ ID NO: 75

ACTCGAGTATGTTACGTGCAAAGGTGATTGTCACCCCCCGAAAGACCATATTGTG SEQ ID NO: 76
ACACACCCTCAGTATCACGCCCAAACATTTACAGCCGCGGTGTCAAAAACCGCG
TGGACGTGGTTAACATCCCTGCTGGGAGGATCAGCCGTAATTATTATAATTGGCT
TGGTGCTGGCTACTATTGTGGCCATGTACGTGCTGACCAACCAGAAACATAATTG
AATACAGCAGCAATTGGCAAGCTGCTTACATAGAACTCGCGGCGATTGGCATGC
CGCCTTAAAATTTTTATTTTATTTTTTCTTTTCTTTTCCGAATCGGATTTTGTTTTTA
ATATTTCAAAAAAAAAAAAAAAAAAAAAAAAATCTAGAAAAAAAAAAAAAAAA
AAAAAAAAAAAAAAAAAAAAAAAAAAAAAAAAAAAAAAAAAAAAAAAAA
AAAAAAAAAAAAAAAAAAAAAAAAAAAAA

-continued

CCTGAATGGACTACGACATAGTCTAGTCCGCCAAGGCCGCCACC

SEQ ID NO: 77

SEQ ID NO: 78

ATGGGCGGCGCATGAGAGAAGCCCAGACCAATTACCTACCCAAAATGGAGAAA

GTTCACGTTGACATCGAGGAAGACAGCCCATTCCTCAGAGCTTTGCAGCGGAGCT

TCCCGCAGTTTGAGGTAGAAGCCAAGCAGGTCACTGATAATGACCATGCTAATG

CCAGAGCGTTTTCGCATCTGGCTTCAAAACTGATCGAAACGGAGGTGGACCCATC

CGACACGATCCTTGACATTGGAAGTGCGCCCGCCCGCAGAATGTATTCTAAGCAC

AAGTATCATTGTATCTGTCCGATGAGATGTGCGGAAGATCCGGACAGATTGTATA

AGTATGCAACTAAGCTGAAGAAAAACTGTAAGGAAATAACTGATAAGGAATTGG

ACAAGAAAATGAAGGAGCTGGCCGCCGTCATGAGCGACCCTGACCTGGAAACTG

AGACTATGTGCCTCCACGACGACGAGTCGTGTCGCTACGAAGGGCAAGTCGCTG

TTTACCAGGATGTATACGCCGTCGACGGCCCCACCAGCCTGTACCACCAGGCCAA

CAAGGGCGTGAGGGTGGCCTACTGGATCGGCTTCGACACCACACCCTTCATGTTC

AAGAACCTGGCCGGCGCCTACCCCAGCTACAGCACCAACTGGGCCGACGAGACC

GTGCTGACCGCCAGGAACATCGGCCTGTGCAGCAGCGACGTGATGGAGAGGAGC

CGGAGAGGCATGAGCATCCTGAGGAAGAAATACCTGAAGCCCAGCAACAACGT

GCTGTTCAGCGTGGGCAGCACCATCTACCACGAGAAGAGGGACCTGCTCAGGAG

CTGGCACCTGCCCAGCGTGTTCCACCTGAGGGGCAAGCAGAACTACACCTGCAG

GTGCGAGACCATCGTGAGCTGCGACGGCTACGTGGTGAAGAGGATCGCCATCAG

CCCCGGCCTGTACGGCAAGCCCAGCGGCTACGCCGCTACAATGCACAGGGAGGG

CTTCCTGTGCTGCAAGGTGACCGACACCCTGAACGGCGAGAGGGTGAGCTTCCC

CGTGTGCACCTACGTGCCCGCCACCCTGTGCGACCAGATGACCGGCATCCTGGCC

ACCGACGTGAGCGCCGACGACGCCCAGAAGCTGCTCGTGGGCCTGAACCAGAGG

ATCGTGGTCAACGGCAGGACCCAGAGGAACACCAACACAATGAAGAACTACCTG

CTGCCCGTGGTGGCCCAGGCTTTCGCCAGGTGGGCCAAGGAGTACAAGGAGGAC

CAGGAAGACGAGAGGCCCCTGGGCCTGAGGGACAGGCAGCTGGTGATGGGCTG

CTGCTGGGCCTTCAGGCGGCACAAGATCACCAGCATCTACAAGAGGCCCGACAC

CCAGACCATCATCAAGGTGAACAGCGACTTCCACAGCTTCGTGCTGCCCAGGATC

GGCAGCAACACCCTGGAGATCGGCCTGAGGACCCGGATCAGGAAGATGCTGGAG

GAACACAAGGAGCCCAGCCCACTGATCACCGCCGAGGACGTGCAGGAGGCCAA

GTGCGCTGCCGACGAGGCCAAGGAGGTGAGGGAGGCCGAGGAACTGAGGGCCG

CCCTGCCACCCCTGGCTGCCGACGTGGAGGAACCCACCCTGGAAGCCGACGTGG

ACCTGATGCTGCAGGAGGCCGGCGCCGGAAGCGTGGAGACACCCAGGGGCCTGA

TCAAGGTGACCAGCTACGACGGCGAGGACAAGATCGGCAGCTACGCCGTGCTGA

GCCCACAGGCCGTGCTGAAGTCCGAGAAGCTGAGCTGCATCCACCCACTGGCCG

AGCAGGTGATCGTGATCACCCACAGCGGCAGGAAGGGCAGGTACGCCGTGGAGC

CCTACCACGGCAAGGTGGTCGTGCCCGAGGGCACGCCATCCCCGTGCAGGACT

TCCAGGCCCTGAGCGAGAGCGCCACCATCGTGTACAACGAGAGGGAGTTCGTGA

ACAGGTACCTGCACCATATCGCCACCCACGGCGGAGCCCTGAACACCGACGAGG

AATACTACAAGACCGTGAAGCCCAGCGAGCACGACGGCGAGTACCTGTACGACA

TCGACAGGAAGCAGTGCGTGAAGAAAGAGCTGGTGACCGGCCTGGGACTGACCG

-continued

```
GCGAGCTGGTGGACCCACCCTTCCACGAGTTCGCCTACGAGAGCCTGAGGACCA
GACCCGCCGCTCCCTACCAGGTGCCCACCATCGGCGTGTACGGCGTGCCCGGCA
GCGGAAAGAGCGGCATCATCAAGAGCGCCGTGACCAAGAAAGACCTGGTGGTC
AGCGCCAAGAAAGAGAACTGCGCCGAGATCATCAGGGACGTGAAGAAGATGAA
AGGCCTGGACGTGAACGCGCGCACCGTGGACAGCGTGCTGCTGAACGGCTGCAA
GCACCCCGTGGAGACCCTGTACATCGACGAGGCCTTCGCTTGCCACGCCGGCACC
CTGAGGGCCCTGATCGCCATCATCAGGCCCAAGAAAGCCGTGCTGTGCGGCGAC
CCCAAGCAGTGCGGCTTCTTCAACATGATGTGCCTGAAGGTGCACTTCAACCACG
AGATCTGCACCCAGGTGTTCCACAAGAGCATCAGCAGGCGGTGCACCAAGAGCG
TGACCAGCGTCGTGAGCACCCTGTTCTACGACAAGAAAATGAGGACCACCAACC
CCAAGGAGACCAAAATCGTGATCGACACCACAGGCAGCACCAAGCCCAAGCAG
GACGACCTGATCCTGACCTGCTTCAGGGGCTGGGTGAAGCAGCTGCAGATCGAC
TACAAGGGCAACGAGATCATGACCGCCGCTGCCAGCCAGGGCCTGACCAGGAAG
GGCGTGTACGCCGTGAGGTACAAGGTGAACGAGAACCCACTGTACGCTCCCACC
AGCGAGCACGTGAACGTGCTGCTGACCAGGACCGAGGACAGGATCGTGTGGAAG
ACCCTGGCCGGCGACCCCTGGATCAAGACCCTGACCGCCAAGTACCCCGGCAAC
TTCACCGCCACCATCGAAGAGTGGCAGGCCGAGCACGACGCCATCATGAGGCAC
ATCCTGGAGAGGCCCGACCCCACCGACGTGTTCCAGAACAAGGCCAACGTGTGC
TGGGCCAAGGCCCTGGTGCCCGTGCTGAAGACCGCCGGCATCGACATGACCACA
GAGCAGTGGAACACCGTGGACTACTTCGAGACCGACAAGGCCCACAGCGCCGAG
ATCGTGCTGAACCAGCTGTGCGTGAGGTTCTTCGGCCTGGACCTGGACAGCGGCC
TGTTCAGCGCCCCCACCGTGCCACTGAGCATCAGGAACAACCACTGGGACAACA
GCCCCAGCCCAAACATGTACGGCCTGAACAAGGAGGTGGTCAGGCAGCTGAGCA
GGCGGTACCCACAGCTGCCCAGGGCCGTGGCCACCGGCAGGGTGTACGACATGA
ACACCGGCACCCTGAGGAACTACGACCCCAGGATCAACCTGGTGCCCGTGAACA
GGCGGCTGCCCCACGCCCTGGTGCTGCACCACAACGAGCACCCACAGAGCGACT
TCAGCTCCTTCGTGAGCAAGCTGAAAGGCAGGACCGTGCTGGTCGTGGGCGAGA
AGCTGAGCGTGCCCGGCAAGATGGTGGACTGGCTGAGCGACAGGCCCGAGGCCA
CCTTCCGGGCCAGGCTGGACCTCGGCATCCCCGGCGACGTGCCCAAGTACGACA
TCATCTTCGTGAACGTCAGGACCCCATACAAGTACCACCATTACCAGCAGTGCGA
GGACCACGCCATCAAGCTGAGCATGCTGACCAAGAAGGCCTGCCTGCACCTGAA
CCCCGGAGGCACCTGCGTGAGCATCGGCTACGGCTACGCCGACAGGGCCAGCGA
GAGCATCATTGGCGCCATCGCCAGGCTGTTCAAGTTCAGCAGGGTGTGCAAACC
CAAGAGCAGCCTGGAGGAAACCGAGGTGCTGTTCGTGTTCATCGGCTACGACCG
GAAGGCCAGGACCCACAACCCCTACAAGCTGAGCAGCACCCTGACAAACATCTA
CACCGGCAGCAGGCTGCACGAGGCCGGCTGCGCCCCAGCTACCACGTGGTCAG
GGGCGATATCGCCACCGCCACCGAGGGCGTGATCATCAACGCTGCCAACAGCAA
GGGCCAGCCCGGAGGCGGAGTGTGCGGCGCCCTGTACAAGAAGTTCCCCGAGAG
CTTCGACCTGCAGCCCATCGAGGTGGGCAAGGCCAGGCTGGTGAAGGGCGCCGC
TAAGCACATCATCCACGCCGTGGGCCCCAACTTCAACAAGGTGAGCGAGGTGGA
```

-continued

```
AGGCGACAAGCAGCTGGCCGAAGCCTACGAGAGCATCGCCAAGATCGTGAACG

ACAATAACTACAAGAGCGTGGCCATCCCACTGCTCAGCACCGGCATCTTCAGCG

GCAACAAGGACAGGCTGACCCAGAGCCTGAACCACCTGCTCACCGCCCTGGACA

CCACCGATGCCGACGTGGCCATCTACTGCAGGGACAAGAAGTGGGAGATGACCC

TGAAGGAGGCCGTGGCCAGGCGGGAGGCCGTGGAAGAGATCTGCATCAGCGAC

GACTCCAGCGTGACCGAGCCCGACGCCGAGCTGGTGAGGGTGCACCCCAAGAGC

TCCCTGGCCGGCAGGAAGGGCTACAGCACCAGCGACGGCAAGACCTTCAGCTAC

CTGGAGGGCACCAAGTTCCACCAGGCCGCTAAGGACATCGCCGAGATCAACGCT

ATGTGGCCCGTGGCCACCGAGGCCAACGAGCAGGTGTGCATGTACATCCTGGGC

GAGAGCATGTCCAGCATCAGGAGCAAGTGCCCCGTGGAGGAAAGCGAGGCCAG

CACACCACCCAGCACCCTGCCCTGCCTGTGCATCCACGCTATGACACCCGAGAGG

GTGCAGCGGCTGAAGGCCAGCAGGCCCGAGCAGATCACCGTGTGCAGCTCCTTC

CCACTGCCCAAGTACAGGATCACCGGCGTGCAGAAGATCCAGTGCAGCCAGCCC

ATCCTGTTCAGCCCAAAGGTGCCCGCCTACATCCACCCCAGGAAGTACCTGGTGG

AGACCCCACCCGTGGACGAGACACCCGAGCCAAGCGCCGAGAACCAGAGCACC

GAGGGCACACCCGAGCAGCCACCCCTGATCACCGAGGACGAGACAAGGACCCG

GACCCCAGAGCCCATCATTATCGAGGAAGAGGAAGAGGACAGCATCAGCCTGCT

GAGCGACGGCCCCACCCACCAGGTGCTGCAGGTGGAGGCCGACATCCACGGCCC

ACCCAGCGTGTCCAGCTCCAGCTGGAGCATCCCACACGCCAGCGACTTCGACGT

GGACAGCCTGAGCATCCTGGACACCCTGGAGGGCGCCAGCGTGACCTCCGGCGC

CACCAGCGCCGAGACCAACAGCTACTTCGCCAAGAGCATGGAGTTCCTGGCCAG

GCCCGTGCCAGCTCCCAGGACCGTGTTCAGGAACCCACCCCACCCAGCTCCCAG

GACCAGGACCCCAAGCCTGGCTCCCAGCAGGGCCTGCAGCAGGACCAGCCTGGT

GAGCACCCCACCCGGCGTGAACAGGGTGATCACCAGGGAGGAACTGGAGGCCCT

GACACCCAGCAGGACCCCCAGCAGGTCCGTGAGCAGGACTAGTCTGGTGTCCAA

CCCACCCGGCGTGAACAGGGTGATCACCAGGGAGGAATTCGAGGCCTTCGTGGC

CCAGCAACAGAGACGGTTCGACGCCGGCGCCTACATCTTCAGCAGCGACACCGG

CCAGGGACACCTGCAGCAAAAGAGCGTGAGGCAGACCGTGCTGAGCGAGGTGG

TGCTGGAGAGGACCGAGCTGGAAATCAGCTACGCCCCCAGGCTGGACCAGGAGA

AGGAGGAACTGCTCAGGAAGAAACTGCAGCTGAACCCCACCCCAGCCAACAGG

AGCAGGTACCAGAGCAGGAAGGTGGAGAACATGAAGGCCATCACCGCCAGGCG

GATCCTGCAGGGCCTGGGACACTACCTGAAGGCCGAGGGCAAGGTGGAGTGCTA

CAGGACCCTGCACCCCGTGCCACTGTACAGCTCCAGCGTGAACAGGGCCTTCTCC

AGCCCCAAGGTGGCCGTGGAGGCCTGCAACGCTATGCTGAAGGAGAACTTCCCC

ACCGTGGCCAGCTACTGCATCATCCCCGAGTACGACGCCTACCTGGACATGGTGG

ACGGCGCCAGCTGCTGCCTGGACACCGCCAGCTTCTGCCCCGCCAAGCTGAGGA

GCTTCCCCAAGAAACACAGCTACCTGGAGCCCACCATCAGGAGCGCCGTGCCCA

GCGCCATCCAGAACACCCTGCAGAACGTGCTGGCCGCTGCCACCAAGAGGAACT

GCAACGTGACCCAGATGAGGGAGCTGCCCGTGCTGGACAGCGCTGCCTTCAACG

TGGAGTGCTTCAAGAAATACGCCTGCAACAACGAGTACTGGGAGACCTTCAAGG

AGAACCCCATCAGGCTGACCGAAGAGAACGTGGTGAACTACATCACCAAGCTGA
```

```
AGGGCCCCAAGGCCGCTGCCCTGTTCGCTAAGACCCACAACCTGAACATGCTGC

AGGACATCCCAATGGACAGGTTCGTGATGGACCTGAAGAGGGACGTGAAGGTGA

CACCCGGCACCAAGCACACCGAGGAGAGGCCCAAGGTGCAGGTGATCCAGGCC

GCTGACCCACTGGCCACCGCCTACCTGTGCGGCATCCACAGGGAGCTGGTGAGG

CGGCTGAACGCCGTGCTGCTGCCCAACATCCACACCCTGTTCGACATGAGCGCCG

AGGACTTCGACGCCATCATCGCCGAGCACTTCCAGCCCGGCGACTGCGTGCTGG

AGACCGACATCGCCAGCTTCGACAAGAGCGAGGATGACGCTATGGCCCTGACCG

CTCTGATGATCCTGGAGGACCTGGGCGTGGACGCCGAGCTGCTCACCCTGATCGA

GGCTGCCTTCGGCGAGATCAGCTCCATCCACCTGCCCACCAAGACCAAGTTCAAG

TTCGGCGCTATGATGAAAAGCGGAATGTTCCTGACCCTGTTCGTGAACACCGTGA

TCAACATTGTGATCGCCAGCAGGGTGCTGCGGGAGAGGCTGACCGGCAGCCCCT

GCGCTGCCTTCATCGGCGACGACAACATCGTGAAGGGCGTGAAAAGCGACAAGC

TGATGGCCGACAGGTGCGCCACCTGGCTGAACATGGAGGTGAAGATCATCGACG

CCGTGGTGGGCGAGAAGGCCCCCTACTTCTGCGGCGGATTCATCCTGTGCGACAG

CGTGACCGGCACCGCCTGCAGGGTGGCCGACCCCCTGAAGAGGCTGTTCAAGCT

GGGCAAGCCACTGGCCGCTGACGATGAGCACGACGATGACAGGCGGAGGGCCCT

GCACGAGGAAAGCACCAGGTGGAACAGGGTGGGCATCCTGAGCGAGCTGTGCA

AGGCCGTGGAGAGCAGGTACGAGACCGTGGGCACCAGCATCATCGTGATGGCTA

TGACCACACTGGCCAGCTCCGTCAAGAGCTTCTCCTACCTGAGGGGGGCCCCTAT

AACTCTCTACGGCTAACCTGAATGGACTACGACATAGTCTAGTCCGCCAAGGCCG

CCACCACTCGAGTATGTTACGTGCAAAGGTGATTGTCACCCCCCGAAAGACCATA

TTGTGACACACCCTCAGTATCACGCCCAAACATTTACAGCCGCGGTGTCAAAAAC

CGCGTGGACGTGGTTAACATCCCTGCTGGGAGGATCAGCCGTAATTATTATAATT

GGCTTGGTGCTGGCTACTATTGTGGCCATGTACGTGCTGACCAACCAGAAACATA

ATTGAATACAGCAGCAATTGGCAAGCTGCTTACATAGAACTCGCGGCGATTGGC

ATGCCGCCTTAAAATTTTTATTTTATTTTTTCTTTTCTTTTCCGAATCGGATTTTGT

TTTTAATATTTCAAAAAAAAAAAAAAAAAAAAAATCTAGAAAAAAAAAA

AAAAAAAAAAAAAAAAAAAAAAAAAAAAAAAAAAAAAAAAAAAAA

AAAAAAAAAAAAAAAAAAAAAAAAAAAAAAAA
```

SEQ ID NO: 79

```
MEKVHVDIEEDSPFLRALQRSFPQFEVEAKQVTDNDHANARAFSHLASKLIETEVDP

SDTILDIGSAPARRMYSKHKYHCICPMRCAEDPDRLYKYATKLKKNCKEITDKELDK

KMKELAAVMSDPDLETETMCLHDDESCRYEGQVAVYQDVYAVDGPTSLYHQANK

GVRVAYWIGFDTTPFMFKNLAGAYPSYSTNWADETVLTARNIGLCSSDVMERSRRG

MSILRKKYLKPSNNVLFSVGSTIYHEKRDLLRSWHLPSVFHLRGKQNYTCRCETIVSC

DGYVVKRIAISPGLYGKPSGYAATMHREGFLCCKVTDTLNGERVSFPVCTYVPATLC

DQMTGILATDVSADDAQKLLVGLNQRIVVNGRTQRNTNTMKNYLLPVVAQAFARW

AKEYKEDQEDERPLGLRDRQLVMGCCWAFRRRHKITSIYKRPDTQTIIKVNSDFHSFV

LPRIGSNTLEIGLRTRIRKMLEEHKEPSPLITAEDVQEAKCAADEAKEVREAEELRAA

LPPLAADVEEPTLEADVDLMLQEAGAGSVETPRGLIKVTSYDGEDKIGSYAVLSPQA

VLKSEKLSCIHPLAEQVIVITHSGRKGRYAVEPYHGKVVVPEGHAIPVQDFQALSESA
```

-continued

TIVYNEREFVNRYLHHIATHGGALNTDEEYYKTVKPSEHDGEYLYDIDRKQCVKKEL
VTGLGLTGELVDPPFHEFAYESLRTRPAAPYQVPTIGVYGVPGSGKSGIIKSAVTKKD
LVVSAKKENCAEIIRDVKKMKGLDVNARTVDSVLLNGCKHPVETLYIDEAFACHAG
TLRALIAIIRPKKAVLCGDPKQCGFFNMMCLKVHFNHEICTQVFHKSISRRCTKSVTS
VVSTLFYDKKMRTTNPKETKIVIDTTGSTKPKQDDLILTCFRGWVKQLQIDYKGNEI
MTAAASQGLTRKGVYAVRYKVNENPLYAPTSEHVNVLLTRTEDRIVWKTLAGDPW
IKTLTAKYPGNFTATIEEWQAEHDAIMRHILERPDPTDVFQNKANVCWAKALVPVL
KTAGIDMTTEQWNTVDYFETDKAHSAEIVLNQLCVRFFGLDLDSGLFSAPTVPLSIR
NNHWDNSPSPNMYGLNKEVVRQLSRRYPQLPRAVATGRVYDMNTGTLRNYDPRIN
LVPVNRRLPHALVLHHNEHPQSDFSSFVSKLKGRTVLVVGEKLSVPGKMVDWLSDR
PEATFRARLDLGIPGDVPKYDIIFVNVRTPYKYHHYQQCEDHAIKLSMLTKKACLHL
NPGGTCVSIGYGYADRASESIIGAIARLFKFSRVCKPKSSLEETEVLFVFIGYDRKART
HNPYKLSSTLTNIYTGSRLHEAGCAPSYHVVRGDIATATEGVIINAANSKGQPGGGV
CGALYKKFPESFDLQPIEVGKARLVKGAAKHIIHAVGPNFNKVSEVEGDKQLAEAYE
SIAKIVNDNNYKSVAIPLLSTGIFSGNKDRLTQSLNHLLTALDTTDADVAIYCRDKKW
EMTLKEAVARREAVEEICISDDSSVTEPDAELVRVHPKSSLAGRKGYSTSDGKTFSYL
EGTKFHQAAKDIAEINAMWPVATEANEQVCMYILGESMSSIRSKCPVEESEASTPPST
LPCLCIHAMTPERVQRLKASRPEQITVCSSFPLPKYRITGVQKIQCSQPILFSPKVPAYI
HPRKYLVETPPVDETPEPSAENQSTEGTPEQPPLITEDETRTRTPEPIIIEEEEEDSISLLS
DGPTHQVLQVEADIHGPPSVSSSSWSIPHASDFDVDSLSILDTLEGASVTSGATSAETN
SYFAKSMEFLARPVPAPRTVFRNPPHPAPRTRTPSLAPSRACSRTSLVSTPPGVNRVIT
REELEALTPSRTPSRSVSRTSLVSNPPGVNRVITREEFEAFVAQQQRRFDAGAYIFSSD
TGQGHLQQKSVRQTVLSEVVLERTELEISYAPRLDQEKEELLRKKLQLNPTPANRSR
YQSRKVENMKAITARRILQGLGHYLKAEGKVECYRTLHPVPLYSSSVNRAFSSPKVA
VEACNAMLKENFPTVASYCIIPEYDAYLDMVDGASCCLDTASFCPAKLRSFPKKHSY
LEPTIRSAVPSAIQNTLQNVLAAATKRNCNVTQMRELPVLDSAAFNVECFKKYACNN
EYWETFKENPIRLTEENVVNYITKLKGPKAAALFAKTHNLNMLQDIPMDRFVMDLK
RDVKVTPGTKHTEERPKVQVIQAADPLATAYLCGIHRELVRRLNAVLLPNIHTLFDM
SAEDFDAIIAEHFQPGDCVLETDIASFDKSEDDAMALTALMILEDLGVDAELLTLIEA
AFGEISSIHLPTKTKFKFGAMMKSGMFLTLFVNTVINIVIASRVLRERLTGSPCAAFIG
DDNIVKGVKSDKLMADRCATWLNMEVKIIDAVVGEKAPYFCGGFILCDSVTGTACR
VADPLKRLFKLGKPLAADDEHDDDRRRALHEESTRWNRVGILSELCKAVESRYETV
GTSIIVMAMTTLASSVKSFSYLRGAPITLYG

SEQ ID NO: 80

MPEKVHVDIEEDSPFLRALQRSFPQFEVEAKQVTDNDHANARAFSHLASKLIETEVD
PSDTILDIGSAPARRMYSKHKYHCICPMRCAEDPDRLYKYATKLKKNCKEITDKELD
KKMKELAAVMSDPDLETETMCLHDDESCRYEGQVAVYQDVYAVDGPTSLYHQAN
KGVRVAYWIGFDTTPFMFKNLAGAYPSYSTNWADETVLTARNIGLCSSDVMERSRR
GMSILRKKYLKPSNNVLFSVGSTIYHEKRDLLRSWHLPSVFHLRGKQNYTCRCETIVS
CDGYVVKRIAISPGLYGKPSGYAATMHREGFLCCKVTDTLNGERVSFPVCTYVPATL
CDQMTGILATDVSADDAQKLLVGLNQRIVVNGRTQRNTNTMKNYLLPVVAQAFAR

-continued

```
WAKEYKEDQEDERPLGLRDRQLVMGCCWAFRRHKITSIYKRPDTQTIIKVNSDFHSF

VLPRIGSNTLEIGLRTRIRKMLEEHKEPSPLITAEDVQEAKCAADEAKEVREAEELRA

ALPPLAADVEEPTLEADVDLMLQEAGAGSVETPRGLIKVTSYDGEDKIGSYAVLSPQ

AVLKSEKLSCIHPLAEQVIVITHSGRKGRYAVEPYHGKVVVPEGHAIPVQDFQALSES

ATIVYNEREFVNRYLHHIATHGGALNTDEEYYKTVKPSEHDGEYLYDIDRKQCVKK

ELVTGLGLTGELVDPPFHEFAYESLRTRPAAPYQVPTIGVYGVPGSGKSGIIKSAVTK

KDLVVSAKKENCAEIIRDVKKMKGLDVNARTVDSVLLNGCKHPVETLYIDEAFACH

AGTLRALIAIIRPKKAVLCGDPKQCGFFNMMCLKVHFNHEICTQVFHKSISRRCTKSV

TSVVSTLFYDKKMRTTNPKETKIVIDTTGSTKPKQDDLILTCFRGWVKQLQIDYKGN

EIMTAAASQGLTRKGVYAVRYKVNENPLYAPTSEHVNVLLTRTEDRIVWKTLAGDP

WIKTLTAKYPGNFTATIEEWQAEHDAIMRHILERPDPTDVFQNKANVCWAKALVPV

LKTAGIDMTTEQWNTVDYFETDKAHSAEIVLNQLCVRFFGLDLDSGLFSAPTVPLSIR

NNHWDNSPSPNMYGLNKEVVRQLSRRYPQLPRAVATGRVYDMNTGTLRNYDPRIN

LVPVNRRLPHALVLHHNEHPQSDFSSFVSKLKGRTVLVVGEKLSVPGKMVDWLSDR

PEATFRARLDLGIPGDVPKYDIIFVNVRTPYKYHHYQQCEDHAIKLSMLTKKACLHL

NPGGTCVSIGYGYADRASESIIGAIARLFKFSRVCKPKSSLEETEVLFVFIGYDRKART

HNPYKLSSTLTNIYTGSRLHEAGCAPSYHVVRGDIATATEGVIINAANSKGQPGGGV

CGALYKKFPESFDLQPIEVGKARLVKGAAKHIIHAVGPNFNKVSEVEGDKQLAEAYE

SIAKIVNDNNYKSVAIPLLSTGIFSGNKDRLTQSLNHLLTALDTTDADVAIYCRDKKW

EMTLKEAVARREAVEEICISDDSSVTEPDAELVRVHPKSSLAGRKGYSTSDGKTFSYL

EGTKFHQAAKDIAEINAMWPVATEANEQVCMYILGESMSSIRSKCPVEESEASTPPST

LPCLCIHAMTPERVQRLKASRPEQITVCSSFPLPKYRITGVQKIQCSQPILFSPKVPAYI

HPRKYLVETPPVDETPEPSAENQSTEGTPEQPPLITEDETRTRTPEPIIIEEEEEDSISLLS

DGPTHQVLQVEADIHGPPSVSSSSWSIPHASDFDVDSLSILDTLEGASVTSGATSAETN

SYFAKSMEFLARPVPAPRTVFRNPPHPAPRTRTPSLAPSRACSRTSLVSTPPGVNRVIT

REELEALTPSRTPSRSVSRTSLVSNPPGVNRVITREEFEAFVAQQQRRFDAGAYIFSSD

TGQGHLQQKSVRQTVLSEVVLERTELEISYAPRLDQEKEELLRKKLQLNPTPANRSR

YQSRKVENMKAITARRILQGLGHYLKAEGKVECYRTLHPVPLYSSSVNRAFSSPKVA

VEACNAMLKENFPTVASYCIIPEYDAYLDMVDGASCCLDTASFCPAKLRSFPKKHSY

LEPTIRSAVPSAIQNTLQNVLAAATKRNCNVTQMRELPVLDSAAFNVECFKKYACNN

EYWETFKENPIRLTEENVVNYITKLKGPKAAALFAKTHNLNMLQDIPMDRFVMDLK

RDVKVTPGTKHTEERPKVQVIQAADPLATAYLCGIHRELVRRLNAVLLPNIHTLFDM

SAEDFDAIIAEHFQPGDCVLETDIASFDKSEDDAMALTALMILEDLGVDAELLTLIEA

AFGEISSIHLPTKTKFKFGAMMKSGMFLTLFVNTVINIVIASRVLRERLTGSPCAAFIG

DDNIVKGVKSDKLMADRCATWLNMEVKIIDAVVGEKAPYFCGGFILCDSVTGTACR

VADPLKRLFKLGKPLAADDEHDDDRRRALHEESTRWNRVGILSELCKAVESRYETV

GTSIIVMAMTTLASSVKSFSYLRGAPITLYG
```

SEQ ID NO: 81

```
MEKVHVDIEEDSPFLRALQRSFPQFEVEAKQVTDNDHANARAFSHLASKLIETEVDP

SDTILDIGSAPARRMYSKHKYHCICPMRCAEDPDRLYKYATKLKKNCKEITDKELDK

KMKELAAVMSDPDLETETMCLHDDESCRYEGQVAVYQDVYAVDGPTSLYHQANK
```

-continued

```
GVRVAYWIGFDTTPFMFKNLAGAYPSYSTNWADETVLTARNIGLCSSDVMERSRRG

MSILRKKYLKPSNNVLFSVGSTIYHEKRDLLRSWHLPSVFHLRGKQNYTCRCETIVSC

DGYVVKRIAISPGLYGKPSGYAATMHREGFLCCKVTDTLNGERVSFPVCTYVPATLC

DQMTGILATDVSADDAQKLLVGLNQRIVVNGRTQRNTNTMKNYLLPVVAQAFARW

AKEYKEDQEDERPLGLRDRQLVMGCCWAFRRHKITSIYKRPDTQTIIKVNSDFHSFV

LPRIGSNTLEIGLRTRIRKMLEEHKEPSPLITAEDIQEAKCAADEAKEVREAEELRAAL

PPLAADFEEPTLEADVDLMLQEAGAGSVETPRGLIKVTSYAGEDKIGSYAVLSPQAV

LKSEKLSCIHPLAEQVIVITHSGRKGRYAVEPYHGKVVVPEGHAIPVQDFQALSESAT

IVYNEREFVNRYLHHIATHGGALNTDEEYYKTVKPSEHDGEYLYDIDRKQCVKKEL

VTGLGLTGELVDPPFHEFAYESLRTRPAAPYQVPTIGVYGVPGSGKSGIIKSAVTKKD

LVVSAKKENCAEIIRDVKKMKGLDVNARTVDSVLLNGCKHPVETLYIDEAFACHAG

TLRALIAIIRPKKAVLCGDPKQCGFFNMMCLKVHFNHEICTQVFHKSISRRCTKSVTS

VVSTLFYDKRMRTTNPKETKIVIDTTGSTKPKQDDLILTCFRGWVKQLQIDYKGNEI

MTAAASQGLTRKGVYAVRYKVNENPLYAPTSEHVNVLLTRTEDRIVWKTLAGDPW

IKILTAKYPGNFTATIEEWQAEHDAIMRHILERPDPTDVFQNKANVCWAKALVPVLK

TAGIDMTTEQWNTVDYFETDKAHSAEIVLNQLCVRFFGLDLDSGLFSAPTVPLSIRN

NHWDNSPSPNMYGLNKEVVRQLSRRYPQLPRAVATGRVYDMNTGTLRNYDPRINL

VPVNRRLPHALVLHHNEHPQSDFSSFVSKLKGRTVLVVGEKLSVPGKKVDWLSDQP

EATFRARLDLGIPGDVPKYDIVFINVRTPYKYHHYQQCEDHAIKLSMLTKKACLHLN

PGGTCVSIGYGYADRASESIIGAIARQFKFSRVCKPKSSHEETEVLFVFIGYDRKARTH

NPYKLSSTLTNIYTGSRLHEAGCAPSYHVVRGDIATATEGVIINAANSKGQPGGGVC

GALYKKFPESFDLQPIEVGKARLVKGAAKHIIHAVGPNFNKVSEVEGDKQLAEAYES

IAKIVNDNNYKSVAIPLLSTGIFSGNKDRLTQSLNHLLTALDTTDADVAIYCRDKKWE

MTLKEAVARREAVEEICISDDSSVTEPDAELVRVHPKSSLAGRKGYSTSDGKTFSYLE

GTKFHQAAKDIAEINAMWPVATEANEQVCMYILGESMSSIRSKCPVEESEASTPPSTL

PCLCIHAMTPERVQRLKASRPEQITVCSSFPLPKYRITGVQKIQCSQPILFSPKVPAYIH

PRKYLVETPPVEETPESPAENQSTEGTPEQPALVNVDATRTRMPEPIIIEEEEEDSISLL

SDGPTHQVLQVEADIHGSPSVSSSSWSIPHASDFDVDSLSILDTLDGASVTSGAVSAET

NSYFARSMEFRARPVPAPRTVFRNPPHPAPRTRTPPLAHSRASSRTSLVSTPPGVNRVI

TREELEALTPSRAPSRSASRTSLVSNPPGVNRVITREEFEAFVAQQQ*RFDAGAYIFSS

DTGQGHLQQKSVRQTVLSEVVLERTELEISYAPRLDQEKEELLRKKLQLNPTPANRS

RYQSRRVENMKAITARRILQGLGHYLKAEGKVECYRTLHPVPLYSSSVNRAFSSPKV

AVEACNAMLKENFPTVASYCIIPEYDAYLDMVDGASCCLDTASFCPAKLRSFPKKHS

YLEPTIRSAVPSAIQNTLQNVLAAATKRNCNVTQMRELPVLDSAAFNVECFKKYACN

NEYWETFKENPIRLTEENVVNYITKLKGPKAAALFAKTHNLNMLQDIPMDRFVMDL

KRDVKVTPGTKHTEERPKVQVIQAADPLATADLCGIHRELVRRLNAVLLPNIHTLFD

MSAEDFDAIIAEHFQPGDCVLETDIASFDKSEDDAMALTALMILEDLGVDAELLTLIE

AAFGEISSIHLPTKTKFKFGAMMKSGMFLTLFVNTVINIVIASRVLRERLTGSPCAAFI
```

-continued

GDDNIVKGVKSDKLMADRCATWLNMEVKIIDAVVGEKAPYFCGGFILCDSVTGTAC

RVADPLKRLFKLGKPLAVDDEHDDDRRRALHEESTRWNRVGILPELCKAVESRYET

VGTSIIVMAMTTLASSVKSFSYLRGAPITLYG*

SEQ ID NO: 82

AGGAAACTTAAGTCAACACAACATATACAAAACAAACGAATCTCAAGCAATCAA

GCATTCTACTTCTATTGCAGCAATTTAAATCATTTCTTTTAAAGCAAAAGCAATTT

TCTGAAAATTTTCACCATTTACGAACGATAGCCACC

SEQ ID NO: 83

ACTCGAGCTAGTGACTGACTAGGATCTGGTTACCACTAAACCAGCCTCAAGAAC

ACCCGAATGGAGTCTCTAAGCTACATAATACCAACTTACACTTACAAAATGTTGT

CCCCCAAAATGTAGCCATTCGTATCTGCTCCTAATAAAAAGAAAGTTTCTTCACA

TTCTAGAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAA

AA

SEQ ID NO: 1

GAGGAAACUU AAGAUGGG

SEQ ID NO: 2

GGAUGGG

SEQ ID NO: 3

GGAUAGG

SEQ ID NO: 4

GGAGAGG

SEQ ID NO: 58

GGGAUGGG

SEQ ID NO: 59

GAGAGG

SEQ ID NO: 60

GAGGG

SEQ ID NO: 61

GAGAUGGG

SEQ ID NO: 62

GAGUGG

SEQ ID NO: 63

GAGGGG

SEQ ID NO: 64

GAGUAGG

SEQ ID NO: 65

GAGUGGG

SEQ ID NO: 66

GAUGGG (RNA sequence for a construct with two subgenomic promoters, Luc, and E3L)

SEQ ID NO: 117 atg

-continued

```
ACCACACCCTTCATGTTCAAGAACCTGGCCGGCGCCTACCCCAGCTACAGCACCAACTGGGCCGACG
AGACCGTGCTGACCGCCAGGAACATCGGCCTGTGCAGCAGCGACGTGATGGAGAGGAGCCGGAGA
GGCATGAGCATCCTGAGGAAGAAATACCTGAAGCCCAGCAACAACGTGCTGTTCAGCGTGGGCAGC
ACCATCTACCACGAGAAGAGGGACCTGCTCAGGAGCTGGCACCTGCCCAGCGTGTTCCACCTGAGG
GGCAAGCAGAACTACACCTGCAGGTGCGAGACCATCGTGAGCTGCGACGGCTACGTGGTGAAGAG
GATCGCCATCAGCCCCGGCCTGTACGGCAAGCCCAGCGGCTACGCCGCTACAATGCACAGGGAGGG
CTTCCTGTGCTGCAAGGTGACCGACACCCTGAACGGCGAGAGGGTGAGCTTCCCCGTGTGCACCTA
CGTGCCCGCCACCCTGTGCGACCAGATGACCGGCATCCTGGCCACCGACGTGAGCGCCGACGACGC
CCAGAAGCTGCTCGTGGGCCTGAACCAGAGGATCGTGGTCAACGGCAGGACCCAGAGGAACACCA
ACACAATGAAGAACTACCTGCTGCCCGTGGTGGCCCAGGCTTTCGCCAGGTGGGCCAAGGAGTACA
AGGAGGACCAGGAAGACGAGAGGCCCCTGGGCCTGAGGGACAGGCAGCTGGTGATGGGCTGCTG
CTGGGCCTTCAGGCGGCACAAGATCACCAGCATCTACAAGAGGCCCGACACCCAGACCATCATCAA
GGTGAACAGCGACTTCCACAGCTTCGTGCTGCCCAGGATCGGCAGCAACACCCTGGAGATCGGCCT
GAGGACCCCGGATCAGGAAGATGCTGGAGGAACACAAGGAGCCCAGCCCACTGATCACCGCCGAGG
ACGTGCAGGAGGCCAAGTGCGCTGCCGACGAGGCCAAGGAGGTGAGGGAGGCCGAGGAACTGAG
GGCCGCCCTGCCACCCCTGGCTGCCGACGTGGAGGAACCCACCCTGGAAGCCGACGTGGACCTGAT
GCTGCAGGAGGCCGGCGCCGGAAGCGTGGAGACACCCAGGGGCCTGATCAAGGTGACCAGCTACG
ACGGCGAGGACAAGATCGGCAGCTACGCCGTGCTGAGCCCACAGGCCGTGCTGAAGTCCGAGAAG
CTGAGCTGCATCCACCCACTGGCCGAGCAGGTGATCGTGATCACCCACAGCGGCAGGAAGGGCAG
GTACGCCGTGGAGCCCTACCACGGCAAGGTGGTCGTGCCCGAGGGCCACGCCATCCCCGTGCAGGA
CTTCCAGGCCCTGAGCGAGAGCGCCACCATCGTGTACAACGAGAGGGAGTTCGTGAACAGGTACCT
GCACCATATCGCCACCCACGGCGGAGCCCTGAACACCGACGAGGAATACTACAAGACCGTGAAGCC
CAGCGAGCACGACGGCGAGTACCTGTACGACATCGACAGGAAGCAGTGCGTGAAGAAAGAGCTGG
TGACCGGCCTGGGACTGACCGGCGAGCTGGTGGACCCACCCTTCCACGAGTTCGCCTACGAGAGCC
TGAGGACCAGACCCGCCGCTCCCTACCAGGTGCCCACCATCGGCGTGTACGGCGTGCCCGGCAGCG
GAAAGAGCGGCATCATCAAGAGCGCCGTGACCAAGAAAGACCTGGTGGTCAGCGCCAAGAAAGAG
AACTGCGCCGAGATCATCAGGGACGTGAAGAAGATGAAAGGCCTGGACGTGAACGCGCGCACCGT
GGACAGCGTGCTGCTGAACGGCTGCAAGCACCCCGTGGAGACCCTGTACATCGACGAGGCCTTCGC
TTGCCACGCCGGCACCCTGAGGGCCCTGATCGCCATCATCAGGCCCAAGAAAGCCGTGCTGTGCGG
CGACCCCAAGCAGTGCGGCTTCTTCAACATGATGTGCCTGAAGGTGCACTTCAACCACGAGATCTGC
ACCCAGGTGTTCCACAAGAGCATCAGCAGGCGGTGCACCAAGAGCGTGACCAGCGTCGTGAGCACC
CTGTTCTACGACAAGAAAATGAGGACCACCAACCCCAAGGAGACCAAAATCGTGATCGACACCACA
GGCAGCACCAAGCCCAAGCAGGACGACCTGATCCTGACCTGCTTCAGGGGCTGGGTGAAGCAGCTG
CAGATCGACTACAAGGGCAACGAGATCATGACCGCCGCTGCCAGCCAGGGCCTGACCAGGAAGGG
CGTGTACGCCGTGAGGTACAAGGTGAACGAGAACCCACTGTACGCTCCCACCAGCGAGCACGTGAA
CGTGCTGCTGACCAGGACCGAGGACAGGATCGTGTGGAAGACCCTGGCCGGCGACCCCTGGATCA
AGACCCTGACCGCCAAGTACCCCGGCAACTTCACCGCCACCATCGAAGAGTGGCAGGCCGAGCACG
ACGCCATCATGAGGCACATCCTGGAGAGGCCCGACCCCACCGACGTGTTCCAGAACAAGGCCAACG
TGTGCTGGGCCAAGGCCCTGGTGCCCGTGCTGAAGACCGCCGGCATCGACATGACCACAGAGCAGT
GGAACACCGTGGACTACTTCGAGACCGACAAGGCCCACAGCGCCGAGATCGTGCTGAACCAGCTGT
GCGTGAGGTTCTTCGGCCTGGACCTGGACAGCGGCCTGTTCAGCGCCCCCACCGTGCCACTGAGCAT
```

-continued

```
CAGGAACAACCACTGGGACAACAGCCCCAGCCCAAACATGTACGGCCTGAACAAGGAGGTGGTCA

GGCAGCTGAGCAGGCGGTACCCACAGCTGCCCAGGGCCGTGGCCACCGGCAGGGTGTACGACATG

AACACCGGCACCCTGAGGAACTACGACCCCAGGATCAACCTGGTGCCCGTGAACAGGCGGCTGCCC

CACGCCCTGGTGCTGCACCACAACGAGCACCCACAGAGCGACTTCAGCTCCTTCGTGAGCAAGCTGA

AAGGCAGGACCGTGCTGGTCGTGGGCGAGAAGCTGAGCGTGCCCGGCAAGATGGTGGACTGGCTG

AGCGACAGGCCCGAGGCCACCTTCCGGGCCAGGCTGGACCTCGGCATCCCCGGCGACGTGCCCAAG

TACGACATCATCTTCGTGAACGTCAGGACCCCATACAAGTACCACCATTACCAGCAGTGCGAGGACC

ACGCCATCAAGCTGAGCATGCTGACCAAGAAGGCCTGCCTGCACCTGAACCCCGGAGGCACCTGCG

TGAGCATCGGCTACGGCTACGCCGACAGGGCCAGCGAGAGCATCATTGGCGCCATCGCCAGGCTGT

TCAAGTTCAGCAGGGTGTGCAAACCCAAGAGCAGCCTGGAGGAAACCGAGGTGCTGTTCGTGTTCA

TCGGCTACGACCGGAAGGCCAGGACCCACAACCCCTACAAGCTGAGCAGCACCCTGACAAACATCT

ACACCGGCAGCAGGCTGCACGAGGCCGGCTGCGCCCCCAGCTACCACGTGGTCAGGGGCGATATC

GCCACCGCCACCGAGGGCGTGATCATCAACGCTGCCAACAGCAAGGGCCAGCCCGGAGGCGGAGT

GTGCGGCGCCCTGTACAAGAAGTTCCCCGAGAGCTTCGACCTGCAGCCCATCGAGGTGGGCAAGGC

CAGGCTGGTGAAGGGCGCCGCTAAGCACATCATCCACGCCGTGGGCCCCAACTTCAACAAGGTGAG

CGAGGTGGAAGGCGACAAGCAGCTGGCCGAAGCCTACGAGAGCATCGCCAAGATCGTGAACGACA

ATAACTACAAGAGCGTGGCCATCCCACTGCTCAGCACCGGCATCTTCAGCGGCAACAAGGACAGGC

TGACCCAGAGCCTGAACCACCTGCTCACCGCCCTGGACACCACCGATGCCGACGTGGCCATCTACTG

CAGGGACAAGAAGTGGGAGATGACCCTGAAGGAGGCCGTGGCCAGGCGGGAGGCCGTGGAAGAG

ATCTGCATCAGCGACGACTCCAGCGTGACCGAGCCCGACGCCGAGCTGGTGAGGGTGCACCCCAAG

AGCTCCCTGGCCGGCAGGAAGGGCTACAGCACCAGCGACGGCAAGACCTTCAGCTACCTGGAGGG

CACCAAGTTCCACCAGGCCGCTAAGGACATCGCCGAGATCAACGCTATGTGGCCCGTGGCCACCGA

GGCCAACGAGCAGGTGTGCATGTACATCCTGGGCGAGAGCATGTCCAGCATCAGGAGCAAGTGCCC

CGTGGAGGAAAGCGAGGCCAGCACACCACCCAGCACCCTGCCCTGCCTGTGCATCCACGCTATGAC

ACCCGAGAGGGTGCAGCGGCTGAAGGCCAGCAGGCCCGAGCAGATCACCGTGTGCAGCTCCTTCCC

ACTGCCCAAGTACAGGATCACCGGCGTGCAGAAGATCCAGTGCAGCCAGCCCATCCTGTTCAGCCCA

AAGGTGCCCGCCTACATCCACCCCAGGAAGTACCTGGTGGAGACCCCACCCGTGGACGAGACACCC

GAGCCAAGCGCCGAGAACCAGAGCACCGAGGGCACACCCGAGCAGCCACCCCTGATCACCGAGGA

CGAGACAAGGACCCGGACCCCAGAGCCCATCATTATCGAGGAAGAGGAAGAGGACAGCATCAGCC

TGCTGAGCGACGGCCCCACCCACCAGGTGCTGCAGGTGGAGGCCGACATCCACGGCCCACCCAGCG

TGTCCAGCTCCAGCTGGAGCATCCCACACGCCAGCGACTTCGACGTGGACAGCCTGAGCATCCTGG

ACACCCTGGAGGGCGCCAGCGTGACCTCCGGCGCCACCAGCGCCGAGACCAACAGCTACTTCGCCA

AGAGCATGGAGTTCCTGGCCAGGCCCGTGCCAGCTCCCAGGACCGTGTTCAGGAACCCACCCCACC

CAGCTCCCAGGACCAGGACCCCAAGCCTGGCTCCCAGCAGGGCCTGCAGCAGGACCAGCCTGGTGA

GCACCCCACCCGGCGTGAACAGGGTGATCACCAGGGAGGAACTGGAGGCCCTGACACCCAGCAGG

ACCCCCAGCAGGTCCGTGAGCAGGACTAGTCTGGTGTCCAACCCACCCGGCGTGAACAGGGTGATC

ACCAGGGAGGAATTCGAGGCCTTCGTGGCCCAGCAACAGAGACGGTTCGACGCCGGCGCCTACATC

TTCAGCAGCGACACCGGCCAGGGACACCTGCAGCAAAAGAGCGTGAGGCAGACCGTGCTGAGCGA

GGTGGTGCTGGAGAGGACCGAGCTGGAAATCAGCTACGCCCCCAGGCTGGACCAGGAGAAGGAG

GAACTGCTCAGGAAGAAACTGCAGCTGAACCCCACCCCAGCCAACAGGAGCAGGTACCAGAGCAG
```

```
-continued
GAAGGTGGAGAACATGAAGGCCATCACCGCCAGGCGGATCCTGCAGGGCCTGGGACACTACCTGA

AGGCCGAGGGCAAGGTGGAGTGCTACAGGACCCTGCACCCCGTGCCACTGTACAGCTCCAGCGTGA

ACAGGGCCTTCTCCAGCCCCAAGGTGGCCGTGGAGGCCTGCAACGCTATGCTGAAGGAGAACTTCC

CCACCGTGGCCAGCTACTGCATCATCCCCGAGTACGACGCCTACCTGGACATGGTGGACGGCGCCA

GCTGCTGCCTGGACACCGCCAGCTTCTGCCCCGCCAAGCTGAGGAGCTTCCCCAAGAAACACAGCTA

CCTGGAGCCCACCATCAGGAGCGCCGTGCCCAGCGCCATCCAGAACACCCTGCAGAACGTGCTGGC

CGCTGCCACCAAGAGGAACTGCAACGTGACCCAGATGAGGGAGCTGCCCGTGCTGGACAGCGCTG

CCTTCAACGTGGAGTGCTTCAAGAAATACGCCTGCAACAACGAGTACTGGGAGACCTTCAAGGAGA

ACCCCATCAGGCTGACCGAAGAGAACGTGGTGAACTACATCACCAAGCTGAAGGGCCCCAAGGCCG

CTGCCCTGTTCGCTAAGACCCACAACCTGAACATGCTGCAGGACATCCCAATGGACAGGTTCGTGAT

GGACCTGAAGAGGGACGTGAAGGTGACACCCGGCACCAAGCACACCGAGGAGAGGCCCAAGGTG

CAGGTGATCCAGGCCGCTGACCCACTGGCCACCGCCTACCTGTGCGGCATCCACAGGGAGCTGGTG

AGGCGGCTGAACGCCGTGCTGCTGCCCAACATCCACACCCTGTTCGACATGAGCGCCGAGGACTTC

GACGCCATCATCGCCGAGCACTTCCAGCCCGGCGACTGCGTGCTGGAGACCGACATCGCCAGCTTC

GACAAGAGCGAGGATGACGCTATGGCCCTGACCGCTCTGATGATCCTGGAGGACCTGGGCGTGGA

CGCCGAGCTGCTCACCCTGATCGAGGCTGCCTTCGGCGAGATCAGCTCCATCCACCTGCCCACCAAG

ACCAAGTTCAAGTTCGGCGCTATGATGAAAAGCGGAATGTTCCTGACCCTGTTCGTGAACACCGTGA

TCAACATTGTGATCGCCAGCAGGGTGCTGCGGGAGAGGCTGACCGGCAGCCCCTGCGCTGCCTTCA

TCGGCGACGACAACATCGTGAAGGGCGTGAAAAGCGACAAGCTGATGGCCGACAGGTGCGCCACC

TGGCTGAACATGGAGGTGAAGATCATCGACGCCGTGGTGGGCGAGAAGGCCCCCTACTTCTGCGGC

GGATTCATCCTGTGCGACAGCGTGACCGGCACCGCCTGCAGGGTGGCCGACCCCCTGAAGAGGCTG

TTCAAGCTGGGCAAGCCACTGGCCGCTGACGATGAGCACGACGATGACAGGCGGAGGGCCCTGCA

CGAGGAAAGCACCAGGTGGAACAGGGTGGGCATCCTGAGCGAGCTGTGCAAGGCCGTGGAGAGC

AGGTACGAGACCGTGGGCACCAGCATCATCGTGATGGCTATGACCACACTGGCCAGCTCCGTCAAG

AGCTTCTCCTACCTGAGGGGGGCCCCTATAACTCTCTACGGCTAACCTGAATGGACTACGACATAGT

CTAgccaccATGagcaagatctacatcgacgagcggagcaacgccgagatcgtgtgcgaggccatcaagaccatcggcatcga gggcgccaccgccgcccagctgaccaggcagctgaacatggagaagcgggaggtgaacaaggccctgtacgacctgcagaggag cgctatggtgtactccagcgacgacatccctccccggtggttcatgaccaccgaggccgacaagcccgacgccgacgctatggccg acgtgatcatcgacgacgtgagcagggagaagtccatgagggaggaccacaagagcttcgacgacgtgatccccgccaagaaga tcatcgactggaagggcgccaaccccgtgaccgtgatcaacgagtactgccagatcaccaggagggactggagcttccggatcga gagcgtgggccccagcaacagccccaccttctacgcctgcgtggacatcgacggcagggtgttcgacaaggccgacggcaagagc aagcgggacgccaagaacaacgccgccaagctggccgtggacaagctgctgggctacgtgatcatccggttcTAAactcgagcta gtgactgactaggatctggttaccactaaaccagcctcaagaacacccgaatggagtctctaagctacataataccaacttacactt acaaaatgttgtcccccaaaatgtagccattcgtatctgctcctaataaaaagaaagtttcttcacattctagAGCTCCGTCAAG

AGCTTCTCCTACCTGAGGGGGGCCCCTATAACTCTCTACGGCTAACCTGAATGGACTACGACATAGT

CTAGCCACCATGGAAGATGCCAAAAACATTAAGAAGGGCCCAGCGCCATTCTACCCACTCGAAGAC

GGGACCGCCGGCGAGCAGCTGCACAAAGCCATGAAGCGCTACGCCCTGGTGCCCGGCACCATCGCC

TTTACCGACGCACATATCGAGGTGGACATTACCTACGCCGAGTACTTCGAGATGAGCGTTCGGCTGG

CAGAAGCTATGAAGCGCTATGGGCTGAATACAAACCATCGGATCGTGGTGTGCAGCGAGAATAGCT

TGCAGTTCTTCATGCCCGTGTTGGGTGCCCTGTTCATCGGTGTGGCTGTGGCCCCAGCTAACGACAT

CTACAACGAGCGCGAGCTGCTGAACAGCATGGGCATCAGCCAGCCCACCGTCGTATTCGTGAGCAA
```

-continued

```
GAAAGGGCTGCAAAAGATCCTCAACGTGCAAAAGAAGCTACCGATCATACAAAAGATCATCATCAT
GGATAGCAAGACCGACTACCAGGGCTTCCAAAGCATGTACACCTTCGTGACTTCCCATTTGCCACCC
GGCTTCAACGAGTACGACTTCGTGCCCGAGAGCTTCGACCGGGACAAAACCATCGCCCTGATCATGA
ACAGTAGTGGCAGTACCGGATTGCCCAAGGGCGTAGCCCTACCGCACCGCACCGCTTGTGTCCGATT
CAGTCATGCCCGCGACCCCATCTTCGGCAACCAGATCATCCCCGACACCGCTATCCTCAGCGTGGTG
CCATTTCACCACGGCTTCGGCATGTTCACCACGCTGGGCTACTTGATCTGCGGCTTTCGGGTCGTGCT
CATGTACCGCTTCGAGGAGGAGCTATTCTTGCGCAGCTTGCAAGACTATAAGATTCAATCTGCCCTG
CTGGTGCCCACACTATTTAGCTTCTTCGCTAAGAGCACTCTCATCGACAAGTACGACCTAAGCAACTT
GCACGAGATCGCCAGCGGCGGGGCGCCGCTCAGCAAGGAGGTAGGTGAGGCCGTGGCCAAACGC
TTCCACCTACCAGGCATCCGACAGGGCTACGGCCTGACAGAAACAACCAGCGCCATTCTGATCACCC
CCGAAGGGGACGACAAGCCTGGCGCAGTAGGCAAGGTGGTGCCCTTCTTCGAGGCTAAGGTGGTG
GACTTGGACACCGGTAAGACACTGGGTGTGAACCAGCGCGGCGAGCTGTGCGTCCGTGGCCCCATG
ATCATGAGCGGCTACGTTAACAACCCCGAGGCTACAAACGCTCTCATCGACAAGGACGGCTGGCTG
CACAGCGGCGACATCGCCTACTGGGACGAGGACGAGCACTTCTTCATCGTGGACCGGCTGAAGTCC
CTGATCAAATACAAGGGCTACCAGGTAGCCCCAGCCGAACTGGAGAGCATCCTGCTGCAACACCCC
AACATCTTCGACGCCGGGGTCGCCGGCCTGCCCGACGACGATGCCGGCGAGCTGCCCGCCGCAGTC
GTCGTGCTGGAACACGGTAAAACCATGACCGAGAAGGAGATCGTGGACTATGTGGCCAGCCAGGTT
ACAACCGCCAAGAAGCTGCGCGGTGGTGTTGTGTTCGTGGACGAGGTGCCTAAAGGACTGACCGG
CAAGTTGGACGCCCGCAAGATCCGCGAGATTCTCATTAAGGCCAAGAAGGGCGGCAAGATCGCCGT
GTAACTCGAGTATGTTACGTGCAAAGGTGATTGTCACCCCCCGAAAGACCATATTGTGACACACCCT
CAGTATCACGCCCAAACATTTACAGCCGCGGTGTCAAAAACCGCGTGGACGTGGTTAACATCCCTGC
TGGGAGGATCAGCCGTAATTATTATAATTGGCTTGGTGCTGGCTACTATTGTGGCCATGTACGTGCT
GACCAACCAGAAACATAATTGAATACAGCAGCAATTGGCAAGCTGCTTACATAGAACTCGCGGCGA
TTGGCATGCCGCCTTAAAATTTTTATTTTATTTTTTCTTTTCTTTTCCGAATCGGATTTTGTTTTTAATAT
TTCAAAAAAAAAAAAAAAAAAAAAAAAATctagAAAAAAAAAAAAAAAAAAAAAAAAAAAAAAAAA
AAAAAAAAAAAAAAAAAAAAAAAAAAAAAAAAAAAAAAAAAAAAAaaaaaaaaaaaaaaaaaaaa
```

(RNA sequence for STARR Fluc IRES-E3L)                                                                                SEQ ID NO: 118

```
AUGGGCGGCGCAUGAGAGAAGCCCAGACCAAUUACCUACCCAAAAUGGAGAAA
GUUCACGUUGACAUCGAGGAAGACAGCCCAUUCCUCAGAGCUUUGCAGCGGAG
CUUCCCGCAGUUUGAGGUAGAAGCCAAGCAGGUCACUGAUAAUGACCAUGCUA
AUGCCAGAGCGUUUUCGCAUCUGGCUUCAAAACUGAUCGAAACGGAGGUGGA
CCCAUCCGACACGAUCCUUGACAUUGGAAGUGCGCCCGCCCGCAGAAUGUAUU
CUAAGCACAAGUAUCAUUGUAUCUGUCCGAUGAGAUGUGCGGAAGAUCCGGA
CAGAUUGUAUAAGUAUGCAACUAAGCUGAAGAAAAACUGUAAGGAAAUAACU
GAUAAGGAAUUGGACAAGAAAAUGAAGGAGCUGGCCGCCGUCAUGAGCGACC
CUGACCUGGAAACUGAGACUAUGUGCCUCCACGACGACGAGUCGUGUCGCUAC
GAAGGGCAAGUCGCUGUUUACCAGGAUGUAUACGCCGUCGACGGCCCCACCAG
CCUGUACCACCAGGCCAACAAGGGCGUGAGGGUGGCCUACUGGAUCGGCUUCG
ACACCACACCCUUCAUGUUCAAGAACCUGGCCGGCGCCUACCCCAGCUACAGC
ACCAACUGGGCCGACGAGACCGUGCUGACCGCCAGGAACAUCGGCCUGUGCAG
```

-continued

CAGCGACGUGAUGGAGAGGAGCCGGAGAGGCAUGAGCAUCCUGAGGAAGAAA
UACCUGAAGCCCAGCAACAACGUGCUGUUCAGCGUGGGCAGCACCAUCUACCA
CGAGAAGAGGGACCUGCUCAGGAGCUGGCACCUGCCCAGCGUGUUCCACCUGA
GGGGCAAGCAGAACUACACCUGCAGGUGCGAGACCAUCGUGAGCUGCGACGGC
UACGUGGUGAAGAGGAUCGCCAUCAGCCCCGGCCUGUACGGCAAGCCCAGCGG
CUACGCCGCUACAAUGCACAGGGAGGGCUUCCUGUGCUGCAAGGUGACCGACA
CCCUGAACGGCGAGAGGGUGAGCUUCCCCGUGUGCACCUACGUGCCCGCCACC
CUGUGCGACCAGAUGACCGGCAUCCUGGCCACCGACGUGAGCGCCGACGACGC
CCAGAAGCUGCUCGUGGGCCUGAACCAGAGGAUCGUGGUCAACGGCAGGACCC
AGAGGAACACCAACACAAUGAAGAACUACCUGCUGCCCGUGGUGGCCCAGGCU
UUCGCCAGGUGGGCCAAGGAGUACAAGGAGGACCAGGAAGACGAGAGGCCCCU
GGGCCUGAGGGACAGGCAGCUGGUGAUGGGCUGCUGCUGGGCCUUCAGGCGGC
ACAAGAUCACCAGCAUCUACAAGAGGCCCGACACCCAGACCAUCAUCAAGGUG
AACAGCGACUUCCACAGCUUCGUGCUGCCCAGGAUCGGCAGCAACACCCUGGA
GAUCGGCCUGAGGACCCGGAUCAGGAAGAUGCUGGAGGAACACAAGGAGCCCA
GCCCACUGAUCACCGCCGAGGACGUGCAGGAGGCCAAGUGCGCUGCCGACGAG
GCCAAGGAGGUGAGGGAGGCCGAGGAACUGAGGGCCGCCCUGCCACCCCUGGC
UGCCGACGUGGAGGAACCCACCCUGGAAGCCGACGUGGACCUGAUGCUGCAGG
AGGCCGGCGCCGGAAGCGUGGAGACACCCAGGGGCCUGAUCAAGGUGACCAGC
UACGACGGCGAGGACAAGAUCGGCAGCUACGCCGUGCUGAGCCCACAGGCCGU
GCUGAAGUCCGAGAAGCUGAGCUGCAUCCACCCACUGGCCGAGCAGGUGAUCG
UGAUCACCCACAGCGGCAGGAAGGGCAGGUACGCCGUGGAGCCCUACCACGGC
AAGGUGGUCGUGCCCGAGGGCCACGCCAUCCCCGUGCAGGACUUCCAGGCCCU
GAGCGAGAGCGCCACCAUCGUGUACAACGAGAGGGAGUUCGUGAACAGGUACC
UGCACCAUAUCGCCACCCACGGCGGAGCCCUGAACACCGACGAGGAAUACUAC
AAGACCGUGAAGCCCAGCGAGCACGACGGCGAGUACCUGUACGACAUCGACAG
GAAGCAGUGCGUGAAGAAAGAGCUGGUGACCGGCCUGGGACUGACCGGCGAG
CUGGUGGACCCACCCUUCCACGAGUUCGCCUACGAGAGCCUGAGGACCAGACC
CGCCGCUCCCUACCAGGUGCCCACCAUCGGCGUGUACGGCGUGCCCGGCAGCG
GAAAGAGCGGCAUCAUCAAGAGCGCCGUGACCAAGAAAGACCUGGUGGUCAGC
GCCAAGAAAGAGAACUGCGCCGAGAUCAUCAGGGACGUGAAGAAGAUGAAAG
GCCUGGACGUGAACGCGCGCACCGUGGACAGCGUGCUGCUGAACGGCUGCAAG
CACCCCGUGGAGACCCUGUACAUCGACGAGGCCUUCGCUUGCCACGCCGGCAC
CCUGAGGGCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCACUUCAAC
CACGAGAUCUGCACCCAGGUGUUCCACAAGAGCAUCAGCAGGCGGUGCACCAA
GAGCGUGACCAGCGUCGUGAGCACCCUGUUCUACGACAAGAAAAUGAGGACCA
CCAACCCCAAGGAGACCAAAAUCGUGAUCGACACCACAGGCAGCACCAAGCCC
AAGCAGGACGACCUGAUCCUGACCUGCUUCAGGGGCUGGGUGAAGCAGCUGCA
GAUCGACUACAAGGGCAACGAGAUCAUGACCGCCGCUGCCAGCCAGGGCCUGA
CCAGGAAGGGCGUGUACGCCGUGAGGUACAAGGUGAACGAGAACCCACUGUAC

-continued

```
GCUCCCACCAGCGAGCACGUGAACGUGCUGCUGACCAGGACCGAGGACAGGAU
CGUGUGGAAGACCCUGGCCGGCGACCCCUGGAUCAAGACCCUGACCGCCAAGU
ACCCCGGCAACUUCACCGCCACCAUCGAAGAGUGGCAGGCCGAGCACGACGCC
AUCAUGAGGCACAUCCUGGAGAGGCCCGACCCCACCGACGUGUUCCAGAACAA
GGCCAACGUGUGCUGGGCCAAGGCCCUGGUGCCCGUGCUGAAGACCGCCGGCA
UCGACAUGACCACAGAGCAGUGGAACACCGUGGACUACUUCGAGACCGACAAG
GCCCACAGCGCCGAGAUCGUGCUGAACCAGCUGUGCGUGAGGUUCUUCGGCCU
GGACCUGGACAGCGGCCUGUUCAGCGCCCCCACCGUGCCACUGAGCAUCAGGA
ACAACCACUGGGACAACAGCCCCAGCCCAAACAUGUACGGCCUGAACAAGGAG
GUGGUCAGGCAGCUGAGCAGGCGGUACCCACAGCUGCCCAGGGCCGUGGCCAC
CGGCAGGGUGUACGACAUGAACACCGGCACCCUGAGGAACUACGACCCCAGGA
UCAACCUGGUGCCCGUGAACAGGCGGCUGCCCCACGCCCUGGUGCUGCACCAC
AACGAGCACCCACAGAGCGACUUCAGCUCCUUCGUGAGCAAGCUGAAAGGCAG
GACCGUGCUGGUCGUGGGCGAGAAGCUGAGCGUGCCCGGCAAGAUGGUGGAC
UGGCUGAGCGACAGGCCCGAGGCCACCUUCCGGGCCAGGCUGGACCUCGGCAU
CCCCGGCGACGUGCCCAAGUACGACAUCAUCUUCGUGAACGUCAGGACCCCAU
ACAAGUACCACCAUUACCAGCAGUGCGAGGACCACGCCAUCAAGCUGAGCAUG
CUGACCAAGAAGGCCUGCCUGCACCUGAACCCCGGAGGCACCUGCGUGAGCAU
CGGCUACGGCUACGCCGACAGGGCCAGCGAGAGCAUCAUUGGCGCCAUCGCCA
GGCUGUUCAAGUUCAGCAGGGUGUGCAAACCCAAGAGCAGCCUGGAGGAAACC
GAGGUGCUGUUCGUGUUCAUCGGCUACGACCGGAAGGCCAGGACCCACAACCC
CUACAAGCUGAGCAGCACCCUGACAAACAUCUACACCGGCAGCAGGCUGCACG
AGGCCGGCUGCGCCCCAGCUACCACGUGGUCAGGGGCGAUAUCGCCACCGCC
ACCGAGGGCGUGAUCAUCAACGCUGCCAACAGCAAGGGCCAGCCCGGAGGCGG
AGUGUGCGGCGCCCUGUACAAGAAGUUCCCCGAGAGCUUCGACCUGCAGCCCA
UCGAGGUGGGCAAGGCCAGGCUGGUGAAGGGCGCCGCUAAGCACAUCAUCCAC
GCCGUGGGCCCCAACUUCAACAAGGUGAGCGAGGUGGAAGGCGACAAGCAGCU
GGCCGAAGCCUACGAGAGCAUCGCCAAGAUCGUGAACGACAAUAACUACAAGA
GCGUGGCCAUCCCACUGCUCAGCACCGGCAUCUUCAGCGGCAACAAGGACAGG
CUGACCCAGAGCCUGAACCACCUGCUCACCGCCCUGGACACCACCGAUGCCGA
CGUGGCCAUCUACUGCAGGGACAAGAAGUGGGAGAUGACCCUGAAGGAGGCC
GUGGCCAGGCGGGAGGCCGUGGAAGAGAUCUGCAUCAGCGACGACUCCAGCGU
GACCGAGCCCGACGCCGAGCUGGUGAGGGUGCACCCCAAGAGCUCCCUGGCCG
GCAGGAAGGGCUACAGCACCAGCGACGGCAAGACCUUCAGCUACCUGGAGGGC
ACCAAGUUCCACCAGGCCGCUAAGGACAUCGCCGAGAUCAACGCUAUGUGGCC
CGUGGCCACCGAGGCCAACGAGCAGGUGUGCAUGUACAUCCUGGGCGAGAGCA
UGUCCAGCAUCAGGAGCAAGUGCCCCGUGGAGGAAAGCGAGGCCAGCACACCA
CCCAGCACCCUGCCCUGCCUGUGCAUCCACGCUAUGACACCCGAGAGGGUGCA
GCGGCUGAAGGCCAGCAGGCCCGAGCAGAUCACCGUGUGCAGCUCCUUCCCAC
UGCCCAAGUACAGGAUCACCGGCGUGCAGAAGAUCCAGUGCAGCCAGCCCAUC
```

-continued

```
CUGUUCAGCCCAAAGGUGCCCGCCUACAUCCACCCCAGGAAGUACCUGGUGGA

GACCCCACCCGUGGACGAGACACCCGAGCCAAGCGCCGAGAACCAGAGCACCG

AGGGCACACCCGAGCAGCCACCCCUGAUCACCGAGGACGAGACAAGGACCCGG

ACCCCAGAGCCCAUCAUUAUCGAGGAAGAGGAAGAGGACAGCAUCAGCCUGCU

GAGCGACGGCCCCACCCACCAGGUGCUGCAGGUGGAGGCCGACAUCCACGGCC

CACCCAGCGUGUCCAGCUCCAGCUGGAGCAUCCCACACGCCAGCGACUUCGAC

GUGGACAGCCUGAGCAUCCUGGACACCCUGGAGGGCGCCAGCGUGACCUCCGG

CGCCACCAGCGCCGAGACCAACAGCUACUUCGCCAAGAGCAUGGAGUUCCUGG

CCAGGCCCGUGCCAGCUCCCAGGACCGUGUUCAGGAACCCACCCCACCCAGCUC

CCAGGACCAGGACCCCAAGCCUGGCUCCCAGCAGGGCCUGCAGCAGGACCAGC

CUGGUGAGCACCCCACCCGGCGUGAACAGGGUGAUCACCAGGGAGGAACUGGA

GGCCCUGACACCCAGCAGGACCCCCAGCAGGUCCGUGAGCAGGACUAGUCUGG

UGUCCAACCCACCCGGCGUGAACAGGGUGAUCACCAGGGAGGAAUUCGAGGCC

UUCGUGGCCCAGCAACAGAGACGGUUCGACGCCGGCGCCUACAUCUUCAGCAG

CGACACCGGCCAGGGACACCUGCAGCAAAAGAGCGUGAGGCAGACCGUGCUGA

GCGAGGUGGUGCUGGAGAGGACCGAGCUGGAAAUCAGCUACGCCCCCAGGCUG

GACCAGGAGAAGGAGGAACUGCUCAGGAAGAAACUGCAGCUGAACCCCACCCC

AGCCAACAGGAGCAGGUACCAGAGCAGGAAGGUGGAGAACAUGAAGGCCAUC

ACCGCCAGGCGGAUCCUGCAGGGCCUGGGACACUACCUGAAGGCCGAGGGCAA

GGUGGAGUGCUACAGGACCCUGCACCCCGUGCCACUGUACAGCUCCAGCGUGA

ACAGGGCCUUCUCCAGCCCCAAGGUGGCCGUGGAGGCCUGCAACGCUAUGCUG

AAGGAGAACUUCCCCACCGUGGCCAGCUACUGCAUCAUCCCCGAGUACGACGC

CUACCUGGACAUGGUGGACGGCGCCAGCUGCUGCCUGGACACCGCCAGCUUCU

GCCCCGCCAAGCUGAGGAGCUUCCCCAAGAAACACAGCUACCUGGAGCCCACC

AUCAGGAGCGCCGUGCCCAGCGCCAUCCAGAACACCCUGCAGAACGUGCUGGC

CGCUGCCACCAAGAGGAACUGCAACGUGACCCAGAUGAGGGAGCUGCCCGUGC

UGGACAGCGCUGCCUUCAACGUGGAGUGCUUCAAGAAAUACGCCUGCAACAAC

GAGUACUGGGAGACCUUCAAGGAGAACCCCAUCAGGCUGACCGAAGAGAACGU

GGUGAACUACAUCACCAAGCUGAAGGGCCCCAAGGCCGCUGCCCUGUUCGCUA

AGACCCACAACCUGAACAUGCUGCAGGACAUCCCAAUGGACAGGUUCGUGAUG

GACCUGAAGAGGGACGUGAAGGUGACACCCGGCACCAAGCACACCGAGGAGAG

GCCCAAGGUGCAGGUGAUCCAGGCCGCUGACCCACUGGCCACCGCCUACCUGU

GCGGCAUCCACAGGGAGCUGGUGAGGCGGCUGAACGCCGUGCUGCUGCCCAAC

AUCCACACCCUGUUCGACAUGAGCGCCGAGGACUUCGACGCCAUCAUCGCCGA

GCACUUCCAGCCCGGCGACUGCGUGCUGGAGACCGACAUCGCCAGCUUCGACA

AGAGCGAGGAUGACGCUAUGGCCCUGACCGCUCUGAUGAUCCUGGAGGACCUG

GGCGUGGACGCCGAGCUGCUCACCCUGAUCGAGGCUGCCUUCGGCGAGAUCAG

CUCCAUCCACCUGCCCACCAAGACCAAGUUCAAGUUCGGCGCUAUGAUGAAAA

GCGGAAUGUUCCUGACCCUGUUCGUGAACACCGUGAUCAACAUUGUGAUCGCC

AGCAGGGUGCUGCGGGAGAGGCUGACCGGCAGCCCCGCGCUGCCUUCAUCGG

CGACGACAACAUCGUGAAGGGCGUGAAAAGCGACAAGCUGAUGGCCGACAGG
```

-continued

```
UGCGCCACCUGGCUGAACAUGGAGGUGAAGAUCAUCGACGCCGUGGUGGGCGA
GAAGGCCCCCUACUUCUGCGGCGGAUUCAUCCUGUGCGACAGCGUGACCGGCA
CCGCCUGCAGGGUGGCCGACCCCCUGAAGAGGCUGUUCAAGCUGGGCAAGCCA
CUGGCCGCUGACGAUGAGCACGACGAUGACAGGCGGAGGGCCCUGCACGAGGA
AAGCACCAGGUGGAACAGGGUGGGCAUCCUGAGCGAGCUGUGCAAGGCCGUG
GAGAGCAGGUACGAGACCGUGGGCACCAGCAUCAUCGUGAUGGCUAUGACCAC
ACUGGCCAGCUCCGUCAAGAGCUUCUCCUACCUGAGGGGGGCCCCUAUAACUC
UCUACGGCUAACCUGAAUGGACUACGACAUAGUCUAGUCCGCCAAGGCCGCCA
CCAUGGAAGAUGCCAAAAACAUUAAGAAGGGCCCAGCGCCAUUCUACCCACUC
GAAGACGGGACCGCCGGCGAGCAGCUGCACAAAGCCAUGAAGCGCUACGCCCU
GGUGCCCGGCACCAUCGCCUUUACCGACGCACAUAUCGAGGUGGACAUUACCU
ACGCCGAGUACUUCGAGAUGAGCGUUCGGCUGGCAGAAGCUAUGAAGCGCUA
UGGGCUGAAUACAAACCAUCGGAUCGUGGUGUGCAGCGAGAAUAGCUUGCAG
UUCUUCAUGCCCGUGUUGGGUGCCCUGUUCAUCGGUGUGGCUGUGGCCCCAGC
UAACGACAUCUACAACGAGCGCGAGCUGCUGAACAGCAUGGGCAUCAGCCAGC
CCACCGUCGUAUUCGUGAGCAAGAAAGGGCUGCAAAAGAUCCUCAACGUGCAA
AAGAAGCUACCGAUCAUACAAAAGAUCAUCAUGGAUAGCAAGACCGACU
ACCAGGGCUUCCAAAGCAUGUACACCUUCGUGACUUCCCAUUUGCCACCCGGC
UUCAACGAGUACGACUUCGUGCCCGAGAGCUUCGACCGGGACAAAACCAUCGC
CCUGAUCAUGAACAGUAGUGGCAGUACCGGAUUGCCCAAGGGCGUAGCCCUAC
CGCACCGCACCGCUUGUGUCCGAUUCAGUCAUGCCCGCGACCCCAUCUUCGGC
AACCAGAUCAUCCCCGACACCGCUAUCCUCAGCGUGGUGCCAUUUCACCACGG
CUUCGGCAUGUUCACCACGCUGGGCUACUUGAUCUGCGGCUUUCGGGUCGUGC
UCAUGUACCGCUUCGAGGAGGAGCUAUUCUUGCGCAGCUUGCAAGACUAUAA
GAUUCAAUCUGCCCUGCUGGUGCCCACACUAUUUAGCUUCUUCGCUAAGAGCA
CUCUCAUCGACAAGUACGACCUAAGCAACUUGCACGAGAUCGCCAGCGGCGGG
GCGCCGCUCAGCAAGGAGGUAGGUGAGGCCGUGGCCAAACGCUUCCACCUACC
AGGCAUCCGACAGGGCUACGGCCUGACAGAAACAACCAGCGCCAUUCUGAUCA
CCCCCGAAGGGGACGACAAGCCUGGCGCAGUAGGCAAGGUGGUGCCCUUCUUC
GAGGCUAAGGUGGUGGACUUGGACACCGGUAAGACACUGGGGUGUGAACCAGC
GCGGCGAGCUGUGCGUCCGUGGCCCCAUGAUCAUGAGCGGCUACGUUAACAAC
CCCGAGGCUACAAACGCUCUCAUCGACAAGGACGGCUGGCUGCACAGCGGCGA
CAUCGCCUACUGGGACGAGGACGAGCACUUCUUCAUCGUGGACCGGCUGAAGU
CCCUGAUCAAAUACAAGGGCUACCAGGUAGCCCCAGCCGAACUGGAGAGCAUC
CUGCUGCAACACCCCAACAUCUUCGACGCCGGGGUCGCCGGCCUGCCCGACGA
CGAUGCCGGCGAGCUGCCCGCCGCAGUCGUCGUGCUGGAACACGGUAAAACCA
UGACCGAGAAGGAGAUCGUGGACUAUGUGGCCAGCCAGGUUACAACCGCCAAG
AAGCUGCGCGGUGGUGUUGUGUUCGUGGACGAGGUGCCUAAAGGACUGACCG
GCAAGUUGGACGCCCGCAAGAUCCGCGAGAUUCUCAUUAAGGCCAAGAAGGGC
GGCAAGAUCGCCGUGUAACUCGAGCCGGAAACGCAAUAGCCGAAAAACAAAAA
```

```
ACAAAAAAAACAAAAAAAAAACCAAAAAAACAAAACACAUUAAAACAGCCUG

UGGGUUGAUCCCACCCACAGGCCCAUUGGGCGCUAGCACUCUGGUAUCACGGU

ACCUUUGUGCGCCUGUUUUAUACCCCUCCCCCAACUGUAACUUAGAAGUAAC

ACACACCGAUCAACAGUCAGCGUGGCACACCAGCCACGUUUUGAUCAAGCACU

UCUGUUACCCCGGACUGAGUAUCAAUAGACUGCUCACGCGGUUGAAGGAGAA

AGCGUUCGUUAUCCGGCCAACUACUUCGAAAAACCUAGUAACACCGUGGAAGU

UGCAGAGUGUUUCGCUCAGCACUACCCCAGUGUAGAUCAGGUCGAUGAGUCAC

CGCAUUCCCCACGGGCGACCGUGGCGGUGGCUGCGUUGGCGGCCUGCCCAUGG

GGAAACCCAUGGGACGCUCUAAUACAGACAUGGUGCGAAGAGUCUAUUGAGC

UAGUUGGUAGUCCUCCGGCCCCUGAAUGCGGCUAAUCCUAACUGCGGAGCACA

CACCCUCAAGCCAGAGGGCAGUGUGUCGUAACGGGCAACUCUGCAGCGGAACC

GACUACUUUGGGUGUCCGUGUUUCAUUUUAUUCCUAUACUGGCUGCUUAUGG

UGACAAUUGAGAGAUCGUUACCAUAUAGCUAUUGGAUUGGCCAUCCGGUGAC

UAAUAGAGCUAUUAUAUAUCCCUUUGUUGGGUUUAUACCACUUAGCUUGAAA

GAGGUUAAAACAUUACAAUUCAUUGUUAAGUUGAAUACAGCAAAAUGAGCAA

GAUCUACAUCGACGAGCGGAGCAACGCCGAGAUCGUGUGCGAGGCCAUCAAGA

CCAUCGGCAUCGAGGGCGCCACCGCCGCCCAGCUGACCAGGCAGCUGAACAUG

GAGAAGCGGGAGGUGAACAAGGCCCUGUACGACCUGCAGAGGAGCGCUAUGG

UGUACUCCAGCGACGACAUCCCUCCCCGGUGGUUCAUGACCACCGAGGCCGAC

AAGCCCGACGCCGACGCUAUGGCCGACGUGAUCAUCGACGACGUGAGCAGGGA

GAAGUCCAUGAGGGAGGACCACAAGAGCUUCGACGACGUGAUCCCCGCCAAGA

AGAUCAUCGACUGGAAGGGCGCCAACCCCGUGACCGUGAUCAACGAGUACUGC

CAGAUCACCAGGAGGGACUGGAGCUUCCGGAUCGAGAGCGUGGGCCCCAGCAA

CAGCCCCACCUUCUACGCCUGCGUGGACAUCGACGGCAGGGUGUUCGACAAGG

CCGACGGCAAGAGCAAGCGGGACGCCAAGAACAACGCCGCCAAGCUGGCCGUG

GACAAGCUGCUGGGCUACGUGAUCAUCCGGUUCUAAACGUAUGUUACGUGCA

AAGGUGAUUGUCACCCCCGAAAGACCAUAUUGUGACACACCCUCAGUAUCAC

GCCCAAACAUUUACAGCCGCGGUGUCAAAAACCGCGUGGACGUGGUUAACAUC

CCUGCUGGGAGGAUCAGCCGUAAUUAUUAUAAUUGGCUUGGUGCUGGCUACU

AUUGUGGCCAUGUACGUGCUGACCAACCAGAAACAUAAUUGAAUACAGCAGC

AAUUGGCAAGCUGCUUACAUAGAACUCGCGGCGAUUGGCAUGCCGCCUUAAAA

UUUUUAUUUUAUUUUUUCUUUUCUUUUCCGAAUCGGAUUUUGUUUUUAAUAU

UUCAAAAAAAAAAAAAAAAAAAAAAAAAUCUAGAAAAAAAAAAAAAAAAAAA

AAAAAAAAAAAAAAAAAAAAAAAAAAAAAAAAAAAAAAAAAAAAAAAAAAAA

AAAAAAAAAAAAAAAAAAAAAAAAAA (RNA sequence for STARR Fluc IRES-E3L (short 3' UTR))  SEQ ID NO: 119

AUGGGCGGCGCAUGAGAGAAGCCCAGACCAAUUACCUACCCAAAAUGGAGAAA

GUUCACGUUGACAUCGAGGAAGACAGCCCAUUCCUCAGAGCUUUGCAGCGGAG

CUUCCCGCAGUUUGAGGUAGAAGCCAAGCAGGUCACUGAUAAUGACCAUGCUA

AUGCCAGAGCGUUUUCGCAUCUGGCUUCAAAACUGAUCGAAACGGAGGUGGA

CCCAUCCGACACGAUCCUUGACAUUGGAAGUGCGCCCGCCCGCAGAAUGUAUU
```

-continued

```
CUAAGCACAAGUAUCAUUGUAUCUGUCCGAUGAGAUGUGCGGAAGAUCCGGA

CAGAUUGUAUAAGUAUGCAACUAAGCUGAAGAAAAACUGUAAGGAAAUAACU

GAUAAGGAAUUGGACAAGAAAAUGAAGGAGCUGGCCGCCGUCAUGAGCGACC

CUGACCUGGAAACUGAGACUAUGUGCCUCCACGACGACGAGUCGUGUCGCUAC

GAAGGGCAAGUCGCUGUUUACCAGGAUGUAUACGCCGUCGACGGCCCCACCAG

CCUGUACCACCAGGCCAACAAGGGCGUGAGGGUGGCCUACUGGAUCGGCUUCG

ACACCACACCCUUCAUGUUCAAGAACCUGGCCGGCGCCUACCCCAGCUACAGC

ACCAACUGGGCCGACGAGACCGUGCUGACCGCCAGGAACAUCGGCCUGUGCAG

CAGCGACGUGAUGGAGAGGAGCCGGAGAGGCAUGAGCAUCCUGAGGAAGAAA

UACCUGAAGCCCAGCAACAACGUGCUGUUCAGCGUGGGCAGCACCAUCUACCA

CGAGAAGAGGGACCUGCUCAGGAGCUGGCACCUGCCCAGCGUGUUCCACCUGA

GGGGCAAGCAGAACUACACCUGCAGGUGCGAGACCAUCGUGAGCUGCGACGGC

UACGUGGUGAAGAGGAUCGCCAUCAGCCCCGGCCUGUACGGCAAGCCCAGCGG

CUACGCCGCUACAAUGCACAGGGAGGGCUUCCUGUGCUGCAAGGUGACCGACA

CCCUGAACGGCGAGAGGGUGAGCUUCCCCGUGUGCACCUACGUGCCCGCCACC

CUGUGCGACCAGAUGACCGGCAUCCUGGCCACCGACGUGAGCGCCGACGACGC

CCAGAAGCUGCUCGUGGGCCUGAACCAGAGGAUCGUGGUCAACGGCAGGACCC

AGAGGAACACCAACACAAUGAAGAACUACCUGCUGCCCGUGGUGGCCCAGGCU

UUCGCCAGGUGGGCCAAGGAGUACAAGGAGGACCAGGAAGACGAGAGGCCCCU

GGGCCUGAGGGACAGGCAGCUGGUGAUGGGCUGCUGCUGGGCCUUCAGGCGGC

ACAAGAUCACCAGCAUCUACAAGAGGCCCGACACCCAGACCAUCAUCAAGGUG

AACAGCGACUUCCACAGCUUCGUGCUGCCCAGGAUCGGCAGCAACACCCUGGA

GAUCGGCCUGAGGACCCGGAUCAGGAAGAUGCUGGAGGAACACAAGGAGCCCA

GCCCACUGAUCACCGCCGAGGACGUGCAGGAGGCCAAGUGCGCUGCCGACGAG

GCCAAGGAGGUGAGGGAGGCCGAGGAACUGAGGGCCGCCCUGCCACCCCUGGC

UGCCGACGUGGAGGAACCCACCCUGGAAGCCGACGUGGACCUGAUGCUGCAGG

AGGCCGGCGCCGGAAGCGUGGAGACACCCAGGGGCCUGAUCAAGGUGACCAGC

UACGACGGCGAGGACAAGAUCGGCAGCUACGCCGUGCUGAGCCCACAGGCCGU

GCUGAAGUCCGAGAAGCUGAGCUGCAUCCACCCACUGGCCGAGCAGGUGAUCG

UGAUCACCCACAGCGGCAGGAAGGGCAGGUACGCCGUGGAGCCCUACCACGGC

AAGGUGGUCGUGCCCGAGGGCCACGCCAUCCCCGUGCAGGACUUCCAGGCCCU

GAGCGAGAGCGCCACCAUCGUGUACAACGAGAGGGAGUUCGUGAACAGGUACC

UGCACCAUAUCGCCACCCACGGCGGAGCCCUGAACACCGACGAGGAAUACUAC

AAGACCGUGAAGCCCAGCGAGCACGACGGCGAGUACCUGUACGACAUCGACAG

GAAGCAGUGCGUGAAGAAAGAGCUGGUGACCGGCCUGGGACUGACCGGCGAG

CUGGUGGACCCACCCUUCCACGAGUUCGCCUACGAGAGCCUGAGGACCAGACC

CGCCGCUCCCUACCAGGUGCCCACCAUCGGCGUGUACGGCGUGCCCGGCAGCG

GAAAGAGCGGCAUCAUCAAGAGCGCCGUGACCAAGAAAGACCUGGUGGUCAGC

GCCAAGAAAGAGAACUGCGCCGAGAUCAUCAGGGACGUGAAGAAGAUGAAAG

GCCUGGACGUGAACGCGCGCACCGUGGACAGCGUGCUGCUGAACGGCUGCAAG
```

-continued

```
CACCCCGUGGAGACCCUGUACAUCGACGAGGCCUUCGCUUGCCACGCCGGCAC

CCUGAGGGCCCUGAUCGCCAUCAUCAGGCCCAAGAAAGCCGUGCUGUGCGGCG

ACCCCAAGCAGUGCGGCUUCUUCAACAUGAUGUGCCUGAAGGUGCACUUCAAC

CACGAGAUCUGCACCCAGGUGUUCCACAAGAGCAUCAGCAGGCGGUGCACCAA

GAGCGUGACCAGCGUCGUGAGCACCCUGUUCUACGACAAGAAAAUGAGGACCA

CCAACCCCAAGGAGACCAAAAUCGUGAUCGACACCACAGGCAGCACCAAGCCC

AAGCAGGACGACCUGAUCCUGACCUGCUUCAGGGGCUGGGUGAAGCAGCUGCA

GAUCGACUACAAGGGCAACGAGAUCAUGACCGCCGCUGCCAGCCAGGGCCUGA

CCAGGAAGGGCGUGUACGCCGUGAGGUACAAGGUGAACGAGAACCCACUGUAC

GCUCCCACCAGCGAGCACGUGAACGUGCUGCUGACCAGGACCGAGGACAGGAU

CGUGUGGAAGACCCUGGCCGGCGACCCCUGGAUCAAGACCCUGACCGCCAAGU

ACCCCGGCAACUUCACCGCCACCAUCGAAGAGUGGCAGGCCGAGCACGACGCC

AUCAUGAGGCACAUCCUGGAGAGGCCCGACCCCACCGACGUGUUCCAGAACAA

GGCCAACGUGUGCUGGGCCAAGGCCCUGGUGCCCGUGCUGAAGACCGCCGGCA

UCGACAUGACCACAGAGCAGUGGAACACCGUGGACUACUUCGAGACCGACAAG

GCCCACAGCGCCGAGAUCGUGCUGAACCAGCUGUGCGUGAGGUUCUUCGGCCU

GGACCUGGACAGCGGCCUGUUCAGCGCCCCCACCGUGCCACUGAGCAUCAGGA

ACAACCACUGGGACAACAGCCCCAGCCCAAACAUGUACGGCCUGAACAAGGAG

GUGGUCAGGCAGCUGAGCAGGCGGUACCCACAGCUGCCCAGGGCCGUGGCCAC

CGGCAGGGUGUACGACAUGAACACCGGCACCCUGAGGAACUACGACCCCAGGA

UCAACCUGGUGCCCGUGAACAGGCGGCUGCCCCACGCCCUGGUGCUGCACCAC

AACGAGCACCCACAGAGCGACUUCAGCUCCUUCGUGAGCAAGCUGAAAGGCAG

GACCGUGCUGGUCGUGGGCGAGAAGCUGAGCGUGCCCGGCAAGAUGGUGGAC

UGGCUGAGCGACAGGCCCGAGGCCACCUUCCGGGCCAGGCUGGACCUCGGCAU

CCCCGGCGACGUGCCCAAGUACGACAUCAUCUUCGUGAACGUCAGGACCCCAU

ACAAGUACCACCAUUACCAGCAGUGCGAGGACCACGCCAUCAAGCUGAGCAUG

CUGACCAAGAAGGCCUGCCUGCACCUGAACCCCGGAGGCACCUGCGUGAGCAU

CGGCUACGGCUACGCCGACAGGGCCAGCGAGAGCAUCAUUGGCGCCAUCGCCA

GGCUGUUCAAGUUCAGCAGGGUGUGCAAACCCAAGAGCAGCCUGGAGGAAACC

GAGGUGCUGUUCGUGUUCAUCGGCUACGACCGGAAGGCCAGGACCCACAACCC

CUACAAGCUGAGCAGCACCCUGACAAACAUCUACACCGGCAGCAGGCUGCACG

AGGCCGGCUGCGCCCCAGCUACCACGUGGUCAGGGGCGAUAUCGCCACCGCC

ACCGAGGGCGUGAUCAUCAACGCUGCCAACAGCAAGGGCCAGCCCGGAGGCGG

AGUGUGCGGCGCCCUGUACAAGAAGUUCCCCGAGAGCUUCGACCUGCAGCCCA

UCGAGGUGGGCAAGGCCAGGCUGGUGAAGGGCGCCGCUAAGCACAUCAUCCAC

GCCGUGGGCCCCAACUUCAACAAGGUGAGCGAGGUGGAAGGCGACAAGCAGCU

GGCCGAAGCCUACGAGAGCAUCGCCAAGAUCGUGAACGACAAUAACUACAAGA

GCGUGGCCAUCCCACUGCUCAGCACCGGCAUCUUCAGCGGCAACAAGGACAGG

CUGACCCAGAGCCUGAACCACCUGCUCACCGCCCUGGACACCACCGAUGCCGA

CGUGGCCAUCUACUGCAGGGACAAGAAGUGGGAGAUGACCCUGAAGGAGGCC

GUGGCCAGGCGGGAGGCCGUGGAAGAGAUCUGCAUCAGCGACGACUCCAGCGU
```

-continued

```
GACCGAGCCCGACGCCGAGCUGGUGAGGGUGCACCCCAAGAGCUCCCUGGCCG

GCAGGAAGGGCUACAGCACCAGCGACGGCAAGACCUUCAGCUACCUGGAGGGC

ACCAAGUUCCACCAGGCCGCUAAGGACAUCGCCGAGAUCAACGCUAUGUGGCC

CGUGGCCACCGAGGCCAACGAGCAGGUGUGCAUGUACAUCCUGGGCGAGAGCA

UGUCCAGCAUCAGGAGCAAGUGCCCCGUGGAGGAAAGCGAGGCCAGCACACCA

CCCAGCACCCUGCCCUGCCUGUGCAUCCACGCUAUGACACCCGAGAGGGUGCA

GCGGCUGAAGGCCAGCAGGCCCGAGCAGAUCACCGUGUGCAGCUCCUUCCCAC

UGCCCAAGUACAGGAUCACCGGCGUGCAGAAGAUCCAGUGCAGCCAGCCCAUC

CUGUUCAGCCCAAAGGUGCCCGCCUACAUCCACCCCAGGAAGUACCUGGUGGA

GACCCCACCCGUGGACGAGACACCCGAGCCAAGCGCCGAGAACCAGAGCACCG

AGGGCACACCCGAGCAGCCACCCCUGAUCACCGAGGACGAGACAAGGACCCGG

ACCCCAGAGCCCAUCAUUAUCGAGGAAGAGGAAGAGGACAGCAUCAGCCUGCU

GAGCGACGGCCCCACCCACCAGGUGCUGCAGGUGGAGGCCGACAUCCACGGCC

CACCCAGCGUGUCCAGCUCCAGCUGGAGCAUCCCACACGCCAGCGACUUCGAC

GUGGACAGCCUGAGCAUCCUGGACACCCUGGAGGGCGCCAGCGUGACCUCCGG

CGCCACCAGCGCCGAGACCAACAGCUACUUCGCCAAGAGCAUGGAGUUCCUGG

CCAGGCCCGUGCCAGCUCCCAGGACCGUGUUCAGGAACCCACCCCACCCAGCUC

CCAGGACCAGGACCCCAAGCCUGGCUCCCAGCAGGGCCUGCAGCAGGACCAGC

CUGGUGAGCACCCCACCCGGCGUGAACAGGGUGAUCACCAGGGAGGAACUGGA

GGCCCUGACACCCAGCAGGACCCCCAGCAGGUCCGUGAGCAGGACUAGUCUGG

UGUCCAACCCACCCGGCGUGAACAGGGUGAUCACCAGGGAGGAAUUCGAGGCC

UUCGUGGCCCAGCAACAGAGACGGUUCGACGCCGGCGCCUACAUCUUCAGCAG

CGACACCGGCCAGGGACACCUGCAGCAAAAGAGCGUGAGGCAGACCGUGCUGA

GCGAGGUGGUGCUGGAGAGGACCGAGCUGGAAAUCAGCUACGCCCCCAGGCUG

GACCAGGAGAAGGAGGAACUGCUCAGGAAGAAACUGCAGCUGAACCCCACCCC

AGCCAACAGGAGCAGGUACCAGAGCAGGAAGGUGGAGAACAUGAAGGCCAUC

ACCGCCAGGCGGAUCCUGCAGGGCUGGGACACUACCUGAAGGCCGAGGGCAA

GGUGGAGUGCUACAGGACCCUGCACCCCGUGCCACUGUACAGCUCCAGCGUGA

ACAGGGCCUUCUCCAGCCCCAAGGUGGCCGUGGAGGCCUGCAACGCUAUGCUG

AAGGAGAACUUCCCCACCGUGGCCAGCUACUGCAUCAUCCCCGAGUACGACGC

CUACCUGGACAUGGUGGACGGCGCCAGCUGCUGCCUGGACACCGCCAGCUUCU

GCCCCGCCAAGCUGAGGAGCUUCCCCAAGAAACACAGCUACCUGGAGCCCACC

AUCAGGAGCGCCGUGCCCAGCGCCAUCCAGAACACCCUGCAGAACGUGCUGGC

CGCUGCCACCAAGAGGAACUGCAACGUGACCCAGAUGAGGGAGCUGCCCGUGC

UGGACAGCGCUGCCUUCAACGUGGAGUGCUUCAAGAAAUACGCCUGCAACAAC

GAGUACUGGGAGACCUUCAAGGAGAACCCCAUCAGGCUGACCGAAGAGAACGU

GGUGAACUACAUCACCAAGCUGAAGGGCCCCAAGGCCGCUGCCCUGUUCGCUA

AGACCCACAACCUGAACAUGCUGCAGGACAUCCCAAUGGACAGGUUCGUGAUG

GACCUGAAGAGGGACGUGAAGGUGACACCCGGCACCAAGCACACCGAGGAGAG

GCCCAAGGUGCAGGUGAUCCAGGCCGCUGACCCACUGGCCACCGCCUACCUGU
```

-continued

```
GCGGCAUCCACAGGGAGCUGGUGAGGCGGCUGAACGCCGUGCUGCUGCCCAAC
AUCCACACCCUGUUCGACAUGAGCGCCGAGGACUUCGACGCCAUCAUCGCCGA
GCACUUCCAGCCCGGCGACUGCGUGCUGGAGACCGACAUCGCCAGCUUCGACA
AGAGCGAGGAUGACGCUAUGGCCCUGACCGCUCUGAUGAUCCUGGAGGACCUG
GGCGUGGACGCCGAGCUGCUCACCCUGAUCGAGGCUGCCUUCGGCGAGAUCAG
CUCCAUCCACCUGCCCACCAAGACCAAGUUCAAGUUCGGCGCUAUGAUGAAAA
GCGGAAUGUUCCUGACCCUGUUCGUGAACACCGUGAUCAACAUUGUGAUCGCC
AGCAGGGUGCUGCGGGAGAGGCUGACCGGCAGCCCCUGCGCUGCCUUCAUCGG
CGACGACAACAUCGUGAAGGGCGUGAAAAGCGACAAGCUGAUGGCCGACAGG
UGCGCCACCUGGCUGAACAUGGAGGUGAAGAUCAUCGACGCCGUGGUGGGCGA
GAAGGCCCCCUACUUCUGCGGCGGAUUCAUCCUGUGCGACAGCGUGACCGGCA
CCGCCUGCAGGGUGGCCGACCCCCUGAAGAGGCUGUUCAAGCUGGGCAAGCCA
CUGGCCGCUGACGAUGAGCACGACGAUGACAGGCGGAGGGCCCUGCACGAGGA
AAGCACCAGGUGGAACAGGGUGGGCAUCCUGAGCGAGCUGUGCAAGGCCGUG
GAGAGCAGGUACGAGACCGUGGGCACCAGCAUCAUCGUGAUGGCUAUGACCAC
ACUGGCCAGCUCCGUCAAGAGCUUCUCCUACCUGAGGGGGGCCCCUAUAACUC
UCUACGGCUAACCUGAAUGGACUACGACAUAGUCUAGUCCGCCAAGGCCGCCA
CCAUGGAAGAUGCCAAAAACAUUAAGAAGGGCCCAGCGCCAUUCUACCCACUC
GAAGACGGGACCGCCGGCGAGCAGCUGCACAAAGCCAUGAAGCGCUACGCCCU
GGUGCCCGGCACCAUCGCCUUUACCGACGCACAUAUCGAGGUGGACAUUACCU
ACGCCGAGUACUUCGAGAUGAGCGUUCGGCUGGCAGAAGCUAUGAAGCGCUA
UGGGCUGAAUACAAACCAUCGGAUCGUGGUGUGCAGCGAGAAUAGCUUGCAG
UUCUUCAUGCCCGUGUUGGGUGCCCUGUUCAUCGGUGUGGCUGUGGCCCAGC
UAACGACAUCUACAACGAGCGCGAGCUGCUGAACAGCAUGGGCAUCAGCCAGC
CCACCGUCGUAUUCGUGAGCAAGAAAGGGCUGCAAAAGAUCCUCAACGUGCAA
AAGAAGCUACCGAUCAUACAAAAGAUCAUCAUCAUGGAUAGCAAGACCGACU
ACCAGGGCUUCCAAAGCAUGUACACCUUCGUGACUUCCCAUUUGCCACCCGGC
UUCAACGAGUACGACUUCGUGCCCGAGAGCUUCGACCGGGACAAAACCAUCGC
CCUGAUCAUGAACAGUAGUGGCAGUACCGGAUUGCCCAAGGGCGUAGCCCUAC
CGCACCGCACCGCUUGUGUCCGAUUCAGUCAUGCCCGCGACCCCAUCUUCGGC
AACCAGAUCAUCCCCGACACCGCUAUCCUCAGCGUGGUGCCAUUUCACCACGG
CUUCGGCAUGUUCACCACGCUGGGCUACUUGAUCUGCGGCUUUCGGGUCGUGC
UCAUGUACCGCUUCGAGGAGGAGCUAUUCUUGCGCAGCUUGCAAGACUAUAA
GAUUCAAUCUGCCCUGCUGGUGCCCACACUAUUUAGCUUCUUCGCUAAGAGCA
CUCUCAUCGACAAGUACGACCUAAGCAACUUGCACGAGAUCGCCAGCGGCGGG
GCGCCGCUCAGCAAGGAGGUAGGUGAGGCCGUGGCCAAACGCUUCCACCUACC
AGGCAUCCGACAGGGCUACGGCCUGACAGAAACAACCAGCGCCAUUCUGAUCA
CCCCCGAAGGGGACGACAAGCCUGGCGCAGUAGGCAAGGUGGUGCCCUUCUUC
GAGGCUAAGGUGGUGGACUUGGACACCGGUAAGACACUGGGUGUGAACCAGC
GCGGCGAGCUGUGCGUCCGUGGCCCCAUGAUCAUGAGCGGCUACGUUAACAAC
CCCGAGGCUACAAACGCUCUCAUCGACAAGGACGGCUGGCUGCACAGCGGCGA
```

-continued

```
CAUCGCCUACUGGGACGAGGACGAGCACUUCUUCAUCGUGGACCGGCUGAAGU
CCCUGAUCAAAUACAAGGGCUACCAGGUAGCCCCAGCCGAACUGGAGAGCAUC
CUGCUGCAACACCCCAACAUCUUCGACGCCGGGGUCGCCGGCCUGCCCGACGA
CGAUGCCGGCGAGCUGCCCGCCGCAGUCGUCGUGCUGGAACACGGUAAAACCA
UGACCGAGAAGGAGAUCGUGGACUAUGUGGCCAGCCAGGUUACAACCGCCAAG
AAGCUGCGCGGUGGUGUUGUGUUCGUGGACGAGGUGCCUAAAGGACUGACCG
GCAAGUUGGACGCCCGCAAGAUCCGCGAGAUUCUCAUUAAGGCCAAGAAGGGC
GGCAAGAUCGCCGUGUAACUCGAGCCGGAAACGCAAUAGCCGAAAAACAAAAA
ACAAAAAAAACAAAAAAAAAACCAAAAAAACAAAACACAUUAAAACAGCCUG
UGGGUUGAUCCCACCCACAGGCCCAUUGGGCGCUAGCACUCUGGUAUCACGGU
ACCUUUGUGCGCCUGUUUUAUACCCCUCCCCCAACUGUAACUUAGAAGUAAC
ACACACCGAUCAACAGUCAGCGUGGCACACCAGCCACGUUUUGAUCAAGCACU
UCUGUUACCCCGGACUGAGUAUCAAUAGACUGCUCACGCGGUUGAAGGAGAA
AGCGUUCGUUAUCCGGCCAACUACUUCGAAAAACCUAGUAACACCGUGGAAGU
UGCAGAGUGUUUCGCUCAGCACUACCCCAGUGUAGAUCAGGUCGAUGAGUCAC
CGCAUUCCCCACGGGCGACCGUGGCGGUGGCUGCGUUGGCGGCCUGCCCAUGG
GGAAACCCAUGGGACGCUCUAAUACAGACAUGGUGCGAAGAGUCUAUUGAGC
UAGUUGGUAGUCCUCCGGCCCCUGAAUGCGGCUAAUCCUAACUGCGGAGCACA
CACCCUCAAGCCAGAGGGCAGUGUGUCGUAACGGGCAACUCUGCAGCGGAACC
GACUACUUUGGGUGUCCGUGUUUCAUUUUAUUCCUAUACUGGCUGCUUAUGG
UGACAAUUGAGAGAUCGUUACCAUAUAGCUAUUGGAUUGGCCAUCCGGUGAC
UAAUAGAGCUAUUAUAUAUCCCUUUGUUGGGUUUAUACCACUUAGCUUGAAA
GAGGUUAAAACAUUACAAUUCAUUGUUAAGUUGAAUACAGCAAAAUGAGCAA
GAUCUACAUCGACGAGCGGAGCAACGCCGAGAUCGUGUGCGAGGCCAUCAAGA
CCAUCGGCAUCGAGGGCGCCACCGCCGCCCAGCUGACCAGGCAGCUGAACAUG
GAGAAGCGGGAGGUGAACAAGGCCCUGUACGACCUGCAGAGGAGCGCUAUGG
UGUACUCCAGCGACGACAUCCCUCCCCGGUGGUUCAUGACCACCGAGGCCGAC
AAGCCCGACGCCGACGCUAUGGCCGACGUGAUCAUCGACGACGUGAGCAGGGA
GAAGUCCAUGAGGGAGGACCACAAGAGCUUCGACGACGUGAUCCCCGCCAAGA
AGAUCAUCGACUGGAAGGGCGCCAACCCCGUGACCGUGAUCAACGAGUACUGC
CAGAUCACCAGGAGGGACUGGAGCUUCCGGAUCGAGAGCGUGGGCCCCAGCAA
CAGCCCCACCUUCUACGCCUGCGUGGACAUCGACGGCAGGGUGUUCGACAAGG
CCGACGGCAAGAGCAAGCGGGACGCCAAGAACAACGCCGCCAAGCUGGCCGUG
GACAAGCUGCUGGGCUACGUGAUCAUCCGGUUCUAAACAAUUGGCAAGCUGCU
UACAUAGAACUCGCGGCGAUUGGCAUGCCGCCUUAAAAUUUUUAUUUUAUUU
UUUCUUUUCUUUUCCGAAUCGGAUUUUGUUUUUAAUAUUUCAAAAAAAAAA
AAAAAAAAAAAAAAUCUAGAAAAAAAAAAAAAAAAAAAAAAAAAAAAAAAA
AAAAAAAAAAAAAAAAAAAAAAAAAAAAAAAAAAAAAAAAAAAAAAAAAAA
AAAAAAAAAAAAAA

What is claimed is:

1. A nucleic acid molecule comprising:

(i) a first polynucleotide encoding one or more viral replication proteins, wherein the first polynucleotide is codon-optimized as compared to a reference polynucleotide of SEQ ID NO:54 encoding the one or more viral replication proteins; and (ii) a second polynucleotide comprising a first heterologous transgene encoding a first antigenic protein or a fragment thereof; and (iii) a 5' untranslated region (UTR) comprising the sequence of SEQ ID NO: 73 or SEQ ID NO:74.

2. The nucleic acid molecule of claim 1, further comprising a 3' untranslated region (UTR).

3. The nucleic acid molecule of claim 1, wherein the first antigenic protein is a viral protein, a bacterial protein, a fungal protein, a protozoan protein, a parasite protein, or a tumor protein.

4. The nucleic acid molecule of claim 3, wherein the viral protein is an orthomyxovirus protein, a paramyxovirus protein, a picornavirus protein, a flavivirus protein, a filovirus protein, a rhabdovirus protein, a togavirus protein, an arterivirus protein, a bunyavirus protein, an arenavirus protein, a reovirus protein, a bornavirus protein, a retrovirus protein, an adenovirus protein, a herpesvirus protein, a polyomavirus protein, a papillomavirus protein, a poxvirus protein, or a hepadnavirus protein.

5. The nucleic acid molecule of claim 3, wherein the first antigenic protein is an influenza virus protein, a respiratory syncytial virus (RSV) protein, a human immunodeficiency virus (HIV) protein, a hepatitis C virus (HCV) protein, a cytomegalovirus (CMV) protein, a Lassa Fever Virus (LFV) protein, an Ebola Virus (EBOV) protein, a *Mycobacterium* protein, a *Bacillus* protein, a *Yersinia* protein, a *Streptococcus* protein, a *Pseudomonas* protein, a *Shigella* protein, a *Campylobacter* protein, a *Salmonella* protein, a *Plasmodium* protein, or a *Toxoplasma* protein.

6. The nucleic acid molecule of claim 3, wherein the tumor protein is a kidney cancer, renal cancer, urinary bladder cancer, prostate cancer, uterine cancer, breast cancer, cervical cancer, ovarian cancer, lung cancer, liver cancer, stomach cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, or sarcoma protein.

7. The nucleic acid molecule of claim 1, wherein the second polynucleotide comprises at least two heterologous transgenes.

8. The nucleic acid molecule of claim 7, wherein a second heterologous transgene encodes a second antigenic protein or a fragment thereof, an immunomodulatory protein, or a reporter protein.

9. The nucleic acid molecule of claim 7, wherein the second polynucleotide further comprises a sequence encoding a 2A peptide, an internal ribosomal entry site (IRES), a subgenomic promoter, or a combination thereof, located between heterologous transgenes.

10. The nucleic acid molecule of claim 7, wherein the first and second heterologous transgenes encode viral proteins, bacterial proteins, fungal proteins, protozoan proteins, parasite proteins, tumor proteins, immunomodulatory proteins, reporter proteins, or any combination thereof.

11. The nucleic acid molecule of claim 1, wherein the first polynucleotide is located 5' of the second polynucleotide.

12. The nucleic acid molecule of claim 11, further comprising an intergenic region located between the first polynucleotide and the second polynucleotide.

13. The nucleic acid molecule of claim 12, wherein the intergenic region comprises a sequence having at least 85% identity to the sequence of SEQ ID NO:77.

14. The nucleic acid molecule of claim 1, wherein the nucleic acid molecule is (a) a DNA molecule; or (b) an RNA molecule, wherein T is substituted with U.

15. The nucleic acid molecule of claim 14, wherein the DNA molecule further comprises a promoter located 5' of the 5' UTR, wherein the promoter is a T7 promoter, a T3 promoter, or an SP6 promoter.

16. The nucleic acid molecule of claim 14, wherein the RNA molecule is a self-replicating RNA molecule.

17. The nucleic acid molecule of claim 14, wherein the RNA molecule further comprises a 5' cap having a Cap 1 structure, a Cap 1 ($^{m6}$A) structure, a Cap 2 structure, or a Cap 0 structure.

18. A pharmaceutical composition comprising the nucleic acid molecule of claim 1 and a lipid formulation.

19. The pharmaceutical composition of claim 18, wherein the lipid formulation comprises an ionizable cationic lipid.

20. The pharmaceutical composition of claim 19, wherein (a) the ionizable cationic lipid has a structure of Formula I:

(I)

or a pharmaceutically acceptable salt thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl; $L^5$ and $L^6$ are each independently selected from the group consisting of a linear $C_1$-$C_{20}$ alkyl and $C_2$-$C_{20}$ alkenyl; $X^5$ is —C(O)O—, whereby —C(O)O—$R^6$ is formed or —OC(O)— whereby —OC(O)—$R^6$ is formed; $X^6$ is —C(O)O— whereby —C(O)O—$R^5$ is formed or —OC(O)— whereby —OC(O)—$R^5$ is formed; $X^7$ is S or O; $L^7$ is absent or lower alkyl; $R^4$ is a linear or branched $C_1$-$C_6$ alkyl; and $R^7$ and $R^8$ are each independently selected from the group consisting of a hydrogen and a linear or branched $C_1$-$C_6$ alkyl; or (b) the ionizable cationic lipid has a structure of

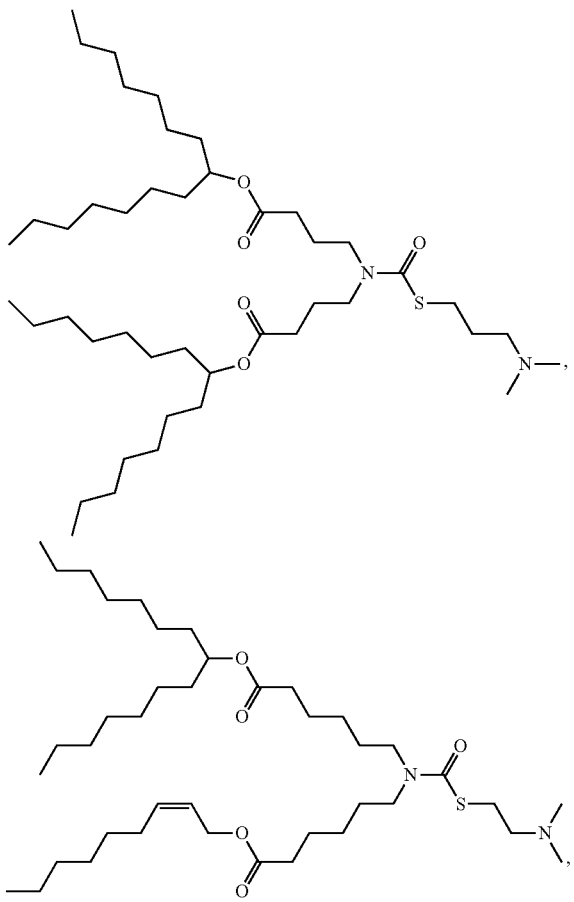

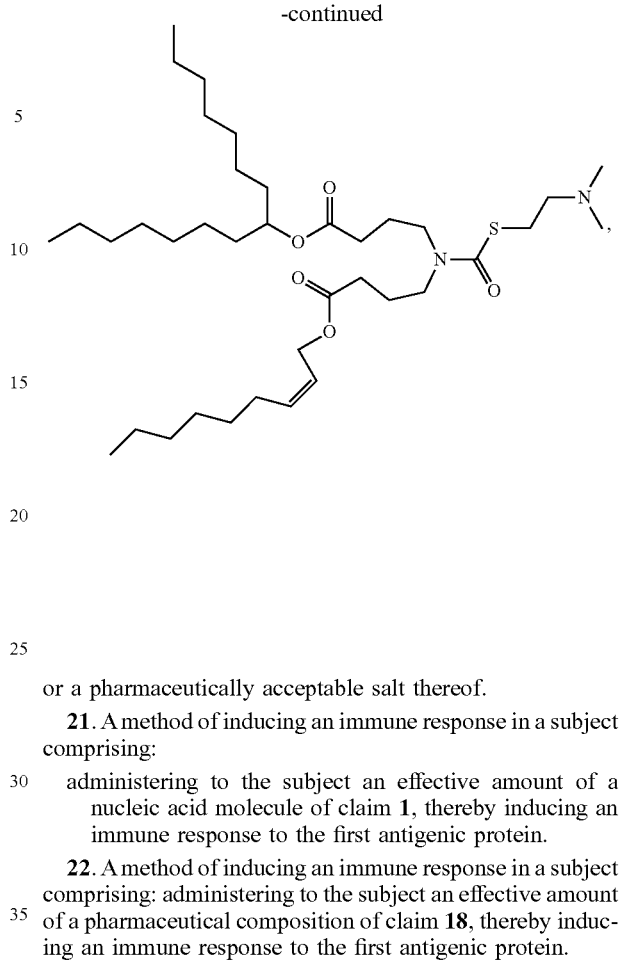

or a pharmaceutically acceptable salt thereof.

21. A method of inducing an immune response in a subject comprising:
administering to the subject an effective amount of a nucleic acid molecule of claim 1, thereby inducing an immune response to the first antigenic protein.

22. A method of inducing an immune response in a subject comprising: administering to the subject an effective amount of a pharmaceutical composition of claim 18, thereby inducing an immune response to the first antigenic protein.

\* \* \* \* \*

```

SEQUENCE LISTING

```
Sequence total quantity: 119
SEQ ID NO: 1                moltype = DNA  length = 18
FEATURE                     Location/Qualifiers
misc_feature                1..18
                            note = Synthetic polynucleotide
source                      1..18
                            mol_type = other DNA
                            organism = synthetic construct
modified_base               15
                            mod_base = OTHER
                            note = uracil
SEQUENCE: 1
gaggaaactt aagatggg                                                         18

SEQ ID NO: 2                moltype =   length =
SEQUENCE: 2
000

SEQ ID NO: 3                moltype =   length =
SEQUENCE: 3
000

SEQ ID NO: 4                moltype =   length =
SEQUENCE: 4
000

SEQ ID NO: 5                moltype = RNA  length = 129
FEATURE                     Location/Qualifiers
misc_feature                1..129
                            note = Synthetic polynucleotide
source                      1..129
                            mol_type = other RNA
                            organism = synthetic construct
SEQUENCE: 5
tcaacacaac atatacaaaa caaacgaatc tcaagcaatc aagcattcta cttctattgc           60
agcaatttaa atcatttctt ttaaagcaaa agcaattttc tgaaaatttt caccatttac          120
gaacgatag                                                                  129

SEQ ID NO: 6                moltype = RNA  length = 28
FEATURE                     Location/Qualifiers
misc_feature                1..28
                            note = Synthetic polynucleotide
source                      1..28
                            mol_type = other RNA
                            organism = synthetic construct
SEQUENCE: 6
attattacat caaaacaaaa agccgcca                                              28

SEQ ID NO: 7                moltype = RNA  length = 245
FEATURE                     Location/Qualifiers
misc_feature                1..245
                            note = Synthetic polynucleotide
source                      1..245
                            mol_type = other RNA
                            organism = synthetic construct
SEQUENCE: 7
cttaaggggg cgctgcctac ggaggtggca gccatctcct tctcggcatc aagcttacca           60
tggtgcccca ggccctgctc ttggtcccgc tgctggtgtt cccctctgc ttcggcaagt           120
tccccatcta caccatcccc gacaagctgg ggccgtggag cccatcgac atccaccacc           180
tgtcctgccc caacaacctc gtggtcgagg acgagggctg caccaacctg agcgggttct          240
cctac                                                                      245

SEQ ID NO: 8                moltype = RNA  length = 177
FEATURE                     Location/Qualifiers
misc_feature                1..177
                            note = Synthetic polynucleotide
source                      1..177
                            mol_type = other RNA
                            organism = synthetic construct
SEQUENCE: 8
tgagtgtcgt acagcctcca ggcccccccc tcccggagga gccatagtgg tctgcggaac           60
cggtgagtac accggaattg ccgggaagac tgggtccttt cttggataaa cccactctat          120
gcccggccat tgggcgtgc ccccgcaaga ctgctagccg agtagtgttg ggttgcg              177

SEQ ID NO: 9                moltype = RNA  length = 89
FEATURE                     Location/Qualifiers
misc_feature                1..89
                            note = Synthetic polynucleotide
```

```
                    source            1..89
                                      mol_type = other RNA
                                      organism = synthetic construct
SEQUENCE: 9
aattattggt taaagaagta tattagtgct aatttccctc cgtttgtcct agcttttctc    60
ttctgtcaac cccacacgcc tttggcaca                                     89

SEQ ID NO: 10       moltype = RNA   length = 569
FEATURE             Location/Qualifiers
misc_feature        1..569
                    note = Synthetic polynucleotide
source              1..569
                    mol_type = other RNA
                    organism = synthetic construct
SEQUENCE: 10
ctccctcccc cccccctaac gttactggcc gaagccgctt ggaataaggc cggtgtgcgt    60
ttgtctatat gttatttcc accatattgc cgtcttttgg caatgtgagg gcccggaaac   120
ctggccctgt cttcttgacg agcattccta ggggtctttc ccctctcgcc aaaggaatgc   180
aaggtctgtt gaatgtcgtg aaggaagcag ttcctctgga agcttcttga agacaaacaa   240
cgtctgtagc gacccttgc aggcagcgga acccccacc tggcgacagg tgcctctgcg    300
gccaaaagcc acgtgtataa gatacacctg caaaggcggc acaaccccag tgccacgttg   360
tgagttggat agttgtggaa agagtcaaat ggctctcctc aagcgtattc aacaaggggc   420
tgaaggatgc ccagaaggta ccccattgta tgggatctga tctggggcct cggtgcacat   480
gctttacgtg tgtttagtcg aggttaaaaa acgtctaggc ccccgaacc acggggacgt    540
ggttttcctt tgaaaaacac gatgataat                                    569

SEQ ID NO: 11       moltype = RNA   length = 44
FEATURE             Location/Qualifiers
misc_feature        1..44
                    note = Synthetic polynucleotide
source              1..44
                    mol_type = other RNA
                    organism = synthetic construct
SEQUENCE: 11
gtcagctttc aaactctttg tttcttgttt gttgattgag aata                    44

SEQ ID NO: 12       moltype = RNA   length = 54
FEATURE             Location/Qualifiers
misc_feature        1..54
                    note = Synthetic polynucleotide
source              1..54
                    mol_type = other RNA
                    organism = synthetic construct
SEQUENCE: 12
ctctcgcctg agaaaaaaaa tccacgaacc aatttctcag caaccagcag cacg          54

SEQ ID NO: 13       moltype = RNA   length = 52
FEATURE             Location/Qualifiers
misc_feature        1..52
                    note = Synthetic polynucleotide
source              1..52
                    mol_type = other RNA
                    organism = synthetic construct
SEQUENCE: 13
acctgtgagg gttcgaagga agtagcagtg tttttgttc ctagaggaag ag            52

SEQ ID NO: 14       moltype = RNA   length = 71
FEATURE             Location/Qualifiers
misc_feature        1..71
                    note = Synthetic polynucleotide
source              1..71
                    mol_type = other RNA
                    organism = synthetic construct
SEQUENCE: 14
acacagaaac attcgcaaaa acaaaatccc agtatcaaaa ttcttctctt tttttcatat    60
ttcgcaaaga c                                                        71

SEQ ID NO: 15       moltype = RNA   length = 52
FEATURE             Location/Qualifiers
misc_feature        1..52
                    note = Synthetic polynucleotide
source              1..52
                    mol_type = other RNA
                    organism = synthetic construct
SEQUENCE: 15
cagaaaaatt tgctacattg tttcacaaac ttcaaatatt attcatttat tt            52

SEQ ID NO: 16       moltype = RNA   length = 158
FEATURE             Location/Qualifiers
```

```
misc_feature           1..158
                       note = Synthetic polynucleotide
source                 1..158
                       mol_type = other RNA
                       organism = synthetic construct
SEQUENCE: 16
ctagtgactg actaggatct ggttaccact aaaccagcct caagaacacc cgaatggagt   60
ctctaagcta cataatacca acttacactt acaaaatgtt gtcccccaaa atgtagccat  120
tcgtatctgc tcctaataaa aagaaagttt cttcacat                          158

SEQ ID NO: 17          moltype = RNA   length = 166
FEATURE                Location/Qualifiers
misc_feature           1..166
                       note = Synthetic polynucleotide
source                 1..166
                       mol_type = other RNA
                       organism = synthetic construct
SEQUENCE: 17
tgcaaggctg gccggaagcc cttgcctgaa agcaagattt cagcctggaa gagggcaaag   60
tggacgggag tggacaggag tggatgcgat aagatgtggt ttgaagctga tgggtgccag  120
ccctgcattg ctgagtcaat caataaagag ctttctttg acccat                  166

SEQ ID NO: 18          moltype = RNA   length = 143
FEATURE                Location/Qualifiers
misc_feature           1..143
                       note = Synthetic polynucleotide
source                 1..143
                       mol_type = other RNA
                       organism = synthetic construct
SEQUENCE: 18
acgccgaagc ctgcagccat gcgaccccac gccaccccgt gcctcctgcc tccgcgcagc   60
ctgcagcggg agaccctgtc cccgccccag ccgtcctcct ggggtggacc ctagtttaat  120
aaagattcac caagtttcac gca                                          143

SEQ ID NO: 19          moltype = RNA   length = 220
FEATURE                Location/Qualifiers
misc_feature           1..220
                       note = Synthetic polynucleotide
source                 1..220
                       mol_type = other RNA
                       organism = synthetic construct
SEQUENCE: 19
tagagcggca aaccctagct acactccata gctagtttct tttttttttg tttttttttt   60
tttttttttt tttttttttt tttttttttc ctttctttc cttctttttt tcctcttttc  120
ttggtggctc catcttagcc ctagtcacgg ctagctgtga aaggtccgtg agccgcatga  180
ctgcagagag tgccgtaact ggtctctctg cagatcatgt                        220

SEQ ID NO: 20          moltype = RNA   length = 170
FEATURE                Location/Qualifiers
misc_feature           1..170
                       note = Synthetic polynucleotide
source                 1..170
                       mol_type = other RNA
                       organism = synthetic construct
SEQUENCE: 20
acacatcaca accacaacct tctcaggcta ccctgagaaa aaaagacatg aagactcagg   60
actcatcttt tctgttggtg taaaatcaac accctaagga acacaaattt ctttaaacat  120
ttgacttctt gtctctgtgc tgcaattaat aaaaaatgga aagaatctac              170

SEQ ID NO: 21          moltype = RNA   length = 110
FEATURE                Location/Qualifiers
misc_feature           1..110
                       note = Synthetic polynucleotide
source                 1..110
                       mol_type = other RNA
                       organism = synthetic construct
SEQUENCE: 21
gctggagcct cggtagccgt tcctcctgcc cgctgggcct cccaacgggc cctcctcccc   60
tccttgcacc ggcccttcct ggtctttgaa taaagtctga gtgggcagca              110

SEQ ID NO: 22          moltype = RNA   length = 123
FEATURE                Location/Qualifiers
misc_feature           1..123
                       note = Synthetic polynucleotide
source                 1..123
                       mol_type = other RNA
                       organism = synthetic construct
SEQUENCE: 22
tagtgcagtc actggcacaa cgcgttgccc ggtaagccaa tcgggtatac acggtcgtca   60
```

```
tactgcagac agggttcttc tactttgcaa gatagtctag agtagtaaaa taaatagtat    120
aag                                                                  123

SEQ ID NO: 23         moltype =    length =
SEQUENCE: 23
000

SEQ ID NO: 24         moltype =    length =
SEQUENCE: 24
000

SEQ ID NO: 25         moltype = RNA   length = 21
FEATURE               Location/Qualifiers
misc_feature          1..21
                      note = Synthetic polynucleotide
source                1..21
                      mol_type = other RNA
                      organism = synthetic construct
SEQUENCE: 25
cacaaagagt aaagaagaac a                                              21

SEQ ID NO: 26         moltype = RNA   length = 21
FEATURE               Location/Qualifiers
misc_feature          1..21
                      note = Synthetic polynucleotide
source                1..21
                      mol_type = other RNA
                      organism = synthetic construct
SEQUENCE: 26
aacactaaaa gtagaagaaa a                                              21

SEQ ID NO: 27         moltype = RNA   length = 21
FEATURE               Location/Qualifiers
misc_feature          1..21
                      note = Synthetic polynucleotide
source                1..21
                      mol_type = other RNA
                      organism = synthetic construct
SEQUENCE: 27
ctcagaaaga taagatcagc c                                              21

SEQ ID NO: 28         moltype = RNA   length = 21
FEATURE               Location/Qualifiers
misc_feature          1..21
                      note = Synthetic polynucleotide
source                1..21
                      mol_type = other RNA
                      organism = synthetic construct
SEQUENCE: 28
aaccaatcga agaaaccaa a                                               21

SEQ ID NO: 29         moltype = RNA   length = 21
FEATURE               Location/Qualifiers
misc_feature          1..21
                      note = Synthetic polynucleotide
source                1..21
                      mol_type = other RNA
                      organism = synthetic construct
SEQUENCE: 29
ctctaatcac caggagtaaa a                                              21

SEQ ID NO: 30         moltype = RNA   length = 21
FEATURE               Location/Qualifiers
misc_feature          1..21
                      note = Synthetic polynucleotide
source                1..21
                      mol_type = other RNA
                      organism = synthetic construct
SEQUENCE: 30
gagagagatc ttaacaaaaa a                                              21

SEQ ID NO: 31         moltype = RNA   length = 21
FEATURE               Location/Qualifiers
misc_feature          1..21
                      note = Synthetic polynucleotide
source                1..21
                      mol_type = other RNA
                      organism = synthetic construct
SEQUENCE: 31
```

```
tgtgtaacaa caacaacaac a                                              21

SEQ ID NO: 32          moltype = RNA   length = 21
FEATURE                Location/Qualifiers
misc_feature           1..21
                       note = Synthetic polynucleotide
source                 1..21
                       mol_type = other RNA
                       organism = synthetic construct
SEQUENCE: 32
ccgcagtagg aagagaaagc c                                              21

SEQ ID NO: 33          moltype = RNA   length = 21
FEATURE                Location/Qualifiers
misc_feature           1..21
                       note = Synthetic polynucleotide
source                 1..21
                       mol_type = other RNA
                       organism = synthetic construct
SEQUENCE: 33
aaaaaaaaaa gaaatcataa a                                              21

SEQ ID NO: 34          moltype = RNA   length = 21
FEATURE                Location/Qualifiers
misc_feature           1..21
                       note = Synthetic polynucleotide
source                 1..21
                       mol_type = other RNA
                       organism = synthetic construct
SEQUENCE: 34
gagagaagaa agaagaagac g                                              21

SEQ ID NO: 35          moltype = RNA   length = 21
FEATURE                Location/Qualifiers
misc_feature           1..21
                       note = Synthetic polynucleotide
source                 1..21
                       mol_type = other RNA
                       organism = synthetic construct
SEQUENCE: 35
caattaaaaa tacttaccaa a                                              21

SEQ ID NO: 36          moltype = RNA   length = 21
FEATURE                Location/Qualifiers
misc_feature           1..21
                       note = Synthetic polynucleotide
source                 1..21
                       mol_type = other RNA
                       organism = synthetic construct
SEQUENCE: 36
gcaaacagag taagcgaaac g                                              21

SEQ ID NO: 37          moltype = RNA   length = 21
FEATURE                Location/Qualifiers
misc_feature           1..21
                       note = Synthetic polynucleotide
source                 1..21
                       mol_type = other RNA
                       organism = synthetic construct
SEQUENCE: 37
gcgaagaaga cgaacgcaaa g                                              21

SEQ ID NO: 38          moltype = RNA   length = 21
FEATURE                Location/Qualifiers
misc_feature           1..21
                       note = Synthetic polynucleotide
source                 1..21
                       mol_type = other RNA
                       organism = synthetic construct
SEQUENCE: 38
ttaggactgt attgactggc c                                              21

SEQ ID NO: 39          moltype = RNA   length = 21
FEATURE                Location/Qualifiers
misc_feature           1..21
                       note = Synthetic polynucleotide
source                 1..21
                       mol_type = other RNA
                       organism = synthetic construct
```

```
SEQUENCE: 39
atcatcggaa ttcggaaaaa g                                                21

SEQ ID NO: 40            moltype = RNA   length = 21
FEATURE                  Location/Qualifiers
misc_feature             1..21
                         note = Synthetic polynucleotide
source                   1..21
                         mol_type = other RNA
                         organism = synthetic construct
SEQUENCE: 40
aaaacaaaag ttaaagcaga c                                                21

SEQ ID NO: 41            moltype = RNA   length = 21
FEATURE                  Location/Qualifiers
misc_feature             1..21
                         note = Synthetic polynucleotide
source                   1..21
                         mol_type = other RNA
                         organism = synthetic construct
SEQUENCE: 41
tttatctcaa ataagaaggc a                                                21

SEQ ID NO: 42            moltype = RNA   length = 21
FEATURE                  Location/Qualifiers
misc_feature             1..21
                         note = Synthetic polynucleotide
source                   1..21
                         mol_type = other RNA
                         organism = synthetic construct
SEQUENCE: 42
ggtggggagg tgagatttct t                                                21

SEQ ID NO: 43            moltype = RNA   length = 21
FEATURE                  Location/Qualifiers
misc_feature             1..21
                         note = Synthetic polynucleotide
source                   1..21
                         mol_type = other RNA
                         organism = synthetic construct
SEQUENCE: 43
tgattaggaa actacaaagc c                                                21

SEQ ID NO: 44            moltype = RNA   length = 21
FEATURE                  Location/Qualifiers
misc_feature             1..21
                         note = Synthetic polynucleotide
source                   1..21
                         mol_type = other RNA
                         organism = synthetic construct
SEQUENCE: 44
catttttcaa tttcataaaa c                                                21

SEQ ID NO: 45            moltype = RNA   length = 21
FEATURE                  Location/Qualifiers
misc_feature             1..21
                         note = Synthetic polynucleotide
source                   1..21
                         mol_type = other RNA
                         organism = synthetic construct
SEQUENCE: 45
ttacttttaa gcccaacaaa a                                                21

SEQ ID NO: 46            moltype = RNA   length = 21
FEATURE                  Location/Qualifiers
misc_feature             1..21
                         note = Synthetic polynucleotide
source                   1..21
                         mol_type = other RNA
                         organism = synthetic construct
SEQUENCE: 46
ggcgtgtgtg tgtgttgttg a                                                21

SEQ ID NO: 47            moltype = RNA   length = 21
FEATURE                  Location/Qualifiers
misc_feature             1..21
                         note = Synthetic polynucleotide
source                   1..21
                         mol_type = other RNA
```

```
                        organism = synthetic construct
SEQUENCE: 47
gtggtgaagg ggaaggttta g                                          21

SEQ ID NO: 48           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 48
ttgttttttt ttggtttggt t                                          21

SEQ ID NO: 49           moltype = DNA  length = 44
FEATURE                 Location/Qualifiers
misc_feature            1..44
                        note = Synthetic polynucleotide
source                  1..44
                        mol_type = other DNA
                        organism = synthetic construct
SEQUENCE: 49
atgggcggcg catgagagaa gcccagacca attacctacc caaa                 44

SEQ ID NO: 50           moltype = DNA  length = 7482
FEATURE                 Location/Qualifiers
misc_feature            1..7482
                        note = Synthetic polynucleotide
source                  1..7482
                        mol_type = other DNA
                        organism = synthetic construct
SEQUENCE: 50
atggagaaag ttcacgttga catcgaggaa gacagcccat tcctcagagc tttgcagcgg    60
agcttcccgc agtttgaggt agaagccaag caggtcactg ataatgacca tgctaatgcc   120
agagcgtttt cgcatctggc ttcaaaactg atcgaaactg aggtggaccc atccgacacg   180
atccttgaca ttggaagtgc gcccgcccgc agaatgtatt ctaagcacaa gtatcattgt   240
atctgtccga tgagatgtgc ggaagatccg gacagattgt ataagtatgc aactaagctg   300
aagaaaaact gtaaggaaat aactgataag gaattggaca agaaaatgaa ggagctggcc   360
gccgtcatga gcgaccctga cctggaaact gagactatgt gcctccacga cgacgagtcg   420
tgtcgctacg aagggcaagt cgctgtttac caggatgtat acgccgtcga cggccccacc   480
agcctgtacc accaggccaa caaggggcgtg agggtggcct actggatcgg cttcgacacc   540
acacccttca tgttcaagaa cctggccggc gcctacccca gctacagcac caactgggcc   600
gacgagaccg tgctgaccgc caggaacatc ggcctgtgca gacgcgacgt gatggagagg   660
agccggagag gcatgagcat cctgaggaag aaatacctga gcccagcaa caacgtgctg   720
ttcagcgtgg gcagcaccat ctaccacgag aagagggacc tgctcaggag ctggcacctg   780
cccagcgtgt tccacctgag gggcaagcag aactacacct gcaggtgcga gaccatcgtg   840
agctgcgacg gctacgtggt gaagaggatc gccatcagcc ccggcctgta cggcaagccc   900
agcggctacg ccgctacaat gcacaggagg gcttcctgt gctgcaaggt gaccgacacc   960
ctgaacggcg agagggtgag cttccccgtg tgcacctacg tgcccgccac cctgtgcgac  1020
cagatgaccg gcatcctggc caccgacgtg agcgccgacg acgcccagaa gctgctcgtg  1080
ggcctgaacc agaggatcgt ggtcaacggc aggacccaga ggaacaccaa cacaatgaag  1140
aactacctgc tgcccgtggt ggcccaggct ttcgccaggt gggccaagga gtacaaggag  1200
gaccaggaag acgagaggcc cctgggcctg agggacaggc agctggtgat gggctgctgc  1260
tgggccttca gcggcacaa gatcaccagc atctacaaga ggcccgacac ccagaccatc  1320
atcaaggtga acagcgactt cgtgctgccca ggatcggcag caacaccctg  1380
gagatcggcc tgaggacccg gatcaggaag atgctggagg aacacaagga gcccagccca  1440
ctgatcaccg ccgaggacgt gcaggaggcc aagtgcgctg ccgacgaggc caaggaggtg  1500
agggaggcca aggaactgag ggccgccctg caccccctgg ctgccgacgt ggaggaaccc  1560
accctggaag ccgacgtgga cctgatgctg caggaggccg gcgccggaag cgtggagaca  1620
cccagggcc tgatcaaggt gaccagctac gacggcgagg acaagatcgg cagctacgcc  1680
gtgctgagcc acaggccgt gctgaagtcc gagaagctga gctgcatcca cccactggcc  1740
gagcaggtga tcgtgatcac ccacagcggc aggaagggca ggtacgccgt ggagccctac  1800
cacggcaagg tggtcgtgcc cgagggccac gccatccccg tgcaggactt ccaggccctg  1860
agcgaggccg ccaccatcgt gtacaacgag agggagttcg tgaacaggta cctgcaccat  1920
atcgccaccg acggcggagc cctgaacacc gacgaggaat actacaagac cgtgaagccc  1980
agcgagcacg acggcgagta cctgtacgac atcgacagga gcagtgcgt gaagaaagag  2040
ctggtgaccg gcctgggact gaccggcgag ctggtgacc caccttcca cgagttcgcc  2100
tacgagagcc tgaggaccag accgcgct ccctaccagg tgcccaccat cggcgtgtac  2160
ggccgcccg gcagcggaaa gagcggcatc atcaagagcg ccgtgaccaa gaagacctg  2220
gtggtcagcg ccaagaaaga gaactgcgcc gagatcatca gggacgtgaa gaagatgaaa  2280
ggcctggacg tgaacgcgcg caccgtggac agcgtgctgc tgaacggctg caagcacccc  2340
gtggagaccc tgtacatcga cgaggccttc gcttgccacg ccggcaccct gagggccctg  2400
atcgccatca tcaggccaa gaagccgtg ctgtgcggcg accccaagca gtgcggcttc  2460
ttcaacatga tgtgctgaa ggtgcacttc aaccacagga tctgcacca ggtgttccac  2520
aagagccatca gcaggcggtg caccaagagc gtgaccagcg tcgtgagcac cctgttctac  2580
gacaagaaaa tgaggaccac caaccccaag gagaccaaaa tcgtgatcga caccacaggc  2640
agcaccaagc ccaagcagga cgacctgatc ctgacctgct tcaggggctg ggtgaagcag  2700
ctgcagatcg actacaaggg caacgagatc atgaccgcc tgccagcca gggcctgacc  2760
aggaagggcg tgtacgccgt gaggtacaag gtgaacgaga cccactgta cgctcccacc  2820
```

```
agcgagcacg tgaacgtgct gctgaccagg accgaggaca ggatcgtgtg gaagaccctg    2880
gccggcgacc cctggatcaa gaccctgacc gccaagtacc ccggcaactt caccgccacc    2940
atcgaagagt ggcaggccga gcacgacgcc atcatgaggc acatcctgga gaggcccgac    3000
cccaccgacg tgttccagaa caaggccaac gtgtgctggg ccaaggccct ggtgcccgtg    3060
ctgaagaccg ccggcatcga catgaccaca gagcagtgga caccgtgga ctacttcgag     3120
accgacaagg cccacagcgc cgagatcgtg ctgaaccagc tgtgcgtgag gttcttcggc    3180
ctggacctgg acagcggcct gttcagcgcc ccaccgtgc cactgagcat caggaacaac     3240
cactgggaca cagcccag cccaaacatg tacggcctga caaggaggt ggtcaggcag       3300
ctgagcaggc ggtacccaca gctgcccagg gccgtggcc ccgagcaggt gtacgacatg     3360
aacaccggca ccctgaggaa ctacgacccc aggatcaacc tggtgcccgt gaacaggcgg    3420
ctgccccacg ccctggtgct gcaccacaac gagcacccac agagcgactt cagctccttc    3480
gtgagcaagc tgaaaggcag gaccgtgctg gtcgtgggcg agaagctgag cgtgcccggc    3540
aagatggtgg actggctgag cgacaggccc gaggccacct tccggccag gctggacctc     3600
ggcatccccg gcgacgtgcc caagtacgac atcatcttcg tgaacgtcag gaccccatac    3660
aagtaccacc attaccagca gtgcgaggac cacgccatca agctgagcat gctgaccaag    3720
aaggcctgcc tgcacctgaa ccccggaggc acctgcgtga gcatcggcta cggctacgcc    3780
gacagggcca gcgagagcat cattggcgcc atcgccaggc tgttcaagtt cagcagggtg    3840
tgcaaacccag agagcagcct ggaggaaacc gaggtgctgt tcgtgttcat cggctacgac    3900
cggaaggcca ggaccacaa cccctacaag ctgagcagca ccctgacaaa catctacacc     3960
ggcagcaggc tgcacgaggc cggctgcgcc ccagctacc acgtggtcag ggcgatatc      4020
gccaccgcca ccgaggcgt gatcatcaac gctgccaaca gcaagggcca gcccggaggc    4080
ggagtgtgcg gcgccctgta caagaagttc cccgagagct tcgacctgca gcccatcgag    4140
gtgggcaagg ccaggctggt gaagggcgcc gctaagcaca tcatccacgc cgtgggcccc    4200
aacttcaaca aggtgagcga ggtggaaggc gacaagcagc tggccgaagc ctacgagagc    4260
atcgccaaga tcgtgaacga caataactac aagagcgtgg ccatcccact gctcagcacc    4320
ggcatcttca gcggcaacaa ggacaggctg acccagagcc tgaaccacct gctccaccgcc    4380
ctggacacca ccgatgccga cgtggccatc tactgcaggg acaagaagtg ggagatgacc    4440
ctgaaggagg ccgtggccag gcgggaggcc gtggaagaga tctgcatcag cgacgactcc    4500
agcgtgaccg agcccgacgc cgagctggtg agggtgcacc caagagctc cctggccggc    4560
aggaagggct acagcaccag cgacggcaag accttcgagc acctggaggg caccaagttc    4620
caccaggccg ctaaggacat cgccgagatc aacgctatgt ggccgtggc caccgaggcc    4680
aacgagcagg tgtgcatgta catcctgggc gagagcatgt ccagcatcag gagcaagtgc    4740
cccgtggagg aaagcgaggc cagcacacca cccagcaccc tgccctgcct gtgcatccac    4800
gctatgacac ccgagagggt gcagcggctg aaggccagca ggccgagca gatcaccgtg    4860
tgcagctcct tcccactgcc caagtacagg atcaccggcg tgcagaagat ccagtgcagc   4920
cagcccatcc tgttcagccc aaaggtgccc gcctacatcc accccaggaa gtacctggtg    4980
gagaccccac ccgtgacga cacccgag ccaagcgccg agaaccagag caccgagggc       5040
acaccgagc agccaccct gatcaccgag gacgagacga ggaccggac ccagagccc        5100
atcattatcg aggaaggaga agggacctgc aggacgacgg ccccacccac                5160
caggtgctgc aggtggaggc cgacatccac ggcccaccca gcgtgtccag ctccagctgg    5220
agcatcccac acgccagcga cttcgacgtg gacagcctga gcatcctgga caccctggag    5280
ggcgccagcg tgacctccgg cgccaccagc gccgagacca cagcctact tcgccaagagc    5340
atggagttcc tggccaggcc cgtgccagct cccaggaccg tgttcaggaa ccacccccac    5400
ccagctccca ggaccaggac cccaagcctg gctcccagca gggcctgcag caggaccagc    5460
ctggtgagca ccccacccgg cgtgaacagg gtgatcacca gggaggaact ggaggccctg    5520
acacccagca ggacccccag caggtccgtg agcaggacta gtctggtgtc caacccaccc    5580
ggcgtgaaca gggtgatcac cagggaggaa ttcgaggcct tcgtggccca gcaacagaga    5640
cggttcgacg ccggcgccta catcttcagc agcgacaccg gccaggacac cctgcagcaa    5700
aagagcgtga ggcagaccgt gctgagcgag gtggtgctgg agaggaccga gctgaaatc     5760
agctacgccc ccaggctgga ccaggagaag gaggaactgc tcaggaagaa actgcagctg    5820
aaccccaccc cagccaacag gagcaggtac cagagcagga ggtggaaga catgaaggcc    5880
atcaccgcca ggcggatcct gcagggcctg ggacactacc tgaagggcca gggcaaggtg    5940
gagtgctaca ggaccctgca cccgtgcca ctgtacagct ccagcgtgaa cagggccttc     6000
tccagcccca aggtggccgt ggaggcctgc aacgctatgc tgaaggagaa cttccccacc    6060
gtggccagct actgcatcat ccccgagtac gacgcctacc tggacatggt ggacggcgcc    6120
agctgctgcc tggacaccgc cagcttctgc cccgccaagc tgaggagctt ccccaagaaa    6180
cacagctacc tggagcccac catcaggagc gccgtgccca cgccatcca gaacaccctg     6240
cagaacgtgc tggccgctgc caccaagagg aactgcaacg tgacccagat gaggagctg    6300
cccgtgctgg acagcgctgc cttcaacgtg gagtgcttca agaaatacgc ctgcaacaac    6360
gagtactggg agaccttcaa ggagaacccc atcaggctga ccgaagaaa cgtggtgaac    6420
tacatcacca gctgaagggg cccaaggcc gctgccctgt cgctaagac ccacaacctg      6480
aacatgctgc aggacatccc aatggacagg ttcgtgatgg acctgaagag ggacgtgaag    6540
gtgacacccg gcaccaagca caccgaggag aggcccaagg tgcaggtgat ccaggccgct    6600
gaccccactgg ccaccgccta cctgtgcggc atccacaggg agctggtgag gcggctgaac    6660
gccgtgctgc tgcccaacat ccacaccctg ttcgacatga gcgccgagga cttcgacgcc    6720
atcatcgccg agcacttcca gcccggcgac tgcgtgctgg agaccgacat cgccagcttc    6780
gacaagagcg aggatgacgc tatggccctg accgctctga tgatcctgga ggacctgggc    6840
gtggacgccg agctgctcac cctgatcgag gctgccttcg gcgagatcag ctccatccac    6900
ctgcccacca agaccaagtt caagttcggc gctatgatga aagcggaat gttcctgacc    6960
ctgttcgtga acaccgtgat caacattgtg atcgccagca gggtgctgcg ggagaggctg    7020
accggcagcc cctgcgctgc cttcatcggc gacgacaaca tcgtgaaggg cgtgaaaagc    7080
gacaagctga tggccgacag gtgcgccacc tggctgaaca tggaggtgaa gatcatcgac    7140
gccgtggtgg gcgagaaggc cccctacttc tgcggcggat tcatcctgtg cgacagcgtg    7200
accggcaccg cctgcaggt ggccgaccc ctgaaggagc tgttcaaget gggcaagcca      7260
ctggccgctg acgatgagca cgacgatgac aggcggaggg ccctgcacga ggaaagcacc    7320
aggtggaaca gggtgggcat cctgagcgag ctgtgcaagg ccgtggagag caggtacgag    7380
accgtggca ccagcatcat cgtgatggct atgaccacac tggccagctc cgtcaagagc     7440
ttctcctacc tgagggggc ccctataact ctctacggct aa                        7482
```

```
SEQ ID NO: 51          moltype = AA  length = 2493
FEATURE                Location/Qualifiers
REGION                 1..2493
                       note = Synthetic polypeptide
source                 1..2493
                       mol_type = protein
                       organism = synthetic construct
SEQUENCE: 51
MEKVHVDIEE DSPFLRALQR SFPQFEVEAK QVTDNDHANA RAFSHLASKL IETEVDPSDT   60
ILDIGSAPAR RMYSKHKYHC ICPMRCAEDP DRLYKYATKL KKNCKEITDK ELDKKMKELA  120
AVMSDPDLET ETMCLHDDES CRYEGQVAVY QDVYAVDGPT SLYHQANKGV RVAYWIGFDT  180
TPFMFKNLAG AYPSYSTNWA DETVLTARNI GLCSSDVMER SRRGMSILRK KYLKPSNNVL  240
FSVGSTIYHE KRDLLRSWHL PSVFHLRGKQ NYTCRCETIV SCDGYVVKRI AISPGLYGKP  300
SGYAATMHRE GFLCCKVTDT LNGERVSFPV CTYVPATLCD QMTGILATDV SADDAQKLLV  360
GLNQRIVVNG RTQRNTNTMK NYLLPVVAQA FARWAKEYKE DQEDERPLGL RDRQLVMGCC  420
WAFRRHKITS IYKRPDTQTI IKVNSDFHSF VLPRIGSNTL EIGLRTRIRK MLEEHKEPSP  480
LITAEDVQEA KCAADEAKEV REAEELRAAL PPLAADVEEP TLEADVDLML QEAGAGSVET  540
PRGLIKVTSY DGEDKIGSYA VLSPQAVLKS EKLSCIHPLA EQVIVITHSG RKGRYAVEPY  600
HGKVVVPEGH AIPVQDFQAL SESATIVYNE REFVNRYLHH IATHGGALNT DEEYYKTVKP  660
SEHDGEYLYD IDRKQCVKKE LVTGLGLTGE LVDPPFHEFA YESLRTRPAA PYQVPTIGVY  720
GVPGSGKSGI IKSAVTKKDL VVSAKKENCA EIIRDVKKMK GLDVNARTVD SVLLNGCKHP  780
VETLYIDEAF ACHAGTLRAL IAIIRPKKAV LCGDPKQCGF FNMMCLKVHF NHEICTQVFH  840
KSISRRCTKS VTSVVSTLFY DKKMRTTNPK ETKIVIDTTG STKPKQDDLI LTCFRGWVKQ  900
LQIDYKGNEI MTAAASQGLT RKGVYAVRYK VNENPLYAPT SEHVNVLLTR TEDRIVWKTL  960
AGDPWIKTLT AKYPGNFTAT IEEWQAEHDA IMRHILERPD PTDVFQNKAN VCWAKALVPV 1020
LKTAGIDMTT EQWNTVDYFE TDKAHSAEIV LNQLCVRFFG LDLDSGLFSA PTVPLSIRNN 1080
HWDNSPSPNM YGLNKEVVRQ LSRRYPQLPR AVATGRVYDM NTGTLRNYDP RINLVPVNRR 1140
LPHALVLHHN EHPQSDFSSF VSKLKGRTVL VVGEKLSVPG KMVDWLSDRP EATFRARLDL 1200
GIPGDVPKYD IIFVNVRTPY KYHHYQQCED HAIKLSMLTK KACLHLNPGG TCVSIGYGYA 1260
DRASESIIGA IARLFKFSRV CKPKSSLEET EVLFVFIGYD RKARTHNPYK LSSTLTNIYT 1320
GSRLHEAGCA PSYHVVRGDI ATATEGVIIN AANSKGQPGG GVCGALYKKF PESFDLQPIE 1380
VGKARLVKGA AKHIIHAVGP NFNKVSEVEG DKQLAEAYES IAKIVNDNNY KSVAIPLLST 1440
GIFSGNKDRL TQSLNHLLTA LDTTADVAI YCRDKKWEMT LKEAVARREA VEEICISDDS 1500
SVTEPDAELV RVHPKSSLAG RKGYSTSDGK TFSYLEGTKF HQAAKDIAEI NAMWPVATEA 1560
NEQVCMYILG ESMSSIRSKC PVEESEASTP PSTLPCLCIH AMTPERVQRL KASRPEQITV 1620
CSSFPLPKYR ITGVQKIQCS QPILFSPKVP AYIHPRKYLV ETPPVEDTPE PSAENQSTEG 1680
TPEQPPLITE DETRTRTPEP IIIEEEEEDS ISLLSDGPTH QVLQVEADIH GPPSVSSSSW 1740
SIPHASDFDV DSLSILDTLE GASVTSGATS AETNSYFAKS MEFLARPVPA PRTVFRNPPH 1800
PAPRTRTPSL APSRACSRTS LVSTPPGVNR VITREELEAL TPSRTPSRSV SRTSLVSNPP 1860
GVNRVITREE FEAFVAQQQR RFDAGAYIFS SDTGQGHLQQ KSVRQTVLSE VVLERTELEI 1920
SYAPRLDQEK EELLRKKLQL NPTPANRSRY QSRKVENMKA ITARRILQGL GHYLKAEGKV 1980
ECYRTLHPVP LYSSSVNRAF SSPKVAVEAC NAMLKENFPT VASYCIIPEY DAYLDMVDGA 2040
SCCLDTASFC PAKLRSFPKK HSYLEPTIRS AVPSAIQNTL QNVLAAATKR NCNVTQMREL 2100
PVLDSAAFNV ECFKKYACNN EYWETFKENP IRLTEENVVN YITKLKGPKA AALFAKTHNL 2160
NMLQDIPMDR FVMDLKRDVK VTPGTKHTEE RPKVQVIQAA DPLATAYLCG IHRELVRRLN 2220
AVLLPNIHTL FDMSAEDFDA IIAEHFQPGD CVLETDIASF DKSEDDAMAL TALMILEDLG 2280
VDAELLTLIE AAFGEISSIH LPTKTKFKFG AMMKSGMFLT LFVNTVINIV IASRVLRERL 2340
TGSPCAAFIG DDNIVKGVKS DKLMADRCAT WLNMEVKIID AVVGEKAPYF CGGFILCDSV 2400
TGTACRVADP LKRLFKLGKP LAADDEHDDD RRRALHEEST RWNRVGILSE LCKAVESRYE 2460
TVGTSIIVMA MTTLASSVKS FSYLRGAPIT LYG                              2493

SEQ ID NO: 52          moltype = DNA  length = 44
FEATURE                Location/Qualifiers
misc_feature           1..44
                       note = Synthetic polynucleotide
source                 1..44
                       mol_type = other DNA
                       organism = synthetic construct
SEQUENCE: 52
cctgaatgga ctacgacata gtctagtccg ccaaggccgc cacc                     44

SEQ ID NO: 53          moltype = DNA  length = 468
FEATURE                Location/Qualifiers
misc_feature           1..468
                       note = Synthetic polynucleotide
source                 1..468
                       mol_type = other DNA
                       organism = synthetic construct
SEQUENCE: 53
actcgagtat gttacgtgca aaggtgattg tcaccccccg aaagaccata ttgtgacaca   60
ccctcagtat cacgcccaaa catttacagc cgcggtgtca aaaccgcgt ggacgtggtt   120
aacatccctg ctgggaggat cagccgtaat tattataatt ggcttggtgc tggctactat  180
tgtggccatg tacgtgctga ccaaccagaa acataattga atacagcagc aattggcaag  240
ctgcttacat agaactcgcg gcgattggca tgccgcctta aattttat tttattttt    300
cttttctttt ccgaatcgga ttttgttttt aatatttcaa aaaaaaaaa aaaaaaaaa    360
aaatctagaa aaaaaaaaa aaaaaaaaaa aaaaaaaaaa aaaaaaaaaa aaaaaaaaaa    420
aaaaaaaaaa aaaaaaaaaa aaaaaaaaaa aaaaaaaaaa aaaaaaaa              468

SEQ ID NO: 54          moltype = DNA  length = 7485
```

| FEATURE | Location/Qualifiers |
|---|---|
| misc_feature | 1..7485 |
| | note = Synthetic polynucleotide |
| source | 1..7485 |
| | mol_type = other DNA |
| | organism = synthetic construct |

SEQUENCE: 54

```
atgcccgaga aggtgcacgt ggacatcgag gaggacagcc ccttcctgag ggccctgcag    60
aggagcttcc cacagttcga agtggaggcc aagcaggtga ccgacaacga ccacgccaac   120
gccagggcct tcagccacct ggccagcaag ctgatcgaga ccgaggtgga ccccagcgac   180
accatcctgg acatcggcag cgccccagcc aggagaatgt acagcaagca caagtaccac   240
tgcatctgcc ccatgaggtg cgccgaggac cccgacaggc tgtacaagta cgccaccaaa   300
ctgaagaaga actgcaagga gatcaccgac aaggagctgg acaagaaaat gaaggagctg   360
gccgccgtga tgagcgaccc cgacctggaa accgagacaa tgtgcctgca cgacgacgag   420
agctgcaggt acgagggcca ggtggccgtc taccaggacg tgtacgccgt cgacggcccc   480
accagcctgt accaccaggc caacaagggc gtgagggtgg cctactggat cggcttcgac   540
accacaccct tcatgttcaa gaacctggcc ggcgcctacc ccagctacag caccaactgg   600
gccgacgaga ccgtgctgac cgccaggaac atcggcctgt gcagcagcga cgtgatgagg   660
aggagccgga gaggcatgag catcctgagg aagaaatacc tgaagcccag caacaacgtg   720
ctgttcagcg tgggcagcac catctaccac gagaagaggg acctgctcag gagctggcac   780
ctgcccagcg tgttccacct gaggggcaag cagaactaca cctgcaggtg cgagaccatc   840
gtgagctgcg acggctacgt ggtgaagagg agcgccatca gccccggcct gtacggcaag   900
cccagcggct acgccgctac aatgcacagg gagggcttcc tgtgctgcaa ggtgaccgac   960
accctgaacg cgcgagagggt gagcttcccc gtgtgcacct acgtgcccgc cacccctgtgc  1020
gaccagatga ccggcatcct ggccaccgac gtgagcgccg acgacgccca gaagctgctc  1080
gtgggcctga accagaggat cgtggtcaac gcgaggaccc agaggaacac caacacaatg  1140
aagaactacc tgctgcccgt ggtgcccag gctttcgcca ggtgggccaa ggagtacaag  1200
gaggaccagg aagacgagag gcccctgggc ctgagggaca ggcagctggt gatgggctgc  1260
tgctgggcct tcaggcggca caagatcacc agcatctaca agaggcccga cacccagacc  1320
atcatcaagg tgaacagcga cttccacagc ttcgtgctgc ccaggatcgg cagcaacacc  1380
ctggagatcg gcctgaggac ccggatcagg aagatgctgg aggaacacaa ggagcccagc  1440
ccactgatca ccgccgagga cgtgcaggag gccaagtgcg ctgccgacga ggccaaggag  1500
gtgagggagg ccgaggaact gagggccgcc ctgccacccc tggctgccga cgtggaggaa  1560
cccacccctgg aagccgacgt ggacctgatg ctgcaggagg ccggcgcgg aagcgtggag  1620
acacccaggg gcctgatcaa ggtgaccagc tacgacggcg aggacaagat cggcagctac  1680
gccgtgctga gcccacaggc cgtgctgaag tccgagaagc tgagctgcat ccacccactg  1740
gccgagcagg tgatcgtgat cacccacagc ggcaggaagg caggtacgc cgtggagccc  1800
taccacggca aggtggtcgt gcccgagggc cacgccatcc ccgtgcagga cttccaggcc  1860
ctgagcgagga gcgccaccat cgtgtacaac gagagggagt tcgtgaacag gtacctgcac  1920
catatcgcca cccacggcgg agccctgaac accgacggag aatactacaa gaccgtgaag  1980
cccagcgagc acgacggcga gtacctgtac gacatcgaca ggaagcagtg cgtgaagaaa  2040
gagctggtga ccggcctggg actgaccggc gagctggtgg acccaccctt ccacgagttc  2100
gcctacgagga gcctgaggac cagacccgcc gctccctacc aggtgcccac catcggcctg  2160
tacgccgtgc ccggcagcgg aaagagcggc atcatcaaga gcgccgtgac caagaaagac  2220
ctggtggtca gcgccaagaa agagaactgc gccgagatca tcagggacgt gaagaagatg  2280
aaaggcctgg acgtgaacgc gcgcaccgtg acagcgtgtc tgctgaacgg ctgcaagcac  2340
cccgtggaca ccctgtacat cgacgaggcc ttcgcttgcc acgccggcac cctgagggcc  2400
ctgatcgcca tcatcaggcc caagaaagcc gtgctgtgcg gcgaccccaa gcagtgcggc  2460
ttcttcaaca tgatgtgcct gaaggtgcac ttcaaccacg atctgcac ccaggtgttc  2520
cacaagagca tcagcaggcg gtgcaccaag agcgtgacca cgtcgtgag cacccctgttc  2580
tacgacaaga aaatgaggac caccaacccc aaggagacca aatcgtgat cgacaccaca  2640
ggcagcacca agcccaagca ggacgacctg atcctgacct gcttcagggg ctgggtgaag  2700
cagctgcaga tcgactacaa gggcaacgag atcatgaccc ccgctgccag ccagggcctg  2760
accaggaagg gcgtgtacgc cgtgaggtac aaggtgaacg agaacccact gtacgctccc  2820
accagcgagc acgtgaacgt gctgctgacc aggaccgagg acaggatcgt gtggaagacc  2880
ctggccggcg acccctggat caagaccctg accgccaagt accccggcaa cttcaccgcc  2940
accatcgaag agtggcaggc cgagcacgac gccatcatga ggcacatcct ggagaggccc  3000
gaccccaccg acgtgttcca gaacaaggcc aacgtgtgct gggccaaggc cctggtgccc  3060
gtgctgaaga ccgccggcat cgacatgacc acagagcagt ggaacaccgt ggactacttc  3120
gagaccgaca aggcccacag cgccgagatc gtgctgaacc agctgtgcgt gaggttcttc  3180
ggcctggacc tggacagcgg cctgttcagc gccccaccg tgccactgag catcaggaac  3240
aaccactggg acaacagccc cagcccaaac atgtacggcc tgaacaagga ggtggtcagg  3300
cagctgagca ggcggtaccc acagctgccc agggccgtgg ccaccggcag ggtgtacgac  3360
atgaacaccg gcaccctgag gaactacgac gccaggatca acctggtgcc cgtgaacagg  3420
cggctgcccc acgccctggt gctgcaccac aacgagcacc acagagcca cttcagctcc  3480
ttcgtgagca agctgaaagg caggaccgtg ctggtcgtgg gcgagaagct gagcgtgccc  3540
ggcaagatgt ggactggct gagcgacagg cccgaggcca ccttccgggc caggctggac  3600
ctcggcatcc ccggcgacgt gcccaagtac gacatcatct tcgtgaacgt caggaccca  3660
tacaagtacc accattacca gcagtgcgga gaccacgcca tcaagctgag catgctgacc  3720
aagaaggcct gcctgcacct gaaccccgga ggcacctgcg tgagcatcgg ctacggctac  3780
gccgacaggg ccagcgagag catcattggc gccatcgcca ggtgttcaa gttcagcagg  3840
gtgtgcaaac caagagcag cctggaggaa ccgaggtgc tgttcgtgtt catcggctac  3900
gaccggaagg ccaggaccca aaccccatac aagctgagca gcaccctgac aaacatctac  3960
accggcacga ggtcgcacga ggccggctgc cccccacagct accacgatca caggggcgat  4020
atcgccaccg ccaccgaggg cgtgatcatc aacgctgaca caagcaaggg ccagcccgga  4080
ggcgagtgt gcgccgcccct gtacaagaag ttccccgaga gcttcgacct gcagcccatc  4140
gaggtgggca aggccaggct ggtgaaggc ccgctaagc acatcatcca cgccgtgggc  4200
cccaacttca caaggtgag cgaggtgaa ggcgacaag agctggccga agcctacgag  4260
agcatcgcca agatcgtgaa cgacaataac tacaagagcg tggccatccc actgctcagc  4320
```

```
accggcatct tcagcggcaa caaggacagg ctgacccaga gcctgaacca ccctgctcacc  4380
gccctggaca ccaccgatgc cgacgtggcc atctactgca gggacaagaa gtgggagatg  4440
accctgaagg aggccgtggc caggcgggag gccgtggaag agatctgcat cagcgacgac  4500
tccagcgtga ccgagcccga cgccgagctg gtgagggtgc accccaagag ctccctggcc  4560
ggcaggaagg gctacagcac cagcgacggc aagaccttca gctacctgga gggcaccgag  4620
ttccaccaga ccgctaagga catcgccgag atcaacgcta tgtggcccgt ggccaccgag  4680
gccaacgagc aggtgtgcat gtacatcctg ggcgagagca tgtccagcat caggagcaag  4740
tgccccgtgg aggaaagcga ggccagcaca ccacccagca ccctgccctg cctgtgcatc  4800
cacgctatga cacccgagag ggtgcagcgg ctgaaggcca caggcccga gcagatcacc  4860
gtgtgcagct ccttcccact gcccaagtac aggatcaccg gcgtgcagaa gatccagtgc  4920
agccagccca tcctgttcag cccaaaggtg cccgcctaca tccacccag gaagtacctg  4980
gtggagaccc caccgtgga cgagacaccc gagccaagcg ccgagaacca gagcaccgag  5040
ggcacacccg agcagccacc cctgatcacc gaggacgaga caaggacccg gacccccagg  5100
cccatcatta tcgaggaaga ggaagaggac agcatcagcc tgctgagcga cggccccacc  5160
caccaggtgc tgcaggtgga ggccgacatc cacggcccac ccagcgtgtc cagctccagc  5220
tggagcatcc cacacgccag cgacttcgac gtggacagcc tgagcatcct ggacaccctg  5280
gagggcgcca gcgtgacctc cggcgccacc agcgccgaga ccaacagcta cttcgccaag  5340
agcatggagt tcctggccag gcccgtgcca gctcccaaga ccgtgtttcag gaacccaccc  5400
cacccagctc caggaccag gaccccaagc ctggctccca gcagggcctg cagcaggacc  5460
agcctggtga gcaccccacc cggcgtgaac agggtgatca ccaggaggaa actgaggcc  5520
ctgacaccca gcaggacccc cagcaggtcc gtgagcagga ctagtctggt gtccaaccca  5580
cccggctgga caggg tgat caccagggag gaattccttc gtgcc ccagcaacag  5640
agacggttcg acgccggcgc ctacatcttc agcagcgaca ccggccaggg acacctgcag  5700
caaaagagcg tgaggcagac cgtgctgagc gaggtggtgc tggagaggac cgagctggaa  5760
atcagctacg ccccaggct ggaccaggag aaggaggaac tgctcaggaa gaaactgcag  5820
ctgaacccca ccccagccaa caggacagg taccagagca ggaaggtgga gaacatgaag  5880
gccatcaccg ccaggcggat cctgcagggc ctgggacact acctgaaggc cgagggcaag  5940
gtggagtgct acaggaccct gcaccccgtg ccactgtaca gctccagcgt gaacagggcc  6000
ttctccagcc ccaaggtggc cgtggaggcc tgcaacgcta tgctgaagga gaacttcccc  6060
accgtggcca gctactgcat catcccag tacgacgcc acctggacat ggtgacggc  6120
gccagctgct gcctggacac cgccagcttc tgccccgcca gctgaggag cttcccaag  6180
aaacacagct acctggagcc caccatcagg agcgccgtgc ccagcgccat ccagaacacc  6240
ctgcagaacg tgctggccgc tgccaccaag aggaactgca acgtgaccca gatgagggag  6300
ctgcccgtgc tggacagcgc tgccttcaac gtggagtgct tcaagaaata cgcctgcaac  6360
aacgagtact gggagaccttt caaggagaac ccccatcagc tgaccgaaga gaacgtggtg  6420
aactacatca ccaagctgaa gggccccaag gccgctgccc tgttcgctaa gacccacaac  6480
ctgaacatgc tgcaggacat cccaatggac caggttcgtga tggacctgaa gagggacgtg  6540
aaggtgacac ccggcaccaa gcacaccgag gagaggccca aggtgcaggt gatccaggcc  6600
gctgaccac tggccaccgc ctacctgtgc ggcatcccaca agcctgt gaggcggctg  6660
aacgccgtgc tgctgcccaa catccacacc ctgttcgaca tgagcgccga ggacttcgac  6720
gccatcatcg ccgagcactt ccagcccggc gactgcgtgc tggagaccga catcgccagc  6780
ttcgacaaga cgaggatga cgctatggcc ctgaccgctc tgatgatcct ggaggacctg  6840
ggcgtggacg ccgagctgct cacccgatc gaggctgcc tcggcgagat cagctccatc  6900
cacctgccca ccaagaccaa gttcaagttc ggcgctatga tgaaaagcgg aatgttcctg  6960
accctgttcg tgaacaccgt gatcaacatt gtgatcgcca gcagggtgct gcgggagagg  7020
ctgaccggca gccctgcgc tgccttcatc ggcgacgaca catcgtgaa gggcgtgaaa  7080
agcgacaagc tgatggccga caggtgcgcc acctggctga acatggaggt gaagatcatc  7140
gacgccgtgg tgggcgagaa ggccccctac ttctgcggcg gattcatcct gtgcgacagc  7200
gtgaccggca ccgcctgcag ggtggccgac ccctgaaga gctgttcaa gctgggcaag  7260
ccactggccg ctgacgatga gcacgacgat gacaggcgga gggccctgca cgaggaaagc  7320
accaggtgaa acagggtggg catcctgagc gagctgtgca aggccgtgca gagcaggtac  7380
gagaccgtgg gcaccagcat catcgtgatg ctatgacca cactggccag ctccgtcaag  7440
agcttctcct acctgagggg ggcccctata actctctacg gctaa            7485

SEQ ID NO: 55         moltype = AA   length = 2494
FEATURE               Location/Qualifiers
REGION                1..2494
                      note = Synthetic polypeptide
source                1..2494
                      mol_type = protein
                      organism = synthetic construct SEQUENCE: 55
MPEKVHVDIE EDSPFLRALQ RSFPQFEVEA KQVTDNDHAN ARAFSHLASK LIETEVDPSD    60
TILDIGSAPA RRMYSKHKYH CICPMRCAED PDRLYKYATK LKKNCKEITD KELDKKMKEL   120
AAVMSDPDLE TETMCLHDDE SCRYEGQVAV YQDVYAVDGP TSLYHQANKG VRVAYWIGFD   180
TTPFMFKNLA GAYPSYSTNW ADETVLTARN IGLCSSDVME RSRRGMSILR KKYLKPSNNV   240
LFSVGSTIYH EKRDLLRSWH LPSVFHLRGK QNYTCRCETI VSCDGYVVKR IAISPGLYGK   300
PSGYAATMHR EGFLCCKVTD TLNGERVSFP VCTYVPATLC DQMTGILATD VSADDAQKLL   360
VGLNQRIVVN GRTQRNTNTM KNYLLPVVAQ AFARWAKEYK EDQEDERPLG LRDRQLVMGC   420
CWAFRRHKIT SIYKRPDTQT IIKVNSDFHS FVLPRIGSNT LEIGLRTRIR KMLEEHKEPS   480
PLITAEDVQE AKCAADEAKE VREAEELRAA LPPLAADVEE PTLEADVDLM LQEAGAGSVE   540
TPRGLIKVTS YDGEDKIGSY AVLSPQAVLK SEKLSCIHPL AEQVIVITHS GRKGRYAVEP   600
YHGKVVVPEG HAIPVQDFQA LSESATIVYN EREFVNRYLH HIATHGGALN TDEEYKTVK   660
PSEHDGEYLY DIDRKQCVKK ELVTGLGLTG ELVDPPFHEF AYESLRTRPA APYQVPTIGV   720
YGVPGSGKSG IIKSAVTKKD LVVSAKKENC AEIIRDVKKM KGLDVNARTV DSVLLNGCKH   780
PVETLYIDEA FACHAGTLRA LIAIIRPKKA VLCGDPKQCG FFNMMCLKVH FNHEICTQVF   840
HKSISRRCTK SVTSVVSTLF YDKKMRTTNP KETKIVIDTT GSTKPKQDDL ILTCFRGWVK   900
QLQIDYKGNE IMTAASQGL TRKGVYAVRY KVNENPLYAP TSEHVNVLLT RTEDRIVWKT   960
LAGDPWIKTL TAKYPGNFTA TIEEWQAEHD AIMRHILERP DPTDVFQNKA NVCWAKALVP  1020
```

```
VLKTAGIDMT  TEQWNTVDYF  ETDKAHSAEI  VLNQLCVRFF  GLDLDSGLFS  APTVPLSIRN  1080
NHWDNSPSPN  MYGLNKEVVR  QLSRRYPQLP  RAVATGRVYD  MNTGTLRNYD  PRINLVPVNR  1140
RLPHALVLHH  NEHPQSDFSS  FVSKLKGRTV  LVVGEKLSVP  GKMVDWLSDR  PEATFRARLD  1200
LGIPGDVPKY  DIIFVNVRTP  YKYHHYQQCE  DHAIKLSMLT  KKACLHLNPG  GTCVSIGYGY  1260
ADRASESIIG  AIARLFKFSR  VCKPKSSLEE  TEVLFVFIGY  DRKARTHNPY  KLSSTLTNIY  1320
TGSRLHEAGC  APSYHVVRGD  IATATEGVII  NAANSKGOPG  GGVCGALYKK  FPESFDLQPI  1380
EVGKARLVKG  AAKHIIHAVG  PNFNKVSEVE  GDKQLAEAYE  SIAKIVNDNN  YKSVAIPLLS  1440
TGIFSGNKDR  LTQSLNHLLT  ALDTTDADVA  IYCRDKKWEM  TLKEAVARRE  AVEEICISDD  1500
SSVTEPDAEL  VRVHPKSSLA  GRKGYSTSDG  KTFSYLEGTK  FHQAAKDIAE  INAMWPVATE  1560
ANEQVCMYIL  GESMSSIRSK  CPVEESEAST  PPSTLPCLCI  HAMTPERVQR  LKASRPEQIT  1620
VCSSFPLPKY  RITGVQKIQC  SQPILFSPKV  PAYIHPRKYL  VETPPVDETP  EPSAENQSTE  1680
GTPEQPPLIT  EDETRTRTPE  PIIIEEEEED  SISLLSDGPT  HQVLQVEADI  HGPPSVSSSS  1740
WSIPHASDFD  VDSLSILDTL  EGASVTSGAT  SAETNSYFAK  SMEFLARPVP  APRTVFRNPP  1800
HPAPRTRTPS  LAPSRACSRT  SLVSTPPGVN  RVITREELEA  LTPSRTPSRS  VSRTSLVSNP  1860
PGVNRVITRE  EFEAFVAQQQ  RRFDAGAYIF  SSDTGQGHLQ  QKSVRQTVLS  EVVLERTELE  1920
ISYAPRLDQE  KEELLRKKLQ  LNPTPANRSR  YQSRKVENMK  AITARRILQG  LGHYLKAEGK  1980
VECYRTLHPV  PLYSSSVNRA  FSSPKVAVEA  CNAMLKENFP  TVASYCIIPE  YDAYLDMVDG  2040
ASCCLDTASF  CPAKLRSFPK  KHSYLEPTIR  SAVPSAIQNT  LQNVLAAATK  RNCNVTQMRE  2100
LPVLDSAAFN  VECFKKYACN  NEYWETFKEN  PIRLTEENVV  NYITKLKGPK  AAALFAKTHN  2160
LNMLQDIPMD  RFVMDLKRDV  KVTPGTKHTE  ERPKVQVIQA  ADPLATAYLC  GIHRELVRRL  2220
NAVLLPNIHT  LFDMSAEDFD  AIIAEHFQPG  DCVLETDIAS  FDKSEDDAMA  LTALMILEDL  2280
GVDAELLTLI  EAAFGEISSI  HLPTKTKFKF  GAMMKSGMPL  TLFVNTVINI  VIASRVLRER  2340
LTGSPCAAFI  GDDNIVKGVK  SDKLMADRCA  TWLNMEVKII  DAVVGEKAPY  FCGGFILCDS  2400
VTGTACRVAD  PLKRLFKLGK  PLAADDEHDD  DRRRALHEES  TRWNRVGILS  ELCKAVESRY  2460
ETVGTSIIVM  AMTTLASSVK  SFSYLRGAPI  TLYG                                2494

SEQ ID NO: 56          moltype = RNA  length = 9739
FEATURE                Location/Qualifiers
misc_feature           1..9739
                       note = Synthetic polynucleotide
source                 1..9739
                       mol_type = other RNA
                       organism = synthetic construct
SEQUENCE: 56
atgggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtcgcccgc  ccgcagaatg tattctaagc acaagtatca ttgtatctgt ccgatgagat     300
gtgcgaaga  tccggacaga ttgtataagt atgcaactaa gctgaagaaa aactgtaagg     360
aaataactga taaggaattg acaagaaaaa tgaaggagct ggccgccgtc atgagcgacc     420
ctgacctgga aactgagact atgtgcctcc acgacgacga gtcgtgtcgc tacgaagggc     480
aagtcgctgt ttaccaggat gtatacgccg tcgacggcc  caccagcctg taccaccagg     540
ccaacaaggg cgtgagggtg gcctactgga tcggcttcga caccacaccc ttcatgttca     600
agaacctggc cggcgcctac cccagctaca gcaccaactg ggccgacgag accgtgctga     660
ccgccaggaa catcggcctg tgcagcagcg acgtgatgga ggaggagccgg agaggcatga     720
gcatcctgag gaaagaatac ctgaagccca gcaacaatcg gctgttcagc gtgggcagca     780
ccatctacca cgagaagagg gacctgctca ggagctggca cctgcccagc gtgttccacc     840
tgaggggcaa gcagaactac acctgcaggt gcgagaccat cgtgagctgc gacggctacg     900
tggtgaagag gatcgccatc agcccccgcc tgtacgccaa cccagcggc  tacgccgcta     960
caatgcacag ggagggcttc ctgtgctgca aggtgaccga caccctgaac gcgcgagagg    1020
tgagcttccc cgtgtgcacc tacgtgcccg ccacccctgtg cgaccagatg accggcatcc    1080
tggccaccga cgtgagcgcc gacgacgccc agaagctgct cgtgggcctg aaccagagga    1140
tcgtggtcaa cggcaggacc cagaggaaca ccaacacaat gaagaactac ctgctgcccg    1200
tggtgccca  ggctttcgcc aggtgggcca aggagtacaa ggaggaccag gaagacgaga    1260
ggccctgggg cctgagggac aggcagctgg tgatgggctg ctgctgggcc ttcaggcggc    1320
acaagatcac cagcatctac aagaggcccg cacccagac  catcatcaag gtgaacagcg    1380
acttccacag cttcgtgctg cccaggatcg gcagcaacac cctggagatc ggcctggagg    1440
cccggatcag gaagatgctg gaggaacaca aggagcccag cccactgatc accgccgagg    1500
acgtgcagga ggccaagtgc gctgccgacg aggccaagga ggtgagggag gccgaggaac    1560
tgagggccgc cctgccaccc ctggctgccg acgtggagga acccaccctg aagccgacg    1620
tggacctgat gctgcaggag gccggcgccg gaagcgtgga gacacccagg ggcctgatca    1680
aggtgaccag ctacgacggc gaggacaaga tcggcagcta cgccgtgctg agcccacagg    1740
ccgtgctgaa gtccgagaag ctgagctgca tccaccact ggccgagcag gtgatcgtga    1800
tcacccacag cggcaggaag ggcaggtacg ccgtggagcc ctaccacggc aaggtggtcg    1860
tgcccgaggg ccacgccatc cccgtgcagg acttccaggc cctgagcgag agcgccacca    1920
tcgtgtacaa cgagagggag ttcgtgaaca ggtacctgca ccatatcgcc acccacggcg    1980
gagccctgaa caccgacgag gaatactaca gaccgtgaa gcccagcgag cacgacggcg    2040
agtacctgta cgacatcgac aggaagcagt gcgtgaagaa agctggtgg accggcctgg    2100
gactgaccgg cgagctggtg gacccaccct tccacgagtt cgcctacgag agcctgagga    2160
ccagacccgc cgctccctac caggtgccca ccatcggcgt gtacgcgtg cccggcagcg    2220
gaaagagcgg catcatcaag agccgcgtga ccaagaaaga cctggtggtc agcgccaaga    2280
aagagaactg cgccgagatc atcagggacg tgaaagaagt gaaggcctg gacgtgaacg    2340
cgcgcccctg ggacaagctg ctgtaacg gctgcaaga ccgtgctgg                   2400
tcgacgaggc cttcgcttgc cacgccggca ccctgagggc cctgatcgcc atcatcaggc    2460
ccaagaaagc cgtgctgtgc ggcgacccca gcagtgcgg cttcttcaac atgatgtgcc    2520
tgaaggtgca cttcaaccac gagatctgca cccaggtgtt ccacaagagc atcagcaggc    2580
ggtgcaccaa gagcgtgacc agctcgtga gcaccctgtt ctacgacaag aaaatgagga    2640
ccaccaaccc aagggagacc aaaaatcgtg  cgacaccac agcagcacc aagcccaagc    2700
```

```
aggacgacct gatcctgacc tgcttcaggg gctgggtgaa gcagctgcag atcgactaca   2760
agggcaacga gatcatgacc gccgctgcca gccagggcct gaccaggaag ggcgtgtacg   2820
ccgtgaggta caaggtgaac gagaacccac tgtacgctcc caccagcgag cacgtgaacg   2880
tgctgctgac caggaccgag gacaggatcg tgtggaagac cctggccggc gacccctgga   2940
tcaagaccct gaccgccaag tacccggca acttcaccgc caccatcgaa gagtggcagg    3000
ccgagcacga cgccatcatg aggcacatcc tggagaggcc cgaccccacc gacgtgttcc   3060
agaacaaggc caacgtgtgc tgggccaagg ccctggtgcc cgtgctgaag accgccggca   3120
tcgacatgac cacagagcag tggaacaccg tggactactt cgagaccgac aaggcccaca   3180
gcgccgagat cgtgctgaac cagctgtgcg tgaggttctt cggcctggac ctggacagcg   3240
gcctgttcag cgcccccacc gtgccactga gcatcaggaa caaccactgg gacaacagcc   3300
ccagcccaaa catgtacggc ctgaacaagg aggtggtcag gcagctgagc aggcggtacc   3360
cacagctgcc cagggccgtg gccaccggca gggtgtacga catgaacacc ggcaccctga   3420
ggaactacga cccaggatc aacctggtgc ccgtgaacag cggctgccc cacgccctgg     3480
tgctgcacca caacgagcac ccacagagcg acttcagctc cttcgtgagc aagctgaaag   3540
gcaggaccgt gctggtcgtg ggcgagaagc tgagcgtgcc cggcaagatg gtggactggc   3600
tgagcgacag gcccgaggcc accttccggg ccaggctgga cctcggcatc ccggcgacg    3660
tgcccaagta cgacatcatc ttcgtgaacg tcaggaccc atacaagtac caccattacc    3720
agcagtgcga ggaccacgcc atcaagctga gcatgctgac caagaaggcc tgcctgcacc   3780
tgaaccccgg aggcacctgc gtgagcatcg gctacggcta cgccgacagg gccagcgaga   3840
gcatcattgg cgccatcgcc aggctgttca agttcagcag ggtgtgcaaa cccaagagca   3900
gcctggagga aaccgaggtg ctgttcgtgt tcatcggcta cgaccggaag gccaggaccc   3960
acaaccccta caagctgagc agcaccctga caaacatcta caccggcagc aggctgacca   4020
aggccggctg cgcccccagc taccacgtgg tcagggcga tatcgccacc gccaccgagg    4080
gcgtgatcat caacgctgcc aacagcaagg gccagcccgg aggcggagtg tgcggcgccc   4140
tgtacaagaa gttccccgag agcttcgacc tgcagcccat cgaggtgggc aaggccaggc   4200
tggtgaaggg cgccgctaag cacatcatcc acgccggcc ccaacttcc aacaaggtga     4260
gcgaggtgga aggcgacaag cagctggccg aagcctacga gagcatcgcc aagatcgtga   4320
acgacaataa ctacaagagc gtggccatcc cactgctcag caccggcatc ttcagcggca   4380
acaaggacag gctgacccag agcctgaacc acctgctcac cgccctggac accaccgatg   4440
ccgacgtggc catctactgc agggacaaga agtgggagat gaccctgaag gaggccgtga   4500
ccaggcggga ggccgtggaa gagatctgca tcagcgacga ctccagcgtg accgagcccg   4560
acgccgagct ggtgagggtg caccccaaga gctccctggc cggcaggaag ggctacagca   4620
ccagcgacgg caagaccttc agctacctgg agggcaccaa gttccaccag gccgctaagg   4680
acatcgccga gatcaacgct atgtggcccg tggccaccga ggccaccgag caggtgtgca   4740
tgtacatcct gggcgagagc atgtccagca tcaggagcaa gtgcccgtg gaggaaagcg    4800
aggccagcac accacccagc accctgccct gcctgtgcat ccacgctatg cacccgaga    4860
gggtgcagcg gctgaaggcc agcagggcg agcagatcac cgtgtgcagc tccttcccac    4920
tgcccaagta caggatcacc ggcgtgcaga gatccagtg cagccagccc atcctgttca    4980
gcccaaaggt gcccgcctac atccacccca ggaagtgacc ggtggagacc ccacccgtgg   5040
acgagacacc cgagccaagc gccgagaacc agagcaccga gggcacaccc gagcagccac   5100
ccctgatcac cgaggacgag acaaggaccc ggaccccaga gccatcatt atcgaggaag   5160
aggaagagga cagcatcagc ctgctgagcg acggccccac ccaccaggtg ctgcaggtgg   5220
aggccgacat ccacggccca cccagcgtgt ccagctccga ctggagcatc ccacacgcca   5280
gcgacttcga cgtggacagc ctgagcatcc tggacaccct ggagggcgcc agcgtgacct   5340
ccggcgccac cagcgccgag accaacagct acttcgccaa gagcatggag ttcctggcca   5400
ggccccgtgcc agctcccagg accgtgttca ggaacccacc ccaccagct cccaggacca   5460
ggaccccaag cctggctccc agcaggcct gcagcaggac cagctggtg agcaccccac    5520
ccggcgtgaa cagggtgatc accagggagg aactgaggc cctgacaccc agcaggaccc   5580
ccagcaggtc cgtgagcagg actagtctgg tgtccaaccc accggcgtg aacagggtga   5640
tcaccaggga ggaattcgag gccttcgtgg cccagcaaca gagacggttc gacgccggcg   5700
cctacatctt cagcagcgac caaaagagc gtgaggcaga                           5760
ccgtgctgag cgaggtggtg ctggagagga ccgagctgga aatcagctac gcccccaggc   5820
tggaccagga gaaggaggaa ctgctcagga gaaactgca gctgaacccc accccagcca   5880
acaggagcag gtaccagagc aggaaggtgg agaacatgaa ggccatcacc gccaggcgga   5940
tcctgcaggg cctgggacac tacctgaagg ccgagggcaa ggtggagtgc tacaggaccc   6000
tgcaccccgt gccactgtac agctccagcg tgaacagggc cttctccagc cccaaggtgg   6060
ccgtggaggc ctgcaacgct atgctgaagg agaacttccc caccgtggcc agctactgca   6120
tcatccccga gtacgacgcc tacctggaca tggtggacgg cgccagctgc tgcctggaca   6180
ccgccagctt ctgccccgcc aagctgagga gcttcccaa gaaacacgc tacctggagc    6240
ccaccatcag gagcgccgtg cccagccca tccagaacac cctgcagaac gtgctggcca   6300
ctgccaccaa gaggaactgc aacgtgaccc agatgaggga gctgcccgtg ctggacagcg   6360
ctgccttcaa cgtggagtgc ttcaagaaat acgcctgcaa caacgagtac tgggagacct   6420
tcaaggagaa ccccatcagg ctgaccgaag agaacgtggt gaactacatc accaagctga   6480
agggcccaa ggccgctgcc ctgttcgcta agacccacaa cctgaacatc ctgcaggaca   6540
tccaatgga caggttcgtg atggacctga gagggacgt gaaggtgaca cccggcacca   6600
agcacaccga ggagaggcc aaggtgcagg tgatccaggc cgctgaccca ctggccaccg   6660
cctacctgtg cggcatccac agggagctgg tgaggcggct gaacgccgtg ctgctgccca   6720
acatccacac cctgttcgac atgagcgccg aggcttcga cgccatccat gccgagcact   6780
tccagcccgg cgactgcgtg ggaaccag acatcgccag cttcgacaag gcgaggatg     6840
acgctatggc cctgaccgct ctgatgatcc tggaggcct gggcgtggac gccgagctgc   6900
tcaccctgat cgaggctgcc ttcgcgaga tcagctccat ccacctgccc accaagacca   6960
agttcaagtt cggcgctatg atgaaaagcg gaatgttcct gacctgttc gtgaacaccg    7020
tgatcaacat tgtgatcgcc agcagggtgc tgcgggagag gctgaccggc agcccctgcg   7080
ctgccttcat cggcgacgac aacatcgtca gggcgtgaa aagcgacac ctgatgcgta    7140
acaggtgcgc cacctggctg aacatggagg tgaagatcat cgacgccgtg gtgggcgaga   7200
aggccccta cttctgcggc ggattcatcc tgtgcgacag cgtgaccggc accgcctgca   7260
gggtggccga ccccctgaag aggctgttca agctgggcaa gccactggcc gctgacgatg   7320
agcacgacga tgacaggcgg agggccctgc acgaggaaag caccaggtgg aacagggtgg   7380
gcatcctgag cgagctgtgc aaggccgtgg agagcaggta cgagaccgtg ggccaccagc   7440
```

```
tcatcgtgat ggctatgacc acactggcca gctccgtcaa gagcttctcc tacctgaggg  7500
gggcccctat aactctctac ggctaacctg aatggactac gacatagtct agtccgccaa  7560
ggccgccacc atgaaggcta tcctggtggt gctgctctac acctttgcca cagccaatgc  7620
tgacaccctg tgtattggct accatgccaa caacagcaca gacacagtgg acacagtgtt  7680
ggagaagaat gtgacagtga cccactctgt gaacctgttg gaggacaaac acaatggcaa  7740
actgtgtaaa ctgaggggag tggctccact gcacctgggc aagtgtaaca ttgctgctg   7800
gattctgggc aaccctgagt gtgagtccct gagcacagcc tcctcctggt cctacattgt  7860
ggagacacca tcctctgaca atggcacttg ttaccctgga gacttcattg actatgagga  7920
actgagggaa caacttttcct ctgtgtcctc ctttgagagg tttgagattt ttccaaagac  7980
ctcctcctgg ccaaaccatg acagcaacaa gggagtgaca gcagcctgtc cacatgctgg  8040
agccaagtcc ttctcaaaga acctgatttg gctggtgaag aagggcaact cctacccaaa  8100
actgagcaag tcctacatca atgacaaggg caaggaggtg ctggtgctgt ggggcatcca  8160
ccacccaagc acctctgctg accaacagtc cctctaccag aatgctgacg cctatgtgtt  8220
tgtgggctcc agcagataca gcaagaagtt caagcctgga attgccatca gaccaaaggt  8280
gagggatcag gagggcagga tgaactacta ctggaccctg gtggaacctg agacaagat   8340
taccttttgag gctacaggca acctggtggt gccaagatat gcctttgcta tggagaggaa  8400
tgctggctct ggcatcatca tctctgacac acctgtccat gactgtaaca ccacttgtca  8460
gacaccaaag ggagccatca acacctccct gccattccag aacatccacc aatcaccat   8520
tggcaagtgt ccaaaatatg tcaagagcac caaactgaga ctggctacag gactgaggaa  8580
catcccaagc atccagagca ggggactgtt ggagccatt gctggcttca ttgagggagg   8640
ctggacaggg atggtggatg gctggtatgg ctaccaccac cagaatgaac agggctctgg  8700
ctatgctgct gacctgaaaa gcacccagaa tgccattgat gagattacca caaaggtaa   8760
ctctgtgatt gagaagatga acacccagtt cacagcagtg ggcaaggagt tcaaccactt  8820
ggagaagagg attgagaacc tgaacaagaa ggtggatgat ggcttcctgg acatctggac  8880
ctacaatgct gaactgctgg tgctgttgga gaatgagagg accctggact accatgacag  8940
caatggcaag aacctctatg agaaggtgag gagccaactt aaaaacaatg ccaaggagat  9000
tggcaatggc tgtttttgagt tctaccacaa gtgtgacaac acttgtatgg agtctgtgaa  9060
gaatggcacc tatgactacc caaaatactc tgaggaggct aaactgaaca gggaggagat  9120
tgatggagtg aaattggaga gcaccaggat ttaccagatc ctggccatct acagcaccgt  9180
ggccagcagc ctggtgctgg tggtgagcct gggcgccatc agcttctgga tgtgcagcaa  9240
cggcagcttg cagtgcagga tctgcatcta aactcgagta tgttacgtgc aaaggtgatt  9300
gtcaccccc gaaagaccat attgtgcac accctcagta tcacgcccaa acatttacag    9360
ccgcggtgtc aaaaaccgcg tggacgtggt taacatccct gctgggagga tcagccgtaa  9420
ttattataat tggcttggtg ctggctacta ttgtggccat gtacgtgctg accaaccaga  9480
aacataattg aatacagcag caattggcaa gctgcttaca tagaactcgc ggcgattggc  9540
atgccgcctt aaaattttta ttttatttt tcttttcttt tccgaatcgg attttgtttt  9600
taatatttca aaaaaaaaa aaaaaaaaa aaaatctaga aaaaaaaaa aaaaaaaaaa     9660
aaaaaaaaaa aaaaaaaaa aaaaaaaaa aaaaaaaaa aaaaaaaaa aaaaaaaaaa      9720
aaaaaaaaaa aaaaaaaaa                                               9739

SEQ ID NO: 57          moltype = RNA   length = 448
FEATURE                Location/Qualifiers
misc_feature           1..448
                       note = Synthetic polynucleotide
source                 1..448
                       mol_type = other RNA
                       organism = synthetic construct
SEQUENCE: 57
gataggcggc gcatgagaga agcccagacc aattacctac ccaaatagga gaaagttcac   60
gttgacatcg aggaagacag cccattcctc agagcttttgc agcggagctt cccgcagttt  120
gaggtagaag ccaagcaggt cactgataat gaccatgcta atgccagagc gttttcgcat  180
ctggcttcaa aactgatcga aacggaggtg gacccatccg acacgatcct tgacattgga  240
atagtcagca tagtacattt catctgacta atactacaac accaccacca tgaatagagg  300
attctttaac atgctcggcc gccgccctt cccggcccc actgccatgt ggaggccgcg    360
gagaaggagg caggcggccc cgggaagcgg agctactaac ttcagcctgc tgaagcaggc  420
tggagacgtg gaggagaacc ctggacct                                     448

SEQ ID NO: 58          moltype =   length =
SEQUENCE: 58
000

SEQ ID NO: 59          moltype =   length =
SEQUENCE: 59
000

SEQ ID NO: 60          moltype =   length =
SEQUENCE: 60
000

SEQ ID NO: 61          moltype =   length =
SEQUENCE: 61
000

SEQ ID NO: 62          moltype =   length =
SEQUENCE: 62
000

SEQ ID NO: 63          moltype =   length =
SEQUENCE: 63
```

```
000

SEQ ID NO: 64           moltype =    length =
SEQUENCE: 64
000

SEQ ID NO: 65           moltype =    length =
SEQUENCE: 65
000

SEQ ID NO: 66           moltype =    length =
SEQUENCE: 66
000

SEQ ID NO: 67           moltype = DNA   length = 30
FEATURE                 Location/Qualifiers
misc_feature            1..30
                        note = Synthetic polynucleotide
source                  1..30
                        mol_type = other DNA
                        organism = synthetic construct
SEQUENCE: 67
atggactacg acatagtcta gtccgccaag                                     30

SEQ ID NO: 68           moltype = DNA   length = 16
FEATURE                 Location/Qualifiers
misc_feature            1..16
                        note = Synthetic polynucleotide
source                  1..16
                        mol_type = other DNA
                        organism = synthetic construct
SEQUENCE: 68
atggactacg acatag                                                    16

SEQ ID NO: 69           moltype = DNA   length = 15
FEATURE                 Location/Qualifiers
misc_feature            1..15
                        note = Synthetic polynucleotide
source                  1..15
                        mol_type = other DNA
                        organism = synthetic construct
SEQUENCE: 69
atggactacg acata                                                     15

SEQ ID NO: 70           moltype =    length =
SEQUENCE: 70
000

SEQ ID NO: 71           moltype =    length =
SEQUENCE: 71
000

SEQ ID NO: 72           moltype = DNA   length = 7482
FEATURE                 Location/Qualifiers
misc_feature            1..7482
                        note = Synthetic polynucleotide
source                  1..7482
                        mol_type = other DNA
                        organism = synthetic construct
SEQUENCE: 72
atggagaaag ttcacgttga catcgaggaa gacagcccat tcctcagagc tttgcagcgg    60
agcttcccgc agtttgaggt agaagccaag caggtcactg ataatgacca tgctaatgcc   120
agagcgtttt cgcatctggc ttcaaaactg atcgaaacgg aggtggaccc atccgacacg   180
atccttgaca ttggaagtgc gcccgcccgc agaatgtatt ctaagcacaa gtatcattgt   240
atctgtccga tgagatgtgc ggaagatccg gacagattgt ataagtatgc aactaagctg   300
aagaaaaact gtaaggaaat aactgataag gaattggaca agaaaatgaa ggagctggcc   360
gccgtcatga gcgaccctga cctggaaact gagactatgt gcctccacga cgacgagtcg   420
tgtcgctacg aagggcaagt cgctgtttac caggatgtat acgcgtcga cggccccacc   480
agcctgtacc accaggccaa caagggcgtg agggtggctg actggatcgg cttcgacacc   540
acacccttca tgttcaagaa cctggccggc gcctacccca gctacagcac caactgggcc   600
gacgagaccg tgctgaccgc caggaacatc ggcctgtgca gcgacgt gatggagagg      660
agccggagag gcatgagcat cctgaggaag aaatacctga gcccagcaa aacgtgctg    720
ttcagcgtgg gcagcaccat ctaccacgag aagagggacc tgctcaggag ctggcacctg   780
cccagcgtgt tccacctgag gggcaagcaa aactacaccc gcagtgcga gaccatcgtg   840
agctgcgacg gctacgtggt gaagaggatc gccatcagcc ccggcctgta cggcaagccc   900
agcggctacc ccgctacaat gcacagggag ggcttcctgt gctgcaaggt gaccgacacc   960
ctgaacggcg agagggtgag cttccccgtg tgcacctacg tgcccgccac cctgtgcgac  1020
cagatgaccg gcatcctggc caccgacgtg agcgccgacg acgcccagaa gctgctcgtg  1080
ggcctgaacc agaggatcgt ggtcaacggc aggacccaga ggaacaccaa cacaatgaag  1140
```

```
aactacctgc tgcccgtggt ggcccaggct ttcgccaggt gggccaagga gtacaaggag  1200
gaccaggaag acgagaggcc cctgggcctg agggacaggc agctggtgat gggctgctgc  1260
tgggccttca ggcggcacaa gatcaccagc atctacaaga ggcccgacac ccagaccatc  1320
atcaaggtga acagcgactt ccacagcttc gtgctgccca ggatcggcag caacaccctg  1380
gagatcggcc tgaggacccg gatcggaag atgctggaga aacacaagga gcccagccca  1440
ctgatcaccg ccgaggacgt gcaggaggcc aagtgcgctg ccgacgaggc caaggaggtg  1500
agggaggccg aggaactgag ggccgccctg ccacccctgg ctgccgacgt ggaggaaccc  1560
accctggaag ccgacgtgga cctgatgctg caggaggccg cgccggaag cgtggagaca  1620
cccagggcc tgatcaaggt gaccagctac gacggcgagg acaagatcgg cagctacgcc  1680
gtgctgagcc cacaggccgt gctgaagtcc gagaagctga gctgcatcca cccactggcc  1740
gagcaggtga tcgtgatcac ccacagcggc aggaagggca ggtacgccgt ggagccctac  1800
cacggcaagg tggtcgtgcc cgagggccac gccatccccg tgcaggactt ccaggccctg  1860
agcgagagcg ccaccatcgt gtacaacgag ggggagttcg tgaacaggta cctgcaccat  1920
atcgccaccc acggcggagc cctgaacacc gacgaggaat actacaagac cgtgaagccc  1980
agcgagcacg acggcgagta cctgtacgac atcgacagga agcagtgcgt gaagaaagag  2040
ctggtgaccg gcctgggact gaccggcgag ctggtggacc cacccttcca cgagttcgcc  2100
tacgagagcc tgaggaccag acccgccgct ccctaccagg tgcccaccat cggcgtgtac  2160
ggcgtgcccg gcagcggaaa gagcgccatc atcaaggacg ccgtgaccaa gaaagacctg  2220
gtggtcagcg ccaagaaaga gaactgcgcc gagatcatca gggacgtgaa gaagatgaaa  2280
ggcctggacg tgaacgcgcg caccgtggac agcgtgctgc tgaacggctg caagcacccc  2340
gtggagaccc tgtacatcga cgaggccttc gcttgccacg ccggcaccct gagggccctg  2400
atcgccatca tcaggcccaa gaaagccgtg ctgtgcggcg accccaagca gtgcggcttc  2460
ttcaacatga tgtgcctgaa ggtgcacttc aaccacagca tctgcaccca ggtgttccac  2520
aagagcatca gcaggcggtg caccaagagc gtgaccagcc tcgtgagcac cctgttctac  2580
gacaagaaaa tgaggaccac caaccccaag gagaccaaaa tcgtgatcga caccacaggc  2640
agcaccaagc ccaagcagga cgacctgatc tgacctgct tcaggggctg ggtgaagcag  2700
ctgcagatcg actacaaggg caacgagatc atgaccgccg ctgccagcca gggcctgacc  2760
aggaagggcc tgtacgccgt gaggtacaag gtgaacgaga acccactgta cgctcccacc  2820
agcgagcacg tgaacgtgct gctgaccagg accgaggaca ggatcgtgtg gaagaccctg  2880
gccggcgacc cctggatcaa gaccctgacc gccaagtacc ccggcaactt caccgccacc  2940
atcgaagagt ggcaggccga gcacgacgcc atcatgaggc acatcctgga gaggcccgac  3000
cccaccgacg tgttccagaa caaggccaac gtgtgctggg ccaaggccct ggtgcccgtg  3060
ctgaagaccc ccggcatcga catgaccaca gagcagtgga acaccgtgga ctacttcgag  3120
accgacaagg cccacagcgc cgagatcgtg ctgaaccgac tgtgcgtgag gttcttcggc  3180
ctggacctgg acagcggcct gttcagcgcc cccaccgtgc cactgagcat caggaacaac  3240
cactgggaca cagccccag cccaaacatg tacggcctga caaggaggt ggtcaggcag  3300
ctgagcaggc ggtacccaca gctgccagg gccgtggcca ccgcagggt gtacgacatg  3360
aacaccggca ccctgaggaa ctacgacccc aggatcaacc tggtgcccgt gaacaggcgg  3420
ctgcccacg ccctggtgct gcaccacaac gagcacccac agagcgactt cagctccttc  3480
gtgagcaagc tgaaaggcag gaccgtgctg tcgtgggcg agaagctgag cgtgcccggc  3540
aagatggtgg actggctgag cgacaggcc gaggccacct tccgggccag gctggacctc  3600
ggcatccccg cgacgtgcc caagtacgac atcatcttcg tgaacgtcag gaccccatac  3660
aagtaccacc attaccagca gtgcgaggac cacgccatca agctgagcat gctgaccaag  3720
aaggcctgcc tgcacctgaa ccccggaggc acctgcgtga gcatcggcta cggctacgcc  3780
gacagggcca gcgagagcat cattggcgcc atcgccaggc tgttcaagtt cagcagggtg  3840
tgcaaaccca agagcagcct ggaggaaacc gaggtgctgt tcgtgttcat cggctacgac  3900
cggaaggcca ggacccacaa cccctacagg ctgagcagca ccctgacaaa catctacacc  3960
ggcagcaggc tgcacgaggc cggctgcgcc cccagctacc acgtggtcag gggcgatatc  4020
gccaccgcca ccgagggcgt gatcatcaac gctgccaaca gcaagggcca gcccggaggc  4080
ggagtgtgcg gcgcgccctgta caagaagttc cccgagagct tcgacctgca gcccatcgag  4140
gtgggcaagg ccaggctggt gaagggcgcc gctaagcaca tcatccacgc cgtgggccc  4200
aacttcaaca aggtgagcga ggtggaaggc gacaagcagc tggccgaagc ctacgagagc  4260
atcgccaaga tcgtgaacga caataactac aagagcgtgg ccatcccact gctcagcacc  4320
ggcatcttca gcggcaacaa ggacaggctg acccagagcc tgaaccacct gctcaccgcc  4380
ctggacacca ccgatgccga cgtggccatc tactgcaagg acaagaagtg ggagatgacc  4440
ctgaaggagg ccgtgccag gcgggaggcc gtggaagaga tctgcatcag cgacgactcc  4500
agcgtgaccg agcccgacgc cgagctggtg agggtgcacc caagagctc cctgccggc  4560
aggaagggct acagcaccag cgacggcaag accttcagct acctggaggg caccaagttc  4620
caccaggcg ctaaggacat cgccgagatc aacgctatgt ggccgtggc caccgaggcc  4680
aacgcaagg tgtgcatgta catcctgggc gagagcatgt ccagcatcag gagcaagtgc  4740
cccgtggagg aaagcgaggc cagcacacca cccagcaccc tgccctgcct gtgcatccac  4800
gctatgacac ccgagagggt gcagcggctg aaggccagca ggcccgagca gatcaccgtg  4860
tgcagctcct tcccactgcc caagtacagg atcaccggcc tgcagaagat ccagtgcagc  4920
cagcccatcc tgttcagccc aaaggtgccc gcctacatcc accaggaa gtacctggtg  4980
gagaccccac ccgtgacga gacacccgag ccaagcgccg agaaccagag caccgagggc  5040
acacccgagc agccaccct gatcaccgag gacgagacaa ggaccgggac cccagagccc  5100
atcattatcg aggaagagga agaggacagc atcagcctgc tgagcgacgg ccccacccac  5160
caggtgctgc aggtggaggc cgacatccac ggcccaccca gcgtgtccag ctccagctgg  5220
agcatcccac acgccagcga cttcgacgtg gacagcctga gcatcctgga caccctggag  5280
ggcgccagcg tgacctccgg cgccaccagc gccgagacca acagctactt cgccaagagc  5340
atggagttcc tggccaggcc cgtgccagct cccaggaccg tgttcaggaa cccaccccac  5400
ccagctccca ggaccaggac cccaagcctg ctcccagca gggcctgcag caggaccagc  5460
ctggtgagca cccccacccgg cgtgaacagg tgatcacca gggaggaact ggaggccctg  5520
acacccagca ggaccccag caggtccgtg agcaggacta gtctggtgtc caacccaccc  5580
ggcgtgaaca gggtgatcac cagggaggaa ttcgaggcct tcgtggccca gcaacagaga  5640
cggttcgacg ccggcgccta catcttcagc agcgacaccg gccagggaca cctgcagcaa  5700
aagagcgtga ggcagaccgt gctgagcgag gtggtgctgg agaggaccga gctggaaatc  5760
agctacgccc ccaggctgga ccaggagaag gaggaactgc tcaggaagaa actgcagctg  5820
aacccccacc cagccaacag gagcaggtac cagagcagga aggtggagaa catgaaggcc  5880
```

```
atcaccgcca ggcggatcct gcagggcctg ggacactacc tgaaggccga gggcaaggtg   5940
gagtgctaca ggaccctgca ccccgtgcca ctgtacagct ccagcgtgaa cagggccttc   6000
tccagcccca aggtggccgt ggaggcctgc aacgctatgc tgaaggagaa cttccccacc   6060
gtggccagct actgcatcat ccccgagtac gacgcctacc tggacatggt ggacggcgcc   6120
agctgctgcc tggacaccgc cagcttctgc cccgccaatc tgaaggagct ccccaagaaa   6180
cacagctacc tggagcccac catcaggagc gccgtgccca gcgccatcca gaacaccctg   6240
cagaacgtgc tggccgctgc caccaagagg aactgcaacg tgacccagat gagggagctg   6300
cccgtgctgg acagcgctgc cttcaacgtg gagtgcttca gaaatacgc ctgcaacaac   6360
gagtactggg agaccttcaa ggagaacccc atcaggctga ccgaagagaa cgtggtgaac   6420
tacatcacca agctgaaggg ccccaaggcc gctgccctgt tcgctaagac ccacaacctg   6480
aacatgctgc aggacatccc aatggacagg ttcgtgatgg acctgaagag ggacgtgaag   6540
gtgacacccg gcaccaagca caccgaggag aggcccaagg tgcaggtgat ccaggccgct   6600
gacccactgg ccaccgccta cctgtgcggc atccacaggg agctggtgag gcggctgaac   6660
gccgtgctgc tgcccaacat ccacaccctg ttcgacatga gcgccgagga cttcgacgcc   6720
atcatcgccc agcacttcca gcccggcgac tgcgtgctgg agaccgacat cgccagcttc   6780
gacaagagcg aggatgacgc tatggccctg accgctctga tgatcctgga ggacctgggc   6840
gtggacgccg agctgctcac cctgatcgag gctgccttcg gcgagatcag ctccatccac   6900
ctgcccacca agaccaagtt caagtccggc gctatgatga aaagcggaat gttcctgacc   6960
ctgttcgtga acaccgtgat caacattgtg atcgccagca gggtgctgcg ggagaggctg   7020
accggcagcc cctgcgctgc cttcatcggc gacgacaaca tcgtgaaggg cgtgaaaagc   7080
gacaagctga tggccgacag gtgcgccacc tggctgaaca tggaggtgaa gatcatcgac   7140
gccgtgtggg gcgagaaggc cccctacttc tgccggcgat tcatcctgtg cgacagcgtg   7200
accggcaccg cctgcagggt ggccgacccc ctgaagaggc tgttcaagct gggcaagcca   7260
ctggccgctg acgatgagca cgacgatgac aggcggaggg ccctgacga ggaaaagcacc   7320
aggtggaaca gggtgggcat cctgagcgag ctgtgcaagg ccgtggagag caggtacgag   7380
accgtgggca ccagcatcat cgtgatggct atgaccacac tggccagctc cgtcaagagc   7440
ttctcctacc tgagggggc ccctataact ctctacggct aa                      7482

SEQ ID NO: 73              moltype = DNA  length = 44
FEATURE                    Location/Qualifiers
misc_feature               1..44
                           note = Synthetic polynucleotide
source                     1..44
                           mol_type = other DNA
                           organism = synthetic construct
SEQUENCE: 73
atgggcggcg catgagagaa gcccagacca attacctacc caaa                    44

SEQ ID NO: 74              moltype = DNA  length = 45
FEATURE                    Location/Qualifiers
misc_feature               1..45
                           note = Synthetic polynucleotide
source                     1..45
                           mol_type = other DNA
                           organism = synthetic construct
SEQUENCE: 74
gatgggcggc gcatgagaga agcccagacc aattacctac ccaaa                   45

SEQ ID NO: 75              moltype = DNA  length = 45
FEATURE                    Location/Qualifiers
misc_feature               1..45
                           note = Synthetic polynucleotide
source                     1..45
                           mol_type = other DNA
                           organism = synthetic construct
SEQUENCE: 75
gataggcggc gcatgagaga agcccagacc aattacctac ccaaa                   45

SEQ ID NO: 76              moltype = DNA  length = 468
FEATURE                    Location/Qualifiers
misc_feature               1..468
                           note = Synthetic polynucleotide
source                     1..468
                           mol_type = other DNA
                           organism = synthetic construct
SEQUENCE: 76
actcgagtat gttacgtgca aaggtgattg tcaccccccg aaagaccata ttgtgacaca    60
ccctcagtat cacgcccaaa catttacagc cgcggtgtca aaaccgcgt ggacgtggtt   120
aacatccctg ctggaggat cagccgtaat tattataatt ggcttggtgc tggctactat   180
tgtggccatg tacgtgctga ccaaccagaa acataattga atacagcagc aattggcaag   240
ctgcttacat agaactcgcg gcgattggca tgccgcctta aattttat tttattttt     300
cttttctttt ccgaatcgga ttttgttttt aatatttcaa aaaaaaaaa aaaaaaaaa    360
aaatctagaa aaaaaaaaa aaaaaaaaa aaaaaaaaa aaaaaaaaa aaaaaaaaa       420
aaaaaaaaaa aaaaaaaaa aaaaaaaaa aaaaaaaaa aaaaaaaa                  468

SEQ ID NO: 77              moltype = DNA  length = 44
FEATURE                    Location/Qualifiers
misc_feature               1..44
                           note = Synthetic polynucleotide
```

```
source              1..44
                    mol_type = other DNA
                    organism = synthetic construct
SEQUENCE: 77
cctgaatgga ctacgacata gtctagtccg ccaaggccgc cacc               44

SEQ ID NO: 78       moltype = DNA  length = 8038
FEATURE             Location/Qualifiers
misc_feature        1..8038
                    note = Synthetic polynucleotide
source              1..8038
                    mol_type = other DNA
                    organism = synthetic construct
SEQUENCE: 78
atgggcggcg catgagagaa gcccagacca attacctacc caaaatggag aaagttcacg   60
ttgacatcga ggaagacagc ccattcctca gagctttgca gcggagcttc cgcagtttg   120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg acaagaaaaa tgaaggagct ggccgccgtc atgagcgacc  420
ctgacctgga aactgagact atgtgcctcc acgacgacga gtcgtgtcgc tacgaaggcc  480
aagtcgctgt ttaccaggat gtatacgccg tcgacggccc caccagcctg taccaccagg  540
ccaacaaggg cgtgagggtg gcctactgga tcggcttcga caccacccc ttcatgttca  600
agaacctggc cggcgcctac cccagctaca gcaccaactg ggccgacgag accgtgctga  660
ccgccaggaa catcggcctg tgcagcagcg acgtgatgga ggagagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacgacaa gccagccggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccaggagg  1140
tcgtggtcaa cggcaggacc cagaggaaca ccaacacaat gaagaactac ctgctgcccg  1200
tggtggccca ggcttttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg aagcgtggga gacacccagg ggcctgatca  1680
aggtgaccag ctacgacggc gaggacaaga tcggcagcta cgccgtgctg agcccacagg  1740
ccgtgctgaa gtccgagaag ctgagctgca tccaccact ggccgagcag gtgatcgtga  1800
tcacccacac cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggaa ttcgtgaaca ggtacctgca ccatatcgcc acccacggca  1980
gagccctgaa caccgacgag gaatactaca agaccgtgaa gcccagcgac acgacggcc  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctcctac caggtgccca ccatcgacgt gtacgacgtg cccggcacgg  2220
gaaagagcgg catcatcaag agcgccgtga ccaagaaaga cctggtggtc agcgccaaga  2280
aagagaactg cgccgagatc atcgggacg tgaagaagat gaaggccctg gacgtgaacg  2340
cgcgcaccgt ggacagcgtg ctgctgaacg gctgcaagca cccccgtggag accctgtaca  2400
tcgacgaggc cttcgcttgc cacgccggca cctgcgaggc cctgatcgcc atcatcaggc  2460
ccaagaaagc cgtgctgtgc ggcgacccca gcagtcgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatggagg  2640
ccaccaaccc caaggacacc aaaatcgtga tcgacaccac aggcagccc aagcccaagc  2700
aggacgacct gatcctgacc tgcttcaggg gctgggtgaa gcagctgcag atcgactaca  2760
agggcaacga gatcatgacc gccgctgcca gccaggcct gaccaggaag ggcgtgtacg  2820
ccgtgaggta caagttgaac gagaaaccac tgtacgctcc caccagcgag cacgtgaacg  2880
tgctgctgac caggaccgag acaggatcg tgtggaagac cctggccggc gacccctgga  2940
tcaagacccct gaccgccaag tacccccggca acttcacgga cagcatcgaa gagtggcagg  3000
ccgagcacga cgccatcatg aggcacatcc tggagaggcc cgaccccacc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccac gtgccactga gcatcaggaa cacctgggac aacactgg  3300
ccagcccaaa catgtacggc ctgaacaagg aggtggtcag gcagctgagc aggcggtacc  3360
cacagctgcc cagggccgtg gccaccggca ggcttgtacga catgaacacc ggcacactga  3420
ggaactacga cccccaggatc aacctggtgc cgtgaacag gcggctgccc cacgcctgg  3480
tgctgcacca caacgagcac ccacagagcg acttcagctc cttcgtgagc aagctgaaag  3540
gcaggaccgt gctggtgtg ggcgagaagc tgagcgtgcc aggcaagatg gtgactggc  3600
tgagcgacag gcccgaggcc accttccggg ccaggctgga cctcggcatc ccggcgacg  3660
tgcccaagta cgacatcatc ttcgtgaacg tcaggacccc atacaagtac caccattacc  3720
agcagtgcga ggaccacgcc atcaagctga gcatgctgac caagaaggcc tgcctgcacc  3780
tgaaccccgg aggcacctgc gtgagcatcg gctacggcta cgccgacagg gccagcgaga  3840
gcatcattgg cgccatcgcc aggcttgttca agttcagcag ggtgtgcaaa cccaagagca  3900
```

-continued

```
gcctggagga aaccgaggtg ctgttcgtgt tcatcggcta cgaccggaag gccaggaccc   3960
acaacccta  caagctgagc agcaccctga caaacatcta caccggcagc aggctgcacg   4020
aggccggctg cgcccccagc taccacgtgg tcagggcga  tatcgccacc gccaccgagg   4080
gcgtgatcat caacgctgcc aacagcaagg ccagcccgg  aggcggagtg tgcggcgccc   4140
tgtacaagaa gttccccgag agcttcgacc tgcagcccat cgaggtgggc aaggccaggc   4200
tggtgaaggg cgccgctaag cacatcatcc acgccgtggg ccccaacttc aacaaggtga   4260
gcgaggtgga aggcgacaag cagctggccg aagcctacga gagcatcgcc aagatcgtga   4320
acgacaataa ctacaagagc gtggccatcc cactgctcag caccggcatc ttcagcggca   4380
acaaggacag gctgacccag agcctgaacc acctgctcac cgccctggac accaccgatg   4440
ccgacgtggc catctactgc agggacaaga agtgggagat gaccctgaag gaggccgtgg   4500
ccaggcggga ggccgtggaa gagatctgca tcagcgacga ctccagcgtg accgagcccg   4560
acgccgagct ggtgagggtg caccccaaga gctccctggc cggcaggaag gctacagca   4620
ccagcgacgg caagaccttc agctacctgg agggcaccaa gttccaccag gccgctaagg   4680
acatcgccga gatcaacgct atgtggcccg tggccaacga ggccagcccc atcctgttca   4740
tgtacatcct gggcgagagc atgtccagca tcaggagcga gtgccccgtg gaggaaagcg   4800
aggccagcac accaccccagc accctgccct gcctgtgcat ccacgctatg cacccgaga   4860
gggtgcagcg gctgaaggcc agcaggcccg agcagatcac cgtgtgcagc tccttcccac   4920
tgcccaagta caggatcacc ggcgtgcaga agatccagtg cagccagccc atcctgttca   4980
gcccaaaggt gcccgcctac atccacccca ggaagtacct ggtggagacc caccccgtgg   5040
acgagacacc cgagccaagc gccgagaacc agagcaccga gggcacaccc gagcagccac   5100
ccctgatcac cgaggacgag acaaggaccc ggacccagag cccatcatt atcgaggaag   5160
aggaagagga cagcatcagc ctgctgagcg acggccccac ccaccaggtg tcaggtggtg   5220
aggccgacat ccacgcccca cccagcgtgt ccagctccag ctggagcatc ccacacgcca   5280
gcgacttcga cgtggacagc ctgagcatcc tggacaccct ggaggcgcc agcgtgacct   5340
ccggcgccac cagcgccgag accaacagct acttcgccaa gagcatggag ttcctggcca   5400
ggcccgtgcc agctcccagg accgtgttca ggaaacccac cccagctcc cccaggacca   5460
ggaccccaag cctggctccc agcagggcct gcagcaggac cagcctggtg agcacccac   5520
ccggcgtgaa caggtgatc accagggag actggaggc cctgacaccc agcaggaccc   5580
ccagcaggtc cgtgagcagg actagtctgg tgtccaaccc acccggcgtg aacagggtga   5640
tcaccaggga ggaattcgag gccttcgtgg cccagcaga ggacggttc gacgccggcg   5700
cctacatctt cagcagcgac accgccagg gacacctgca gcaaaagagc gtgaggcaga   5760
ccgtgctgag cgaggtggtg ctggagagga ccgagctgga aatcagctac gccccaggc   5820
tggaccagga gaaggaggaa ctgctcagga gaaactgca gctgaacccc accccagca   5880
acaggagcag gtaccagagc aggaaggtgg agaacatgaa ggccatcacc gccaggcgga   5940
tcctgactgg acctgggacac tacctgaagg ccgagggcaa ggtggagtgc tacaggaccc   6000
tgcacccgt gccactgtac agctccagcg tgaacagggc cttctccagc cccaaggtgg   6060
ccgtggaggc ctgcaacgct atgctgaagg agaacttccc caccgtgcc agctactgca   6120
tcatccccga gtacgacgcc tacctggaca tggtggacgg cgccagctgc tgcctggaca   6180
ccgccagctt ctgccccgcc aagctgagga gcttcccaa gaaacacgc tacctggagc   6240
ccaccatcag gagcgccgtg cccagcgcca tccagaacac cctgcagaac gtgctggcca   6300
ctgccaccaa gaggaactgc aacgtgaccc agatgaggga gctgcccgtg ctggacagcg   6360
ctgccttcaa cgtggagtgc ttcaagaaat acgcctgcaa caacgagtac tgggagacct   6420
tcaaggagaa ccccatcagg ctgaccgaag agaacgtggt gaactacatc accaagccga   6480
agggccccaa ggccgctgcc ctgttcgcta gacccacaa cctgaacatg ctgcaggaca   6540
tcccaatgga caggttcgtg atggacctga gagggacgt gaaggtgaca cccggcacca   6600
agcacaccga ggagaggccc aaggtgcagg tgatccaggc cgctgaccca ctggccaccg   6660
cctacctgtg cggcatccac aagggacgtg tgaggcggct gaaccgcgtg ctgctgccca   6720
acatccacac cctgttcgac atgagcgccg aggacttga cgccatcatc gccgagcact   6780
tccagccgcg cgactgcgtg ctggagaccg acatcgccag cttcgacaag agcgaggatg   6840
acgctatggc cctgaccgct ctgatgatcc tggaggacct gggcgtggac gccgagctgc   6900
tcacctgat cgaggctgcc ttcggcgaga tcagctccat ccacctgcc accaagacca   6960
agttcaagtt cggcgctatg atgaaaagcg gaatgttcct gacctgtc gtgaacaccg   7020
tgatcaacat tgtgatcgcc agcagggtgc tgcgggagag gctgaccggc agccctgcg   7080
ctgccttcat cggcgacgac aacatcgtga agggcgtgaa aagcgacaag ctgatggccg   7140
acaggtgcgc cacctggctg aacatggagg tgaagatcat cgacgccgtg gtgggcgaga   7200
aggcccccta cttctgcggc ggattcatcc tgtgcgacag cgtgaccggc accgcctgca   7260
gggtggccga ccccctgaag aggctgttca agctgggcaa gccactggcc gctgacatgt   7320
agcacgacga tgacaggcgg agggccctgc acgaggaaag caccaggtgg aacagggtga   7380
gcatcctgag cgagctgtgc aaggccgtgg agagcaggta cgagaccgtg ggcaccagca   7440
tcatcgtgat ggctatgacc acactggcca gctccgtcaa gagcttctcc tacctgaggg   7500
gggcccctat aactctctac ggctaacctg aatggactac gacatagtct agtccgccaa   7560
ggccgccacc actcgagtat gttacgtgca aggtgattg tcaccccccg aaagaccata   7620
ttgtgacaca ccctcagtat cacgcccaaa catttacagc cgcggtgtca aaaaccgcgt   7680
ggacgtggtt aacatccctg ctgggaggat cagccgtaat tattataatt ggcttggttg   7740
tggctactat tgtggccatg tacgtgctga ccaaccagaa acataattga atacagcagc   7800
aattggcaag ctgcttacat agaactgcgc gcgattggca tgccgcctta aaattttttat   7860
tttatttttt cttttctttt ccgaatcgga ttttgtttttt aatatttcaa aaaaaaaaa   7920
aaaaaaaaa  aaatctagaa aaaaaaaaa aaaaaaaaa aaaaaaaaa aaaaaaaaa     7980
aaaaaaaaaa aaaaaaaaa aaaaaaaaa aaaaaaaaa aaaaaaaaa aaaaaaaa       8038
```

```
SEQ ID NO: 79         moltype = AA  length = 2493
FEATURE               Location/Qualifiers
REGION                1..2493
                      note = Synthetic polypeptide
source                1..2493
                      mol_type = protein
                      organism = synthetic construct
SEQUENCE: 79
MEKVHVDIEE DSPFLRALQR SFPQFEVEAK QVTDNDHANA RAFSHLASKL IETEVDPSDT   60
```

```
ILDIGSAPAR RMYSKHKYHC ICPMRCAEDP DRLYKYATKL KKNCKEITDK ELDKKMKELA    120
AVMSDPDLET ETMCLHDDES CRYEGQVAVY QDVYAVDGPT SLYHQANKGV RVAYWIGFDT    180
TPFMFKNLAG AYPSYSTNWA DETVLTARNI GLCSSDVMER SRRGMSILRK KYLKPSNNVL    240
FSVGSTIYHE KRDLLRSWHL PSVFHLRGKQ NYTCRCETIV SCDGYVVKRI AISPGLYGKP    300
SGYAATMHRE GFLCCKVTDT LNGERVSFPV CTYVPATLCD QMTGILATDV SADDAQKLLV    360
GLNQRIVVNG RTQRNTNTMK NYLLPVVAQA FARWAKEYKE DQEDERPLGL RDRQLVMGCC    420
WAFRRHKITS IYKRPDTQTI IKVNSDFHSF VLPRIGSNTL EIGLRTRIRK MLEEHKEPSP    480
LITAEDVQEA KCAADEAKEV REAEELRAAL PPLAADVEEP TLEADVDLML QEAGAGSVET    540
PRGLIKVTSY DGEDKIGSYA VLSPQAVLKS EKLSCIHPLA EQVIVITHSG RKGRYAVEPY    600
HGKVVVPEGH AIPVQDFQAL SESATIVYNE REFVNRYLHH IATHGGALNT DEEYYKTVKP    660
SEHDGEYLYD IDRKQCVKKE LVTGLGLTGE LVDPPFHEFA YESLRTRPAA PYQVPTIGVY    720
GVPGSGKSGI IKSAVTKKDL VVSAKKENCA EIIRDVKKMK GLDVNARTVD SVLLNGCKHP    780
VETLYIDEAF ACHAGTLRAL IAIIRPKKAV LCGDPKQCGF FNMMCLKVHF NHEICTQVFH    840
KSISRRCTKS VTSVVSTLFY DKKMRTTNPK ETKIVIDTTG STKPKQDDLI LTCFRGWVKQ    900
LQIDYKGNEI MTAAASQGLT RKGVYAVRYK VNENPLYAPT SEHVNVLLTR TEDRIVWKTL    960
AGDPWIKTLT AKYPGNFTAT IEEWQAEHDA IMRHILERPD PTDVFQNKAN VCWAKALVPV   1020
LKTAGIDMTT EQWNTVDYFE TDKAHSAEIV LNQLCVRFFG LDLDSGLFSA PTVPLSIRNN   1080
HWDNSPSPNM YGLNKEVVRQ LSRRYPQLPR AVATGRVYDM NTGTLRNYDP RINLVPVNRR   1140
LPHALVLHHN EHPQSDFSSF VSKLKGRTVL VVGEKLSVPG KMVDWLSDRP EATFRARLDL   1200
GIPGDVPKYD IIFVNVRTPY KYHHYQQCED HAIKLSMLTK KACLHLNPGG TCVSIGYGYA   1260
DRASESIIGA IARLFKFSRV CKPKSSLEET EVLFVFIGYD RKARTHNPYK LSSTLTNIYT   1320
GSRLHEAGCA PSYHVVRGDI ATATEGVIIN AANSKGQPGG GVCGALYKKF PESFDLQPIE   1380
VGKARLVKGA AKHIIHAVGP NFNKVSEVEG DKQLAEAYES IAKIVNDNNY KSVAIPLLST   1440
GIFSGNKDRL TQSLNHLLTA LDTTADVAI  YCRDKKWEMT LKEAVARREA VEEICISDDS   1500
SVTEPDAELV RVHPKSSLAG RKGYSTSDGK TFSYLEGTKF HQAAKDIAEI NAMWPVATEA   1560
NEQVCMYILG ESMSSIRSKC PVEESEASTP PSTLPCLCIH AMTPERVQRL KASRPEQITV   1620
CSSFPLPKYR ITGVQKIQCS QPILFSPKVP AYIHPRKYLV ETPPVDETPE PSAENQSTEG   1680
TPEQPPLITE DETRTRTPEP IIIEEEEDS  ISLLSDGPTH QVLQVEADIH GPPSVSSSSW   1740
SIPHASDFDV DSLSILDTLE GASVTSGATS AETNSYFAKS MEFLARPVPA PRTVFRNPPH   1800
PAPRTRTPSL APSRACSRTS LVSTPPGVNR VITREELEAL TPSRTPSRSV SRTSLVSNPP   1860
GVNRVITREE FEAFVAQQQR RFDAGAYIFS SDTGQGHLQQ KSVRQTVLSE VVLERTELEI   1920
SYAPRLDQEK EELLRKKLQL NPTPANRSRY QSRKVENMKA ITARRILQGL GHYLKAEGKV   1980
ECYRTLHPVP LYSSSVNRAF SSPKVAVEAC NAMLKENFPT VASYCIIPEY DAYLDMVDGA   2040
SCCLDTASFC PAKLRSFPKK HSYLEPTIRS AVPSAIQNTL QNVLAAATKR NCNVTQMREL   2100
PVLDSAAFNV ECFKKYACNN EYWETFKENP IRLTEENVVN YITKLKGPKA AALFAKTHNL   2160
NMLQDIPMDR FVMDLKRDVK VTPGTKHTEE RPKVQVIQAA DPLATAYLCG IHRELVRRLN   2220
AVLLPNIHTL FDMSAEDFDA IIAEHFQPGD CVLETDIASF DKSEDDAMAL TALMILEDLG   2280
VDAELLTLIE AAFGEISSIH LPTKTKFKFG AMMKSGMPLT LFVNTVINIV IASRVLRERL   2340
TGSPCAAFIG DDNIVKGVKS DKLMADRCAT WLNMEVKIID AVVGEKAPYF CGGFILCDSV   2400
TGTACRVADP LKRLFKLGKP LAADDEHDDD RRRALHEEST RWNRVGILSE LCKAVESRYE   2460
TVGTSIIVMA MTTLASSVKS FSYLRGAPIT LYG                                2493

SEQ ID NO: 80         moltype = AA  length = 2494
FEATURE               Location/Qualifiers
REGION                1..2494
                      note = Synthetic polypeptide
source                1..2494
                      mol_type = protein
                      organism = synthetic construct
SEQUENCE: 80
MPEKVHVDIE EDSPFLRALQ RSFPQFEVEA KQVTDNDHAN ARAFSHLASK LIETEVDPSD     60
TILDIGSAPA RRMYSKHKYH CICPMRCAED PDRLYKYATK LKKNCKEITD KELDKKMKEL    120
AAVMSDPDLE TETMCLHDDE SCRYEGQVAV YQDVYAVDGP TSLYHQANKG VRVAYWIGFD    180
TTPFMFKNLA GAYPSYSTNW ADETVLTARN IGLCSSDVME RSRRGMSILR KKYLKPSNNV    240
LFSVGSTIYH EKRDLLRSWH LPSVFHLRGK QNYTCRCETI VSCDGYVVKR IAISPGLYGK    300
PSGYAATMHR EGFLCCKVTD TLNGERVSFP VCTYVPATLC DQMTGILATD VSADDAQKLL    360
VGLNQRIVVN GRTQRNTNTM KNYLLPVVAQ AFARWAKEYK EDQEDERPLG LRDRQLVMGC    420
CWAFRRHKIT SIYKRPDTQT IIKVNSDFHS FVLPRIGSNT LEIGLRTRIR KMLEEHKEPS    480
PLITAEDVQE AKCAADEAKE VREAEELRAA LPPLAADVEE PTLEADVDLM LQEAGAGSVE    540
TPRGLIKVTS YDGEDKIGSY AVLSPQAVLK SEKLSCIHPL AEQVIVITHS GRKGRYAVEP    600
YHGKVVVPEG HAIPVQDFQA LSESATIVYN EREFVNRYLH HIATHGGALN TDEEYYKTVK    660
PSEHDGEYLY DIDRKQCVKK ELVTGLGLTG ELVDPPFHEF AYESLRTRPA APYQVPTIGV    720
YGVPGSGKSG IIKSAVTKKD LVVSAKKENC AEIIRDVKKM KGLDVNARTV DSVLLNGCKH    780
PVETLYIDEA FACHAGTLRA LIAIIRPKKA VLCGDPKQCG FFNMMCLKVH FNHEICTQVF    840
HKSISRRCTK SVTSVVSTLF YDKKMRTTNP KETKIVIDTT GSTKPKQDDL ILTCFRGWVK    900
QLQIDYKGNE IMTAAASQGL TRKGVYAVRY KVNENPLYAP TSEHVNVLLT RTEDRIVWKT    960
LAGDPWIKTL TAKYPGNFTA TIEEWQAEHD AIMRHILERP DPTDVFQNKA NVCWAKALVP   1020
VLKTAGIDMT TEQWNTVDYF ETDKAHSAEI VLNQLCVRFF GLDLDSGLFS APTVPLSIRN   1080
NHWDNSPSPN MYGLNKEVVR QLSRRYPQLP RAVATGRVYD MNTGTLRNYD PRINLVPVNR   1140
RLPHALVLHH NEHPQSDFSS FVSKLKGRTV LVVGEKLSVP GKMVDWLSDR PEATFRARLD   1200
LGIPGDVPKY DIIFVNVRTP YKYHHYQQCE DHAIKLSMLT KKACLHLNPG GTCVSIGYGY   1260
ADRASESIIG AIARLFKFSR VCKPKSSLEE TEVLFVFIGY DRKARTHNPY KLSSTLTNIY   1320
TGSRLHEAGC APSYHVVRGD IATATEGVII NAANSKGQPG GGVCGALYKK FPESFDLQPI   1380
EVGKARLVKG AAKHIIHAVG PNFNKVSEVE GDKQLAEAYE SIAKIVNDNN YKSVAIPLLS   1440
TGIFSGNKDR LTQSLNHLLT ALDTTADVAI YCRDKKWEMT LKEAVARREA VEEICISDD    1500
SSVTEPDAEL VRVHPKSSLA GRKGYSTSDG KTFSYLEGTK FHQAAKDIAE INAMWPVATE   1560
ANEQVCMYIL GESMSSIRSK CPVEESEAST PPSTLPCLCI HAMTPERVQR LKASRPEQIT   1620
VCSSFPLPKY RITGVQKIQC SQPILFSPKV PAYIHPRKYL VETPPVDETP EPSAENQSTE   1680
GTPEQPPLIT EDETRTRTPE PIIIEEEEED SISLLSDGPT HQVLQVEADI HGPPSVSSSS   1740
```

```
WSIPHASDFD VDSLSILDTL EGASVTSGAT SAETNSYFAK SMEFLARPVP APRTVFRNPP 1800
HPAPRTRTPS LAPSRACSRT SLVSTPPGVN RVITREELEA LTPSRTPSRS VSRTSLVSNP 1860
PGVNRVITRE EFEAFVAQQQ RRFDAGAYIF SSDTGQGHLQ QKSVRQTVLS EVVLERTELE 1920
ISYAPRLDQE KEELLRKKLQ LNPTPANRSR YQSRKVENMK AITARRILQG LGHYLKAEGK 1980
VECYRTLHPV PLYSSSVNRA FSSPKVAVEA CNAMLKENFP TVASYCIIPE YDAYLDMVDG 2040
ASCCLDTASF CPAKLRSFPK KHSYLEPTIR SAVPSAIQNT LQNVLAAATK RNCNVTQMRE 2100
LPVLDSAAFN VECFKKYACN NEYWETFKEN PIRLTEENVV NYITKLKGPK AAALFAKTHN 2160
LNMLQDIPMD RFVMDLKRDV KVTPGTKHTE ERPKVQVIQA ADPLATAYLC GIHRELVRRL 2220
NAVLLPNIHT LFDMSAEDFD AIIAEHFQPG DCVLETDIAS FDKSEDDAMA LTALMILEDL 2280
GVDAELLTLI EAAFGEISSI HLPTKTKFKF GAMMKSGMFL TLFVNTVINI VIASRVLRER 2340
LTGSPCAAFI GDDNIVKGVK SDKLMADRCA TWLNMEVKII DAVVGEKAPY FCGGFILCDS 2400
VTGTACRVAD PLKRLFKLGK PLAADDEHDD DRRRALHEES TRWNRVGILS ELCKAVESRY 2460
ETVGTSIIVM AMTTLASSVK SFSYLRGAPI TLYG                             2494

SEQ ID NO: 81          moltype = AA  length = 2492
FEATURE                Location/Qualifiers
REGION                 1..2492
                       note = Synthetic polypeptide
source                 1..2492
                       mol_type = protein
                       organism = synthetic construct
SEQUENCE: 81
MEKVHVDIEE DSPFLRALQR SFPQFEVEAK QVTDNDHANA RAFSHLASKL IETEVDPSDT 60
ILDIGSAPAR RMYSKHKYHC ICPMRCAEDP DRLYKYATKL KKNCKEITDK ELDKKMKELA 120
AVMSDPDLET ETMCLHDDES CRYEGQVAVY QDVYAVDGPT SLYHQANKGV RVAYWIGFDT 180
TPFMFKNLAG AYPSYSTNWA DETVLTARNI GLCSSDVMER SRRGMSILRK KYLKPSNNVL 240
FSVGSTIYHE KRDLLRSWHL PSVFHLRGKQ NYTCRCETIV SCDGYVVKRI AISPGLYGKP 300
SGYAATMHRE GFLCCKVTDT LNGERVSFPV CTYVPATLCD QMTGILATDV SADDAQKLLV 360
GLNQRIVVNG RTQRNTNTMK NYLLPVVAQA FARWAKEYKE DQEDERPLGL RDRQLVMGCC 420
WAFRRHKITS IYKRPDTQTI IKVNSDFHSF VLPRIGSNTL EIGLRTRIRK MLEEHKEPSP 480
LITAEDIQEA KCAADEAKEV REAEELRAAL PPLAADFEEP TLEADVDLML QEAGAGSVET 540
PRGLIKVTSY AGEDKIGSYA VLSPQAVLKS EKLSCIHPLA EQVIVITHSG RKGRYAVEPY 600
HGKVVVPEGH AIPVQDFQAL SESATIVYNE REFVNRYLHH IATHGGALNT DEEYYKTVKP 660
SEHDGEYLYD IDRKQCVKKE LVTGLGLTGE LVDPPFHEPA YESLRTRPAA PYQVPTIGVY 720
GVPGSGKSGI IKSAVTKKDL VVSAKKENCA EIIRDVKKMK GLDVNARTVD SVLLNGCKHP 780
VETLYIDEAF ACHAGTLRAL IAIIRPKKAV LCGDPKQCGF FNMMCLKVHF NHEICTQVFH 840
KSISRRCTKS VTSVVSTLFY DKRMTTNPK ETKIVIDTTG STKPKQDDLI LTCFRGWVKQ 900
LQIDYKGNEI MTAAASQGLT RKGVYAVRYK VNENPLYAPT SEHVNVLLTR TEDRIVWKTL 960
AGDPWIKILT AKYPGNFTAT IEEWQAEHDA IMRHILERPD PTDVFQNKAN VCWAKALVPV 1020
LKTAGIDMTT EQWNTVDYFE TDKAHSAEIV LNQLCVRFFG LDLDSGLFSA PTVPLSIRNN 1080
HWDNSPSPNM YGLNKEVVRQ LSRRYPQLPR AVATGRVYDM NTGTLRNYDP RINLVPVNRR 1140
LPHALVLHHN EHPQSDFSSF VSKLKGRTVL VVGEKLSVPG KKVDWLSDQP EATFRARLDL 1200
GIPGDVPKYD IVFINVRTPY KYHHYQQCED HAIKLSMLTK KACLHLNPGG TCVSIGYGYA 1260
DRASESIIGA IARQFKFSRV CKPKSSHEET EVLFVFIGYD RKARTHNPYK LSSTLTNIYT 1320
GSRLHEAGCA PSYHVRGDI ATATEGVIIN AANSKGQPGG GVCGALYKKF PESFDLQPIE 1380
VGKARLVKGA AKHIIHAVGP NFNKVSEVEG DKQLAEAYES IAKIVNDNNY KSVAIPLLST 1440
GIFSGNKDRL TQSLNHLLTA LDTTDADVAI YCRDKKWEMT LKEAVARREA VEEICISDDS 1500
SVTEPDAELV RVHPKSSLAG RKGYSTSDGK TFSYLEGTKF HQAAKDIAEI NAMWPVATEA 1560
NEQVCMYILG ESMSSIRSKC PVEESEASTP PSTLPCLCIH AMTEPERVQRL KASRPEQITV 1620
CSSFPLPKYR ITGVQKIQCS QPILFSPKVP AYIHPRKYLV ETPPVEETPE SPAENQSTEG 1680
TPEQPALVNV DATRTRMPEP IIIEEEEEDS ISLLSDGPTH QVLQVEADIH GSPSVSSSSW 1740
SIPHASDFDV DSLSILDTLD GASVTSGAVS AETNSYFARS MEFRARPVPA PRTVFRNPPH 1800
PAPRTRTPPL AHSRASSRTS LVSTPPGVNR VITREELEAL TPSRAPSRSA SRTSLVSNPP 1860
GVNRVITREE FEAFVAQQQR FDAGAYIFSS DTGQGHLQQK SVRQTVLSEV VLERTELEIS 1920
YAPRLDQEEE ELLRKKLQLN PTPANRSRYQ SRRVENMKAI TARRILQGLG HYLKAEGKVE 1980
CYRTLHPVPL YSSSVNRAFS SPKVAVEACN AMLKENFPTV ASYCIIPEYD AYLDMVDGAS 2040
CCLDTASFCP AKLRSFPKKH SYLEPTIRSA VPSAIQNTLQ NVLAAATKRN CNVTQMRELP 2100
VLDSAAFNVE CFKKYACNNE YWETFKENPI RLTEENVVNY ITKLKGPKAA ALFAKTHNLN 2160
MLQDIPMDRF VMDLKRDVKV TPGTKHTEER PKVQVIQAPL ATADLCGI HRELVRRLNA 2220
VLLPNIHTLF DMSAEDFDAI IAEHFQPGDC VLETDIASFD KSEDDAMALT ALMILEDLGV 2280
DAELLTLIEA AFGEISSIHL PTKTKFKFGA MMKSGMFLTL FVNTVINIVI ASRVLRERLT 2340
GSPCAAFIGD DNIVKGVKSD KLMADRCATW LNMEVKIIDA VVGEKAPYFC GGFILCDSVT 2400
GTACRVADPL KRLFKLGKPL AVDDEHDDDR RRALHEESTR WNRVGILPEL CKAVESRYET 2460
VGTSIIVMAM TTLASSVKSF SYLRGAPITL YG                               2492

SEQ ID NO: 82          moltype = DNA  length = 146
FEATURE                Location/Qualifiers
misc_feature           1..146
                       note = Synthetic polynucleotide
source                 1..146
                       mol_type = other DNA
                       organism = synthetic construct
SEQUENCE: 82
aggaaactta agtcaacaca acatatacaa aacaaacgaa tctcaagcaa tcaagcattc 60
tacttctatt gcagcaattt aaatcatttc ttttaaagca aaagcaattt tctgaaaatt 120
ttcaccattt acgaacgata gccacc                                     146

SEQ ID NO: 83          moltype = DNA  length = 270
FEATURE                Location/Qualifiers
```

```
misc_feature         1..270
                     note = Synthetic polynucleotide
source               1..270
                     mol_type = other DNA
                     organism = synthetic construct
SEQUENCE: 83
actcgagcta gtgactgact aggatctggt taccactaaa ccagcctcaa gaacacccga    60
atggagtctc taagctacat aataccaact tacacttaca aaatgttgtc ccccaaaatg   120
tagccattcg tatctgctcc taataaaaag aaagtttctt cacattctag aaaaaaaaaa   180
aaaaaaaaaa aaaaaaaaaa aaaaaaaaaa aaaaaaaaaa aaaaaaaaaa aaaaaaaaaa   240
aaaaaaaaaa aaaaaaaaaa aaaaaaaaaa                                    270

SEQ ID NO: 84        moltype = RNA  length = 1653
FEATURE              Location/Qualifiers
misc_feature         1..1653
                     note = Synthetic polynucleotide
source               1..1653
                     mol_type = other RNA
                     organism = synthetic construct
SEQUENCE: 84
atggaagatg ccaaaaacat taagaagggc ccagcgccat tctacccact cgaagacggg    60
accgccggcg agcagctgca caaagccatg aagcgctacg ccctggtgcc cggcaccatc   120
gcctttaccg acgcacatat cgaggtggac attacctacg ccgagtactt cgagatgagc   180
gttcggctgg cagaagctat gaagcgctat gggctgaata caaaccatcg gatcgtggtg   240
tgcagcgaga atagcttgca gttcttcatg cccgtgttgg tgccctgtt catcggtgtg    300
gctgtggccc cagctaacga catctacaac gagcgcgagc tgctgaacag catgggcatc   360
agccagccca ccgtcgtatt cgtgagcaag aaagggctgc aaaagatcct caacgtgcaa   420
aagaagctac cgatcataca aaagatcatc atcatggata gcaagaccga ctaccagggc   480
ttccaaagca tgtacacctt cgtgacttcc catttgccac ccggcttcaa cgagtacgac   540
ttcgtgcccg agagcttcga ccgggacaaa accatcgccc tgatcatgaa cagtagtggc   600
agtaccggat tgcccaaggg cgtagcccta ccgcaccgca ccgcttgtgt ccgattcagt   660
catgcccgcg accccatctt cggcaaccag atcatccccg acaccgctat cctcagcgtg   720
gtgccatttc accacggctt cggcatgttc accacgctgg gctacttgat ctgcggcttt   780
cgggtcgtgc tcatgtaccg cttcgaggag gagctattct tgcgcagctt gcaagactat   840
aagattcaat ctgccctgct ggtgcccaca ctatttagct tcttcgctaa gagcactctc   900
atcgacaagt acgacctaag caacttgcac gagatcgcca cggcggggc gccgctcagc   960
aaggaggtag gtgaggccgt ggccaaacgc ttccacctac caggcatccg acagggctac  1020
ggcctgacag aaacaaccag cgccattctg atcacccccg aaggggacga caagcctggc  1080
gcagtaggca aggtggtgcc cttcttcgag gctaaggtgg tggacttgga caccggtaag  1140
acactgggtg tgaaccagcg cggcgagctg tgcgtccgtg gccccatgat catgagcggc  1200
tacgttaaca ccccgaggc tacaaacgct ctcatcgaca aggacggctg gctgcacagc  1260
ggcgacatcg cctactggga cgaggacgag cacttcttca tcgtggaccg gctgaagtcc  1320
ctgatcaaat acaagggcta ccaggtagcc ccagccgaac tggagagcat cctgctgcaa  1380
caccccaaca tcttcgacgc cggggtcgcc ggcctgcccg acgacgatgc cggcgagctg  1440
cccgccgcag tcgtcgtgct ggaacacggt aaaaccatga ccgagaagga gatcgtggac  1500
tatgtggcca gccaggttac aaccgccaag aagctgcgcg gtggtgttgt gttcgtggac  1560
gaggtgccta aggactgac cggcaagttg gacgcccgca agatccgcga gattctcatt  1620
aaggccaaga agggcggcaa gatcgccgtg taa                               1653

SEQ ID NO: 85        moltype = RNA  length = 1653
FEATURE              Location/Qualifiers
misc_feature         1..1653
                     note = Synthetic polynucleotide
source               1..1653
                     mol_type = other RNA
                     organism = synthetic construct
SEQUENCE: 85
atggaagatg ccaaaaacat taagaagggc ccagcgccat tctacccact cgaagacggg    60
accgccggcg agcagctgca caaagccatg aagcgctacg ccctggtgcc cggcaccatc   120
gcctttaccg acgcacatat cgaggtggac attacctacg ccgagtactt cgagatgagc   180
gttcggctgg cagaagctat gaagcgctat gggctgaata caaaccatcg gatcgtggtg   240
tgcagcgaga atagcttgca gttcttcatg cccgtgttgg tgccctgtt catcggtgtg    300
gctgtggccc cagctaacga catctacaac gagcgcgagc tgctgaacag catgggcatc   360
agccagccca ccgtcgtatt cgtgagcaag aaagggctgc aaaagatcct caacgtgcaa   420
aagaagctac cgatcataca aaagatcatc atcatggata gcaagaccga ctaccagggc   480
ttccaaagca tgtacacctt cgtgacttcc catttgccac ccggcttcaa cgagtacgac   540
ttcgtgcccg agagcttcga ccgggacaaa accatcgccc tgatcatgaa cagtagtggc   600
agtaccggat tgcccaaggg cgtagcccta ccgcaccgca ccgcttgtgt ccgattcagt   660
catgcccgcg accccatctt cggcaaccag atcatccccg acaccgctat cctcagcgtg   720
gtgccatttc accacggctt cggcatgttc accacgctgg gctacttgat ctgcggcttt   780
cgggtcgtgc tcatgtaccg cttcgaggag gagctattct tgcgcagctt gcaagactat   840
aagattcaat ctgccctgct ggtgcccaca ctatttagct tcttcgctaa gagcactctc   900
atcgacaagt acgacctaag caacttgcac gagatcgcca cggcggggc gccgctcagc   960
aaggaggtag gtgaggccgt ggccaaacgc ttccacctac caggcatccg acagggctac  1020
ggcctgacag aaacaaccag cgccattctg atcacccccg aaggggacga caagcctggc  1080
gcagtaggca aggtggtgcc cttcttcgag gctaaggtgg tggacttgga caccggtaag  1140
acactgggtg tgaaccagcg cggcgagctg tgcgtccgtg gccccatgat catgagcggc  1200
tacgttaaca ccccgaggc tacaaacgct ctcatcgaca aggacggctg gctgcacagc  1260
ggcgacatcg cctactggga cgaggacgag cacttcttca tcgtggaccg gctgaagtcc  1320
```

```
ctgatcaaat acaagggcta ccaggtagcc ccagccgaac tggagagcat cctgctgcaa    1380
caccccaaca tcttcgacgc cggggtcgcc ggcctgcccg acgacgatgc cggcgagctg    1440
cccgccgcag tcgtcgtgct ggaacacggt aaaaccatga ccgagaagga gatcgtggac    1500
tatgtggcca gccaggttac aaccgccaag aagctgcgcg tggtgttgt gttcgtggac     1560
gaggtgccta aaggactgac cggcaagttg gacgcccgca gatccgcga gattctcatt     1620
aaggccaaga agggcggcaa gatcgccgtg taa                                 1653

SEQ ID NO: 86          moltype = RNA   length = 1653
FEATURE                Location/Qualifiers
misc_feature           1..1653
                       note = Synthetic polynucleotide
source                 1..1653
                       mol_type = other RNA
                       organism = synthetic construct
SEQUENCE: 86
atggaagatg ccaaaaacat taagaagggc ccagcgccat tctacccact cgaagacggg    60
accgccggcg agcagctgca caaagccatg aagcgctacg ccctggtgcc cggcaccatc    120
gcctttaccg acgcacatat cgaggtggac attacctacg ccgagtactt cgagatgagc    180
gttcggctgg cagaagctat gaagcgctat gggctgaata caaaccatcg gatcgtggtg    240
tgcagcgaga atagcttgca gttcttcatg cccgtgttgg gtgccctgtt catcggtgtg    300
gctgtggccc cagctaacga catctacaac gagcgcgagc tgctgaacag catgggcatc    360
agccagccca ccgtcgtatt cgtgagcaag aaagggctga aaaagatcct caacgtgcaa    420
aagaagctac cgatcataca aaagatcatc atcatggata gcaagaccga ctaccagggc    480
ttccaaagca tgtacacctt cgtgacttcc catttgccac ccggcttcaa cgagtacgac    540
ttcgtgcccg agagcttcga ccgggacaaa accatcgccc tgatcatgaa cagtagtggc    600
agtaccggat tgcccaaggg cgtagcccta ccgcaccgca ccgcttgtgt ccgattcagt    660
catgcccgcg accccatctt cggcaaccag atcatcccg acaccgctat cctcagcgtg    720
gtgccatttc accacggctt cggcatgttc accacgctgg gctacttgat ctgcggcttt    780
cgggtcgtgc tcatgtaccg cttcgaggag gagctattct tgcgcagctt gcaagactat    840
aagattcaat ctgccctgct ggtgcccaca ctatttagct tcttcgctaa gagcactctc    900
atcgacaagt acgacctaag caacttgcac gagatcgcca gcggcgggc gccgctcagc    960
aaggaggtag gtgaggccgt ggccaaacgc ttccacctac caggcatccg acagggctac    1020
ggcctgacga aacaaccagc gccattctg atcacccccg aaggggacga caagcctggc    1080
gcagtaggca aggtggtgcc cttcttcgag gctaaggtgg tggacttgga caccggtaag    1140
acactggggt gaaccagcg cggcgagctg tgcgtccgtg gcccatgat cgatgagcggc    1200
tacgttaaca accccgaggc tacaaacgct ctcatcgaca aggacggctg gctgcacagc    1260
ggcgacatcg cctactggga cgaggacgag cacttcttca tcgtggaccg gctgaagtcc    1320
ctgatcaaat acaagggcta ccaggtagcc ccagccgaac tggagagcat cctgctgcaa    1380
caccccaaca tcttcgacgc cggggtcgcc ggcctgcccg acgacgatgc cggcgagctg    1440
cccgccgcag tcgtcgtgct ggaacacggt aaaaccatga ccgagaagga gatcgtggac    1500
tatgtggcca gccaggttac aaccgccaag aagctgcgcg tggtgttgt gttcgtggac     1560
gaggtgccta aaggactgac cggcaagttg gacgcccgca gatccgcga gattctcatt     1620
aaggccaaga agggcggcaa gatcgccgtg taa                                 1653

SEQ ID NO: 87          moltype = RNA   length = 57
FEATURE                Location/Qualifiers
misc_feature           1..57
                       note = Synthetic polynucleotide
source                 1..57
                       mol_type = other RNA
                       organism = synthetic construct
SEQUENCE: 87
atgaagttgg tggttgtggg ggccgggggt gttggcaaaa gcgcccttac aatttga        57

SEQ ID NO: 88          moltype = RNA   length = 66
FEATURE                Location/Qualifiers
misc_feature           1..66
                       note = Synthetic polynucleotide
source                 1..66
                       mol_type = other RNA
                       organism = synthetic construct
SEQUENCE: 88
atggatccta gacgctacgc cccaatgatc cgaccagcaa aactcgatgt acttccgagg    60
aactga                                                               66

SEQ ID NO: 89          moltype = RNA   length = 837
FEATURE                Location/Qualifiers
misc_feature           1..837
                       note = Synthetic polynucleotide
source                 1..837
                       mol_type = other RNA
                       organism = synthetic construct
SEQUENCE: 89
atgagagtga cagcccctag aaccttactg cttctgcttt ggggagctgt tgctctgaca    60
gagacatggg ctggatctct gagcgaggtg accggccagg gcctgtgcat cggcgccgtg    120
cccaagaccc accaggtgct gtgcaacacc cccagaagac cagcgacgg cagctactac    180
ctggccgctc ccaccggcac cacctgggcc tgcagcaccg gcctgacccc ttgcatcagc    240
accaccatcc tgaacctgac caccgactac tgcgtgctgg tggagctgtg gcccagggtg    300
acctaccaca gccccagcta cgcctaccac cagttcgaga ggagggccaa gtacaagagg    360
```

```
gagcccgtga gcctgaccct ggccctgctg ctgggcggcc tgacaatggg cggcatcgcc   420
gccggcgtgg gcaccggcac caccgccctg gtggccaccc agcagttcca gcagctgcag   480
gccgccatgc acgacgacct gaaggaggtg gagaagtcca tcaccaacct ggagaagtcc   540
ctgaccagcc tgagcgaggt ggtgctgcag aacaggaggg gcctggacct gctgttcctg   600
aaggagggcg gcctgtgcgc cgccctgaag gaggagtgct gcctgtacgc cgaccacacc   660
ggcctggtga tcgtgggcat tgtcgctggc ctggccgtcc tcgccgtggt ggtgattgga   720
gctgtggtcg cagctgttat gtgcagaaga aagtcatccg gcggaaaggg aggctcctac   780
tctcaggctg cttctgctac agtgcctaga gctcttatgt gtttatctca gctgtaa      837

SEQ ID NO: 90             moltype = RNA  length = 378
FEATURE                   Location/Qualifiers
misc_feature              1..378
                          note = Synthetic polynucleotide
source                    1..378
                          mol_type = other RNA
                          organism = synthetic construct
SEQUENCE: 90
atgagagtga cagcccctag aaccttactg cttctgcttt ggggagctgt tgctctgaca   60
gagacatggg ctggatctta ccacagcccc agctacgcct accaccagtt cgagaggggg   120
ggaggaggct ccgggggagg aggctccctg aagatcagcc aggccgtgca cgccgcccac   180
gccgagatca acgaggccgg ccgggaggtg atcgtgggca ttgtcgctgg cctggccgtc   240
ctcgccgtgg tggtgattgg agctgtggtc gcagctgtta tgtgcagaag aaagtcatcc   300
ggcggaaagg gaggctccta ctctcaggct gcttctgcta cagtgcctag agctcttatg   360
tgtttatctc agctgtaa                                                 378

SEQ ID NO: 91             moltype = RNA  length = 876
FEATURE                   Location/Qualifiers
misc_feature              1..876
                          note = Synthetic polynucleotide
source                    1..876
                          mol_type = other RNA
                          organism = synthetic construct
SEQUENCE: 91
atgagagtga cagcccctag aaccttactg cttctgcttt ggggagctgt tgctctgaca   60
gagacatggg ctggatctct gagcgaggtg accggccagg gcctgtgcat cggcgccgtg   120
cccaagaccc accaggtgct gtgcaacacc cccagaagga ccagcgacgg cagctactac   180
ctggccgctc ccaccggcac cacctgggcc tgcagcaccg gcctgacccc ttgcatcagc   240
accaccatcc tgaacctgac caccgactac tgcgtgctgg tggagctgtg gcccagggtg   300
acctaccaca gcccagcta cgcctaccac cagttcgaga ggggccaa gtacaagagg      360
gagcccgtga gcctgaccct ggccctgctg ctgggcggcc tgacaatggg cggcatcgcc   420
gccggcgtgg gcaccggcac caccgccctg gtggccaccc agcagttcca gcagctgcag   480
gccgccatgc acgacgacct gaaggaggtg gagaagtcca tcaccaacct ggagaagtcc   540
ctgaccagcc tgagcgaggt ggtgctgcag aacaggaggg gcctggacct gctgttcctg   600
aaggagggcg gcctgtgcgc cgccctgaag gaggagtgct gcctgtacgc cgaccacacc   660
ggcctggtga tcgtgggcat tgtcgctggc ctggccgtcc tcgccgtggt ggtgattgga   720
gctgtggtcg cagctgttat gtgcagaaga aagtcatccg gcggaaaggg aggctcctac   780
tctcaggctg cttctgctac agtgcctaga gctcttatgt gtttatctca gctgggcggc   840
ggaggcagcg actacaagga cgacgatgac aagtaa                             876

SEQ ID NO: 92             moltype = RNA  length = 417
FEATURE                   Location/Qualifiers
misc_feature              1..417
                          note = Synthetic polynucleotide
source                    1..417
                          mol_type = other RNA
                          organism = synthetic construct
SEQUENCE: 92
atgagagtga cagcccctag aaccttactg cttctgcttt ggggagctgt tgctctgaca   60
gagacatggg ctggatctta ccacagcccc agctacgcct accaccagtt cgagaggggg   120
ggaggaggct ccgggggagg aggctccctg aagatcagcc aggccgtgca cgccgcccac   180
gccgagatca acgaggccgg ccgggaggtg atcgtgggca ttgtcgctgg cctggccgtc   240
ctcgccgtgg tggtgattgg agctgtggtc gcagctgtta tgtgcagaag aaagtcatcc   300
ggcggaaagg gaggctccta ctctcaggct gcttctgcta cagtgcctag agctcttatg   360
tgtttatctc agctgggcgg cggaggcagc gactacaagg acgacgatga caagtaa      417

SEQ ID NO: 93             moltype = AA  length = 550
FEATURE                   Location/Qualifiers
REGION                    1..550
                          note = Synthetic polypeptide
source                    1..550
                          mol_type = protein
                          organism = synthetic construct
SEQUENCE: 93
MEDAKNIKKG PAPFYPLEDG TAGEQLHKAM KRYALVPGTI AFTDAHIEVD ITYAEYFEMS   60
VRLAEAMKRY GLNTNHRIVV CSENSLQFFM PVLGALFIGV AVAPANDIYN ERELLNSMGI   120
SQPTVVFVSK KGLQKILNVQ KKLPIIQKII IMDSKTDYQG FQSMYTFVTS HLPPGFNEYD   180
FVPESFDRDK TIALIMNSSG STGLPKGVAL PHRTACVRFS HARDPIFGNQ IIPDTAILSV   240
VPFHHGFGMF TTLGYLICGF RVVLMYRFEE ELFLRSLQDY KIQSALLVPT LFSFFAKSTL   300
IDKYDLSNLH EIASGGAPLS KEVGEAVAKR FHLPGIRQGY GLTETTSAIL ITPEGDDKPG   360
```

| | |
|---|---|
| AVGKVVPFFE AKVVDLDTGK TLGVNQRGEL CVRGPMIMSG YVNNPEATNA LIDKDGWLHS | 420 |
| GDIAYWDEDE HFFIVDRLKS LIKYKGYQVA PAELESILLQ HPNIFDAGVA GLPDDDAGEL | 480 |
| PAAVVVLEHG KTMTEKEIVD YVASQVTTAK KLRGGVVFVD EVPKGLTGKL DARKIREILI | 540 |
| KAKKGGKIAV | 550 |

```
SEQ ID NO: 94            moltype = AA   length = 18
FEATURE                  Location/Qualifiers
REGION                   1..18
                         note = Synthetic polypeptide
source                   1..18
                         mol_type = protein
                         organism = synthetic construct
SEQUENCE: 94
MKLVVVGAGG VGKSALTI                                                 18

SEQ ID NO: 95            moltype = AA   length = 21
FEATURE                  Location/Qualifiers
REGION                   1..21
                         note = Synthetic polypeptide
source                   1..21
                         mol_type = protein
                         organism = synthetic construct
SEQUENCE: 95
MDPRRYAPMI RPAKLDVLPR N                                             21

SEQ ID NO: 96            moltype = AA   length = 278
FEATURE                  Location/Qualifiers
REGION                   1..278
                         note = Synthetic polypeptide
source                   1..278
                         mol_type = protein
                         organism = synthetic construct
SEQUENCE: 96
MRVTAPRTLL LLLWGAVALT ETWAGSLSEV TGQGLCIGAV PKTHQVLCNT TQKTSDGSYY    60
LAAPTGTTWA CSTGLTPCIS TTILNLTTDY CVLVELWPRV TYHSPSYAYH QFERRAKYKR  120
EPVSLTLALL LGGGLTMGGIA AGVGTGTTAL VATQQFQQLQ AAMHDDLKEV EKSITNLEKS  180
LTSLSEVVLQ NRRGLDLLFL KEGGLCAALK EECCLYADHT GLVIVGIVAG LAVLAVVVIG  240
AVVAAVMCRR KSSGGKGGSY SQAASATVPR ALMCLSQL                          278

SEQ ID NO: 97            moltype = AA   length = 125
FEATURE                  Location/Qualifiers
REGION                   1..125
                         note = Synthetic polypeptide
source                   1..125
                         mol_type = protein
                         organism = synthetic construct
SEQUENCE: 97
MRVTAPRTLL LLLWGAVALT ETWAGSYHSP SYAYHQFERG GGGSGGGGSL KISQAVHAAH    60
AEINEAGREV IVGIVAGLAV LAVVVIGAVV AAVMCRRKSS GGKGGSYSQA ASATVPRALM  120
CLSQL                                                              125

SEQ ID NO: 98            moltype = AA   length = 291
FEATURE                  Location/Qualifiers
REGION                   1..291
                         note = Synthetic polypeptide
source                   1..291
                         mol_type = protein
                         organism = synthetic construct
SEQUENCE: 98
MRVTAPRTLL LLLWGAVALT ETWAGSLSEV TGQGLCIGAV PKTHQVLCNT TQKTSDGSYY    60
LAAPTGTTWA CSTGLTPCIS TTILNLTTDY CVLVELWPRV TYHSPSYAYH QFERRAKYKR  120
EPVSLTLALL LGGGLTMGGIA AGVGTGTTAL VATQQFQQLQ AAMHDDLKEV EKSITNLEKS  180
LTSLSEVVLQ NRRGLDLLFL KEGGLCAALK EECCLYADHT GLVIVGIVAG LAVLAVVVIG  240
AVVAAVMCRR KSSGGKGGSY SQAASATVPR ALMCLSQLGG GGSDYKDDDD K           291

SEQ ID NO: 99            moltype = AA   length = 138
FEATURE                  Location/Qualifiers
REGION                   1..138
                         note = Synthetic polypeptide
source                   1..138
                         mol_type = protein
                         organism = synthetic construct
SEQUENCE: 99
MRVTAPRTLL LLLWGAVALT ETWAGSYHSP SYAYHQFERG GGGSGGGGSL KISQAVHAAH    60
AEINEAGREV IVGIVAGLAV LAVVVIGAVV AAVMCRRKSS GGKGGSYSQA ASATVPRALM  120
CLSQLGGGGS DYKDDDDK                                                138

SEQ ID NO: 100           moltype = RNA  length = 9690
FEATURE                  Location/Qualifiers
```

```
misc_feature         1..9690
                     note = Synthetic polynucleotide
source               1..9690
                     mol_type = other RNA
                     organism = synthetic construct
SEQUENCE: 100
atgggcggcg catgagagaa gcccagacca attacctacc caaaatggag aaagttcacg    60
ttgacatcga ggaagacagc ccattcctca gagctttgca gcggagcttc ccgcagtttg   120
aggtagaagc caagcaggtc actgataatg accatgctaa tgccagagcg ttttcgcatc   180
tggcttcaaa actgatcgaa acggaggtgg acccatccga cacgatcctt gacattggaa   240
gtgcgcccgc ccgcagaatg tattctaagc acaagtatca ttgtatctgt ccgatgagat   300
gtgcggaaga tccggacaga ttgtataagt atgcaactaa gctgaagaaa aactgtaagg   360
aaataactga taaggaattg acaagaaaaa tgaaggagct ggccgccgtc atgagcgacc   420
ctgacctgga aactgagact atgtgcctcc acgacgacga gtcgtgtcgc tacgaaggcg   480
aagtcgctgt ttaccaggat gtatacgccg tcgacggccc caccagcctg taccaccagg   540
ccaacaaggg cgtgagggtg gcctactgga tcggcttcga caccacaccc ttcatgttca   600
agaacctggc cggcgcctac cccagctaca gcaccaactg gccgacgag accgtgctga   660
ccgccaggaa catcggcctg tgcagcagcg acgtgatgga ggaggcatga   720
gcatcctgag gaagaaatac ctgaagccca gcaacaacgt gctgttcagc gtgggcagca   780
ccatctacca cgagaagagg gacctgctca ggagctggca cctgcccagc gtgttccacc   840
tgaggggcaa gcagaactac acctgcaggt gcgagaccat cgtgagctgc gacggctacg   900
tggtgaagag gatcgccatc agcccccggcc tgtacggcaa gccagcggcc tacgccgcta   960
caatgcacag ggagggcttc ctgtgctgca aggtgaccga cacctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgccccg    1200
tggtggccca ggcttccgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacc cctggagatc ggcctgaagga  1440
cccgatcga gaagatgctg gaggaacaca aggagcccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga cccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccaccccact ggccgagcag gtgatcgtga  1800
tcacccacac cggcaggaag ggcaggtacg ccgtggagcc ctaccacggc aaggtggtcg  1860
tgcccgaggg ccacgccatc cccgtgcagg acttccagcc cctgagcgag agcgccacca  1920
tcgtgtacaa cgagagggag ttcgtgaaca gtacctgca ccatatccgc acccacggcg  1980
gagccctgaa caccgacgag gaatactaca gaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagaccgc cgctccctac caggtgccca ccatcgcgt gtacggcgtg cccggcacgg  2220
gaaagagcgg catcatcaag agcgccgtga ccaagaaaga cctggtggtc agcgccaaga  2280
aagagaactg cgccgagatc atcagggacg tgaagaagat gaaggccctg gacgtgaacg  2340
cgcgcaccgt ggacagcgtg ctgctgaacg gctgcaagca cccccgtggag accctgtaca  2400
tcgacgaggc cttcgcttgc cacgccgcca ccctgagggc cctgatcgcc atcatcaggc  2460
ccaagaaagc cgtgctgtgc ggcgacccca gcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagccagcac  2700
aggacgacct gatcctgacc tgcttcaggg gctgggtgaa gcagctgcag atcgactaca  2760
agggcaacga gatcatgacc gccgctgcca gccaggcct gaccaggaag ggcgtgtacg  2820
ccgtgaggta caaggtgaac gagaacccac tgtacgctcc caccagcgag cacgtgaacg  2880
tgctgcgac caggaccgag gacaggatcg tgtggaagac cctggccggc gacccctgga  2940
tcaagaccct gaccgccaag taccccggca acttcaccgc caccatcgaa gagtggcagg  3000
ccgagcacga cgccatcatg aggcacatcc tggagaggcc cgaccccacc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcacccgtga  3420
ggaactacga cccaggatc aacctggtgc ccgtgaacag gcggctgccc cacgccctga  3480
tgctgcacca caacgagcac ccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc ccggcgacg  3660
tgcccaagta cgacatcatc ttcgtgaacg tcaggaccct atacaagtac caccattacc  3720
agcagtgcga ggaccacgcc atcaagctga gcatgctgac caagaaggcc tgcctgcacc  3780
tgaaccccgg aggcacctgc gtgagcatcg ctacggcta cgccgacagg gccagcgaga  3840
gcatcattgg cgccatcgcc aggctgttca gttcagcagc ggtgtgcaaa cccaagagca  3900
gcctggagga accgaggtg ctgttcgtgt tcatcggcta cgaccggaag gccagaccct  3960
acaaccccta caagctgagc agcaccctga caaacatcta caccgcagc aggctgcacg  4020
aggccgctg cgccccagc taccacgtgg tcagggcga tatcgccacc gaccaccgga  4080
gcgtgatcat caacgctgcc aacagcaagg ccagcccgg aggcgagtg tgcggccccc  4140
tgtacaagaa gtccccgag agcttcgacc tgcagcccat cgaggtgggc aaggccaggc  4200
tggtgaaggg cgccgctaag cacatcatcc acgccgtgggg cccaacttc aacaggtga   4260
gcgaggtgga aggcgacaag cagctggccg aagcctacga gagcatcgcc aagatcgtga  4320
acgacaataa ctacaagagc gtggccatcc cactgctcag caccggcatc ttcagcggca  4380
```

```
acaaggacag gctgacccag agcctgaacc acctgctcac cgccctggac accaccgatg   4440
ccgacgtggc catctactgc agggacaaga agtgggagat gaccctgaag gaggccgtgg   4500
ccaggcggga ggccgtggaa gagatctgca tcagcgacga ctccagcgtg accgagcccg   4560
acgccgagct ggtgagggtg caccccaaga gctccctggc cggcaggaag ggctacagca   4620
ccagcgacga caagacctcc agctacctgg agggcaccaa gttccaccag gccgctaagg   4680
acatcgccga gatcaacgct atgtggcccg tggccaccga ggccaacgag caggtgtgca   4740
tgtacatcct gggcgagagc atgtccagca tcaggagcaa gtgccccgtg gagaaagcg   4800
aggccagcac accacccagc accctgccct gcctgtgcat ccacgctatg acacccgaga   4860
gggtgcagcg gctgaaggcc agcaggcccg agcagatcac cgtgtgcagc tccttcccac   4920
tgcccaagta caggatcacc ggcgtgcaga agatccagtg cagccagccc atcctgttca   4980
gcccaaaggt gcccgcctac atccacccca ggaagtacct ggtggagacc ccacccgtgg   5040
acgagacacc cgagccaagc gccgagaacc agagcaccga gggcacaccc gagcagccac   5100
ccctgatcac cgaggacgag acaaggaccc ggaccccaga gcccatcatt atcgaggaag   5160
aggaagagga cagcatcagc ctgctgagcg acggcccaca ccaccaggtg ctgcaggtgg   5220
aggccgacat ccacgcccca cccagcgtgt ccagctccag ctggagcatc ccacacgcca   5280
gcgacttcga cgtggacagc ctgagcatcc tggacaccct ggagggcgcc agcgtgacct   5340
ccggcgccac cagcgccgag accaacagct acttcgccaa gagcatggag ttcctggcca   5400
ggcccgtgcc agctcccagg accgtgttca ggaacccacc ccaccagct ccacaggacca   5460
ggaccccaag cctggctccc agcagggcct gcagcaggac cagcctggtg agcaccccac   5520
ccggcgtgaa cagggtgatc accagggagg aactggaggc cctgacaccc agcaggaccc   5580
ccagcaggtc cgtgagcagg actagtctgg tgtccaaccc acccggcgtg aacagggtga   5640
tcaccaggga ggaattcgag gccttcgtgg cccagcaaca gagacggttc gacgccggcg   5700
cctacatctt cagcagcgac accgccagg gacaccgtga gcaaaagagc gtgaggcaga   5760
ccgtgctgag cgaggtggtg ctggagagga ccgagctgga aatcagctac gccccaggc   5820
tggaccagga gaaggaggaa ctgctcagga agaaactgca gctgaacccc accccagcca   5880
acaggacgag gtaccagagc aggaaggtga agaacatgaa ggccatcaac gccaggcgga   5940
tcctgcaggg cctgggacac tacctgaagg ccgagggcaa ggtggagtgc tacaggaccc   6000
tgcaccccgt gccactgtac agctccagcg tgaacagggc cttctccagc cccaaggtgg   6060
ccgtggaggc ctgcaacgct atgctgaagg agaacttccc caccgtggcc agctactgca   6120
tcatcccgga gtacgacgcc tacctggaca tggtggacga cgccagctgc tgcctggaca   6180
ccgccagctt ctgccccgcc aagctgagga gcttcccaa gaaacacgca tacctggagc   6240
ccaccatcag gagcgccgtg cccagcgcca tccagaacac cctgcagaac gtgctggccg   6300
ctgccaccaa gaggaactgc aacgtgaccc agatgaggga gctgcccgtg ctggacagcg   6360
ctgccttcaa cgtggagtgc ttcaagaaat acgcctgcaa caacgagtac tgggagaact   6420
tcaaggagaa ccccatcagg ctgaccgaag agaacgtggt gaactacatc accaagctga   6480
agggccccaa ggccgctgcc ctgttcgcta gacccacaa cctgaacatg ctgcaggaca   6540
tcccaatgga caggttcgtg atggacctga agggacgt gaaggtgaca cccggcacca   6600
agcacaccga ggagaggccc aaggtgcagg tgatccaggc cgctgaccca ctggccaccg   6660
cctacctgtg cggcatccac aagggactga tgaggccgtg tgctgctgcca   6720
acatccacac cctgttcgac atgagcgcg aggacttcga cgccatcatc gccgagcact   6780
tccagcccgg cgactgcgtg ctggagaccg acatcgccag cttcgacaag agcgaggatg   6840
acgctatggc cctgaccgct ctgatgatcc tggaggacct gggcgtggac gccgagctgc   6900
tcaccctgat cgaggctgcc ttcggcgaga tcagctccat ccacctgccc accaagacca   6960
agttcaagtt cggcgctatg atgaaaagcg aatgttcctc gacctgttc gtgaacaccg   7020
tgatcaacat tgtgatcgcc agcagggtgc tgcgggagag gctgaccggc agcccctgcg   7080
ctgccttcat cggcgacgac aacatcgtga agggcgtgaa aagcgacaag ctgatggccg   7140
acaggtgcgc cacctggctg aacatggagg tgaagatcat cgacgccgtg gtggggcgaga   7200
aggcccccta cttctgcggc ggattcatcc tgtgcgacag cgtgaccggc accgcctgca   7260
gggtggccga ccccctgaag aggctgttca agctgggcaa gccactggcc gctgacgatg   7320
agcacgacga tgacaggcgg agggccctgc acgaggaaag caccaggtgg aacagggtgg   7380
gcatcctgag cgagctgtgc aaggccgtgg agagcaggta ggcaccagca   7440
tcatcgtgat ggctatgacc acactggcca gctccgtcaa gagcttctcc tacctgaggg   7500
gggccctat aactctctac ggctaacctg aatggactac gacatagtct agtccgccaa   7560
ggccgccacc atgaagatg ccaaaaacat taagaagggc ccagcgccat ctacccact   7620
cgaagacggg accgccggcg agcagctgca caaagccatg aagcgctacg ccctggtgcc   7680
cggcaccatc gcctttaccg acgcacatat cgaggtggac attacctacg ccgagtactt   7740
cgagatgagc gttcggctgg cagaagctat gaagcgctat gggctgaata caaaccatcg   7800
gatcgtggtg tgcagcgaga atagcttgca gttcttcatg cccgtgttgg gtgccctgtt   7860
catcggtgtg gctgtggccc cagctaacga catctacaac gagcgcgagc tgctgaacag   7920
catgggcatc agccagccca cgtcgtatt cgtgagcaag aaagggctgc aaaagatcct   7980
caacgtgcaa aagaagctac cgatcataca aagatcatc atcatggata gcaagaccga   8040
ctaccagggc ttccaaagca tgtacacctt cgtgacttcc catttgccac ccggcttcaa   8100
cgagtacgac ttcgtgcccg agagcttcga ccgggacaaa accatcgccc tgatcatgaa   8160
cagtagtgac agtaccggat tgcccaaggg cgtagcccta ccgcaccgca ccgcttgtga   8220
ccgattcagt catgcccgcg accccatctt cggcaaccag atcatccccg accgctat   8280
cctcagcgtg gtgccatttc accacggctt cggcatgttc accacgctgg gctacttgat   8340
ctgcggcttt cgggtcgtgc tcatgtaccg cttcgaggag gagctattct tgcgcagctt   8400
gcaagactat aagattcaat ctgccctgct ggtgccaca ctatttagct tcttcgctaa   8460
gagcactctc atcgacaagt acgacctaag caacttgcac gagatcgcca gcgggcgggc   8520
gccgctcagc aaggaggtag gtgaggccgt ggcaaacgc ttccacctac caggcatccg   8580
acagggctac ggcctgacag aaacaaccag cgccattctg atcaccccg aagggggacga   8640
caagcctggc gcagtaggca aggtggtgcc cttcttcgag gctaaggtgg tggacttgga   8700
caccggtaag acactgggtg tgaaccagcg cggcgagctg tgcgtccgtg gccccatgat   8760
catgagcgga tacgttaaca acccggagc tacaaacgct ctcatcgaca aggacctg   8820
gctgcacagc ggcgacatcg cctactggga cgaggacgag cacttcttca tcgtggaccg   8880
gctgaagtcc ctgatcaaat acaagggcta ccaggtagcc ccagcgaac tggagagcat   8940
cctgctgcaa caccccaaca tcttcgacgc cggggtcgcc ggcctgcccg acgacgatgc   9000
cggcgagctg cccgccgcag tcgtcgtgct ggaacacggt aaaaccatga ccgagaagga   9060
gatcgtggac tatgtggcca gccaggttac aaccgccaag aagctgcgcg gtgtgttgt   9120
```

```
gttcgtggac gaggtgccta aaggactgac cggcaagttg gacgcccgca agatccgcga  9180
gattctcatt aaggccaaga agggcggcaa gatcgccgtg taactcgagt atgttacgtg  9240
caaaggtgat tgtcaccccc cgaaagacca tattgtgaca caccctcagt atcacgccca  9300
aacatttaca gccgcggtgt caaaaaccgc gtggacgtgg ttaacatccc tgctgggagg  9360
atcagccgta attattataa ttggcttggt gctggctact attgtggcca tgtacgtgct  9420
gaccaaccag aaacataatt gaatacagca gcaattggca agctgcttac atagaactgc  9480
cggcgattgg catgccgcct taaaatttt attttatttt ttcttttctt ttccgaatcg  9540
gattttgttt ttaatatttc aaaaaaaaaa aaaaaaaaaa aaaatctag aaaaaaaaaa  9600
aaaaaaaaaa aaaaaaaaaa aaaaaaaaaa aaaaaaaaaa aaaaaaaaaa aaaaaaaaaa  9660
aaaaaaaaaa aaaaaaaaaa aaaaaaaaaa                                 9690

SEQ ID NO: 101        moltype = RNA   length = 9773
FEATURE               Location/Qualifiers
misc_feature          1..9773
                      note = Synthetic polynucleotide
source                1..9773
                      mol_type = other RNA
                      organism = synthetic construct
SEQUENCE: 101
attgacggcg tagtacacac tattgaatca aacagccgac caattgcact accatcacaa    60
tggagaagcc agtagtaaac gtagacgtag accccccagag tccgtttgtc gtgcaactgc   120
aaaaaagctt cccgcaattt gaggtagtag cacagcaggt cactccaaat gaccatgcta   180
atgccagagc attttcgcat ctggccagta aactaatcga gctggaggtt cctaccacag   240
cgacgatctt ggacataggc agcgcaccgg ctcgtagaat gttttccgag caccagtatc   300
attgtgtctg ccccatgcgt agtccagaag acccggaccg catgatgaaa tatgccagta   360
aactggcgga aaaagcgtgc aagattacaa acaagaactt gcatgaagga attaaggatc   420
tccggaccgt acttgatacg ccggatgctg aaacaccatc gctctgcttt cacaacgatg   480
ttacctgcaa catgcgtgcc gaatattccg tcatgcagga cgtgtatatc aacgctcccg   540
gaactatcta tcatcaggct atgaaaggcg tgcggaccct gtactggatt ggcttcgaca   600
ccacccagtt catgttctcg gctatggcag gttcgtaccc tgcctacaac accaactggg   660
ccgacgagaa agtccttgaa gcgcgtaaca tcggactttg cagcacaaag ctgagtgaag   720
gtaggacagg aaaattgtcg ataatgagga agaaggagtt gaagcccggg tcgcgggttt   780
atttctccgt aggatcgaca ctttatccag aacacagagc cagcttgcag agctggcatc   840
ttccatcggt gttccacttg aatggaaagc agtcgtacac ttgccgctgt gatacagtgg   900
tgagttgcga aggctacgta gtgaagaaaa tcaccatcag tccgggatc acgggagaaa   960
ccgtgggata cgcggttaca cacaatagcg agggcttctt gctatgcaaa gttactgaca  1020
cagtaaaagg agaacgggta tcgttccctg tgtgcacgta catcccggcc accatatgcg  1080
atcagatgac tggtataatg gccacggata tatcacctga cgatgcacaa aaacttctgg  1140
ttgggctcaa ccagcgaatt gtcattaacg gtaggactaa caggaacacc aacaccatcg  1200
aaaattacct tctgccgatc atagcacaag ggttcagcaa atgggctaag gagcgcaagg  1260
atgatcttga taacgagaaa atgctgggta ctagagaacg caagcttacg tatggctgct  1320
tgtgggcgtt tcgcactaag aaagtacatt cgttttatcg cccacctgga acgcagacct  1380
gcgtaaaagt cccagcctct tttagcgctt ttcccatgtc gtccgtatgg agcacctctt  1440
tgcccatgtc gctgaggcag aaattgaaac tggcattgca accaagaag gaggaaaaac  1500
tgctgcaggt ctcggaggaa ttagtcatgg aggccaaggc tgcttttgag gatgctcagg  1560
aggaagccag agcggagaag ctccgagaag cacttccacc attagtggca gacaaaggca  1620
tcgaggcgac cgcagaagtt gtctgcgaag tggagggcgt ccaggcggca atcggagcag  1680
cattagttga aacccccgcgc ggtcacgtaa ggataatacc tcaagcaaat gaccgtatga  1740
tcggacagta tatcgttgtc tcgcaaaact ctgtgctgaa gaatgccaaa ctcgcaccag  1800
cgcacccgct agcagatcag gttaagatca taacacactc cggaagatca ggaaggtacg  1860
cggtcgaacc atacgacgct aaagtactga tgccagcagg aggtgccgta ccatgcgcga  1920
aattcctagc actgagtgag agcgccacgt tagtgtacaa cgaaagagag tttgtgaacc  1980
gcaaactata ccacattgcc atgcatggcc ccgccaagaa tacagaagag gagcagtaca  2040
aggttacaaa ggcagagctt gcagaaacag agtacgtgtt tgacgtggac aagaagcgtt  2100
gcgttaagaa ggaagaagcc tcaggtctgg tcctctcggg agaactgacc aacccctcct  2160
atcatgagct agctctggag ggactgaaga cccgaccttgc ggtcccgtac aaggtcgaaa  2220
caataggagt gataggcaca ccgggggtcgg gcaagtcagc tattatcaag tcaactgtca  2280
cggcacgaga tcttgttacc agcggaaaga agaaaattg tcgcgaaatt gaggccgacg  2340
tgctaagact gaggggtatg cagattacgt cgaagacagt agattcggtt atgctcaacg  2400
gatgccacaa agccgtagaa gtgctgtacg ttgacgaagc gttcgcgtgc cacgcaggag  2460
cactacttgc cttgattgct atcgtcaggc cccgcaagaa ggtagtacta tgcggagacc  2520
ccatgcaatg cggattcttc aacatgatgc aactaaaggt acatttcaat caccctgaaa  2580
aagacatatg caccaagaca ttctacaagt atatctcccg gcgttgcaca cagccagtta  2640
cagctattgt atcgacactg cattacgatg gaaagatgaa aaccacgaac ccgtgcaaga  2700
agaacattga aatcgatatt acaggggcca caaagccgaa gccagggat atcatcctga  2760
catgttttccg cggtgggtt aagcaattgc aaatcgacta tccccgacat gaagtaatga  2820
cagccgcggc ctcacaaggg ctaaccagaa aaggagtgta tgccgtccgg caaaaagtca  2880
atgaaaaccc actgtacgcg atcacatcag agcatgtcaa cgtgttgctc acccgcactg  2940
aggacaggt agtgtggaaa accttgcagg gcgacccatg gattaagcag ctcactaaca  3000
tacctaaagg aaactttcag gctactatag aggactggga agctgaacac aagggaataa  3060
ttgctgcaat aaacagcccc actccccgtt ccaatccgtt cagctgcaag accaacgttt  3120
gctgggcgaa agcattggaa ccgatactag ccacggccgg tatcgtactt accggttgcc  3180
agtggagcga actgttccca cagttgcgcg atgacaaacc acattcggcc attacgcct  3240
tagacgtaat ttgcattaag ttttcggca tggttgac aagcggactg ttttctaaac  3300
agagcatccc actaacgtac catcccgccg attcagcagg gccgtagct cattgggaca  3360
acagcccagg aacccgcaag tatgggtacg atcacgccat tgccgccgaa ctctcccgta  3420
gatttccggt gttccagcta gctgggaagg gcacacaact tgatttgcag acggggagaa  3480
ccagagttat ctctgcacag cataaacctgg tcccggtgaa ccgcaatctt cctcacgcct  3540
tagtcccgga gtacaaggag aagcaacccg gcccggtcga aaaattcttg aaccagttca  3600
```

```
aacaccactc agtacttgtg gtatcagagg aaaaaattga agctccccgt aagagaatcg  3660
aatggatcgc cccgattggc atagccggtg cagataagaa ctacaacctg gctttcgggt  3720
ttccgccgca ggcacggtac gacctggtgt tcatcaacat tggaactaaa tacagaaacc  3780
accactttca gcagtgcgaa gaccatgcgg cgaccttaaa aacccctttcg cgttcggccc  3840
tgaattgcct taacccagga ggcaccctcg tggtgaagtc ctatggctac gccgaccgca  3900
acagtgagga cgtagtcacc gctcttgcca gaaagtttgt cagggtgtct gcagcgagac  3960
cagattgtgt ctcaagcaat acagaaatgt acctgatttt ccgacaacta gacaacagcc  4020
gtacacggca attcaccccg caccatctga attgcgtgat ttcgtccgtg tatgagggta  4080
caagagatgg agttggagcc gcgccgtcat accgcaccaa aagggagaat attgctgact  4140
gtcaaggaga agcagttgtc aacgcagcca atccgctggg tagaccaggc gaaggagtct  4200
gccgtgccat ctataaacgt tggccgacca gttttaccga ttcagccacg gagacaggca  4260
ccgcaagaat gactgtgtgc ctaggaaaga aagtgatcca cgcggtcggc cctgatttcc  4320
ggaagcaccc agaagcagaa gccttgaaat tgctacaaaa cgcctaccat gcagtggcag  4380
acttagtaaa tgaacataac atcaagtctg tcgccattcc actgctatct acaggcattt  4440
acgcagccgg aaaagaccgc cttgaagtat cacttaactg cttgacaacc gcgctagaca  4500
gaactgacgc ggacgtaacc atctattgcc tggataagaa gtggaaggaa agaatcgacg  4560
cggcactcca acttaaggag tctgtaacag agctgaagga tgaagatatg gagatcgacg  4620
atgagttagt atggatccat ccagacagtt gcttgaaggg aagaaaggga ttcagtacta  4680
caaaaggaaa attgtattcg tacttcgaag gcaccaaatt ccatcaagca gcaaaagaca  4740
tggcggagat aaaggtcctg ttccctaatg accaggaaag taatgaacaa ctgtgtgcct  4800
acatattggg tgagaccatg gaagcaatcc gcgaaaagtg cccggtcgac cataaccccgt  4860
cgtctagccc gcccaaaacg ttgccgtgcc tttgcatgta tgccatgacg ccagaaaggg  4920
tccacagact tagaagcaat aacgtcaaag aagttacagt atgctcctcc accccccttc  4980
ctaagcacaa aattaagaat gttcagaagg ttcagtgcac gaaagtagtc ctgtttaatc  5040
cgcacactcc cgcattcgtt cccgccgta agtacataga agtgccagaa cagcctaccg  5100
ctcctcctgc acaggccgag gaggccccccg aagttgtagc gacaccgtca ccatctacag  5160
ctgataacac ctcgcttgat gtcacagaca tctcactgga tatggatgac agtagcgaag  5220
gctcactttt ttcgagcttt agcggatcgg acaactctat tactagtatg acagttggt   5280
cgtcaggacc tagttcacta gagatagtag accgaaggca ggtggtggtg gctgacgttc  5340
atgccgtcca agagcctgcc cctattccac cgccaaggct aaagaagatg gcccgcctgg  5400
cagcggcaag aaaagagccc actccaccgg caagcaatag ctctgagtcc ctccacctct  5460
cttttggtgg ggtatccatg tccctcggat caattttcga cggagagacg gcccgccagg  5520
cagcggtaca accccctggca acaggcccca cggatgtgcc tatgtctttc ggatcgtttt  5580
ccgacggaga gattgatgag ctgagccgca gagtaactga gtccgaaccc gtcctgtttg  5640
gatcatttga accgggcgaa gtgaactcaa ttatatcgtc ccgatcagcc gtatctttc   5700
ctctacgcaa gcagagacgt agacgcagga gcaggaggac tgaatactga ctaaccgggg  5760
taggtgggta catattttcg acggacacag gccctgggca cttgcaaaag aagtccgttc  5820
tgcagaacca gcttacagaa ccgaccttgg agcgcaatgt cctggaaaga attcatgccc  5880
cggtgctcga cacgtcgaaa gaggaacaac tcaaactcag gtaccagatg atgcccaccg  5940
aagccaacaa aagtaggtac cagtctcgta aagtagaaaa tcagaaagcc ataaccactg  6000
agcgactact gtcaggacta cgactgtata actctgccac agatcagcca gaatgctata  6060
agatcaccta tccgaaacca ttgtactcca gtagcgtacc ggcgaactac tccgatccac  6120
agttcgctgt agctgtctgt aacaactatc tgcatgacga ctatccgaca gtagcatctt  6180
atcagattac tgacgagtac gatgcttact tggatatggt agacgggaca gtcgcctgcc  6240
tggacactgc aaccttctgc cccgctaagc ttagaagtta cccgaaaaaa catgagtata  6300
gagccccgaa tatccgcagt gcggttccat cagcgatgca gaacacgcta caaaatgtgc  6360
tcattgccgc aactaaaaga aattgcaacg tcacgcagat gcgtgaactg ccaacactgg  6420
actcagcgac attcaatgtc gaatgcttc gaaaatatgc atgtaatgac gagtattggg  6480
aggagttcgc tcggaagcca attaggatta ccactgagtt tgtcaccgca tatgtagcta  6540
gactgaaagg ccctaaggcc gccgcactat ttgcaaagac gtataatttg gtcccattgc  6600
aagaagtgcc tatggataga ttcgtcatgg acatgaaaga agacgtgaaa gttacaccag  6660
gcacgaaaca cacagaagaa agaccgaaag tacaagtgat acaagccgca gaaccccctgg  6720
cgactgctta cttatgcggg attcaccggg aattagtgcg taggcttacg gccgtcttgc  6780
ttccaaacat tcacacgctt tttgacatgt cggcggagga ttttgatgca atcatagcag  6840
aacacttcaa gcaaggcgac ccggtactgg agacggatat cgcatcattc acgcaaaagc  6900
aagacgacgc tatggcgtta accggtctga tgatcttgga ggacctgggt gtggatcaac  6960
cactactcga cttgatcgag tgcgcctttt gagaaatatc atccaccat ctacctacgg   7020
gtactcgttt taaattcggg gcgatgatga aatccggaat gttcctcaca cttttttgtca  7080
acacagtttt gaatgtcgtt atcgccagca gagtactaga ggagcgggctt aaaacgtcca  7140
gatgtgcagc gttcattggc gacgacaaca tcatacatgg agtagtatct gacaaagaaa  7200
tggctgagag gtgcgccacc tggctcaaca tggaggttaa gatcatcgac gcagtcatcg  7260
gtgagagacc accttacttc tgcggcggat ttatcttgca agattcggtt acttccacag  7320
cgtgccgcgt ggcggatccc ctgaaaaggc tgtttaagtt gggtaaaccg ctcccagccg  7380
acgacgaga agacgaagac agaagacgcg tctcgttgta tgaaacaaag ggtggttta   7440
gagtaggtat aacaggcact ttagcagtgg ccgtgacgac ccggtatgag gtagacaata  7500
ttacacctgt cctactggca ttgagaactt ttgcccagag caaaagagca ttccaagcca  7560
tcagagggga aataaagcat ctctacgtgt gtcctaaata gtcagcatag tacatttcat  7620
ctgactaata ctacaacacc accaccatgg aagatgccaa aaacattaag aagggcccca  7680
cgccattcta cccactcgaa gacgggaccg ccggcgaaca gctgcacaag gcatgaagc   7740
gctacgccct ggtgcccggc accatcgcct ttaccgacgc acatatcgag gtggacatta  7800
cctacgccga gtacttcgag atgagcgttc ggctggcaga agctatgaag cgctatgggc  7860
tgaatacaaa ccatcggatc gtggtgtgca gcgagaataag cttgcagttc ttcatgcccg  7920
tgttgggtgc cctgttcatc ggtgtggctg tggccccagc taacgacatc tacaacgagc  7980
gcgagctgct gaacagcatg ggcatcagcc agcccacccgt cgtattcgtg agcaagaaag  8040
ggctgcaaaa gatcctcaac gtgcaaaaga agctaccgat catacaaaag atcatcatca  8100
tggatagcaa gaccgactac cagggcttcc aaagcatgta cacctctgtg acttccatt   8160
tgccacccgg cttcaacgag tacgacttcg tgcccgagag cttcgaccgg acaaaacca   8220
tcgccctgat catgaacagt agtggcagta ccggattgcc caagggcgta gcctaccgc   8280
accgcaccgc ttgtgtccga ttcagtcatg cccgcgaccc catcttcggc aaccagatca  8340
```

```
tccccgacac cgctatcctc agcgtggtgc catttcacca cggcttcggc atgttcacca    8400
cgctgggcta cttgatctgc ggctttcggg tcgtgctcat gtaccgcttc gaggaggagc    8460
tattcttgcg cagcttgcaa gactataaga ttcaatctgc cctgctggtg cccacactat    8520
ttagcttctt cgctaagagc actctcatcg acaagtacga cctaagcaac ttgcacgaga    8580
tcgccagcgg cggggcgccg ctcagcaagg aggtaggtga gccgtggcc aaacgcttcc    8640
acctaccagg catccgacag ggctacggcc tgacagaaac aaccagcgcc attctgatca    8700
cccccgaagg ggacgacaag cctggcgcag taggcaaggt ggtgcccttc ttcgaggcta    8760
aggtggtgga cttggacacc ggtaagacac tgggtgtgaa ccagcgcggc gagctgtgcg    8820
tccgtggccc catgatcatg agcggctacg ttaacaccc cgaggctaca aacgctctca    8880
tcgacaagga cggctggctg cacagcggcg acatcgccta ctgggacgag gacgagcact    8940
tcttcatcgt ggaccggctg aagtccctga tcaaatacaa gggctaccag gtagcccag    9000
ccgaactgga gagcatcctg ctgcaacacc ccaacatctt cgacgccggg gtcgccggcc    9060
tgcccgacga cgatgccggc gagctgcccg ccgcagtcgt cgtgctggaa cacggtaaaa    9120
ccatgaccga gaaggagatc gtggactatg tggccagcca ggttacaaac gccaagaagc    9180
tgcgcggtgg tgttgtgttc gtggacgagg tgcctaaagg actgaccggc aagttggacg    9240
cccgcaagat ccgcgagatt ctcattaagg ccaagaaggg cggcaagatc gccgtgtaaa    9300
cgcgtgctag accatggatc ctagacgcta cgccccaatg atccgaccag caaaactcga    9360
tgtacttccg aggaactgat gtgcataatg catcaggctg gtacattaga tccccgctta    9420
ccgcgggcaa tatagcaaca ctaaaaactc gatgtacttc cgaggaagcg cagtgcataa    9480
tgctgcgcag tgttgccaca taaccactat attaaccatt tatctagcgg acgccaaaaa    9540
ctcaatgtat ttctgaggaa gcgtggtgca taatgccacg cagcgtctgc ataacttta    9600
ttatttcttt tattaatcaa caaaattttg ttttaaact ttcaaaaaaa aaaaaaaaa    9660
aaaaaaatc tagaaaaaaa aaaaaaaaa aaaaaaaaa aaaaaaaaa aaaaaaaaa    9720
aaaaaaaaa aaaaaaaaa aaaaaaaaa aaaaaaaaa aaaaaaaaa aaa          9773

SEQ ID NO: 102         moltype = RNA  length = 2086
FEATURE                Location/Qualifiers
misc_feature           1..2086
                       note = Synthetic polynucleotide
source                 1..2086
                       mol_type = other RNA
                       organism = synthetic construct
SEQUENCE: 102
aggaaactta agtcaacaca acatatacaa aacaaacgaa tctcaagcaa tcaagcattc      60
tacttctatt gcagcaattt aaatcatttc ttttaaagca aaagcaattt tctgaaaatt    120
ttcaccattt acgaacgata gccatggaag atgccaaaaa cattaagaag ggcccagcgc    180
cattctaccc actcgaagac gggaccgccg gcgagcagct gcacaaagcc atgaagcgct    240
acgccctggt gcccggcacc atcgccttta ccgacgcaca tatcgaggtg gacattacct    300
acgccgagta cttcgagatg agcgttcggc tggcagaagc tgtgaagcgc tatgggctga    360
atacaaacca tcggatcgtg gtgtgcagcg agaatagctt gcagttcttc atgcccgtgt    420
tgggtgccct gttcatcggt gtggctgtgg ccccagctaa cgacatctac aacgagcgcg    480
agctgctgaa cagcatgggc atcagccagc ccaccgtcgt attcgtgagc aagaaagggc    540
tgcaaaagat cctcaacgtg caaaagaagc taccgatcat acaaaagatc atcatcatgg    600
atagcaagac cgactaccag ggcttccaaa gcatgtacac cttcgtgact tcccatttgc    660
cacccggctt caacgagtac gacttcgtgc ccgagagctt cgaccgggac aaaaccatcg    720
ccctgatcat gaacagtagt ggcagtaccg gattgcccaa gggcgtagcc ctaccgcacc    780
gcaccgcttg tgtccgattc agtcatgccc gcgaccccat cttcggcaac cagatcatcc    840
ccgacaccgc tatcctcagc gtggtgccat tcaccacgg cttcggcatg ttcaccacgc    900
tgggctactt gatctgcggc tttcgggtcg tgctcatgta ccgcttcgag gaggagctat    960
tcttgcgcag cttgcaagac tataagatcc aatctgccct gctggtgccc acactattta   1020
gcttcttcgc taagagcact ctcatcgaca agtacgacct aagcaacttg cacgagatcg   1080
ccagcggcgg ggcgccgctc agcaaggagg taggtgaggc cgtggccaaa cgcttccacc   1140
taccaggcat ccgacagggc tacggcctga cagaaacaac cagcgccatt ctgatcaccc   1200
ccgagggga cgacaagcct ggcgcagtag gcaaggtggt gcccttcttc gaggctaagg   1260
tggtggactt ggacaccggt aagacactgg gtgtgaacca gcgcggcgag ctgtgcgtca   1320
gtggccccat gatcatgagc ggctacgtta acaccccga ggctacaaac gctctcatcg   1380
acaaggacgg ctggctgcac agcggcgaca tcgcctactg ggacgaggac gagcacttct   1440
tcatcgtgga ccggctgaag tccctgatca aatacaaggg ctaccaggta gccccagccg   1500
aactggagag catcctgctg caacacccca acatcttcga cgcggggtc gccggcctgc   1560
ccgacgacga tgccggcgag ctgcccgccg cagtcgtcgt gctggaacac ggtaaaacca   1620
tgaccgagaa ggagatcgtg gactatgtgg ccagccaggt tacaaccgcc aagaagctgc   1680
gcggtggtgt tgtgttcgtg gacgaggtgc ctaaaggact gaccggcaag ttggacgccc   1740
gcaagatccg cgagattctc attaaggcca agaagggcgg caagatcgcc gtgtaactcg   1800
agctagtgac tgactaggat ctggttacca ctaaaccagc ctcaagaaca cccgaatcg   1860
gtctctaagc tacataatac caacttacac ttacaaaatg ttgtccccca aaatgtagcc   1920
attcgtatct gctcctaata aaagaaagt tccttcacat tctagaaaaa aaaaaaaaa   1980
aaaaaaaaa aaaaaaaaa aaaaaaaaa aaaaaaaaa aaaaaaaaa aaaaaaaaa   2040
aaaaaaaaa aaaaaaaaa aaaaaaaaa aaaaaaaaa aaaaaa                 2086

SEQ ID NO: 103         moltype = RNA  length = 8095
FEATURE                Location/Qualifiers
misc_feature           1..8095
                       note = Synthetic polynucleotide
source                 1..8095
                       mol_type = other RNA
                       organism = synthetic construct
SEQUENCE: 103
atgggcggcg catgagagaa gcccagacca attacctacc caaaatggag aaagttcacg      60
ttgacatcga ggaagacagc ccattcctca gagctttgca gcggagcttc ccgcagtttg    120
```

```
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgccg tcgacggccc caccagcctg taccaccagg    540
ccaacaaggg cgtgagggtg gcctactgga tcggcttcga caccacaccc ttcatgttca    600
agaacctggc cggcgcctac cccagctaca gcaccaactg ggccgacgag accgtgctga    660
ccgccaggaa catcggcctg tgcagcagcg acgtgatgga gaggagccgg agaggcatga    720
gcatcctgag gaagaaatac ctgaagccca gcaacaacgt gctgttcagc gtgggcagca    780
ccatctacca cgagaagagg gacctgctca ggagctggca cctgcccagc gtgttccacc    840
tgaggggcaa gcagaactac acctgcaggt gcgagaccat cgtgagctgc gacggctacg    900
tggtgaagag gatcgccatc agccccggcc tgtacggcaa gccagcggc tacgccgcta    960
caatgcacag ggagggcttc ctgtgctgca aggtgaccga caccctgaac ggcgagaggg   1020
tgagcttccc cgtgtgcacc tacgtgcccg ccacccgtgt cgaccagatg accggcatcc   1080
tggccaccga cgtgagcgcc gacgacgccc agaagctgct cgtgggcctg aaccagagga   1140
tcgtgaagac cggcaggacc cagaggaaca ccaacacaat gaagaactac ctgctgcccg   1200
tggtggccca ggctttcgcc aggtgggcca aggagtacaa ggaggaccag gaagacgaga   1260
ggcccctggg cctgagggac aggcagctgg tgatgggctg ctgctgggcc ttcaggcggc   1320
acaagatcac cagcatctac aagaggcccg acacccagac catcatcaag gtgaacagcg   1380
acttccacag cttcgtgctg cccaggatcg gcagcaacac cctggagatc ggcctgagga   1440
cccggatcag gaagatgctg gaggaacaca aggagcccca cccactgatc accgccgagg   1500
acgtgcagga ggccaagtgc gctgccgacg aggccaagga ggtgagggag gccgaggaac   1560
tgagggccgc cctgccaccc ctggctgccg acgtggagga acccaccctg aagccgacg   1620
tggacctgat gctgcaggag gccggccgcg gaagcgtgga gacccggag ggcctgatca   1680
aggtgaccag ctacgacggc gaggacaaga tcggcagcta cgccgtgctg agcccacagg   1740
ccgtgctgaa gtccgagaag ctgagctgca tccaccccact ggccgagcag gtgatcgtga   1800
tcacccacag cggcaggaag ggcaggtacg ccgtggagcc ctaccacggc aaggtggtcg   1860
tgcccgaggg ccacgccatc cccgtgcagg acttccaggc cctgagcgag agcgccacca   1920
tcgtgtacaa cgagagggag ttcgtgaaca ggtacctgca ccatatcgcc acccacggcg   1980
gagccctgaa caccgacgag gaatactaca agaccgtgaa gccagcgag cacgacggcg   2040
agtacctgta cgacatcgac aggaagcagt gcgtgaagaa agagctggtg accggcctgg   2100
gactgaccgg cgagctggtg gacccacccct tccacgagtt cgcctacgag agcctgagga   2160
ccagacccgc cgctccctac caggtgccca ccatcggcgt gtacggcgtg cccggcagcg   2220
gaaagagcgg catcatcaag agcgccgtga ccaagaaaga cctggtggtc agcgccaaga   2280
aagagaactg cgccgagatc atcagggacg tgaaagaagat gaaaggcctg gacgtgaacg   2340
cgcgcaccgt ggacagcgtg ctgctgaacg gctgcaagca cccgtggag accctgtaca   2400
tcgacgaggc cttcgcttgc cacgcgggca ccctgagggc cctgatcgcc atcatcaggc   2460
ccaagaaagc cgtgctgtgc ggcgacccca agcagtgcgg cttcttcaac atgatgtgcc   2520
tgaaggtgca cttcaaccac gagatctgca cccaggtgtt ccacaagagc atcagcaggc   2580
ggtgcaccaa gagcgtgacc agcgtcgtga gcaccctgtt ctacgacaag aaaatgagga   2640
ccaccaaccc caaggagacc aaaatcgtga tcgacaccac aggcagcacc aagcccaagc   2700
aggacgacct gatcctgacc tgcttcaggg gctgggtgaa gcagctgcag atcgactaca   2760
agggcaacga gatcatgacc gccgctgcca gccagggcct gaccaggaag ggcgtgtacg   2820
ccgtgaggta caaggtgaac gagaacccac tgtacgctcc caccagcgag cacgtgaacg   2880
tgctgctgac caggaccgag gacaggatcg tgtggaagac ctgccgggc gaccccctga   2940
tcaagaccct gaccgccaag taccccggca cttcaccgc caccatcgaa gagtggcagg   3000
ccgagcacga cgccatcatg aggcacatcc tggagaggcc cgaccccacc gacgtgttcc   3060
agaacaaggc caacgtgtgc tgggccaagg ccctggtgcc cgtgctgaag accgccggca   3120
tcgacatgac cacagagcag tggaacaccg tggactactt cgagaccgac aaggcccaca   3180
gcgccgagat cgtgctgaac cagctgtgcg tgaggttctt cggcctggac ctggacagcg   3240
gcctgttcag cgcccccacc gtgccactga gcatcaggaa caaccactgg gacaacagcc   3300
ccagcccaaa catgtacggc ctgaacaagg aggtggtcag gcagctgagc aggcggtacc   3360
cacagctgcc caggggccgt gccaccggca gggtgtacga catgaacacc ggcaccctgg   3420
ggaactacga ccccaggatc aacctggtgc ccgtgaacag gcggctgccc acgccctgg   3480
tgctgcacca acgagcac ccacagagcg acttcagctc cttcgtgagc aagctgaaag   3540
gcaggaccgt gctggtcgtg ggcgagagc tgagcgtgcc cggcaagatg gtggactggc   3600
tgagcgacag gccgagggcc accttccggg ccaggctgga cctcggcatc cccggcgacg   3660
tgcccaagta cgacatcatc ttcgtgaacg tcaggacccc atacaagtac caccattacc   3720
agcagtgcga ggaccacgcc atcaagctga catgctgac caagaaggcc tgcctgcacc   3780
tgaacccgg aggcacctgc gtgagcatcg gctacggcta cgccgacagg gccagcgaga   3840
gcatcattgg cgccatcgcc aggctgttca gttcagcag ggtgtgcaaa cccaagagca   3900
gcctggagga aaccgaggtg ctgttcgtgt tcatcggcta cgaccggaca cgcaggaccc   3960
acaaccccta caagctgagc agcacctga caaacatcta caccggcagc aggctgcacg   4020
aggccggctg cgccccagc taccacgtgg tcagggcga tatcgccacc gccaccgagg   4080
gcgtgatcat caacgctgcc aacagcaagg gccagcccgg aggcggagtg tgcggcgccc   4140
tgtacaagaa gttccccgag agcttcgacc tgcagcccat cgaggtgggc aaggccaggc   4200
tggtgaaggg cgccgctaag cacatcatcc acgccgtggg ccccaacttc aacaaggtga   4260
gcgaggtgga aggcgacaag cagctggccg aagcctacga gagcatcgcc aagatcgtga   4320
acgacaataa ctacaagagc gtggccatcc cactgctcag caccggcatc ttcagcggca   4380
acaaggacag gctgacccag agcctgaacc acctgctcac cgcctggac accaccgatg   4440
ccgacgtggc catctactgc agggacaaga agtgggagat gacctgaag gaggccgtgg   4500
ccaggcggga ggcctgggaa gagatctgca gcagcagcag cagcaggccgagg   4560
acgccgagct ggtgagggtg cacccccaag actcccggc cggcaggag ggctacagca   4620
ccagcacgg caagacctc agctacctgg agggcaccaa gttccacacg gccgctaagg   4680
acatcgccga gatcaacgct atgtggcccg tggccaccga ggccaacgag caggtgtgca   4740
tgtacatcct gggcgagagc atgtccagca tcaggagcaa gtgcccgtg gagaaagcg   4800
aggccagcac accacccagc accctgccct gcctgtgcat ccacgctatg acacccgaga   4860
```

```
gggtgcagcg gctgaaggcc agcaggcccg agcagatcac cgtgtgcagc tccttcccac   4920
tgcccaagta caggatcacc ggcgtgcaga agatccagtg cagccagccc atcctgttca   4980
gcccaaaggt gcccgcctac atccacccca ggaagtacct ggtggagacc ccacccgtgg   5040
acgagacacc cgagccaagc gccgagaacc agagcaccga gggcacaccc gagcagccac   5100
ccctgatcac cgaggacgag acaaggaccc ggaccccaga gcccatcatt atcgaggaag   5160
aggaagagga cagcatcagc ctgctgagcg acgcccccac ccaccaggtg ctgcaggtgg   5220
aggccgacat ccacggccca cccagcgtgt ccagctccag ctggagcatc ccacacgcca   5280
gcgacttcga cgtggacagc ctgagcatcc tggacaccct ggagggcgcc agcgtgacct   5340
ccggcgccac cagcgccgag accaacagct acttcgccaa gagcatggag ttcctggcca   5400
ggcccgtgcc agctcccagg accgtgttca ggaacccacc ccacccagct cccaggacca   5460
ggacccccaag cctggctccc agcagggcct gcagcaggac cagcctggtg agcaccccac   5520
ccggcgtgaa cagggtgatc accagggagg aactggaggc cctgcacccc agcaggaccc   5580
ccagcaggtc cgtgagcagg actagtctgg tgtccaaccc accggctgtg aacagggtga   5640
tcaccaggga ggaattcgag gccttcgtgg cccagcaaca gagacggttc gacgccggcg   5700
cctacatctt cagcagcgac accggccagg gacacctgga gcaaaagagc gtgaggcaga   5760
ccgtgctgag cgaggtggtg ctggagagga ccgagctgga aatcagctac gccccaggc    5820
tggaccagga gaaggaggaa ctgctcagga agaaactgca gctgaacccc accccagcca   5880
acaggagcag gtaccagagc aggaaggtgg agaacatgaa ggccatcacc gccaggcgga   5940
tcctgcaggg cctgggacac tacctgaagg ccgagggcaa ggtggagtgc tacaggaccc   6000
tgcaccccgt gccactgtac agctccagcg tgaacagggc cttctccagc cccaaggtgg   6060
ccgtggaggc ctgcaacgct atgctgaagg agaacttccc caccgtggcc agctactgca   6120
tcatccccga gtacgacgcc tacctggaca tggtggacgg ccagctgc tgcctggaca    6180
ccgccagctt ctgccccgcc aagctgagga gcttccccaa gaaacacagc tacctggagc   6240
ccaccatcag gagcgccgtg cccagcgcca tccagaacac cctgcagaac gtgctggccg   6300
ctgccaccaa gaggaactgc aacgtgaccc agatgaggga gctgcccgtg ctggacagcg   6360
ctgccttcaa cgtggagtgc ttcaagaaat acgcctgcaa caacgagtac tgggagacct   6420
tcaaggagaa ccccatcagg ctgaccgaag agaacgtggt gaactacatc accaagctga   6480
agggccccaa ggccgctgcc ctgttcgcta gacccacaa cctgaacatg ctgcaggaca   6540
tcccaatgga caggttcgtg atggacctga gagggacgt gaaggtgaca cccggcacca   6600
agcacaccga ggagaggccc aaggtgcagg tgatccagc cgctgaccca ctggccaccg   6660
cctacctgtg cggcatccac agggagctgg tgaggcggct gaacgccgtg ctgctgccca   6720
acatccacac cctgttcgac atgagcgccg aggacttcga cgccatcatc gccgagcact   6780
tccagccccg cgactgcgtg ctggagaccg acatcgccag cttcgacaag agcgaggatg   6840
acgctatggc cctgaccgct ctgatgatcc tggaggacct gggcgtggac gccagctgc   6900
tcaccctgat cgaggctgcc ttcggcgaga tcagctccat ccacctgccc accaagacca   6960
agttcaagtt cggcgctatg atgaaaagcg aatgttcct gaccctgttc gtgaacaccg    7020
tgatcaacat tgtgatcgcc agcagggtgc tgcgggagag gctgaccggc agcccctgcg   7080
ctgccttcat cggcgacgac aacatcgtga agggcgtgaa aagcgacaag ctgatggccg   7140
acaggtgcgc cacctggctg aacatggagg tgaagatcat cgacgccgtg gtgggcagga   7200
aggcccccta cttctgcggc ggattcatcc tgtgcgacag cgtgaccggc accgcctgca   7260
gggtggccga ccccctgaag aggctgttca agctgggcaa gccactggcc gctgacgatg   7320
agcacgacga tgacaggcgg agggccctgc acgaggaaag caccaggtgg aacagggtgg   7380
gcatcctgag cgagctgtgc aaggccgtgg agagccagta cgagaccgtg ggcaccagca   7440
tcatcgtgat ggctatgacc acactggcca gctccgtcaa gagcttctcc tacctgaggg   7500
gggccctat aactctctac ggctaacctg aatggactac gacatagtct agtccgccaa    7560
ggccgccacc catgaagttg gtggttgtgg gggccgggg tgttggcaaa agcgcccta    7620
caatttgact cgagtatgtt acgtgcaaag gtgattgtca ccccccgaaa gaccatattg    7680
tgacacaccc tcagtatcac gcccaaacat ttacagccgc ggtgtcaaaa accgcgtgga   7740
cgtggttaac atccctgctg ggaggatcag ccgtaattat tataattggc ttggtgctgg   7800
ctactattgt ggcatgtac gtgctgacca ccagaaaca taattgaata cagcagcaat    7860
tggcaagctg cttacataga actcgcggcg atggcatgc cgccttaaaa tttttatttt   7920
attttttctt ttcttttccg aatcggattt tgttttttaat attttcaaaaa aaaaaaaaaa   7980
aaaaaaaaaa tctagaaaaa aaaaaaaaaa aaaaaaaaaa aaaaaaaaaa aaaaaaaaaa   8040
aaaaaaaaaa aaaaaaaaaa aaaaaaaaaa aaaaaaaaaa aaaaaaaaaa aaaaa        8095

SEQ ID NO: 104         moltype = RNA    length = 8120
FEATURE                Location/Qualifiers
misc_feature           1..8120
                       note = Synthetic polynucleotide
source                 1..8120
                       mol_type = other RNA
                       organism = synthetic construct
SEQUENCE: 104
attgacggcg tagtacacac tattgaatca aacagccgac caattgcact accatcacaa     60
tggagaagcc agtagtaaac gtagacgtag accccccagag tccgtttgtc gtgcaactgc    120
aaaaaagctt cccgcaattt gaggtagtag cacagcaggt cactccaaat gaccatgcta    180
atgccagagc attttcgcat ctggccagta aactaatcga gctggaggtt cctaccacag    240
cgacgatctt ggacataggc agcgcaccgg ctcgtagaat gttttccgag caccagtatc    300
attgtgtctg ccccatgcgt agtccagaag acccggacca catgatgaaa tatgccagta    360
aactggcgga aaaagcgtgc aagattacaa caagaacttt gcatgagaag attaaggatc    420
tccgaccgt acttgatacg ccggatgctg aaacaccatc gctctgcttt cacaacgatg     480
ttacctgcaa catgcgtgcc gaatattccg tcatgcagga cgtgtatatc aacgctcccg    540
gaactatcta tcatcaggct atgaaaggcg tgcggaccc gtactggatt ggcttcgaca    600
ccacccagtt catgttctcg gctatgcag gttcgtactac accaacctgg     660
ccgacgagaa agtccttgaa gcgcgtaaca tcggactttg cagcacaaag ctgagtgaag    720
gtaggacagg aaaattgtcg ataatgagga agaaggagtt gaagcccggg tcgcgggttt    780
atttctccgt aggatcgaca ctttatccag aacacagagc cagcttgcag agctggcatc    840
ttccatcggg gttccacttg aatggaaagc agtcgtacac ttgccgctgt gatacagtgg    900
tgagttgcga aggctacgta gtgaagaaaa tcaccatcag tccgggatc acgggagaaa    960
```

-continued

```
ccgtgggata cgcggttaca cacaatagcg agggcttctt gctatgcaaa gttactgaca 1020
cagtaaaagg agaacgggta tcgttccctg tgtgcacgta catcccggcc accatatgcg 1080
atcagatgac tggtataatg gccacggata tatcacctga cgatgcacaa aaacttctgg 1140
ttgggctcaa ccagcgaatt gtcattaacg gtaggactaa caggaacacc aacaccatgc 1200
aaaattacct tctgccgatc atagcacaag ggttcagcaa atgggctaag gagcgcaagg 1260
atgatcttga taacgagaaa atgctggtta ctagagaacg caagcttacg tatggctgct 1320
tgtgggcgtt tcgcactaag aaagtacatt cgttttatcg cccacctgga acgcagacct 1380
gcgtaaaagt cccagcctct tttagcgctt ttcccatgtc gtccgtatgg acgacctctt 1440
tgcccatgtc gctgaggcag aaattgaaac tggcattgca accaaagaag gaggaaaaac 1500
tgctgcaggt ctcggaggaa ttagtcatgg aggccaaggc tgcttttgag gatgctcagg 1560
aggaagccag agcggagaag ctccgagaag cacttccacc attagtggca gacaaaggca 1620
tcgaggcagc cgcagaagtt gtctgcgaag tggaggggct ccaggcggac atcggagcag 1680
cattagttga accccgcgc ggtcacgtaa ggataatacc tcaagcaaat gaccgtgatga 1740
tcggacagta tatcgttgtc tcgccaaact ctgtgctgaa gaatgccaaa ctcgcaccag 1800
cgcacccgct agcagatcag gttaagatca taacacactc cggaagatca ggaaggtacg 1860
cggtcgaacc atacgacgct aaagtactga tgccagcagg aggtgccgta ccatggccag 1920
aattcctagc actgagtgag agcgccacgt tagtgtacaa cgaaagagag tttgtgaacc 1980
gcaaactata ccacattgcc atgcatggcc ccgccaagaa tacagaagag gagcagtaca 2040
aggttacaaa ggcagagctt gcagaaacag agtacgtgtt tgacgtggac aagaagcgtt 2100
gcgttaagaa ggaagaagcc tcaggtctgg tcctctcggg agaactgacc aaccctccct 2160
atcatgagct agctctggag ggactgaaga cccgacctgc ggtcccgtac aaggtcgaaa 2220
caataggagt gataggcaca ccgggggtcgg gcaagtcgga tattatcaag tcaactgtca 2280
cggcacgaga tcttgttacc agcggaaaga aagaaaattg tcgcgaaatt gaggccgacg 2340
tgctaagact gagggtatg cagattacgt cgaagacagt agattcggtt atgctcaacg 2400
gatgccacaa agccgtagaa gtgctgtacg ttgacgaagc gttcgcgtgc cacgcaggag 2460
cactacttgc cttgattgct atcgtcaggc cccgcaagaa ggtagtacta tgccgagacc 2520
ccatgcaatg cggattcttc aacatgatgc aactaaaggt acatttcaat cacccctgaaa 2580
aagacatatg caccaagaca ttctacaagt atatctcccg gcgttgcaca cagccagtta 2640
cagctattgt atcgacactg cattacgatg gaaagatgaa aaccacgaac ccgtgcaaga 2700
agaacattga aatcgatatt acaggggcca caaagccgga gccaggggat atcatcctga 2760
catgtttccg cgggtggggtt aagcaattgc aaatcgacta tcccggacat gaagtaatga 2820
cagccgcggc ctcacaaggg ctaaccagaa aaggagtgta tgccgtccgg caaaaagtca 2880
atgaaaaccc actgtacgcg atcacatcag agcatgtgaa cgtgttgctc acccgcactg 2940
aggacaggct agtgtgtgaaa accttgcagg gcgacccatg gattaagcag ctcactaaca 3000
taccaaagg aaactttcag gctactatag aggactggga agctgaaaca aagggaataa 3060
ttgctgcaat aaacagcccc actccccgtg ccaatccgtt cagctgcaag accaacgttt 3120
gctgggcgaa agcattggaa ccgatactag ccacggccgg tatcgtactt accggttgcc 3180
agtggagcga actgttccca cagtttgcgg atgacaaacc acattcggcc atttacgcct 3240
tagacgtaat ttgcattaag tttttcggca tggacttgac aagcggacta ttttctaaac 3300
agagcatccc actaacgtac catccccgcc attcagcgag gccggtagct cattgggaca 3360
acagcccagg aacccgcaag tatgggtacg atcacgccat tgccgccgaa ctctcccgta 3420
gatttccggt gttccagcta gctgggaagg gcacacaact tgatttgcag acggggagaa 3480
ccagattat ctctgcacag cataacctgg tcccggtgaa ccgcaatctt cctcacgcct 3540
tagtccccga gtacaaggag aagcaacccg gcccggtcga aaattcttg aaccagttca 3600
aacaccactc agtacttgtg gtatcagagg aaaaaattga agctcccgt aagagaatcg 3660
aatggatcgc cccgattggc atagccggtg cagataagaa ctacaacctg gctttcgggt 3720
ttccgccgca ggcacggtac gacctggtgt tcatcaacat tggaactaaa tacagaaacc 3780
accactttca gcagtgcgaa gaccatgcgg cgaccttaaa aacccttcg cgttcggccc 3840
tgaattgcct taaccagga ggcacccctcg tggtgaagtc ctatggctac gccgaccgca 3900
acagtgagga cgtagtcacc gctcttgcca gaaagtttgt cagggtgtct gcagcgacc 3960
cagattgtgt ctcaagcaat acagaaatgt acctgatttt ccgacaacta gacaacaccg 4020
gtacacggca attcaccccg caccatctga attgcgtgat ttcgtccgtg tatgaggta 4080
caagagatgg agttggagcc cgccgtcat accgcaccaa aagggagaat attgctgact 4140
gtcaagagga agcagttgtc aacgcagcca atccgctggg tagaccaggc gaaggagtct 4200
gccgtgccat ctataaacgt tggccgacca gttttaccga ttcagccacg gagacaggca 4260
ccgcaagaat gactgtgtgc ctaggaaaga aagtgatcca cgcggtcggc cctgatttcc 4320
ggaagcaccc agaagcagaa gccttgaaat tgctacaaaa cgcctaccat gcagtggcag 4380
acttagtaaa tgaacataac atcaagtctg tcgccattcc actgctatct acaggcattt 4440
acgcagccgg aaaaagaccg cttgaagtat cacttaactg cttgacaaac gcgctagaca 4500
gaactgacgc ggacgtaacc atctattgcc tggataagaa gtggaaggaa agaatcgacg 4560
cggcactcca acttaaggag tctgtaacag agctgaagga tgaagatatg gagatcgacg 4620
atgagttagt atggatccat ccagacagtt gcttgaaggg aagaaaggga ttcagtacta 4680
caaaaggaaa attgtattcg tacttcgaag gcaccaaatt ccatcaagca gcaaagaca 4740
tggcggagat aaaggtcctg ttccctaatg accaggaaag taatgaacaa ctgtgtgcct 4800
acatattggg tgagaccatg gaagcaatcc gcgaaaagtg cccggtcgac cataacccgt 4860
cgtctagccc gccccaaaacg ttgccgtgcc tttgcatgta tgccatgacg ccagaaaggg 4920
tccacagact tagaagcaat aacgtcaaag aagttacagt atgctcctcc accccccttc 4980
ctaagcacaa aattaagaat gttcagaagg ttcagtgcac gaaagtagtc ctgtttaatc 5040
cgcacactcc cgcattcgtt ccgcccgta agtacatga agtgccagaa cagcctaccg 5100
ctcctcctgc acaggccgag gaggccccg aagttgtagc gacaccgtca ccatctacag 5160
ctgataacac ctcgcttgat gtcacagaca tctcactgga tatggatgac agtagcgaag 5220
gctcactttt ttcgagcttt agcggatcgg acaactctat tactagtatg gacagttggt 5280
cgtcaggacc tagttcacta gagatagtag accgaaggca ggtggtggtg gctgacgttc 5340
atgcgtccca agagcctgcc tcgcaaggct aaagaagatg gccgcctga 5400
cagcggcaag aaaagagccc actccaccgg caagcaatag ctctgagtcc ctccacctct 5460
cttttggtgg ggtatccatg tccctcggat caatttcga cggagagacg gcccgccagg 5520
cagcggtaca cccctggca acaggccca cggatgtgcc tatgtctttc ggatcgtttt 5580
ccgacggaga gattgatgag ctgagccgca gagtaactga gtccgaaccc gtcctgtttg 5640
gatcatttga accgggcgaa gtgaactcaa ttatatcgtc ccgatcagcc gtatctttc 5700
```

```
ctctacgcaa gcagagacgt agacgcagga gcaggaggac tgaatactga ctaaccgggg   5760
taggtgggta catattttcg acggacacag gccctgggca cttgcaaaag aagtccgttc   5820
tgcagaacca gcttacagaa ccgaccttgg agcgcaatgt cctggaaaga attcatgccc   5880
cggtgctcga cacgtcgaaa gaggaacaac tcaaactcag gtaccagatg atgcccaccg   5940
aagccaacaa aagtaggtac cagtctcgta aagtagaaaa tcagaaagcc ataaccactg   6000
agcgactact gtcaggacta cgactgtata actctgccac agatcagcca gaatgctata   6060
agatcaccta tccgaaacca ttgtactcca gtagcgtacc ggcgaactac tccgatccac   6120
agttcgctgt agctgtctgt aacaactatc tgcatgagaa ctatccgaca gtagcatctt   6180
atcagattac tgacgagtac gatgcttact tggatatggt agacgggaca gtcgcctgcc   6240
tggacactgc aaccttctgc cccgctaagc ttagaagtta cccgaaaaaa catgagtata   6300
gagccccgaa tatccgcagt gcggttccat cagcgatgca gaacacgcta caaaatgtgc   6360
tcattgccgc aactaaaaga aattgcaacg tcacgcagat gcgtgaactg ccaacactgg   6420
actcagcgca attcaatgtc gaatgctttc gaaaatatgc atgtaatgac gagtattggg   6480
aggagttcgc tcggaagcca attaggatta ccactgagtt tgtcaccgca tatgtagcta   6540
gactgaaagg ccctaaggcc gccgcactat ttgcaaagac gtataatttg gtcccattgc   6600
aagaagtgcc tatggataga ttcgtcatgg acatgaaaag agacgtgaaa gttacaccag   6660
gcacgaaaca cacagaagaa agaccgaaag tacaagtgat acaagccgca gaaccctcg   6720
cgactgctta cttatgcggg attcaccggg aattagtacg taggcttacg gccgtcttgc   6780
ttccaaacat tcacacgctt tttgacatgt cggcggagga ttttgatgcg aatcatagcag   6840
aacacttcaa gcaaggcgac ccggtactgg agacggatat cgcatcattc gacaaaagcc   6900
aagacgacgc tatggcgtta accggtctga tgatcttgga ggacctgggt gtggatcaac   6960
cactactcga cttgatcgag tgcgcctttg gagaaatatc atccacccat ctacctacgg   7020
gtactcgttt taaattcggg gcgatgatga atccggaat gttcctcaca cttttttgtca   7080
acacagtttt gaattcgtt atcgccagca gagtactaga ggagcggctt aaaacgtcca   7140
gatgtgcagc gttcattggc gacgacaaca tcatacatgg agtagtatct gacaaagaaa   7200
tggctgagag gtgcgccacc tggctcaaca tggaggttaa gatcatcgac agcagtcatcg   7260
gtgagagacc accttacttc tgcggcgat ttatcttgca agattcggtt acttccacag   7320
cgtgccgcgt ggcggatccc ctgaaaaggc tgtttaagtt gggtaaaccg ctcccagccg   7380
acgacgagca agacgaagac agaagacgcg ctctgctaga tgaaacaaag gcgtggttta   7440
gagtaggtat aacaggcact ttagcagtgg ccgtgacgac ccggtatgag gtagacaata   7500
ttacacctgt cctactggca ttgagaactt tgcccagag caaaagagca ttccaagcca   7560
tcagagggga aataaagcat ctctacggtg tcctaaaata gtcagcatag tacatttcat   7620
ctgactaata ctacaacacc accaccacgc gtgctagacc atggatccta gacgctacgc   7680
cccaatgatc cgaccagcaa aactcgatgt acttccgagg aactgatgtg cataatgcat   7740
caggctggta cattagatcc ccgcttaccg cgggcaatat agcacactaa aaaactcgat   7800
gtacttccga ggaagcgcag tgcataatgc tgcgcagtgt tgccacataa ccactatatt   7860
aaccatttat ctagcggacg ccaaaaactc aatgtatttc tgaggaagcg tggtgcataa   7920
tgccacgcag cgtctgcata actttttatta tttctttat taatcaacaa aattttgttt   7980
ttaacatttc aaaaaaaaaa aaaaaaaaaa aaaaatctag aaaaaaaaaa aaaaaaaaa   8040
aaaaaaaaaa aaaaaaaaaa aaaaaaaaaa aaaaaaaaa aaaaaaaaaa aaaaaaaaa   8100
aaaaaaaaaa aaaaaaaaaa                                                8120

SEQ ID NO: 105         moltype = RNA  length = 8875
FEATURE                Location/Qualifiers
misc_feature           1..8875
                       note = Synthetic polynucleotide
source                 1..8875
                       mol_type = other RNA
                       organism = synthetic construct
SEQUENCE: 105
atgggcggcg catgagagaa gcccagacca attacctacc caaaatggag aaagttcacg    60
ttgacatcga ggaagacagc ccattcctca gagctttgca gcggagcttc ccgcagtttg   120
aggtagaagc caagcaggtc actgataatg accatgctaa tgccagagcg ttttcgcatc   180
tggcttcaaa actgatcgaa acggaggtgg acccatccga cacgtccctt gacattgaa   240
gtcgcccgc ccgcagaatg tattctaagc acaagtatca ttgtatctgt ccgatgagat   300
gtgcggaaga tccggacaga ttgtataagt atgcaactaa gctgaagaaa aactgtaagg   360
aaataactga taaggaattg gacaagaaaa tgaaggagct ggccgccgtc atgagcgacc   420
ctgacctgga aactgagact atgtgcctcc acgacgacga gtcgtgtcgc tacgaagggc   480
aagtcgctgt ttaccaggat gtatacgccg tcgacggccc caccagcgta taccaccagg   540
ccaacaaggg cgtgagggtg cgctactgga tcggcttcga caccaccacc ttcatgttca   600
agaacctggc cggcgcctac cccagctaca gcaccaactg ggccgacgag accgtgctga   660
ccgccaggaa catcggcctg tgcagcagcg acgtgatgga ggagccggag aggcatga    720
gcatcctgag gaagaaatac ctgaagccca gcaacaacgt gctgttcagc gtgggcagca   780
ccatctcacc cgagaagagg gacctgctca gagctctgca cctgcccagc gtgttccaaa   840
tgaggggcaa gcagaactac acctgcaggt gcgagaccat cgtgagctgc gacggctacg   900
tggtgaagag gatcgccatc agcccggct gtacggcaa gccagcggc tacgccgcta   960
caatgcacag ggagggcttc ctgtgctgca aggtgaccga caccctgaac ggcgagaggg  1020
tgagcttccc cgtgtgcacc tacgtgcccg ccacctgtg cgaccagatg accggcatcc  1080
tggccaccga cgtgagcgcc gacgacgccc agaagtctgc gtgggcctg aaccagagga  1140
tcgtggtcaa cggcaggacc cagaggaaca ccaacacaat gaagaactac ctgctgcccg  1200
tggtggccca ggctttcgcc agtgtggca ggagtacaa ggaggaccag gaagacgaga  1260
ggcccctggg cctgagggac aggcagctgg tgatgggctg ctgctggcc ttcaggcgc   1320
acaagatcac cagcatctac aagagcccg acacccagac catcatcaag gtgaacagcg  1380
acttccacag cttcgtgctg cccaggatcg gcagcaacc cctggagatc ggcctggga  1440
cccggatcag gaagatgctg gaggaacaca aggagccca ccactgatc accgccgagg   1500
acgtgcagga ggccaagtgc gctgccgacg aggccaagga ggtgaggag gccgaggaac   1560
tgagggccgc cctgccaccc ctggctgccg acgtggagga acccacctg gaagccgacg   1620
tggacctgat gctgcaggag gccggcgccg gaagcgtgga gacacccagg ggcctgatca   1680
aggtgaccag ctacgacggc gaggacaaga tcggcagcta cgccgtgctg agcccacagg   1740
```

```
ccgtgctgaa gtccgagaag ctgagctgca tccacccact ggccgagcag gtgatcgtga  1800
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgca gccagccgac gacgacggcg  2040
agtacctgta cgacatcgac aggaagcagt gcgtgaagaa agagctggtg accggcctga  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca cccgtggag acctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcacccgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
agggcaacga gatcatgacc gccgctgcca gccagggcct gaccaggaag gacgctgtacg  2820
ccgtgaggta caaggtgaac gagaacccac tgtacgctcc caccagcgag cacgtgaacg  2880
tgctgctgac caggaccgag gacaggatcg tgtggaagac cctggccggc gacccctgga  2940
tcaagaccct gaccgccaag taccccgcga acttcaccgc caccatcgaa gagtggcagg  3000
ccgagcacga cgccatcatg aggcacatcc tggagagcgc cgaccccacc gctgttcc    3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccacc gtgccactga gcatcagaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcacctga   3420
ggaactacga ccccaggatc aacctggtgc ccgtgaacag gcggctgccc cacgccctgg  3480
tgctgcacca caacgagcac ccacagagcg actttcagtc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc ccggcgacg   3660
tgcccaagta cgacatcatc ttcgtgaacg tcaggacccc atacaagtac accattacc   3720
agcagtgcga ggaccacgcc atcaagctga gcatgctgac caagaaggcc tgcctgcacc  3780
tgaaccccgg aggcacctgc gtgagcatcg gctacgctca cgccgacagg gccagcgaga  3840
gcatcattgg cgccatgccc aggctgttca agttcagcag ggtgtgcaaa cccaagagca  3900
gcctggagga aaccgaggtg ctgttcgtgt catcggcta cgaccggaag gccaggaccc    3960
acaaccccta caagctgagc agcacctga caaaatctcta caccggcagc aggctgcacg  4020
aggccggctg cgcccccage taccacgtgg tcaggggcga tatcgccacc gccaccgagg  4080
gcgtgatcat caacgctgcc aacagcaagg gccagcccgg aggcggagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg cccccaacttc aacaaggtga  4260
gcgaggtgga aggcgacaag cagctggccg aagcctacga aggcatcgcc aagatcgtga  4320
acgacaataa ctacaagagc gtggccatcc cactgctcag caccggcatc ttcagcggca  4380
acaaggacag gctgacccag agcctgaacc acctgctcac cgcccttggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgagggtg cacccaaga gctccggc cggcaggaag ggctacagca     4620
ccagcgacgg caagaccttc agctacctgg agggcaccaa gttccaccag gccgctaagg  4680
acatcgccga gatcaacgct atgtggcccg tggccaccga ggcaacgag caggtgtgca   4740
tgtacatcct gggcgagagc atgtccagca tcaggagaa gtgccccgtg gaggaaagcg  4800
aggccagcac accacccagc accctgcct gcctgtgcat ccacgctatg acacccgaga   4860
gggtgcagcg gctgaaggcc agcaggcccg agcagatcac cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagcc ccacccgtga    5040
acgagacacc cgagccaagc gccgagaacc agagcaccga gggcacaccc gagcagccac  5100
ccctgatcac cgaggacgag caaggaccg ggacccaga gccatcatt atcgaggaag      5160
aggaagagga cagcatcagc ctgctgagcg acggccccac ccaccaggtg ctgcaggtgg  5220
aggccgacat ccacggccca cccagcgtgt ccagctccag ctggagcatc ccaccacgca  5280
gcgacttcga cgtggacagc ctgagcatcc tggacaccct ggagggcgcc agcgtggacc  5340
ccggcgccac cagcgccgag accaacagct acttcgccaa gagcatggag ttcctggcca  5400
ggcccgtgcc agctcccagg accgtgttca ggaacccacc ccaccagct cccaggacca   5460
ggaccccaag cctggctccc agcagggcct gcagcaggac cagcctggtg agcacccac    5520
ccggctgaa cagggtgatc accaggggagg aactggaggc cctgacaccc agcagaaccc  5580
ccagcaggtc cgtgagcagg actagtctgg tgtccaaccc accggcgtg aacagggtga    5640
tcaccaggga ggaattcgag gccttcgtgg cccagcaaca gagacggttc gacgccggcg  5700
cctacatctt cagcagcgac accggccagg acacctgca gcaaagagc gtgaggcaga    5760
ccgtgctgag cgaggtggtg ctggagagga ccgagctgga aatcagctac gcccccaggc  5820
tggaccagga gaaggaggaa ctgctcagga agaaactgca gctgaacccc accccagcca  5880
acaggagcag gtaccagagc aggaaggtgg agaacatgga ggcatcacc gccaggcgga    5940
tcctgcaggg cctgggacac tacctgaagg ccgaggcaa ggtggagtgc tacaggaccc    6000
tgcacccccgt gccactgtac agctccagcg tgaacaggc cttctccage cccaaggtgg    6060
ccgtggaggc ctgcaacgct atgctgaagg agaacttccc caccgtggcc agctactgca  6120
tcatcccga gtacgacgcc taccggaca tggtggacgc cgtcctggaca                6180
ccgcagcctt ctgccccgcc aagctgagga gcttccccaa gaaacacagc tacctggagc  6240
caccatcag gagccgcgtg cccagcgcca tccagaacac cctgcagaac gtgctggccg    6300
ctgccaccaa gaggaactgc aacgtgaccc cagatgaggga gctgccccgtg ctggacagcg  6360
ctgccttcaa cgtggagtgc ttcaagaaat acgcctgcaa caacgagtac tgggagacct  6420
tcaaggagaa cccccatcagg ctgaccgaag agaacgtggt gaactacatc accaagctga  6480
```

```
agggccccaa ggccgctgcc ctgttcgcta agacccacaa cctgaacatg ctgcaggaca    6540
tcccaatgga caggttcgtg atggacctga gagggacgt gaaggtgaca cccggccacca    6600
agcacaccga ggagaggccc aaggtgcagg tgatccaggc cgctgaccca ctggccaccg    6660
cctacctgtg cggcatccac agggagctgg tgaggcggct gaacgccgtg ctgctgccca    6720
acatccacac cctgttcgac atgagcgccc aggacttcga cgccatcatc gccgagcact    6780
tccagcccgg cgactgcgtg ctggagaccg acatcgccag cttcgacaag agcgaggatg    6840
acgctatggc cctgaccgct ctgatgatcc tggaggacct gggcgtggac gccgagctgc    6900
tcaccctgat cgaggctgcc ttcggcgaga tcagctccat ccacctgccc accaagacca    6960
agttcaagtt cggcgctatg atgaaaagcg gaatgcttct gaccctgttc gtgaacaccg    7020
tgatcaacat tgtgatcgcc agcagggtgc tgcgggagag gctgaccggc agccctgcg    7080
ctgccttcat cggcgacgac aacatcgtga agggcgtgaa aagcgacaag ctgatggccg    7140
acaggtgcgc cacctggctg aacatggagg tgaagatcat cgacgccgtg gtgggcgaga    7200
aggcccccta cttctgcggc ggattcatcc tgtgcgacag cgtgaccggc accgcctgca    7260
gggtggccga ccccctgaag aggctgttca agctgggcaa gccactggcc gctgacgatg    7320
agcacgacga tgacaggcgg agggccctgc acgaggaaag caccaggtgg aacagggtgg    7380
gcatcctgag cgagctgtgc aaggccgtgg agagcaggta cgagaccgtg ggcaccagca    7440
tcatcgtgat ggctatgacc acactggcca gctccgtcaa gagcttctcc tacctgaggg    7500
gggccctat aactctctac ggctaacctg aatggactac gacatagtct agtccgccaa    7560
ggccgccacc atgagagtga cagccccta g aaccttactg cttctgcttt ggggagctgt    7620
tgctctgaca gagacatggg ctggatctct gagcgaggtg accggccagg gcctgtgcat    7680
cggcgccgtg cccaagaccc accaggtgct gtgcaacacc cccagaagaa ccagcgacgg    7740
cagctactac ctggccgctc ccaccggcac cacctggcc tgcagcaccg cctgaccc    7800
ttgcatcagc accaccatcc tgaacctgac caccgactac tgcgtgctgg tggagctgtg    7860
gcccagggtg acctaccaca gcccagcta cgcctaccac cagttcgaga ggagggccaa    7920
gtacaagagg gagcccgtga gcctgaccct ggccctgctg ctgggcggcc tgacaatggg    7980
cggcatcgcc gccggcgtgg gcaccggcac caccgcctg gtggccaccc agcagttcca    8040
gcagctgcag gccgccatgc acgacgacct gaaggaggtg gagaagtcca tcaccaacct    8100
ggagaagtcc ctgaccagcc tgagcgaggt ggtgctgcag aacaggaggg gcctggacct    8160
gctgttcctg aaggagggcg gcctgtgcgc cgccctgaag gaggagtgct gcctgtacgc    8220
cgaccacacc ggcctggtga tcgtgggcat tgtcgctggc gtgccgtcc tcgccgtggt    8280
ggtgattgga gctgtggtcg cagctgttat gtgcagaaga aagtcatccg gcggaaaggg    8340
aggctcctac tctcaggctg cttctgctac agtgcctaga gctcttatgt gtttatctca    8400
gctgtaaact cgagtatgtt acgtgcaaag gtgattgtca cccccgaaa gaccatatg    8460
tgacacaccc tcagtatcac gcccaaaacat ttacagccgc ggtgtcaaaa gccgcgtgga    8520
cgtggttaac atccctgctg ggaggatcag ccgtaattat tataattggc ttggtgctgg    8580
ctactattgt ggccatgtac gtgctgacca accagaaaca taattgaata cagcagcaat    8640
tggcaagctg cttacataga actcgcggcg attggcatgc cgccttaaaa ttttattt    8700
atttttctt ttcttttccg aatcggattt tgttttaat atttcaaaaa aaaaaaaaaa    8760
aaaaaaaaaa tctagaaaaa aaaaaaaaaa aaaaaaaaaa aaaaaaaaaa aaaaaaaaaa    8820
aaaaaaaaaa aaaaaaaaaa aaaaaaaaaa aaaaaaaaaa aaaaa                  8875

SEQ ID NO: 106        moltype = RNA   length = 8416
FEATURE               Location/Qualifiers
misc_feature          1..8416
                      note = Synthetic polynucleotide
source                1..8416
                      mol_type = other RNA
                      organism = synthetic construct
SEQUENCE: 106
atgggcggcg catgagagaa gcccagacca attacctacc caaaatggag aaagttcacg     60
ttgacatcga ggaagacagc ccattcctca gagctttgca gcggagcttc ccgcagttg    120
aggtagaagc caagcaggtc actgataatg accatgctaa tgccagagcg ttttcgcatc    180
tggcttcaaa actgatcgaa acggaggtgg acccatccga cacgatccct gacattggaa    240
gtgcgcccgc ccgcagaatg tattctaagc acaagtatca ttgtatctgt ccgatgagat    300
gtgcggagga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgccg tcgacggccc caccagcctg taccaccagg    540
ccaacaaggg cgtgagggtg gcctactgga tcggcttcga caccacaccc ttcatgttca    600
agaacctggc cggcgcctac ccagctacag gcaccaactg ggccgacgag accgtgctga    660
ccgcaggaa catcggcctg tgcagcagcg acgtgatgga gagcggcag agaggcatga    720
gcatcctgag gaagaaatac ctgaagccca gcaacaacgt gctgttcagc gtgggcagca    780
ccatctacca cgagaagagg gacctgctca ggagctggca cctgcccagc gtgttccacc    840
tgaggggcaa gcagaactac acctgcaggt gcgagaccat cgtgagctgc gacggctacg    900
tggtgaagag gatcgccatc agccccggcc tgtacggcaa gccagcggc tacgccgcta    960
caatgcacag ggagggcttc ctgtgctgca aggtgaccga caccctgaac ggcgagaggg   1020
tgagcttccc cgtgtgcacc tacgtgcccg ccaccctgtg cgaccagatg accggcatcc   1080
tggccaccga cgtgagcgcc gacgacgcc agaagctgct cgtgggcctg aaccagagga   1140
tcgtcgtcaa cggcagacga cagaggaaca ccaacaat gaagaactac ctgctgccca   1200
tggtggccca ggctttcgcc aagtgggcca aggagtacaa ggaggaccag aagacgaga   1260
ggcccctggg cctgagggac aggcagctgg tgatgggctc tgctggggcc ttcaggcggc   1320
acaagatcac cagcatctac aagaggcccg acacccagac atcatcaag gtgaacagcg   1380
acttccacag cttcgtgctg cccaggatcg gcagcaacac cctggagatc ggcctgagga   1440
cccggataga gaagatgctg gaggaacaca aggagcccac cactgctgca acgcgctaca   1500
acgtgcagga ggccaagtgc gctgccgacg aggccaagga ggtgagggag gccgaggaac   1560
tgagggccgc cctgccaccc ctggctgccg acgtgagggag acccaccctg aagccgacg   1620
tggacctgat gctgcaggag gccggcgccg aagcgtgga cacccagggc ctgatca     1680
aggtgaccag ctacgacggc gaggacaaga tcggcagcta cgccgtgctg agcccacagg   1740
ccgtgctgaa gtccgagaag ctgagctgca tccacccact ggccgagcag gtgatcgtga   1800
```

-continued

```
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgac agcctgagga  2160
ccagacccgc cgctccctac caggtgccca ccatcggcgt gtacggcgtg cccggcagcg  2220
gaaagagcgc catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgaccccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
agggcaacga gatcatgacc gccgctgcca gccagggcct gaccaggaag ggcgtgtacg  2820
ccgtgaggta caaggtgaac gagaacccac tgtacgctcc ccagcgcac cacgtgaacg  2880
tgctgctgac caggaccgag gacaggatcg tgtggaagaa ccctggccgg cgaccctgga  2940
tcaagaccct gaccgccaag tacccggca acttcaccgc caccatcgaa gagtggcagg  3000
ccgagcacga cgccatcatg aggcacatcc tggagaggcc cgaccccacc gacgtgttcc  3060
agaacaaggc caacgtgtgc tgggccaagg ccctggtgcc cgtgctgaag accgccgaca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgccccacc gtgccactga gcatcaggaa caaccactgg gacaacagcc  3300
ccagcccaaa catgtacggc ctgaacaagg aggtggtcag gcagctggcc agcggtacc  3360
cacagctgcc cagggccgtg gccaccggca gggtgtacga catgaacacc ggcacctga  3420
ggaactacga ccccaggatc aacctggtgc ccgtgaacag gcggctgccc cacgccctgg  3480
tgctgccaca caacgagcac ccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc cccggcgacg  3660
tgcccaagta cgacatcatc ttcgtgaacg tcaggacccc atacaagtac caccattacc  3720
agcagtgcga ggaccacgcc atcaagctga gcatgctgac caagaaggcc tgcctgcacc  3780
tgaaccccgg aggcacctgc gtgagcatcg gctacggcta cgccgacagg gccagcgaga  3840
gcatcattgg cgccatcgcc aggctgttca gttcagcag ggtgtgcaaa cccaagagca  3900
gcctggagga aaccgaggtg ctgttcgtgt tcatcggcta cgaccggaag gccaggaccc  3960
acaaccccta caagctgagc agcacccgca caaacatcta caccggcagc aggctgcacg  4020
aggccggctg cgccccacc taccacgtgg tcaggggcga tatcgcacc gccaccgagg  4080
gcgtgatcat caacgctgcc aacagcaagg gccagccggc aggcgagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg cccaacttc aacaaggtga  4260
gcgaggtgga aggcgacaag cagctggccg aagcctacga gagcatcgcc aagatcgtga  4320
acgacaataa ctacaagagc gtggccatcc cactgctcag cgccggcatc ttcagcggca  4380
acaaggacag gctgacccag agcctgaacc acctgctcac cgccctggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgaggtg caccccaaga gctccctggc cggcaggaag ggctacagca  4620
ccagcgacgg caagaccttc agctacctgg agggcaccaa gttccaccag gccgctaagg  4680
acatcgccga gatcaacgct atgtggcccc tggccaccga ggccaacgag caggtgtgca  4740
tgtacatcct gggcgagagc atgtccagca tcaggagcaa gtgccccgtg gagaaagcgg  4800
aggccagcac accaccagc acctgccct gcctgtgcat ccacgctatg acaccgaga  4860
gggtgcagcg gctgaaggcc agcaggcccg agcagatcca cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagacc ccaccgtgg  5040
acgagacacc cgagccaagc gccgagaacc agagcaccga gggcacaccc gagcagccac  5100
ccctgatcac cgaggacgag acaaggaccc ggaccccaga gccatcatt atcgaggaag  5160
aggaagagga cagcatcagc ctgctgagcg acggcccacc ccaccaggtg ctgcaggtgg  5220
aggccgacat ccacgcccca cccagcgtgt ccagctccag ctggagcatc ccacacgcca  5280
gcgacttcga cgtggacagc ctgagcatcc tggacaccct ggagggcgcc agcgtgacct  5340
ccggcgccac cagcgccgag accaacagct acttcgccaa gagcatggac ttcctggcca  5400
ggcccgtgcc agctcccagg accgtgttca gaaccacc ccaccagct cccaggacca  5460
ggaccccaag cctggctccc agcagggcct gcagcaggac cagcctggtg agcaccccac  5520
ccggcgtgaa cagggtgatc accagggagg aactggaggc cctgacaccc agcaggaccc  5580
ccagcaggtc cgtgagcagg actagtctgg tgtccaaccc accggcgtg aacagggtga  5640
tcaccaggga ggaattcgag gccttcgtgg cccagcaaca gagacggttc gacgccggcc  5700
cctacatctt cagcagcgac accggccagg acacctgca gcaaaagagc gtgaggcaga  5760
ccgtgctgag cgaggtggtg ctggagagga ccgagctgga aatcagctac gccccaggc  5820
tggaccagga gaaggaggaa ctgctcagga gaaactgca gctgaacacc acccagcca  5880
acaggacagg gtaccagagc aggaaggtgg agaacatgaa ggccatcacc gccaggcgga  5940
tcctgcaggg cctgggacac tacctgaagg ccgaggcaa ggtggagtgc tacaggaccc  6000
tgcacccgt gccactgtac agctccagcg tgaacagggc cttctccagc cccaaggtgg  6060
ccgtggaggc ctgcaacgct atgctgaagg agaacttccc caccgtggcc agctactgca  6120
tcatcccga gtacgacgcc tacctggaca tggtggacgg cgccagctgc tgcctggaca  6180
cgccacgctt cttcccaga agctgagga gcttcccaca gaaacacgac tacctggagc  6240
ccaccatcag gagcgccgtg cccagcgcca tccagaacac cctgcagaac gtgctggccg  6300
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggcccaa ggccgctgcc ctgttcgcta agaccccaca ccctgaacatg ctgcaggaca  6540
```

```
tcccaatgga caggttcgtg atggacctga agagggacgt gaaggtgaca cccggcacca   6600
agcacaccga ggagaggccc aaggtgcagg tgatccaggc cgctgaccca ctggccaccg   6660
cctacctgtg cggcatccac agggagctgg tgaggcggct gaacgccgtg ctgctgccca   6720
acatccacac cctgttcgac atgagcgccg aggacttcga cgccatcatc gccgagcact   6780
tccagcccgg cgactgcgtg ctggacaccg acatcgccga cttcgacaag agcgaggatg   6840
acgctatggc cctgaccgct ctgatgatcc tggaggacct gggcgtggac gccgagctgc   6900
tcaccctgat cgaggctgcc ttcggcgaga tcagctccat ccacctgccc accaagacca   6960
agttcaagtt cggcgctatg atgaaaagcg gaatgttcct gaccctgttc gtgaacaccg   7020
tgatcaacat tgtgatcgcc agcagggtgc tgcgggagag gctgaccggc agccctgcg   7080
ctgccttcat cggcgacgac aacatcgtga agcgcaag ctgatgccga                7140
acaggtgcgc cacctggctg aacatggagg tgaagatcat cgacgccgtg gtgggcgaga   7200
aggcccccta cttctgcggc ggattcatcc tgtgcgacag cgtgaccggc accgcctgca   7260
gggtggccga cccccctgaag aggctgttca agctgggcaa gccactggcc gctgacgatg   7320
agcacgacga tgacaggcgg agggccctgc acgaggaaga caccaggtgg aacagggtgg   7380
gcatcctgag cgagctgtgc aaggccgtgg agagcaggta cgagaccgtg ggcaccagca   7440
tcatcgtgat ggctatgacc acactggcca gctccgtcaa gagcttctcc tacctgaggg   7500
gggccctat aactctctac ggctaacctg aatggactac gacatagtct agtccgccaa   7560
ggccgccacc atgagagtga cagccctag aaccttactg cttctgcttt ggggagctgt   7620
tgctctgaca gagacatggg ctggatctta ccacagcccc agctacgcct accaccagtt   7680
cgagaggggg ggaggaggct ccgggggagg aggctccctg aagatcagcc aggccgtgca   7740
cgccgcccac gccgagatca acgaggccgg ccgggaggtc atcgtgggca ttgtcgctgg   7800
cctggccgtc ctcgccgtgg tggtgattgg agctgtgggc cgagctgtta tgtgcagaag   7860
aaagtcatcc ggcggaaagg gaggctccta ctctcaggct gcttctgcta cagtgcctag   7920
agctcttatg tgtttatctc agctgtaaac tcgagtatgt tacgtgcaaa ggtgattgtc   7980
acccccccgaa agaccatatt gtgacacacc ctcagtatca cgcccaaaca tttacagccg   8040
cggtgtcaaa aaccgcgtgg acgtggttaa catccctgcc ggggaggatca gccgtaatta   8100
ttataattgg cttggtgctg gctactattg tggccatgta cgtgctgacc aaccagaaac   8160
ataattgaat acagcagcaa ttggcaagct gcttacatag aactcgcggc gattggcatg   8220
ccgccttaaa atttttattt tatttttttct tttcttttcc gaatcggatt tgtttttaa    8280
tatttcaaaa aaaaaaaaaaa aaaaaaaaa atctagaaaa aaaaaaaaaa aaaaaaaaaa    8340
aaaaaaaaaa aaaaaaaaaa aaaaaaaaa aaaaaaaaa aaaaaaaaa aaaaaaaaaa       8400
aaaaaaaaaa aaaaaa                                                    8416

SEQ ID NO: 107           moltype = RNA   length = 8914
FEATURE                  Location/Qualifiers
misc_feature             1..8914
                         note = Synthetic polynucleotide
source                   1..8914
                         mol_type = other RNA
                         organism = synthetic construct
SEQUENCE: 107
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggacaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgccg tcgacgccc caccagcctg taccaccagg    540
ccaacaaggg cgtgaggtg gcctactgga tcggcttcga caccaccccc ttcatgtctca    600
agaacctggc cggcgcctac cccagctaca gcaccaactg gccgacgag accgtgctga    660
ccgcaggaa catcggcctg tgcagcgcg acgtgatgga ggagccggg agaggcatga       720
gcatcctgag gaagaaatac ctgaagccca gcaacaacgt gctgttcagc gtgggcagca    780
ccatcctacc cgagaaagag gacctgctca ggagctggca cctgcccagc gtgttccaca    840
tgaggggcaa gcagaactac acctgcaggt gcgagaccat cgtgagctgc gacggctacg    900
tggtgaagag gatcgccatc agccccggct gtacggcaa gccagcggc tacgccgcta     960
caatgcacag ggagggcttc ctgtgctgca aggtgaccga cacccctgaac ggcgagaggg   1020
tgagcttccc cgtgtgcacc tacgtgcccg ccacccgtg cgaccagatg accggcatcc    1080
tggccaccga cgtgagcgcc gacgacgccc agaagcgtgct cgtgggcctg aaccagagca    1140
tcgtggtcaa cggcaggacc cagaggaaca ccaaacacaat gaagaactac ctgctgcccg    1200
tggtggccca ggctttcgcc agtgggcca aggagtacaa ggaggaccag gaagacgaga    1260
ggcccctggg cctgagggac aggcagctgg tgatgggctg ctgctgggcc ttcaggcggc    1320
acaagatcac cagcatctac aagaggcccg acacccagac catcatcaag tgaacagcg    1380
acttccacag cttcgtgctg ccaggatcg gcagcaacac cctggagatc ggcctgagga    1440
cccgatcag gaagatgctg gagaacaca aggagcccag cccactgatc accgccagg     1500
acgtgcagga ggccaagtgc gctgccgacg aggccaagga ggtgagggag gccgaggaac    1560
tgagggccgc cctgccaccc ctggctgccg acgtggagga accccagg gaaggcgacg    1620
tggacctgat gctgcaggag gccgggcgcg gaagcgtgga gacaccccag ggcctgatca    1680
aggtgaccag ctacgacggc gaggacaaga tcggcagcta cgccgtgctg agcccacagg    1740
ccgtgctgaa gtccgagaag ctgagctgca tccaccccact ggccgagcag gtgatcgtga    1800
tcacccacac cggcaggaag ggcaggtacg ccgtggagcc caccacggc aaggtggtgg    1860
tgcccgaggg ccacgccatc ccgtgcagg acttccagggc cctgagcgag agcgccacca    1920
tcgtgtacaa cgagagggga ttcgtgacaa ggtacctgca ccatatcgac accccaccgg    1980
gagccctgaa caccgacgag gaatactaca agaccgtgaa gcccagcgag cacgacggcg    2040
agtacctgta cgacatcgac aggaagcagt gcgtgaagaa agagctggtg accggcctgg    2100
gactgaccgc cgagctggtg gacccaccct tccacgagtt cgcctacgag agcctgagga    2160
ccagacccgc cgctccctac caggtgccca tcggcgtgt acgcgtgc cccggcagcg     2220
gaaagagcgg catcatcaag agcgccgtga ccaagaagga cctggtggtc agcgccaaga    2280
```

-continued

```
aagagaactg cgccgagatc atcagggacg tgaagaagat gaaaggcctg gacgtgaacg 2340
cgcgcaccgt ggacagcgtg ctgctgaacg gctgcaagca cccgtggag accctgtaca 2400
tcgacgaggc cttcgcttgc cacgccggca ccctgagggc cctgatcgcc atcatcaggc 2460
ccaagaaagc cgtgctgtgc ggcgacccca agcagtgcgg cttcttcaac atgatgtgcc 2520
tgaaggtgca cttcaaccac gagatctgca cccaggtgtt ccacaagagc atcagcaggc 2580
ggtgcaccaa gagcgtgacc agcgtcgtga gcaccctgtt ctacgacaag aaaatgagga 2640
ccaccaaccc caaggagacc aaaatcgtga tcgacaccac aggcagcacc aagcccaagc 2700
aggacgacct gatcctgacc tgcttcaggg gctgggtgaa gcagctgcag atcgactaca 2760
agggcaacga gatcatgacc gccgctgcca gccagggcct gaccaggaag ggcgtgtacg 2820
ccgtgaggta caaggtgaac gagaacccac tgtacgctcc caccagcgag cacgtgaacg 2880
tgctgctgac caggaccgag gacaggatcg tgtggaagac cctggccggc gacccctgga 2940
tcaagaccct gaccgccaag taccccggca acttcaccgc caccatcgaa gagtggcagg 3000
ccgagcacga cgccatcatg aggcacatct tggagaggcc cgaccccacc gacgtgttcc 3060
agaacaaggc caacgtgtgc tgggccaagg ccctggtgac cgtgctgaag accgccggca 3120
tcgacatgac cacagagcag tggaacaccg tggactactt cgagaccgac aaggcccaca 3180
gcgccgagat cgtgctgaac cagctgtgcg tgaggttctt cggcctggac ctggacagcg 3240
gcctgttcag cgcccccacc gtgccactga gcatcaggaa caaccactgg gacaacagcc 3300
ccagcccaaa catgtacggc ctgaacaagg aggtggtcag gcagctgagc aggcggtacc 3360
cacagctgcc cagggccgtg gccaccggca gggtgtacga catgaacacc ggcaccctga 3420
ggaactacga ccccaggatc aacctggtgc ccgtgaacag gcggctgccc cacgccctgg 3480
tgctgcacca caacgagcac ccacagagcg acttcagctc cttcgtgagc aagctgaaag 3540
gcaggaccgt gctggtcgtg ggcgagaagc tgagcgtgcc cggcaagatg gtggactggc 3600
tgagcgacag gcccgaggcc accttccggg ccaggctgga cctcggcatc cccggcgacg 3660
tgcccaagta cgacatcatc ttcgtgaacg tcaggacccc atacaagtac caccattacc 3720
agcagtgcga ggaccacgcc atcaagctga gcatgctgac caagaaggcc tgcctgcacc 3780
tgaaccccgg aggcaccgtgc gtgagcatcg gctacgacta tcaggccgag gccagcgaga 3840
gcatcattgg cgccatcgcc aggctgttca agttcagcag ggtgtgcaaa cccaagagca 3900
gcctggagga aaccgaggtg ctgttcgtgt tcatcggcta cgaccggaag gccaggaccc 3960
acaaccccta caagctgagc agcaccctga caaacatcta caccggcagc aggctgcacg 4020
aggccggctg cgcccccagc taccacgtgg tcagggcga tatcgccacc gccaccgagg 4080
gcgtgatcat caacgctgcc aacagcaagg gccagcccgg aggcggagtg tgcggcgccc 4140
tgtacaagaa gttccccgag agcttcgacc tgcagcccat cgaggtgggc aaggccaggc 4200
tggtgaaggg cgccgctaag cacatcatcc acgccgtggg cccccaacttc aacaaggtga 4260
gcgaggtgga aggcgacaag cagctggccg aagcctacga gagcatcgcc aagatcgtga 4320
acgacaataa ctacaagagc gtggccatcc cactgctcag caccggcatc ttcagcggca 4380
acaaggacag gctgacccag agcctgaacc acctgctcac cgccctggac accaccgatg 4440
ccgacgtggc catctactgc agggacaaga agtgggagat gacccctgaag gaggccgtgg 4500
ccaggcggga ggccgtggaa gagatctgca tcagcgacga ctccagcgtg accgagcccg 4560
acgccgagct ggtgagggtg caccccaaga gctccctggc cggcaggaag ggctacagca 4620
ccagcgacgg caagaccttc agctactgg agggcaccaa gttccaccag gccgctaagg 4680
acatcgccga gatcaacgct atgtggcccg tggccaccga ggccaacgag caggtgtgca 4740
tgtacatcct gggcgagagc atgtccagca tcaggagcaa gtgccccgtg gagaaagcg 4800
aggccagcac accaccagc accctgccct gcctgtgcat ccagctatg acacccgagg 4860
gggtgcagcg gctgaaggcc agcaggcccg agcagatcca cgtgtgcagc tccttcccac 4920
tgcccaagta caggatcacc ggcgtgcaga agatccagtg cagccagccc atcctgttca 4980
gcccaaaggt gcccgcctac atccacccca ggaagtacct ggtggagacc ccacccgtgg 5040
acgagacacc cgagccaagc gccgagaacc agagcaccga gggcacaccc gagcagccac 5100
ccctgatcac cgaggacgag acaaggaccc ggacccaga gccatcatt atcgaggaag 5160
aggaagagga cagcatcagc ctgctgagcg acggccccac ccaccaggtg ctgcaggtgg 5220
aggccgacat ccacggccca cccagcgtgt ccagctccag ctggagcatc ccacacgcca 5280
gcgacttcga cgtggacagc cgtgagcatcc tggacacact ggagggcgcc agcgtgacct 5340
ccggcgccac cagcgccgag accaacagct acttcgccaa gagcatggag ttcctggcca 5400
ggcccgtgcc agctcccagg accgtgttca ggaacccacc ccaccagct cccaggacca 5460
ggaccccaag cctggctccc agcagggcct gcagcaggac cagcctggtg agcaccccac 5520
ccggcgtgaa cagggtgatc accagggagg aactggaggc cctgacaccc agcaggaccc 5580
ccagcaggtc cgtgagcagg actagtctgg tgtccaaccc acccggcgtg aacagggtga 5640
tcaccaggga ggaattcgag gccttcgtgg cccagcaaca gagacggttc gacgccggcg 5700
cctacatctt cagcagcgac accggccagg gacacctgca gcaaagagc gtgaggcaga 5760
ccgtgctgag cgaggtggtg ctggagagga ccgagctgga aatcagctac gccccaggc 5820
tggaccagga gaaggaggaa ctgctcagga gaaactgca gctgaacccc acccagcca 5880
acaggagcag gtaccagagc aggaaggtgg agaacatgaa ggccatcacc gccaggcgga 5940
tcctgcaggg cctgggacac tacctgaagg ccgaggcaa ggtggagtgc tacaggaccc 6000
tgcacccgt gccactgtac agctccagcg tgaacagggc cttctccagc ccaaggtgg 6060
ccgtggaggc ctgcaacgct atgctgaagg agaacttccc caccgtgagc gctactgca 6120
tcatccccga gtacgacgcc tacctggaca tggtggacgg cgccagctgc tgcctggaca 6180
ccgccagctt ctgccccgcc aagctgagga gcttccccaa gaaacacagc tacctggagc 6240
caccatcag gagcgccgtg cccagcgcca tccagaacac cctgcagaac gtgctggccg 6300
ctgccaccaa caggaactgc aacgtgaccc agatgagga gctgcccgtg ctggacagcg 6360
ctgccttcaa cgtggagtgc ttcaagaaat acgcctgcaa caacagtac tgggagacct 6420
tcaaggagaa cccatcagg ctgaccgaag agaacgtggt gaactacatc accaagctga 6480
agggccccaa ggccgctgcc ctgttcgcta gacccacaa cctgaacatg ctgcaggaca 6540
tcccaatgga caggttcgtg atggacctga agagggacgt gaaggtgaca cccggcacca 6600
agcacaccga ggagagggccc aaggtgcagg tgatccaggc cgctgaccca ctggcaccg 6660
cctacctgtg cggcatccac aagggcgtg tgaggcggct gtgctgccca 6720
acatccacac cctgttcgac atgagcgccg aggacttcga cgccatcatc gccgagcact 6780
tccagcccgg cgactgcgtg ctggagaccg acatcgccag cttcgacaag agcgaggatg 6840
acgctatggc cctgaccgct ctgatgatcc tggaggacct gggcgtggac gccgagctgc 6900
tcaccctgat cgaggctgcc ttcggcgaga tcagctccat ccacctgccc accaagacca 6960
agttcaagtt cggcgctatg atgaaaagcg gaatgttcct gaccctgttc gtgaacaccg 7020
```

```
tgatcaacat tgtgatcgcc agcagggtgc tgcgggagag gctgaccggc agccctgcg    7080
ctgccttcat cggcgacgac aacatcgtga agggcgtgaa aagcgacaag ctgatggccg    7140
acaggtgcgc cacctggctg aacatggagg tgaagatcat cgacgccgtg gtgggcgaga    7200
aggcccccta cttctgcggc ggattcatcc tgtgcgacag cgtgaccggc accgcctgca    7260
gggtgccga ccccctgaag aggctgttca agctgggcga gccactgcgc gctgacgatg    7320
agcacgacga tgacaggcgg agggccctgc acgaggaaag caccaggtgg aacagggtgg    7380
gcatcctgag cgagctgtgc aaggccgtgg agagcaggta cgagaccgtg ggcaccagca    7440
tcatcgtgat ggctatgacc acactggcca gctccgtcaa gagcttctcc tacctgaggg    7500
gggcccctat aactctctac ggctaacctg aatggactac gacatagtct agtccgccaa    7560
ggccgccacc atgagagtga cagccctag aaccttactg cttctgcttt ggggagctgt    7620
tgctctgaca gagacatggg ctggatctct gagcgaggtg accggccagg gctgtgcat    7680
cggcgccgtg cccaagaccc accaggtgct gtgcaacacc cccagaaga ccagcgacgg    7740
cagctactac ctggccgctc ccaccggcac cacctgggc tgcagcaccg gcctgacccc    7800
ttgcatcagc accaccatcc tgaacctgac caccgactac tgctgctgg tggagctgtg    7860
gcccagggtg acctaccaca gccccagcta cgcctaccac cagttcgaga ggagggccaa    7920
gtacaagagg gagcccgtga gcctgaccct ggccctgctg ctgggcggcc tgacaatggg    7980
cggcatcgcc gccggcgtgg gcaccggcac caccgccctg gtggccaccc agcagttcca    8040
gcagctgcag gccgccatgc acgacgacct gaaggagg gagaagtcca tcaccaacct    8100
ggagaagtcc ctgaccagcc tgagcgaggt ggtgctgcag aacaggaggg gcctggacct    8160
gctgttcctg aaggaggggg gcctgtgcgc cgccctgaag gaggagtgct gcctgtacgc    8220
cgaccacacc ggcctggtga tcgtgggcat tgtcgctggc ctggccgtcc tcgccgtggt    8280
ggtgattgga gctgtggtcg cagctgttat gtgcagaaga aagtcatccg gcggaaaggg    8340
aggctcctac tctcaggctg cttctgctac agtgcctaga gctcttatgt gtttatctca    8400
gctgggcggc ggaggcagcg actacaagga cgacgatgac aagtaaactc gagtatgtta    8460
cgtgcaaagg tgattgtcac cccccgaaag accatattgt gacacaccct cagtatcacg    8520
cccaaacatt tacagccgcg gtgtcaaaaa ccgcgtggac gtggttaaca tccctgctgg    8580
gaggatcagc cgtaattatt ataattggct tggtgctgac tactattgtg gccatgtacg    8640
tgctgaccaa ccagaaacat aattgaatac agcagcaatt ggcaagctgc ttacatagaa    8700
ctcgcggcga ttggcatgcc gccttaaat ttttattttta tttttctttt ttctttccga    8760
atcggatttt gttttttata tttcaaaaaa aaaaaaaaa aaaaaaaat ctagaaaaaa    8820
aaaaaaaaaa aaaaaaaaaa aaaaaaaaaa aaaaaaaaaa aaaaaaaaaa aaaaaaaaaa    8880
aaaaaaaaaa aaaaaaaaaa aaaaaaaaaa aaaa                                8914

SEQ ID NO: 108         moltype = RNA    length = 8455
FEATURE                Location/Qualifiers
misc_feature           1..8455
                       note = Synthetic polynucleotide
source                 1..8455
                       mol_type = other RNA
                       organism = synthetic construct
SEQUENCE: 108
atgggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg gacaagaaaa tgaaggagct ggccgccgtc atgagcgacc     420
ctgacctgga aactgagact atgtgcctcc acgacgacga gtcgtgtcgc tacgaagggc     480
aagtcgctgt ttaccaggat gtatacgccg tcgacgccc caccagcctg taccaccagg     540
ccaacaaggg cgtgaggggg gcctactgga tcggcttcga caccacaccc ttcatgttca     600
agaacctggc cggcgcctac cccagctaca gcaccaactg ggccgacgag accgtgctga     660
ccgcaggaa catcggcctg tgcagcagcg acgtgatgga ggagccggg agaggcatga     720
gcatcctgag gaagaaatac ctgaagccca gcaacaacgt gctgttcagc gtgggcagca     780
ccatctacca cgaaaagagg gacctgctca ggagctgcac cgtgttccac     840
tgagggggcaa gcagaactac acctgcaggt gcgagaccat cgtgagctgc gacggctacg     900
tggtgaagag gatcgccatc agcccggcc tgtacggcaa gccagcggc tacgccgcta     960
caatgcacag ggaggggcttc ctgtgctgca aggtgaccga caccctgaac ggcgagaggg    1020
tgagcttccc cgtgtgcacc tacgtgcccg ccaccctgtg cgaccagatg accggcatcc    1080
tggccaccga cgtgagcgcc gacgacgcc cgtgggcctg cgtgggcacg aaccagagga    1140
tcgtggtcaa cggcaggacc cagaggaaca ccaacacaat gaagaactac ctgctgcccg    1200
tggtggccca ggctttcgcc agtgggcca aggagtacaa ggaggaccag gaagacgaga    1260
ggcccctggg cctgagggac aggcagctgg tgatgggctg ctgctgggcc ttcaggcggc    1320
acaagatcac cagcatctac aagagggccc acaccccagc catcatgaag ctgaacgtga    1380
acttccacag cttcgtgctg cccaggatcg gcagcaacac cctggagatc ggcctgagga    1440
cccgatcag gaagatgctg gaggaacaca agagcccag ccactgatc accgccgagg     1500
acgtgcagga ggcaagtgc gctgccgacg aggccaagga ggtgaggggag gccgaggaac    1560
tgaggggccgc cctgccaccc ctggctgccg acgtggagga acccaccagg gaagccgacg    1620
tggacctgat gctgcaggcc gccggcgccg gaagcgtgga gaccccagg ggctgatca    1680
aggtgaccag ctacgacggc gaggacaaga tcgcagcta cgccgtgctg agcccacagg    1740
ccgtgctgaa gtccgagaag ctgagctgca tccaccact ggccgagcag gtgatcgtga    1800
tcacccacag cggcaggaag gcaggtacg ccgtggagcc ctaccacggc aaggtggtcg    1860
tgccccgagg ccacgccatc cccgtgcagg acttccaggc cctgagcgag agcgccacca    1920
tcgtgtacaa cgagagggga ttcgtgaaca ggtacctgca ccatatcgac acccacgcg    1980
gagccctgaa caccgacgag gaatactaca gaccgtgaa gccagcgag cacgacggcg    2040
agtacctgta cgacatcgac aggaagcagt gcgtgaagaa agagctggtg accggcctgg    2100
gactgaccgc cgagctggtg gacccacccct tccacgagtt cgcctacgag agcctgagga    2160
ccagaccgc cgctccctac caggtgccca ccatcggcgt gtacggcgtg cccggcagcg    2220
gaaagagcgg catcatcaag agcgccgtga ccaagaaaga cctggtggtc agcgccaaga    2280
```

```
aagagaactg cgccgagatc atcagggacg tgaagaagat gaaaggcctg gacgtgaacg 2340
cgcgcaccgt ggacagcgtg ctgctgaacg gctgcaagca cccgtggag accctgtaca 2400
tcgacgaggc cttcgcttgc cacgccggca ccctgagggc cctgatcgcc atcatcaggc 2460
ccaagaaagc cgtgctgtgc ggcgacccca agcagtgcgg cttcttcaac atgatgtgcc 2520
tgaaggtgca cttcaaccac gagatctgca cccaggtgtt ccacaagagc atcagcaggc 2580
ggtgcaccaa gagcgtgacc agcgtcgtga gcacccctgtt ctacgacaag aaaatgagga 2640
ccaccaaccc caaggagacc aaaatcgtga tcgacaccac aggcagcacc aagcccaagc 2700
aggacgacct gatcctgacc tgcttcaggg gctgggtgaa gcagctgcag atcgactaca 2760
agggcaacga gatcatgacc gccgctgcca gccagggcct gaccaggaag ggcgtgtacg 2820
ccgtgaggta caaggtgaac gagaacccac tgtacgctcc caccagcgag cacgtgaacg 2880
tgctgctgac caggaccgag gacaggatcg tgtggaagac cctggccggc gacccctgga 2940
tcaagaccct gaccgccaag taccccggca acttcaccgc caccatcgaa gagtggcagg 3000
ccgagcacga cgccatcatg aggcacatcc tggagaggcc cgaccccacc gacgtgttcc 3060
agaacaaggc caacgtgtgc tgggccaagg ccctggtgac ccgtgctgaag accgccgcca 3120
tcgacatgac cacagagcag tggaacaccg tggactactt cgagaccgac aaggcccaca 3180
gcgccgagat cgtgctgaac cagctgtgcg tgaggttctt cggcctggac ctggacagcg 3240
gcctgttcag cgcccccacc gtgccactga gcatcaggaa caaccactgg gacaacagcc 3300
ccagcccaaa catgtacggc ctgaacaagg aggtggtcag gcagctgacc aggcggtacc 3360
cacagctgcc cagggccgtg gccaccggca gggtgtacga catgaacacc ggcaccctga 3420
ggaactacga ccccaggatc aacctggtgc ccgtgaacag gcggctgccc cacgccctgg 3480
tgctgcacca acgagcac ccacagagcg acttcagctc cttcgtgagc aagctgaaag 3540
gcaggaccgt gctggtcgtg ggcgagaagc tgagcgtgcc cggcaagatg gtggactggc 3600
tgagcgacag gcccgaggcc accttccggg ccaggctgga cctcggcatc ccgggcgacg 3660
tgcccaagta cgacatcatc ttcgtgaacg tcaggacccc atacaagtac caccattacc 3720
agcagtgcga ggaccacgcc atcaagctga gcatgctgac caagaaggcc tgcctgcacc 3780
tgaaccccgg aggcaccctgc gtgagcatcg gctacgccta cagctgggcc ggcacggcga 3840
gcatcattgg cgccatcgcc aggctgttca agttcagcag ggtgtgcaaa cccaagagca 3900
gcctggagga aaccgaggtg ctgttcgtgt tcatcggcta cgaccggaag gccaggaccc 3960
acaaccccta caagctgagc agcaccctga caaacatcta caccggcagc aggctgcacg 4020
aggccgctg cgcccccagc taccacgtgg tcaggggcga tatcgccacc gccaccgagg 4080
gcgtgatcat caacgctgcc aacagcaagg gccagcccgg aggcggagtg tgcggcgccc 4140
tgtacaagaa gttccccgag agcttcgacc tgcagcccat cgaggtgggc aaggccaggc 4200
tggtgaaggg cgccgctaag cacatcatcc acgccgtggg ccccaacttc aacaaggtga 4260
gcgaggtgga aggcgacaag cagctggccg aagcctacga gagcatcgcc aagatcgtga 4320
acgacaataa ctacaagagc gtggccatcc cactgctcag caccggcatc ttcagcggca 4380
acaaggacag gctgacccag agcctgaacc acctgctcac cgccctggac accaccgatg 4440
ccgacgtggc catctactgc agggacaaga agtgggagat gaccctgaag gaggccgtgg 4500
ccaggcggga ggccgtggaa gagatctgca tcagcgacga ctccagcgtg accgagcccg 4560
acgccgagct ggtgagggtg caccccaaga gctccctggc cggcaggaag ggctacagca 4620
ccagcgacgg caagaccttc agctactggg agggcaccaa gttccaccag gccgctaagg 4680
acatcgccga gatcaacgct atgtggcccg tggccaccga ggccaacgag caggtgtgca 4740
tgtacatcct gggcgagagc atgtccagca tcaggagcaa gtgccccgtg gagaaagcg 4800
aggcagcac accaccagc accctgccct gcctgtgcat ccacgctatg acacccgagg 4860
gggtgcagcg gctgaaggcc agcaggcccg agcagatcca cgtgtgcagc tccttcccac 4920
tgcccaagta caggatcacc ggcgtgcaga agatccagtg cagccagccc atcctgttca 4980
gcccaaaggt gcccgcctac atccacccca ggaagtacct ggtggagacc ccacccgtgg 5040
acgagacacc cgagccaagc gccgagaacc agagcaccga gggcacaccc gagcagccac 5100
ccctgatcac cgaggacgag acaaggaccc ggacccagaa gcccatcatt atcgaggaag 5160
aggaagagga cagcatcagc ctgctgagcg acggccccac ccaccaggtg ctgcaggtgg 5220
aggccgacat ccacggccca cccagcgtgt ccagctccag ctggagcatc ccacacgcca 5280
gcgacttcga cgtggacacg ctgagcatcc tggacacctt ggagggcgcc agcgtgacct 5340
ccggcgccac cagcgccgag accaacagct acttcgccaa gagcatggag ttcctgcca 5400
ggcccgtgcc agctcccagg accgtgttca ggaacccacc ccaccagct cccaggacca 5460
ggaccccaag cctggctccc agcagggcct gcagcaggac cagcctggtg agcacccac 5520
ccggcgtgaa cagggtgatc accagggagg aactggaggc cctgacaccc agcaggaccc 5580
ccagcaggtc cgtgagcagg actagtctgg tgtccaaccc acccggcgtg aacagggtga 5640
tcaccaggga ggaattcgag gccttcgtgg cccagcaaca gagacggttc gacgccggcg 5700
cctacatctt cagcagcgac accggccagg gacacctgca gcaaaagagc gtgaggcaga 5760
ccgtgctgag cgaggtggtg ctggagagga ccgagctgga aatcagctac gccccccagc 5820
tggaccagga gaaggaggaa ctgctcagga gaaactgca gctgaacccc accccagcca 5880
acaggagcag gtaccagagc aggaaggtgg agaacatgaa ggccatcacc gccaggcgga 5940
tcctgcaggg cctgggacac tacctgaagg ccgaggcaa ggtggagtgc tacaggaccc 6000
tgcacccgt gccactgtac agctccagcg tgaacagggc cttctccagc cccaaggtgg 6060
ccgtggaggc ctgcaacgct atgctgaagg agaacttccc caccgtgacg gctactgca 6120
tcatcccga gtacgacgcc tacctggaca tggtggacgg cgccagctgc tgcctggaca 6180
ccgccagctt ctgccccgcc aagctgagga gcttccccaa gaaacacagc tacctggagc 6240
ccaccatcag gagcgccgtg cccagcgcca tccagaacac cctgcagaac gtgctggccg 6300
ctgccaccaa ggagaactgc aacgtgacc agatgaggga gctgcccgtg ctggacagcg 6360
ctgccttcaa cgtggagtgc ttcaagaaat acgcctgcaa caacgagtac tgggagacct 6420
tcaaggagaa ccccatcagg ctgaccgaag agaacgtggt gaactacatc accaagctga 6480
agggccccaa ggccgctgcc ctgttcgcta gacccacaa cctgaacatg ctgcaggaca 6540
tcccaatgga caggttcgtg atggacctga agagggacgt gaaggtgaca cccggcacca 6600
agcacaccga ggagagggcc aaggtgcagg tgatccaggc cgctgaccca ctggccaccg 6660
cctacctgtg cggcatccac aagggcctgg tgaggcggct ctgctgccca 6720
acatccacac cctgttcgac atgagcgccg aggacttcga cgccatcatc gccgagcact 6780
tccagcccgg cgactgcgtg ctggagaccg acatcgccag cttcgacaag agcgaggatg 6840
acgctatggc cctgaccgct ctgatgatcc tggaggacct gggcgtggac gccgagctgc 6900
tcaccctgat cgaggctgcc ttcggcgaga tcagctccat ccacctgccc accaagacca 6960
agttcaagtt cggcgctatg atgaaaagcg gaatgttcct gaccctgttc gtgaacaccg 7020
```

```
                                          -continued
tgatcaacat tgtgatcgcc agcagggtgc tgcgggagag gctgaccggc agccctgcg      7080
ctgccttcat cggcgacgac aacatcgtga agggcgtgaa aagcgacaag ctgatggccg      7140
acaggtgcgc cacctggctg aacatggagg tgaagatcat cgacgccgtg gtgggcgaga     7200
aggcccccta cttctgcggc ggattcatcc tgtgcgacag cgtgaccggc accgcctgca     7260
gggtggccga ccccctgaag aggctgttca agctgggcaa gccactggcc gctgacgatg     7320
agcacgacga tgacaggcgg agggccctgc acgaggaaag caccaggtgg aacagggtgg     7380
gcatcctgag cgagctgtgc aaggccgtgg agagcaggta cgagaccgtg ggcaccagca     7440
tcatcgtgat ggctatgacc acactggcca gctccgtcaa gagcttctcc tacctgaggg     7500
gggcccctat aactctctac ggctaacctg aatggactac aacatagtct agtccgcaa     7560
ggccgccacc atgagagtga cagccctag aaccttactg cttctgcttt ggggagctgt     7620
tgctctgaca gagacatggg ctggatctta ccacagcccc agctacgcct accaccagtt     7680
cgagaggggg ggaggaggct ccgggggagg aggctccctg aagatcagcc aggccgtgca     7740
cgccgccac gccgagatca acgaggccgg ccgggaggtg atcgtgggca ttgtcgctgg     7800
cctggccgtc ctcgccgtgg tggtgattgg agctgtggtc gcagctgtta tgtgcagaag     7860
aaagtcatcc ggcggaaagg gaggctccta ctctcaggct gcttctgcta cagtgcctag     7920
agctcttatg tgtttatctc agctgggcgg cggaggcagc gactacaagg acgacgatga     7980
caagtaaact cgagtatgtt acgtgcaaag gtgattgtca cccccgaaa gaccatattg      8040
tgacacaccc tcagtatcac gcccaaacat ttacagccgc ggtgtcaaaa accgcgtgga    8100
cgtggttaac atccctgctg ggaggatcag ccgtaattat tataattggc ttggtgctgg    8160
ctactattgt ggccatgtac gtgctgacca accagaaaca taattgaata cagcagcaat   8220
tggcaagctg cttacataga actcgcgcg attggcatgc cgccttaaaa ttttttattt    8280
attttttctt ttcttttccg aatcggattt tgttttttaat atttcaaaaa aaaaaaaaaa  8340
aaaaaaaaaa tctagaaaaa aaaaaaaaaa aaaaaaaaaa aaaaaaaaaa aaaaaaaaaa  8400
aaaaaaaaaa aaaaaaaaaa aaaaaaaaaa aaaaaaaaaa aaaaa                    8455

SEQ ID NO: 109           moltype = AA   length = 2512
FEATURE                  Location/Qualifiers
REGION                   1..2512
                         note = Synthetic polypeptide
source                   1..2512
                         mol_type = protein
                         organism = synthetic construct
SEQUENCE: 109
MEKPVVNVDV DPQSPFVVQL QKSFPQFEVV AQQVTPNDHA NARAFSHLAS KLIELEVPTT     60
ATILDIGSAP ARRMFSEHQY HCVCPMRSPE DPDRMMKYAS KLAEKACKIT NKNLHEKIKD    120
LRTVLDTPDA ETPSLCFHND VTCNMRAEYS VMQDVYINAP GTIYHQAMKG VRTLYWIGFD    180
TTQFMFSAMA GSYPAYNTNW ADEKVLEARN IGLCSTKLSE GRTGKLSIMR KKELKPGSRV    240
YFSVGSTLYP EHRASLQSWH LPSVFHLNGK QSYTCRCDTV VSCEGYVVKK ITISPGITGE    300
TVGYAVTHNS EGFLLCKVTD TVKGERVSFP VCTYIPATIC DQMTGIMATD ISPDDAQKLL    360
VGLNQRIVIN GRTNRNTNTM QNYLLPIIAQ GFSKWAKERK DDLDNEKMLG TRERKLTYGC    420
LWAFRTKKVH SFYRPPGTQT CVKVPASFSA FPMSSVWTTS LPMSLRQKLK LALQPKKEEK    480
LLQVSEELVM EAKAAFEDAQ EEARAEKLRE ALPPLVADKG IEAAAEVVCE VEGLQADIGA    540
ALVETPRGHV RIIPQANDRM IGQYIVVSPN SVLKNAKLAP AHPLADQVKI ITHSGRSGRY    600
AVEPYDAKVL MPAGGAVPWP EFLALSESAT LVYNEREFVN RKLYHIAMHG PAKNTEEEQY    660
KVTKAELAET EYVFDVKKR CVKKEEASGL VLSGELTNPP YHELALEGLK TRPAVPYKVE    720
TIGVIGTPGS GKSAIIKSTV TARDLVTSGK KENCREIEAD VLRLRGMQIT SKTVDSVMLN    780
GCHKAVEVLV VDEAFACHAG ALLALIAIVR PRKKVVLCGD PMQCGFFNMM QLKVHFNHPE    840
KDICTKTFYK YISRRCTQPV TAIVSTLHYD GKMKTTNPCK KNIEIDITGA TKPKPGDIIL    900
TCFRGWVKQL QIDYPGHEVM TAAASQGLTR KGVYAVRQKV NENPLYAITS EHVNVLLTRT    960
EDRLVWKTLQ GDPWIKQLTN IPKGNFQATI EDWEAEHKGI IAAINSPTPR ANPFSCKTNV   1020
CWAKALEPIL ATAGIVLTGC QWSELFPQFA DDKPHSAIYA LDVICIKFFG MDLTSGLFSK   1080
QSIPLTYHPA DSRAPVAHWD NSPGTRKYGY DHAIAAELSR RFPVFQLAGK GTQLDLQTGR   1140
TRVISAQHNL VPVNRNLPHA LVPEYKEKQP GPVEKFLNQF KHHSVLVVSE EKIEAPRKRI   1200
EWIAPIGIAG ADKNYNLAFG FPPQARYDLV FINIGTKYRN HHFQQCEDHA ATLKTLSRSA   1260
LNCLNPGGTL VVKSYGYADR NSEDVVTALA RKFVRVSAAR PDCVSSNTEM YLIFRQLDNS   1320
RTRQFTPHHL NCVISSVYEG TRDGVGAAPS YRTKRENIAD CQEEAVVNAA NPLGRPGEGV   1380
CRAIYKRWPT SFTDSATETG TARMTVCLGK KVIHAVGPDF RKHPEAEALK LLQNAYHAVA   1440
DLVNEHNIKS VAIPLLSTGI YAAGKDRLEV SLNCLTTALD RTDADVTIYC LDKKWKERID   1500
AALQLKESVT ELKDEDMEID DELVWIHPDS CLKGRKGFST TKGKLYSYFE GTKFHQAAKD   1560
MAEIKVLFPN DQESNEQLCA YILGETMEAI REKCPVDHNP SSSPPKTLPC LCMYAMTPER   1620
VHRLRSNNVK EVTVCSSTPL PKHKIKNVQK VQCTKVVLFN PHTPAFVPAR KYIEVPEQPT   1680
APPAQAEEAP EVVATPSPST ADNTSLDVTD ISLDMDDSSE GSLFSSFSGS DNSITSMDSW   1740
SSGPSSLEIV DRRQVVVADV HAVQEPAPIP PPRLKKMARL AAARKEPTPP ASNSSESLHL   1800
SFGGVSMSLG SIFDGETARQ AAVQPLATGR TDVPMSFGSF SDGEIDELSR RVTESEPVLF   1860
GSFEPGEVNS IISSRSAVSF PLRKQRRRRR SRRTEYLTGV GGYIFSTDTG PGHLQKKSVL   1920
QNQLTEPTLE RNVLERIHAP VLDTSKEEQL KLRYQMMPTE ANKSRYQSRK VENQKAITTE   1980
RLLSGLRLYN SATDQPECYK ITYPKPLYSS SVPANYSDPQ FAVAVCNNYL HENYPTVASY   2040
QITDEYDAYL DMVDGTVACL DTATFCPAKL RSYPKKHEYR APNIRSAVPS AMQNTLQNVL   2100
IAATKRNCNV TQMRELPTLD SATFNVECFR KYACNDEYWE EFARKPIRIT TEFVTAYVAR   2160
LKGPKAAALF AKTYNLVPLQ EVPMDRFVMD MKRDVKVTPG TKHTEERPKV QVIQAAEPLA   2220
TAYLCGIHRE LVRRLTAVLL PNIHTLFDMS AEDFDAIIAE HFKQGDPVLE TDIASFDKSQ   2280
DDAMALTGLM ILEDLGVDQP LLDLIECAFG EISSTHLPTG TRFKFGAMMK SGMFLTLFVN   2340
TVLNVVIASR VLEERLKTSR CAAFIGDDNI IHGVVLDKHEYR AERCATWLNM EVKIIDAVIG   2400
ERPPYFCGGF ILQDSVTSTA CRVADPLKRL FKLGKPLPAD DEQDEDRRRA LLDETKAWFR   2460
VGITGTLAVA VTTRYEVDNI TPVLLALRTF AQSKRAFQAI RGEIKHLYGG PK             2512

SEQ ID NO: 110           moltype = AA   length = 9
FEATURE                  Location/Qualifiers
REGION                   1..9
```

```
                        note = Synthetic polypeptide
source                  1..9
                        mol_type = protein
                        organism = synthetic construct
SEQUENCE: 110
SPSYVYHQF                                                                   9

SEQ ID NO: 111          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 111
SPSYAYHQF                                                                   9

SEQ ID NO: 112          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 112
TPHPARIGL                                                                   9

SEQ ID NO: 113          moltype = RNA   length = 1701
FEATURE                 Location/Qualifiers
misc_feature            1..1701
                        note = Synthetic polynucleotide
source                  1..1701
                        mol_type = other RNA
                        organism = synthetic construct
SEQUENCE: 113
atgaaggcta tcctggtggt gctgctctac acctttgcca cagccaatgc tgacaccctg      60
tgtattggct accatgccaa caacagcaca gacacagtgg acacagtgtt ggagaagaat     120
gtgacagtga cccactctgt gaacctgttg gaggacaaac acaatggcaa actgtgtaaa     180
ctgagggag tggctccact gcacctgggc aagtgtaaca ttgctggctg gattctgggc     240
aaccctgagt gtgagtccct gagcacagcc tcctcctggt cctacattgt ggagacacca     300
tcctctgaca atggcacttg ttaccctgga gacttcattg actatgagga actgagggaa     360
caactttcct ctgtgtcctc ctttgagagg tttgagattt ttccaaagac ctcctcctgg     420
ccaaaccatg acagcaacaa gggagtgaca gcagcctgtc cacatggctg agccaagtcc     480
ttctacaaga acctgatttg gctggtgaag aagggcaact cctacccaaa actgagcaag     540
tcctacatca tgacaagggg caaggaggtg ctggtgctgt ggggcatcca ccacccaagc     600
acctctgctg ccaacagtc cctctaccag aatgctgacg cctatgtgtt tgtgggctcc     660
agcagataca gcaagaagtt caagcctgag attgccatca gaccaaaggt gagggatcag     720
gagggcagga tgaactacta ctggaccctg gtggaacctg gagacaagat tacctttgag     780
gctacaggca acctggtggt gccaagatat gcctttgcta tggagaggaa tgctggctct     840
ggcatcatca tctctgacac acctgtccat gactgtaaca ccacttgtca gacaccaaag     900
ggagccatca cacctcccct gccattccag aacatccacc caatcaccat tggcaagtgt     960
ccaaaatatg tcaagagcac caaactgaga ctggctacag gactgaggaa catcccaagc    1020
atccagagca ggggactgtt tggagccatt gctggcttca ttgagggagg ctggacaggg    1080
atggtggatg gctggtatgg ctaccaccac cagaatgaac agggctctgg ctatgctgct    1140
gacctgaaaa gcacccagaa tgccattgat gagattacca acaaggtgaa ctctgtgatt    1200
gagaagatga acacccagtt cacagcagtg ggcaaggagt tcaaccactt ggagaagagg    1260
attgagaacc tgaacaagaa ggtggatgat ggcttcctgg acatctggac ctacaatgct    1320
gaactgctgg tgctgttgga gaatgagagg accctggact accatgacag caatgtgaag    1380
aacctctatg agaaggtgag gagccaactt aaaaacaatg ccaaggagat tggcaatggc    1440
tgttttgagt tctaccacaa gtgtgacaac acttgtatgg agtctgtgaa gaatggcacc    1500
tatgactacc caaaatactc tgaggaggct aaactgaaca gggaggagat tgatggagtg    1560
aaattggaga gcaccaggat ttaccagatc ctggccatct acagcaccgt ggccagcagc    1620
ctggtgctgg tggtgagcct gggcgccatc agcttctgga tgtgcagcaa cggcagcttg    1680
cagtgcagga tctgcatcta a                                              1701

SEQ ID NO: 114          moltype = AA   length = 566
FEATURE                 Location/Qualifiers
REGION                  1..566
                        note = Synthetic polypeptide
source                  1..566
                        mol_type = protein
                        organism = synthetic construct
SEQUENCE: 114
MKAILVVLLY TFATANADTL CIGYHANNST DTVDTVLEKN VTVTHSVNLL EDKHNGKLCK      60
LRGVAPLHLG KCNIAGWILG NPECESLSTA SSWSYIVETP SSDNGTCYPG DFIDYEELRE     120
QLSSVSSFER FEIFPKTSSW PNHDSNKGVT AACPHAGAKS FYKNLIWLVK KGNSYPKLSK     180
SYINDKGKEV LVLWGIHHPS TSADQQSLYQ NADAYVFVGS SRYSKKFKPE IAIRPKVRDQ     240
EGRMNYYWTL VEPGDKITFE ATGNLVVPRY AFAMERNAGS GIIISDTPVH DCNTTCQTPK     300
GAINTSLPFQ NIHPITIGKC PKYVKSTKLR LATGLRNIPS IQSRGLFGAI AGFIEGGWTG     360
```

```
MVDGWYGYHH QNEQGSGYAA DLKSTQNAID EITNKVNSVI EKMNTQFTAV GKEFNHLEKR   420
IENLNKKVDD GFLDIWTYNA ELLVLLENER TLDYHDSNVK NLYEKVRSQL KNNAKEIGNG   480
CFEFYHKCDN TCMESVKNGT YDYPKYSEEA KLNREEIDGV KLESTRIYQI LAIYSTVASS   540
LVLVVSLGAI SFWMCSNGSL QCRICI                                       566

SEQ ID NO: 115        moltype = RNA   length = 9911
FEATURE               Location/Qualifiers
misc_feature          1..9911
                      note = Synthetic polynucleotide
source                1..9911
                      mol_type = other RNA
                      organism = synthetic construct
SEQUENCE: 115
gataggcggc gcatgagaga agcccagacc aattacctac ccaaatagga gaaagttcac    60
gttgacatcg aggaagacag cccattcctc agagctttgc agcggagctt cccgcagttt   120
gaggtagaag ccaagcaggt cactgataat gaccatgcta atgccagagc gttttcgcat   180
ctggcttcaa aactgatcga aacggaggtg gacccatccg acacgatcct tgacattgga   240
atagtcagca tagtacattt catctgacta atactacaac accaccacca tgaatagagg   300
attctttaac atgctcggcc gccgcccctt cccggccccc actgccatgt ggaggccgcg   360
gagaaggagg caggcggccc cgggaagcgg agctactaac ttcagcctgc tgaagcaggc   420
tggagacgtg gaggagaacc ctggacctga aaagttcac gttgacatcg aggaagacag    480
cccattcctc agagctttgc agcggagctt cccgcagttt gaggtagaag ccaagcaggt   540
cactgataat gaccatgcta atgccagagc gttttcgcat ctggcttcaa aactgatcga   600
aacggaggtg gacccatccg acacgatcct tgacattgga agtgcgcccg cccgcagaat   660
gtattctaag cacaagtatc attgtatctg tccgatgaga tgtgcggaag atccggacag   720
attgtataag tatgcaacta agctgaagaa aaactgaaga gaaataactg ataaggaatt   780
ggacaagaaa atgaaggagc tcgccgcgcg catgagcgca cctgacctgg aaactgagac   840
tatgtgcctc cacgacgacg agtcgtgtcg ctacgaaggg caagtcgctg tttaccagga   900
tgtatacgcg gttgacggac cgacaagtct ctatcaccaa gccaataagg gagttagagt   960
cgcctactgg ataggctttg acaccacccc ttttatgtt aagaacttgg ctggagcata   1020
tccatcatac tctaccaact gggccgacga aaccgtgtta acggctcgta acataggcct   1080
atgcagctct gacgttatgg agcggtcacg tagagggatg tccattctta gaaagaagta   1140
tttgaaacca tccaacaatg ttctattctc tgttggctcg accatctacc acgagaagag   1200
ggacttactg aggagctggc acctgccgtc tgtatttcac ttacgtggca agcaaaatta   1260
cacatgtcgg tgtgagacta tagttagttg cgacgggtac gtcgttaaaa gaatagctat   1320
cagtccaggc ctgtatggga agccttcagg ctatgctgct acgatgcacc gcagggatt    1380
cttgtgctgc aaagtgacag acacattgaa cggggagagg gtctcttttc ccgtgtgcac   1440
gtatgtgcca gctacattgt gtgaccaaat gactggcata ctggcaacag atgtcagtgc   1500
ggacgacgtg caaaaactgc tggttggcct caaccagcgt atagtcgtca acggtcgcac   1560
ccagagaaac accaatacca tgaaaaatta ccttttgccc gtagtggccc aggcatttgc   1620
taggtgggca aaggaatata aggaagatca agaagatgaa aggccactag gactacgaga   1680
tagacagtta gtcatggggt gttgttgggc ttttagaagg cacaagataa catctattta   1740
taagcgcccg gatacccaaa ccatcatcaa agtgaacagc gatttccact cattcgtgct   1800
gcccaggata ggcagtaaca cattggagat cgggctgaga acaagaatca ggaaaatgtt   1860
agaggagcac aaggagccgt cacctctcat taccgccgag gacgtacaag aagctaagtg   1920
cgcagccgat gaggctaagg aggtgcgtga agccgaggag ttgcgcgcag ctctaccacc   1980
tttggcagct gatgttgagg agcccactct ggaagccgat gtcgacttga tgttacaaga   2040
ggctgggggc ggctcagtgg agacacctcg tggcttgata aaggttacca gctacgatgg   2100
cgaggacaag atcggctctt acgctgtgct ttctccgcag gctgtactca agagtgaaaa   2160
attatcttgc atccaccctc tcgctgaaca agtcatagtg ataacacact ctggccgaaa   2220
agggcgttat gccgtggaac cataccatgg taaagtaggt gtgccagagg gacatgccat   2280
acccgtccag gactttcaag ctctgagtga aagtgccacc attgtgtaca acgaacgtga   2340
gttcgtaaac aggtacctgc accatattgc cacacatgga ggagcgctga acactgatga   2400
agaatattac aaaactgtca gcccagcga gcacgacggc gaatacctgt acgacatcga   2460
caggaaacag tgcgtcaaga aagaactagt cactgggcta gggctcacag gcgagctggt   2520
ggatcctccc ttccatgaat tcgcctacga gagtctgaga acacgaccag ccgctccta    2580
ccaagtacca accataggg tgtatggcgt gccaggatca ggcaagtctg catcattaa    2640
aagcgcagtc accaaaaaag atcagtggt gagcgccaag aaagaaaact gtgcagaaat   2700
tataagggac gtcaagaaaa tgaaaggct ggacgtcaat gccagaactg tggactcagt   2760
gctcttgaat ggatgcaaac acccgtaga gaccctgtat attgacgaag cttttgcttg   2820
tcatgcaggt actctcagag cgctcatagc cattataaga cctaaaaagg cagtgctctg   2880
cggggatccc aaacagtgcg gttttttaa catgatgtgc ctgaaagtgc attttaacca   2940
cgagatttgc acacaagtct ccacaaaag catctctcgc cgttcacta aatctgtgac   3000
ttcggtcgtc tcaaccttgt tttacgacaa aaaatgaga acgaccat cgaaagagac   3060
taagattgtg attgacacta ccggcagtac caaacctaag caggacgatc tcattctcac   3120
ttgtttcaga gggtgggtga agcagttgca aatagattac aaaggcaacg aataatgac    3180
ggcagctgcc tctcaagggc tgacccgtaa aggtgtgtat gccgttcggt acaaggtgaa   3240
tgaaaatcct ctgtacgcac ccacctctga acatgtgaac gtcctgaaac ccgcacgga    3300
ggaccgcatc gtgtggaaa cactagccgg cgacccatg ataaaaacc tgactgccaa    3360
gtaccctggg aatttcactg ccacgataga ggagtgcaa gcagagcatg atgccatcat   3420
gaggcacatc ttggagagac ggaccctac cgacgtcttc cagaataagg caaacgtgtg   3480
ttgggccaag gctttagtgc cggtgctgaa gaccgctggc atagacatga ccactgaaca   3540
atggaacact gtggattatt tgaaacggaa aaaagctcac tcagcagaga tagtattgaa   3600
ccaactgtg ctgaggtct ttggactcga tgtctattc ctgcacccac   3660
tgttccgtta tccattagga ataatcactg ggataactcc ccgtcgccta acatgtacgg   3720
gctgaataaa gaagtggtcc gtcagctctc tcgcaggtac ccacaactgc ctcgggcagt   3780
tgccactgga agagtctatg acatgaacac tggtacactg cgcaattatg atccgcgcat   3840
aaacctagta cctgtaaaca gaagactgcc tcatgcttta gtcctccacc ataatgaaca   3900
cccacagagt gactttttctt cattcgtcag caaattgaag ggcagaactg tcctggtggt   3960
```

```
cggggaaaag ttgtccgtcc caggcaaaat ggttgactgg ttgtcagacc ggcctgaggc    4020
taccttcaga gctcggctgg atttaggcat cccaggtgat gtgcccaaat atgacataat    4080
atttgttaat gtgaggaccc catataaata ccatcactat cagcagtgtg aagaccatgc    4140
cattaagctt agcatgttga ccaagaaagc ttgtctgcat ctgaatcccg gcggaacctg    4200
tgtcagcata ggttatggtt acgctgacag ggccagcgaa agcatcattg gtgctatagc    4260
gcggcagttc aagttttccc gggtatgcaa accgaaatcc tcacttgaag agacggaagt    4320
tctgttttgta ttcattgggt acgatcgcaa ggcccgtacg cacaatcctt acaagctttc    4380
atcaaccttg accaacattt atacaggttc cagactccac gaagccggat gtgcaccctc    4440
atatcatgtg gtgcgagggg atattgccac ggccaccgaa ggagtgatta taaatgctgc    4500
taacagcaaa ggacaacctg gcggaggggt gtgcggagcg ctgtataaga aattcccgga    4560
aagcttcgat ttacagccga tcgaagtagg aaaagcgcga ctggtcaaag gtgcagctaa    4620
acatatcatt catgccgtag gaccaaactt caacaaagtt tcggaggttg aaggtgacaa    4680
acagttggca gaggcttatg agtccatcgc taagattgtc aacgataaca attacaagtc    4740
agtagcgatt ccactgttgt ccaccggcat cttttccggg aacaaagatc gactaaccca    4800
atcattgaac catttgctga cagctttaga caccactgat gcagatgtag ccatatactg    4860
cagggacaag aaatgggaaa tgactctcaa ggaagcagtg gctaggagag aagcagtgga    4920
ggagatatgc atatccgacg actcttcagt gacagaacct gatgcagagc tggtgagggt    4980
gcatccgaag agttctttgg ctggaaggaa gggctacagc acaagcgatg gcaaaactt     5040
ctcatatttg gaagggacca agtttcacca ggcggccaag gatatagcag aaattaatgc    5100
catgtggccc gttgcaacgg aggccaatga gcaggtatgc atgtatatcc tcggagaaag    5160
catgagcagt attaggtcga aatgcccgt cgaagagtcg gaagcctcca caccacctag    5220
cacgctgcct tgcttgtgca tccatgccat gactccagaa agatacagc gcctaaaagc    5280
ctcacgtcca gaacaaatta ctgtgtgctc atccttttcca ttgccaagt atagaatcac    5340
tggtgtgcag aagatccaat gctcccagcc tatattgttc tcaccgaaag tgcctgcgta    5400
tattcatcca aggaagtatc tcgtggaaac accaccggta gacgagactc cggagccatc    5460
ggcagagaac caatccacag aggggacacc tgaacaacca ccacttataa ccgaggatga    5520
gaccaggact agaacgcctg agccgatcat catcgaagag gaagaagagg atagcataag    5580
tttgctgtca gatggcccga cccaccaggt gctgcaagtc gaggcagaca ttcacgggcc    5640
gccctctgta tctagctcat cctggtccat tcctcatgca tccgactttg atgtggacag    5700
tttatccata cttgacaccc tggagggagc tagcgtgacc agcggggcaa cgtcagccga    5760
gactaactct tacttcgcaa agagtatgga gtttctggcg cgaccggtgc ctgcgcctcg    5820
aacagtattc aggaaccctc cacatcccgc tccgcgcaca agaaccgtc cacttgcacc    5880
cagcaggcc tgctcgagaa ccagcctagt ttccaccccg ccaggcgtga ataggtggat    5940
cactagagag gagctcgagg cgcttaccc gtcacgcact cctagcaggt cggtctcgga    6000
aaccagcctg gtctccaacc cgccaggcgt aaataggtgg attacaagag aggagtttga    6060
ggcgttcgta gcacaacaac aatgacggtt tgatgcgggt gcatacatct tttcctccga    6120
caccggtcaa gggcatttac aacaaaaatc agtaaggcaa acggtgctat ccgaagtggt    6180
gttggagagg accgaattgg agatttcgta tgccccgcgc ctcgaccaag aaaaagaaga    6240
attactacgc aagaaattac agttaaatcc cacacctgct aacagaagca gataccagtc    6300
caggaaggtg gagaacatga agccataac agctagacgt attctgcaag gcctagggca    6360
ttatttgaag gcagaaggaa aagtggagtg ctaccgaacc ctgcatcctg ttccctttgta    6420
ttcatctagt gtgaaccgtg ccttttcaag ccccaaggtc gcagtggaag cctgtaacgc    6480
catgttgaaa gagaacttcc cgactgtggc ttcttactgt attattccag agtacgatgc    6540
ctatttggac atggttgacg gagcttcatg ctgcttagac actgccagtt tttgccctgc    6600
aaagctgcgc agctttccaa agaaacactc ctatttggaa cccacaatac gatcggcagt    6660
gccttcagcg atccagaaca cgctccgaaa cgtcctggca gctgccacaa aaagaaattg    6720
caatgtcacg caaatgagag aattgcccgt attggattcg gccgcttta atgtggaatg    6780
cttcaagaaa tatgcgtgta ataatgaata ttgggaaacg tttaaagaaa acccccatcag    6840
gcttactgaa gaaaacgtgg taaattacat taccaaatta aaaggaccaa aagctgctgc    6900
tcttttttcgcg aagacacata atttgaatat gttgcaggac ataccaatgg acaggtttgt    6960
aatgacttta aagagagacg tgaaagtgac tccaggaaca aaacatactg aagaacggcc    7020
caaggtacag gtgatccagg ctgccgatcc gctagcaaca gcgtatctgt gcggaatcca    7080
ccgagagctg gttaggagat taaatgcggt cctgcttccg aacattcata ccactgtttga    7140
tatgtcggct gaagactttg acgctattat agccgagcac ttccagcctg gggattgtgt    7200
tctggaaact gacatcgcgt cgtttgataa aagtgaggac gacgccatgg ctctgaccgc    7260
gttaatgatt ctggaagact taggtgtgga cgcagagctg ttgacgctga ttgaggcgga    7320
tttcggcgaa atttcatcaa cactttgct cactaaaact aaatttaaat tcggagccat    7380
gatgaaatct ggaatgttcc tcacactgtt tgtgaacaca gtcattaaca ttgtaatcgc    7440
aagcagagtg ttgagagaac ggctaaccgg atcaccatgt gcagcattca ttggagatga    7500
caatatcgtg aaaggagtca atcggacaa attaatgcga gacaggtgcg ccacctggtt    7560
gaatatggaa gtcaagatta tagatgctgt ggtgggcgag aaagcgcctt atttctgtgg    7620
agggtttatt ttgtgtgact ccgtgaccgg cacagcgtgc cgtgtggcag accccctaaa    7680
aaggctgttt aagcttggca aacctctggc agcagacgat gaacatgatg atgacaggag    7740
aagggcatta catgaagagt caacacgctg gaaccgagtg ggtattcttt cagagctgtg    7800
caaggcagta gaatcaaggt atgaaaccgt aggaacttcc atcatagtta tggccatgac    7860
tactctagct agcagtgtta aatcattcag ctacctgaga ggggcccta taactctcta    7920
cggctaacct gaatggacta cgacatagtc tagtccgcca agatatcgca ccatggaaga    7980
tgccaaaaac attaagaagg gcccagcgcc attctacccca ctcggaagacg ggacgcgg    8040
cgagcagctc cacaaagcc tgaagcgcta cgccctggtg cccggcacca tcgcctttac    8100
cgacgcacat atcgaggtgg acattaccta cgccgagtac ttcgagatga gcgttcggct    8160
ggcagaagct atgaagcgct atgggctgaa tacaaaccat cggatcgtgg tgtgcagcga    8220
gaatagcttg cagttcttca tgcccgtgtt gggtgccctg ttcatcggtg tggctgtggc    8280
cccagctaac gacatctaca acgagcgcga gctgctgaac agcatgggca tcagcagcc    8340
caccgtcgta ttcgtgagca agaaagggct caaaatcgcc aaaaagatc cgatcataa    8400
accgatcata caaagatca tcatcatgga tagcaagacc gactaccagg gcttccaaag    8460
catgtacacc ttcgtgactt cccatttgcc accggcttc aacgagtacg acttcgtgcc    8520
cgagagcttc gaccgggaca aaaccatcgc cctgatcatg aacagtagtg gcagtaccgg    8580
attgcccaag ggcgtagccc taccgcaccg caccgcttgt gtccgattca gtcatgcccg    8640
cgaccccatc ttcggcaacc agatcatccc cgacaccgct atcctcagcg tggtgccatt    8700
```

```
tcaccacggc ttcggcatgt tcaccacgct gggctacttg atctgcggct ttcgggtcgt    8760
gctcatgtac cgcttcgagg aggagctatt cttgcgcagc ttgcaagact ataagattca    8820
atctgccctg ctggtgccca cactatttag cttcttcgct aagagcactc tcatcgacaa    8880
gtacgaccta agcaacttgc acgagatcgc cagcggcggg gcgccgctca gcaaggaggt    8940
aggtgaggcc gtgccaaaac gcttccacct accaggcatc cgacagggct acggcctgac    9000
agaaacaacc agcgccattc tgatcacccc cgaaggggac gacaagcctg cgcagtagg     9060
caaggtggtg cccttcttcg aggctaaggt ggtggacttg gacaccggta agacactggg    9120
tgtgaaccag cgcggcgagc tgtgcgtccg tggccccatg atcatgagcg ctacgttaa     9180
caaccccgag gctacaaacg ctctcatcga caaggacggc tggctgcaca gcggcgacat    9240
cgcctactgg gacgaggacg agcacttctt catcgtcgac cggctgaagt ccctgatcaa    9300
atacaagggc taccaggtag ccccagccga actggagagc atcctgctgc aacaccccaa    9360
catcttcgac gccggggtcg ccggcctgcc cgacgacgat gccggcgagc tgcccgccgc    9420
agtcgtcgtg ctgaacacg gtaaaaccat gaccgagaag gagatcgtgg actatgtggc     9480
cagccaggtt acaaccgcca agaagctgcg cggtggtgtt gtgttcgtgg acgaggtgcc    9540
taaaggactg accggcaagt tggacgcccg caagatccgc gagattctca ttaaggccaa    9600
gaagggcggc aagatcgccg tgtaaggcgc gccgtttaaa cggccggcct taattaagta    9660
acgatacagc agcaattggc aagctgctta catagaactc gcggcgattg gcatgccgcc    9720
ttaaaatttt tattttattt tttcttttct tttccgaatc ggattttgtt tttaatattt    9780
caaaaaaaaa aaaaaaaaaa aaaaaatcta gaaaaaaaaa aaaaaaaaaa aaaaaaaaaa    9840
aaaaaaaaaa aaaaaaaaaa aaaaaaaaaa aaaaaaaaaa aaaaaaaaaa aaaaaaaaaa    9900
aaaaaaaaaa a                                                          9911

SEQ ID NO: 116        moltype = RNA   length = 2117
FEATURE               Location/Qualifiers
misc_feature          1..2117
                      note = Synthetic polynucleotide
source                1..2117
                      mol_type = other RNA
                      organism = synthetic construct
SEQUENCE: 116
aggaaactta agtcaacaca acatatacaa aacaaacgaa tctcaagcaa tcaagcattc      60
tacttctatt gcagcaattt aaatcatttc ttttaaagca aaagcaattt tctgaaaatt     120
ttcaccattt acgaacgata gccaccatga aggctatcct ggtggtgctg ctctacacct     180
ttgccacagc caatgctgac accctgtgta ttggctacca tgccaacaac agcacagaca     240
cagtggacac agtgttggag aagaatgtca cagtgaccca ctctgtgaac ctgttggagg     300
acaaacacaa tggcaaactg tgtaaactga ggggagtggc tccactgcac ctgggcaagt     360
gtaacattgc tggctggatt ctgggcaacc ctgagtgtga gtccctgagc acagcctcct     420
cctggtccta cattgtggag acaccatcct ctgacaatgg cacttgttac cctggagact     480
tcattgacta tgaggaactg agggaacaac tttcctctgt gcctcctttt gagaggtttg     540
agattttttcc aaagacctcc tcctggccaa accatgacag caacaaggga gtgcagcag     600
cctgtccaca tgctggagcc aagtcttct acaagaacct gatttggctg gtgaagaagg      660
gcaactccta cccaaaactg agcaagtcct acatcaatga caagggcaag gaggtgctgg     720
tgctgtgggg catccaccac ccaagcacct ctgctgacca acagccctc taccagaata     780
ctgacgccta tgtgtttgtg ggctccagca gatacagcaa gaagttcaag cctgagattg     840
ccatcagacc aaaggtgagg gatcaggagg caggatgaa ctactactgg accctggtgg      900
aacctggaga caagattacc tttgaggcta caggcaacct ggtggtgcca agatatgcct     960
ttgctatgga gaggaatgct ggctctggca tcatcatctc tgacacacct gtccatgact    1020
gtaacaccac ttgtcagaca ccaaaggag ccatcaacac ctccctgcca ttccagaaca     1080
tccacccaat caccattggc aagtgtccaa aatatgtcaa gagcaccaaa ctgagactgg    1140
ctacaggact gaggaacatc ccaagcatcc agagcagggg actgtttgga gccattgctg    1200
gcttcattga gggaggctgg acagggatgg tggatgctg gtatgctac caccaccaga     1260
atgaacaggg ctctggctat gctgctgacc tgaaaagcac ccagaatgcc attgatgaga    1320
ttaccaacaa ggtgaactct gtgattgaga agatgaacac ccagttcaca gcagtgggca    1380
aggagttcaa ccacttggag aagagattg agaacctgaa caaggaggtg gatgatggct     1440
tcctggacat ctggacctac aatgctgaac tgctggtgct gttggagaat gagaggaccc    1500
tggactacca tgacagcaat gtgaagaacc tctatgagaa ggtgaggagc caacttaaaa    1560
acaatgccaa ggagattggc aatggctgtt tgagttcta ccacaagtgt gacaacactt     1620
gtatggagtc tgtgaagaat ggcacctatg actacccaaa atactctgag gaggctaaac    1680
tgaacaggga ggagattgat ggagtgaaat tggagagcac caggatttac cagatcctgg    1740
ccatctacag caccgtggcc agcagcctgg tgctggtggt gagcctgggc gccatcagct    1800
tctggatgtg cagcaacggc agcttgcagt gcaggatctg catctaaact cgagctagtg    1860
actgactagg atctggttac cactaaacca gcctcaagaa cacccgaatg gagtctctaa    1920
gctacataat accaacttac acttacaaaa tgttgtcccc caaaatgtag ccattcgtat    1980
ctgctcctaa taaaaagaaa gtttcttcac attctagaaa aaaaaaaaaa aaaaaaaaaa    2040
aaaaaaaaaa aaaaaaaaaa aaaaaaaaaa aaaaaaaaaa aaaaaaaaaa aaaaaaaaaa    2100
aaaaaaaaaa aaaaaaa                                                   2117

SEQ ID NO: 117        moltype = DNA   length = 10508
FEATURE               Location/Qualifiers
misc_feature          1..10508
                      note = Synthetic polynucleotide
source                1..10508
                      mol_type = other DNA
                      organism = synthetic construct
SEQUENCE: 117
atgggcggcg catgagagaa gcccagacca attacctacc caaatggag aaagttcacg       60
ttgacatcga ggaagacagc ccattcctca gagctttgca gcggagcttc cgcagtttg      120
aggtagaagc caagcaggtc actgataatg accatgctaa tgccagagcg ttttcgcatc     180
tggcttcaaa actgatcgaa acggaggtgg acccatccga cacgatcctt gacattggaa     240
```

```
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgccg tcgacggccc caccagcctg taccaccagg    540
ccaacaaggg cgtgagggtg gcctactgga tcggcttcga caccacaccc ttcatgttca    600
agaacctggc cggcgcctac cccagctaca gcaccaactg ggccgacgag accgtgctga    660
ccgccaggaa catcggcctg tgcagcagcg acgtgatgga gaggagccgg agaggcatga    720
gcatcctgag gaagaaatac ctgaagccca gcaacaacgt gctgttcagc gtgggcagca    780
ccatctacca cgagaagagg gacctgctca ggagctggca cctgcccagc gtgttccacc    840
tgaggggcaa gcagaactac acctgcaggt gcgagaccat cgtgagctgc gacggctacg    900
tggtgaagag gatcgccatc agcccgccc tgtacggcaa gcccagcggc tacgccgcta    960
caatgcacag ggagggcttc ctgtgctgca aggtgaccga caccctgaac ggcgagaggg   1020
tgagcttccc cgtgtgcacc tacgtgcccg ccacccctgtg cgaccagatg accggcactg   1080
tggccaccga cgtgagcgcc gacgacgccc agaagctgct cgtgggcctg aaccagagga   1140
tcgtggtcaa cggcaggacc cagaggaaca ccaacacaat gaagaactac ctgctgcccg   1200
tggtggccca ggctttcgcc aggtgggcca aggagtacaa ggaggaccag gaagacgaga   1260
ggccccttggg cctgagggac aggcagctgg tgatgggctg ctgctgggcc ttcaggcggc   1320
acaagatcac cagcatctac aagaggcccg acacccagac catcatcaag gtgaacagcg   1380
acttccacag cttcgtgctg cccaggatcg gcagcaacac cctggagatc ggcctgagga   1440
cccggatcag gaagatgctg gaggaacaca aggagcccag cccactgatc accgccgagg   1500
acgtgcagga ggccaagtgc gctgccgacg aggccaagaa ggtgagggag gcgaggaac   1560
tgagggccgc cctgccaccc ctggctgccg acgtggagga acccaccctg gaagccgacg   1620
tggacctgat gctgcaggag gccggcgccg gaagcgtgga gacacccagg ggcctgatca   1680
aggtgaccag ctacgacggc gaggacaaga tcggcagcta cgccgtgctg agcccacagg   1740
ccgtgctgaa gtccgagaag ctgagctgca tccacccact ggccgagcag gtgatcgtga   1800
tcacccacag cggcaggaag ggcaggtacg ccgtggagcc ctaccacggc aaggtggtcg   1860
tgcccgaggg ccacgccatc cccgtgcagg acttccaggc cctgagcgag agcgccacca   1920
tcgtgtacaa cgagagggag ttcgtgaaca ggtacctgca ccatatcgcc acccacggcg   1980
gagccctgaa caccgacgag gaatactaca agaccgacga gccccacgag   2040
agtacctgta cgacatcgac aggaagcagt gcgtgaagaa agagctggtg accggcctga   2100
gactgaccgg cgagctggtg gacccaccct tccacgagtt cgcctacgag agcctgagga   2160
ccagacccgc cgctccctac caggtgccca ccatcggcgt gtacggcgtg cccggcagcg   2220
gaaagagcgg catcatcaag agcgccgtga ccaagaaaga cctggtggtc agcgccaaga   2280
aagagaactg cgccgagatc atcagggacg tgaagaagat gaaaggcctg gacgtgaacg   2340
cgcgcaccgt ggacagcgtg ctgctgaacg gctgcaagca cccccgtggag accctgtaca   2400
tcgacgagcc cttcgcttgc cacgccggca ccctgagggc cctgatcgcc atcatcaggc   2460
ccaagaaagc cgtgctgtgc ggcgaccccca agcagtgcgg cttcttcaac atgatgtgcc   2520
tgaaggtgca cttcaaccac gagatctgca ccaggttgtt caacaagagc atcagcaggc   2580
ggtgcaccaa gagcgtgacc agcgtcgtga gcacctgtt ctacgacaag aaaatgagga   2640
ccaccaaccc caaggagacc aaaatcgtga tcgacaccac aggcagcacc aagcccaagc   2700
aggacgacct gatcctgacc tgcttcaggg gctgggtgaa gcagctgcag atcgactaca   2760
agggcaacga gatcatgacc gccgctgcca gccagggcct gaccaggaag gcgtgtacg   2820
ccgtgaggta caaggtgaac gagaacccac tgtacgctcc caccagcgag cacgtgaacg   2880
tgctgctgac caggaccgag gacaggatcg tgtggaagac cctggccggc gacccctgga   2940
tcaagaccct gaccgccaag taccccgca acttcaccgc caccatcgaa gagtggcagg   3000
ccgagccga cgcatcatg aggacatc tggagaggcc cgaccccacc gacctgtcc   3060
agaacaaggc caacgtgtgc tgggccaagg ccctggtgcc cgtgctgaag accgccggca   3120
tcgacatgac cacagagcag tggaacaccg tggactactt cgagaccgac aaggccaca   3180
gcgccgagat cgtgctgaac cagctgtgcg tgaggttctt cggcctggac ctggacagcg   3240
gccttgttcag cgccccccacc gtgccactga gcatcaggaa caaccactgg gacaacgaca   3300
ccagcccaaa catgtacggc ctgaacaagg aggtggtcag gcagctgagc aggcggtacc   3360
cacagctgcc cagggccgtg gccaccggca gggtgtacga catgaacacc ggcacccctga   3420
ggaactacga ccccaggatc aacctggtgc cgtgaacag cgggctgccc cacgccctgg   3480
tgctgcaaca acgagcac ccacagagcg acttcagctc cttcgtgagc aagctgaaag   3540
gcaggaccgt gctggtcgtg ggcgagaagc tgagcgtgcc cggcaagatg gtggactggc   3600
tgagcgacag gcccgaggcc accttccggg ccaggctgga cctcggcatc ccggcgacg   3660
tgcccaagta cgacatcatc ttcgtgaacg tcaggaccc atacaagtac caccattacc   3720
agcagtgcga ggaccacgcc atcaagctga gcatgctgac caagaaggcc tgcctgcacc   3780
tgaaccccgg aggcacctgc gtgagcatcg gctacgccta cgccgacagg gccaagacga   3840
gcatcattgg cgccatcgcc aggctgttca agttcagcag ggtgtgcaaa cccaagcagca   3900
gcctggagga aaccgaggtg ctgttcgtgt catcggcta cgaccggaag gccaggaccc   3960
acaacccccta caagctgagc agcaccctga caaatcta caccggcagc aggctgcacg   4020
aggccgctg cgccccagc taccacgtgg tcaggggcga tatcgccacc gccaccgagg   4080
gcgtgatcat caacgctgcc aacagcaagg gccagcccgg aggcggagtg tgcggcgccc   4140
tgtacaagaa gttccccgag agcttcgacc tgcagcccat cgaggtgggc aaggccaggc   4200
tggtgaaggg cgccgctaag cacatcatcc acgccgtggg ccccaacttc aacaaggtga   4260
gcgaggtgga aggcgacaag cagctggccg aagcctacga gagcatcgcc aagatcgtga   4320
acgacaataa ctacaagagc gtggccatcc cactgctcag caccggccat ttcagcggca   4380
acaaggacag gctgacccag agcctgaacc acctgctcac cgcctcgga ccaccgatg   4440
ccgacgtggc catctactgc aggacaagaa gtgggagat acctgaag aggccgtgg   4500
ccaggcggga ggccgtggaa gagatctgca tcagcgacga ctccagcgtg accgagcccg   4560
acgccgagct ggtgagggtg caccccaaga gctccctggc cggcaggaag gctacagca   4620
ccagcgacga caagaccttc agctacctgg aggcaccaa gttcaacaag gctaagaag   4680
acatcgccga gatcaacgct atgtggcccg tggccaccga ggccaacgag caggtgtgca   4740
tgtacatcct gggcgagagc atgtccagca tcaggcagaa gtgccccgtg gagaaagcg   4800
aggcagcac accacccagc accctgccct gcctgtgcat ccacgctatg acacccgaga   4860
gggtgcagcg gctgaaggcc agcaggccg agcagatcac cgtgtgcagc tccttcccac   4920
tgcccaagta caggatcacc ggcgtgcaga agatccagtg cagccagccc atcctgttca   4980
```

```
gcccaaaggt gcccgcctac atccacccca ggaagtacct ggtggagacc ccacccgtgg   5040
acgagacacc cgagccaagc gccgagaacc agagcaccga gggcacaccc gagcagccac   5100
ccctgatcac cgaggacgag acaaggaccc ggaccccaga gcccatcatt atcgaggaag   5160
aggaagagga cagcatcagc ctgctgagcg acggccccac ccaccaggtg ctgcaggtgg   5220
aggccgacat ccacggccca cccagcgtgt ccagctccag ctggagcatc ccacacgcca   5280
gcgacttcga cgtggacagc ctgagcatcc tggacacccc ggagggcgcc agcgtgacct   5340
ccggcgccac cagcgccgag accaacagct acttcgccaa gagcatggag ttcctggcca   5400
ggcccgtgcc agctcccagg accgtgttca ggaacccacc ccacccagct cccaggacca   5460
ggaccccaag cctggctccc agcagggcct gcagcaggac cagcctggtg agcaccccac   5520
ccggcgtgaa cagggtgatc accaggyagg aactggaggc cctgacaccc agcaggaccc   5580
ccagcaggtc cgtgagcagg actagtctgg tgtccaaccc acccggcgtg aacagggtga   5640
tcaccaggga ggaattcgag gccttcgtgg cccagcaaca gagacggttc gacgccggcg   5700
cctacatctt cagcagcgac accggccagg acacctgca gcaaaagagc gtgaggcaga   5760
ccgtgctgag cgaggtggtg ctggagagga ccgagctgga aatcagctac gcccccagcc   5820
tggaccagga gaaggaggaa ctgctcagga gaaactgca gctgaacccc accccagcca   5880
acaggagcag gtaccagagc aggaaggtgg agaaacatgaa ggccatcacc gccaggcgga   5940
tcctgcaggg cctgggacac tacctgaagg ccgagggcaa ggtggagtgc tacaggaccc   6000
tgcaccccgt gccactgtac agctccagcg tgaacaggac cttctccagc cccaaggtgg   6060
ccgtggaggc ctgcaacgct atgctgaagg agaacttccc caccgtggcc agctactgca   6120
tcatccccga gtacgacgcc tacctggaca tggtggacgg cgccagctgc tgcctggaca   6180
ccgccagctt ctgccccgcc aagctgagga gcttccccaa gaaacacagc tacctggagc   6240
ccaccatcag gagcgccgtg cccagcgcca tccagaacac cctgcagaac gtgctggccg   6300
ctgccaccaa gaggaactgc aacgtgaccc agatgaggga gctgcccgtg ctggacagcg   6360
ctgccttcaa cgtggagtgc ttcaagaaat acgcctgcaa caacgagtac tgggagacct   6420
tcaaggagaa ccccatcagg ctgaccgaag agaacgtggt gaactacatc accaagctga   6480
agggccccaa ggccgctgcc ctgttcgcta agaccсaacct gaacatg ctgcaggaca   6540
tcccaatgga caggttcgtg atggacctga gagggacgt gaaggtgaca cccggcacca   6600
agcacaccgg ggagaggccc aaggtgcagg tgatccaggc cgctgaccca ctggccaccg   6660
cctacctgtg cggcatccac agggagctgg tgaggcggct gaacgccgtg ctgctgccca   6720
acatccacac cctgttcgac atgagcgccg aggacttcga ccccatcatc ctgccgagcc   6780
tccagcccgg cgactgcgtg ctggagaccg acatcgccag cttcgacaag agcgaggatg   6840
acgctatggc cctgaccgct ctgatgatcc tggaggacct gggcgtggac gccgagctgc   6900
tcaccctgat cgaggctgcc ttcggcgaga tcagctccat ccacctgccc accaagacca   6960
agttcaagtt cggcgctatg atgaaaagcg gaatgttcct gaccctgttc gtgaacaccg   7020
tgatcaacat tgtgatcgcc agcagggtgc tgcgggagag gctgaccggc agcccctgg   7080
ctgccttcat cggcgacgac aacatcgtga agggcgtgaa aagcgacaag ctgatggccg   7140
acaggtgcgc cacctggctg aacatggagg tgaagatcat cgacgccgtg gtgggcgaga   7200
aggcccccta cttctgcggc ggattcatcc tgtgcgacag cgtgaccggc accgcctgca   7260
gggtgtacgc ccccctgaag aggctgttca gctgggcaa gccactggcc gctgacgatg   7320
agcacgacga tgacaggcgg agggccctgc acgaggaaag caccaggtgg aacagggtgg   7380
gcatcctgag cgagctgtgc aaggccgtgg agagcaggta cgagaccgtg ggcaccagca   7440
tcatcgtgat ggctatgacc acactggcca gctccgtcaa gagcttctcc tacctgaggg   7500
gggccctat aactctctac ggctaacctg aatggactac gacatagtct agccaccatg   7560
agcaagatct acatcgacga gcggagcaac gccgagatcg tgtgcgaggc catcaagacc   7620
atcggcatcg agggcgccac cgccgcccag ctgaccaggc agctgaacat ggagaagcgg   7680
gaggtgaaca aggccctgta cgacctgcag aggagcgcta tggtgtactc cagcgacgac   7740
atcccctccc ggtggttcat gaccaccgag gccgacaagc ccgacgccga cgctatggcc   7800
gacgtgatca tcgacgacgt gagcaggag aagtccatga gggaggacca caagagcttc   7860
gacgacgtga tccccgccaa gaagatcatc gactggaagg gcgccaaccc cgtgaccgtg   7920
atcaacgagt actgccagat caccaggagg gactggagct tccggatcga gagcgtgggc   7980
cccagaaaca gccccaccct ctacgcctgc gtggacatcc acggcagggt gttccagaag   8040
gccgacggca agagcaagcg ggacgccaag aacaacgccg ccaagctggc cgtggacaag   8100
ctgctgggct acgtgatcat ccggttctaa actcgagcta gtgactgact aggatctggt   8160
taccactaaa ccagcctcaa gaacacccga atggagtctc taagctacat aataccaact   8220
tacacttaca aaatgttgtc ccccaaaatg tagccattcg tatctgctcc taataaaaag   8280
aaagtttctt cacattctag agctccgtca agagcttctc ctacctgagg ggggccccta   8340
taactctcta cggctaacct gaatggacta cgacatagtc tagccaccat ggaagatgcc   8400
aaaaacatta agaagggccc agcgccattc tacccactcg aagacgggac cgccggcgag   8460
cagctgcaca aagccatgaa gcgctacgcc ctggtgcccg gcaccatcgc ctttaccgac   8520
gcacatatcg aggtggacat tacctacgcc gagtacttcg agatgagcgt tcggctggca   8580
gaagctatga agcgctatgg gctgaataca aaccatcgga tcgtggtgtg cagcgagaat   8640
agcttgcagt tcttcatgcc cgtgttgggt gccctgttca tcggtgtggc tgtggcccca   8700
gctaacgaca tctacaacga gcgcgagctg ctgaacagca tgggcatcag ccagcccacc   8760
gtcgtattcg tgagcaagaa agggctgcaa aagatcctca acgtgcaaaa gaagctaccg   8820
atcatacaaa agatcatcat catggatagc aagaccgact accagggctt ccaaagcatg   8880
tacaccttcg tgacttccca tttgccaccc ggcttcaacg agtacgactt cgtgcccgag   8940
agcttcgacc gggacaaaac catcgccctg atcatgaaca gtagtggcag taccggattg   9000
cccaagggcg tagcccctacc gcaccgcacc gcttgtgtcc gattcagtca tgcccgcgac   9060
cccatcttcg gcaaccagat catccccgac aagcggttca gccatcac gccatttcac   9120
cacggcttcg gcatgttcac cacgctgggc tacttgatcc gcggctttcg ggtcgtgctc   9180
atgtaccgct tcgaggagga gctattcttg cgcagcttgc aagactataa gattcaatct   9240
gccctgctgt gcccacact atttagcttc ttcgctaaga gcactctcat cgacaagtac   9300
gacctaagca acttgcacga atcgccagc ggcggggcg cgctcagcaa ggaggtaggt   9360
gagccgtgg caaaggctt ccacctacca gcatcgcag agggctaccg cctgacagaa   9420
acaaccagcg ccattctgat cacccccgaa gggacgaca agcctggcgc agtaggcaag   9480
gtggtgccct cttcgaggc taaggtggtg gacttggaca ccgtaagac actgggtgtg   9540
aaccagcgcg cgagctgtg cgtccgtggc cccatgatca tgagcggcta cgttaacaac   9600
cccgaggcta caaacgctct catcgacaag gacggctggc tgcacagcgg cgacatcgcc   9660
tactgggacg aggacgagca cttcttcatc gtggaccggc tgaagtccct gatcaaatac   9720
```

```
aagggctacc aggtagcccc agccgaactg gagagcatcc tgctgcaaca ccccaacatc    9780
ttcgacgccg gggtcgccgg cctgcccgac gacgatgccg gcgagctgcc cgccgcagtc    9840
gtcgtgctgg aacacggtaa aaccatgacc gagaaggaga tcgtggacta tgtggccagc    9900
caggttacaa ccgccaagaa gctgcgcggt ggtgttgtgt tcgtggacga ggtgcctaaa    9960
ggactgaccg gcaagttgga cgcccgcaag atccgcgcaa ttctcattaa ggccaagaag   10020
ggcggcaaga tcgccgtgta actcgagtat gttacgtgca aaggtgattg tcaccccccg   10080
aaagaccata ttgtgacaca ccctcagtat cacgcccaaa catttacagc cgcggtgtca   10140
aaaaccgcgt ggacgtggtt aacatccctg ctgggaggat cagccgtaat tattataatt   10200
ggcttggtgc tggctactat tgtggccatg tacgtgctga ccaaccagaa acataattga   10260
atacagcagc aattggcaag ctgcttacat agaactcgcg gcgattggca tgccgcctta   10320
aaattttttat tttatttttt ctttctttt ccgaatcgga ttttgttttt aatatttcaa   10380
aaaaaaaaaa aaaaaaaaaa aaatctagaa aaaaaaaaaa aaaaaaaaaa aaaaaaaaaa   10440
aaaaaaaaaa aaaaaaaaaa aaaaaaaaaa aaaaaaaaaa aaaaaaaaaa aaaaaaaaaa   10500
aaaaaaaa                                                            10508

SEQ ID NO: 118         moltype = RNA   length = 11075
FEATURE                Location/Qualifiers
misc_feature           1..11075
                       note = Synthetic polynucleotide
source                 1..11075
                       mol_type = other RNA
                       organism = synthetic construct
SEQUENCE: 118
atgggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatcgt ccgatgagat      300
gtgcggaaga tccggacaga ttgtataagt atgcaactaa gctgaagaaa aactgtaagg     360
aaataactga taaggaattg gacaagaaaa tgaaggagct ggccgccgtc atgagcgacc     420
ctgacctgga aactgagact atgtgcctcc acgacgacga gtcgtgtcgc tacgaaggcc     480
aagtcgctgt ttaccaggat gtatacgccg tcgacggccc caccagcctg taccaccagg     540
ccaacaaggg cgtgagggtg gcctactgga tcggcttcga caccacaccc ttcatgttca     600
agaacctggc cggcgcctac cccagctaca gcaccaactg ggccgacgag accgtgctga     660
ccgccaggaa catcggcctg tgcagcagcg acgtgatgga gaggagccgg agaggcatga     720
gcatcctgag gaagaaatac ctgaagccca gcaacaacgt gctgttcagc gtgggcagca     780
ccatctacca cgaagagagg gacctgctca ggagctggca cctgcccagc gtgttccacc     840
tgagggcaa gcagaactac acctgcaggt gcgagaccat cgtgagctgc gacggctacg     900
tggtgaagag gatcgccatc agccccggcc tgtacggcaa gccagcgaa tacgccgcca     960
caatgcacag ggagggcttc ctgtgctgca aggtgaccga caccctgaac ggcgagaggg    1020
tgagcttccc cgtgtgcacc tacgtgcccg ccacccctgtg cgaccagatg accggcatcc    1080
tggccaccga cgtgagcgcc gacgacgccc agaagctgct cgtgggcctg aaccagagga    1140
tcgtcgtcaa cggcagaca cagaggaaca ccaacacaat gaagaactac ctgctgcccg     1200
tggtggccca ggctttcgcc aggtgggcca aggagtacaa ggaggaccag gaagacgaga    1260
ggccctgg cctgagggac aggcagctgg tgatgggctc tgctgggcc ttcaggcggc       1320
acaagatcac cagcatctac aagaggcccg acacccagac catcatcaag gtgaacagcg    1380
acttccacag cttcgtgctg cccaggatcg gcagcaacac ctgggagtc ggcctgagga    1440
cccggatcag cgaagatgctg gaggaacaca aggagcccag cccactgatc accgccgagg    1500
acgtgcagga ggccaagtgc gctgccgacg aggccaagga ggtgagggag gccgaggaac    1560
tgagggcccgc cctgccaccc ctggctgccg acgtggagga acccacctg gaagccgacg    1620
tggacctgat gctgcaggag gccgccgccg gaagcgtga gacccagg ggcctgatca       1680
aggtgaccag ctacgacggc gaggacaaga tcgcagcta cgccgtgctg agcccacagg    1740
ccgtgctgaa gtccgagaag ctgagctgca tccaccccact ggcgagcag gtgatcgtga    1800
tcacccacag cggcaggaag ggcaggtacg ccgtggagcc ctaccacggc aaggtggtcg    1860
tgcccgaggg ccacgccatc cccgtgcagg acttccaggg cctgagcgag agcgccacca    1920
tcgtgtacaa cgagagggag ttcgtgaaca ggtacctgca ccatatcgcc acccacggca    1980
gagccctgaa caccgacgag gaatactaca gaccgtgaa gcccagcgag cacgacggcg    2040
agtacctgta cgacatcgac aggaagcagt gcgtgaagaa agagctggtg accggcctgg    2100
gactgaccgg cgagctggtg gacccaccct tccacgagtt cgcctacgaa agctgagga    2160
ccagacccgc cgctcccctac caggtgccca atcgcgt gtacgccgtg cccggcagcg     2220
gaaagagcgg catcatcaag agcgccgtga ccaagaaaga cctggtggtc agcgccaaga    2280
aagagaactg cgccgagatc atcagggacg tgaagaagat gaaggcctg gacgtgaacg    2340
cgcgcaccgt ggacagcgtg ctgctgaacg gctgcaagca cccgtggag accctgtaca    2400
tcgacgagc cttcgcttgc cacgccggca cctgaggc ctgatcgcc atcatcaggg       2460
ccaagaaagc cgtgctgtgc ggcgaccca agcagtgcgg cttcttcaac atgatgtgcc    2520
tgaaggtgca cttcaaccac gagatctgca cccaggtgtt ccacaagagc atcagcaggc    2580
ggtgcaccaa gagcgtgacc agcgtcgtga gcacctgtt ctacgacaag aaaatggagga    2640
ccaccaaccc caaggagaga aaaatcgtga tcgaccacaa aggcagcac aagcccaagc    2700
aggacgacct gatcctgacc tgcttcaggg gctgggtgaa gcagctgcag atcgactaca    2760
agggccaacga gatcatgacc gccgctgcca gccaggcct gaccaggaag ggcgtgtacg    2820
ccgtgaggta caaggtgaac gagaacccac tgtacgctcc caccagcgag cacgtgaacg    2880
tgctgctgac caggaccgag gacaggatcg tgtggaagac cctggccggc gacccctgga    2940
tcaagaccct gaccgccaag taccccgca acttcaccgc caccatcgaa gagtggcagg    3000
ccgagccgga cgccatcatg aggcacatcg tggagggcc gacccccgtc gacgtgttcc    3060
agaacaaggc caacgtgtgc tgggccaaga gcctggtgcc cgtgctgaag accgccggca    3120
tcgacatgac cacagagcag tggaacaccg tggactactt cgagaccgac aaggcccaca    3180
gcgccgagat cgtgctgaac cagctgtgcg tgaggttctt cggcctggac ctggacagcg    3240
gcctgttcag cgccccacc gtgccactga gcatcaggaa caaccactgg gacaacagcc    3300
ccagcccaaa catgtacggc ctgaacaagg aggtggtcag gcagctgagc aggcggtacc    3360
```

```
cacagctgcc cagggccgtg gccaccggca gggtgtacga catgaacacc ggcaccctga   3420
ggaactacga ccccaggatc aacctggtgc ccgtgaacag gcggctgccc cacgccctgg   3480
tgctgcacca acgagcac ccacagagcg acttcagctc cttcgtgagc aagctgaaag      3540
gcaggaccgt gctggtcgtg ggcgagaagc tgagcgtgcc cggcaagatg gtggactggc   3600
tgagcgacag gcccgaggcc accttccggg ccaggctgga cctcggcgca ccggcgacg    3660
tgcccaagta cgacatcatc ttcgtgaacg tcaggacccc atacaagtac caccattacc   3720
agcagtgcga ggaccacgcc atcaagctga gcatgctgac caagaaggcc tgcctgcacc   3780
tgaaccccgg aggcacctgc gtgagcatcg gctacggcta cgccgacagg gccagcgaga   3840
gcatcattgg cgccatcgcc aggctgttca agttcagcag ggtgtgcaaa cccaagagca   3900
gcctggagga aaccgaggtg ctgttcgtgt tcatcggcta cgaccggaag gccaggaccc   3960
acaaccccta caagctgagc agcaccctga caaacatcta caccggcagc aggctgcacg   4020
aggccggctg cgcccccagc taccacgtgg tcagggcga tatcgccacc gccaccgagg    4080
gcgtgatcat caacgctgcc aacagcaagg ccagcccgg aggcggagtg tgcggcgccc    4140
tgtacaagaa gttccccgag agcttcgacc tgcagcccat cgaggtgggc aaggccaggc   4200
tggtgaaggg cgccgctaag cacatcatcc acgccgtggg ccccaacttc aacaaggtga   4260
gcgaggtgga aggcgacaag cagctggccg aagcctacga gagcatcgcc aagatcgtga   4320
acgacaataa ctacaagagc gtggccatcc cactgctcag caccggcatc ttcagcggca   4380
acaaggacag gctgacccag agcctgaacc acctgctcac cgccctggac accaccgatg   4440
ccgacgtggc catctactgc agggacaaga agtgggagat gaccctgaag gaggccgtgg   4500
ccaggcggga ggccgtggaa gagatctgca tcaggcgacga ctccagcgtg accgagcccg   4560
acgccgagct ggtgagggtg caccccaaga gctccctggc cggcaggaag ggctacagca   4620
ccagcgacgg caagaccttc agctacctgg agggaccaa gttccaccag gccgctaagg    4680
acatcgccga gatcaacgct atgtggcccg tggccaccga ggccaacgag caggtgtgca   4740
tgtacatcct gggcgagagc atgtccagca tcaggagcaa gtgccccgtg gagaaagcg    4800
aggccagcac accacccagc accctgccct gcctgtgcat ccacgctatg acacccgaga   4860
gggtgacgcg gctgaaggcc caggcccg agcagatcac cgtgtgcagc tccttcccac    4920
tgcccaagta caggatcacc ggcgtgcaga agatccagtg cagccagccc atcctgttca   4980
gcccaaaggt gcccgcctac atccacccca ggaagtacct ggtggagacc ccaccgtgg    5040
acgagacacc cgagccaagc gccgagaacc agagcaccga gggcacaccc gagcagccac   5100
ccctgatcac cgaggacgag acaaggaccc ggacccccaga gccatcatt atcgaggaag   5160
aggaagagga cagcatcagc ctgctgagcg acgcccccac ccaccaggtg ctgcaggtga   5220
aggccgacat ccacggccca cccagcgtgt ccagctccag ctggagcatc ccacacgcca   5280
gcgacttcga cgtggacagc ctgagcatcc tggacaccct ggagggcgcc agcgtgacct   5340
ccggcgccac cagcgccgag accaacagct acttcgcaa gagcatggag ttcctggcca    5400
ggcccgtgcc agctcccagg accgtgttca ggaacccacc ccacccagct cccagaccca   5460
ggaccccaag cctggctccc agcagggcct gcagcaggac cagcctggtg agcaccccac   5520
ccggcgtgaa cagggtgatc accagggagg aactggaggc cctgacaccc agcaggaccc   5580
ccagcaggtc cgtgagcagg actagtctgg tgtccaaccc accggctgt aacagggtga    5640
tcaccaggga ggaattcgag gccttcgtgg cccagcaaca gagacggttc gacgccggcg   5700
cctacatctt cagcagcgac accggccagg gacacctgga gcaaaagagc gtgaggcaga   5760
ccgtgctgag cgaggtggtg ctggagagga ccgagctgga aatcagctac gcccccaggc   5820
tggaccagga gaaggaggaa ctgctcagga gaaaactgca gctgaacccc accccagcca   5880
acaggacgcag gtaccagagc aggaaggtgg agaacatgaa ggccatcacc gccaggcgga   5940
tcctgcaggg cctgggacac tacctgaagg ccgagggcaa ggtggagtgc tacaggaccc   6000
tgcacccgt gccactgtac agctccagcg tgaacagggc cttctccagc cccaaggtgg    6060
ccgtggaggc ctgcaacgct atgctgaagg agaacttccc caccgtggcc agctactgca   6120
tcatccccga gtacgacgcc tacctggaca tggtggacgg cgcagcctgc tgcctggaca   6180
ccgccagctt ctgccccgcc aagctgagga gcttccccaa gaaacacagc tacctggagc   6240
ccaccatcag gagcgccgtg cccagcgcca tccagaacac cctgcagaac gtgctggccg   6300
ctgccaccaa gaggaactgc aacgtgaccc agatgagga gctgcccgtg ctggacagcg   6360
ctgccttcaa cgtggagtgc ttcaagaaat acgcctgcaa caacgagtac tgggagacct   6420
tcaaggagaa ccccatcagg ctgaccgaag agaacgtggt gaactacatc accaagctga   6480
agggccccaa ggccgctgcc ctgttcgcta gacccacaa cctgaacatg ctgcaggaca    6540
tcccaatgga caggttcgtg atggacctga gagggacgt gaaggtgaca cccggcacca   6600
agcacaccga ggagaggccc aaggtgcagg tgatccagcc cgctgaccca ctggccaccg   6660
cctacctgtg cggcatccac agggagctgg tgaggcggct gaacgccgtg ctgctgccca   6720
acatccacac cctgttcgac atgagcgccg aggacttcga cgccatcatc gccgagcact   6780
tccagcccg cgactgcgtg ctggagaccg acatcgccag cttcgacaag agcgaggatg   6840
acgctatggc cctgaccgct ctgatgatcc tggaggacct gggcgtggac gccagctga    6900
tcaccctgat cgaggctgcc ttcggcgaga tcagctccat ccacctgccc accaagacca   6960
agttcaagtt cggcgctatg atgaaaagcg gaatgttcct gaccctgttc gtgaacaccg   7020
tgatcaacat tgtgatcgcc agcagggtgc tgcgggagag gctgaccggc agccctgcg    7080
ctgccttcat cggcgacgac aacatcgtga agggcgtgaa aagcgacaag ctgatggccg   7140
acaggtgcgc cacctggctg aacatggagg tgaagatcat cgacgccgtg gtgggcagga   7200
aggcccccta cttctgcggc ggattcatcc tgtgcgacag cgtgaccggc accgcctgca   7260
gggtggccga ccccctgaag aggctgttca agctgggcaa gccactggcc gctgacatgg   7320
agcacgacga tgacaggcgg aggggccctgc acgaggaaag caccaggtgg aacagggtgg   7380
gcatcctgag cgagctgtgc aaggccgtgg agagcaggta cgagccgtg ggcaccagca    7440
tcatcgtgat ggctatgacc acactggcca gctccgtcaa gagcttctcc tacctgaggg   7500
gggcccctat aactctctac ggctaacctg aatggactac gacatagtct agtccgccaa   7560
gccgccacc atgaaagatg ccaaaaacat taagaagggc ccagcgccat ctacccact    7620
cgaagacggg accgccggcg agcagctgca caaagccatg aagcgctacg ccctggtgcc   7680
cggcaccatc gcctttaccg acgcacatat cgaggtggac attactacg ccgagtactt     7740
cgagatgagc gttcggctgg cagaagctat gaagcgctat gggctgaata caaaccatcg   7800
gatcgtggtg tgcagcgaga atagcttgca gttcttcatg cccgtgttgg gtgcctgtt     7860
catcggtgtg gctgtggccc cagctaacga catctacaac gagcgcgagc tgctgaacag   7920
catgggcatc agccagccca ccgtcgtatt cgtgagcaag aaagggctgc aaaagatcct   7980
caacgtgcaa aagaagctac cgatcataca aaagatcatc atcatggata gcaagaccga   8040
ctaccagggc ttccaaagca tgtacacctt cgtgacttcc catttgccac ccggcttcaa   8100
```

```
cgagtacgac ttcgtgcccg agagcttcga ccgggacaaa accatcgccc tgatcatgaa   8160
cagtagtggc agtaccggat tgcccaaggg cgtagcccta ccgcaccgca ccgcttgtgt   8220
ccgattcagt catgcccgcg accccatctt cggcaaccag atcatccccg acaccgctat   8280
cctcagcgtg gtgccatttc accacggctt cggcatgttc accacgctgg gctacttgat   8340
ctgcggcttt cgggtcgtgc tcatgtaccg cttcgaggag gagctattct tgcgcagctt   8400
gcaagactat aagattcaat ctgccctgct ggtgcccaca ctatttagct tcttcgctaa   8460
gagcactctc atcgacaagt acgacctaag caacttgcac gagatcgcca gcggcggggc   8520
gccgctcagc aaggaggtag gtgaggccgt ggccaaacgc ttccacctac caggcatccg   8580
acagggctac ggcctgacag aaacaaccag cgccattctg atcacccccg aaggggacga   8640
caagcctggc gcagtaggca aggtggtgcc ctctcttcgag gctaaggtgg tggacttgga   8700
caccggtaag acactgggtg tgaaccagcg cggcgagctg tgcgtccgtg gcccatgat    8760
catgagcggc tacgttaaca accccgaggc tacaaacgct ctcatcgaca aggacgctg    8820
gctgcacagc ggcgacatcg cctactggga cgaggacgag cacttcttca tcgtggaccg   8880
gctgaagtcc ctgatcaaat acaagggcta ccaggtagcc ccagccgaac tggagagcat   8940
cctgctgcaa caccccaaca tcttcgacgc cgggtcgcc ggcctgcccg acgacgatgc    9000
cggcgagctg cccgccgcag tcgtcgtgct ggaacacggt aaaaccatga ccgagaagga   9060
gatcgtggac tatgtggcca gccaggttac aaccgccaag aagctgcgcg tggtgttgt    9120
gttcgtggac gaggtgccta aaggacgac cggcaagttg gcgacccgca agatccgcga   9180
gattctcatt aaggccaaga agggcggcaa gatcgccgtg taactcgagc cggaaacgaa   9240
atagccgaaa aacaaaaac aaaaaaaca aaaaaaaaac caaaaaaaca aaacacatta    9300
aaacagcctg tgggttgatc ccaccccacg gcccattggg cgctagcact ctggtatcac   9360
ggtaccttg tgcgcctgtt ttataccccc tcccccaact gtaacttaga agtaacacac    9420
accgatcaac agtcagcgtg gcacaccagc cacgtttga tcaagcactt ctgttacccc    9480
ggactgagta tcaatagact gctcacgcgg ttgaaggaga aagcgttcgt tatccggcca   9540
actacttcga aaaacctagt aacaccgtgg aagttcaga gtgtttcgct cagcactacc    9600
ccagtgtaga tcaggtcgat gagtcaccgc attccccacg ggcgaccgtg gggtggctg    9660
cgttggcggc ctgcccatgg ggaaacccat gggacgctct aatacagaca tggtgcgaag   9720
agtctattga gctagttggt agtcctccgg cccctgaatg cggctaatcc taactgcgga   9780
gcacacaccc tcaagccaga gggcagtgtg tcgtaacggg caactctgca gcggaaccga   9840
ctactttggg tgtccgtgtt tcatttttatt cctatactgg ctgcttatgg tgacaattga   9900
gagatcgtta ccatatagct attggattgg ccatccggtg actaatagag ctattatata   9960
tccctttgtt gggtttatac cacttagctt gaaagaggtt aaaacattac aattcattgt  10020
taagttgaat acagcaaaat gagcaagatc tacatcgacg agcggagcaa cgccgagatc  10080
gtgtgcgagg ccatcaagac catcggcatc gagggcgcca ccgccgccca gctgaccagg  10140
cagctgaaca tggagaagcg ggaggtgaac aaggccctgt acgacctgca gagggagcgt  10200
atggtgtact ccagcgacga catccctccc cggtggttca tgaccaccga ggccgacaag  10260
cccgacgccg acgctatggc cgacgtgatc atcgacgacg tgagcaggga gaagtccatg  10320
agggaggacc acaagagctt cgacgacgtg atccccgcca agaagatcat cgactggaag  10380
ggcgccaacc ccgtgaccgt gatcaacgag tactgccaga tcaccaggag ggactggagc  10440
ttccggatcg agagcgtggg ccccсagcaac agccccacct tctacgcctg cgtggacatc  10500
gacggcaggg tgttcgacaa ggccgacggc aagagcaagc gggacgccaa gaacaacgcc  10560
gccaagctgg ccgtggacaa gctgctgggc tacgtgatca tccggttcta aacgtatgtt  10620
acgtgcaaag gtgattgtca ccccccgaaa gaccatattg tgacacaccc tcagtatcac  10680
gcccaaacat ttacagccgc ggtgtcaaaa accgcgtgga cgtggttaac atccctgctg  10740
ggaggatcag ccgtaattat tataattggc ttggtgctgg ctactattgt ggccatgtac  10800
gtgctgacca accagaaaca taattgaata cagcagcaat tggcaagctg cttacataga  10860
actcgcggcg attggcatgc cgccttaaaa tttttatttt atttttttctt ttcttttccg  10920
aatcggattt tgtttttaat atttcaaaaa aaaaaaaaaa aaaaaaaaaa tctagaaaaa  10980
aaaaaaaaaa aaaaaaaaaa aaaaaaaaaa aaaaaaaaaa aaaaaaaaaa aaaaaaaaaa  11040
aaaaaaaaaa aaaaaaaaaa aaaaaaaaaa aaaaa                              11075

SEQ ID NO: 119         moltype = RNA   length = 10851
FEATURE                Location/Qualifiers
misc_feature           1..10851
                       note = Synthetic polynucleotide
source                 1..10851
                       mol_type = other RNA
                       organism = synthetic construct
SEQUENCE: 119
atgggcggcg catgagagaa gcccagacca attacctacc caaatggag aaagttcacg      60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg acaagaaaaa tgaaggagct ggccgccgtc atgagcgacc    420
ctgacctgga aactgagact atgtgcctcc acgacgacga gtcgtgtcgc tacgaagggc    480
aagtcgctgt ttaccaggat gtatacgccg tcgacggcc caccagcctg taccaccagg    540
ccaacaaggg cgtgagggtg gcctactgga tcggcttcga caccacaccc ttcatgttca    600
agaacctggc cggcgcctac cccagctaca gcaccaactg ggccgacgag accgtgctga    660
ccgccaggaa catcggcctg tgcagcagcg acgtgatgga ggagccgg agaggcatga    720
gcatcctgag gaagaaatac ctgaagccca gcaacaacgt gctgttcagc gtgggcagca    780
ccatctacca cgagaagagg gacctgctca ggagctggca cctgcccagc gtgttccacc    840
tgaggggcaa gcagaactac acctgcaggt gcgagcacat gggcgctag                900
tggtgaagag gatcgccatc agccccggcc tgtacggcaa gcccagcggc tacgccgcta    960
caatgcacag ggagggcttc ctgtgctgca aggtgaccga caccctgaac ggcgagaggg   1020
tgagcttccc cgtgtgcacc tacgtgcccg ccaccсctgtg cgaccagatg accggcatcc   1080
tggccaccga cgtgagcgcc gacgacgccc agaagctgct cgtgggcctg aaccaggaga   1140
tcgtggtcaa cggcaggacc cagaggaaca ccaacacaat gaagaactac ctgctgcccg   1200
```

-continued

```
tggtggccca ggctttcgcc aggtgggcca aggagtacaa ggaggaccag gaagacgaga    1260
ggcccctggg cctgagggac aggcagctgg tgatgggctg ctgctgggcc ttcaggcggc    1320
acaagatcac cagcatctac aagaggcccg acacccagac catcatcaag gtgaacagcg    1380
acttccacag cttcgtgctg cccaggatcg gcagcaacac cctggagatc ggcctgagga    1440
cccggatcag gaagatgctg gaggaacaca aggagcccac cccactgatc accgccgagg    1500
acgtgcagga ggccaagtgc gctgccgacg aggccaagga ggtgagggag gccgaggaac    1560
tgagggccgc cctgccaccc ctggctgccg acgtggagga acccaccctg gaagccgacg    1620
tggacctgat gctgcaggag gccggcgccg gaagcgtgga gacacccagg ggcctgatca    1680
aggtgaccag ctacgacggc gaggacaaga tcggcagcta cgccgtgctg agcccacagg    1740
ccgtgctgaa gtccgagaag ctgagctgca tccaccccact ggccgagcag gtgatcgtga    1800
tcacccacag cggcaggaag ggcaggtacg ccgtggagcc ctaccacggc aaggtggtcg    1860
tgcccgaggg ccacgccatc cccgtgcagg acttccaggc cctgagcgag agcgccacca    1920
tcgtgtacaa cgagagggag ttcgtgaaca ggtacctgca ccatatcgcc acccacggcg    1980
gagccctgaa caccgacgag gaatactaca agaccgtgga gcccagccag cacgacggcg    2040
agtacctgta cgacatcgac aggaagcagt gcgtgaagaa agagctggtg accggcctgg    2100
gactgaccgg cgagctggtg gacccacccct tccacgagtt cgcctacgag agcctgagga    2160
ccagaccgc cgctccctac caggtgccca ccatcggcgt gtacgcgtg cccggcagcg    2220
gaaagagcgg catcatcaag agcgccgtga ccaagaaaga cctggtggtc agcgccaaga    2280
aagagaactg cgccgagatc atcagggacg tgaagaagat gaaaggcctg gacgtgaacg    2340
cgcgcaccgt ggacagcgtg ctgctgaacg gctgcaagca ccccgtggag accctgtaca    2400
tcgacgaggc cttcgcttgc cacgccggca ccctgagggc cctgatcgcc atcatcaggc    2460
ccaagaaagc cgtgctgtgc ggcgacccca agcagtgcgg cttcttcaac atgatgtgcc    2520
tgaaggtgca cttcaaccac gagatctgca cccaggtgtt ccacaagagc atcagcaggc    2580
ggtgcaccaa gagcgtgacc agcgtcgtga gcacccctgtt ctacgacaag aaaatgagga    2640
ccaccaaccc caaggagacc aaaatcgtga tcgacaccac aggcagcacc aagcccaagc    2700
aggacgagct gatcctgacc tgcttcaggg gctgggtgga gcagctgcag atcgactaca    2760
agggcaacga gatcatgacc gccgctgcca gccagggcct gaccaggaag ggcgtgtacg    2820
ccgtgaggta caaggtgaac gagaacccac tgtacgctcc caccagcgag cacgtgaacg    2880
tgctgctgac caggaccgag gacaggatcg tgtggaagac cctggccggc gacccctgga    2940
tcaagaccct gaccgccaag tacccccggca acttcaccgc caccatcgaa gagtggcagg    3000
ccgagcacga cgccatcatg aggcacatcc tggagaggcc cgaccccacc gacgtgttcc    3060
agaacaaggc caacgtgtgc tgggccaagg ccctggtgcc cgtgctgaag accgccggca    3120
tcgacatgac cacagagcag tggaacaccg tggactactt cgagaccgac aaggcccaca    3180
gcgccgagat cgtgctgaac cagctgtgcg tgaggttctt cggcctggac ctggacagcg    3240
gcctgttcag cgccccccacc gtgccactga gcatcaggaa caaccactgg gacaacagcc    3300
ccagcccaaa catgtacggc ctgaacaagg aggtggtcag gcagctgagc aggcggtacc    3360
cacagctgcc cagggccgtg gccaccggca gggtgtacga catgaacacc ggcacccctga    3420
ggaactacga ccccaggatc aacctggtgc ccgtgaacag cggctgcccc cacgcctggg    3480
tgctgcacca caacgagcac ccacagagcg cttcagctc cttcgtgagc aagctgaaag    3540
gcaggaccgt gctggtcgtg ggcgagaagc tgagcgtgcc cggcaagatg gtggactggc    3600
tgagcgacag gcccgaggcc accttccggg ccaggctgga cctcggcatc ccggcgacg    3660
tgcccaagta cgacatcatc ttcgtgaacg tcaggacccc atacaagtac caccattacc    3720
agcagtgcga ggaccacgcc atcaagctga gcatgctgac caagaaggcc tgcctgcacc    3780
tgaaccccgg aggcacctgc gtgagcatcg gctacggcta cgccgacagg gccagcgaga    3840
gcatcattgg cgccatcgcc aggctgttca gttcagcag ggtgtgcaaa cccaagagca    3900
gcctggagga aaccgaggtg ctgttcgtgt tcatcggcta cgaccggaag gccaggaccc    3960
acaaccccta caagctgagc agcaccctga caaacatcca caccggcagc aggctgcacg    4020
aggccggctg cgcccccagc taccacgtgg tcagggcga tatcgccacc gccaccgagg    4080
gcgtgatcat caacgctgcc aacagcaagg gccagcccgg aggcggagtg tgcggcgccc    4140
tgtacaagaa gttccccgag agcttcgacc tgcagcccat cgaggtgggc aaggccaggc    4200
tggtgaaggg cgccgctaag cacatcatcc acgccgtggg cccccaacttc aacaaggtga    4260
gcgaggtgga aggcgacaag cagctggccg aagcctacga gagcatcgcc aagatcgtga    4320
acgacaataa ctacaagagc gtggccatcc cactgctcag caccggcatc ttcagcggca    4380
acaaggacag gctgacccag agcctgaacc acctgctcac cgccctggac accaccgatg    4440
ccgacgtggc catctactgc agggacaaga agtgggagat gaccctggag gaggccgtga    4500
ccaggcggga ggccgtgaaa gagatctgca tcagcgacga ctccagcgtg accgagcccg    4560
acgccgagct ggtgagggtg caccccaaga gctccctggc cggcaggaag ggctacagca    4620
ccagcgacgg caagaccttc agctacctgg agggcaccaa gttccaccag gccgctaagg    4680
acatcgccga gatcaacgct atgtggcccc tggccaacga ggccaacgag caggtgtgca    4740
tgtacatcct gggcgagagc atgtccagca tcaggagcaa gtgccccgtg gaggaaagcg    4800
aggccagcac accacccagc accctgcccct gcctgtgcat ccacgctatg acacccgaga    4860
gggtcagcg gctgaaggcc agcaggcccg agcagatcac cgtgtgcagc tccttcccac    4920
tgcccaagta caggatcacc ggcgtgcaga agatccagtg cagccagccc atcctgttca    4980
gcccaaaggt gcccgcctac atccaccccca ggaagtgacct ggtggaccc cccaccagcc    5040
acgagacacc cgagccaagc gccgagaacc agagcaccga gggcacaccc gagcagccac    5100
ccctgatcac cgaggacgag acaaggaccc ggaccccaga gccatcatt atcgaggaag    5160
aggaagagga cagcatcagc ctgctgagcg acggccccac ccaccaggtg ctgcaggtgg    5220
aggccgacat ccacggccca cccagcgtgt ccagctccga ctggagcatc ccacacgcca    5280
gcgacttcga cgtggacgcc gtgagcatcc tggaccctt ggagggcgcc agcgtgacct    5340
ccggcgccac cagcgccgag accaacagct acttcgccaa gagcatgaag ttcctgccca    5400
ggcccgtgcc agctcccagg accgtgttca ggaacccacc ccaccagct cccaggacca    5460
ggaccccaag cctggctccc agcagggcct gcagcaggac cagcctggtg agcacccacc    5520
ccggcgtgaa cagggtgatc accagggagg aactggaggc cctgacaccc agcaggaccc    5580
ccagcaggtc cgtgagcagg actagtctgg tgtccaaccc agccggtg aacagggtga    5640
tcaccagggga ggaattcgag gccttcgtgg ccccagcaaca gagacggttc gacgccggcg    5700
cctacatctt cagcagcgac accgccagg acacctgca gcaaaagagc gtgaggcaga    5760
ccgtgctgag cgaggtggtg ctggagagga ccgagctgga aatcagctac gcccccagcc    5820
tggaccagga gaaggaggaa ctgctcagga gaaactgca gctgaacccc accccagcca    5880
acaggagcag gtaccagagc aggaaggtgg agaacatgaa ggccatcacc gccaggcgga    5940
```

-continued

```
tcctgcaggg cctgggacac tacctgaagg ccgagggcaa ggtggagtgc tacaggaccc    6000
tgcaccccgt gccactgtac agctccagcg tgaacagggc cttctccagc cccaaggtgg    6060
ccgtggaggc ctgcaacgct atgctgaagg agaacttccc caccgtggcc agctactgca    6120
tcatccccga gtacgacgcc tacctggaca tggtggacgg cgccagctgc tgcctggaca    6180
ccgccagctt ctgccccgcc aagctgagga gcttcccaa gaaacacagc tacctggagc    6240
ccaccatcag gagcgccgtg cccagcgcca tccagaacac cctgcagaac gtgctgccg    6300
ctgccaccaa gaggaactgc aacgtgaccc agatgaggga gctgcccgtg ctggacagcg    6360
ctgccttcaa cgtggagtgc ttcaagaaat acgcctgcaa caacgagtac tgggagacct    6420
tcaaggagaa ccccatcagg ctgaccgaag agaacgtggt gaactacatc accaagctga    6480
agggccccaa ggccgctgcc ctgttcgcta agacccacaa cctgaacatg ctgcaggaca    6540
tcccaatgga caggttcgtg atggacctga gagggacgt gaaggtgaca cccggcacca    6600
agcacaccga ggagaggccc aaggtgcagg tgatccaggc cgctgaccca ctggccaccg    6660
cctacctgtg cggcatccac agggagctgg tgaggcggct gaacgccgtg ctgctgccca    6720
acatccacac cctgttcgac atgagcgccg aggacttcga cgccatcatc gccgagcact    6780
tccagcccgg cgactgcgtg ctggagaccg acatcgccag cttcgacaag agcgaggatg    6840
acgctatggc cctgaccgct ctgatgatcc tggaggacct gggcgtggac gccgagctgc    6900
tcaccctgat cgaggctgcc ttcggcgaga tcagctccat ccacctgccc accaagacca    6960
agttcaagtt cggcgctatg atgaaaagcg gaatgttcct gaccctgttc gtgaacaccg    7020
tgatcaacat tgtgatcgcc agcagggtgc tgcgggagag gctgaccggc agccctgcg    7080
ctgccttcat cggcgacgac aacatcgtga agggcgtgaa aagcgacaag ctgatggccg    7140
acaggtgcgc cacctggctg aacatggagg tgaagatcat cgacgccgtg gtgggcgaga    7200
aggccccta cttctgcggc ggattcatcc tgtgcgacag cgtgaccggc agcgcctgca    7260
gggtggccga cccctgaag aggctgttca agctgggcag gccactggcc gctgacgatg    7320
agcacgacga tgacaggcgg aggggcccac acgaggaaag caccaggtgg aacagggtgg    7380
gcatcctgag cgagctgtgc aaggccgtgg agagcaggta cgagaccgtg ggcaccagca    7440
tcatcgtgat ggctatgacc acactggcca gctccgtcaa gagcttctcc tacctgaggg    7500
gggccctat aactctctac ggctaacctg aatggactac gacatagtct agtccgccaa    7560
ggccgccacc atggaagatg ccaaaaacat taagaagggc ccagcgccat tctacccact    7620
cgaagacggg accgccggcg agcagctgca caaagccatg aagcgctacg ccctggtgcc    7680
cggcaccatc gccttaccg acgcacatat cgaggtggac attacctacg ccgagtactt    7740
cgagatgagc gttcggctgg cagaagctat gaagcgctat gggctgaata caaaccatcg    7800
gatcgtggtg tgcagcgaga atagcttgca gttcttcatg cccgtgttgg gtgccctgtt    7860
catcggtgtg gctgtggccc cagctaacga catctacaac gagcgcgagc tgctgaacag    7920
catgggcatc agcagcccca cgtcgtatt cgtgagcaag aaagggctgc aaaagatcct    7980
caacgtgcaa aagaagctac cgatcataca aagatcatc atcatggata gcaagaccga    8040
ctaccagggc ttccaaagca tgtacaccct cgtgacttcc catttgccac ccggcttcaa    8100
cgagtacgac ttcgtgcccg agagcttcga ccgggacaaa accatcgccc tgatcatgaa    8160
cagtagtggc agtaccggat tgcccaaggg cgtagcccta ccgcaccgca ccgccttgtgt    8220
ccgattcagt catgccgcg accccatctt cggcaaccag atcatccccg acaccgctat    8280
cctcagcgtg gtgccatttc accacggctt cggcatgttc accacgctgg gctactgat    8340
ctgcggcttt cgggtcgtgc tcatgtaccg cttcgaggag gagctattct gcgcagctt    8400
gcaagactat aagattcaat ctgccctgct ggtgcccaca ctatttagct tcttcgctaa    8460
gagcactctc atcgacaagt acgacctaag caacttgcac gagatcgcca gcggcggggc    8520
gccgctcagc aaggaggtag gtgaggccgt ggccaaacgc ttccaccta caggcatccg    8580
acagggctac ggcctgacag aaacaaccag cgccattctg atcaccccgg aagggacga    8640
caagcctggc gcagtaggca aggtggtgcc cttcttcgag gctaaggtgg tggacttga    8700
caccggtaag acactgggtg tgaaccagcg cggcgagctg tgcgtccgtg gccccatgat    8760
catgagcggc tacgttaaca acccgagc tacaaacgct ctcatcgaca aggacgctg    8820
gctgcacagc ggcgacatcg cctactggga cgaggacgag cacttcttca tcgtggaccg    8880
gctgaagtcc ctgatcaaat acaagggcta ccaggtagcc ccagccgaac tggagagcat    8940
cctgctgcaa caccccaaca tcttcgacgc cgggtgcc ggcctgcccg acgacgatgc    9000
cggcgagctg cccgccgcag tcgtcgtgct ggaacacggt aaaaaccatga ccgagaagga    9060
gatcgtggac tatgtggcca gccaggttac aaccgccaag aagctgcgcg gtggtgttgt    9120
gttcgtggac gaggtgccta aaggactgac cggcaagttg gacgcccgca agatccgcga    9180
gattctcatt aaggccaaga agggccgcaa gatcgccgtg taactcgagc cggaaacgca    9240
atagccgaaa aacaaaaaac aaaaaaaaca aaaaaaaac caaaaaaaca aaacacatta    9300
aaacagcctg tgggttgatc ccacccacag gcccattggg cgctagcact ctggtatcac    9360
ggtaccttg tgcgcctgtt ttataccccc tcccccaact gtaacttaga agtaacacac    9420
accgatcaac agtcagcgtg gcacaccaac acgtttttga tcaagcactt ctgttacccc    9480
ggactgagta tcaatagact gctcacgcgg ttgaaggaga aagcgttcgt tatccggcca    9540
actacttcga aaaacctagt aacaccgtgg aagttgcaga gtgtttcgct cagcactacc    9600
ccagtgtaga tcaggtcgat gagtcaccgc attcccacg ggcgaccgtg gcggtggctg    9660
cgttggcggc ctgcccatgg ggaaacccat gggacgctct aatacagaca tggtgcgaag    9720
agtctattga gctagttggt agtcctccgg cccctgaatg tcgtcaatcc taactgcgga    9780
gcacacaccc tcaagccaga gggcagtgtg tcgtaacggg caactctgca gcggaaccga    9840
ctactttggg tgtccgtgtt tcattttatt cctatactgg ctgcttatgg tgacaattga    9900
gagatcgtta ccatatagct attggattgg ccatccggtg actaatagag ctattatata    9960
tccctttgtt gggtttatac cacttagctt gaaagaggtt aaaacattac aattcattgt   10020
taagttgaat acagcaaaat gagcaagatc tacatcgacg agcggagcaa cgccgagatc   10080
gtgtgcgagg ccatcaagac catcggcatc gagggcgcca ccgccgccca gctgaccagg   10140
cagctgaaca tggagaagcg ggaggtgaac aaggcccctgt acgacctgca gaggagcgct   10200
atggtgtact ccagcgacga catccctccc cggtggttca tgaccaccga ggccgacaag   10260
cccgacgccg acgctatggc cgacgtgatc atcgacacg tgagcaggga gaagtccatg   10320
agggaggacc aaaagagctt cgacgacgtg atcccgca agaagatcat cgactggaag   10380
ggcgccaacc ccgtgaccgt gatcaacgag tactgccaga tcaccaggag ggactggagc   10440
ttccggatcg agagcgtggg cccagcaac agccccacct tctacgcctg cgtggacatc   10500
gacgcagggg tgttcgacaa ggccgacggc aagagcaagc gggacgccaa gaacaacgcc   10560
gccaagctgc ccgtggacaa gctgctgggc tacgtgatca tccggttcta aacaattggc   10620
aagctgctta catagaactc gcggcgattg gcatgccgcc ttaaaatttt tattttattt   10680
```

-continued

```
tttcttttct tttccgaatc ggattttgtt tttaatattt caaaaaaaaa aaaaaaaaaa  10740
aaaaaatcta gaaaaaaaaa aaaaaaaaaa aaaaaaaaaa aaaaaaaaaa aaaaaaaaaa  10800
aaaaaaaaaa aaaaaaaaaa aaaaaaaaaa aaaaaaaaaa aaaaaaaaaa a           10851
```